US012774457B2

(12) United States Patent
Wessells et al.

(10) Patent No.: US 12,774,457 B2
(45) Date of Patent: Oct. 27, 2026

(54) GENE EDITING SYSTEMS COMPRISING AN RNA GUIDE TARGETING HYDROXYACID OXIDASE 1 (HAO1) AND USES THEREOF

(71) Applicant: Arbor Biotechnologies, Inc., Cambridge, MA (US)

(72) Inventors: Quinton Norman Wessells, Cambridge, MA (US); Jeffrey Raymond Haswell, Needham, MA (US); Tia Marie Ditommaso, Newton, MA (US); Noah Michael Jakimo, San Francisco, CA (US); Sejuti Sengupta, Ashland, MA (US)

(73) Assignee: Arbor Biotechnologies, Inc., Cambridge, MA (US)

( * ) Notice: Subject to any disclaimer, the term of this patent is extended or adjusted under 35 U.S.C. 154(b) by 1080 days.

(21) Appl. No.: 17/832,038

(22) Filed: Jun. 3, 2022

(65) Prior Publication Data

US 2023/0032141 A1 Feb. 2, 2023

Related U.S. Application Data

(60) Provisional application No. 63/300,727, filed on Jan. 19, 2022, provisional application No. 63/292,889, filed on Dec. 22, 2021, provisional application No. 63/225,046, filed on Jul. 23, 2021, provisional application No. 63/197,073, filed on Jun. 4, 2021.

(51) Int. Cl.

| | |
|---|---|
| ***C12N 9/22*** | (2006.01) |
| ***A61K 31/7105*** | (2006.01) |
| ***A61K 38/46*** | (2006.01) |
| ***A61K 48/00*** | (2006.01) |
| ***A61P 13/12*** | (2006.01) |
| ***C12N 15/11*** | (2006.01) |
| ***C12N 15/113*** | (2010.01) |
| ***C12N 15/86*** | (2006.01) |
| ***C12N 15/88*** | (2006.01) |
| ***C12N 15/90*** | (2006.01) |

(52) U.S. Cl.

CPC ............ *C12N 9/22* (2013.01); *A61K 31/7105* (2013.01); *A61K 38/465* (2013.01); *A61P 13/12* (2018.01); *C12N 15/11* (2013.01); *C12N 15/1137* (2013.01); *C12N 15/86* (2013.01); *C12N 15/88* (2013.01); *C12N 15/907* (2013.01); *C12Y 101/03015* (2013.01); *A61K 48/00* (2013.01); *C12N 2310/20* (2017.05); *C12N 2750/14143* (2013.01); *C12N 2800/80* (2013.01)

(58) Field of Classification Search

None

See application file for complete search history.

(56) References Cited

FOREIGN PATENT DOCUMENTS

| | | | |
|---|---|---|---|
| CN | 112195164 | A | 1/2021 |
| WO | WO 2015/100436 | A1 | 7/2015 |
| WO | WO 2019/178427 | A1 | 9/2019 |
| WO | WO 2020/028327 | A1 | 2/2020 |
| WO | 2020069296 | A1 | 4/2020 |
| WO | 2020132659 | A1 | 6/2020 |
| WO | WO 2021/202800 | A1 | 10/2021 |
| WO | WO 2021/257730 | A2 | 12/2021 |

OTHER PUBLICATIONS

U.S. Appl. No. 18/052,801, filed Nov. 4, 2022, Wessells et al.

[No Author Listed], Cas12i nickase variant Cas12i2-6.1, SEQ ID No: 18. Geneseq Database Accession No. BIV42112. From CN 112195164 A. Jan. 8, 2021.

Mcgaw et al., Engineered Cas1212 is a versatile high-efficiency platform for therapeutic genome editing. Nat Commun. May 20, 2022;13(1):2833(1-11).

Zheng et al., CRISPR/Cas9-mediated metabolic pathway reprogramming in a novel humanized rat model ameliorates primary hyperoxaluria type 1. Kidney Int. Oct. 2020;98(4):947-957. Epub May 25, 2020.

U.S. Appl. No. 18/565,575, filed Nov. 30, 2023, Quinton Norman Wessells et al.

Zabaleta et al. (Dec. 2018) "CRISPR/Cas9-Mediated Glycolate Oxidase Disruption is an Efficacious and Safe Treatment for Primary Hyperoxaluria Type I", Nature Communications, 9(1):9 pages.

Zheng et al. (Aug. 27, 2020) "Knockdown of Lactate Dehydrogenase by Adeno-Associated Virus-Delivered CRISPR/Cas9 System Alleviates Primary Hyperoxaluria Type 1", Clinical and Translational Medicine, 10(8):e261(13 pages).

Gao et al., Engineered Cpf1 variants with altered PAM specificities. Nat Biotechnol. Aug. 2017;35(8):789-792. Epub Jun. 5, 2017.

Huang et al., Structural basis for two metal-ion catalysis of DNA cleavage by Cas1212. Nat Commun. Oct. 16, 2020;11(1):5241. 28 pages.

Slaymaker et al., Rationally engineered Cas9 nucleases with improved specificity. Science. Jan. 1, 2016;351(6268):84-8. Epub Dec. 1, 2015.

(Continued)

*Primary Examiner* — Christopher M Babic

*Assistant Examiner* — Kimberly A Aron

(74) *Attorney, Agent, or Firm* — Lathrop GPM LLP; Malaika O.D. Tyson

(57) ABSTRACT

Provided herein are gene editing systems and/or compositions comprising RNA guides targeting HAO1 for use in genetic editing of the HAO1 gene. Also provide herein are methods of using the gene editing system for introducing edits to the HAO1 gene and/or for treatment of primary hyperoxaluria (PH), and processes for characterizing the gene editing system.

14 Claims, 10 Drawing Sheets

Specification includes a Sequence Listing.

(56) References Cited

OTHER PUBLICATIONS

Strecker et al., Engineering of CRISPR-Cas12b for human genome editing. Nat Commun. Jan. 22, 2019;10(1):212. 29 pages.
International Preliminary Report on Patentability for PCT International Application No. PCT/US2022/032144, dated Nov. 21, 2023.
International Search Report and Written Opinion for PCT International Application No. PCT/US2022/032144, mailed May 12, 2022.
Japan Patent Office, Office Action for Application No. JP 2023-574534, dated May 19, 2026. Machine English Translation included.

SEQUENCE LISTING

```
<160> NUMBER OF SEQ ID NOS: 1097

<210> SEQ ID NO 1
<211> LENGTH: 36
<212> TYPE: RNA
<213> ORGANISM: Artificial Sequence
<220> FEATURE:
<223> OTHER INFORMATION: Synthetic

<400> SEQUENCE: 1
```

guugcaaaac ccaagaaauc cgucuuucau ugacgg 36

<210> SEQ ID NO 2
<211> LENGTH: 36
<212> TYPE: RNA
<213> ORGANISM: Artificial Sequence
<220> FEATURE:
<223> OTHER INFORMATION: Synthetic

<400> SEQUENCE: 2
aauagcggcc cuaagaaauc cgucuuucau ugacgg 36

<210> SEQ ID NO 3
<211> LENGTH: 36
<212> TYPE: RNA
<213> ORGANISM: Artificial Sequence
<220> FEATURE:
<223> OTHER INFORMATION: Synthetic

<400> SEQUENCE: 3
auuggaacug gcgagaaauc cgucuuucau ugacgg 36

<210> SEQ ID NO 4
<211> LENGTH: 36
<212> TYPE: RNA
<213> ORGANISM: Artificial Sequence
<220> FEATURE:
<223> OTHER INFORMATION: Synthetic

<400> SEQUENCE: 4
ccagcaacac cuaagaaauc cgucuuucau ugacgg 36

<210> SEQ ID NO 5
<211> LENGTH: 36
<212> TYPE: RNA
<213> ORGANISM: Artificial Sequence
<220> FEATURE:
<223> OTHER INFORMATION: Synthetic

<400> SEQUENCE: 5
cggcgcucga auaggaaauc cgucuuucau ugacgg 36

<210> SEQ ID NO 6
<211> LENGTH: 36
<212> TYPE: RNA
<213> ORGANISM: Artificial Sequence
<220> FEATURE:
<223> OTHER INFORMATION: Synthetic

<400> SEQUENCE: 6
guggcaacac cuaagaaauc cgucuuucau ugacgg 36

<210> SEQ ID NO 7
<211> LENGTH: 36
<212> TYPE: RNA
<213> ORGANISM: Artificial Sequence
<220> FEATURE:
<223> OTHER INFORMATION: Synthetic

<400> SEQUENCE: 7
guugcaacac cuaagaaauc cgucuuucau ugacgg 36

<210> SEQ ID NO 8
<211> LENGTH: 36
<212> TYPE: RNA

<213> ORGANISM: Artificial Sequence
<220> FEATURE:
<223> OTHER INFORMATION: Synthetic

<400> SEQUENCE: 8
guugcaaugc cuaagaaauc cgucuuucau ugacgg 36

<210> SEQ ID NO 9
<211> LENGTH: 34
<212> TYPE: RNA
<213> ORGANISM: Artificial Sequence
<220> FEATURE:
<223> OTHER INFORMATION: Synthetic

<400> SEQUENCE: 9
gcaacaccua agaaauccgu cuuucauuga cggg 34

<210> SEQ ID NO 10
<211> LENGTH: 23
<212> TYPE: RNA
<213> ORGANISM: Artificial Sequence
<220> FEATURE:
<223> OTHER INFORMATION: Synthetic

<400> SEQUENCE: 10
agaaauccgu cuuucauuga cgg 23

<210> SEQ ID NO 11
<211> LENGTH: 30
<212> TYPE: DNA
<213> ORGANISM: Artificial Sequence
<220> FEATURE:
<223> OTHER INFORMATION: Synthetic

<400> SEQUENCE: 11
cctggaaaat gctgcaatat tatcagccaa 30

<210> SEQ ID NO 12
<211> LENGTH: 30
<212> TYPE: DNA
<213> ORGANISM: Artificial Sequence
<220> FEATURE:
<223> OTHER INFORMATION: Synthetic

<400> SEQUENCE: 12
tcttacctgg aaaatgctgc aatattatca 30

<210> SEQ ID NO 13
<211> LENGTH: 30
<212> TYPE: DNA
<213> ORGANISM: Artificial Sequence
<220> FEATURE:
<223> OTHER INFORMATION: Synthetic

<400> SEQUENCE: 13
cttacctgga aaatgctgca atattatcag 30

<210> SEQ ID NO 14
<211> LENGTH: 30
<212> TYPE: DNA
<213> ORGANISM: Artificial Sequence
<220> FEATURE:
<223> OTHER INFORMATION: Synthetic

<400> SEQUENCE: 14
ttacctggaa aatgctgcaa tattatcagc 30

<210> SEQ ID NO 15
<211> LENGTH: 30
<212> TYPE: DNA
<213> ORGANISM: Artificial Sequence
<220> FEATURE:
<223> OTHER INFORMATION: Synthetic

<400> SEQUENCE: 15
tcagccaaag tttcttcatc atttgcccca 30

<210> SEQ ID NO 16
<211> LENGTH: 30
<212> TYPE: DNA
<213> ORGANISM: Artificial Sequence
<220> FEATURE:
<223> OTHER INFORMATION: Synthetic

<400> SEQUENCE: 16
cttcatcatt tgccccagac ctgtaatagt 30

<210> SEQ ID NO 17
<211> LENGTH: 30
<212> TYPE: DNA
<213> ORGANISM: Artificial Sequence
<220> FEATURE:
<223> OTHER INFORMATION: Synthetic

<400> SEQUENCE: 17
ttcatcattt gccccagacc tgtaatagtc 30

<210> SEQ ID NO 18
<211> LENGTH: 30
<212> TYPE: DNA
<213> ORGANISM: Artificial Sequence
<220> FEATURE:
<223> OTHER INFORMATION: Synthetic

<400> SEQUENCE: 18
atcatttgcc ccagacctgt aatagtcata 30

<210> SEQ ID NO 19
<211> LENGTH: 30
<212> TYPE: DNA
<213> ORGANISM: Artificial Sequence
<220> FEATURE:
<223> OTHER INFORMATION: Synthetic

<400> SEQUENCE: 19
gccccagacc tgtaatagtc atatatagac 30

<210> SEQ ID NO 20
<211> LENGTH: 30
<212> TYPE: DNA
<213> ORGANISM: Artificial Sequence
<220> FEATURE:
<223> OTHER INFORMATION: Synthetic

<400> SEQUENCE: 20
ccccagacct gtaatagtca tatatagact 30

<210> SEQ ID NO 21
<211> LENGTH: 30
<212> TYPE: DNA
<213> ORGANISM: Artificial Sequence
<220> FEATURE:

<223> OTHER INFORMATION: Synthetic

<400> SEQUENCE: 21
aaaaaataaa ttttcttacc tggaaaatgc 30

<210> SEQ ID NO 22
<211> LENGTH: 30
<212> TYPE: DNA
<213> ORGANISM: Artificial Sequence
<220> FEATURE:
<223> OTHER INFORMATION: Synthetic

<400> SEQUENCE: 22
ggaagtactg atttagcatg ttgttcataa 30

<210> SEQ ID NO 23
<211> LENGTH: 30
<212> TYPE: DNA
<213> ORGANISM: Artificial Sequence
<220> FEATURE:
<223> OTHER INFORMATION: Synthetic

<400> SEQUENCE: 23
agcatgttgt tcataatcat tgatacaaat 30

<210> SEQ ID NO 24
<211> LENGTH: 30
<212> TYPE: DNA
<213> ORGANISM: Artificial Sequence
<220> FEATURE:
<223> OTHER INFORMATION: Synthetic

<400> SEQUENCE: 24
gcatgttgtt cataatcatt gatacaaatt 30

<210> SEQ ID NO 25
<211> LENGTH: 30
<212> TYPE: DNA
<213> ORGANISM: Artificial Sequence
<220> FEATURE:
<223> OTHER INFORMATION: Synthetic

<400> SEQUENCE: 25
ttcataatca ttgatacaaa ttagccgggg 30

<210> SEQ ID NO 26
<211> LENGTH: 30
<212> TYPE: DNA
<213> ORGANISM: Artificial Sequence
<220> FEATURE:
<223> OTHER INFORMATION: Synthetic

<400> SEQUENCE: 26
ataatcattg atacaaatta gccgggggag 30

<210> SEQ ID NO 27
<211> LENGTH: 30
<212> TYPE: DNA
<213> ORGANISM: Artificial Sequence
<220> FEATURE:
<223> OTHER INFORMATION: Synthetic

<400> SEQUENCE: 27
atacaaatta gccgggggag cattttcaca 30

<210> SEQ ID NO 28
<211> LENGTH: 30
<212> TYPE: DNA
<213> ORGANISM: Artificial Sequence
<220> FEATURE:
<223> OTHER INFORMATION: Synthetic

<400> SEQUENCE: 28
gccgggggag cattttcaca ggttattgct 30

<210> SEQ ID NO 29
<211> LENGTH: 30
<212> TYPE: DNA
<213> ORGANISM: Artificial Sequence
<220> FEATURE:
<223> OTHER INFORMATION: Synthetic

<400> SEQUENCE: 29
tcacaggtta ttgctatccc agatggagtt 30

<210> SEQ ID NO 30
<211> LENGTH: 30
<212> TYPE: DNA
<213> ORGANISM: Artificial Sequence
<220> FEATURE:
<223> OTHER INFORMATION: Synthetic

<400> SEQUENCE: 30
cacaggttat tgctatccca gatggagttc 30

<210> SEQ ID NO 31
<211> LENGTH: 30
<212> TYPE: DNA
<213> ORGANISM: Artificial Sequence
<220> FEATURE:
<223> OTHER INFORMATION: Synthetic

<400> SEQUENCE: 31
acaggttatt gctatcccag atggagttcg 30

<210> SEQ ID NO 32
<211> LENGTH: 30
<212> TYPE: DNA
<213> ORGANISM: Artificial Sequence
<220> FEATURE:
<223> OTHER INFORMATION: Synthetic

<400> SEQUENCE: 32
gaagtactga tttagcatgt tgttcataat 30

<210> SEQ ID NO 33
<211> LENGTH: 30
<212> TYPE: DNA
<213> ORGANISM: Artificial Sequence
<220> FEATURE:
<223> OTHER INFORMATION: Synthetic

<400> SEQUENCE: 33
taaaaaataa atttcttac ctggaaaatg 30

<210> SEQ ID NO 34
<211> LENGTH: 30
<212> TYPE: DNA
<213> ORGANISM: Artificial Sequence
<220> FEATURE:
<223> OTHER INFORMATION: Synthetic

<400> SEQUENCE: 34
aaaaataaat tttcttacct ggaaaatgct 30

<210> SEQ ID NO 35
<211> LENGTH: 30
<212> TYPE: DNA
<213> ORGANISM: Artificial Sequence
<220> FEATURE:
<223> OTHER INFORMATION: Synthetic

<400> SEQUENCE: 35
aaaacatgat tttaaaaaat aaattttctt 30

<210> SEQ ID NO 36
<211> LENGTH: 30
<212> TYPE: DNA
<213> ORGANISM: Artificial Sequence
<220> FEATURE:
<223> OTHER INFORMATION: Synthetic

<400> SEQUENCE: 36
tatcaatgat tatgaacaac atgctaaatc 30

<210> SEQ ID NO 37
<211> LENGTH: 30
<212> TYPE: DNA
<213> ORGANISM: Artificial Sequence
<220> FEATURE:
<223> OTHER INFORMATION: Synthetic

<400> SEQUENCE: 37
tgaacaacat gctaaatcag tacttccaaa 30

<210> SEQ ID NO 38
<211> LENGTH: 30
<212> TYPE: DNA
<213> ORGANISM: Artificial Sequence
<220> FEATURE:
<223> OTHER INFORMATION: Synthetic

<400> SEQUENCE: 38
caaagtctat atatgactat tacaggtctg 30

<210> SEQ ID NO 39
<211> LENGTH: 30
<212> TYPE: DNA
<213> ORGANISM: Artificial Sequence
<220> FEATURE:
<223> OTHER INFORMATION: Synthetic

<400> SEQUENCE: 39
caggtctggg gcaaatgatg aagaaacttt 30

<210> SEQ ID NO 40
<211> LENGTH: 30
<212> TYPE: DNA
<213> ORGANISM: Artificial Sequence
<220> FEATURE:
<223> OTHER INFORMATION: Synthetic

<400> SEQUENCE: 40
ggctgataat attgcagcat tttccaggta 30

<210> SEQ ID NO 41
<211> LENGTH: 30

<212> TYPE: DNA
<213> ORGANISM: Artificial Sequence
<220> FEATURE:
<223> OTHER INFORMATION: Synthetic

<400> SEQUENCE: 41
gctgataata ttgcagcatt ttccaggtaa 30

<210> SEQ ID NO 42
<211> LENGTH: 30
<212> TYPE: DNA
<213> ORGANISM: Artificial Sequence
<220> FEATURE:
<223> OTHER INFORMATION: Synthetic

<400> SEQUENCE: 42
cagcattttc caggtaagaa aatttatttt 30

<210> SEQ ID NO 43
<211> LENGTH: 30
<212> TYPE: DNA
<213> ORGANISM: Artificial Sequence
<220> FEATURE:
<223> OTHER INFORMATION: Synthetic

<400> SEQUENCE: 43
tccaggtaag aaaatttatt ttttaaaatc 30

<210> SEQ ID NO 44
<211> LENGTH: 30
<212> TYPE: DNA
<213> ORGANISM: Artificial Sequence
<220> FEATURE:
<223> OTHER INFORMATION: Synthetic

<400> SEQUENCE: 44
ccaggtaaga aaatttattt tttaaaatca 30

<210> SEQ ID NO 45
<211> LENGTH: 30
<212> TYPE: DNA
<213> ORGANISM: Artificial Sequence
<220> FEATURE:
<223> OTHER INFORMATION: Synthetic

<400> SEQUENCE: 45
aaacatgatt ttaaaaaata aattttctta 30

<210> SEQ ID NO 46
<211> LENGTH: 30
<212> TYPE: DNA
<213> ORGANISM: Artificial Sequence
<220> FEATURE:
<223> OTHER INFORMATION: Synthetic

<400> SEQUENCE: 46
attttttaaa atcatgtttt aaaattacac 30

<210> SEQ ID NO 47
<211> LENGTH: 30
<212> TYPE: DNA
<213> ORGANISM: Artificial Sequence
<220> FEATURE:
<223> OTHER INFORMATION: Synthetic

<400> SEQUENCE: 47
caggtaagaa aatttatttt ttaaaatcat 30

<210> SEQ ID NO 48
<211> LENGTH: 30
<212> TYPE: DNA
<213> ORGANISM: Artificial Sequence
<220> FEATURE:
<223> OTHER INFORMATION: Synthetic

<400> SEQUENCE: 48
tttaaaatca tgttttaaaa ttacacaaag 30

<210> SEQ ID NO 49
<211> LENGTH: 30
<212> TYPE: DNA
<213> ORGANISM: Artificial Sequence
<220> FEATURE:
<223> OTHER INFORMATION: Synthetic

<400> SEQUENCE: 49
ttaaaatcat gttttaaaat tacacaaaga 30

<210> SEQ ID NO 50
<211> LENGTH: 30
<212> TYPE: DNA
<213> ORGANISM: Artificial Sequence
<220> FEATURE:
<223> OTHER INFORMATION: Synthetic

<400> SEQUENCE: 50
taaaatcatg ttttaaaatt acacaaagac 30

<210> SEQ ID NO 51
<211> LENGTH: 30
<212> TYPE: DNA
<213> ORGANISM: Artificial Sequence
<220> FEATURE:
<223> OTHER INFORMATION: Synthetic

<400> SEQUENCE: 51
aaaatcatgt tttaaaatta cacaaagacc 30

<210> SEQ ID NO 52
<211> LENGTH: 30
<212> TYPE: DNA
<213> ORGANISM: Artificial Sequence
<220> FEATURE:
<223> OTHER INFORMATION: Synthetic

<400> SEQUENCE: 52
aaatcatgtt ttaaaattac acaaagaccg 30

<210> SEQ ID NO 53
<211> LENGTH: 30
<212> TYPE: DNA
<213> ORGANISM: Artificial Sequence
<220> FEATURE:
<223> OTHER INFORMATION: Synthetic

<400> SEQUENCE: 53
gtgtaatttt aaaacatgat tttaaaaaat 30

<210> SEQ ID NO 54
<211> LENGTH: 30
<212> TYPE: DNA
<213> ORGANISM: Artificial Sequence
<220> FEATURE:
<223> OTHER INFORMATION: Synthetic

<400> SEQUENCE: 54
tgtaatttta aaacatgatt ttaaaaaata 30

<210> SEQ ID NO 55
<211> LENGTH: 30
<212> TYPE: DNA
<213> ORGANISM: Artificial Sequence
<220> FEATURE:
<223> OTHER INFORMATION: Synthetic

<400> SEQUENCE: 55
taaaacatga ttttaaaaaa taaattttct 30

<210> SEQ ID NO 56
<211> LENGTH: 30
<212> TYPE: DNA
<213> ORGANISM: Artificial Sequence
<220> FEATURE:
<223> OTHER INFORMATION: Synthetic

<400> SEQUENCE: 56 tttttaaaa tcatgtttta aaattacaca 30

<210> SEQ ID NO 57
<211> LENGTH: 30
<212> TYPE: DNA
<213> ORGANISM: Artificial Sequence
<220> FEATURE:
<223> OTHER INFORMATION: Synthetic

<400> SEQUENCE: 57
gtatcaatga ttatgaacaa catgctaaat 30

<210> SEQ ID NO 58
<211> LENGTH: 24
<212> TYPE: DNA
<213> ORGANISM: Artificial Sequence
<220> FEATURE:
<223> OTHER INFORMATION: Synthetic

<400> SEQUENCE: 58
ttgctatccc agatggagtt cgtt 24

<210> SEQ ID NO 59
<211> LENGTH: 21
<212> TYPE: DNA
<213> ORGANISM: Artificial Sequence
<220> FEATURE:
<223> OTHER INFORMATION: Synthetic

<400> SEQUENCE: 59
ctatcccaga tggagttcgt t 21

<210> SEQ ID NO 60
<211> LENGTH: 30
<212> TYPE: DNA
<213> ORGANISM: Artificial Sequence
<220> FEATURE:
<223> OTHER INFORMATION: Synthetic

<400> SEQUENCE: 60
ttttttaatt ctagatggaa gctgtatcca 30

<210> SEQ ID NO 61
<211> LENGTH: 30
<212> TYPE: DNA
<213> ORGANISM: Artificial Sequence
<220> FEATURE:
<223> OTHER INFORMATION: Synthetic

<400> SEQUENCE: 61
attttatttt ttaattctag atggaagctg 30

<210> SEQ ID NO 62
<211> LENGTH: 30
<212> TYPE: DNA
<213> ORGANISM: Artificial Sequence
<220> FEATURE:
<223> OTHER INFORMATION: Synthetic

<400> SEQUENCE: 62
attttttaat tctagatgga agctgtatcc 30

<210> SEQ ID NO 63
<211> LENGTH: 30
<212> TYPE: DNA
<213> ORGANISM: Artificial Sequence
<220> FEATURE:
<223> OTHER INFORMATION: Synthetic

<400> SEQUENCE: 63
tattttttaa ttctagatgg aagctgtatc 30

<210> SEQ ID NO 64
<211> LENGTH: 30
<212> TYPE: DNA
<213> ORGANISM: Artificial Sequence
<220> FEATURE:
<223> OTHER INFORMATION: Synthetic

<400> SEQUENCE: 64
ttttattttt taattctaga tggaagctgt 30

<210> SEQ ID NO 65
<211> LENGTH: 30
<212> TYPE: DNA
<213> ORGANISM: Artificial Sequence
<220> FEATURE:
<223> OTHER INFORMATION: Synthetic

<400> SEQUENCE: 65
aaaaataaaa taaaataaaa ggctttagag 30

<210> SEQ ID NO 66
<211> LENGTH: 30
<212> TYPE: DNA
<213> ORGANISM: Artificial Sequence
<220> FEATURE:
<223> OTHER INFORMATION: Synthetic

<400> SEQUENCE: 66
attttatttt atttttaat tctagatgga 30

<210> SEQ ID NO 67
<211> LENGTH: 30
<212> TYPE: DNA
<213> ORGANISM: Artificial Sequence
<220> FEATURE:
<223> OTHER INFORMATION: Synthetic

<400> SEQUENCE: 67
tattttattt tattttttaa ttctagatgg 30

<210> SEQ ID NO 68
<211> LENGTH: 30
<212> TYPE: DNA
<213> ORGANISM: Artificial Sequence
<220> FEATURE:
<223> OTHER INFORMATION: Synthetic

<400> SEQUENCE: 68
tgaaactcta aagcctttta ttttatttta 30

<210> SEQ ID NO 69
<211> LENGTH: 30
<212> TYPE: DNA
<213> ORGANISM: Artificial Sequence
<220> FEATURE:
<223> OTHER INFORMATION: Synthetic

<400> SEQUENCE: 69
tttaattcta gatggaagct gtatccaagg 30

<210> SEQ ID NO 70
<211> LENGTH: 30
<212> TYPE: DNA
<213> ORGANISM: Artificial Sequence
<220> FEATURE:
<223> OTHER INFORMATION: Synthetic

<400> SEQUENCE: 70
ttttatttta ttttttaatt ctagatggaa 30

<210> SEQ ID NO 71
<211> LENGTH: 30
<212> TYPE: DNA
<213> ORGANISM: Artificial Sequence
<220> FEATURE:
<223> OTHER INFORMATION: Synthetic

<400> SEQUENCE: 71
ttaattctag atggaagctg tatccaagga 30

<210> SEQ ID NO 72
<211> LENGTH: 30
<212> TYPE: DNA
<213> ORGANISM: Artificial Sequence
<220> FEATURE:
<223> OTHER INFORMATION: Synthetic

<400> SEQUENCE: 72
tattttattt tttaattcta gatggaagct 30

<210> SEQ ID NO 73
<211> LENGTH: 30
<212> TYPE: DNA
<213> ORGANISM: Artificial Sequence
<220> FEATURE:
<223> OTHER INFORMATION: Synthetic

<400> SEQUENCE: 73
catctagaat taaaaaataa aataaaataa 30

<210> SEQ ID NO 74

<211> LENGTH: 30
<212> TYPE: DNA
<213> ORGANISM: Artificial Sequence
<220> FEATURE:
<223> OTHER INFORMATION: Synthetic

<400> SEQUENCE: 74
taattctaga tggaagctgt atccaaggat 30

<210> SEQ ID NO 75
<211> LENGTH: 30
<212> TYPE: DNA
<213> ORGANISM: Artificial Sequence
<220> FEATURE:
<223> OTHER INFORMATION: Synthetic

<400> SEQUENCE: 75
aattctagat ggaagctgta tccaaggatg 30

<210> SEQ ID NO 76
<211> LENGTH: 30
<212> TYPE: DNA
<213> ORGANISM: Artificial Sequence
<220> FEATURE:
<223> OTHER INFORMATION: Synthetic

<400> SEQUENCE: 76
attctagatg gaagctgtat ccaaggatgc 30

<210> SEQ ID NO 77
<211> LENGTH: 30
<212> TYPE: DNA
<213> ORGANISM: Artificial Sequence
<220> FEATURE:
<223> OTHER INFORMATION: Synthetic

<400> SEQUENCE: 77
tagatggaag ctgtatccaa ggatgctccg 30

<210> SEQ ID NO 78
<211> LENGTH: 30
<212> TYPE: DNA
<213> ORGANISM: Artificial Sequence
<220> FEATURE:
<223> OTHER INFORMATION: Synthetic

<400> SEQUENCE: 78
ctgaaacaga tctgtcgact tctgttttag 30

<210> SEQ ID NO 79
<211> LENGTH: 30
<212> TYPE: DNA
<213> ORGANISM: Artificial Sequence
<220> FEATURE:
<223> OTHER INFORMATION: Synthetic

<400> SEQUENCE: 79
taggacagag ggtcagcatg ccaatatgtg 30

<210> SEQ ID NO 80
<211> LENGTH: 30
<212> TYPE: DNA
<213> ORGANISM: Artificial Sequence
<220> FEATURE:
<223> OTHER INFORMATION: Synthetic

<400> SEQUENCE: 80
aggacagagg gtcagcatgc caatatgtgt 30

<210> SEQ ID NO 81
<211> LENGTH: 30
<212> TYPE: DNA
<213> ORGANISM: Artificial Sequence
<220> FEATURE:
<223> OTHER INFORMATION: Synthetic

<400> SEQUENCE: 81
ggacagaggg tcagcatgcc aatatgtgtg 30

<210> SEQ ID NO 82
<211> LENGTH: 30
<212> TYPE: DNA
<213> ORGANISM: Artificial Sequence
<220> FEATURE:
<223> OTHER INFORMATION: Synthetic

<400> SEQUENCE: 82
ccactgtgag aggtaggagg aagattgtca 30

<210> SEQ ID NO 83
<211> LENGTH: 30
<212> TYPE: DNA
<213> ORGANISM: Artificial Sequence
<220> FEATURE:
<223> OTHER INFORMATION: Synthetic

<400> SEQUENCE: 83
tgttttagga cagagggtca gcatgccaat 30

<210> SEQ ID NO 84
<211> LENGTH: 30
<212> TYPE: DNA
<213> ORGANISM: Artificial Sequence
<220> FEATURE:
<223> OTHER INFORMATION: Synthetic

<400> SEQUENCE: 84
gcctccttct gtccctgtgg tgacaatctt 30

<210> SEQ ID NO 85
<211> LENGTH: 30
<212> TYPE: DNA
<213> ORGANISM: Artificial Sequence
<220> FEATURE:
<223> OTHER INFORMATION: Synthetic

<400> SEQUENCE: 85
tcaccacagg gacagaagga ggctaacgtt 30

<210> SEQ ID NO 86
<211> LENGTH: 30
<212> TYPE: DNA
<213> ORGANISM: Artificial Sequence
<220> FEATURE:
<223> OTHER INFORMATION: Synthetic

<400> SEQUENCE: 86
cggagcatcc ttggatacag cttccatcta 30

<210> SEQ ID NO 87
<211> LENGTH: 30
<212> TYPE: DNA

<213> ORGANISM: Artificial Sequence
<220> FEATURE:
<223> OTHER INFORMATION: Synthetic

<400> SEQUENCE: 87
agcaacattc cggagcatcc ttggatacag 30

<210> SEQ ID NO 88
<211> LENGTH: 30
<212> TYPE: DNA
<213> ORGANISM: Artificial Sequence
<220> FEATURE:
<223> OTHER INFORMATION: Synthetic

<400> SEQUENCE: 88
cagcaacatt ccggagcatc cttggataca 30

<210> SEQ ID NO 89
<211> LENGTH: 30
<212> TYPE: DNA
<213> ORGANISM: Artificial Sequence
<220> FEATURE:
<223> OTHER INFORMATION: Synthetic

<400> SEQUENCE: 89
gatacagctt ccatctagaa ttaaaaaata 30

<210> SEQ ID NO 90
<211> LENGTH: 30
<212> TYPE: DNA
<213> ORGANISM: Artificial Sequence
<220> FEATURE:
<223> OTHER INFORMATION: Synthetic

<400> SEQUENCE: 90
ctcctacctc tcacagtggc aagctcgccg 30

<210> SEQ ID NO 91
<211> LENGTH: 30
<212> TYPE: DNA
<213> ORGANISM: Artificial Sequence
<220> FEATURE:
<223> OTHER INFORMATION: Synthetic

<400> SEQUENCE: 91
tgtccctgtg gtgacaatct tcctcctacc 30

<210> SEQ ID NO 92
<211> LENGTH: 30
<212> TYPE: DNA
<213> ORGANISM: Artificial Sequence
<220> FEATURE:
<223> OTHER INFORMATION: Synthetic

<400> SEQUENCE: 92
gcatgctgac cctctgtcct aaaacagaag 30

<210> SEQ ID NO 93
<211> LENGTH: 30
<212> TYPE: DNA
<213> ORGANISM: Artificial Sequence
<220> FEATURE:
<223> OTHER INFORMATION: Synthetic

<400> SEQUENCE: 93
cctgggcaac cgtctggatg atgtgcgtaa 30

<210> SEQ ID NO 94
<211> LENGTH: 30
<212> TYPE: DNA
<213> ORGANISM: Artificial Sequence
<220> FEATURE:
<223> OTHER INFORMATION: Synthetic

<400> SEQUENCE: 94
aatctgttac gcacatcatc cagacggttg 30

<210> SEQ ID NO 95
<211> LENGTH: 30
<212> TYPE: DNA
<213> ORGANISM: Artificial Sequence
<220> FEATURE:
<223> OTHER INFORMATION: Synthetic

<400> SEQUENCE: 95
gaatctgtta cgcacatcat ccagacggtt 30

<210> SEQ ID NO 96
<211> LENGTH: 30
<212> TYPE: DNA
<213> ORGANISM: Artificial Sequence
<220> FEATURE:
<223> OTHER INFORMATION: Synthetic

<400> SEQUENCE: 96
tggcggcagt ttgaatctgt tacgcacatc 30

<210> SEQ ID NO 97
<211> LENGTH: 30
<212> TYPE: DNA
<213> ORGANISM: Artificial Sequence
<220> FEATURE:
<223> OTHER INFORMATION: Synthetic

<400> SEQUENCE: 97
cctgagttgt ggcggcagtt tgaatctgtt 30

<210> SEQ ID NO 98
<211> LENGTH: 30
<212> TYPE: DNA
<213> ORGANISM: Artificial Sequence
<220> FEATURE:
<223> OTHER INFORMATION: Synthetic

<400> SEQUENCE: 98
gcctcagctc ggggcccaca tgatcatggt 30

<210> SEQ ID NO 99
<211> LENGTH: 30
<212> TYPE: DNA
<213> ORGANISM: Artificial Sequence
<220> FEATURE:
<223> OTHER INFORMATION: Synthetic

<400> SEQUENCE: 99
cgcctcagct cggggcccac atgatcatgg 30

<210> SEQ ID NO 100
<211> LENGTH: 30
<212> TYPE: DNA
<213> ORGANISM: Artificial Sequence
<220> FEATURE:

<223> OTHER INFORMATION: Synthetic

<400> SEQUENCE: 100
aaactgccgc cacaactcag gtaaccatga 30

<210> SEQ ID NO 101
<211> LENGTH: 30
<212> TYPE: DNA
<213> ORGANISM: Artificial Sequence
<220> FEATURE:
<223> OTHER INFORMATION: Synthetic

<400> SEQUENCE: 101
tgacagtgga cacaccttac ctgggcaacc 30

<210> SEQ ID NO 102
<211> LENGTH: 30
<212> TYPE: DNA
<213> ORGANISM: Artificial Sequence
<220> FEATURE:
<223> OTHER INFORMATION: Synthetic

<400> SEQUENCE: 102
atcatcccct ttctttctca gcctgtcagt 30

<210> SEQ ID NO 103
<211> LENGTH: 30
<212> TYPE: DNA
<213> ORGANISM: Artificial Sequence
<220> FEATURE:
<223> OTHER INFORMATION: Synthetic

<400> SEQUENCE: 103
gctgcaactg tatatctaca aggaccgaga 30

<210> SEQ ID NO 104
<211> LENGTH: 30
<212> TYPE: DNA
<213> ORGANISM: Artificial Sequence
<220> FEATURE:
<223> OTHER INFORMATION: Synthetic

<400> SEQUENCE: 104
aagaagtggc ggaagctggt cctgaggcac 30

<210> SEQ ID NO 105
<211> LENGTH: 30
<212> TYPE: DNA
<213> ORGANISM: Artificial Sequence
<220> FEATURE:
<223> OTHER INFORMATION: Synthetic

<400> SEQUENCE: 105
ctgggccacc tcctcaattg aagaagtggc 30

<210> SEQ ID NO 106
<211> LENGTH: 30
<212> TYPE: DNA
<213> ORGANISM: Artificial Sequence
<220> FEATURE:
<223> OTHER INFORMATION: Synthetic

<400> SEQUENCE: 106
agttcctggg ccacctcctc aattgaagaa 30

<210> SEQ ID NO 107
<211> LENGTH: 30
<212> TYPE: DNA
<213> ORGANISM: Artificial Sequence
<220> FEATURE:
<223> OTHER INFORMATION: Synthetic

<400> SEQUENCE: 107
tcagcctgtc agtccctggg aacgggcatg 30

<210> SEQ ID NO 108
<211> LENGTH: 30
<212> TYPE: DNA
<213> ORGANISM: Artificial Sequence
<220> FEATURE:
<223> OTHER INFORMATION: Synthetic

<400> SEQUENCE: 108
ctcagcctgt cagtccctgg gaacgggcat 30

<210> SEQ ID NO 109
<211> LENGTH: 30
<212> TYPE: DNA
<213> ORGANISM: Artificial Sequence
<220> FEATURE:
<223> OTHER INFORMATION: Synthetic

<400> SEQUENCE: 109
tttctcagcc tgtcagtccc tgggaacggg 30

<210> SEQ ID NO 110
<211> LENGTH: 30
<212> TYPE: DNA
<213> ORGANISM: Artificial Sequence
<220> FEATURE:
<223> OTHER INFORMATION: Synthetic

<400> SEQUENCE: 110
ctttctcagc ctgtcagtcc ctgggaacgg 30

<210> SEQ ID NO 111
<211> LENGTH: 30
<212> TYPE: DNA
<213> ORGANISM: Artificial Sequence
<220> FEATURE:
<223> OTHER INFORMATION: Synthetic

<400> SEQUENCE: 111
cgcacatcat ccagacggtt gcccaggtaa 30

<210> SEQ ID NO 112
<211> LENGTH: 30
<212> TYPE: DNA
<213> ORGANISM: Artificial Sequence
<220> FEATURE:
<223> OTHER INFORMATION: Synthetic

<400> SEQUENCE: 112
gtgacagtgg acacacctta cctgggcaac 30

<210> SEQ ID NO 113
<211> LENGTH: 30
<212> TYPE: DNA
<213> ORGANISM: Artificial Sequence
<220> FEATURE:
<223> OTHER INFORMATION: Synthetic

<400> SEQUENCE: 113
cccaggtaag gtgtgtccac tgtcacaaat 30

<210> SEQ ID NO 114
<211> LENGTH: 30
<212> TYPE: DNA
<213> ORGANISM: Artificial Sequence
<220> FEATURE:
<223> OTHER INFORMATION: Synthetic

<400> SEQUENCE: 114
gttggctgca actgtatatc tacaaggacc 30

<210> SEQ ID NO 115
<211> LENGTH: 30
<212> TYPE: DNA
<213> ORGANISM: Artificial Sequence
<220> FEATURE:
<223> OTHER INFORMATION: Synthetic

<400> SEQUENCE: 115
tctgcctgcc gcactagctt cttggtgact 30

<210> SEQ ID NO 116
<211> LENGTH: 30
<212> TYPE: DNA
<213> ORGANISM: Artificial Sequence
<220> FEATURE:
<223> OTHER INFORMATION: Synthetic

<400> SEQUENCE: 116
tagcccatct tctctgcctg ccgcactagc 30

<210> SEQ ID NO 117
<211> LENGTH: 30
<212> TYPE: DNA
<213> ORGANISM: Artificial Sequence
<220> FEATURE:
<223> OTHER INFORMATION: Synthetic

<400> SEQUENCE: 117
ccagggactg acaggctgag aaagaaaggg 30

<210> SEQ ID NO 118
<211> LENGTH: 30
<212> TYPE: DNA
<213> ORGANISM: Artificial Sequence
<220> FEATURE:
<223> OTHER INFORMATION: Synthetic

<400> SEQUENCE: 118
aggaggtggc ccaggaactc aacatcatgc 30

<210> SEQ ID NO 119
<211> LENGTH: 30
<212> TYPE: DNA
<213> ORGANISM: Artificial Sequence
<220> FEATURE:
<223> OTHER INFORMATION: Synthetic

<400> SEQUENCE: 119
ttcaattgag gaggtggccc aggaactcaa 30

<210> SEQ ID NO 120
<211> LENGTH: 30

<212> TYPE: DNA
<213> ORGANISM: Artificial Sequence
<220> FEATURE:
<223> OTHER INFORMATION: Synthetic

<400> SEQUENCE: 120
cgccacttct tcaattgagg aggtggccca 30

<210> SEQ ID NO 121
<211> LENGTH: 30
<212> TYPE: DNA
<213> ORGANISM: Artificial Sequence
<220> FEATURE:
<223> OTHER INFORMATION: Synthetic

<400> SEQUENCE: 121
aattgaggag gtggcccagg aactcaacat 30

<210> SEQ ID NO 122
<211> LENGTH: 30
<212> TYPE: DNA
<213> ORGANISM: Artificial Sequence
<220> FEATURE:
<223> OTHER INFORMATION: Synthetic

<400> SEQUENCE: 122
tagatataca gttgcagcca acgaagtgcc 30

<210> SEQ ID NO 123
<211> LENGTH: 30
<212> TYPE: DNA
<213> ORGANISM: Artificial Sequence
<220> FEATURE:
<223> OTHER INFORMATION: Synthetic

<400> SEQUENCE: 123
tcggtccttg tagatataca gttgcagcca 30

<210> SEQ ID NO 124
<211> LENGTH: 30
<212> TYPE: DNA
<213> ORGANISM: Artificial Sequence
<220> FEATURE:
<223> OTHER INFORMATION: Synthetic

<400> SEQUENCE: 124
gtgacttctc ggtccttgta gatatacagt 30

<210> SEQ ID NO 125
<211> LENGTH: 30
<212> TYPE: DNA
<213> ORGANISM: Artificial Sequence
<220> FEATURE:
<223> OTHER INFORMATION: Synthetic

<400> SEQUENCE: 125
ttggtgactt ctcggtcctt gtagatatac 30

<210> SEQ ID NO 126
<211> LENGTH: 30
<212> TYPE: DNA
<213> ORGANISM: Artificial Sequence
<220> FEATURE:
<223> OTHER INFORMATION: Synthetic

<400> SEQUENCE: 126
cagccaacga agtgcctcag gaccagcttc 30

<210> SEQ ID NO 127
<211> LENGTH: 30
<212> TYPE: DNA
<213> ORGANISM: Artificial Sequence
<220> FEATURE:
<223> OTHER INFORMATION: Synthetic

<400> SEQUENCE: 127
ctaatttggc aaatttctca ttttatgcat 30

<210> SEQ ID NO 128
<211> LENGTH: 30
<212> TYPE: DNA
<213> ORGANISM: Artificial Sequence
<220> FEATURE:
<223> OTHER INFORMATION: Synthetic

<400> SEQUENCE: 128
atcctaaaat aagaaatgca taaaatgaga 30

<210> SEQ ID NO 129
<211> LENGTH: 30
<212> TYPE: DNA
<213> ORGANISM: Artificial Sequence
<220> FEATURE:
<223> OTHER INFORMATION: Synthetic

<400> SEQUENCE: 129
aagtagagaa ataaacgaac ctctcaaaat 30

<210> SEQ ID NO 130
<211> LENGTH: 30
<212> TYPE: DNA
<213> ORGANISM: Artificial Sequence
<220> FEATURE:
<223> OTHER INFORMATION: Synthetic

<400> SEQUENCE: 130
tctacttgaa ttcatactga ctttgtgatc 30

<210> SEQ ID NO 131
<211> LENGTH: 30
<212> TYPE: DNA
<213> ORGANISM: Artificial Sequence
<220> FEATURE:
<223> OTHER INFORMATION: Synthetic

<400> SEQUENCE: 131
taatttggca aatttctcat tttatgcatt 30

<210> SEQ ID NO 132
<211> LENGTH: 30
<212> TYPE: DNA
<213> ORGANISM: Artificial Sequence
<220> FEATURE:
<223> OTHER INFORMATION: Synthetic

<400> SEQUENCE: 132
tatgcatttc ttattttagg atgaaaaatt 30

<210> SEQ ID NO 133
<211> LENGTH: 30
<212> TYPE: DNA
<213> ORGANISM: Artificial Sequence
<220> FEATURE:
<223> OTHER INFORMATION: Synthetic

<400> SEQUENCE: 133
gcaaatttct cattttatgc atttcttatt 30

<210> SEQ ID NO 134
<211> LENGTH: 30
<212> TYPE: DNA
<213> ORGANISM: Artificial Sequence
<220> FEATURE:
<223> OTHER INFORMATION: Synthetic

<400> SEQUENCE: 134
ctcattttat gcatttctta ttttaggatg 30

<210> SEQ ID NO 135
<211> LENGTH: 30
<212> TYPE: DNA
<213> ORGANISM: Artificial Sequence
<220> FEATURE:
<223> OTHER INFORMATION: Synthetic

<400> SEQUENCE: 135
tcattttatg catttcttat tttaggatga 30

<210> SEQ ID NO 136
<211> LENGTH: 30
<212> TYPE: DNA
<213> ORGANISM: Artificial Sequence
<220> FEATURE:
<223> OTHER INFORMATION: Synthetic

<400> SEQUENCE: 136
catcctaaaa taagaaatgc ataaaatgag 30

<210> SEQ ID NO 137
<211> LENGTH: 30
<212> TYPE: DNA
<213> ORGANISM: Artificial Sequence
<220> FEATURE:
<223> OTHER INFORMATION: Synthetic

<400> SEQUENCE: 137
ggcaaatttc tcattttatg catttcttat 30

<210> SEQ ID NO 138
<211> LENGTH: 30
<212> TYPE: DNA
<213> ORGANISM: Artificial Sequence
<220> FEATURE:
<223> OTHER INFORMATION: Synthetic

<400> SEQUENCE: 138
tcatcctaaa ataagaaatg cataaaatga 30

<210> SEQ ID NO 139
<211> LENGTH: 30
<212> TYPE: DNA
<213> ORGANISM: Artificial Sequence
<220> FEATURE:
<223> OTHER INFORMATION: Synthetic

<400> SEQUENCE: 139
tcctcaggag aaaatgataa agtactggtt 30

<210> SEQ ID NO 140
<211> LENGTH: 30
<212> TYPE: DNA
<213> ORGANISM: Artificial Sequence
<220> FEATURE:
<223> OTHER INFORMATION: Synthetic

<400> SEQUENCE: 140 aaaattttc atcctaaaat aagaaatgca 30

<210> SEQ ID NO 141
<211> LENGTH: 30
<212> TYPE: DNA
<213> ORGANISM: Artificial Sequence
<220> FEATURE:
<223> OTHER INFORMATION: Synthetic

<400> SEQUENCE: 141
caaaattttt catcctaaaa taagaaatgc 30

<210> SEQ ID NO 142
<211> LENGTH: 30
<212> TYPE: DNA
<213> ORGANISM: Artificial Sequence
<220> FEATURE:
<223> OTHER INFORMATION: Synthetic

<400> SEQUENCE: 142
ctcaggagaa aatgataaag tactggtttc 30

<210> SEQ ID NO 143
<211> LENGTH: 30
<212> TYPE: DNA
<213> ORGANISM: Artificial Sequence
<220> FEATURE:
<223> OTHER INFORMATION: Synthetic

<400> SEQUENCE: 143
cctcaggaga aaatgataaa gtactggttt 30

<210> SEQ ID NO 144
<211> LENGTH: 30
<212> TYPE: DNA
<213> ORGANISM: Artificial Sequence
<220> FEATURE:
<223> OTHER INFORMATION: Synthetic

<400> SEQUENCE: 144
atgcatttct tattttagga tgaaaaattt 30

<210> SEQ ID NO 145
<211> LENGTH: 30
<212> TYPE: DNA
<213> ORGANISM: Artificial Sequence
<220> FEATURE:
<223> OTHER INFORMATION: Synthetic

<400> SEQUENCE: 145
gccacatatg cagcaagtcc actgtcgtct 30

<210> SEQ ID NO 146
<211> LENGTH: 30
<212> TYPE: DNA
<213> ORGANISM: Artificial Sequence
<220> FEATURE:
<223> OTHER INFORMATION: Synthetic

<400> SEQUENCE: 146
agccacatat gcagcaagtc cactgtcgtc 30

<210> SEQ ID NO 147
<211> LENGTH: 30
<212> TYPE: DNA
<213> ORGANISM: Artificial Sequence
<220> FEATURE:
<223> OTHER INFORMATION: Synthetic

<400> SEQUENCE: 147
ctttagccac atatgcagca agtccactgt 30

<210> SEQ ID NO 148
<211> LENGTH: 30
<212> TYPE: DNA
<213> ORGANISM: Artificial Sequence
<220> FEATURE:
<223> OTHER INFORMATION: Synthetic

<400> SEQUENCE: 148
ccagctgata gatgggtcta ttgctttagc 30

<210> SEQ ID NO 149
<211> LENGTH: 30
<212> TYPE: DNA
<213> ORGANISM: Artificial Sequence
<220> FEATURE:
<223> OTHER INFORMATION: Synthetic

<400> SEQUENCE: 149
atatcttccc agctgataga tgggtctatt 30

<210> SEQ ID NO 150
<211> LENGTH: 30
<212> TYPE: DNA
<213> ORGANISM: Artificial Sequence
<220> FEATURE:
<223> OTHER INFORMATION: Synthetic

<400> SEQUENCE: 150
gatatcttcc cagctgatag atgggtctat 30

<210> SEQ ID NO 151
<211> LENGTH: 30
<212> TYPE: DNA
<213> ORGANISM: Artificial Sequence
<220> FEATURE:
<223> OTHER INFORMATION: Synthetic

<400> SEQUENCE: 151
tcagccattt gatatcttcc cagctgatag 30

<210> SEQ ID NO 152
<211> LENGTH: 30
<212> TYPE: DNA
<213> ORGANISM: Artificial Sequence
<220> FEATURE:
<223> OTHER INFORMATION: Synthetic

<400> SEQUENCE: 152
gcaatgatgt cagtcttctc agccatttga 30

<210> SEQ ID NO 153

<211> LENGTH: 30
<212> TYPE: DNA
<213> ORGANISM: Artificial Sequence
<220> FEATURE:
<223> OTHER INFORMATION: Synthetic

<400> SEQUENCE: 153
ttcatcctaa aataagaaat gcataaaatg 30

<210> SEQ ID NO 154
<211> LENGTH: 30
<212> TYPE: DNA
<213> ORGANISM: Artificial Sequence
<220> FEATURE:
<223> OTHER INFORMATION: Synthetic

<400> SEQUENCE: 154
tgcatttctt attttaggat gaaaaatttt 30

<210> SEQ ID NO 155
<211> LENGTH: 30
<212> TYPE: DNA
<213> ORGANISM: Artificial Sequence
<220> FEATURE:
<223> OTHER INFORMATION: Synthetic

<400> SEQUENCE: 155
ggatgaaaaa ttttgaaacc agtactttat 30

<210> SEQ ID NO 156
<211> LENGTH: 30
<212> TYPE: DNA
<213> ORGANISM: Artificial Sequence
<220> FEATURE:
<223> OTHER INFORMATION: Synthetic

<400> SEQUENCE: 156
ttattttagg atgaaaaatt ttgaaaccag 30

<210> SEQ ID NO 157
<211> LENGTH: 30
<212> TYPE: DNA
<213> ORGANISM: Artificial Sequence
<220> FEATURE:
<223> OTHER INFORMATION: Synthetic

<400> SEQUENCE: 157
ccaattgttg caaagggcat tttgagaggt 30

<210> SEQ ID NO 158
<211> LENGTH: 30
<212> TYPE: DNA
<213> ORGANISM: Artificial Sequence
<220> FEATURE:
<223> OTHER INFORMATION: Synthetic

<400> SEQUENCE: 158
ttgcaaaggg cattttgaga ggttcgttta 30

<210> SEQ ID NO 159
<211> LENGTH: 30
<212> TYPE: DNA
<213> ORGANISM: Artificial Sequence
<220> FEATURE:
<223> OTHER INFORMATION: Synthetic

<400> SEQUENCE: 159
gcaacaattg gcaatgatgt cagtcttctc 30

<210> SEQ ID NO 160
<211> LENGTH: 30
<212> TYPE: DNA
<213> ORGANISM: Artificial Sequence
<220> FEATURE:
<223> OTHER INFORMATION: Synthetic

<400> SEQUENCE: 160
caaagggcat tttgagaggt tcgtttattt 30

<210> SEQ ID NO 161
<211> LENGTH: 30
<212> TYPE: DNA
<213> ORGANISM: Artificial Sequence
<220> FEATURE:
<223> OTHER INFORMATION: Synthetic

<400> SEQUENCE: 161
tgagaggttc gtttatttct ctacttgaat 30

<210> SEQ ID NO 162
<211> LENGTH: 30
<212> TYPE: DNA
<213> ORGANISM: Artificial Sequence
<220> FEATURE:
<223> OTHER INFORMATION: Synthetic

<400> SEQUENCE: 162
gagaggttcg tttatttctc tacttgaatt 30

<210> SEQ ID NO 163
<211> LENGTH: 30
<212> TYPE: DNA
<213> ORGANISM: Artificial Sequence
<220> FEATURE:
<223> OTHER INFORMATION: Synthetic

<400> SEQUENCE: 163
agaggttcgt ttatttctct acttgaattc 30

<210> SEQ ID NO 164
<211> LENGTH: 30
<212> TYPE: DNA
<213> ORGANISM: Artificial Sequence
<220> FEATURE:
<223> OTHER INFORMATION: Synthetic

<400> SEQUENCE: 164
gtttatttct ctacttgaat tcatactgac 30

<210> SEQ ID NO 165
<211> LENGTH: 30
<212> TYPE: DNA
<213> ORGANISM: Artificial Sequence
<220> FEATURE:
<223> OTHER INFORMATION: Synthetic

<400> SEQUENCE: 165
atttctctac ttgaattcat actgactttg 30

<210> SEQ ID NO 166
<211> LENGTH: 30
<212> TYPE: DNA

<213> ORGANISM: Artificial Sequence
<220> FEATURE:
<223> OTHER INFORMATION: Synthetic

<400> SEQUENCE: 166
tttctctact tgaattcata ctgactttgt 30

<210> SEQ ID NO 167
<211> LENGTH: 30
<212> TYPE: DNA
<213> ORGANISM: Artificial Sequence
<220> FEATURE:
<223> OTHER INFORMATION: Synthetic

<400> SEQUENCE: 167
ctctacttga attcatactg actttgtgat 30

<210> SEQ ID NO 168
<211> LENGTH: 30
<212> TYPE: DNA
<213> ORGANISM: Artificial Sequence
<220> FEATURE:
<223> OTHER INFORMATION: Synthetic

<400> SEQUENCE: 168
ctgcatatgt ggctaaagca atagacccat 30

<210> SEQ ID NO 169
<211> LENGTH: 30
<212> TYPE: DNA
<213> ORGANISM: Artificial Sequence
<220> FEATURE:
<223> OTHER INFORMATION: Synthetic

<400> SEQUENCE: 169
cttattttag gatgaaaaat tttgaaacca 30

<210> SEQ ID NO 170
<211> LENGTH: 30
<212> TYPE: DNA
<213> ORGANISM: Artificial Sequence
<220> FEATURE:
<223> OTHER INFORMATION: Synthetic

<400> SEQUENCE: 170
gagacgacag tggacttgct gcatatgtgg 30

<210> SEQ ID NO 171
<211> LENGTH: 30
<212> TYPE: DNA
<213> ORGANISM: Artificial Sequence
<220> FEATURE:
<223> OTHER INFORMATION: Synthetic

<400> SEQUENCE: 171
tggagacgac agtggacttg ctgcatatgt 30

<210> SEQ ID NO 172
<211> LENGTH: 30
<212> TYPE: DNA
<213> ORGANISM: Artificial Sequence
<220> FEATURE:
<223> OTHER INFORMATION: Synthetic

<400> SEQUENCE: 172
tcctgaggaa aattttggag acgacagtgg 30

<210> SEQ ID NO 173
<211> LENGTH: 30
<212> TYPE: DNA
<213> ORGANISM: Artificial Sequence
<220> FEATURE:
<223> OTHER INFORMATION: Synthetic

<400> SEQUENCE: 173
ctcctgagga aaattttgga gacgacagtg 30

<210> SEQ ID NO 174
<211> LENGTH: 30
<212> TYPE: DNA
<213> ORGANISM: Artificial Sequence
<220> FEATURE:
<223> OTHER INFORMATION: Synthetic

<400> SEQUENCE: 174
tctcctgagg aaaattttgg agacgacagt 30

<210> SEQ ID NO 175
<211> LENGTH: 30
<212> TYPE: DNA
<213> ORGANISM: Artificial Sequence
<220> FEATURE:
<223> OTHER INFORMATION: Synthetic

<400> SEQUENCE: 175
tcattttctc ctgaggaaaa ttttggagac 30

<210> SEQ ID NO 176
<211> LENGTH: 30
<212> TYPE: DNA
<213> ORGANISM: Artificial Sequence
<220> FEATURE:
<223> OTHER INFORMATION: Synthetic

<400> SEQUENCE: 176
atcattttct cctgaggaaa attttggaga 30

<210> SEQ ID NO 177
<211> LENGTH: 30
<212> TYPE: DNA
<213> ORGANISM: Artificial Sequence
<220> FEATURE:
<223> OTHER INFORMATION: Synthetic

<400> SEQUENCE: 177
aaaccagtac tttatcattt tctcctgagg 30

<210> SEQ ID NO 178
<211> LENGTH: 30
<212> TYPE: DNA
<213> ORGANISM: Artificial Sequence
<220> FEATURE:
<223> OTHER INFORMATION: Synthetic

<400> SEQUENCE: 178
gaaaccagta ctttatcatt ttctcctgag 30

<210> SEQ ID NO 179
<211> LENGTH: 30
<212> TYPE: DNA
<213> ORGANISM: Artificial Sequence
<220> FEATURE:

<223> OTHER INFORMATION: Synthetic

<400> SEQUENCE: 179
tgaaaccagt actttatcat tttctcctga 30

<210> SEQ ID NO 180
<211> LENGTH: 30
<212> TYPE: DNA
<213> ORGANISM: Artificial Sequence
<220> FEATURE:
<223> OTHER INFORMATION: Synthetic

<400> SEQUENCE: 180
aggatgaaaa attttgaaac cagtacttta 30

<210> SEQ ID NO 181
<211> LENGTH: 30
<212> TYPE: DNA
<213> ORGANISM: Artificial Sequence
<220> FEATURE:
<223> OTHER INFORMATION: Synthetic

<400> SEQUENCE: 181
taggatgaaa aattttgaaa ccagtacttt 30

<210> SEQ ID NO 182
<211> LENGTH: 30
<212> TYPE: DNA
<213> ORGANISM: Artificial Sequence
<220> FEATURE:
<223> OTHER INFORMATION: Synthetic

<400> SEQUENCE: 182
ttttaggatg aaaaattttg aaaccagtac 30

<210> SEQ ID NO 183
<211> LENGTH: 30
<212> TYPE: DNA
<213> ORGANISM: Artificial Sequence
<220> FEATURE:
<223> OTHER INFORMATION: Synthetic

<400> SEQUENCE: 183
ggagacgaca gtggacttgc tgcatatgtg 30

<210> SEQ ID NO 184
<211> LENGTH: 30
<212> TYPE: DNA
<213> ORGANISM: Artificial Sequence
<220> FEATURE:
<223> OTHER INFORMATION: Synthetic

<400> SEQUENCE: 184
caacaattgg caatgatgtc agtcttctca 30

<210> SEQ ID NO 185
<211> LENGTH: 29
<212> TYPE: DNA
<213> ORGANISM: Artificial Sequence
<220> FEATURE:
<223> OTHER INFORMATION: Synthetic

<400> SEQUENCE: 185
aattcatact gactttgtga tcctttgtg 29

<210> SEQ ID NO 186
<211> LENGTH: 24
<212> TYPE: DNA
<213> ORGANISM: Artificial Sequence
<220> FEATURE:
<223> OTHER INFORMATION: Synthetic

<400> SEQUENCE: 186
atactgactt tgtgatcctt tgtg 24

<210> SEQ ID NO 187
<211> LENGTH: 30
<212> TYPE: DNA
<213> ORGANISM: Artificial Sequence
<220> FEATURE:
<223> OTHER INFORMATION: Synthetic

<400> SEQUENCE: 187
agttacagtt tccctaaggt gcttgtttta 30

<210> SEQ ID NO 188
<211> LENGTH: 30
<212> TYPE: DNA
<213> ORGANISM: Artificial Sequence
<220> FEATURE:
<223> OTHER INFORMATION: Synthetic

<400> SEQUENCE: 188
aagccatgtt taacagcctc cctggcatca 30

<210> SEQ ID NO 189
<211> LENGTH: 30
<212> TYPE: DNA
<213> ORGANISM: Artificial Sequence
<220> FEATURE:
<223> OTHER INFORMATION: Synthetic

<400> SEQUENCE: 189
acagcctccc tggcatcatc acctggagag 30

<210> SEQ ID NO 190
<211> LENGTH: 30
<212> TYPE: DNA
<213> ORGANISM: Artificial Sequence
<220> FEATURE:
<223> OTHER INFORMATION: Synthetic

<400> SEQUENCE: 190
aacagcctcc ctggcatcat cacctggaga 30

<210> SEQ ID NO 191
<211> LENGTH: 30
<212> TYPE: DNA
<213> ORGANISM: Artificial Sequence
<220> FEATURE:
<223> OTHER INFORMATION: Synthetic

<400> SEQUENCE: 191
gacaccaaga tcccattcaa gccatgttta 30

<210> SEQ ID NO 192
<211> LENGTH: 30
<212> TYPE: DNA
<213> ORGANISM: Artificial Sequence
<220> FEATURE:
<223> OTHER INFORMATION: Synthetic

<400> SEQUENCE: 192
tcgagcccca tgattcgaca ccaagatccc 30

<210> SEQ ID NO 193
<211> LENGTH: 30
<212> TYPE: DNA
<213> ORGANISM: Artificial Sequence
<220> FEATURE:
<223> OTHER INFORMATION: Synthetic

<400> SEQUENCE: 193
gcgtctgcca aaactcacag tggctggcac 30

<210> SEQ ID NO 194
<211> LENGTH: 30
<212> TYPE: DNA
<213> ORGANISM: Artificial Sequence
<220> FEATURE:
<223> OTHER INFORMATION: Synthetic

<400> SEQUENCE: 194
gcagacgcta agatttcctt ttggagttcc 30

<210> SEQ ID NO 195
<211> LENGTH: 30
<212> TYPE: DNA
<213> ORGANISM: Artificial Sequence
<220> FEATURE:
<223> OTHER INFORMATION: Synthetic

<400> SEQUENCE: 195
tggcagacgc taagatttcc ttttggagtt 30

<210> SEQ ID NO 196
<211> LENGTH: 30
<212> TYPE: DNA
<213> ORGANISM: Artificial Sequence
<220> FEATURE:
<223> OTHER INFORMATION: Synthetic

<400> SEQUENCE: 196
gtgtcgaatc atggggctcg acaactcgat 30

<210> SEQ ID NO 197
<211> LENGTH: 30
<212> TYPE: DNA
<213> ORGANISM: Artificial Sequence
<220> FEATURE:
<223> OTHER INFORMATION: Synthetic

<400> SEQUENCE: 197
ggcagacgct aagatttcct tttggagttc 30

<210> SEQ ID NO 198
<211> LENGTH: 30
<212> TYPE: DNA
<213> ORGANISM: Artificial Sequence
<220> FEATURE:
<223> OTHER INFORMATION: Synthetic

<400> SEQUENCE: 198
aacatggctt gaatgggatc ttggtgtcga 30

<210> SEQ ID NO 199
<211> LENGTH: 30

<212> TYPE: DNA
<213> ORGANISM: Artificial Sequence
<220> FEATURE:
<223> OTHER INFORMATION: Synthetic

<400> SEQUENCE: 199
ctctctccag gtgatgatgc cagggaggct 30

<210> SEQ ID NO 200
<211> LENGTH: 30
<212> TYPE: DNA
<213> ORGANISM: Artificial Sequence
<220> FEATURE:
<223> OTHER INFORMATION: Synthetic

<400> SEQUENCE: 200
actctctcca ggtgatgatg ccagggaggc 30

<210> SEQ ID NO 201
<211> LENGTH: 30
<212> TYPE: DNA
<213> ORGANISM: Artificial Sequence
<220> FEATURE:
<223> OTHER INFORMATION: Synthetic

<400> SEQUENCE: 201
tactctctcc aggtgatgat gccagggagg 30

<210> SEQ ID NO 202
<211> LENGTH: 30
<212> TYPE: DNA
<213> ORGANISM: Artificial Sequence
<220> FEATURE:
<223> OTHER INFORMATION: Synthetic

<400> SEQUENCE: 202
ttttactctc tccaggtgat gatgccaggg 30

<210> SEQ ID NO 203
<211> LENGTH: 30
<212> TYPE: DNA
<213> ORGANISM: Artificial Sequence
<220> FEATURE:
<223> OTHER INFORMATION: Synthetic

<400> SEQUENCE: 203
cctaaggtgc ttgttttact ctctccaggt 30

<210> SEQ ID NO 204
<211> LENGTH: 30
<212> TYPE: DNA
<213> ORGANISM: Artificial Sequence
<220> FEATURE:
<223> OTHER INFORMATION: Synthetic

<400> SEQUENCE: 204
ccctaaggtg cttgttttac tctctccagg 30

<210> SEQ ID NO 205
<211> LENGTH: 30
<212> TYPE: DNA
<213> ORGANISM: Artificial Sequence
<220> FEATURE:
<223> OTHER INFORMATION: Synthetic

<400> SEQUENCE: 205
cagtttccct aaggtgcttg ttttactctc 30

<210> SEQ ID NO 206
<211> LENGTH: 30
<212> TYPE: DNA
<213> ORGANISM: Artificial Sequence
<220> FEATURE:
<223> OTHER INFORMATION: Synthetic

<400> SEQUENCE: 206
aatgggatct tggtgtcgaa tcatggggct 30

<210> SEQ ID NO 207
<211> LENGTH: 24
<212> TYPE: DNA
<213> ORGANISM: Artificial Sequence
<220> FEATURE:
<223> OTHER INFORMATION: Synthetic

<400> SEQUENCE: 207
ccttttggag ttcccatttc catc 24

<210> SEQ ID NO 208
<211> LENGTH: 23
<212> TYPE: DNA
<213> ORGANISM: Artificial Sequence
<220> FEATURE:
<223> OTHER INFORMATION: Synthetic

<400> SEQUENCE: 208
cttttggagt tcccatttcc atc 23

<210> SEQ ID NO 209
<211> LENGTH: 24
<212> TYPE: DNA
<213> ORGANISM: Artificial Sequence
<220> FEATURE:
<223> OTHER INFORMATION: Synthetic

<400> SEQUENCE: 209
gggaaactgt aacttaacag gcag 24

<210> SEQ ID NO 210
<211> LENGTH: 30
<212> TYPE: DNA
<213> ORGANISM: Artificial Sequence
<220> FEATURE:
<223> OTHER INFORMATION: Synthetic

<400> SEQUENCE: 210
caactttctt ttcttttatg atctttaagt 30

<210> SEQ ID NO 211
<211> LENGTH: 30
<212> TYPE: DNA
<213> ORGANISM: Artificial Sequence
<220> FEATURE:
<223> OTHER INFORMATION: Synthetic

<400> SEQUENCE: 211
cggttggcca tggctctgag tggtaagact 30

<210> SEQ ID NO 212
<211> LENGTH: 30
<212> TYPE: DNA
<213> ORGANISM: Artificial Sequence
<220> FEATURE:
<223> OTHER INFORMATION: Synthetic

<400> SEQUENCE: 212
gccatggctc tgagtggtaa gactcattct 30

<210> SEQ ID NO 213
<211> LENGTH: 30
<212> TYPE: DNA
<213> ORGANISM: Artificial Sequence
<220> FEATURE:
<223> OTHER INFORMATION: Synthetic

<400> SEQUENCE: 213
ttgtttacaa ctttcttttc ttttatgatc 30

<210> SEQ ID NO 214
<211> LENGTH: 30
<212> TYPE: DNA
<213> ORGANISM: Artificial Sequence
<220> FEATURE:
<223> OTHER INFORMATION: Synthetic

<400> SEQUENCE: 214
tttacaactt tcttttcttt tatgatcttt 30

<210> SEQ ID NO 215
<211> LENGTH: 30
<212> TYPE: DNA
<213> ORGANISM: Artificial Sequence
<220> FEATURE:
<223> OTHER INFORMATION: Synthetic

<400> SEQUENCE: 215
acaactttct tttcttttat gatctttaag 30

<210> SEQ ID NO 216
<211> LENGTH: 30
<212> TYPE: DNA
<213> ORGANISM: Artificial Sequence
<220> FEATURE:
<223> OTHER INFORMATION: Synthetic

<400> SEQUENCE: 216
aagatcataa aagaaaagaa agttgtaaac 30

<210> SEQ ID NO 217
<211> LENGTH: 30
<212> TYPE: DNA
<213> ORGANISM: Artificial Sequence
<220> FEATURE:
<223> OTHER INFORMATION: Synthetic

<400> SEQUENCE: 217
tctattttat atattcattt ctttgtccag 30

<210> SEQ ID NO 218
<211> LENGTH: 30
<212> TYPE: DNA
<213> ORGANISM: Artificial Sequence
<220> FEATURE:
<223> OTHER INFORMATION: Synthetic

<400> SEQUENCE: 218
ccactcagag ccatggccaa ccggaattct 30

<210> SEQ ID NO 219
<211> LENGTH: 30
<212> TYPE: DNA
<213> ORGANISM: Artificial Sequence
<220> FEATURE:
<223> OTHER INFORMATION: Synthetic

<400> SEQUENCE: 219
ttcctttagt atctcgagga catcttgaac 30

<210> SEQ ID NO 220
<211> LENGTH: 30
<212> TYPE: DNA
<213> ORGANISM: Artificial Sequence
<220> FEATURE:
<223> OTHER INFORMATION: Synthetic

<400> SEQUENCE: 220
ctttagtatc tcgaggacat cttgaacacc 30

<210> SEQ ID NO 221
<211> LENGTH: 30
<212> TYPE: DNA
<213> ORGANISM: Artificial Sequence
<220> FEATURE:
<223> OTHER INFORMATION: Synthetic

<400> SEQUENCE: 221
agtatctcga ggacatcttg aacacctttc 30

<210> SEQ ID NO 222
<211> LENGTH: 30
<212> TYPE: DNA
<213> ORGANISM: Artificial Sequence
<220> FEATURE:
<223> OTHER INFORMATION: Synthetic

<400> SEQUENCE: 222
gtatctcgag gacatcttga acacctttct 30

<210> SEQ ID NO 223
<211> LENGTH: 30
<212> TYPE: DNA
<213> ORGANISM: Artificial Sequence
<220> FEATURE:
<223> OTHER INFORMATION: Synthetic

<400> SEQUENCE: 223
aagatgtcct cgagatacta aaggaagaat 30

<210> SEQ ID NO 224
<211> LENGTH: 30
<212> TYPE: DNA
<213> ORGANISM: Artificial Sequence
<220> FEATURE:
<223> OTHER INFORMATION: Synthetic

<400> SEQUENCE: 224
taaacaagaa tgagtcttac cactcagagc 30

<210> SEQ ID NO 225
<211> LENGTH: 30
<212> TYPE: DNA
<213> ORGANISM: Artificial Sequence
<220> FEATURE:
<223> OTHER INFORMATION: Synthetic

<400> SEQUENCE: 225
gggggagaaa ggtgttcaag atgtcctcga 30

<210> SEQ ID NO 226
<211> LENGTH: 30
<212> TYPE: DNA
<213> ORGANISM: Artificial Sequence
<220> FEATURE:
<223> OTHER INFORMATION: Synthetic

<400> SEQUENCE: 226
ccaggtaact ggacaaagaa atgaatatat 30

<210> SEQ ID NO 227
<211> LENGTH: 30
<212> TYPE: DNA
<213> ORGANISM: Artificial Sequence
<220> FEATURE:
<223> OTHER INFORMATION: Synthetic

<400> SEQUENCE: 227
acttggttag ggggagaaag gtgttcaaga 30

<210> SEQ ID NO 228
<211> LENGTH: 30
<212> TYPE: DNA
<213> ORGANISM: Artificial Sequence
<220> FEATURE:
<223> OTHER INFORMATION: Synthetic

<400> SEQUENCE: 228
cacttggtta gggggagaaa ggtgttcaag 30

<210> SEQ ID NO 229
<211> LENGTH: 30
<212> TYPE: DNA
<213> ORGANISM: Artificial Sequence
<220> FEATURE:
<223> OTHER INFORMATION: Synthetic

<400> SEQUENCE: 229
tcacttggtt agggggagaa aggtgttcaa 30

<210> SEQ ID NO 230
<211> LENGTH: 30
<212> TYPE: DNA
<213> ORGANISM: Artificial Sequence
<220> FEATURE:
<223> OTHER INFORMATION: Synthetic

<400> SEQUENCE: 230
tgaatcactc tgtatctttt cacttggtta 30

<210> SEQ ID NO 231
<211> LENGTH: 30
<212> TYPE: DNA
<213> ORGANISM: Artificial Sequence
<220> FEATURE:
<223> OTHER INFORMATION: Synthetic

<400> SEQUENCE: 231
gttctgaatc actctgtatc ttttcacttg 30

<210> SEQ ID NO 232

<211> LENGTH: 30
<212> TYPE: DNA
<213> ORGANISM: Artificial Sequence
<220> FEATURE:
<223> OTHER INFORMATION: Synthetic

<400> SEQUENCE: 232
agttctgaat cactctgtat cttttcactt 30

<210> SEQ ID NO 233
<211> LENGTH: 30
<212> TYPE: DNA
<213> ORGANISM: Artificial Sequence
<220> FEATURE:
<223> OTHER INFORMATION: Synthetic

<400> SEQUENCE: 233
acagtaaaac aaatgaataa aacaagtcag 30

<210> SEQ ID NO 234
<211> LENGTH: 30
<212> TYPE: DNA
<213> ORGANISM: Artificial Sequence
<220> FEATURE:
<223> OTHER INFORMATION: Synthetic

<400> SEQUENCE: 234
caggtaactg gacaaagaaa tgaatatata 30

<210> SEQ ID NO 235
<211> LENGTH: 30
<212> TYPE: DNA
<213> ORGANISM: Artificial Sequence
<220> FEATURE:
<223> OTHER INFORMATION: Synthetic

<400> SEQUENCE: 235
aacacctttc tccccctaac caagtgaaaa 30

<210> SEQ ID NO 236
<211> LENGTH: 30
<212> TYPE: DNA
<213> ORGANISM: Artificial Sequence
<220> FEATURE:
<223> OTHER INFORMATION: Synthetic

<400> SEQUENCE: 236
gctttccagg taactggaca aagaaatgaa 30

<210> SEQ ID NO 237
<211> LENGTH: 30
<212> TYPE: DNA
<213> ORGANISM: Artificial Sequence
<220> FEATURE:
<223> OTHER INFORMATION: Synthetic

<400> SEQUENCE: 237
gggcttagct ttccaggtaa ctggacaaag 30

<210> SEQ ID NO 238
<211> LENGTH: 30
<212> TYPE: DNA
<213> ORGANISM: Artificial Sequence
<220> FEATURE:
<223> OTHER INFORMATION: Synthetic

<400> SEQUENCE: 238
ggggcttagc tttccaggta actggacaaa 30

<210> SEQ ID NO 239
<211> LENGTH: 30
<212> TYPE: DNA
<213> ORGANISM: Artificial Sequence
<220> FEATURE:
<223> OTHER INFORMATION: Synthetic

<400> SEQUENCE: 239
tggggagacc aatcgtttgg ggcttagctt 30

<210> SEQ ID NO 240
<211> LENGTH: 30
<212> TYPE: DNA
<213> ORGANISM: Artificial Sequence
<220> FEATURE:
<223> OTHER INFORMATION: Synthetic

<400> SEQUENCE: 240
gtggggagac caatcgtttg gggcttagct 30

<210> SEQ ID NO 241
<211> LENGTH: 30
<212> TYPE: DNA
<213> ORGANISM: Artificial Sequence
<220> FEATURE:
<223> OTHER INFORMATION: Synthetic

<400> SEQUENCE: 241
gttaggggga gaaaggtgtt caagatgtcc 30

<210> SEQ ID NO 242
<211> LENGTH: 30
<212> TYPE: DNA
<213> ORGANISM: Artificial Sequence
<220> FEATURE:
<223> OTHER INFORMATION: Synthetic

<400> SEQUENCE: 242 ctcccctaa ccaagtgaaa agatacagag 30

<210> SEQ ID NO 243
<211> LENGTH: 30
<212> TYPE: DNA
<213> ORGANISM: Artificial Sequence
<220> FEATURE:
<223> OTHER INFORMATION: Synthetic

<400> SEQUENCE: 243
tactgtcaag ttgtctattt tatatattca 30

<210> SEQ ID NO 244
<211> LENGTH: 30
<212> TYPE: DNA
<213> ORGANISM: Artificial Sequence
<220> FEATURE:
<223> OTHER INFORMATION: Synthetic

<400> SEQUENCE: 244
agaactaaat cagtctgact tgttttattc 30

<210> SEQ ID NO 245
<211> LENGTH: 30
<212> TYPE: DNA

<213> ORGANISM: Artificial Sequence
<220> FEATURE:
<223> OTHER INFORMATION: Synthetic

<400> SEQUENCE: 245
aataatgtga ctctattaac actgaattgt 30

<210> SEQ ID NO 246
<211> LENGTH: 30
<212> TYPE: DNA
<213> ORGANISM: Artificial Sequence
<220> FEATURE:
<223> OTHER INFORMATION: Synthetic

<400> SEQUENCE: 246
tggcagaaca tcaatctggg gaaagaaaag 30

<210> SEQ ID NO 247
<211> LENGTH: 30
<212> TYPE: DNA
<213> ORGANISM: Artificial Sequence
<220> FEATURE:
<223> OTHER INFORMATION: Synthetic

<400> SEQUENCE: 247
ctggcagaac atcaatctgg ggaaagaaaa 30

<210> SEQ ID NO 248
<211> LENGTH: 30
<212> TYPE: DNA
<213> ORGANISM: Artificial Sequence
<220> FEATURE:
<223> OTHER INFORMATION: Synthetic

<400> SEQUENCE: 248
cacagcctcc acaatttctg gcagaacatc 30

<210> SEQ ID NO 249
<211> LENGTH: 30
<212> TYPE: DNA
<213> ORGANISM: Artificial Sequence
<220> FEATURE:
<223> OTHER INFORMATION: Synthetic

<400> SEQUENCE: 249
ccttccacag cctccacaat ttctggcaga 30

<210> SEQ ID NO 250
<211> LENGTH: 30
<212> TYPE: DNA
<213> ORGANISM: Artificial Sequence
<220> FEATURE:
<223> OTHER INFORMATION: Synthetic

<400> SEQUENCE: 250
caccttccct tccacagcct ccacaatttc 30

<210> SEQ ID NO 251
<211> LENGTH: 30
<212> TYPE: DNA
<213> ORGANISM: Artificial Sequence
<220> FEATURE:
<223> OTHER INFORMATION: Synthetic

<400> SEQUENCE: 251
cgcacacccc cgtccaggaa gacttccacc 30

<210> SEQ ID NO 252
<211> LENGTH: 30
<212> TYPE: DNA
<213> ORGANISM: Artificial Sequence
<220> FEATURE:
<223> OTHER INFORMATION: Synthetic

<400> SEQUENCE: 252
ccgcacaccc ccgtccagga agacttccac 30

<210> SEQ ID NO 253
<211> LENGTH: 30
<212> TYPE: DNA
<213> ORGANISM: Artificial Sequence
<220> FEATURE:
<223> OTHER INFORMATION: Synthetic

<400> SEQUENCE: 253
agaacatcag tgcctttccg cacacccccg 30

<210> SEQ ID NO 254
<211> LENGTH: 30
<212> TYPE: DNA
<213> ORGANISM: Artificial Sequence
<220> FEATURE:
<223> OTHER INFORMATION: Synthetic

<400> SEQUENCE: 254
cagaacatca gtgcctttcc gcacaccccc 30

<210> SEQ ID NO 255
<211> LENGTH: 30
<212> TYPE: DNA
<213> ORGANISM: Artificial Sequence
<220> FEATURE:
<223> OTHER INFORMATION: Synthetic

<400> SEQUENCE: 255
gcgccaagag ccagagcttt cagaacatca 30

<210> SEQ ID NO 256
<211> LENGTH: 30
<212> TYPE: DNA
<213> ORGANISM: Artificial Sequence
<220> FEATURE:
<223> OTHER INFORMATION: Synthetic

<400> SEQUENCE: 256
gtctccccac aaacacagcc ttggcgccaa 30

<210> SEQ ID NO 257
<211> LENGTH: 30
<212> TYPE: DNA
<213> ORGANISM: Artificial Sequence
<220> FEATURE:
<223> OTHER INFORMATION: Synthetic

<400> SEQUENCE: 257
cctggaaagc taagccccaa acgattggtc 30

<210> SEQ ID NO 258
<211> LENGTH: 30
<212> TYPE: DNA
<213> ORGANISM: Artificial Sequence
<220> FEATURE:

<223> OTHER INFORMATION: Synthetic

<400> SEQUENCE: 258
tccagttacc tggaaagcta agccccaaac 30

<210> SEQ ID NO 259
<211> LENGTH: 30
<212> TYPE: DNA
<213> ORGANISM: Artificial Sequence
<220> FEATURE:
<223> OTHER INFORMATION: Synthetic

<400> SEQUENCE: 259
gtccagttac ctggaaagct aagccccaaa 30

<210> SEQ ID NO 260
<211> LENGTH: 30
<212> TYPE: DNA
<213> ORGANISM: Artificial Sequence
<220> FEATURE:
<223> OTHER INFORMATION: Synthetic

<400> SEQUENCE: 260
tttgtccagt tacctggaaa gctaagcccc 30

<210> SEQ ID NO 261
<211> LENGTH: 30
<212> TYPE: DNA
<213> ORGANISM: Artificial Sequence
<220> FEATURE:
<223> OTHER INFORMATION: Synthetic

<400> SEQUENCE: 261
ctttgtccag ttacctggaa agctaagccc 30

<210> SEQ ID NO 262
<211> LENGTH: 30
<212> TYPE: DNA
<213> ORGANISM: Artificial Sequence
<220> FEATURE:
<223> OTHER INFORMATION: Synthetic

<400> SEQUENCE: 262
ttttattcat ttgttttact gtcaagttgt 30

<210> SEQ ID NO 263
<211> LENGTH: 30
<212> TYPE: DNA
<213> ORGANISM: Artificial Sequence
<220> FEATURE:
<223> OTHER INFORMATION: Synthetic

<400> SEQUENCE: 263
tattcatttg ttttactgtc aagttgtcta 30

<210> SEQ ID NO 264
<211> LENGTH: 30
<212> TYPE: DNA
<213> ORGANISM: Artificial Sequence
<220> FEATURE:
<223> OTHER INFORMATION: Synthetic

<400> SEQUENCE: 264
attcatttgt tttactgtca agttgtctat 30

<210> SEQ ID NO 265
<211> LENGTH: 30
<212> TYPE: DNA
<213> ORGANISM: Artificial Sequence
<220> FEATURE:
<223> OTHER INFORMATION: Synthetic

<400> SEQUENCE: 265
ttcatttgtt ttactgtcaa gttgtctatt 30

<210> SEQ ID NO 266
<211> LENGTH: 30
<212> TYPE: DNA
<213> ORGANISM: Artificial Sequence
<220> FEATURE:
<223> OTHER INFORMATION: Synthetic

<400> SEQUENCE: 266
atttgtttta ctgtcaagtt gtctatttta 30

<210> SEQ ID NO 267
<211> LENGTH: 30
<212> TYPE: DNA
<213> ORGANISM: Artificial Sequence
<220> FEATURE:
<223> OTHER INFORMATION: Synthetic

<400> SEQUENCE: 267
gttttactgt caagttgtct attttatata 30

<210> SEQ ID NO 268
<211> LENGTH: 30
<212> TYPE: DNA
<213> ORGANISM: Artificial Sequence
<220> FEATURE:
<223> OTHER INFORMATION: Synthetic

<400> SEQUENCE: 268
tccccctaac caagtgaaaa gatacagagt 30

<210> SEQ ID NO 269
<211> LENGTH: 30
<212> TYPE: DNA
<213> ORGANISM: Artificial Sequence
<220> FEATURE:
<223> OTHER INFORMATION: Synthetic

<400> SEQUENCE: 269
ttttactgtc aagttgtcta ttttatatat 30

<210> SEQ ID NO 270
<211> LENGTH: 30
<212> TYPE: DNA
<213> ORGANISM: Artificial Sequence
<220> FEATURE:
<223> OTHER INFORMATION: Synthetic

<400> SEQUENCE: 270
actgtcaagt tgtctatttt atatattcat 30

<210> SEQ ID NO 271
<211> LENGTH: 30
<212> TYPE: DNA
<213> ORGANISM: Artificial Sequence
<220> FEATURE:
<223> OTHER INFORMATION: Synthetic

<400> SEQUENCE: 271
ctgtcaagtt gtctatttta tatattcatt 30

<210> SEQ ID NO 272
<211> LENGTH: 30
<212> TYPE: DNA
<213> ORGANISM: Artificial Sequence
<220> FEATURE:
<223> OTHER INFORMATION: Synthetic

<400> SEQUENCE: 272
tatatattca tttctttgtc cagttacctg 30

<210> SEQ ID NO 273
<211> LENGTH: 30
<212> TYPE: DNA
<213> ORGANISM: Artificial Sequence
<220> FEATURE:
<223> OTHER INFORMATION: Synthetic

<400> SEQUENCE: 273
atatattcat ttctttgtcc agttacctgg 30

<210> SEQ ID NO 274
<211> LENGTH: 30
<212> TYPE: DNA
<213> ORGANISM: Artificial Sequence
<220> FEATURE:
<223> OTHER INFORMATION: Synthetic

<400> SEQUENCE: 274
tatattcatt tctttgtcca gttacctgga 30

<210> SEQ ID NO 275
<211> LENGTH: 30
<212> TYPE: DNA
<213> ORGANISM: Artificial Sequence
<220> FEATURE:
<223> OTHER INFORMATION: Synthetic

<400> SEQUENCE: 275
atttctttgt ccagttacct ggaaagctaa 30

<210> SEQ ID NO 276
<211> LENGTH: 30
<212> TYPE: DNA
<213> ORGANISM: Artificial Sequence
<220> FEATURE:
<223> OTHER INFORMATION: Synthetic

<400> SEQUENCE: 276
gcgccaaggc tgtgtttgtg gggagaccaa 30

<210> SEQ ID NO 277
<211> LENGTH: 30
<212> TYPE: DNA
<213> ORGANISM: Artificial Sequence
<220> FEATURE:
<223> OTHER INFORMATION: Synthetic

<400> SEQUENCE: 277
tgaaagctct ggctcttggc gccaaggctg 30

<210> SEQ ID NO 278
<211> LENGTH: 30

<212> TYPE: DNA
<213> ORGANISM: Artificial Sequence
<220> FEATURE:
<223> OTHER INFORMATION: Synthetic

<400> SEQUENCE: 278
tggaggctgt ggaagggaag gtggaagtct 30

<210> SEQ ID NO 279
<211> LENGTH: 30
<212> TYPE: DNA
<213> ORGANISM: Artificial Sequence
<220> FEATURE:
<223> OTHER INFORMATION: Synthetic

<400> SEQUENCE: 279
ttgaactttt ctttccccag attgatgttc 30

<210> SEQ ID NO 280
<211> LENGTH: 30
<212> TYPE: DNA
<213> ORGANISM: Artificial Sequence
<220> FEATURE:
<223> OTHER INFORMATION: Synthetic

<400> SEQUENCE: 280
tgccagaaat tgtggaggct gtggaaggga 30

<210> SEQ ID NO 281
<211> LENGTH: 30
<212> TYPE: DNA
<213> ORGANISM: Artificial Sequence
<220> FEATURE:
<223> OTHER INFORMATION: Synthetic

<400> SEQUENCE: 281
atgttctgcc agaaattgtg gaggctgtgg 30

<210> SEQ ID NO 282
<211> LENGTH: 30
<212> TYPE: DNA
<213> ORGANISM: Artificial Sequence
<220> FEATURE:
<223> OTHER INFORMATION: Synthetic

<400> SEQUENCE: 282
cccagattga tgttctgcca gaaattgtgg 30

<210> SEQ ID NO 283
<211> LENGTH: 30
<212> TYPE: DNA
<213> ORGANISM: Artificial Sequence
<220> FEATURE:
<223> OTHER INFORMATION: Synthetic

<400> SEQUENCE: 283
ccccagattg atgttctgcc agaaattgtg 30

<210> SEQ ID NO 284
<211> LENGTH: 30
<212> TYPE: DNA
<213> ORGANISM: Artificial Sequence
<220> FEATURE:
<223> OTHER INFORMATION: Synthetic

<400> SEQUENCE: 284
tttccccaga ttgatgttct gccagaaatt 30

<210> SEQ ID NO 285
<211> LENGTH: 30
<212> TYPE: DNA
<213> ORGANISM: Artificial Sequence
<220> FEATURE:
<223> OTHER INFORMATION: Synthetic

<400> SEQUENCE: 285
ctttccccag attgatgttc tgccagaaat 30

<210> SEQ ID NO 286
<211> LENGTH: 30
<212> TYPE: DNA
<213> ORGANISM: Artificial Sequence
<220> FEATURE:
<223> OTHER INFORMATION: Synthetic

<400> SEQUENCE: 286
tctttcccca gattgatgtt ctgccagaaa 30

<210> SEQ ID NO 287
<211> LENGTH: 30
<212> TYPE: DNA
<213> ORGANISM: Artificial Sequence
<220> FEATURE:
<223> OTHER INFORMATION: Synthetic

<400> SEQUENCE: 287
aacttttctt tccccagatt gatgttctgc 30

<210> SEQ ID NO 288
<211> LENGTH: 30
<212> TYPE: DNA
<213> ORGANISM: Artificial Sequence
<220> FEATURE:
<223> OTHER INFORMATION: Synthetic

<400> SEQUENCE: 288
atagagtcac attattgaac ttttctttcc 30

<210> SEQ ID NO 289
<211> LENGTH: 30
<212> TYPE: DNA
<213> ORGANISM: Artificial Sequence
<220> FEATURE:
<223> OTHER INFORMATION: Synthetic

<400> SEQUENCE: 289
agtgttaata gagtcacatt attgaacttt 30

<210> SEQ ID NO 290
<211> LENGTH: 30
<212> TYPE: DNA
<213> ORGANISM: Artificial Sequence
<220> FEATURE:
<223> OTHER INFORMATION: Synthetic

<400> SEQUENCE: 290
ctggacgggg gtgtgcggaa aggcactgat 30

<210> SEQ ID NO 291
<211> LENGTH: 23
<212> TYPE: DNA
<213> ORGANISM: Artificial Sequence
<220> FEATURE:
<223> OTHER INFORMATION: Synthetic

<400> SEQUENCE: 291
cttttctttt atgatcttta agt 23

<210> SEQ ID NO 292
<211> LENGTH: 22
<212> TYPE: DNA
<213> ORGANISM: Artificial Sequence
<220> FEATURE:
<223> OTHER INFORMATION: Synthetic

<400> SEQUENCE: 292
ttttctttta tgatctttaa gt 22

<210> SEQ ID NO 293
<211> LENGTH: 30
<212> TYPE: DNA
<213> ORGANISM: Artificial Sequence
<220> FEATURE:
<223> OTHER INFORMATION: Synthetic

<400> SEQUENCE: 293
tttcagggtg ccagaatgtg aaagtcatcg 30

<210> SEQ ID NO 294
<211> LENGTH: 30
<212> TYPE: DNA
<213> ORGANISM: Artificial Sequence
<220> FEATURE:
<223> OTHER INFORMATION: Synthetic

<400> SEQUENCE: 294
ttttttcagg gtgccagaat gtgaaagtca 30

<210> SEQ ID NO 295
<211> LENGTH: 30
<212> TYPE: DNA
<213> ORGANISM: Artificial Sequence
<220> FEATURE:
<223> OTHER INFORMATION: Synthetic

<400> SEQUENCE: 295
taagctcagg ttcaaagtgt tggtaatgcc 30

<210> SEQ ID NO 296
<211> LENGTH: 30
<212> TYPE: DNA
<213> ORGANISM: Artificial Sequence
<220> FEATURE:
<223> OTHER INFORMATION: Synthetic

<400> SEQUENCE: 296
atattaaatg tatgcattat tttttcaggg 30

<210> SEQ ID NO 297
<211> LENGTH: 30
<212> TYPE: DNA
<213> ORGANISM: Artificial Sequence
<220> FEATURE:
<223> OTHER INFORMATION: Synthetic

<400> SEQUENCE: 297
agttcatatt aaatgtatgc attatttttt 30

<210> SEQ ID NO 298
<211> LENGTH: 30
<212> TYPE: DNA
<213> ORGANISM: Artificial Sequence
<220> FEATURE:
<223> OTHER INFORMATION: Synthetic

<400> SEQUENCE: 298
ttcagggtgc cagaatgtga aagtcatcga 30

<210> SEQ ID NO 299
<211> LENGTH: 30
<212> TYPE: DNA
<213> ORGANISM: Artificial Sequence
<220> FEATURE:
<223> OTHER INFORMATION: Synthetic

<400> SEQUENCE: 299
aatgtatgca ttattttttc agggtgccag 30

<210> SEQ ID NO 300
<211> LENGTH: 30
<212> TYPE: DNA
<213> ORGANISM: Artificial Sequence
<220> FEATURE:
<223> OTHER INFORMATION: Synthetic

<400> SEQUENCE: 300
tcagggtgcc agaatgtgaa agtcatcgac 30

<210> SEQ ID NO 301
<211> LENGTH: 30
<212> TYPE: DNA
<213> ORGANISM: Artificial Sequence
<220> FEATURE:
<223> OTHER INFORMATION: Synthetic

<400> SEQUENCE: 301
gccgtttcca agatctgaca gtgcacaata 30

<210> SEQ ID NO 302
<211> LENGTH: 30
<212> TYPE: DNA
<213> ORGANISM: Artificial Sequence
<220> FEATURE:
<223> OTHER INFORMATION: Synthetic

<400> SEQUENCE: 302
agggtgccag aatgtgaaag tcatcgacaa 30

<210> SEQ ID NO 303
<211> LENGTH: 30
<212> TYPE: DNA
<213> ORGANISM: Artificial Sequence
<220> FEATURE:
<223> OTHER INFORMATION: Synthetic

<400> SEQUENCE: 303
gtgaggaaaa atcctttggc cgtttccaag 30

<210> SEQ ID NO 304
<211> LENGTH: 30
<212> TYPE: DNA
<213> ORGANISM: Artificial Sequence
<220> FEATURE:
<223> OTHER INFORMATION: Synthetic

<400> SEQUENCE: 304
ggccgtttcc aagatctgac agtgcacaat 30

<210> SEQ ID NO 305
<211> LENGTH: 30
<212> TYPE: DNA
<213> ORGANISM: Artificial Sequence
<220> FEATURE:
<223> OTHER INFORMATION: Synthetic

<400> SEQUENCE: 305
cattcagttc atattaaatg tatgcattat 30

<210> SEQ ID NO 306
<211> LENGTH: 30
<212> TYPE: DNA
<213> ORGANISM: Artificial Sequence
<220> FEATURE:
<223> OTHER INFORMATION: Synthetic

<400> SEQUENCE: 306
ccaagatctg acagtgcaca atattttccc 30

<210> SEQ ID NO 307
<211> LENGTH: 30
<212> TYPE: DNA
<213> ORGANISM: Artificial Sequence
<220> FEATURE:
<223> OTHER INFORMATION: Synthetic

<400> SEQUENCE: 307
caagatctga cagtgcacaa tattttccca 30

<210> SEQ ID NO 308
<211> LENGTH: 30
<212> TYPE: DNA
<213> ORGANISM: Artificial Sequence
<220> FEATURE:
<223> OTHER INFORMATION: Synthetic

<400> SEQUENCE: 308
cagggtgcca gaatgtgaaa gtcatcgaca 30

<210> SEQ ID NO 309
<211> LENGTH: 30
<212> TYPE: DNA
<213> ORGANISM: Artificial Sequence
<220> FEATURE:
<223> OTHER INFORMATION: Synthetic

<400> SEQUENCE: 309
ttgcattcag ttcatattaa atgtatgcat 30

<210> SEQ ID NO 310
<211> LENGTH: 30
<212> TYPE: DNA
<213> ORGANISM: Artificial Sequence
<220> FEATURE:
<223> OTHER INFORMATION: Synthetic

<400> SEQUENCE: 310
gaggtagcaa acactaaggt gaaaagataa 30

<210> SEQ ID NO 311

<211> LENGTH: 30
<212> TYPE: DNA
<213> ORGANISM: Artificial Sequence
<220> FEATURE:
<223> OTHER INFORMATION: Synthetic

<400> SEQUENCE: 311
agacaacgtc atcccctggc aggctaaagt 30

<210> SEQ ID NO 312
<211> LENGTH: 30
<212> TYPE: DNA
<213> ORGANISM: Artificial Sequence
<220> FEATURE:
<223> OTHER INFORMATION: Synthetic

<400> SEQUENCE: 312
aattgtaagc tcaggttcaa agtgttggta 30

<210> SEQ ID NO 313
<211> LENGTH: 30
<212> TYPE: DNA
<213> ORGANISM: Artificial Sequence
<220> FEATURE:
<223> OTHER INFORMATION: Synthetic

<400> SEQUENCE: 313
ttaaattgta agctcaggtt caaagtgttg 30

<210> SEQ ID NO 314
<211> LENGTH: 30
<212> TYPE: DNA
<213> ORGANISM: Artificial Sequence
<220> FEATURE:
<223> OTHER INFORMATION: Synthetic

<400> SEQUENCE: 314
aaacagtggt tcttaaattg taagctcagg 30

<210> SEQ ID NO 315
<211> LENGTH: 30
<212> TYPE: DNA
<213> ORGANISM: Artificial Sequence
<220> FEATURE:
<223> OTHER INFORMATION: Synthetic

<400> SEQUENCE: 315
aaaacagtgg ttcttaaatt gtaagctcag 30

<210> SEQ ID NO 316
<211> LENGTH: 30
<212> TYPE: DNA
<213> ORGANISM: Artificial Sequence
<220> FEATURE:
<223> OTHER INFORMATION: Synthetic

<400> SEQUENCE: 316
catgtcttta aaacagtggt tcttaaattg 30

<210> SEQ ID NO 317
<211> LENGTH: 30
<212> TYPE: DNA
<213> ORGANISM: Artificial Sequence
<220> FEATURE:
<223> OTHER INFORMATION: Synthetic

<400> SEQUENCE: 317
acatgtcttt aaaacagtgg ttcttaaatt 30

<210> SEQ ID NO 318
<211> LENGTH: 30
<212> TYPE: DNA
<213> ORGANISM: Artificial Sequence
<220> FEATURE:
<223> OTHER INFORMATION: Synthetic

<400> SEQUENCE: 318
tgtttacatg tctttaaaac agtggttctt 30

<210> SEQ ID NO 319
<211> LENGTH: 30
<212> TYPE: DNA
<213> ORGANISM: Artificial Sequence
<220> FEATURE:
<223> OTHER INFORMATION: Synthetic

<400> SEQUENCE: 319
acctgtattc tgtttacatg tctttaaaac 30

<210> SEQ ID NO 320
<211> LENGTH: 30
<212> TYPE: DNA
<213> ORGANISM: Artificial Sequence
<220> FEATURE:
<223> OTHER INFORMATION: Synthetic

<400> SEQUENCE: 320
ttaacctgta ttctgtttac atgtctttaa 30

<210> SEQ ID NO 321
<211> LENGTH: 30
<212> TYPE: DNA
<213> ORGANISM: Artificial Sequence
<220> FEATURE:
<223> OTHER INFORMATION: Synthetic

<400> SEQUENCE: 321
attaacctgt attctgttta catgtcttta 30

<210> SEQ ID NO 322
<211> LENGTH: 30
<212> TYPE: DNA
<213> ORGANISM: Artificial Sequence
<220> FEATURE:
<223> OTHER INFORMATION: Synthetic

<400> SEQUENCE: 322
tttattaacc tgtattctgt ttacatgtct 30

<210> SEQ ID NO 323
<211> LENGTH: 30
<212> TYPE: DNA
<213> ORGANISM: Artificial Sequence
<220> FEATURE:
<223> OTHER INFORMATION: Synthetic

<400> SEQUENCE: 323
tcccatctgt attatttttt ttcagcatgt 30

<210> SEQ ID NO 324
<211> LENGTH: 30
<212> TYPE: DNA

<213> ORGANISM: Artificial Sequence
<220> FEATURE:
<223> OTHER INFORMATION: Synthetic

<400> SEQUENCE: 324
gtaaaattgg aggtagcaaa cactaaggtg 30

<210> SEQ ID NO 325
<211> LENGTH: 30
<212> TYPE: DNA
<213> ORGANISM: Artificial Sequence
<220> FEATURE:
<223> OTHER INFORMATION: Synthetic

<400> SEQUENCE: 325
agtaaaattg gaggtagcaa acactaaggt 30

<210> SEQ ID NO 326
<211> LENGTH: 30
<212> TYPE: DNA
<213> ORGANISM: Artificial Sequence
<220> FEATURE:
<223> OTHER INFORMATION: Synthetic

<400> SEQUENCE: 326
gacaacgtca tcccctggca ggctaaagtg 30

<210> SEQ ID NO 327
<211> LENGTH: 30
<212> TYPE: DNA
<213> ORGANISM: Artificial Sequence
<220> FEATURE:
<223> OTHER INFORMATION: Synthetic

<400> SEQUENCE: 327
ttattgcatt cagttcatat taaatgtatg 30

<210> SEQ ID NO 328
<211> LENGTH: 30
<212> TYPE: DNA
<213> ORGANISM: Artificial Sequence
<220> FEATURE:
<223> OTHER INFORMATION: Synthetic

<400> SEQUENCE: 328
cccatctgta ttattttttt tcagcatgta 30

<210> SEQ ID NO 329
<211> LENGTH: 30
<212> TYPE: DNA
<213> ORGANISM: Artificial Sequence
<220> FEATURE:
<223> OTHER INFORMATION: Synthetic

<400> SEQUENCE: 329
ttcagcatgt attacttgac aaagagacac 30

<210> SEQ ID NO 330
<211> LENGTH: 30
<212> TYPE: DNA
<213> ORGANISM: Artificial Sequence
<220> FEATURE:
<223> OTHER INFORMATION: Synthetic

<400> SEQUENCE: 330
ttttttttca gcatgtatta cttgacaaag 30

<210> SEQ ID NO 331
<211> LENGTH: 30
<212> TYPE: DNA
<213> ORGANISM: Artificial Sequence
<220> FEATURE:
<223> OTHER INFORMATION: Synthetic

<400> SEQUENCE: 331
attgcttttg acttttcaat gggtgtccta 30

<210> SEQ ID NO 332
<211> LENGTH: 30
<212> TYPE: DNA
<213> ORGANISM: Artificial Sequence
<220> FEATURE:
<223> OTHER INFORMATION: Synthetic

<400> SEQUENCE: 332
cttttgactt ttcaatgggt gtcctaggaa 30

<210> SEQ ID NO 333
<211> LENGTH: 30
<212> TYPE: DNA
<213> ORGANISM: Artificial Sequence
<220> FEATURE:
<223> OTHER INFORMATION: Synthetic

<400> SEQUENCE: 333
tgacttttca atgggtgtcc taggaacctt 30

<210> SEQ ID NO 334
<211> LENGTH: 30
<212> TYPE: DNA
<213> ORGANISM: Artificial Sequence
<220> FEATURE:
<223> OTHER INFORMATION: Synthetic

<400> SEQUENCE: 334
gacttttcaa tgggtgtcct aggaaccttt 30

<210> SEQ ID NO 335
<211> LENGTH: 30
<212> TYPE: DNA
<213> ORGANISM: Artificial Sequence
<220> FEATURE:
<223> OTHER INFORMATION: Synthetic

<400> SEQUENCE: 335
acttttcaat gggtgtccta ggaacctttt 30

<210> SEQ ID NO 336
<211> LENGTH: 30
<212> TYPE: DNA
<213> ORGANISM: Artificial Sequence
<220> FEATURE:
<223> OTHER INFORMATION: Synthetic

<400> SEQUENCE: 336
tcaatgggtg tcctaggaac cttttagaaa 30

<210> SEQ ID NO 337
<211> LENGTH: 30
<212> TYPE: DNA
<213> ORGANISM: Artificial Sequence
<220> FEATURE:

<223> OTHER INFORMATION: Synthetic

<400> SEQUENCE: 337
caatgggtgt cctaggaacc ttttagaaag 30

<210> SEQ ID NO 338
<211> LENGTH: 30
<212> TYPE: DNA
<213> ORGANISM: Artificial Sequence
<220> FEATURE:
<223> OTHER INFORMATION: Synthetic

<400> SEQUENCE: 338
aatgggtgtc ctaggaacct tttagaaaga 30

<210> SEQ ID NO 339
<211> LENGTH: 30
<212> TYPE: DNA
<213> ORGANISM: Artificial Sequence
<220> FEATURE:
<223> OTHER INFORMATION: Synthetic

<400> SEQUENCE: 339
tagaaagaaa tggactttca tcctggaaat 30

<210> SEQ ID NO 340
<211> LENGTH: 30
<212> TYPE: DNA
<213> ORGANISM: Artificial Sequence
<220> FEATURE:
<223> OTHER INFORMATION: Synthetic

<400> SEQUENCE: 340
agaaagaaat ggactttcat cctggaaata 30

<210> SEQ ID NO 341
<211> LENGTH: 30
<212> TYPE: DNA
<213> ORGANISM: Artificial Sequence
<220> FEATURE:
<223> OTHER INFORMATION: Synthetic

<400> SEQUENCE: 341
gaaagaaatg gactttcatc ctggaaatat 30

<210> SEQ ID NO 342
<211> LENGTH: 30
<212> TYPE: DNA
<213> ORGANISM: Artificial Sequence
<220> FEATURE:
<223> OTHER INFORMATION: Synthetic

<400> SEQUENCE: 342
catcctggaa atatattaac tgttaaaaag 30

<210> SEQ ID NO 343
<211> LENGTH: 30
<212> TYPE: DNA
<213> ORGANISM: Artificial Sequence
<220> FEATURE:
<223> OTHER INFORMATION: Synthetic

<400> SEQUENCE: 343
atcctggaaa tatattaact gttaaaaaga 30

<210> SEQ ID NO 344
<211> LENGTH: 30
<212> TYPE: DNA
<213> ORGANISM: Artificial Sequence
<220> FEATURE:
<223> OTHER INFORMATION: Synthetic

<400> SEQUENCE: 344
actgttaaaa agaaaacatt gaaaatgtgt 30

<210> SEQ ID NO 345
<211> LENGTH: 30
<212> TYPE: DNA
<213> ORGANISM: Artificial Sequence
<220> FEATURE:
<223> OTHER INFORMATION: Synthetic

<400> SEQUENCE: 345
aaaagaaaac attgaaaatg tgtttagaca 30

<210> SEQ ID NO 346
<211> LENGTH: 30
<212> TYPE: DNA
<213> ORGANISM: Artificial Sequence
<220> FEATURE:
<223> OTHER INFORMATION: Synthetic

<400> SEQUENCE: 346
cattgctttt gacttttcaa tgggtgtcct 30

<210> SEQ ID NO 347
<211> LENGTH: 30
<212> TYPE: DNA
<213> ORGANISM: Artificial Sequence
<220> FEATURE:
<223> OTHER INFORMATION: Synthetic

<400> SEQUENCE: 347
ccatctgtat tattttttt cagcatgtat 30

<210> SEQ ID NO 348
<211> LENGTH: 30
<212> TYPE: DNA
<213> ORGANISM: Artificial Sequence
<220> FEATURE:
<223> OTHER INFORMATION: Synthetic

<400> SEQUENCE: 348
tttcattgct tttgactttt caatgggtgt 30

<210> SEQ ID NO 349
<211> LENGTH: 30
<212> TYPE: DNA
<213> ORGANISM: Artificial Sequence
<220> FEATURE:
<223> OTHER INFORMATION: Synthetic

<400> SEQUENCE: 349
tatttcattg cttttgactt ttcaatgggt 30

<210> SEQ ID NO 350
<211> LENGTH: 30
<212> TYPE: DNA
<213> ORGANISM: Artificial Sequence
<220> FEATURE:
<223> OTHER INFORMATION: Synthetic

<400> SEQUENCE: 350
aaaatgtgtt tagacaacgt catcccctgg 30

<210> SEQ ID NO 351
<211> LENGTH: 30
<212> TYPE: DNA
<213> ORGANISM: Artificial Sequence
<220> FEATURE:
<223> OTHER INFORMATION: Synthetic

<400> SEQUENCE: 351
tttttcagca tgtattactt gacaaagaga 30

<210> SEQ ID NO 352
<211> LENGTH: 30
<212> TYPE: DNA
<213> ORGANISM: Artificial Sequence
<220> FEATURE:
<223> OTHER INFORMATION: Synthetic

<400> SEQUENCE: 352
ttttcagcat gtattacttg acaaagagac 30

<210> SEQ ID NO 353
<211> LENGTH: 30
<212> TYPE: DNA
<213> ORGANISM: Artificial Sequence
<220> FEATURE:
<223> OTHER INFORMATION: Synthetic

<400> SEQUENCE: 353
tttcagcatg tattacttga caaagagaca 30

<210> SEQ ID NO 354
<211> LENGTH: 30
<212> TYPE: DNA
<213> ORGANISM: Artificial Sequence
<220> FEATURE:
<223> OTHER INFORMATION: Synthetic

<400> SEQUENCE: 354
tcagcatgta ttacttgaca aagagacact 30

<210> SEQ ID NO 355
<211> LENGTH: 30
<212> TYPE: DNA
<213> ORGANISM: Artificial Sequence
<220> FEATURE:
<223> OTHER INFORMATION: Synthetic

<400> SEQUENCE: 355
cagcatgtat tacttgacaa agagacactg 30

<210> SEQ ID NO 356
<211> LENGTH: 30
<212> TYPE: DNA
<213> ORGANISM: Artificial Sequence
<220> FEATURE:
<223> OTHER INFORMATION: Synthetic

<400> SEQUENCE: 356
agcatgtatt acttgacaaa gagacactgt 30

<210> SEQ ID NO 357
<211> LENGTH: 30

<212> TYPE: DNA
<213> ORGANISM: Artificial Sequence
<220> FEATURE:
<223> OTHER INFORMATION: Synthetic

<400> SEQUENCE: 357
cttgacaaag agacactgtg cagagggtga 30

<210> SEQ ID NO 358
<211> LENGTH: 30
<212> TYPE: DNA
<213> ORGANISM: Artificial Sequence
<220> FEATURE:
<223> OTHER INFORMATION: Synthetic

<400> SEQUENCE: 358
acaaagagac actgtgcaga gggtgaccac 30

<210> SEQ ID NO 359
<211> LENGTH: 30
<212> TYPE: DNA
<213> ORGANISM: Artificial Sequence
<220> FEATURE:
<223> OTHER INFORMATION: Synthetic

<400> SEQUENCE: 359
cccacttcaa tacaaagggt gtcgttcttt 30

<210> SEQ ID NO 360
<211> LENGTH: 30
<212> TYPE: DNA
<213> ORGANISM: Artificial Sequence
<220> FEATURE:
<223> OTHER INFORMATION: Synthetic

<400> SEQUENCE: 360
aatacaaagg gtgtcgttct tttccaacaa 30

<210> SEQ ID NO 361
<211> LENGTH: 30
<212> TYPE: DNA
<213> ORGANISM: Artificial Sequence
<220> FEATURE:
<223> OTHER INFORMATION: Synthetic

<400> SEQUENCE: 361
ttttccaaca aaatagcaat cccttttatt 30

<210> SEQ ID NO 362
<211> LENGTH: 30
<212> TYPE: DNA
<213> ORGANISM: Artificial Sequence
<220> FEATURE:
<223> OTHER INFORMATION: Synthetic

<400> SEQUENCE: 362
tccaacaaaa tagcaatccc ttttatttca 30

<210> SEQ ID NO 363
<211> LENGTH: 30
<212> TYPE: DNA
<213> ORGANISM: Artificial Sequence
<220> FEATURE:
<223> OTHER INFORMATION: Synthetic

<400> SEQUENCE: 363
ccaacaaaat agcaatccct tttatttcat 30

<210> SEQ ID NO 364
<211> LENGTH: 30
<212> TYPE: DNA
<213> ORGANISM: Artificial Sequence
<220> FEATURE:
<223> OTHER INFORMATION: Synthetic

<400> SEQUENCE: 364
caacaaaata gcaatccctt ttatttcatt 30

<210> SEQ ID NO 365
<211> LENGTH: 30
<212> TYPE: DNA
<213> ORGANISM: Artificial Sequence
<220> FEATURE:
<223> OTHER INFORMATION: Synthetic

<400> SEQUENCE: 365
atttcattgc ttttgacttt tcaatgggtg 30

<210> SEQ ID NO 366
<211> LENGTH: 30
<212> TYPE: DNA
<213> ORGANISM: Artificial Sequence
<220> FEATURE:
<223> OTHER INFORMATION: Synthetic

<400> SEQUENCE: 366
aaagtgttgg taatgcctga ttcacaactt 30

<210> SEQ ID NO 367
<211> LENGTH: 30
<212> TYPE: DNA
<213> ORGANISM: Artificial Sequence
<220> FEATURE:
<223> OTHER INFORMATION: Synthetic

<400> SEQUENCE: 367
ctctctaaga agtaacatac atcctaaaac 30

<210> SEQ ID NO 368
<211> LENGTH: 30
<212> TYPE: DNA
<213> ORGANISM: Artificial Sequence
<220> FEATURE:
<223> OTHER INFORMATION: Synthetic

<400> SEQUENCE: 368
acaactttga gaaggtagca ctggagagaa 30

<210> SEQ ID NO 369
<211> LENGTH: 30
<212> TYPE: DNA
<213> ORGANISM: Artificial Sequence
<220> FEATURE:
<223> OTHER INFORMATION: Synthetic

<400> SEQUENCE: 369
accttagtgt ttgctacctc caattttact 30

<210> SEQ ID NO 370
<211> LENGTH: 30
<212> TYPE: DNA
<213> ORGANISM: Artificial Sequence
<220> FEATURE:
<223> OTHER INFORMATION: Synthetic

<400> SEQUENCE: 370
gtgtttgcta cctccaattt tactaaagga 30

<210> SEQ ID NO 371
<211> LENGTH: 30
<212> TYPE: DNA
<213> ORGANISM: Artificial Sequence
<220> FEATURE:
<223> OTHER INFORMATION: Synthetic

<400> SEQUENCE: 371
gctacctcca attttactaa aggatacagc 30

<210> SEQ ID NO 372
<211> LENGTH: 30
<212> TYPE: DNA
<213> ORGANISM: Artificial Sequence
<220> FEATURE:
<223> OTHER INFORMATION: Synthetic

<400> SEQUENCE: 372
ctacctccaa ttttactaaa ggatacagca 30

<210> SEQ ID NO 373
<211> LENGTH: 30
<212> TYPE: DNA
<213> ORGANISM: Artificial Sequence
<220> FEATURE:
<223> OTHER INFORMATION: Synthetic

<400> SEQUENCE: 373
tactaaagga tacagcactt tagcctgcca 30

<210> SEQ ID NO 374
<211> LENGTH: 30
<212> TYPE: DNA
<213> ORGANISM: Artificial Sequence
<220> FEATURE:
<223> OTHER INFORMATION: Synthetic

<400> SEQUENCE: 374
actaaaggat acagcacttt agcctgccag 30

<210> SEQ ID NO 375
<211> LENGTH: 30
<212> TYPE: DNA
<213> ORGANISM: Artificial Sequence
<220> FEATURE:
<223> OTHER INFORMATION: Synthetic

<400> SEQUENCE: 375
ctaaaggata cagcacttta gcctgccagg 30

<210> SEQ ID NO 376
<211> LENGTH: 30
<212> TYPE: DNA
<213> ORGANISM: Artificial Sequence
<220> FEATURE:
<223> OTHER INFORMATION: Synthetic

<400> SEQUENCE: 376
agcctgccag gggatgacgt tgtctaaaca 30

<210> SEQ ID NO 377
<211> LENGTH: 30
<212> TYPE: DNA
<213> ORGANISM: Artificial Sequence
<220> FEATURE:
<223> OTHER INFORMATION: Synthetic

<400> SEQUENCE: 377
gcctgccagg ggatgacgtt gtctaaacac 30

<210> SEQ ID NO 378
<211> LENGTH: 30
<212> TYPE: DNA
<213> ORGANISM: Artificial Sequence
<220> FEATURE:
<223> OTHER INFORMATION: Synthetic

<400> SEQUENCE: 378
caccttagtg tttgctacct ccaattttac 30

<210> SEQ ID NO 379
<211> LENGTH: 30
<212> TYPE: DNA
<213> ORGANISM: Artificial Sequence
<220> FEATURE:
<223> OTHER INFORMATION: Synthetic

<400> SEQUENCE: 379
tctaaacaca ttttcaatgt tttcttttta 30

<210> SEQ ID NO 380
<211> LENGTH: 30
<212> TYPE: DNA
<213> ORGANISM: Artificial Sequence
<220> FEATURE:
<223> OTHER INFORMATION: Synthetic

<400> SEQUENCE: 380
caatgttttc tttttaacag ttaatatatt 30

<210> SEQ ID NO 381
<211> LENGTH: 30
<212> TYPE: DNA
<213> ORGANISM: Artificial Sequence
<220> FEATURE:
<223> OTHER INFORMATION: Synthetic

<400> SEQUENCE: 381
aatgttttct ttttaacagt taatatattt 30

<210> SEQ ID NO 382
<211> LENGTH: 30
<212> TYPE: DNA
<213> ORGANISM: Artificial Sequence
<220> FEATURE:
<223> OTHER INFORMATION: Synthetic

<400> SEQUENCE: 382
tctttttaac agttaatata tttccaggat 30

<210> SEQ ID NO 383
<211> LENGTH: 30
<212> TYPE: DNA
<213> ORGANISM: Artificial Sequence
<220> FEATURE:
<223> OTHER INFORMATION: Synthetic

<400> SEQUENCE: 383 cttttttaaca gttaatatat ttccaggatg 30

<210> SEQ ID NO 384
<211> LENGTH: 30
<212> TYPE: DNA
<213> ORGANISM: Artificial Sequence
<220> FEATURE:
<223> OTHER INFORMATION: Synthetic

<400> SEQUENCE: 384
tttttaacag ttaatatatt tccaggatga 30

<210> SEQ ID NO 385
<211> LENGTH: 30
<212> TYPE: DNA
<213> ORGANISM: Artificial Sequence
<220> FEATURE:
<223> OTHER INFORMATION: Synthetic

<400> SEQUENCE: 385
ttaacagtta atatatttcc aggatgaaag 30

<210> SEQ ID NO 386
<211> LENGTH: 30
<212> TYPE: DNA
<213> ORGANISM: Artificial Sequence
<220> FEATURE:
<223> OTHER INFORMATION: Synthetic

<400> SEQUENCE: 386
taacagttaa tatatttcca ggatgaaagt 30

<210> SEQ ID NO 387
<211> LENGTH: 30
<212> TYPE: DNA
<213> ORGANISM: Artificial Sequence
<220> FEATURE:
<223> OTHER INFORMATION: Synthetic

<400> SEQUENCE: 387
aacagttaat atatttccag gatgaaagtc 30

<210> SEQ ID NO 388
<211> LENGTH: 30
<212> TYPE: DNA
<213> ORGANISM: Artificial Sequence
<220> FEATURE:
<223> OTHER INFORMATION: Synthetic

<400> SEQUENCE: 388
acagttaata tatttccagg atgaaagtcc 30

<210> SEQ ID NO 389
<211> LENGTH: 30
<212> TYPE: DNA
<213> ORGANISM: Artificial Sequence
<220> FEATURE:
<223> OTHER INFORMATION: Synthetic

<400> SEQUENCE: 389
tcaatgtttt ctttttaaca gttaatatat 30

<210> SEQ ID NO 390

<211> LENGTH: 30
<212> TYPE: DNA
<213> ORGANISM: Artificial Sequence
<220> FEATURE:
<223> OTHER INFORMATION: Synthetic

<400> SEQUENCE: 390
atatatttcc aggatgaaag tccatttctt 30

<210> SEQ ID NO 391
<211> LENGTH: 30
<212> TYPE: DNA
<213> ORGANISM: Artificial Sequence
<220> FEATURE:
<223> OTHER INFORMATION: Synthetic

<400> SEQUENCE: 391
tcaccttagt gtttgctacc tccaatttta 30

<210> SEQ ID NO 392
<211> LENGTH: 30
<212> TYPE: DNA
<213> ORGANISM: Artificial Sequence
<220> FEATURE:
<223> OTHER INFORMATION: Synthetic

<400> SEQUENCE: 392
ataaacaatg agatcattat cttttcacct 30

<210> SEQ ID NO 393
<211> LENGTH: 30
<212> TYPE: DNA
<213> ORGANISM: Artificial Sequence
<220> FEATURE:
<223> OTHER INFORMATION: Synthetic

<400> SEQUENCE: 393
tctctaagaa gtaacataca tcctaaaaca 30

<210> SEQ ID NO 394
<211> LENGTH: 30
<212> TYPE: DNA
<213> ORGANISM: Artificial Sequence
<220> FEATURE:
<223> OTHER INFORMATION: Synthetic

<400> SEQUENCE: 394
ggatatattc agacactaaa gatgtgattg 30

<210> SEQ ID NO 395
<211> LENGTH: 30
<212> TYPE: DNA
<213> ORGANISM: Artificial Sequence
<220> FEATURE:
<223> OTHER INFORMATION: Synthetic

<400> SEQUENCE: 395
gatatattca gacactaaag atgtgattgg 30

<210> SEQ ID NO 396
<211> LENGTH: 30
<212> TYPE: DNA
<213> ORGANISM: Artificial Sequence
<220> FEATURE:
<223> OTHER INFORMATION: Synthetic

<400> SEQUENCE: 396
agacactaaa gatgtgattg gaaatctaca 30

<210> SEQ ID NO 397
<211> LENGTH: 30
<212> TYPE: DNA
<213> ORGANISM: Artificial Sequence
<220> FEATURE:
<223> OTHER INFORMATION: Synthetic

<400> SEQUENCE: 397
gaaatctaca ttcaaagaag tatcaccaat 30

<210> SEQ ID NO 398
<211> LENGTH: 30
<212> TYPE: DNA
<213> ORGANISM: Artificial Sequence
<220> FEATURE:
<223> OTHER INFORMATION: Synthetic

<400> SEQUENCE: 398
aaagaagtat caccaattac cgccacccat 30

<210> SEQ ID NO 399
<211> LENGTH: 30
<212> TYPE: DNA
<213> ORGANISM: Artificial Sequence
<220> FEATURE:
<223> OTHER INFORMATION: Synthetic

<400> SEQUENCE: 399
ccgccaccca ttccaattct ctccagtgct 30

<210> SEQ ID NO 400
<211> LENGTH: 30
<212> TYPE: DNA
<213> ORGANISM: Artificial Sequence
<220> FEATURE:
<223> OTHER INFORMATION: Synthetic

<400> SEQUENCE: 400
caattctctc cagtgctacc ttctcaaagt 30

<210> SEQ ID NO 401
<211> LENGTH: 30
<212> TYPE: DNA
<213> ORGANISM: Artificial Sequence
<220> FEATURE:
<223> OTHER INFORMATION: Synthetic

<400> SEQUENCE: 401
tctccagtgc taccttctca aagttgtgaa 30

<210> SEQ ID NO 402
<211> LENGTH: 30
<212> TYPE: DNA
<213> ORGANISM: Artificial Sequence
<220> FEATURE:
<223> OTHER INFORMATION: Synthetic

<400> SEQUENCE: 402
tcttttcacc ttagtgtttg ctacctccaa 30

<210> SEQ ID NO 403
<211> LENGTH: 30
<212> TYPE: DNA

<213> ORGANISM: Artificial Sequence
<220> FEATURE:
<223> OTHER INFORMATION: Synthetic

<400> SEQUENCE: 403
tcaaagttgt gaatcaggca ttaccaacac 30

<210> SEQ ID NO 404
<211> LENGTH: 30
<212> TYPE: DNA
<213> ORGANISM: Artificial Sequence
<220> FEATURE:
<223> OTHER INFORMATION: Synthetic

<400> SEQUENCE: 404
ccaacacttt gaacctgagc ttacaattta 30

<210> SEQ ID NO 405
<211> LENGTH: 30
<212> TYPE: DNA
<213> ORGANISM: Artificial Sequence
<220> FEATURE:
<223> OTHER INFORMATION: Synthetic

<400> SEQUENCE: 405
gaacctgagc ttacaattta agaaccactg 30

<210> SEQ ID NO 406
<211> LENGTH: 30
<212> TYPE: DNA
<213> ORGANISM: Artificial Sequence
<220> FEATURE:
<223> OTHER INFORMATION: Synthetic

<400> SEQUENCE: 406
aacctgagct tacaatttaa gaaccactgt 30

<210> SEQ ID NO 407
<211> LENGTH: 30
<212> TYPE: DNA
<213> ORGANISM: Artificial Sequence
<220> FEATURE:
<223> OTHER INFORMATION: Synthetic

<400> SEQUENCE: 407
caatttaaga accactgttt taaagacatg 30

<210> SEQ ID NO 408
<211> LENGTH: 30
<212> TYPE: DNA
<213> ORGANISM: Artificial Sequence
<220> FEATURE:
<223> OTHER INFORMATION: Synthetic

<400> SEQUENCE: 408
aagaaccact gttttaaaga catgtaaaca 30

<210> SEQ ID NO 409
<211> LENGTH: 30
<212> TYPE: DNA
<213> ORGANISM: Artificial Sequence
<220> FEATURE:
<223> OTHER INFORMATION: Synthetic

<400> SEQUENCE: 409
agaaccactg ttttaaagac atgtaaacag 30

<210> SEQ ID NO 410
<211> LENGTH: 30
<212> TYPE: DNA
<213> ORGANISM: Artificial Sequence
<220> FEATURE:
<223> OTHER INFORMATION: Synthetic

<400> SEQUENCE: 410
taaagacatg taaacagaat acaggttaat 30

<210> SEQ ID NO 411
<211> LENGTH: 30
<212> TYPE: DNA
<213> ORGANISM: Artificial Sequence
<220> FEATURE:
<223> OTHER INFORMATION: Synthetic

<400> SEQUENCE: 411
aaagacatgt aaacagaata caggttaata 30

<210> SEQ ID NO 412
<211> LENGTH: 30
<212> TYPE: DNA
<213> ORGANISM: Artificial Sequence
<220> FEATURE:
<223> OTHER INFORMATION: Synthetic

<400> SEQUENCE: 412
aagacatgta aacagaatac aggttaataa 30

<210> SEQ ID NO 413
<211> LENGTH: 30
<212> TYPE: DNA
<213> ORGANISM: Artificial Sequence
<220> FEATURE:
<223> OTHER INFORMATION: Synthetic

<400> SEQUENCE: 413
tgaatcaggc attaccaaca ctttgaacct 30

<210> SEQ ID NO 414
<211> LENGTH: 30
<212> TYPE: DNA
<213> ORGANISM: Artificial Sequence
<220> FEATURE:
<223> OTHER INFORMATION: Synthetic

<400> SEQUENCE: 414
gtaatgcctg attcacaact ttgagaaggt 30

<210> SEQ ID NO 415
<211> LENGTH: 30
<212> TYPE: DNA
<213> ORGANISM: Artificial Sequence
<220> FEATURE:
<223> OTHER INFORMATION: Synthetic

<400> SEQUENCE: 415
ccaggatgaa agtccatttc tttctaaaag 30

<210> SEQ ID NO 416
<211> LENGTH: 30
<212> TYPE: DNA
<213> ORGANISM: Artificial Sequence
<220> FEATURE:

<223> OTHER INFORMATION: Synthetic

<400> SEQUENCE: 416
atttctctct aagaagtaac atacatccta 30

<210> SEQ ID NO 417
<211> LENGTH: 30
<212> TYPE: DNA
<213> ORGANISM: Artificial Sequence
<220> FEATURE:
<223> OTHER INFORMATION: Synthetic

<400> SEQUENCE: 417
acattctggc accctgaaaa aataatgcat 30

<210> SEQ ID NO 418
<211> LENGTH: 30
<212> TYPE: DNA
<213> ORGANISM: Artificial Sequence
<220> FEATURE:
<223> OTHER INFORMATION: Synthetic

<400> SEQUENCE: 418
tggcaccctg aaaaaataat gcatacattt 30

<210> SEQ ID NO 419
<211> LENGTH: 30
<212> TYPE: DNA
<213> ORGANISM: Artificial Sequence
<220> FEATURE:
<223> OTHER INFORMATION: Synthetic

<400> SEQUENCE: 419
tttctctcta agaagtaaca tacatcctaa 30

<210> SEQ ID NO 420
<211> LENGTH: 30
<212> TYPE: DNA
<213> ORGANISM: Artificial Sequence
<220> FEATURE:
<223> OTHER INFORMATION: Synthetic

<400> SEQUENCE: 420
ccaaaaatgc tttatttctc tctaagaagt 30

<210> SEQ ID NO 421
<211> LENGTH: 30
<212> TYPE: DNA
<213> ORGANISM: Artificial Sequence
<220> FEATURE:
<223> OTHER INFORMATION: Synthetic

<400> SEQUENCE: 421
ttagagagaa ataaagcatt tttgggaaga 30

<210> SEQ ID NO 422
<211> LENGTH: 30
<212> TYPE: DNA
<213> ORGANISM: Artificial Sequence
<220> FEATURE:
<223> OTHER INFORMATION: Synthetic

<400> SEQUENCE: 422
cttcttagag agaaataaag catttttggg 30

<210> SEQ ID NO 423
<211> LENGTH: 30
<212> TYPE: DNA
<213> ORGANISM: Artificial Sequence
<220> FEATURE:
<223> OTHER INFORMATION: Synthetic

<400> SEQUENCE: 423
ggatgtatgt tacttcttag agagaaataa 30

<210> SEQ ID NO 424
<211> LENGTH: 30
<212> TYPE: DNA
<213> ORGANISM: Artificial Sequence
<220> FEATURE:
<223> OTHER INFORMATION: Synthetic

<400> SEQUENCE: 424
aggatgtatg ttacttctta gagagaaata 30

<210> SEQ ID NO 425
<211> LENGTH: 30
<212> TYPE: DNA
<213> ORGANISM: Artificial Sequence
<220> FEATURE:
<223> OTHER INFORMATION: Synthetic

<400> SEQUENCE: 425
taggatgtat gttacttctt agagagaaat 30

<210> SEQ ID NO 426
<211> LENGTH: 30
<212> TYPE: DNA
<213> ORGANISM: Artificial Sequence
<220> FEATURE:
<223> OTHER INFORMATION: Synthetic

<400> SEQUENCE: 426
cacattctgg caccctgaaa aaataatgca 30

<210> SEQ ID NO 427
<211> LENGTH: 30
<212> TYPE: DNA
<213> ORGANISM: Artificial Sequence
<220> FEATURE:
<223> OTHER INFORMATION: Synthetic

<400> SEQUENCE: 427
gtgtctgaat atatccaaat gttttaggat 30

<210> SEQ ID NO 428
<211> LENGTH: 30
<212> TYPE: DNA
<213> ORGANISM: Artificial Sequence
<220> FEATURE:
<223> OTHER INFORMATION: Synthetic

<400> SEQUENCE: 428
caatcacatc tttagtgtct gaatatatcc 30

<210> SEQ ID NO 429
<211> LENGTH: 30
<212> TYPE: DNA
<213> ORGANISM: Artificial Sequence
<220> FEATURE:
<223> OTHER INFORMATION: Synthetic

<400> SEQUENCE: 429
ccaatcacat ctttagtgtc tgaatatatc 30

<210> SEQ ID NO 430
<211> LENGTH: 30
<212> TYPE: DNA
<213> ORGANISM: Artificial Sequence
<220> FEATURE:
<223> OTHER INFORMATION: Synthetic

<400> SEQUENCE: 430
aatgtagatt tccaatcaca tctttagtgt 30

<210> SEQ ID NO 431
<211> LENGTH: 30
<212> TYPE: DNA
<213> ORGANISM: Artificial Sequence
<220> FEATURE:
<223> OTHER INFORMATION: Synthetic

<400> SEQUENCE: 431
gaatgtagat ttccaatcac atctttagtg 30

<210> SEQ ID NO 432
<211> LENGTH: 30
<212> TYPE: DNA
<213> ORGANISM: Artificial Sequence
<220> FEATURE:
<223> OTHER INFORMATION: Synthetic

<400> SEQUENCE: 432
tttgaatgta gatttccaat cacatcttta 30

<210> SEQ ID NO 433
<211> LENGTH: 30
<212> TYPE: DNA
<213> ORGANISM: Artificial Sequence
<220> FEATURE:
<223> OTHER INFORMATION: Synthetic

<400> SEQUENCE: 433
gtgatacttc tttgaatgta gatttccaat 30

<210> SEQ ID NO 434
<211> LENGTH: 30
<212> TYPE: DNA
<213> ORGANISM: Artificial Sequence
<220> FEATURE:
<223> OTHER INFORMATION: Synthetic

<400> SEQUENCE: 434
gaatgggtgg cggtaattgg tgatacttct 30

<210> SEQ ID NO 435
<211> LENGTH: 30
<212> TYPE: DNA
<213> ORGANISM: Artificial Sequence
<220> FEATURE:
<223> OTHER INFORMATION: Synthetic

<400> SEQUENCE: 435
agaaggtagc actggagaga attggaatgg 30

<210> SEQ ID NO 436
<211> LENGTH: 30

<212> TYPE: DNA
<213> ORGANISM: Artificial Sequence
<220> FEATURE:
<223> OTHER INFORMATION: Synthetic

<400> SEQUENCE: 436
gagaaggtag cactggagag aattggaatg 30

<210> SEQ ID NO 437
<211> LENGTH: 30
<212> TYPE: DNA
<213> ORGANISM: Artificial Sequence
<220> FEATURE:
<223> OTHER INFORMATION: Synthetic

<400> SEQUENCE: 437
agtgtctgaa tatatccaaa tgttttagga 30

<210> SEQ ID NO 438
<211> LENGTH: 30
<212> TYPE: DNA
<213> ORGANISM: Artificial Sequence
<220> FEATURE:
<223> OTHER INFORMATION: Synthetic

<400> SEQUENCE: 438
caggatgaaa gtccatttct ttctaaaagg 30

<210> SEQ ID NO 439
<211> LENGTH: 30
<212> TYPE: DNA
<213> ORGANISM: Artificial Sequence
<220> FEATURE:
<223> OTHER INFORMATION: Synthetic

<400> SEQUENCE: 439
tcgatgactt tcacattctg gcaccctgaa 30

<210> SEQ ID NO 440
<211> LENGTH: 30
<212> TYPE: DNA
<213> ORGANISM: Artificial Sequence
<220> FEATURE:
<223> OTHER INFORMATION: Synthetic

<400> SEQUENCE: 440
cctcaccaat gtcttgtcga tgactttcac 30

<210> SEQ ID NO 441
<211> LENGTH: 30
<212> TYPE: DNA
<213> ORGANISM: Artificial Sequence
<220> FEATURE:
<223> OTHER INFORMATION: Synthetic

<400> SEQUENCE: 441
tttctaaaag gttcctagga cacccattga 30

<210> SEQ ID NO 442
<211> LENGTH: 30
<212> TYPE: DNA
<213> ORGANISM: Artificial Sequence
<220> FEATURE:
<223> OTHER INFORMATION: Synthetic

<400> SEQUENCE: 442
ctaaaaggtt cctaggacac ccattgaaaa 30

<210> SEQ ID NO 443
<211> LENGTH: 30
<212> TYPE: DNA
<213> ORGANISM: Artificial Sequence
<220> FEATURE:
<223> OTHER INFORMATION: Synthetic

<400> SEQUENCE: 443
taaaaggttc ctaggacacc cattgaaaag 30

<210> SEQ ID NO 444
<211> LENGTH: 30
<212> TYPE: DNA
<213> ORGANISM: Artificial Sequence
<220> FEATURE:
<223> OTHER INFORMATION: Synthetic

<400> SEQUENCE: 444
ctaggacacc cattgaaaag tcaaaagcaa 30

<210> SEQ ID NO 445
<211> LENGTH: 30
<212> TYPE: DNA
<213> ORGANISM: Artificial Sequence
<220> FEATURE:
<223> OTHER INFORMATION: Synthetic

<400> SEQUENCE: 445
aaaagtcaaa agcaatgaaa taaaagggat 30

<210> SEQ ID NO 446
<211> LENGTH: 30
<212> TYPE: DNA
<213> ORGANISM: Artificial Sequence
<220> FEATURE:
<223> OTHER INFORMATION: Synthetic

<400> SEQUENCE: 446
ctattttgtt ggaaaagaac gacacccttt 30

<210> SEQ ID NO 447
<211> LENGTH: 30
<212> TYPE: DNA
<213> ORGANISM: Artificial Sequence
<220> FEATURE:
<223> OTHER INFORMATION: Synthetic

<400> SEQUENCE: 447
tgttggaaaa gaacgacacc ctttgtattg 30

<210> SEQ ID NO 448
<211> LENGTH: 30
<212> TYPE: DNA
<213> ORGANISM: Artificial Sequence
<220> FEATURE:
<223> OTHER INFORMATION: Synthetic

<400> SEQUENCE: 448
gttggaaaag aacgacaccc tttgtattga 30

<210> SEQ ID NO 449
<211> LENGTH: 30
<212> TYPE: DNA
<213> ORGANISM: Artificial Sequence
<220> FEATURE:
<223> OTHER INFORMATION: Synthetic

<400> SEQUENCE: 449
ttggaaaaga acgacaccct ttgtattgaa 30

<210> SEQ ID NO 450
<211> LENGTH: 30
<212> TYPE: DNA
<213> ORGANISM: Artificial Sequence
<220> FEATURE:
<223> OTHER INFORMATION: Synthetic

<400> SEQUENCE: 450
ctcaccaatg tcttgtcgat gactttcaca 30

<210> SEQ ID NO 451
<211> LENGTH: 30
<212> TYPE: DNA
<213> ORGANISM: Artificial Sequence
<220> FEATURE:
<223> OTHER INFORMATION: Synthetic

<400> SEQUENCE: 451
gaaaagaacg acaccctttg tattgaagtg 30

<210> SEQ ID NO 452
<211> LENGTH: 30
<212> TYPE: DNA
<213> ORGANISM: Artificial Sequence
<220> FEATURE:
<223> OTHER INFORMATION: Synthetic

<400> SEQUENCE: 452
tattgaagtg gggaattaca gactgtggtc 30

<210> SEQ ID NO 453
<211> LENGTH: 30
<212> TYPE: DNA
<213> ORGANISM: Artificial Sequence
<220> FEATURE:
<223> OTHER INFORMATION: Synthetic

<400> SEQUENCE: 453
aagtggggaa ttacagactg tggtcaccct 30

<210> SEQ ID NO 454
<211> LENGTH: 30
<212> TYPE: DNA
<213> ORGANISM: Artificial Sequence
<220> FEATURE:
<223> OTHER INFORMATION: Synthetic

<400> SEQUENCE: 454
cagactgtgg tcaccctctg cacagtgtct 30

<210> SEQ ID NO 455
<211> LENGTH: 30
<212> TYPE: DNA
<213> ORGANISM: Artificial Sequence
<220> FEATURE:
<223> OTHER INFORMATION: Synthetic

<400> SEQUENCE: 455
gtcaagtaat acatgctgaa aaaaaataat 30

<210> SEQ ID NO 456
<211> LENGTH: 30
<212> TYPE: DNA
<213> ORGANISM: Artificial Sequence
<220> FEATURE:
<223> OTHER INFORMATION: Synthetic

<400> SEQUENCE: 456
tcaagtaata catgctgaaa aaaaataata 30

<210> SEQ ID NO 457
<211> LENGTH: 30
<212> TYPE: DNA
<213> ORGANISM: Artificial Sequence
<220> FEATURE:
<223> OTHER INFORMATION: Synthetic

<400> SEQUENCE: 457
tgcactgtca gatcttggaa acggccaaag 30

<210> SEQ ID NO 458
<211> LENGTH: 30
<212> TYPE: DNA
<213> ORGANISM: Artificial Sequence
<220> FEATURE:
<223> OTHER INFORMATION: Synthetic

<400> SEQUENCE: 458
gaaacggcca aaggattttt cctcaccaat 30

<210> SEQ ID NO 459
<211> LENGTH: 30
<212> TYPE: DNA
<213> ORGANISM: Artificial Sequence
<220> FEATURE:
<223> OTHER INFORMATION: Synthetic

<400> SEQUENCE: 459
ttcctcacca atgtcttgtc gatgactttc 30

<210> SEQ ID NO 460
<211> LENGTH: 30
<212> TYPE: DNA
<213> ORGANISM: Artificial Sequence
<220> FEATURE:
<223> OTHER INFORMATION: Synthetic

<400> SEQUENCE: 460
tcctcaccaa tgtcttgtcg atgactttca 30

<210> SEQ ID NO 461
<211> LENGTH: 30
<212> TYPE: DNA
<213> ORGANISM: Artificial Sequence
<220> FEATURE:
<223> OTHER INFORMATION: Synthetic

<400> SEQUENCE: 461
gtattgaagt ggggaattac agactgtggt 30

<210> SEQ ID NO 462
<211> LENGTH: 30
<212> TYPE: DNA
<213> ORGANISM: Artificial Sequence
<220> FEATURE:
<223> OTHER INFORMATION: Synthetic

<400> SEQUENCE: 462
ctttctaaaa ggttcctagg acacccattg 30

<210> SEQ ID NO 463
<211> LENGTH: 28
<212> TYPE: DNA
<213> ORGANISM: Artificial Sequence
<220> FEATURE:
<223> OTHER INFORMATION: Synthetic

<400> SEQUENCE: 463
gagagaaata aagcattttt gggaagaa 28

<210> SEQ ID NO 464
<211> LENGTH: 27
<212> TYPE: DNA
<213> ORGANISM: Artificial Sequence
<220> FEATURE:
<223> OTHER INFORMATION: Synthetic

<400> SEQUENCE: 464
aatatgaact gaatgcaata ataatca 27

<210> SEQ ID NO 465
<211> LENGTH: 26
<212> TYPE: DNA
<213> ORGANISM: Artificial Sequence
<220> FEATURE:
<223> OTHER INFORMATION: Synthetic

<400> SEQUENCE: 465
atatgaactg aatgcaataa taatca 26

<210> SEQ ID NO 466
<211> LENGTH: 30
<212> TYPE: RNA
<213> ORGANISM: Artificial Sequence
<220> FEATURE:
<223> OTHER INFORMATION: Synthetic

<400> SEQUENCE: 466
ccuggaaaau gcugcaauau uaucagccaa 30

<210> SEQ ID NO 467
<211> LENGTH: 30
<212> TYPE: RNA
<213> ORGANISM: Artificial Sequence
<220> FEATURE:
<223> OTHER INFORMATION: Synthetic

<400> SEQUENCE: 467
ucuuaccugg aaaaugcugc aauauuauca 30

<210> SEQ ID NO 468
<211> LENGTH: 30
<212> TYPE: RNA
<213> ORGANISM: Artificial Sequence
<220> FEATURE:
<223> OTHER INFORMATION: Synthetic

<400> SEQUENCE: 468
cuuaccugga aaaugcugca auauuaucag 30

<210> SEQ ID NO 469

<211> LENGTH: 30
<212> TYPE: RNA
<213> ORGANISM: Artificial Sequence
<220> FEATURE:
<223> OTHER INFORMATION: Synthetic

<400> SEQUENCE: 469
uuaccuggaa aaugcugcaa uauuaucagc 30

<210> SEQ ID NO 470
<211> LENGTH: 30
<212> TYPE: RNA
<213> ORGANISM: Artificial Sequence
<220> FEATURE:
<223> OTHER INFORMATION: Synthetic

<400> SEQUENCE: 470
ucagccaaag uuucuucauc auuugcccca 30

<210> SEQ ID NO 471
<211> LENGTH: 30
<212> TYPE: RNA
<213> ORGANISM: Artificial Sequence
<220> FEATURE:
<223> OTHER INFORMATION: Synthetic

<400> SEQUENCE: 471
cuucaucauu ugccccagac cuguaauagu 30

<210> SEQ ID NO 472
<211> LENGTH: 30
<212> TYPE: RNA
<213> ORGANISM: Artificial Sequence
<220> FEATURE:
<223> OTHER INFORMATION: Synthetic

<400> SEQUENCE: 472
uucaucauuu gccccagacc uguaauaguc 30

<210> SEQ ID NO 473
<211> LENGTH: 30
<212> TYPE: RNA
<213> ORGANISM: Artificial Sequence
<220> FEATURE:
<223> OTHER INFORMATION: Synthetic

<400> SEQUENCE: 473
aucauuugcc ccagaccugu aauagucaua 30

<210> SEQ ID NO 474
<211> LENGTH: 30
<212> TYPE: RNA
<213> ORGANISM: Artificial Sequence
<220> FEATURE:
<223> OTHER INFORMATION: Synthetic

<400> SEQUENCE: 474
gccccagacc uguaauaguc auauauagac 30

<210> SEQ ID NO 475
<211> LENGTH: 30
<212> TYPE: RNA
<213> ORGANISM: Artificial Sequence
<220> FEATURE:
<223> OTHER INFORMATION: Synthetic

<400> SEQUENCE: 475
ccccagaccu guaauaguca uauauagacu 30

<210> SEQ ID NO 476
<211> LENGTH: 30
<212> TYPE: RNA
<213> ORGANISM: Artificial Sequence
<220> FEATURE:
<223> OTHER INFORMATION: Synthetic

<400> SEQUENCE: 476
aaaaaauaaa uuuucuuacc uggaaaaugc 30

<210> SEQ ID NO 477
<211> LENGTH: 30
<212> TYPE: RNA
<213> ORGANISM: Artificial Sequence
<220> FEATURE:
<223> OTHER INFORMATION: Synthetic

<400> SEQUENCE: 477
ggaaguacug auuuagcaug uuguucauaa 30

<210> SEQ ID NO 478
<211> LENGTH: 30
<212> TYPE: RNA
<213> ORGANISM: Artificial Sequence
<220> FEATURE:
<223> OTHER INFORMATION: Synthetic

<400> SEQUENCE: 478
agcauguugu ucauaaucau ugauacaaau 30

<210> SEQ ID NO 479
<211> LENGTH: 30
<212> TYPE: RNA
<213> ORGANISM: Artificial Sequence
<220> FEATURE:
<223> OTHER INFORMATION: Synthetic

<400> SEQUENCE: 479
gcauguuguu cauaaucauu gauacaaauu 30

<210> SEQ ID NO 480
<211> LENGTH: 30
<212> TYPE: RNA
<213> ORGANISM: Artificial Sequence
<220> FEATURE:
<223> OTHER INFORMATION: Synthetic

<400> SEQUENCE: 480
uucauaauca uugauacaaa uuagccgggg 30

<210> SEQ ID NO 481
<211> LENGTH: 30
<212> TYPE: RNA
<213> ORGANISM: Artificial Sequence
<220> FEATURE:
<223> OTHER INFORMATION: Synthetic

<400> SEQUENCE: 481
auaaucauug auacaaauua gccgggggag 30

<210> SEQ ID NO 482
<211> LENGTH: 30
<212> TYPE: RNA

<213> ORGANISM: Artificial Sequence
<220> FEATURE:
<223> OTHER INFORMATION: Synthetic

<400> SEQUENCE: 482
auacaaauua gccgggggag cauuuucaca 30

<210> SEQ ID NO 483
<211> LENGTH: 30
<212> TYPE: RNA
<213> ORGANISM: Artificial Sequence
<220> FEATURE:
<223> OTHER INFORMATION: Synthetic

<400> SEQUENCE: 483
gccgggggag cauuuucaca gguuauugcu 30

<210> SEQ ID NO 484
<211> LENGTH: 30
<212> TYPE: RNA
<213> ORGANISM: Artificial Sequence
<220> FEATURE:
<223> OTHER INFORMATION: Synthetic

<400> SEQUENCE: 484
ucacagguua uugcuauccc agauggaguu 30

<210> SEQ ID NO 485
<211> LENGTH: 30
<212> TYPE: RNA
<213> ORGANISM: Artificial Sequence
<220> FEATURE:
<223> OTHER INFORMATION: Synthetic

<400> SEQUENCE: 485
cacagguuau ugcuauccca gauggaguuc 30

<210> SEQ ID NO 486
<211> LENGTH: 30
<212> TYPE: RNA
<213> ORGANISM: Artificial Sequence
<220> FEATURE:
<223> OTHER INFORMATION: Synthetic

<400> SEQUENCE: 486
acagguuauu gcuaucccag auggaguucg 30

<210> SEQ ID NO 487
<211> LENGTH: 30
<212> TYPE: RNA
<213> ORGANISM: Artificial Sequence
<220> FEATURE:
<223> OTHER INFORMATION: Synthetic

<400> SEQUENCE: 487
gaaguacuga uuuagcaugu uguucauaau 30

<210> SEQ ID NO 488
<211> LENGTH: 30
<212> TYPE: RNA
<213> ORGANISM: Artificial Sequence
<220> FEATURE:
<223> OTHER INFORMATION: Synthetic

<400> SEQUENCE: 488
uaaaaaauaa auuuucuuac cuggaaaaug 30

<210> SEQ ID NO 489
<211> LENGTH: 30
<212> TYPE: RNA
<213> ORGANISM: Artificial Sequence
<220> FEATURE:
<223> OTHER INFORMATION: Synthetic

<400> SEQUENCE: 489
aaaaauaaau uuucuuaccu ggaaaaugcu 30

<210> SEQ ID NO 490
<211> LENGTH: 30
<212> TYPE: RNA
<213> ORGANISM: Artificial Sequence
<220> FEATURE:
<223> OTHER INFORMATION: Synthetic

<400> SEQUENCE: 490
aaaacaugau uuuaaaaaau aaauuuucuu 30

<210> SEQ ID NO 491
<211> LENGTH: 30
<212> TYPE: RNA
<213> ORGANISM: Artificial Sequence
<220> FEATURE:
<223> OTHER INFORMATION: Synthetic

<400> SEQUENCE: 491
uaucaaugau uaugaacaac augcuaaauc 30

<210> SEQ ID NO 492
<211> LENGTH: 30
<212> TYPE: RNA
<213> ORGANISM: Artificial Sequence
<220> FEATURE:
<223> OTHER INFORMATION: Synthetic

<400> SEQUENCE: 492
ugaacaacau gcuaaaucag uacuuccaaa 30

<210> SEQ ID NO 493
<211> LENGTH: 30
<212> TYPE: RNA
<213> ORGANISM: Artificial Sequence
<220> FEATURE:
<223> OTHER INFORMATION: Synthetic

<400> SEQUENCE: 493
caaagucuau auaugacuau uacaggucug 30

<210> SEQ ID NO 494
<211> LENGTH: 30
<212> TYPE: RNA
<213> ORGANISM: Artificial Sequence
<220> FEATURE:
<223> OTHER INFORMATION: Synthetic

<400> SEQUENCE: 494
caggucuggg gcaaaugaug aagaaacuuu 30

<210> SEQ ID NO 495
<211> LENGTH: 30
<212> TYPE: RNA
<213> ORGANISM: Artificial Sequence
<220> FEATURE:

<223> OTHER INFORMATION: Synthetic

<400> SEQUENCE: 495
ggcugauaau auugcagcau uuuccaggua 30

<210> SEQ ID NO 496
<211> LENGTH: 30
<212> TYPE: RNA
<213> ORGANISM: Artificial Sequence
<220> FEATURE:
<223> OTHER INFORMATION: Synthetic

<400> SEQUENCE: 496
gcugauaaua uugcagcauu uuccagguaa 30

<210> SEQ ID NO 497
<211> LENGTH: 30
<212> TYPE: RNA
<213> ORGANISM: Artificial Sequence
<220> FEATURE:
<223> OTHER INFORMATION: Synthetic

<400> SEQUENCE: 497
cagcauuuuc cagguaagaa aauuuauuuu 30

<210> SEQ ID NO 498
<211> LENGTH: 30
<212> TYPE: RNA
<213> ORGANISM: Artificial Sequence
<220> FEATURE:
<223> OTHER INFORMATION: Synthetic

<400> SEQUENCE: 498
uccagguaag aaaauuuauu uuuuaaaauc 30

<210> SEQ ID NO 499
<211> LENGTH: 30
<212> TYPE: RNA
<213> ORGANISM: Artificial Sequence
<220> FEATURE:
<223> OTHER INFORMATION: Synthetic

<400> SEQUENCE: 499
ccagguaaga aaauuuauuu uuuaaaauca 30

<210> SEQ ID NO 500
<211> LENGTH: 30
<212> TYPE: RNA
<213> ORGANISM: Artificial Sequence
<220> FEATURE:
<223> OTHER INFORMATION: Synthetic

<400> SEQUENCE: 500
aaacaugauu uuaaaaaaua aauuuucuua 30

<210> SEQ ID NO 501
<211> LENGTH: 30
<212> TYPE: RNA
<213> ORGANISM: Artificial Sequence
<220> FEATURE:
<223> OTHER INFORMATION: Synthetic

<400> SEQUENCE: 501
auuuuuuaaa aucauguuuu aaaauuacac 30

<210> SEQ ID NO 502
<211> LENGTH: 30
<212> TYPE: RNA
<213> ORGANISM: Artificial Sequence
<220> FEATURE:
<223> OTHER INFORMATION: Synthetic

<400> SEQUENCE: 502
cagguaagaa aauuuauuuu uuaaaaucau 30

<210> SEQ ID NO 503
<211> LENGTH: 30
<212> TYPE: RNA
<213> ORGANISM: Artificial Sequence
<220> FEATURE:
<223> OTHER INFORMATION: Synthetic

<400> SEQUENCE: 503
uuuaaaauca uguuuuaaaa uuacacaaag 30

<210> SEQ ID NO 504
<211> LENGTH: 30
<212> TYPE: RNA
<213> ORGANISM: Artificial Sequence
<220> FEATURE:
<223> OTHER INFORMATION: Synthetic

<400> SEQUENCE: 504
uuaaaaucau guuuuaaaau uacacaaaga 30

<210> SEQ ID NO 505
<211> LENGTH: 30
<212> TYPE: RNA
<213> ORGANISM: Artificial Sequence
<220> FEATURE:
<223> OTHER INFORMATION: Synthetic

<400> SEQUENCE: 505
uaaaaucaug uuuuaaaauu acacaaagac 30

<210> SEQ ID NO 506
<211> LENGTH: 30
<212> TYPE: RNA
<213> ORGANISM: Artificial Sequence
<220> FEATURE:
<223> OTHER INFORMATION: Synthetic

<400> SEQUENCE: 506
aaaaucaugu uuuaaaauua cacaaagacc 30

<210> SEQ ID NO 507
<211> LENGTH: 30
<212> TYPE: RNA
<213> ORGANISM: Artificial Sequence
<220> FEATURE:
<223> OTHER INFORMATION: Synthetic

<400> SEQUENCE: 507
aaaucauguu uuaaaauuac acaaagaccg 30

<210> SEQ ID NO 508
<211> LENGTH: 30
<212> TYPE: RNA
<213> ORGANISM: Artificial Sequence
<220> FEATURE:
<223> OTHER INFORMATION: Synthetic

<400> SEQUENCE: 508
guguaauuuu aaaacaugau uuuaaaaaau 30

<210> SEQ ID NO 509
<211> LENGTH: 30
<212> TYPE: RNA
<213> ORGANISM: Artificial Sequence
<220> FEATURE:
<223> OTHER INFORMATION: Synthetic

<400> SEQUENCE: 509
uguaauuuua aaacaugauu uuaaaaaaua 30

<210> SEQ ID NO 510
<211> LENGTH: 30
<212> TYPE: RNA
<213> ORGANISM: Artificial Sequence
<220> FEATURE:
<223> OTHER INFORMATION: Synthetic

<400> SEQUENCE: 510
uaaaacauga uuuuaaaaaa uaaauuuucu 30

<210> SEQ ID NO 511
<211> LENGTH: 30
<212> TYPE: RNA
<213> ORGANISM: Artificial Sequence
<220> FEATURE:
<223> OTHER INFORMATION: Synthetic

<400> SEQUENCE: 511
uuuuuuaaaa ucauguuuua aaauuacaca 30

<210> SEQ ID NO 512
<211> LENGTH: 30
<212> TYPE: RNA
<213> ORGANISM: Artificial Sequence
<220> FEATURE:
<223> OTHER INFORMATION: Synthetic

<400> SEQUENCE: 512
guaucaauga uuaugaacaa caugcuaaau 30

<210> SEQ ID NO 513
<211> LENGTH: 24
<212> TYPE: RNA
<213> ORGANISM: Artificial Sequence
<220> FEATURE:
<223> OTHER INFORMATION: Synthetic

<400> SEQUENCE: 513
uugcuauccc agauggaguu cguu 24

<210> SEQ ID NO 514
<211> LENGTH: 21
<212> TYPE: RNA
<213> ORGANISM: Artificial Sequence
<220> FEATURE:
<223> OTHER INFORMATION: Synthetic

<400> SEQUENCE: 514
cuaucccaga uggaguucgu u 21

<210> SEQ ID NO 515
<211> LENGTH: 30

<212> TYPE: RNA
<213> ORGANISM: Artificial Sequence
<220> FEATURE:
<223> OTHER INFORMATION: Synthetic

<400> SEQUENCE: 515
uuuuuuaauu cuagauggaa gcuguaucca 30

<210> SEQ ID NO 516
<211> LENGTH: 30
<212> TYPE: RNA
<213> ORGANISM: Artificial Sequence
<220> FEATURE:
<223> OTHER INFORMATION: Synthetic

<400> SEQUENCE: 516
auuuuauuuu uuaauucuag auggaagcug 30

<210> SEQ ID NO 517
<211> LENGTH: 30
<212> TYPE: RNA
<213> ORGANISM: Artificial Sequence
<220> FEATURE:
<223> OTHER INFORMATION: Synthetic

<400> SEQUENCE: 517
auuuuuuaau ucuagaugga agcuguaucc 30

<210> SEQ ID NO 518
<211> LENGTH: 30
<212> TYPE: RNA
<213> ORGANISM: Artificial Sequence
<220> FEATURE:
<223> OTHER INFORMATION: Synthetic

<400> SEQUENCE: 518
uauuuuuuaa uucuagaugg aagcuguauc 30

<210> SEQ ID NO 519
<211> LENGTH: 30
<212> TYPE: RNA
<213> ORGANISM: Artificial Sequence
<220> FEATURE:
<223> OTHER INFORMATION: Synthetic

<400> SEQUENCE: 519
uuuuauuuuu uaauucuaga uggaagcugu 30

<210> SEQ ID NO 520
<211> LENGTH: 30
<212> TYPE: RNA
<213> ORGANISM: Artificial Sequence
<220> FEATURE:
<223> OTHER INFORMATION: Synthetic

<400> SEQUENCE: 520
aaaaauaaaa uaaaauaaaa ggcuuuagag 30

<210> SEQ ID NO 521
<211> LENGTH: 30
<212> TYPE: RNA
<213> ORGANISM: Artificial Sequence
<220> FEATURE:
<223> OTHER INFORMATION: Synthetic

<400> SEQUENCE: 521
auuuuauuuu auuuuuuaau ucuagaugga 30

<210> SEQ ID NO 522
<211> LENGTH: 30
<212> TYPE: RNA
<213> ORGANISM: Artificial Sequence
<220> FEATURE:
<223> OTHER INFORMATION: Synthetic

<400> SEQUENCE: 522
uauuuuauuu uauuuuuuaa uucuagaugg 30

<210> SEQ ID NO 523
<211> LENGTH: 30
<212> TYPE: RNA
<213> ORGANISM: Artificial Sequence
<220> FEATURE:
<223> OTHER INFORMATION: Synthetic

<400> SEQUENCE: 523
ugaaacucua aagccuuuua uuuuauuuua 30

<210> SEQ ID NO 524
<211> LENGTH: 30
<212> TYPE: RNA
<213> ORGANISM: Artificial Sequence
<220> FEATURE:
<223> OTHER INFORMATION: Synthetic

<400> SEQUENCE: 524
uuuaauucua gauggaagcu guauccaagg 30

<210> SEQ ID NO 525
<211> LENGTH: 30
<212> TYPE: RNA
<213> ORGANISM: Artificial Sequence
<220> FEATURE:
<223> OTHER INFORMATION: Synthetic

<400> SEQUENCE: 525
uuuuauuuua uuuuuuaauu cuagauggaa 30

<210> SEQ ID NO 526
<211> LENGTH: 30
<212> TYPE: RNA
<213> ORGANISM: Artificial Sequence
<220> FEATURE:
<223> OTHER INFORMATION: Synthetic

<400> SEQUENCE: 526
uuaauucuag auggaagcug uauccaagga 30

<210> SEQ ID NO 527
<211> LENGTH: 30
<212> TYPE: RNA
<213> ORGANISM: Artificial Sequence
<220> FEATURE:
<223> OTHER INFORMATION: Synthetic

<400> SEQUENCE: 527
uauuuuauuu uuuaauucua gauggaagcu 30

<210> SEQ ID NO 528
<211> LENGTH: 30
<212> TYPE: RNA
<213> ORGANISM: Artificial Sequence
<220> FEATURE:
<223> OTHER INFORMATION: Synthetic

<400> SEQUENCE: 528
caucuagaau uaaaaaauaa aauaaaauaa 30

<210> SEQ ID NO 529
<211> LENGTH: 30
<212> TYPE: RNA
<213> ORGANISM: Artificial Sequence
<220> FEATURE:
<223> OTHER INFORMATION: Synthetic

<400> SEQUENCE: 529
uaauucuaga uggaagcugu auccaaggau 30

<210> SEQ ID NO 530
<211> LENGTH: 30
<212> TYPE: RNA
<213> ORGANISM: Artificial Sequence
<220> FEATURE:
<223> OTHER INFORMATION: Synthetic

<400> SEQUENCE: 530
aauucuagau ggaagcugua uccaaggaug 30

<210> SEQ ID NO 531
<211> LENGTH: 30
<212> TYPE: RNA
<213> ORGANISM: Artificial Sequence
<220> FEATURE:
<223> OTHER INFORMATION: Synthetic

<400> SEQUENCE: 531
auucuagaug gaagcuguau ccaaggaugc 30

<210> SEQ ID NO 532
<211> LENGTH: 30
<212> TYPE: RNA
<213> ORGANISM: Artificial Sequence
<220> FEATURE:
<223> OTHER INFORMATION: Synthetic

<400> SEQUENCE: 532
uagauggaag cuguauccaa ggaugcuccg 30

<210> SEQ ID NO 533
<211> LENGTH: 30
<212> TYPE: RNA
<213> ORGANISM: Artificial Sequence
<220> FEATURE:
<223> OTHER INFORMATION: Synthetic

<400> SEQUENCE: 533
cugaaacaga ucugucgacu ucuguuuuag 30

<210> SEQ ID NO 534
<211> LENGTH: 30
<212> TYPE: RNA
<213> ORGANISM: Artificial Sequence
<220> FEATURE:
<223> OTHER INFORMATION: Synthetic

<400> SEQUENCE: 534
uaggacagag ggucagcaug ccaauaugug 30

<210> SEQ ID NO 535
<211> LENGTH: 30
<212> TYPE: RNA
<213> ORGANISM: Artificial Sequence
<220> FEATURE:
<223> OTHER INFORMATION: Synthetic

<400> SEQUENCE: 535
aggacagagg gucagcaugc caauaugugu 30

<210> SEQ ID NO 536
<211> LENGTH: 30
<212> TYPE: RNA
<213> ORGANISM: Artificial Sequence
<220> FEATURE:
<223> OTHER INFORMATION: Synthetic

<400> SEQUENCE: 536
ggacagaggg ucagcaugcc aauaugugug 30

<210> SEQ ID NO 537
<211> LENGTH: 30
<212> TYPE: RNA
<213> ORGANISM: Artificial Sequence
<220> FEATURE:
<223> OTHER INFORMATION: Synthetic

<400> SEQUENCE: 537
ccacugugag agguaggagg aagauuguca 30

<210> SEQ ID NO 538
<211> LENGTH: 30
<212> TYPE: RNA
<213> ORGANISM: Artificial Sequence
<220> FEATURE:
<223> OTHER INFORMATION: Synthetic

<400> SEQUENCE: 538
uguuuuagga cagaggguca gcaugccaau 30

<210> SEQ ID NO 539
<211> LENGTH: 30
<212> TYPE: RNA
<213> ORGANISM: Artificial Sequence
<220> FEATURE:
<223> OTHER INFORMATION: Synthetic

<400> SEQUENCE: 539
gccuccuucu gucccugugg ugacaaucuu 30

<210> SEQ ID NO 540
<211> LENGTH: 30
<212> TYPE: RNA
<213> ORGANISM: Artificial Sequence
<220> FEATURE:
<223> OTHER INFORMATION: Synthetic

<400> SEQUENCE: 540
ucaccacagg gacagaagga ggcuaacguu 30

<210> SEQ ID NO 541
<211> LENGTH: 30
<212> TYPE: RNA
<213> ORGANISM: Artificial Sequence
<220> FEATURE:
<223> OTHER INFORMATION: Synthetic

<400> SEQUENCE: 541
cggagcaucc uuggauacag cuuccaucua 30

<210> SEQ ID NO 542
<211> LENGTH: 30
<212> TYPE: RNA
<213> ORGANISM: Artificial Sequence
<220> FEATURE:
<223> OTHER INFORMATION: Synthetic

<400> SEQUENCE: 542
agcaacauuc cggagcaucc uuggauacag 30

<210> SEQ ID NO 543
<211> LENGTH: 30
<212> TYPE: RNA
<213> ORGANISM: Artificial Sequence
<220> FEATURE:
<223> OTHER INFORMATION: Synthetic

<400> SEQUENCE: 543
cagcaacauu ccggagcauc cuuggauaca 30

<210> SEQ ID NO 544
<211> LENGTH: 30
<212> TYPE: RNA
<213> ORGANISM: Artificial Sequence
<220> FEATURE:
<223> OTHER INFORMATION: Synthetic

<400> SEQUENCE: 544
gauacagcuu ccaucuagaa uuaaaaaaua 30

<210> SEQ ID NO 545
<211> LENGTH: 30
<212> TYPE: RNA
<213> ORGANISM: Artificial Sequence
<220> FEATURE:
<223> OTHER INFORMATION: Synthetic

<400> SEQUENCE: 545
cuccuaccuc ucacaguggc aagcucgccg 30

<210> SEQ ID NO 546
<211> LENGTH: 30
<212> TYPE: RNA
<213> ORGANISM: Artificial Sequence
<220> FEATURE:
<223> OTHER INFORMATION: Synthetic

<400> SEQUENCE: 546
ugucccugug gugacaaucu uccuccuacc 30

<210> SEQ ID NO 547
<211> LENGTH: 30
<212> TYPE: RNA
<213> ORGANISM: Artificial Sequence
<220> FEATURE:
<223> OTHER INFORMATION: Synthetic

<400> SEQUENCE: 547
gcaugcugac ccucuguccu aaaacagaag 30

<210> SEQ ID NO 548

<211> LENGTH: 30
<212> TYPE: RNA
<213> ORGANISM: Artificial Sequence
<220> FEATURE:
<223> OTHER INFORMATION: Synthetic

<400> SEQUENCE: 548
ccugggcaac cgucuggaug augugcguaa 30

<210> SEQ ID NO 549
<211> LENGTH: 30
<212> TYPE: RNA
<213> ORGANISM: Artificial Sequence
<220> FEATURE:
<223> OTHER INFORMATION: Synthetic

<400> SEQUENCE: 549
aaucuguuac gcacaucauc cagacgguug 30

<210> SEQ ID NO 550
<211> LENGTH: 30
<212> TYPE: RNA
<213> ORGANISM: Artificial Sequence
<220> FEATURE:
<223> OTHER INFORMATION: Synthetic

<400> SEQUENCE: 550
gaaucuguua cgcacaucau ccagacgguu 30

<210> SEQ ID NO 551
<211> LENGTH: 30
<212> TYPE: RNA
<213> ORGANISM: Artificial Sequence
<220> FEATURE:
<223> OTHER INFORMATION: Synthetic

<400> SEQUENCE: 551
uggcggcagu uugaaucugu uacgcacauc 30

<210> SEQ ID NO 552
<211> LENGTH: 30
<212> TYPE: RNA
<213> ORGANISM: Artificial Sequence
<220> FEATURE:
<223> OTHER INFORMATION: Synthetic

<400> SEQUENCE: 552
ccugaguugu ggcggcaguu ugaaucuguu 30

<210> SEQ ID NO 553
<211> LENGTH: 30
<212> TYPE: RNA
<213> ORGANISM: Artificial Sequence
<220> FEATURE:
<223> OTHER INFORMATION: Synthetic

<400> SEQUENCE: 553
gccucagcuc ggggcccaca ugaucauggu 30

<210> SEQ ID NO 554
<211> LENGTH: 30
<212> TYPE: RNA
<213> ORGANISM: Artificial Sequence
<220> FEATURE:
<223> OTHER INFORMATION: Synthetic

<400> SEQUENCE: 554
cgccucagcu cggggcccac augaucaugg 30

<210> SEQ ID NO 555
<211> LENGTH: 30
<212> TYPE: RNA
<213> ORGANISM: Artificial Sequence
<220> FEATURE:
<223> OTHER INFORMATION: Synthetic

<400> SEQUENCE: 555
aaacugccgc cacaacucag guaaccauga 30

<210> SEQ ID NO 556
<211> LENGTH: 30
<212> TYPE: RNA
<213> ORGANISM: Artificial Sequence
<220> FEATURE:
<223> OTHER INFORMATION: Synthetic

<400> SEQUENCE: 556
ugacagugga cacaccuuac cugggcaacc 30

<210> SEQ ID NO 557
<211> LENGTH: 30
<212> TYPE: RNA
<213> ORGANISM: Artificial Sequence
<220> FEATURE:
<223> OTHER INFORMATION: Synthetic

<400> SEQUENCE: 557 aucaucccu uucuuucuca gccugucagu 30

<210> SEQ ID NO 558
<211> LENGTH: 30
<212> TYPE: RNA
<213> ORGANISM: Artificial Sequence
<220> FEATURE:
<223> OTHER INFORMATION: Synthetic

<400> SEQUENCE: 558
gcugcaacug uauaucuaca aggaccgaga 30

<210> SEQ ID NO 559
<211> LENGTH: 30
<212> TYPE: RNA
<213> ORGANISM: Artificial Sequence
<220> FEATURE:
<223> OTHER INFORMATION: Synthetic

<400> SEQUENCE: 559
aagaaguggc ggaagcuggu ccugaggcac 30

<210> SEQ ID NO 560
<211> LENGTH: 30
<212> TYPE: RNA
<213> ORGANISM: Artificial Sequence
<220> FEATURE:
<223> OTHER INFORMATION: Synthetic

<400> SEQUENCE: 560
cugggccacc uccucaauug aagaaguggc 30

<210> SEQ ID NO 561
<211> LENGTH: 30
<212> TYPE: RNA

<213> ORGANISM: Artificial Sequence
<220> FEATURE:
<223> OTHER INFORMATION: Synthetic

<400> SEQUENCE: 561
aguuccuggg ccaccuccuc aauugaagaa 30

<210> SEQ ID NO 562
<211> LENGTH: 30
<212> TYPE: RNA
<213> ORGANISM: Artificial Sequence
<220> FEATURE:
<223> OTHER INFORMATION: Synthetic

<400> SEQUENCE: 562
ucagccuguc agucccuggg aacgggcaug 30

<210> SEQ ID NO 563
<211> LENGTH: 30
<212> TYPE: RNA
<213> ORGANISM: Artificial Sequence
<220> FEATURE:
<223> OTHER INFORMATION: Synthetic

<400> SEQUENCE: 563
cucagccugu cagucccugg gaacgggcau 30

<210> SEQ ID NO 564
<211> LENGTH: 30
<212> TYPE: RNA
<213> ORGANISM: Artificial Sequence
<220> FEATURE:
<223> OTHER INFORMATION: Synthetic

<400> SEQUENCE: 564
uuucucagcc ugucaguccc ugggaacggg 30

<210> SEQ ID NO 565
<211> LENGTH: 30
<212> TYPE: RNA
<213> ORGANISM: Artificial Sequence
<220> FEATURE:
<223> OTHER INFORMATION: Synthetic

<400> SEQUENCE: 565
cuuucucagc cugucagucc cugggaacgg 30

<210> SEQ ID NO 566
<211> LENGTH: 30
<212> TYPE: RNA
<213> ORGANISM: Artificial Sequence
<220> FEATURE:
<223> OTHER INFORMATION: Synthetic

<400> SEQUENCE: 566
cgcacaucau ccagacgguu gcccagguaa 30

<210> SEQ ID NO 567
<211> LENGTH: 30
<212> TYPE: RNA
<213> ORGANISM: Artificial Sequence
<220> FEATURE:
<223> OTHER INFORMATION: Synthetic

<400> SEQUENCE: 567
gugacagugg acacaccuua ccugggcaac 30

<210> SEQ ID NO 568
<211> LENGTH: 30
<212> TYPE: RNA
<213> ORGANISM: Artificial Sequence
<220> FEATURE:
<223> OTHER INFORMATION: Synthetic

<400> SEQUENCE: 568
cccagguaag guguguccac ugucacaaau 30

<210> SEQ ID NO 569
<211> LENGTH: 30
<212> TYPE: RNA
<213> ORGANISM: Artificial Sequence
<220> FEATURE:
<223> OTHER INFORMATION: Synthetic

<400> SEQUENCE: 569
guuggcugca acuguauauc uacaaggacc 30

<210> SEQ ID NO 570
<211> LENGTH: 30
<212> TYPE: RNA
<213> ORGANISM: Artificial Sequence
<220> FEATURE:
<223> OTHER INFORMATION: Synthetic

<400> SEQUENCE: 570
ucugccugcc gcacuagcuu cuuggugacu 30

<210> SEQ ID NO 571
<211> LENGTH: 30
<212> TYPE: RNA
<213> ORGANISM: Artificial Sequence
<220> FEATURE:
<223> OTHER INFORMATION: Synthetic

<400> SEQUENCE: 571
uagcccaucu ucucugccug ccgcacuagc 30

<210> SEQ ID NO 572
<211> LENGTH: 30
<212> TYPE: RNA
<213> ORGANISM: Artificial Sequence
<220> FEATURE:
<223> OTHER INFORMATION: Synthetic

<400> SEQUENCE: 572
ccagggacug acaggcugag aaagaaaggg 30

<210> SEQ ID NO 573
<211> LENGTH: 30
<212> TYPE: RNA
<213> ORGANISM: Artificial Sequence
<220> FEATURE:
<223> OTHER INFORMATION: Synthetic

<400> SEQUENCE: 573
aggagguggc ccaggaacuc aacaucaugc 30

<210> SEQ ID NO 574
<211> LENGTH: 30
<212> TYPE: RNA
<213> ORGANISM: Artificial Sequence
<220> FEATURE:

<223> OTHER INFORMATION: Synthetic

<400> SEQUENCE: 574
uucaauugag gagguggccc aggaacucaa 30

<210> SEQ ID NO 575
<211> LENGTH: 30
<212> TYPE: RNA
<213> ORGANISM: Artificial Sequence
<220> FEATURE:
<223> OTHER INFORMATION: Synthetic

<400> SEQUENCE: 575
cgccacuucu ucaauugagg agguggccca 30

<210> SEQ ID NO 576
<211> LENGTH: 30
<212> TYPE: RNA
<213> ORGANISM: Artificial Sequence
<220> FEATURE:
<223> OTHER INFORMATION: Synthetic

<400> SEQUENCE: 576
aauugaggag guggcccagg aacucaacau 30

<210> SEQ ID NO 577
<211> LENGTH: 30
<212> TYPE: RNA
<213> ORGANISM: Artificial Sequence
<220> FEATURE:
<223> OTHER INFORMATION: Synthetic

<400> SEQUENCE: 577
uagauauaca guugcagcca acgaagugcc 30

<210> SEQ ID NO 578
<211> LENGTH: 30
<212> TYPE: RNA
<213> ORGANISM: Artificial Sequence
<220> FEATURE:
<223> OTHER INFORMATION: Synthetic

<400> SEQUENCE: 578
ucgguccuug uagauauaca guugcagcca 30

<210> SEQ ID NO 579
<211> LENGTH: 30
<212> TYPE: RNA
<213> ORGANISM: Artificial Sequence
<220> FEATURE:
<223> OTHER INFORMATION: Synthetic

<400> SEQUENCE: 579
gugacuucuc gguccuugua gauauacagu 30

<210> SEQ ID NO 580
<211> LENGTH: 30
<212> TYPE: RNA
<213> ORGANISM: Artificial Sequence
<220> FEATURE:
<223> OTHER INFORMATION: Synthetic

<400> SEQUENCE: 580
uuggugacuu cucgguccuu guagauauac 30

<210> SEQ ID NO 581
<211> LENGTH: 30
<212> TYPE: RNA
<213> ORGANISM: Artificial Sequence
<220> FEATURE:
<223> OTHER INFORMATION: Synthetic

<400> SEQUENCE: 581
cagccaacga agugccucag gaccagcuuc 30

<210> SEQ ID NO 582
<211> LENGTH: 30
<212> TYPE: RNA
<213> ORGANISM: Artificial Sequence
<220> FEATURE:
<223> OTHER INFORMATION: Synthetic

<400> SEQUENCE: 582
cuaauuuggc aaauuucuca uuuuaugcau 30

<210> SEQ ID NO 583
<211> LENGTH: 30
<212> TYPE: RNA
<213> ORGANISM: Artificial Sequence
<220> FEATURE:
<223> OTHER INFORMATION: Synthetic

<400> SEQUENCE: 583
auccuaaaau aagaaaugca uaaaaugaga 30

<210> SEQ ID NO 584
<211> LENGTH: 30
<212> TYPE: RNA
<213> ORGANISM: Artificial Sequence
<220> FEATURE:
<223> OTHER INFORMATION: Synthetic

<400> SEQUENCE: 584
aaguagagaa auaaacgaac cucucaaaau 30

<210> SEQ ID NO 585
<211> LENGTH: 30
<212> TYPE: RNA
<213> ORGANISM: Artificial Sequence
<220> FEATURE:
<223> OTHER INFORMATION: Synthetic

<400> SEQUENCE: 585
ucuacuugaa uucauacuga cuuugugauc 30

<210> SEQ ID NO 586
<211> LENGTH: 30
<212> TYPE: RNA
<213> ORGANISM: Artificial Sequence
<220> FEATURE:
<223> OTHER INFORMATION: Synthetic

<400> SEQUENCE: 586
uaauuuggca aauuucucau uuuaugcauu 30

<210> SEQ ID NO 587
<211> LENGTH: 30
<212> TYPE: RNA
<213> ORGANISM: Artificial Sequence
<220> FEATURE:
<223> OTHER INFORMATION: Synthetic

<400> SEQUENCE: 587
uaugcauuuc uuauuuuagg augaaaaauu 30

<210> SEQ ID NO 588
<211> LENGTH: 30
<212> TYPE: RNA
<213> ORGANISM: Artificial Sequence
<220> FEATURE:
<223> OTHER INFORMATION: Synthetic

<400> SEQUENCE: 588
gcaaauuucu cauuuuaugc auuucuuauu 30

<210> SEQ ID NO 589
<211> LENGTH: 30
<212> TYPE: RNA
<213> ORGANISM: Artificial Sequence
<220> FEATURE:
<223> OTHER INFORMATION: Synthetic

<400> SEQUENCE: 589
cucauuuuau gcauuucuua uuuuaggaug 30

<210> SEQ ID NO 590
<211> LENGTH: 30
<212> TYPE: RNA
<213> ORGANISM: Artificial Sequence
<220> FEATURE:
<223> OTHER INFORMATION: Synthetic

<400> SEQUENCE: 590
ucauuuuaug cauuucuuau uuuaggauga 30

<210> SEQ ID NO 591
<211> LENGTH: 30
<212> TYPE: RNA
<213> ORGANISM: Artificial Sequence
<220> FEATURE:
<223> OTHER INFORMATION: Synthetic

<400> SEQUENCE: 591
cauccuaaaa uaagaaaugc auaaaaugag 30

<210> SEQ ID NO 592
<211> LENGTH: 30
<212> TYPE: RNA
<213> ORGANISM: Artificial Sequence
<220> FEATURE:
<223> OTHER INFORMATION: Synthetic

<400> SEQUENCE: 592
ggcaaauuuc ucauuuuaug cauuucuuau 30

<210> SEQ ID NO 593
<211> LENGTH: 30
<212> TYPE: RNA
<213> ORGANISM: Artificial Sequence
<220> FEATURE:
<223> OTHER INFORMATION: Synthetic

<400> SEQUENCE: 593
ucauccuaaa auaagaaaug cauaaaauga 30

<210> SEQ ID NO 594
<211> LENGTH: 30

<212> TYPE: RNA
<213> ORGANISM: Artificial Sequence
<220> FEATURE:
<223> OTHER INFORMATION: Synthetic

<400> SEQUENCE: 594
uccucaggag aaaaugauaa aguacugguu 30

<210> SEQ ID NO 595
<211> LENGTH: 30
<212> TYPE: RNA
<213> ORGANISM: Artificial Sequence
<220> FEATURE:
<223> OTHER INFORMATION: Synthetic

<400> SEQUENCE: 595
aaaauuuuuc auccuaaaau aagaaaugca 30

<210> SEQ ID NO 596
<211> LENGTH: 30
<212> TYPE: RNA
<213> ORGANISM: Artificial Sequence
<220> FEATURE:
<223> OTHER INFORMATION: Synthetic

<400> SEQUENCE: 596
caaaauuuuu cauccuaaaa uaagaaaugc 30

<210> SEQ ID NO 597
<211> LENGTH: 30
<212> TYPE: RNA
<213> ORGANISM: Artificial Sequence
<220> FEATURE:
<223> OTHER INFORMATION: Synthetic

<400> SEQUENCE: 597
cucaggagaa aaugauaaag uacugguuuc 30

<210> SEQ ID NO 598
<211> LENGTH: 30
<212> TYPE: RNA
<213> ORGANISM: Artificial Sequence
<220> FEATURE:
<223> OTHER INFORMATION: Synthetic

<400> SEQUENCE: 598
ccucaggaga aaaugauaaa guacugguuu 30

<210> SEQ ID NO 599
<211> LENGTH: 30
<212> TYPE: RNA
<213> ORGANISM: Artificial Sequence
<220> FEATURE:
<223> OTHER INFORMATION: Synthetic

<400> SEQUENCE: 599
augcauuucu uauuuuagga ugaaaaauuu 30

<210> SEQ ID NO 600
<211> LENGTH: 30
<212> TYPE: RNA
<213> ORGANISM: Artificial Sequence
<220> FEATURE:
<223> OTHER INFORMATION: Synthetic

<400> SEQUENCE: 600
gccacauaug cagcaagucc acugucgucu 30

<210> SEQ ID NO 601
<211> LENGTH: 30
<212> TYPE: RNA
<213> ORGANISM: Artificial Sequence
<220> FEATURE:
<223> OTHER INFORMATION: Synthetic

<400> SEQUENCE: 601
agccacauau gcagcaaguc cacugucguc 30

<210> SEQ ID NO 602
<211> LENGTH: 30
<212> TYPE: RNA
<213> ORGANISM: Artificial Sequence
<220> FEATURE:
<223> OTHER INFORMATION: Synthetic

<400> SEQUENCE: 602
cuuuagccac auaugcagca aguccacugu 30

<210> SEQ ID NO 603
<211> LENGTH: 30
<212> TYPE: RNA
<213> ORGANISM: Artificial Sequence
<220> FEATURE:
<223> OTHER INFORMATION: Synthetic

<400> SEQUENCE: 603
ccagcugaua gaugggucua uugcuuuagc 30

<210> SEQ ID NO 604
<211> LENGTH: 30
<212> TYPE: RNA
<213> ORGANISM: Artificial Sequence
<220> FEATURE:
<223> OTHER INFORMATION: Synthetic

<400> SEQUENCE: 604
auaucuuccc agcugauaga ugggucuauu 30

<210> SEQ ID NO 605
<211> LENGTH: 30
<212> TYPE: RNA
<213> ORGANISM: Artificial Sequence
<220> FEATURE:
<223> OTHER INFORMATION: Synthetic

<400> SEQUENCE: 605
gauaucuucc cagcugauag augggucuau 30

<210> SEQ ID NO 606
<211> LENGTH: 30
<212> TYPE: RNA
<213> ORGANISM: Artificial Sequence
<220> FEATURE:
<223> OTHER INFORMATION: Synthetic

<400> SEQUENCE: 606
ucagccauuu gauaucuucc cagcugauag 30

<210> SEQ ID NO 607
<211> LENGTH: 30
<212> TYPE: RNA
<213> ORGANISM: Artificial Sequence
<220> FEATURE:
<223> OTHER INFORMATION: Synthetic

<400> SEQUENCE: 607
gcaaugaugu cagucuucuc agccauuuga 30

<210> SEQ ID NO 608
<211> LENGTH: 30
<212> TYPE: RNA
<213> ORGANISM: Artificial Sequence
<220> FEATURE:
<223> OTHER INFORMATION: Synthetic

<400> SEQUENCE: 608
uucauccuaa aauaagaaau gcauaaaaug 30

<210> SEQ ID NO 609
<211> LENGTH: 30
<212> TYPE: RNA
<213> ORGANISM: Artificial Sequence
<220> FEATURE:
<223> OTHER INFORMATION: Synthetic

<400> SEQUENCE: 609
ugcauuucuu auuuuaggau gaaaaauuuu 30

<210> SEQ ID NO 610
<211> LENGTH: 30
<212> TYPE: RNA
<213> ORGANISM: Artificial Sequence
<220> FEATURE:
<223> OTHER INFORMATION: Synthetic

<400> SEQUENCE: 610
ggaugaaaaa uuuugaaacc aguacuuuau 30

<210> SEQ ID NO 611
<211> LENGTH: 30
<212> TYPE: RNA
<213> ORGANISM: Artificial Sequence
<220> FEATURE:
<223> OTHER INFORMATION: Synthetic

<400> SEQUENCE: 611
uuauuuuagg augaaaaauu uugaaaccag 30

<210> SEQ ID NO 612
<211> LENGTH: 30
<212> TYPE: RNA
<213> ORGANISM: Artificial Sequence
<220> FEATURE:
<223> OTHER INFORMATION: Synthetic

<400> SEQUENCE: 612
ccaauuguug caaagggcau uuugagaggu 30

<210> SEQ ID NO 613
<211> LENGTH: 30
<212> TYPE: RNA
<213> ORGANISM: Artificial Sequence
<220> FEATURE:
<223> OTHER INFORMATION: Synthetic

<400> SEQUENCE: 613
uugcaaaggg cauuuugaga gguucguuua 30

<210> SEQ ID NO 614
<211> LENGTH: 30
<212> TYPE: RNA
<213> ORGANISM: Artificial Sequence
<220> FEATURE:
<223> OTHER INFORMATION: Synthetic

<400> SEQUENCE: 614
gcaacaauug gcaaugaugu cagucuucuc 30

<210> SEQ ID NO 615
<211> LENGTH: 30
<212> TYPE: RNA
<213> ORGANISM: Artificial Sequence
<220> FEATURE:
<223> OTHER INFORMATION: Synthetic

<400> SEQUENCE: 615
caaagggcau uuugagaggu ucguuuauuu 30

<210> SEQ ID NO 616
<211> LENGTH: 30
<212> TYPE: RNA
<213> ORGANISM: Artificial Sequence
<220> FEATURE:
<223> OTHER INFORMATION: Synthetic

<400> SEQUENCE: 616
ugagagguuc guuuauuucu cuacuugaau 30

<210> SEQ ID NO 617
<211> LENGTH: 30
<212> TYPE: RNA
<213> ORGANISM: Artificial Sequence
<220> FEATURE:
<223> OTHER INFORMATION: Synthetic

<400> SEQUENCE: 617
gagagguucg uuuauuucuc uacuugaauu 30

<210> SEQ ID NO 618
<211> LENGTH: 30
<212> TYPE: RNA
<213> ORGANISM: Artificial Sequence
<220> FEATURE:
<223> OTHER INFORMATION: Synthetic

<400> SEQUENCE: 618
agagguucgu uuauuucucu acuugaauuc 30

<210> SEQ ID NO 619
<211> LENGTH: 30
<212> TYPE: RNA
<213> ORGANISM: Artificial Sequence
<220> FEATURE:
<223> OTHER INFORMATION: Synthetic

<400> SEQUENCE: 619
guuuauuucu cuacuugaau ucauacugac 30

<210> SEQ ID NO 620
<211> LENGTH: 30
<212> TYPE: RNA
<213> ORGANISM: Artificial Sequence
<220> FEATURE:
<223> OTHER INFORMATION: Synthetic

<400> SEQUENCE: 620
auuucucuac uugaauucau acugacuuug 30

<210> SEQ ID NO 621
<211> LENGTH: 30
<212> TYPE: RNA
<213> ORGANISM: Artificial Sequence
<220> FEATURE:
<223> OTHER INFORMATION: Synthetic

<400> SEQUENCE: 621
uuucucuacu ugaauucaua cugacuuugu 30

<210> SEQ ID NO 622
<211> LENGTH: 30
<212> TYPE: RNA
<213> ORGANISM: Artificial Sequence
<220> FEATURE:
<223> OTHER INFORMATION: Synthetic

<400> SEQUENCE: 622
cucuacuuga auucauacug acuuugugau 30

<210> SEQ ID NO 623
<211> LENGTH: 30
<212> TYPE: RNA
<213> ORGANISM: Artificial Sequence
<220> FEATURE:
<223> OTHER INFORMATION: Synthetic

<400> SEQUENCE: 623
cugcauaugu ggcuaaagca auagacccau 30

<210> SEQ ID NO 624
<211> LENGTH: 30
<212> TYPE: RNA
<213> ORGANISM: Artificial Sequence
<220> FEATURE:
<223> OTHER INFORMATION: Synthetic

<400> SEQUENCE: 624
cuuauuuuag gaugaaaaau uuugaaacca 30

<210> SEQ ID NO 625
<211> LENGTH: 30
<212> TYPE: RNA
<213> ORGANISM: Artificial Sequence
<220> FEATURE:
<223> OTHER INFORMATION: Synthetic

<400> SEQUENCE: 625
gagacgacag uggacuugcu gcauaugugg 30

<210> SEQ ID NO 626
<211> LENGTH: 30
<212> TYPE: RNA
<213> ORGANISM: Artificial Sequence
<220> FEATURE:
<223> OTHER INFORMATION: Synthetic

<400> SEQUENCE: 626
uggagacgac aguggacuug cugcauaugu 30

<210> SEQ ID NO 627

<211> LENGTH: 30
<212> TYPE: RNA
<213> ORGANISM: Artificial Sequence
<220> FEATURE:
<223> OTHER INFORMATION: Synthetic

<400> SEQUENCE: 627
uccugaggaa aauuuuggag acgacagugg 30

<210> SEQ ID NO 628
<211> LENGTH: 30
<212> TYPE: RNA
<213> ORGANISM: Artificial Sequence
<220> FEATURE:
<223> OTHER INFORMATION: Synthetic

<400> SEQUENCE: 628
cuccugagga aaauuuugga gacgacagug 30

<210> SEQ ID NO 629
<211> LENGTH: 30
<212> TYPE: RNA
<213> ORGANISM: Artificial Sequence
<220> FEATURE:
<223> OTHER INFORMATION: Synthetic

<400> SEQUENCE: 629
ucuccugagg aaaauuuugg agacgacagu 30

<210> SEQ ID NO 630
<211> LENGTH: 30
<212> TYPE: RNA
<213> ORGANISM: Artificial Sequence
<220> FEATURE:
<223> OTHER INFORMATION: Synthetic

<400> SEQUENCE: 630
ucauuuucuc cugaggaaaa uuuuggagac 30

<210> SEQ ID NO 631
<211> LENGTH: 30
<212> TYPE: RNA
<213> ORGANISM: Artificial Sequence
<220> FEATURE:
<223> OTHER INFORMATION: Synthetic

<400> SEQUENCE: 631
aucauuuucu ccugaggaaa auuuuggaga 30

<210> SEQ ID NO 632
<211> LENGTH: 30
<212> TYPE: RNA
<213> ORGANISM: Artificial Sequence
<220> FEATURE:
<223> OTHER INFORMATION: Synthetic

<400> SEQUENCE: 632
aaaccaguac uuuaucauuu ucuccugagg 30

<210> SEQ ID NO 633
<211> LENGTH: 30
<212> TYPE: RNA
<213> ORGANISM: Artificial Sequence
<220> FEATURE:
<223> OTHER INFORMATION: Synthetic

<400> SEQUENCE: 633
gaaaccagua cuuuaucauu uucuccugag 30

<210> SEQ ID NO 634
<211> LENGTH: 30
<212> TYPE: RNA
<213> ORGANISM: Artificial Sequence
<220> FEATURE:
<223> OTHER INFORMATION: Synthetic

<400> SEQUENCE: 634
ugaaaccagu acuuuaucau uuucuccuga 30

<210> SEQ ID NO 635
<211> LENGTH: 30
<212> TYPE: RNA
<213> ORGANISM: Artificial Sequence
<220> FEATURE:
<223> OTHER INFORMATION: Synthetic

<400> SEQUENCE: 635
aggaugaaaa auuuugaaac caguacuuua 30

<210> SEQ ID NO 636
<211> LENGTH: 30
<212> TYPE: RNA
<213> ORGANISM: Artificial Sequence
<220> FEATURE:
<223> OTHER INFORMATION: Synthetic

<400> SEQUENCE: 636
uaggaugaaa aauuuugaaa ccaguacuuu 30

<210> SEQ ID NO 637
<211> LENGTH: 30
<212> TYPE: RNA
<213> ORGANISM: Artificial Sequence
<220> FEATURE:
<223> OTHER INFORMATION: Synthetic

<400> SEQUENCE: 637
uuuuaggaug aaaaauuuug aaaccaguac 30

<210> SEQ ID NO 638
<211> LENGTH: 30
<212> TYPE: RNA
<213> ORGANISM: Artificial Sequence
<220> FEATURE:
<223> OTHER INFORMATION: Synthetic

<400> SEQUENCE: 638
ggagacgaca guggacuugc ugcauaugug 30

<210> SEQ ID NO 639
<211> LENGTH: 30
<212> TYPE: RNA
<213> ORGANISM: Artificial Sequence
<220> FEATURE:
<223> OTHER INFORMATION: Synthetic

<400> SEQUENCE: 639
caacaauugg caaugauguc agucuucuca 30

<210> SEQ ID NO 640
<211> LENGTH: 29
<212> TYPE: RNA

<213> ORGANISM: Artificial Sequence
<220> FEATURE:
<223> OTHER INFORMATION: Synthetic

<400> SEQUENCE: 640
aauucauacu gacuuuguga uccuuugug 29

<210> SEQ ID NO 641
<211> LENGTH: 24
<212> TYPE: RNA
<213> ORGANISM: Artificial Sequence
<220> FEATURE:
<223> OTHER INFORMATION: Synthetic

<400> SEQUENCE: 641
auacugacuu ugugauccuu ugug 24

<210> SEQ ID NO 642
<211> LENGTH: 30
<212> TYPE: RNA
<213> ORGANISM: Artificial Sequence
<220> FEATURE:
<223> OTHER INFORMATION: Synthetic

<400> SEQUENCE: 642
aguuacaguu ucccuaaggu gcuuguuuua 30

<210> SEQ ID NO 643
<211> LENGTH: 30
<212> TYPE: RNA
<213> ORGANISM: Artificial Sequence
<220> FEATURE:
<223> OTHER INFORMATION: Synthetic

<400> SEQUENCE: 643
aagccauguu uaacagccuc ccuggcauca 30

<210> SEQ ID NO 644
<211> LENGTH: 30
<212> TYPE: RNA
<213> ORGANISM: Artificial Sequence
<220> FEATURE:
<223> OTHER INFORMATION: Synthetic

<400> SEQUENCE: 644
acagccuccc uggcaucauc accuggagag 30

<210> SEQ ID NO 645
<211> LENGTH: 30
<212> TYPE: RNA
<213> ORGANISM: Artificial Sequence
<220> FEATURE:
<223> OTHER INFORMATION: Synthetic

<400> SEQUENCE: 645
aacagccucc cuggcaucau caccuggaga 30

<210> SEQ ID NO 646
<211> LENGTH: 30
<212> TYPE: RNA
<213> ORGANISM: Artificial Sequence
<220> FEATURE:
<223> OTHER INFORMATION: Synthetic

<400> SEQUENCE: 646
gacaccaaga ucccauucaa gccauguuua 30

<210> SEQ ID NO 647
<211> LENGTH: 30
<212> TYPE: RNA
<213> ORGANISM: Artificial Sequence
<220> FEATURE:
<223> OTHER INFORMATION: Synthetic

<400> SEQUENCE: 647
ucgagcccca ugauucgaca ccaagauccc 30

<210> SEQ ID NO 648
<211> LENGTH: 30
<212> TYPE: RNA
<213> ORGANISM: Artificial Sequence
<220> FEATURE:
<223> OTHER INFORMATION: Synthetic

<400> SEQUENCE: 648
gcgucugcca aaacucacag uggcuggcac 30

<210> SEQ ID NO 649
<211> LENGTH: 30
<212> TYPE: RNA
<213> ORGANISM: Artificial Sequence
<220> FEATURE:
<223> OTHER INFORMATION: Synthetic

<400> SEQUENCE: 649
gcagacgcua agauuuccuu uuggaguucc 30

<210> SEQ ID NO 650
<211> LENGTH: 30
<212> TYPE: RNA
<213> ORGANISM: Artificial Sequence
<220> FEATURE:
<223> OTHER INFORMATION: Synthetic

<400> SEQUENCE: 650
uggcagacgc uaagauuucc uuuuggaguu 30

<210> SEQ ID NO 651
<211> LENGTH: 30
<212> TYPE: RNA
<213> ORGANISM: Artificial Sequence
<220> FEATURE:
<223> OTHER INFORMATION: Synthetic

<400> SEQUENCE: 651
gugucgaauc auggggcucg acaacucgau 30

<210> SEQ ID NO 652
<211> LENGTH: 30
<212> TYPE: RNA
<213> ORGANISM: Artificial Sequence
<220> FEATURE:
<223> OTHER INFORMATION: Synthetic

<400> SEQUENCE: 652
ggcagacgcu aagauuuccu uuuggaguuc 30

<210> SEQ ID NO 653
<211> LENGTH: 30
<212> TYPE: RNA
<213> ORGANISM: Artificial Sequence
<220> FEATURE:

<223> OTHER INFORMATION: Synthetic

<400> SEQUENCE: 653
aacauggcuu gaaugggauc uuggugucga 30

<210> SEQ ID NO 654
<211> LENGTH: 30
<212> TYPE: RNA
<213> ORGANISM: Artificial Sequence
<220> FEATURE:
<223> OTHER INFORMATION: Synthetic

<400> SEQUENCE: 654
cucucuccag gugaugaugc cagggaggcu 30

<210> SEQ ID NO 655
<211> LENGTH: 30
<212> TYPE: RNA
<213> ORGANISM: Artificial Sequence
<220> FEATURE:
<223> OTHER INFORMATION: Synthetic

<400> SEQUENCE: 655
acucucucca ggugaugaug ccagggaggc 30

<210> SEQ ID NO 656
<211> LENGTH: 30
<212> TYPE: RNA
<213> ORGANISM: Artificial Sequence
<220> FEATURE:
<223> OTHER INFORMATION: Synthetic

<400> SEQUENCE: 656
uacucucucc aggugaugau gccagggagg 30

<210> SEQ ID NO 657
<211> LENGTH: 30
<212> TYPE: RNA
<213> ORGANISM: Artificial Sequence
<220> FEATURE:
<223> OTHER INFORMATION: Synthetic

<400> SEQUENCE: 657
uuuuacucuc uccaggugau gaugccaggg 30

<210> SEQ ID NO 658
<211> LENGTH: 30
<212> TYPE: RNA
<213> ORGANISM: Artificial Sequence
<220> FEATURE:
<223> OTHER INFORMATION: Synthetic

<400> SEQUENCE: 658
ccuaaggugc uuguuuuacu cucuccaggu 30

<210> SEQ ID NO 659
<211> LENGTH: 30
<212> TYPE: RNA
<213> ORGANISM: Artificial Sequence
<220> FEATURE:
<223> OTHER INFORMATION: Synthetic

<400> SEQUENCE: 659
cccuaaggug cuuguuuuac ucucuccagg 30

<210> SEQ ID NO 660
<211> LENGTH: 30
<212> TYPE: RNA
<213> ORGANISM: Artificial Sequence
<220> FEATURE:
<223> OTHER INFORMATION: Synthetic

<400> SEQUENCE: 660
caguuucccu aaggugcuug uuuuacucuc 30

<210> SEQ ID NO 661
<211> LENGTH: 30
<212> TYPE: RNA
<213> ORGANISM: Artificial Sequence
<220> FEATURE:
<223> OTHER INFORMATION: Synthetic

<400> SEQUENCE: 661
aaugggaucu uggugucgaa ucauggggcu 30

<210> SEQ ID NO 662
<211> LENGTH: 24
<212> TYPE: RNA
<213> ORGANISM: Artificial Sequence
<220> FEATURE:
<223> OTHER INFORMATION: Synthetic

<400> SEQUENCE: 662
ccuuuuggag uucccauuuc cauc 24

<210> SEQ ID NO 663
<211> LENGTH: 23
<212> TYPE: RNA
<213> ORGANISM: Artificial Sequence
<220> FEATURE:
<223> OTHER INFORMATION: Synthetic

<400> SEQUENCE: 663
cuuuuggagu ucccauuucc auc 23

<210> SEQ ID NO 664
<211> LENGTH: 24
<212> TYPE: RNA
<213> ORGANISM: Artificial Sequence
<220> FEATURE:
<223> OTHER INFORMATION: Synthetic

<400> SEQUENCE: 664
gggaaacugu aacuuaacag gcag 24

<210> SEQ ID NO 665
<211> LENGTH: 30
<212> TYPE: RNA
<213> ORGANISM: Artificial Sequence
<220> FEATURE:
<223> OTHER INFORMATION: Synthetic

<400> SEQUENCE: 665
caacuuucuu uucuuuuaug aucuuuaagu 30

<210> SEQ ID NO 666
<211> LENGTH: 30
<212> TYPE: RNA
<213> ORGANISM: Artificial Sequence
<220> FEATURE:
<223> OTHER INFORMATION: Synthetic

<400> SEQUENCE: 666
cgguuggcca uggcucugag ugguaagacu 30

<210> SEQ ID NO 667
<211> LENGTH: 30
<212> TYPE: RNA
<213> ORGANISM: Artificial Sequence
<220> FEATURE:
<223> OTHER INFORMATION: Synthetic

<400> SEQUENCE: 667
gccauggcuc ugagugguaa gacucauucu 30

<210> SEQ ID NO 668
<211> LENGTH: 30
<212> TYPE: RNA
<213> ORGANISM: Artificial Sequence
<220> FEATURE:
<223> OTHER INFORMATION: Synthetic

<400> SEQUENCE: 668
uuguuuacaa cuuucuuuuc uuuuaugauc 30

<210> SEQ ID NO 669
<211> LENGTH: 30
<212> TYPE: RNA
<213> ORGANISM: Artificial Sequence
<220> FEATURE:
<223> OTHER INFORMATION: Synthetic

<400> SEQUENCE: 669
uuuacaacuu ucuuuucuuu uaugaucuuu 30

<210> SEQ ID NO 670
<211> LENGTH: 30
<212> TYPE: RNA
<213> ORGANISM: Artificial Sequence
<220> FEATURE:
<223> OTHER INFORMATION: Synthetic

<400> SEQUENCE: 670
acaacuuucu uuucuuuuau gaucuuuaag 30

<210> SEQ ID NO 671
<211> LENGTH: 30
<212> TYPE: RNA
<213> ORGANISM: Artificial Sequence
<220> FEATURE:
<223> OTHER INFORMATION: Synthetic

<400> SEQUENCE: 671
aagaucauaa aagaaaagaa aguuguaaac 30

<210> SEQ ID NO 672
<211> LENGTH: 30
<212> TYPE: RNA
<213> ORGANISM: Artificial Sequence
<220> FEATURE:
<223> OTHER INFORMATION: Synthetic

<400> SEQUENCE: 672
ucuauuuuau auauucauuu cuuuguccag 30

<210> SEQ ID NO 673
<211> LENGTH: 30

<212> TYPE: RNA
<213> ORGANISM: Artificial Sequence
<220> FEATURE:
<223> OTHER INFORMATION: Synthetic

<400> SEQUENCE: 673
ccacucagag ccauggccaa ccggaauucu 30

<210> SEQ ID NO 674
<211> LENGTH: 30
<212> TYPE: RNA
<213> ORGANISM: Artificial Sequence
<220> FEATURE:
<223> OTHER INFORMATION: Synthetic

<400> SEQUENCE: 674
uuccuuuagu aucucgagga caucuugaac 30

<210> SEQ ID NO 675
<211> LENGTH: 30
<212> TYPE: RNA
<213> ORGANISM: Artificial Sequence
<220> FEATURE:
<223> OTHER INFORMATION: Synthetic

<400> SEQUENCE: 675
cuuuaguauc ucgaggacau cuugaacacc 30

<210> SEQ ID NO 676
<211> LENGTH: 30
<212> TYPE: RNA
<213> ORGANISM: Artificial Sequence
<220> FEATURE:
<223> OTHER INFORMATION: Synthetic

<400> SEQUENCE: 676
aguaucucga ggacaucuug aacaccuuuc 30

<210> SEQ ID NO 677
<211> LENGTH: 30
<212> TYPE: RNA
<213> ORGANISM: Artificial Sequence
<220> FEATURE:
<223> OTHER INFORMATION: Synthetic

<400> SEQUENCE: 677
guaucucgag gacaucuuga acaccuuucu 30

<210> SEQ ID NO 678
<211> LENGTH: 30
<212> TYPE: RNA
<213> ORGANISM: Artificial Sequence
<220> FEATURE:
<223> OTHER INFORMATION: Synthetic

<400> SEQUENCE: 678
aagauguccu cgagauacua aaggaagaau 30

<210> SEQ ID NO 679
<211> LENGTH: 30
<212> TYPE: RNA
<213> ORGANISM: Artificial Sequence
<220> FEATURE:
<223> OTHER INFORMATION: Synthetic

<400> SEQUENCE: 679
uaaacaagaa ugagucuuac cacucagagc 30

<210> SEQ ID NO 680
<211> LENGTH: 30
<212> TYPE: RNA
<213> ORGANISM: Artificial Sequence
<220> FEATURE:
<223> OTHER INFORMATION: Synthetic

<400> SEQUENCE: 680
gggggagaaa gguguucaag auguccucga 30

<210> SEQ ID NO 681
<211> LENGTH: 30
<212> TYPE: RNA
<213> ORGANISM: Artificial Sequence
<220> FEATURE:
<223> OTHER INFORMATION: Synthetic

<400> SEQUENCE: 681
ccagguaacu ggacaaagaa augaauauau 30

<210> SEQ ID NO 682
<211> LENGTH: 30
<212> TYPE: RNA
<213> ORGANISM: Artificial Sequence
<220> FEATURE:
<223> OTHER INFORMATION: Synthetic

<400> SEQUENCE: 682
acuugguuag ggggagaaag guguucaaga 30

<210> SEQ ID NO 683
<211> LENGTH: 30
<212> TYPE: RNA
<213> ORGANISM: Artificial Sequence
<220> FEATURE:
<223> OTHER INFORMATION: Synthetic

<400> SEQUENCE: 683
cacuugguua gggggagaaa gguguucaag 30

<210> SEQ ID NO 684
<211> LENGTH: 30
<212> TYPE: RNA
<213> ORGANISM: Artificial Sequence
<220> FEATURE:
<223> OTHER INFORMATION: Synthetic

<400> SEQUENCE: 684
ucacuugguu agggggagaa agguguucaa 30

<210> SEQ ID NO 685
<211> LENGTH: 30
<212> TYPE: RNA
<213> ORGANISM: Artificial Sequence
<220> FEATURE:
<223> OTHER INFORMATION: Synthetic

<400> SEQUENCE: 685
ugaaucacuc uguaucuuuu cacuugguua 30

<210> SEQ ID NO 686
<211> LENGTH: 30
<212> TYPE: RNA
<213> ORGANISM: Artificial Sequence
<220> FEATURE:
<223> OTHER INFORMATION: Synthetic

<400> SEQUENCE: 686
guucugaauc acucuguauc uuuucacuug 30

<210> SEQ ID NO 687
<211> LENGTH: 30
<212> TYPE: RNA
<213> ORGANISM: Artificial Sequence
<220> FEATURE:
<223> OTHER INFORMATION: Synthetic

<400> SEQUENCE: 687
aguucugaau cacucuguau cuuuucacuu 30

<210> SEQ ID NO 688
<211> LENGTH: 30
<212> TYPE: RNA
<213> ORGANISM: Artificial Sequence
<220> FEATURE:
<223> OTHER INFORMATION: Synthetic

<400> SEQUENCE: 688
acaguaaaac aaaugaauaa aacaagucag 30

<210> SEQ ID NO 689
<211> LENGTH: 30
<212> TYPE: RNA
<213> ORGANISM: Artificial Sequence
<220> FEATURE:
<223> OTHER INFORMATION: Synthetic

<400> SEQUENCE: 689
cagguaacug gacaaagaaa ugaauauaua 30

<210> SEQ ID NO 690
<211> LENGTH: 30
<212> TYPE: RNA
<213> ORGANISM: Artificial Sequence
<220> FEATURE:
<223> OTHER INFORMATION: Synthetic

<400> SEQUENCE: 690
aacaccuuuc ucccccuaac caagugaaaa 30

<210> SEQ ID NO 691
<211> LENGTH: 30
<212> TYPE: RNA
<213> ORGANISM: Artificial Sequence
<220> FEATURE:
<223> OTHER INFORMATION: Synthetic

<400> SEQUENCE: 691
gcuuuccagg uaacuggaca aagaaaugaa 30

<210> SEQ ID NO 692
<211> LENGTH: 30
<212> TYPE: RNA
<213> ORGANISM: Artificial Sequence
<220> FEATURE:
<223> OTHER INFORMATION: Synthetic

<400> SEQUENCE: 692
gggcuuagcu uuccagguaa cuggacaaag 30

<210> SEQ ID NO 693
<211> LENGTH: 30
<212> TYPE: RNA
<213> ORGANISM: Artificial Sequence
<220> FEATURE:
<223> OTHER INFORMATION: Synthetic

<400> SEQUENCE: 693
ggggcuuagc uuuccaggua acuggacaaa 30

<210> SEQ ID NO 694
<211> LENGTH: 30
<212> TYPE: RNA
<213> ORGANISM: Artificial Sequence
<220> FEATURE:
<223> OTHER INFORMATION: Synthetic

<400> SEQUENCE: 694
uggggagacc aaucguuugg ggcuuagcuu 30

<210> SEQ ID NO 695
<211> LENGTH: 30
<212> TYPE: RNA
<213> ORGANISM: Artificial Sequence
<220> FEATURE:
<223> OTHER INFORMATION: Synthetic

<400> SEQUENCE: 695
guggggagac caaucguuug gggcuuagcu 30

<210> SEQ ID NO 696
<211> LENGTH: 30
<212> TYPE: RNA
<213> ORGANISM: Artificial Sequence
<220> FEATURE:
<223> OTHER INFORMATION: Synthetic

<400> SEQUENCE: 696
guuaggggga gaaagguguu caagaugucc 30

<210> SEQ ID NO 697
<211> LENGTH: 30
<212> TYPE: RNA
<213> ORGANISM: Artificial Sequence
<220> FEATURE:
<223> OTHER INFORMATION: Synthetic

<400> SEQUENCE: 697
cucccccuaa ccaagugaaa agauacagag 30

<210> SEQ ID NO 698
<211> LENGTH: 30
<212> TYPE: RNA
<213> ORGANISM: Artificial Sequence
<220> FEATURE:
<223> OTHER INFORMATION: Synthetic

<400> SEQUENCE: 698
uacugucaag uugucuauuu uauauauuca 30

<210> SEQ ID NO 699
<211> LENGTH: 30
<212> TYPE: RNA
<213> ORGANISM: Artificial Sequence
<220> FEATURE:
<223> OTHER INFORMATION: Synthetic

<400> SEQUENCE: 699
agaacuaaau cagucugacu uguuuuauuc 30

<210> SEQ ID NO 700
<211> LENGTH: 30
<212> TYPE: RNA
<213> ORGANISM: Artificial Sequence
<220> FEATURE:
<223> OTHER INFORMATION: Synthetic

<400> SEQUENCE: 700
aauaauguga cucuauuaac acugaauugu 30

<210> SEQ ID NO 701
<211> LENGTH: 30
<212> TYPE: RNA
<213> ORGANISM: Artificial Sequence
<220> FEATURE:
<223> OTHER INFORMATION: Synthetic

<400> SEQUENCE: 701
uggcagaaca ucaaucuggg gaaagaaaag 30

<210> SEQ ID NO 702
<211> LENGTH: 30
<212> TYPE: RNA
<213> ORGANISM: Artificial Sequence
<220> FEATURE:
<223> OTHER INFORMATION: Synthetic

<400> SEQUENCE: 702
cuggcagaac aucaaucugg ggaaagaaaa 30

<210> SEQ ID NO 703
<211> LENGTH: 30
<212> TYPE: RNA
<213> ORGANISM: Artificial Sequence
<220> FEATURE:
<223> OTHER INFORMATION: Synthetic

<400> SEQUENCE: 703
cacagccucc acaauuucug gcagaacauc 30

<210> SEQ ID NO 704
<211> LENGTH: 30
<212> TYPE: RNA
<213> ORGANISM: Artificial Sequence
<220> FEATURE:
<223> OTHER INFORMATION: Synthetic

<400> SEQUENCE: 704
ccuuccacag ccuccacaau uucuggcaga 30

<210> SEQ ID NO 705
<211> LENGTH: 30
<212> TYPE: RNA
<213> ORGANISM: Artificial Sequence
<220> FEATURE:
<223> OTHER INFORMATION: Synthetic

<400> SEQUENCE: 705
caccuucccu uccacagccu ccacaauuuc 30

<210> SEQ ID NO 706

<211> LENGTH: 30
<212> TYPE: RNA
<213> ORGANISM: Artificial Sequence
<220> FEATURE:
<223> OTHER INFORMATION: Synthetic

<400> SEQUENCE: 706
cgcacacccc cguccaggaa gacuuccacc 30

<210> SEQ ID NO 707
<211> LENGTH: 30
<212> TYPE: RNA
<213> ORGANISM: Artificial Sequence
<220> FEATURE:
<223> OTHER INFORMATION: Synthetic

<400> SEQUENCE: 707
ccgcacaccc ccguccagga agacuuccac 30

<210> SEQ ID NO 708
<211> LENGTH: 30
<212> TYPE: RNA
<213> ORGANISM: Artificial Sequence
<220> FEATURE:
<223> OTHER INFORMATION: Synthetic

<400> SEQUENCE: 708
agaacaucag ugccuuuccg cacaccccg 30

<210> SEQ ID NO 709
<211> LENGTH: 30
<212> TYPE: RNA
<213> ORGANISM: Artificial Sequence
<220> FEATURE:
<223> OTHER INFORMATION: Synthetic

<400> SEQUENCE: 709
cagaacauca gugccuuucc gcacaccccc 30

<210> SEQ ID NO 710
<211> LENGTH: 30
<212> TYPE: RNA
<213> ORGANISM: Artificial Sequence
<220> FEATURE:
<223> OTHER INFORMATION: Synthetic

<400> SEQUENCE: 710
gcgccaagag ccagagcuuu cagaacauca 30

<210> SEQ ID NO 711
<211> LENGTH: 30
<212> TYPE: RNA
<213> ORGANISM: Artificial Sequence
<220> FEATURE:
<223> OTHER INFORMATION: Synthetic

<400> SEQUENCE: 711
gucuccccac aaacacagcc uuggcgccaa 30

<210> SEQ ID NO 712
<211> LENGTH: 30
<212> TYPE: RNA
<213> ORGANISM: Artificial Sequence
<220> FEATURE:
<223> OTHER INFORMATION: Synthetic

<400> SEQUENCE: 712
ccuggaaagc uaagccccaa acgauugguc 30

<210> SEQ ID NO 713
<211> LENGTH: 30
<212> TYPE: RNA
<213> ORGANISM: Artificial Sequence
<220> FEATURE:
<223> OTHER INFORMATION: Synthetic

<400> SEQUENCE: 713
uccaguuacc uggaaagcua agccccaaac 30

<210> SEQ ID NO 714
<211> LENGTH: 30
<212> TYPE: RNA
<213> ORGANISM: Artificial Sequence
<220> FEATURE:
<223> OTHER INFORMATION: Synthetic

<400> SEQUENCE: 714
guccaguuac cuggaaagcu aagccccaaa 30

<210> SEQ ID NO 715
<211> LENGTH: 30
<212> TYPE: RNA
<213> ORGANISM: Artificial Sequence
<220> FEATURE:
<223> OTHER INFORMATION: Synthetic

<400> SEQUENCE: 715
uuuguccagu uaccuggaaa gcuaagcccc 30

<210> SEQ ID NO 716
<211> LENGTH: 30
<212> TYPE: RNA
<213> ORGANISM: Artificial Sequence
<220> FEATURE:
<223> OTHER INFORMATION: Synthetic

<400> SEQUENCE: 716
cuuuguccag uuaccuggaa agcuaagccc 30

<210> SEQ ID NO 717
<211> LENGTH: 30
<212> TYPE: RNA
<213> ORGANISM: Artificial Sequence
<220> FEATURE:
<223> OTHER INFORMATION: Synthetic

<400> SEQUENCE: 717
uuuuauucau uuguuuuacu gucaaguugu 30

<210> SEQ ID NO 718
<211> LENGTH: 30
<212> TYPE: RNA
<213> ORGANISM: Artificial Sequence
<220> FEATURE:
<223> OTHER INFORMATION: Synthetic

<400> SEQUENCE: 718
uauucauuug uuuuacuguc aaguugucua 30

<210> SEQ ID NO 719
<211> LENGTH: 30
<212> TYPE: RNA

<213> ORGANISM: Artificial Sequence
<220> FEATURE:
<223> OTHER INFORMATION: Synthetic

<400> SEQUENCE: 719
auucauuugu uuuacuguca aguugucuau 30

<210> SEQ ID NO 720
<211> LENGTH: 30
<212> TYPE: RNA
<213> ORGANISM: Artificial Sequence
<220> FEATURE:
<223> OTHER INFORMATION: Synthetic

<400> SEQUENCE: 720
uucauuuguu uuacugucaa guugucuauu 30

<210> SEQ ID NO 721
<211> LENGTH: 30
<212> TYPE: RNA
<213> ORGANISM: Artificial Sequence
<220> FEATURE:
<223> OTHER INFORMATION: Synthetic

<400> SEQUENCE: 721
auuuguuuua cugucaaguu gucuauuuua 30

<210> SEQ ID NO 722
<211> LENGTH: 30
<212> TYPE: RNA
<213> ORGANISM: Artificial Sequence
<220> FEATURE:
<223> OTHER INFORMATION: Synthetic

<400> SEQUENCE: 722
guuuuacugu caaguugucu auuuuauaua 30

<210> SEQ ID NO 723
<211> LENGTH: 30
<212> TYPE: RNA
<213> ORGANISM: Artificial Sequence
<220> FEATURE:
<223> OTHER INFORMATION: Synthetic

<400> SEQUENCE: 723
ucccccuaac caagugaaaa gauacagagu 30

<210> SEQ ID NO 724
<211> LENGTH: 30
<212> TYPE: RNA
<213> ORGANISM: Artificial Sequence
<220> FEATURE:
<223> OTHER INFORMATION: Synthetic

<400> SEQUENCE: 724
uuuuacuguc aaguugucua uuuuauauau 30

<210> SEQ ID NO 725
<211> LENGTH: 30
<212> TYPE: RNA
<213> ORGANISM: Artificial Sequence
<220> FEATURE:
<223> OTHER INFORMATION: Synthetic

<400> SEQUENCE: 725
acugucaagu ugucuauuuu auauauucau 30

<210> SEQ ID NO 726
<211> LENGTH: 30
<212> TYPE: RNA
<213> ORGANISM: Artificial Sequence
<220> FEATURE:
<223> OTHER INFORMATION: Synthetic

<400> SEQUENCE: 726
cugucaaguu gucuauuuua uauauucauu 30

<210> SEQ ID NO 727
<211> LENGTH: 30
<212> TYPE: RNA
<213> ORGANISM: Artificial Sequence
<220> FEATURE:
<223> OTHER INFORMATION: Synthetic

<400> SEQUENCE: 727
uauauauuca uuucuuuguc caguuaccug 30

<210> SEQ ID NO 728
<211> LENGTH: 30
<212> TYPE: RNA
<213> ORGANISM: Artificial Sequence
<220> FEATURE:
<223> OTHER INFORMATION: Synthetic

<400> SEQUENCE: 728
auauauucau uucuuugucc aguuaccugg 30

<210> SEQ ID NO 729
<211> LENGTH: 30
<212> TYPE: RNA
<213> ORGANISM: Artificial Sequence
<220> FEATURE:
<223> OTHER INFORMATION: Synthetic

<400> SEQUENCE: 729
uauauucauu ucuuugucca guuaccugga 30

<210> SEQ ID NO 730
<211> LENGTH: 30
<212> TYPE: RNA
<213> ORGANISM: Artificial Sequence
<220> FEATURE:
<223> OTHER INFORMATION: Synthetic

<400> SEQUENCE: 730
auuucuuugu ccaguuaccu ggaaagcuaa 30

<210> SEQ ID NO 731
<211> LENGTH: 30
<212> TYPE: RNA
<213> ORGANISM: Artificial Sequence
<220> FEATURE:
<223> OTHER INFORMATION: Synthetic

<400> SEQUENCE: 731
gcgccaaggc uguguuugug gggagaccaa 30

<210> SEQ ID NO 732
<211> LENGTH: 30
<212> TYPE: RNA
<213> ORGANISM: Artificial Sequence
<220> FEATURE:

<223> OTHER INFORMATION: Synthetic

<400> SEQUENCE: 732
ugaaagcucu ggcucuuggc gccaaggcug 30

<210> SEQ ID NO 733
<211> LENGTH: 30
<212> TYPE: RNA
<213> ORGANISM: Artificial Sequence
<220> FEATURE:
<223> OTHER INFORMATION: Synthetic

<400> SEQUENCE: 733
uggaggcugu ggaagggaag guggaagucu 30

<210> SEQ ID NO 734
<211> LENGTH: 30
<212> TYPE: RNA
<213> ORGANISM: Artificial Sequence
<220> FEATURE:
<223> OTHER INFORMATION: Synthetic

<400> SEQUENCE: 734
uugaacuuuu cuuuccccag auugauguuc 30

<210> SEQ ID NO 735
<211> LENGTH: 30
<212> TYPE: RNA
<213> ORGANISM: Artificial Sequence
<220> FEATURE:
<223> OTHER INFORMATION: Synthetic

<400> SEQUENCE: 735
ugccagaaau uguggaggcu guggaaggga 30

<210> SEQ ID NO 736
<211> LENGTH: 30
<212> TYPE: RNA
<213> ORGANISM: Artificial Sequence
<220> FEATURE:
<223> OTHER INFORMATION: Synthetic

<400> SEQUENCE: 736
auguucugcc agaaauugug gaggcugugg 30

<210> SEQ ID NO 737
<211> LENGTH: 30
<212> TYPE: RNA
<213> ORGANISM: Artificial Sequence
<220> FEATURE:
<223> OTHER INFORMATION: Synthetic

<400> SEQUENCE: 737
cccagauuga uguucugcca gaaauugugg 30

<210> SEQ ID NO 738
<211> LENGTH: 30
<212> TYPE: RNA
<213> ORGANISM: Artificial Sequence
<220> FEATURE:
<223> OTHER INFORMATION: Synthetic

<400> SEQUENCE: 738
ccccagauug auguucugcc agaaauugug 30

<210> SEQ ID NO 739
<211> LENGTH: 30
<212> TYPE: RNA
<213> ORGANISM: Artificial Sequence
<220> FEATURE:
<223> OTHER INFORMATION: Synthetic

<400> SEQUENCE: 739
uuuccccaga uugauguucu gccagaaauu 30

<210> SEQ ID NO 740
<211> LENGTH: 30
<212> TYPE: RNA
<213> ORGANISM: Artificial Sequence
<220> FEATURE:
<223> OTHER INFORMATION: Synthetic

<400> SEQUENCE: 740
cuuuccccag auugauguuc ugccagaaau 30

<210> SEQ ID NO 741
<211> LENGTH: 30
<212> TYPE: RNA
<213> ORGANISM: Artificial Sequence
<220> FEATURE:
<223> OTHER INFORMATION: Synthetic

<400> SEQUENCE: 741
ucuuucccca gauugauguu cugccagaaa 30

<210> SEQ ID NO 742
<211> LENGTH: 30
<212> TYPE: RNA
<213> ORGANISM: Artificial Sequence
<220> FEATURE:
<223> OTHER INFORMATION: Synthetic

<400> SEQUENCE: 742
aacuuuucuu uccccagauu gauguucugc 30

<210> SEQ ID NO 743
<211> LENGTH: 30
<212> TYPE: RNA
<213> ORGANISM: Artificial Sequence
<220> FEATURE:
<223> OTHER INFORMATION: Synthetic

<400> SEQUENCE: 743
auagagucac auuauugaac uuuucuuucc 30

<210> SEQ ID NO 744
<211> LENGTH: 30
<212> TYPE: RNA
<213> ORGANISM: Artificial Sequence
<220> FEATURE:
<223> OTHER INFORMATION: Synthetic

<400> SEQUENCE: 744
aguguuaaua gagucacauu auugaacuuu 30

<210> SEQ ID NO 745
<211> LENGTH: 30
<212> TYPE: RNA
<213> ORGANISM: Artificial Sequence
<220> FEATURE:
<223> OTHER INFORMATION: Synthetic

<400> SEQUENCE: 745
cuggacgggg gugugcggaa aggcacugau 30

<210> SEQ ID NO 746
<211> LENGTH: 23
<212> TYPE: RNA
<213> ORGANISM: Artificial Sequence
<220> FEATURE:
<223> OTHER INFORMATION: Synthetic

<400> SEQUENCE: 746
cuuuucuuuu augaucuuua agu 23

<210> SEQ ID NO 747
<211> LENGTH: 22
<212> TYPE: RNA
<213> ORGANISM: Artificial Sequence
<220> FEATURE:
<223> OTHER INFORMATION: Synthetic

<400> SEQUENCE: 747
uuuucuuuua ugaucuuuaa gu 22

<210> SEQ ID NO 748
<211> LENGTH: 30
<212> TYPE: RNA
<213> ORGANISM: Artificial Sequence
<220> FEATURE:
<223> OTHER INFORMATION: Synthetic

<400> SEQUENCE: 748
uuucagggug ccagaaugug aaagucaucg 30

<210> SEQ ID NO 749
<211> LENGTH: 30
<212> TYPE: RNA
<213> ORGANISM: Artificial Sequence
<220> FEATURE:
<223> OTHER INFORMATION: Synthetic

<400> SEQUENCE: 749
uuuuuucagg gugccagaau gugaaaguca 30

<210> SEQ ID NO 750
<211> LENGTH: 30
<212> TYPE: RNA
<213> ORGANISM: Artificial Sequence
<220> FEATURE:
<223> OTHER INFORMATION: Synthetic

<400> SEQUENCE: 750
uaagcucagg uucaaagugu ugguaaugcc 30

<210> SEQ ID NO 751
<211> LENGTH: 30
<212> TYPE: RNA
<213> ORGANISM: Artificial Sequence
<220> FEATURE:
<223> OTHER INFORMATION: Synthetic

<400> SEQUENCE: 751
auauuaaaug uaugcauuau uuuuucaggg 30

<210> SEQ ID NO 752
<211> LENGTH: 30

<212> TYPE: RNA
<213> ORGANISM: Artificial Sequence
<220> FEATURE:
<223> OTHER INFORMATION: Synthetic

<400> SEQUENCE: 752
aguucauauu aaauguaugc auuauuuuuu 30

<210> SEQ ID NO 753
<211> LENGTH: 30
<212> TYPE: RNA
<213> ORGANISM: Artificial Sequence
<220> FEATURE:
<223> OTHER INFORMATION: Synthetic

<400> SEQUENCE: 753
uucagggugc cagaauguga aagucaucga 30

<210> SEQ ID NO 754
<211> LENGTH: 30
<212> TYPE: RNA
<213> ORGANISM: Artificial Sequence
<220> FEATURE:
<223> OTHER INFORMATION: Synthetic

<400> SEQUENCE: 754
aauguaugca uuauuuuuuc agggugccag 30

<210> SEQ ID NO 755
<211> LENGTH: 30
<212> TYPE: RNA
<213> ORGANISM: Artificial Sequence
<220> FEATURE:
<223> OTHER INFORMATION: Synthetic

<400> SEQUENCE: 755
ucagggugcc agaaugugaa agucaucgac 30

<210> SEQ ID NO 756
<211> LENGTH: 30
<212> TYPE: RNA
<213> ORGANISM: Artificial Sequence
<220> FEATURE:
<223> OTHER INFORMATION: Synthetic

<400> SEQUENCE: 756
gccguuucca agaucugaca gugcacaaua 30

<210> SEQ ID NO 757
<211> LENGTH: 30
<212> TYPE: RNA
<213> ORGANISM: Artificial Sequence
<220> FEATURE:
<223> OTHER INFORMATION: Synthetic

<400> SEQUENCE: 757
agggugccag aaugugaaag ucaucgacaa 30

<210> SEQ ID NO 758
<211> LENGTH: 30
<212> TYPE: RNA
<213> ORGANISM: Artificial Sequence
<220> FEATURE:
<223> OTHER INFORMATION: Synthetic

<400> SEQUENCE: 758
gugaggaaaa auccuuuggc cguuuccaag 30

<210> SEQ ID NO 759
<211> LENGTH: 30
<212> TYPE: RNA
<213> ORGANISM: Artificial Sequence
<220> FEATURE:
<223> OTHER INFORMATION: Synthetic

<400> SEQUENCE: 759
ggccguuucc aagaucugac agugcacaau 30

<210> SEQ ID NO 760
<211> LENGTH: 30
<212> TYPE: RNA
<213> ORGANISM: Artificial Sequence
<220> FEATURE:
<223> OTHER INFORMATION: Synthetic

<400> SEQUENCE: 760
cauucaguuc auauuaaaug uaugcauuau 30

<210> SEQ ID NO 761
<211> LENGTH: 30
<212> TYPE: RNA
<213> ORGANISM: Artificial Sequence
<220> FEATURE:
<223> OTHER INFORMATION: Synthetic

<400> SEQUENCE: 761
ccaagaucug acagugcaca auauuuuccc 30

<210> SEQ ID NO 762
<211> LENGTH: 30
<212> TYPE: RNA
<213> ORGANISM: Artificial Sequence
<220> FEATURE:
<223> OTHER INFORMATION: Synthetic

<400> SEQUENCE: 762
caagaucuga cagugcacaa uauuuuccca 30

<210> SEQ ID NO 763
<211> LENGTH: 30
<212> TYPE: RNA
<213> ORGANISM: Artificial Sequence
<220> FEATURE:
<223> OTHER INFORMATION: Synthetic

<400> SEQUENCE: 763
cagggugcca gaaugugaaa gucaucgaca 30

<210> SEQ ID NO 764
<211> LENGTH: 30
<212> TYPE: RNA
<213> ORGANISM: Artificial Sequence
<220> FEATURE:
<223> OTHER INFORMATION: Synthetic

<400> SEQUENCE: 764
uugcauucag uucauauuaa auguaugcau 30

<210> SEQ ID NO 765
<211> LENGTH: 30
<212> TYPE: RNA
<213> ORGANISM: Artificial Sequence
<220> FEATURE:
<223> OTHER INFORMATION: Synthetic

<400> SEQUENCE: 765
gagguagcaa acacuaaggu gaaaagauaa 30

<210> SEQ ID NO 766
<211> LENGTH: 30
<212> TYPE: RNA
<213> ORGANISM: Artificial Sequence
<220> FEATURE:
<223> OTHER INFORMATION: Synthetic

<400> SEQUENCE: 766
agacaacguc auccccuggc aggcuaaagu 30

<210> SEQ ID NO 767
<211> LENGTH: 30
<212> TYPE: RNA
<213> ORGANISM: Artificial Sequence
<220> FEATURE:
<223> OTHER INFORMATION: Synthetic

<400> SEQUENCE: 767
aauuguaagc ucagguucaa aguguuggua 30

<210> SEQ ID NO 768
<211> LENGTH: 30
<212> TYPE: RNA
<213> ORGANISM: Artificial Sequence
<220> FEATURE:
<223> OTHER INFORMATION: Synthetic

<400> SEQUENCE: 768
uuaaauugua agcucagguu caaaguguug 30

<210> SEQ ID NO 769
<211> LENGTH: 30
<212> TYPE: RNA
<213> ORGANISM: Artificial Sequence
<220> FEATURE:
<223> OTHER INFORMATION: Synthetic

<400> SEQUENCE: 769
aaacaguggu ucuuaaauug uaagcucagg 30

<210> SEQ ID NO 770
<211> LENGTH: 30
<212> TYPE: RNA
<213> ORGANISM: Artificial Sequence
<220> FEATURE:
<223> OTHER INFORMATION: Synthetic

<400> SEQUENCE: 770
aaaacagugg uucuuaaauu guaagcucag 30

<210> SEQ ID NO 771
<211> LENGTH: 30
<212> TYPE: RNA
<213> ORGANISM: Artificial Sequence
<220> FEATURE:
<223> OTHER INFORMATION: Synthetic

<400> SEQUENCE: 771
caugucuuua aaacaguggu ucuuaaauug 30

<210> SEQ ID NO 772
<211> LENGTH: 30
<212> TYPE: RNA
<213> ORGANISM: Artificial Sequence
<220> FEATURE:
<223> OTHER INFORMATION: Synthetic

<400> SEQUENCE: 772
acaugucuuu aaaacagugg uucuuaaauu 30

<210> SEQ ID NO 773
<211> LENGTH: 30
<212> TYPE: RNA
<213> ORGANISM: Artificial Sequence
<220> FEATURE:
<223> OTHER INFORMATION: Synthetic

<400> SEQUENCE: 773
uguuuacaug ucuuuaaaac agugguucuu 30

<210> SEQ ID NO 774
<211> LENGTH: 30
<212> TYPE: RNA
<213> ORGANISM: Artificial Sequence
<220> FEATURE:
<223> OTHER INFORMATION: Synthetic

<400> SEQUENCE: 774
accuguauuc uguuuacaug ucuuuaaaac 30

<210> SEQ ID NO 775
<211> LENGTH: 30
<212> TYPE: RNA
<213> ORGANISM: Artificial Sequence
<220> FEATURE:
<223> OTHER INFORMATION: Synthetic

<400> SEQUENCE: 775
uuaaccugua uucuguuuac augucuuuaa 30

<210> SEQ ID NO 776
<211> LENGTH: 30
<212> TYPE: RNA
<213> ORGANISM: Artificial Sequence
<220> FEATURE:
<223> OTHER INFORMATION: Synthetic

<400> SEQUENCE: 776
auuaaccugu auucuguuua caugucuuua 30

<210> SEQ ID NO 777
<211> LENGTH: 30
<212> TYPE: RNA
<213> ORGANISM: Artificial Sequence
<220> FEATURE:
<223> OTHER INFORMATION: Synthetic

<400> SEQUENCE: 777
uuuauuaacc uguauucugu uuacaugucu 30

<210> SEQ ID NO 778
<211> LENGTH: 30
<212> TYPE: RNA
<213> ORGANISM: Artificial Sequence
<220> FEATURE:
<223> OTHER INFORMATION: Synthetic

<400> SEQUENCE: 778
ucccaucugu auuauuuuuu uucagcaugu 30

<210> SEQ ID NO 779
<211> LENGTH: 30
<212> TYPE: RNA
<213> ORGANISM: Artificial Sequence
<220> FEATURE:
<223> OTHER INFORMATION: Synthetic

<400> SEQUENCE: 779
guaaaauugg agguagcaaa cacuaaggug 30

<210> SEQ ID NO 780
<211> LENGTH: 30
<212> TYPE: RNA
<213> ORGANISM: Artificial Sequence
<220> FEATURE:
<223> OTHER INFORMATION: Synthetic

<400> SEQUENCE: 780
aguaaaauug gagguagcaa acacuaaggu 30

<210> SEQ ID NO 781
<211> LENGTH: 30
<212> TYPE: RNA
<213> ORGANISM: Artificial Sequence
<220> FEATURE:
<223> OTHER INFORMATION: Synthetic

<400> SEQUENCE: 781
gacaacguca uccccuggca ggcuaaagug 30

<210> SEQ ID NO 782
<211> LENGTH: 30
<212> TYPE: RNA
<213> ORGANISM: Artificial Sequence
<220> FEATURE:
<223> OTHER INFORMATION: Synthetic

<400> SEQUENCE: 782
uuauugcauu caguucauau uaaauguaug 30

<210> SEQ ID NO 783
<211> LENGTH: 30
<212> TYPE: RNA
<213> ORGANISM: Artificial Sequence
<220> FEATURE:
<223> OTHER INFORMATION: Synthetic

<400> SEQUENCE: 783
cccaucugua uuauuuuuuu ucagcaugua 30

<210> SEQ ID NO 784
<211> LENGTH: 30
<212> TYPE: RNA
<213> ORGANISM: Artificial Sequence
<220> FEATURE:
<223> OTHER INFORMATION: Synthetic

<400> SEQUENCE: 784
uucagcaugu auuacuugac aaagagacac 30

<210> SEQ ID NO 785

<211> LENGTH: 30
<212> TYPE: RNA
<213> ORGANISM: Artificial Sequence
<220> FEATURE:
<223> OTHER INFORMATION: Synthetic

<400> SEQUENCE: 785
uuuuuuuuca gcauguauua cuugacaaag 30

<210> SEQ ID NO 786
<211> LENGTH: 30
<212> TYPE: RNA
<213> ORGANISM: Artificial Sequence
<220> FEATURE:
<223> OTHER INFORMATION: Synthetic

<400> SEQUENCE: 786
auugcuuuug acuuuucaau gggugucca 30

<210> SEQ ID NO 787
<211> LENGTH: 30
<212> TYPE: RNA
<213> ORGANISM: Artificial Sequence
<220> FEATURE:
<223> OTHER INFORMATION: Synthetic

<400> SEQUENCE: 787
cuuuugacuu uucaaugggu guccuaggaa 30

<210> SEQ ID NO 788
<211> LENGTH: 30
<212> TYPE: RNA
<213> ORGANISM: Artificial Sequence
<220> FEATURE:
<223> OTHER INFORMATION: Synthetic

<400> SEQUENCE: 788
ugacuuuuca augggugucc uaggaaccuu 30

<210> SEQ ID NO 789
<211> LENGTH: 30
<212> TYPE: RNA
<213> ORGANISM: Artificial Sequence
<220> FEATURE:
<223> OTHER INFORMATION: Synthetic

<400> SEQUENCE: 789
gacuuuucaa ugggugucu aggaaccuuu 30

<210> SEQ ID NO 790
<211> LENGTH: 30
<212> TYPE: RNA
<213> ORGANISM: Artificial Sequence
<220> FEATURE:
<223> OTHER INFORMATION: Synthetic

<400> SEQUENCE: 790
acuuuucaau gggugucca ggaaccuuuu 30

<210> SEQ ID NO 791
<211> LENGTH: 30
<212> TYPE: RNA
<213> ORGANISM: Artificial Sequence
<220> FEATURE:
<223> OTHER INFORMATION: Synthetic

<400> SEQUENCE: 791
ucaaugggug uccuaggaac cuuuuagaaa 30

<210> SEQ ID NO 792
<211> LENGTH: 30
<212> TYPE: RNA
<213> ORGANISM: Artificial Sequence
<220> FEATURE:
<223> OTHER INFORMATION: Synthetic

<400> SEQUENCE: 792
caaugggugu ccuaggaacc uuuuagaaag 30

<210> SEQ ID NO 793
<211> LENGTH: 30
<212> TYPE: RNA
<213> ORGANISM: Artificial Sequence
<220> FEATURE:
<223> OTHER INFORMATION: Synthetic

<400> SEQUENCE: 793 aaugggugue cuaggaaccu uuuagaaaga 30

<210> SEQ ID NO 794
<211> LENGTH: 30
<212> TYPE: RNA
<213> ORGANISM: Artificial Sequence
<220> FEATURE:
<223> OTHER INFORMATION: Synthetic

<400> SEQUENCE: 794
uagaaagaaa uggacuuuca uccuggaaau 30

<210> SEQ ID NO 795
<211> LENGTH: 30
<212> TYPE: RNA
<213> ORGANISM: Artificial Sequence
<220> FEATURE:
<223> OTHER INFORMATION: Synthetic

<400> SEQUENCE: 795
agaaagaaau ggacuuucau ccuggaaaua 30

<210> SEQ ID NO 796
<211> LENGTH: 30
<212> TYPE: RNA
<213> ORGANISM: Artificial Sequence
<220> FEATURE:
<223> OTHER INFORMATION: Synthetic

<400> SEQUENCE: 796
gaaagaaaug gacuuucauc cuggaaauau 30

<210> SEQ ID NO 797
<211> LENGTH: 30
<212> TYPE: RNA
<213> ORGANISM: Artificial Sequence
<220> FEATURE:
<223> OTHER INFORMATION: Synthetic

<400> SEQUENCE: 797
cauccuggaa auauauuaac uguuaaaaag 30

<210> SEQ ID NO 798
<211> LENGTH: 30
<212> TYPE: RNA

<213> ORGANISM: Artificial Sequence
<220> FEATURE:
<223> OTHER INFORMATION: Synthetic

<400> SEQUENCE: 798
auccuggaaa uauauuaacu guuaaaaaga 30

<210> SEQ ID NO 799
<211> LENGTH: 30
<212> TYPE: RNA
<213> ORGANISM: Artificial Sequence
<220> FEATURE:
<223> OTHER INFORMATION: Synthetic

<400> SEQUENCE: 799
acuguuaaaa agaaaacauu gaaaaugugu 30

<210> SEQ ID NO 800
<211> LENGTH: 30
<212> TYPE: RNA
<213> ORGANISM: Artificial Sequence
<220> FEATURE:
<223> OTHER INFORMATION: Synthetic

<400> SEQUENCE: 800
aaaagaaaac auugaaaaug uguuuagaca 30

<210> SEQ ID NO 801
<211> LENGTH: 30
<212> TYPE: RNA
<213> ORGANISM: Artificial Sequence
<220> FEATURE:
<223> OTHER INFORMATION: Synthetic

<400> SEQUENCE: 801
cauugcuuuu gacuuuucaa ugggugucc u 30

<210> SEQ ID NO 802
<211> LENGTH: 30
<212> TYPE: RNA
<213> ORGANISM: Artificial Sequence
<220> FEATURE:
<223> OTHER INFORMATION: Synthetic

<400> SEQUENCE: 802
ccaucuguau uauuuuuuuu cagcauguau 30

<210> SEQ ID NO 803
<211> LENGTH: 30
<212> TYPE: RNA
<213> ORGANISM: Artificial Sequence
<220> FEATURE:
<223> OTHER INFORMATION: Synthetic

<400> SEQUENCE: 803
uuucauugcu uuugacuuuu caaugggugu 30

<210> SEQ ID NO 804
<211> LENGTH: 30
<212> TYPE: RNA
<213> ORGANISM: Artificial Sequence
<220> FEATURE:
<223> OTHER INFORMATION: Synthetic

<400> SEQUENCE: 804
uauuucauug cuuuugacuu uucaaugggu 30

<210> SEQ ID NO 805
<211> LENGTH: 30
<212> TYPE: RNA
<213> ORGANISM: Artificial Sequence
<220> FEATURE:
<223> OTHER INFORMATION: Synthetic

<400> SEQUENCE: 805
aaaauguguu uagacaacgu cauccccugg 30

<210> SEQ ID NO 806
<211> LENGTH: 30
<212> TYPE: RNA
<213> ORGANISM: Artificial Sequence
<220> FEATURE:
<223> OTHER INFORMATION: Synthetic

<400> SEQUENCE: 806
uuuuucagca uguauuacuu gacaaagaga 30

<210> SEQ ID NO 807
<211> LENGTH: 30
<212> TYPE: RNA
<213> ORGANISM: Artificial Sequence
<220> FEATURE:
<223> OTHER INFORMATION: Synthetic

<400> SEQUENCE: 807
uuuucagcau guauuacuug acaaagagac 30

<210> SEQ ID NO 808
<211> LENGTH: 30
<212> TYPE: RNA
<213> ORGANISM: Artificial Sequence
<220> FEATURE:
<223> OTHER INFORMATION: Synthetic

<400> SEQUENCE: 808
uuucagcaug uauuacuuga caaagagaca 30

<210> SEQ ID NO 809
<211> LENGTH: 30
<212> TYPE: RNA
<213> ORGANISM: Artificial Sequence
<220> FEATURE:
<223> OTHER INFORMATION: Synthetic

<400> SEQUENCE: 809
ucagcaugua uuacuugaca aagagacacu 30

<210> SEQ ID NO 810
<211> LENGTH: 30
<212> TYPE: RNA
<213> ORGANISM: Artificial Sequence
<220> FEATURE:
<223> OTHER INFORMATION: Synthetic

<400> SEQUENCE: 810
cagcauguau uacuugacaa agagacacug 30

<210> SEQ ID NO 811
<211> LENGTH: 30
<212> TYPE: RNA
<213> ORGANISM: Artificial Sequence
<220> FEATURE:

<223> OTHER INFORMATION: Synthetic

<400> SEQUENCE: 811
agcauguauu acuugacaaa gagacacugu 30

<210> SEQ ID NO 812
<211> LENGTH: 30
<212> TYPE: RNA
<213> ORGANISM: Artificial Sequence
<220> FEATURE:
<223> OTHER INFORMATION: Synthetic

<400> SEQUENCE: 812
cuugacaaag agacacugug cagaggguga 30

<210> SEQ ID NO 813
<211> LENGTH: 30
<212> TYPE: RNA
<213> ORGANISM: Artificial Sequence
<220> FEATURE:
<223> OTHER INFORMATION: Synthetic

<400> SEQUENCE: 813
acaaagagac acugugcaga gggugaccac 30

<210> SEQ ID NO 814
<211> LENGTH: 30
<212> TYPE: RNA
<213> ORGANISM: Artificial Sequence
<220> FEATURE:
<223> OTHER INFORMATION: Synthetic

<400> SEQUENCE: 814
cccacuucaa uacaaagggu gucguucuuu 30

<210> SEQ ID NO 815
<211> LENGTH: 30
<212> TYPE: RNA
<213> ORGANISM: Artificial Sequence
<220> FEATURE:
<223> OTHER INFORMATION: Synthetic

<400> SEQUENCE: 815
aauacaaagg gugucguucu uuuccaacaa 30

<210> SEQ ID NO 816
<211> LENGTH: 30
<212> TYPE: RNA
<213> ORGANISM: Artificial Sequence
<220> FEATURE:
<223> OTHER INFORMATION: Synthetic

<400> SEQUENCE: 816
uuuuccaaca aaauagcaau cccuuuuauu 30

<210> SEQ ID NO 817
<211> LENGTH: 30
<212> TYPE: RNA
<213> ORGANISM: Artificial Sequence
<220> FEATURE:
<223> OTHER INFORMATION: Synthetic

<400> SEQUENCE: 817
uccaacaaaa uagcaauccc uuuuauuuca 30

<210> SEQ ID NO 818
<211> LENGTH: 30
<212> TYPE: RNA
<213> ORGANISM: Artificial Sequence
<220> FEATURE:
<223> OTHER INFORMATION: Synthetic

<400> SEQUENCE: 818
ccaacaaaau agcaaucccu uuuauuucau 30

<210> SEQ ID NO 819
<211> LENGTH: 30
<212> TYPE: RNA
<213> ORGANISM: Artificial Sequence
<220> FEATURE:
<223> OTHER INFORMATION: Synthetic

<400> SEQUENCE: 819
caacaaaaua gcaaucccuu uuauuucauu 30

<210> SEQ ID NO 820
<211> LENGTH: 30
<212> TYPE: RNA
<213> ORGANISM: Artificial Sequence
<220> FEATURE:
<223> OTHER INFORMATION: Synthetic

<400> SEQUENCE: 820
auuucauugc uuuugacuuu ucaaugggug 30

<210> SEQ ID NO 821
<211> LENGTH: 30
<212> TYPE: RNA
<213> ORGANISM: Artificial Sequence
<220> FEATURE:
<223> OTHER INFORMATION: Synthetic

<400> SEQUENCE: 821
aaaguguugg uaaugccuga uucacaacuu 30

<210> SEQ ID NO 822
<211> LENGTH: 30
<212> TYPE: RNA
<213> ORGANISM: Artificial Sequence
<220> FEATURE:
<223> OTHER INFORMATION: Synthetic

<400> SEQUENCE: 822
cucucuaaga aguaacauac auccuaaaac 30

<210> SEQ ID NO 823
<211> LENGTH: 30
<212> TYPE: RNA
<213> ORGANISM: Artificial Sequence
<220> FEATURE:
<223> OTHER INFORMATION: Synthetic

<400> SEQUENCE: 823
acaacuuuga gaagguagca cuggagagaa 30

<210> SEQ ID NO 824
<211> LENGTH: 30
<212> TYPE: RNA
<213> ORGANISM: Artificial Sequence
<220> FEATURE:
<223> OTHER INFORMATION: Synthetic

<400> SEQUENCE: 824
accuuagugu uugcuaccuc caauuuuacu 30

<210> SEQ ID NO 825
<211> LENGTH: 30
<212> TYPE: RNA
<213> ORGANISM: Artificial Sequence
<220> FEATURE:
<223> OTHER INFORMATION: Synthetic

<400> SEQUENCE: 825
guguuugcua ccuccaauuu uacuaaagga 30

<210> SEQ ID NO 826
<211> LENGTH: 30
<212> TYPE: RNA
<213> ORGANISM: Artificial Sequence
<220> FEATURE:
<223> OTHER INFORMATION: Synthetic

<400> SEQUENCE: 826
gcuaccucca auuuuacuaa aggauacagc 30

<210> SEQ ID NO 827
<211> LENGTH: 30
<212> TYPE: RNA
<213> ORGANISM: Artificial Sequence
<220> FEATURE:
<223> OTHER INFORMATION: Synthetic

<400> SEQUENCE: 827
cuaccuccaa uuuuacuaaa ggauacagca 30

<210> SEQ ID NO 828
<211> LENGTH: 30
<212> TYPE: RNA
<213> ORGANISM: Artificial Sequence
<220> FEATURE:
<223> OTHER INFORMATION: Synthetic

<400> SEQUENCE: 828
uacuaaagga uacagcacuu uagccugcca 30

<210> SEQ ID NO 829
<211> LENGTH: 30
<212> TYPE: RNA
<213> ORGANISM: Artificial Sequence
<220> FEATURE:
<223> OTHER INFORMATION: Synthetic

<400> SEQUENCE: 829
acuaaaggau acagcacuuu agccugccag 30

<210> SEQ ID NO 830
<211> LENGTH: 30
<212> TYPE: RNA
<213> ORGANISM: Artificial Sequence
<220> FEATURE:
<223> OTHER INFORMATION: Synthetic

<400> SEQUENCE: 830
cuaaaggaua cagcacuuua gccugccagg 30

<210> SEQ ID NO 831
<211> LENGTH: 30

<212> TYPE: RNA
<213> ORGANISM: Artificial Sequence
<220> FEATURE:
<223> OTHER INFORMATION: Synthetic

<400> SEQUENCE: 831
agccugccag gggaugacgu ugucuaaaca 30

<210> SEQ ID NO 832
<211> LENGTH: 30
<212> TYPE: RNA
<213> ORGANISM: Artificial Sequence
<220> FEATURE:
<223> OTHER INFORMATION: Synthetic

<400> SEQUENCE: 832
gccugccagg ggaugacguu gucuaaacac 30

<210> SEQ ID NO 833
<211> LENGTH: 30
<212> TYPE: RNA
<213> ORGANISM: Artificial Sequence
<220> FEATURE:
<223> OTHER INFORMATION: Synthetic

<400> SEQUENCE: 833
caccuuagug uuugcuaccu ccaauuuuac 30

<210> SEQ ID NO 834
<211> LENGTH: 30
<212> TYPE: RNA
<213> ORGANISM: Artificial Sequence
<220> FEATURE:
<223> OTHER INFORMATION: Synthetic

<400> SEQUENCE: 834
ucuaaacaca uuuucaaugu uuucuuuuua 30

<210> SEQ ID NO 835
<211> LENGTH: 30
<212> TYPE: RNA
<213> ORGANISM: Artificial Sequence
<220> FEATURE:
<223> OTHER INFORMATION: Synthetic

<400> SEQUENCE: 835
caauguuuuc uuuuuaacag uuaauauauu 30

<210> SEQ ID NO 836
<211> LENGTH: 30
<212> TYPE: RNA
<213> ORGANISM: Artificial Sequence
<220> FEATURE:
<223> OTHER INFORMATION: Synthetic

<400> SEQUENCE: 836
aauguuuucu uuuuaacagu uaauauauuu 30

<210> SEQ ID NO 837
<211> LENGTH: 30
<212> TYPE: RNA
<213> ORGANISM: Artificial Sequence
<220> FEATURE:
<223> OTHER INFORMATION: Synthetic

<400> SEQUENCE: 837
ucuuuuuaac aguuaaauaua uuuccaggau 30

<210> SEQ ID NO 838
<211> LENGTH: 30
<212> TYPE: RNA
<213> ORGANISM: Artificial Sequence
<220> FEATURE:
<223> OTHER INFORMATION: Synthetic

<400> SEQUENCE: 838
cuuuuuaaca guuaaauauau uuccaggaug 30

<210> SEQ ID NO 839
<211> LENGTH: 30
<212> TYPE: RNA
<213> ORGANISM: Artificial Sequence
<220> FEATURE:
<223> OTHER INFORMATION: Synthetic

<400> SEQUENCE: 839
uuuuuaacag uuaaauauauu uccaggauga 30

<210> SEQ ID NO 840
<211> LENGTH: 30
<212> TYPE: RNA
<213> ORGANISM: Artificial Sequence
<220> FEATURE:
<223> OTHER INFORMATION: Synthetic

<400> SEQUENCE: 840
uuaacaguua auauauuucc aggaugaaag 30

<210> SEQ ID NO 841
<211> LENGTH: 30
<212> TYPE: RNA
<213> ORGANISM: Artificial Sequence
<220> FEATURE:
<223> OTHER INFORMATION: Synthetic

<400> SEQUENCE: 841
uaacaguuaa uauauuucca ggaugaaagu 30

<210> SEQ ID NO 842
<211> LENGTH: 30
<212> TYPE: RNA
<213> ORGANISM: Artificial Sequence
<220> FEATURE:
<223> OTHER INFORMATION: Synthetic

<400> SEQUENCE: 842
aacaguuaau auauuuccag gaugaaaguc 30

<210> SEQ ID NO 843
<211> LENGTH: 30
<212> TYPE: RNA
<213> ORGANISM: Artificial Sequence
<220> FEATURE:
<223> OTHER INFORMATION: Synthetic

<400> SEQUENCE: 843
acaguuaaua uauuuccagg augaaagucc 30

<210> SEQ ID NO 844
<211> LENGTH: 30
<212> TYPE: RNA
<213> ORGANISM: Artificial Sequence
<220> FEATURE:
<223> OTHER INFORMATION: Synthetic

<400> SEQUENCE: 844
ucaauguuuu cuuuuuaaca guuaauauau 30

<210> SEQ ID NO 845
<211> LENGTH: 30
<212> TYPE: RNA
<213> ORGANISM: Artificial Sequence
<220> FEATURE:
<223> OTHER INFORMATION: Synthetic

<400> SEQUENCE: 845
auauauuucc aggaugaaag uccauuucuu 30

<210> SEQ ID NO 846
<211> LENGTH: 30
<212> TYPE: RNA
<213> ORGANISM: Artificial Sequence
<220> FEATURE:
<223> OTHER INFORMATION: Synthetic

<400> SEQUENCE: 846
ucaccuuagu guuugcuacc uccaauuuua 30

<210> SEQ ID NO 847
<211> LENGTH: 30
<212> TYPE: RNA
<213> ORGANISM: Artificial Sequence
<220> FEATURE:
<223> OTHER INFORMATION: Synthetic

<400> SEQUENCE: 847
auaaacaaug agaucauuau cuuuucaccu 30

<210> SEQ ID NO 848
<211> LENGTH: 30
<212> TYPE: RNA
<213> ORGANISM: Artificial Sequence
<220> FEATURE:
<223> OTHER INFORMATION: Synthetic

<400> SEQUENCE: 848
ucucuaagaa guaacauaca uccuaaaaca 30

<210> SEQ ID NO 849
<211> LENGTH: 30
<212> TYPE: RNA
<213> ORGANISM: Artificial Sequence
<220> FEATURE:
<223> OTHER INFORMATION: Synthetic

<400> SEQUENCE: 849
ggauauauuc agacacuaaa gaugugauug 30

<210> SEQ ID NO 850
<211> LENGTH: 30
<212> TYPE: RNA
<213> ORGANISM: Artificial Sequence
<220> FEATURE:
<223> OTHER INFORMATION: Synthetic

<400> SEQUENCE: 850
gauauauuca gacacuaaag augugauugg 30

<210> SEQ ID NO 851
<211> LENGTH: 30
<212> TYPE: RNA
<213> ORGANISM: Artificial Sequence
<220> FEATURE:
<223> OTHER INFORMATION: Synthetic

<400> SEQUENCE: 851
agacacuaaa gaugugauug gaaaucuaca 30

<210> SEQ ID NO 852
<211> LENGTH: 30
<212> TYPE: RNA
<213> ORGANISM: Artificial Sequence
<220> FEATURE:
<223> OTHER INFORMATION: Synthetic

<400> SEQUENCE: 852
gaaaucuaca uucaaagaag uaucaccaau 30

<210> SEQ ID NO 853
<211> LENGTH: 30
<212> TYPE: RNA
<213> ORGANISM: Artificial Sequence
<220> FEATURE:
<223> OTHER INFORMATION: Synthetic

<400> SEQUENCE: 853
aaagaaguau caccaauuac cgccacccau 30

<210> SEQ ID NO 854
<211> LENGTH: 30
<212> TYPE: RNA
<213> ORGANISM: Artificial Sequence
<220> FEATURE:
<223> OTHER INFORMATION: Synthetic

<400> SEQUENCE: 854
ccgccaccca uuccaauucu cuccagugcu 30

<210> SEQ ID NO 855
<211> LENGTH: 30
<212> TYPE: RNA
<213> ORGANISM: Artificial Sequence
<220> FEATURE:
<223> OTHER INFORMATION: Synthetic

<400> SEQUENCE: 855
caauucucuc cagugcuacc uucucaaagu 30

<210> SEQ ID NO 856
<211> LENGTH: 30
<212> TYPE: RNA
<213> ORGANISM: Artificial Sequence
<220> FEATURE:
<223> OTHER INFORMATION: Synthetic

<400> SEQUENCE: 856
ucuccagugc uaccuucuca aaguugugaa 30

<210> SEQ ID NO 857
<211> LENGTH: 30
<212> TYPE: RNA
<213> ORGANISM: Artificial Sequence
<220> FEATURE:
<223> OTHER INFORMATION: Synthetic

<400> SEQUENCE: 857
ucuuuucacc uuaguguuug cuaccuccaa 30

<210> SEQ ID NO 858
<211> LENGTH: 30
<212> TYPE: RNA
<213> ORGANISM: Artificial Sequence
<220> FEATURE:
<223> OTHER INFORMATION: Synthetic

<400> SEQUENCE: 858
ucaaaguugu gaaucaggca uuaccaacac 30

<210> SEQ ID NO 859
<211> LENGTH: 30
<212> TYPE: RNA
<213> ORGANISM: Artificial Sequence
<220> FEATURE:
<223> OTHER INFORMATION: Synthetic

<400> SEQUENCE: 859
ccaacacuuu gaaccugagc uuacaauuua 30

<210> SEQ ID NO 860
<211> LENGTH: 30
<212> TYPE: RNA
<213> ORGANISM: Artificial Sequence
<220> FEATURE:
<223> OTHER INFORMATION: Synthetic

<400> SEQUENCE: 860
gaaccugagc uuacaauuua agaaccacug 30

<210> SEQ ID NO 861
<211> LENGTH: 30
<212> TYPE: RNA
<213> ORGANISM: Artificial Sequence
<220> FEATURE:
<223> OTHER INFORMATION: Synthetic

<400> SEQUENCE: 861
aaccugagcu uacaauuuaa gaaccacugu 30

<210> SEQ ID NO 862
<211> LENGTH: 30
<212> TYPE: RNA
<213> ORGANISM: Artificial Sequence
<220> FEATURE:
<223> OTHER INFORMATION: Synthetic

<400> SEQUENCE: 862
caauuuaaga accacuguuu uaaagacaug 30

<210> SEQ ID NO 863
<211> LENGTH: 30
<212> TYPE: RNA
<213> ORGANISM: Artificial Sequence
<220> FEATURE:
<223> OTHER INFORMATION: Synthetic

<400> SEQUENCE: 863
aagaaccacu guuuuaaaga cauguaaaca 30

<210> SEQ ID NO 864

<211> LENGTH: 30
<212> TYPE: RNA
<213> ORGANISM: Artificial Sequence
<220> FEATURE:
<223> OTHER INFORMATION: Synthetic

<400> SEQUENCE: 864
agaaccacug uuuuaaagac auguaaacag 30

<210> SEQ ID NO 865
<211> LENGTH: 30
<212> TYPE: RNA
<213> ORGANISM: Artificial Sequence
<220> FEATURE:
<223> OTHER INFORMATION: Synthetic

<400> SEQUENCE: 865
uaaagacaug uaaacagaau acagguuaau 30

<210> SEQ ID NO 866
<211> LENGTH: 30
<212> TYPE: RNA
<213> ORGANISM: Artificial Sequence
<220> FEATURE:
<223> OTHER INFORMATION: Synthetic

<400> SEQUENCE: 866
aaagacaugu aaacagaaua cagguuaaua 30

<210> SEQ ID NO 867
<211> LENGTH: 30
<212> TYPE: RNA
<213> ORGANISM: Artificial Sequence
<220> FEATURE:
<223> OTHER INFORMATION: Synthetic

<400> SEQUENCE: 867
aagacaugua aacagaauac agguuaauaa 30

<210> SEQ ID NO 868
<211> LENGTH: 30
<212> TYPE: RNA
<213> ORGANISM: Artificial Sequence
<220> FEATURE:
<223> OTHER INFORMATION: Synthetic

<400> SEQUENCE: 868
ugaaucaggc auuaccaaca cuuugaaccu 30

<210> SEQ ID NO 869
<211> LENGTH: 30
<212> TYPE: RNA
<213> ORGANISM: Artificial Sequence
<220> FEATURE:
<223> OTHER INFORMATION: Synthetic

<400> SEQUENCE: 869
guaaugccug auucacaacu uugagaaggu 30

<210> SEQ ID NO 870
<211> LENGTH: 30
<212> TYPE: RNA
<213> ORGANISM: Artificial Sequence
<220> FEATURE:
<223> OTHER INFORMATION: Synthetic

<400> SEQUENCE: 870
ccaggaugaa aguccauuuc uuucuaaaag 30

<210> SEQ ID NO 871
<211> LENGTH: 30
<212> TYPE: RNA
<213> ORGANISM: Artificial Sequence
<220> FEATURE:
<223> OTHER INFORMATION: Synthetic

<400> SEQUENCE: 871
auuucucucu aagaaguaac auacauccua 30

<210> SEQ ID NO 872
<211> LENGTH: 30
<212> TYPE: RNA
<213> ORGANISM: Artificial Sequence
<220> FEATURE:
<223> OTHER INFORMATION: Synthetic

<400> SEQUENCE: 872
acauucuggc acccugaaaa aauaaugcau 30

<210> SEQ ID NO 873
<211> LENGTH: 30
<212> TYPE: RNA
<213> ORGANISM: Artificial Sequence
<220> FEATURE:
<223> OTHER INFORMATION: Synthetic

<400> SEQUENCE: 873
uggcacccug aaaaaauaau gcauacauuu 30

<210> SEQ ID NO 874
<211> LENGTH: 30
<212> TYPE: RNA
<213> ORGANISM: Artificial Sequence
<220> FEATURE:
<223> OTHER INFORMATION: Synthetic

<400> SEQUENCE: 874
uuucucucua agaaguaaca uacauccuaa 30

<210> SEQ ID NO 875
<211> LENGTH: 30
<212> TYPE: RNA
<213> ORGANISM: Artificial Sequence
<220> FEATURE:
<223> OTHER INFORMATION: Synthetic

<400> SEQUENCE: 875
ccaaaaaugc uuuauuucuc ucuaagaagu 30

<210> SEQ ID NO 876
<211> LENGTH: 30
<212> TYPE: RNA
<213> ORGANISM: Artificial Sequence
<220> FEATURE:
<223> OTHER INFORMATION: Synthetic

<400> SEQUENCE: 876
uuagagagaa auaaagcauu uuugggaaga 30

<210> SEQ ID NO 877
<211> LENGTH: 30
<212> TYPE: RNA

<213> ORGANISM: Artificial Sequence
<220> FEATURE:
<223> OTHER INFORMATION: Synthetic

<400> SEQUENCE: 877
cuucuuagag agaaauaaag cauuuuuggg 30

<210> SEQ ID NO 878
<211> LENGTH: 30
<212> TYPE: RNA
<213> ORGANISM: Artificial Sequence
<220> FEATURE:
<223> OTHER INFORMATION: Synthetic

<400> SEQUENCE: 878
ggauguaugu uacuucuuag agagaaauaa 30

<210> SEQ ID NO 879
<211> LENGTH: 30
<212> TYPE: RNA
<213> ORGANISM: Artificial Sequence
<220> FEATURE:
<223> OTHER INFORMATION: Synthetic

<400> SEQUENCE: 879
aggauguaug uuacuucuua gagagaaaua 30

<210> SEQ ID NO 880
<211> LENGTH: 30
<212> TYPE: RNA
<213> ORGANISM: Artificial Sequence
<220> FEATURE:
<223> OTHER INFORMATION: Synthetic

<400> SEQUENCE: 880
uaggauguau guuacuucuu agagagaaau 30

<210> SEQ ID NO 881
<211> LENGTH: 30
<212> TYPE: RNA
<213> ORGANISM: Artificial Sequence
<220> FEATURE:
<223> OTHER INFORMATION: Synthetic

<400> SEQUENCE: 881
cacauucugg cacccugaaa aaauaaugca 30

<210> SEQ ID NO 882
<211> LENGTH: 30
<212> TYPE: RNA
<213> ORGANISM: Artificial Sequence
<220> FEATURE:
<223> OTHER INFORMATION: Synthetic

<400> SEQUENCE: 882
gugucugaau auauccaaau guuuuaggau 30

<210> SEQ ID NO 883
<211> LENGTH: 30
<212> TYPE: RNA
<213> ORGANISM: Artificial Sequence
<220> FEATURE:
<223> OTHER INFORMATION: Synthetic

<400> SEQUENCE: 883
caaucacauc uuuagugucu gaauauaucc 30

<210> SEQ ID NO 884
<211> LENGTH: 30
<212> TYPE: RNA
<213> ORGANISM: Artificial Sequence
<220> FEATURE:
<223> OTHER INFORMATION: Synthetic

<400> SEQUENCE: 884
ccaaucacau cuuuaguguc ugaauauauc 30

<210> SEQ ID NO 885
<211> LENGTH: 30
<212> TYPE: RNA
<213> ORGANISM: Artificial Sequence
<220> FEATURE:
<223> OTHER INFORMATION: Synthetic

<400> SEQUENCE: 885
aauguagauu uccaaucaca ucuuuagugu 30

<210> SEQ ID NO 886
<211> LENGTH: 30
<212> TYPE: RNA
<213> ORGANISM: Artificial Sequence
<220> FEATURE:
<223> OTHER INFORMATION: Synthetic

<400> SEQUENCE: 886
gaauguagau uuccaaucac aucuuuagug 30

<210> SEQ ID NO 887
<211> LENGTH: 30
<212> TYPE: RNA
<213> ORGANISM: Artificial Sequence
<220> FEATURE:
<223> OTHER INFORMATION: Synthetic

<400> SEQUENCE: 887
uuugaaugua gauuuccaau cacaucuuua 30

<210> SEQ ID NO 888
<211> LENGTH: 30
<212> TYPE: RNA
<213> ORGANISM: Artificial Sequence
<220> FEATURE:
<223> OTHER INFORMATION: Synthetic

<400> SEQUENCE: 888
gugauacuuc uuugaaugua gauuuccaau 30

<210> SEQ ID NO 889
<211> LENGTH: 30
<212> TYPE: RNA
<213> ORGANISM: Artificial Sequence
<220> FEATURE:
<223> OTHER INFORMATION: Synthetic

<400> SEQUENCE: 889
gaaugggugg cgguaauugg ugauacuucu 30

<210> SEQ ID NO 890
<211> LENGTH: 30
<212> TYPE: RNA
<213> ORGANISM: Artificial Sequence
<220> FEATURE:

<223> OTHER INFORMATION: Synthetic

<400> SEQUENCE: 890
agaagguagc acuggagaga auuggaaugg 30

<210> SEQ ID NO 891
<211> LENGTH: 30
<212> TYPE: RNA
<213> ORGANISM: Artificial Sequence
<220> FEATURE:
<223> OTHER INFORMATION: Synthetic

<400> SEQUENCE: 891
gagaagguag cacuggagag aauuggaaug 30

<210> SEQ ID NO 892
<211> LENGTH: 30
<212> TYPE: RNA
<213> ORGANISM: Artificial Sequence
<220> FEATURE:
<223> OTHER INFORMATION: Synthetic

<400> SEQUENCE: 892
agugucugaa uauauccaaa uguuuuagga 30

<210> SEQ ID NO 893
<211> LENGTH: 30
<212> TYPE: RNA
<213> ORGANISM: Artificial Sequence
<220> FEATURE:
<223> OTHER INFORMATION: Synthetic

<400> SEQUENCE: 893
caggaugaaa guccauuucu uucuaaaagg 30

<210> SEQ ID NO 894
<211> LENGTH: 30
<212> TYPE: RNA
<213> ORGANISM: Artificial Sequence
<220> FEATURE:
<223> OTHER INFORMATION: Synthetic

<400> SEQUENCE: 894
ucgaugacuu ucacauucug gcacccugaa 30

<210> SEQ ID NO 895
<211> LENGTH: 30
<212> TYPE: RNA
<213> ORGANISM: Artificial Sequence
<220> FEATURE:
<223> OTHER INFORMATION: Synthetic

<400> SEQUENCE: 895
ccucaccaau gucuugucga ugacuuucac 30

<210> SEQ ID NO 896
<211> LENGTH: 30
<212> TYPE: RNA
<213> ORGANISM: Artificial Sequence
<220> FEATURE:
<223> OTHER INFORMATION: Synthetic

<400> SEQUENCE: 896
uuucuaaaag guuccuagga cacccauuga 30

<210> SEQ ID NO 897
<211> LENGTH: 30
<212> TYPE: RNA
<213> ORGANISM: Artificial Sequence
<220> FEATURE:
<223> OTHER INFORMATION: Synthetic

<400> SEQUENCE: 897
cuaaaagguu ccuaggacac ccauugaaaa 30

<210> SEQ ID NO 898
<211> LENGTH: 30
<212> TYPE: RNA
<213> ORGANISM: Artificial Sequence
<220> FEATURE:
<223> OTHER INFORMATION: Synthetic

<400> SEQUENCE: 898
uaaaagguuc cuaggacacc cauugaaaag 30

<210> SEQ ID NO 899
<211> LENGTH: 30
<212> TYPE: RNA
<213> ORGANISM: Artificial Sequence
<220> FEATURE:
<223> OTHER INFORMATION: Synthetic

<400> SEQUENCE: 899
cuaggacacc cauugaaaag ucaaaagcaa 30

<210> SEQ ID NO 900
<211> LENGTH: 30
<212> TYPE: RNA
<213> ORGANISM: Artificial Sequence
<220> FEATURE:
<223> OTHER INFORMATION: Synthetic

<400> SEQUENCE: 900
aaaagucaaa agcaaugaaa uaaaagggau 30

<210> SEQ ID NO 901
<211> LENGTH: 30
<212> TYPE: RNA
<213> ORGANISM: Artificial Sequence
<220> FEATURE:
<223> OTHER INFORMATION: Synthetic

<400> SEQUENCE: 901
cuauuuuguu ggaaaagaac gacacccuuu 30

<210> SEQ ID NO 902
<211> LENGTH: 30
<212> TYPE: RNA
<213> ORGANISM: Artificial Sequence
<220> FEATURE:
<223> OTHER INFORMATION: Synthetic

<400> SEQUENCE: 902
uguuggaaaa gaacgacacc cuuuguauug 30

<210> SEQ ID NO 903
<211> LENGTH: 30
<212> TYPE: RNA
<213> ORGANISM: Artificial Sequence
<220> FEATURE:
<223> OTHER INFORMATION: Synthetic

<400> SEQUENCE: 903
guuggaaaag aacgacaccc uuuguauuga 30

<210> SEQ ID NO 904
<211> LENGTH: 30
<212> TYPE: RNA
<213> ORGANISM: Artificial Sequence
<220> FEATURE:
<223> OTHER INFORMATION: Synthetic

<400> SEQUENCE: 904
uuggaaaaga acgacacccu uuguauugaa 30

<210> SEQ ID NO 905
<211> LENGTH: 30
<212> TYPE: RNA
<213> ORGANISM: Artificial Sequence
<220> FEATURE:
<223> OTHER INFORMATION: Synthetic

<400> SEQUENCE: 905
cucaccaaug ucuugucgau gacuuucaca 30

<210> SEQ ID NO 906
<211> LENGTH: 30
<212> TYPE: RNA
<213> ORGANISM: Artificial Sequence
<220> FEATURE:
<223> OTHER INFORMATION: Synthetic

<400> SEQUENCE: 906
gaaaagaacg acacccuuug uauugaagug 30

<210> SEQ ID NO 907
<211> LENGTH: 30
<212> TYPE: RNA
<213> ORGANISM: Artificial Sequence
<220> FEATURE:
<223> OTHER INFORMATION: Synthetic

<400> SEQUENCE: 907
uauugaagug gggaauuaca gacugugguc 30

<210> SEQ ID NO 908
<211> LENGTH: 30
<212> TYPE: RNA
<213> ORGANISM: Artificial Sequence
<220> FEATURE:
<223> OTHER INFORMATION: Synthetic

<400> SEQUENCE: 908
aaguggggaa uuacagacug uggucacccu 30

<210> SEQ ID NO 909
<211> LENGTH: 30
<212> TYPE: RNA
<213> ORGANISM: Artificial Sequence
<220> FEATURE:
<223> OTHER INFORMATION: Synthetic

<400> SEQUENCE: 909
cagacugugg ucacccucug cacagugucu 30

<210> SEQ ID NO 910
<211> LENGTH: 30

<212> TYPE: RNA
<213> ORGANISM: Artificial Sequence
<220> FEATURE:
<223> OTHER INFORMATION: Synthetic

<400> SEQUENCE: 910
gucaaguaau acaugcugaa aaaaaauaau 30

<210> SEQ ID NO 911
<211> LENGTH: 30
<212> TYPE: RNA
<213> ORGANISM: Artificial Sequence
<220> FEATURE:
<223> OTHER INFORMATION: Synthetic

<400> SEQUENCE: 911
ucaaguaaua caugcugaaa aaaaauaaua 30

<210> SEQ ID NO 912
<211> LENGTH: 30
<212> TYPE: RNA
<213> ORGANISM: Artificial Sequence
<220> FEATURE:
<223> OTHER INFORMATION: Synthetic

<400> SEQUENCE: 912
ugcacuguca gaucuuggaa acggccaaag 30

<210> SEQ ID NO 913
<211> LENGTH: 30
<212> TYPE: RNA
<213> ORGANISM: Artificial Sequence
<220> FEATURE:
<223> OTHER INFORMATION: Synthetic

<400> SEQUENCE: 913
gaaacggcca aaggauuuuu ccucaccaau 30

<210> SEQ ID NO 914
<211> LENGTH: 30
<212> TYPE: RNA
<213> ORGANISM: Artificial Sequence
<220> FEATURE:
<223> OTHER INFORMATION: Synthetic

<400> SEQUENCE: 914
uuccucacca augucuuguc gaugacuuuc 30

<210> SEQ ID NO 915
<211> LENGTH: 30
<212> TYPE: RNA
<213> ORGANISM: Artificial Sequence
<220> FEATURE:
<223> OTHER INFORMATION: Synthetic

<400> SEQUENCE: 915
uccucaccaa ugucuugucg augacuuuca 30

<210> SEQ ID NO 916
<211> LENGTH: 30
<212> TYPE: RNA
<213> ORGANISM: Artificial Sequence
<220> FEATURE:
<223> OTHER INFORMATION: Synthetic

<400> SEQUENCE: 916
guauugaagu ggggaauuac agacuguggu 30

<210> SEQ ID NO 917
<211> LENGTH: 30
<212> TYPE: RNA
<213> ORGANISM: Artificial Sequence
<220> FEATURE:
<223> OTHER INFORMATION: Synthetic

<400> SEQUENCE: 917
cuuucuaaaa gguuccuagg acacccauug 30

<210> SEQ ID NO 918
<211> LENGTH: 28
<212> TYPE: RNA
<213> ORGANISM: Artificial Sequence
<220> FEATURE:
<223> OTHER INFORMATION: Synthetic

<400> SEQUENCE: 918
gagagaaaua aagcauuuuu gggaagaa 28

<210> SEQ ID NO 919
<211> LENGTH: 27
<212> TYPE: RNA
<213> ORGANISM: Artificial Sequence
<220> FEATURE:
<223> OTHER INFORMATION: Synthetic

<400> SEQUENCE: 919
aauaugaacu gaaugcaaua auaauca 27

<210> SEQ ID NO 920
<211> LENGTH: 26
<212> TYPE: RNA
<213> ORGANISM: Artificial Sequence
<220> FEATURE:
<223> OTHER INFORMATION: Synthetic

<400> SEQUENCE: 920
auaugaacug aaugcaauaa uaauca 26

<210> SEQ ID NO 921
<211> LENGTH: 3162
<212> TYPE: DNA
<213> ORGANISM: Artificial Sequence
<220> FEATURE:
<223> OTHER INFORMATION: Synthetic

<400> SEQUENCE: 921
atgagcagcg cgatcaaaag ctacaagagc gttctgcgtc cgaacgagcg taagaaccaa 60
ctgctgaaaa gcaccattca gtgcctggaa gacggtagcg cgttcttttt caagatgctg 120
caaggcctgt ttggtggcat caccccggag attgttcgtt tcagcaccga acaggagaaa 180
cagcaacagg atatcgcgct gtggtgcgcg gttaactggt tccgtccggt gagccaagac 240
agcctgaccc acaccattgc gagcgataac ctggtggaga agtttgagga atactatggt 300
ggcaccgcga gcgacgcgat caaacagtac ttcagcgcga gcattggcga aagctactat 360
tggaacgact gccgtcaaca gtactatgat ctgtgccgtg agctgggtgt tgaggtgagc 420
gacctgaccc atgatctgga gatcctgtgc cgtgaaaagt gcctggcggt tgcgaccgag 480
agcaaccaga acaacagcat cattagcgtt ctgtttggca ccggcgaaaa agaggaccgt 540
agcgtgaaac tgcgtatcac caagaaaatt ctggaggcga tcagcaacct gaaagaaatc 600

```
ccgaagaacg ttgcgccgat tcaagagatc attctgaacg tggcgaaagc gaccaaggaa    660
accttccgtc aggtgtatgc gggtaacctg ggtgcgccga gcaccctgga gaaatttatc    720
gcgaaggacg gccaaaaaga gttcgatctg aagaaactgc agaccgacct gaagaaagtt    780
attcgtggta aaagcaagga gcgtgattgg tgctgccagg aagagctgcg tagctacgtg    840
gagcaaaaca ccatccagta tgacctgtgg gcgtggggcg aaatgttcaa caaagcgcac    900
accgcgctga aaatcaagag cacccgtaac tacaactttg cgaagcaacg tctggaacag    960
ttcaaagaga ttcagagcct gaacaacctg ctggttgtga agaagctgaa cgactttttc   1020
gatagcgaat tttcagcgg cgaggaaacc tacaccatct gcgttcacca tctgggtggc   1080
aaggacctga gcaaactgta taaggcgtgg gaggatgatc cggcggaccc ggaaaacgcg   1140
attgtggttc tgtgcgacga tctgaaaaac aactttaaga aagagccgat ccgtaacatt   1200
ctgcgttaca tcttcaccat tcgtcaagaa tgcagcgcgc aggacatcct ggcggcggcg   1260
aagtacaacc aacagctgga tcgttataaa agccaaaagg cgaacccgag cgttctgggt   1320
aaccagggct ttacctggac caacgcggtg atcctgccgg agaaggcgca gcgtaacgac   1380
cgtccgaaca gcctggatct gcgtatttgg ctgtacctga aactgcgtca cccggacggt   1440
cgttggaaga aacaccatat cccgttctac gatacccgtt tcttccaaga aatttatgcg   1500
gcgggcaaca gcccggttga cacctgccag tttcgtaccc cgcgtttcgg ttatcacctg   1560
ccgaaactga ccgatcagac cgcgatccgt gttaacaaga aacatgtgaa agcggcgaag   1620
accgaggcgc gtattcgtct ggcgatccaa cagggcaccc tgccggtgag caacctgaag   1680
atcaccgaaa ttagcgcgac catcaacagc aaaggtcaag tgcgtattcc ggttaagttt   1740
gacgtgggtc gtcaaaaagg caccctgcag atcggtgacc gtttctgcgg ctacgatcaa   1800
aaccagaccg cgagccacgc gtatagcctg tgggaagtgg ttaaagaggg tcaataccat   1860
aaagagctgg gctgctttgt tcgtttcatc agcagcggtg acatcgtgag cattaccgag   1920
aaccgtggca accaatttga tcagctgagc tatgaaggtc tggcgtaccc gcaatatgcg   1980
gactggcgta agaaagcgag caagttcgtg agcctgtggc agatcaccaa gaaaaacaag   2040
aaaaaggaaa tcgtgaccgt tgaagcgaaa gagaagtttg acgcgatctg caagtaccag   2100
ccgcgtctgt ataaattcaa caaggagtac gcgtatctgc tgcgtgatat tgttcgtggc   2160
aaaagcctgg tggaactgca acagattcgt caagagatct ttcgtttcat tgaacaggac   2220
tgcggtgtta cccgtctggg cagcctgagc ctgagcaccc tggaaaccgt gaaagcggtt   2280
aagggtatca tttacagcta ttttagcacc gcgctgaacg cgagcaagaa caacccgatc   2340
agcgacgaac agcgtaaaga gtttgatccg gaactgttcg cgctgctgga aaagctggag   2400
ctgattcgta cccgtaaaaa gaaacaaaaa gtggaacgta tcgcgaacag cctgattcag   2460
acctgcctgg agaacaacat caagttcatt cgtggtgaag gcgacctgag caccaccaac   2520
aacgcgacca agaaaaaggc gaacagccgt agcatggatt ggttggcgcg tggtgttttt   2580
aacaaaatcc gtcaactggc gccgatgcac aacattaccc tgttcggttg cggcagcctg   2640
tacaccagcc accaggaccc gctggtgcat cgtaacccgg ataaagcgat gaagtgccgt   2700
tgggcggcga tcccggttaa ggacattggc gattgggtgc tgcgtaagct gagccaaaac   2760
ctgcgtgcga aaaacatcgg caccggcgag tactatcacc aaggtgttaa agagttcctg   2820
agccattatg aactgcagga cctggaggaa gagctgctga agtggcgtag cgatcgtaaa   2880
agcaacattc cgtgctgggt gctgcagaac cgtctggcgg agaagctggg caacaaagaa   2940
```

```
gcggtggttt acatcccggt tcgtggtggc cgtatttatt ttgcgaccca caaggtggcg   3000

accggtgcgg tgagcatcgt tttcgaccaa aaacaagtgt gggtttgcaa cgcggatcat   3060

gttgcggcgg cgaacatcgc gctgaccgtg aagggtattg gcgaacaaag cagcgacgaa   3120

gagaacccgg atggtagccg tatcaaactg cagctgacca gc                      3162


<210> SEQ ID NO 922
<211> LENGTH: 1054
<212> TYPE: PRT
<213> ORGANISM: Artificial Sequence
<220> FEATURE:
<223> OTHER INFORMATION: Synthetic

<400> SEQUENCE: 922

Met Ser Ser Ala Ile Lys Ser Tyr Lys Ser Val Leu Arg Pro Asn Glu
1               5                   10                  15

Arg Lys Asn Gln Leu Leu Lys Ser Thr Ile Gln Cys Leu Glu Asp Gly
            20                  25                  30

Ser Ala Phe Phe Phe Lys Met Leu Gln Gly Leu Phe Gly Gly Ile Thr
        35                  40                  45

Pro Glu Ile Val Arg Phe Ser Thr Glu Gln Glu Lys Gln Gln Gln Asp
    50                  55                  60

Ile Ala Leu Trp Cys Ala Val Asn Trp Phe Arg Pro Val Ser Gln Asp
65                  70                  75                  80

Ser Leu Thr His Thr Ile Ala Ser Asp Asn Leu Val Glu Lys Phe Glu
                85                  90                  95

Glu Tyr Tyr Gly Gly Thr Ala Ser Asp Ala Ile Lys Gln Tyr Phe Ser
            100                 105                 110

Ala Ser Ile Gly Glu Ser Tyr Tyr Trp Asn Asp Cys Arg Gln Gln Tyr
        115                 120                 125

Tyr Asp Leu Cys Arg Glu Leu Gly Val Glu Val Ser Asp Leu Thr His
    130                 135                 140

Asp Leu Glu Ile Leu Cys Arg Glu Lys Cys Leu Ala Val Ala Thr Glu
145                 150                 155                 160

Ser Asn Gln Asn Asn Ser Ile Ile Ser Val Leu Phe Gly Thr Gly Glu
                165                 170                 175

Lys Glu Asp Arg Ser Val Lys Leu Arg Ile Thr Lys Lys Ile Leu Glu
            180                 185                 190

Ala Ile Ser Asn Leu Lys Glu Ile Pro Lys Asn Val Ala Pro Ile Gln
        195                 200                 205

Glu Ile Ile Leu Asn Val Ala Lys Ala Thr Lys Glu Thr Phe Arg Gln
    210                 215                 220

Val Tyr Ala Gly Asn Leu Gly Ala Pro Ser Thr Leu Glu Lys Phe Ile
225                 230                 235                 240

Ala Lys Asp Gly Gln Lys Glu Phe Asp Leu Lys Lys Leu Gln Thr Asp
                245                 250                 255

Leu Lys Lys Val Ile Arg Gly Lys Ser Lys Glu Arg Asp Trp Cys Cys
            260                 265                 270

Gln Glu Glu Leu Arg Ser Tyr Val Glu Gln Asn Thr Ile Gln Tyr Asp
        275                 280                 285

Leu Trp Ala Trp Gly Glu Met Phe Asn Lys Ala His Thr Ala Leu Lys
    290                 295                 300

Ile Lys Ser Thr Arg Asn Tyr Asn Phe Ala Lys Gln Arg Leu Glu Gln
305                 310                 315                 320

Phe Lys Glu Ile Gln Ser Leu Asn Asn Leu Leu Val Val Lys Lys Leu
```

```
                325                 330                 335

Asn Asp Phe Phe Asp Ser Glu Phe Phe Ser Gly Glu Glu Thr Tyr Thr
            340                 345                 350

Ile Cys Val His His Leu Gly Gly Lys Asp Leu Ser Lys Leu Tyr Lys
        355                 360                 365

Ala Trp Glu Asp Asp Pro Ala Asp Pro Glu Asn Ala Ile Val Val Leu
    370                 375                 380

Cys Asp Asp Leu Lys Asn Asn Phe Lys Lys Glu Pro Ile Arg Asn Ile
385                 390                 395                 400

Leu Arg Tyr Ile Phe Thr Ile Arg Gln Glu Cys Ser Ala Gln Asp Ile
                405                 410                 415

Leu Ala Ala Ala Lys Tyr Asn Gln Gln Leu Asp Arg Tyr Lys Ser Gln
            420                 425                 430

Lys Ala Asn Pro Ser Val Leu Gly Asn Gln Gly Phe Thr Trp Thr Asn
        435                 440                 445

Ala Val Ile Leu Pro Glu Lys Ala Gln Arg Asn Asp Arg Pro Asn Ser
    450                 455                 460

Leu Asp Leu Arg Ile Trp Leu Tyr Leu Lys Leu Arg His Pro Asp Gly
465                 470                 475                 480

Arg Trp Lys Lys His His Ile Pro Phe Tyr Asp Thr Arg Phe Phe Gln
                485                 490                 495

Glu Ile Tyr Ala Ala Gly Asn Ser Pro Val Asp Thr Cys Gln Phe Arg
            500                 505                 510

Thr Pro Arg Phe Gly Tyr His Leu Pro Lys Leu Thr Asp Gln Thr Ala
        515                 520                 525

Ile Arg Val Asn Lys Lys His Val Lys Ala Ala Lys Thr Glu Ala Arg
    530                 535                 540

Ile Arg Leu Ala Ile Gln Gln Gly Thr Leu Pro Val Ser Asn Leu Lys
545                 550                 555                 560

Ile Thr Glu Ile Ser Ala Thr Ile Asn Ser Lys Gly Gln Val Arg Ile
                565                 570                 575

Pro Val Lys Phe Asp Val Gly Arg Gln Lys Gly Thr Leu Gln Ile Gly
            580                 585                 590

Asp Arg Phe Cys Gly Tyr Asp Gln Asn Gln Thr Ala Ser His Ala Tyr
        595                 600                 605

Ser Leu Trp Glu Val Val Lys Glu Gly Gln Tyr His Lys Glu Leu Gly
    610                 615                 620

Cys Phe Val Arg Phe Ile Ser Ser Gly Asp Ile Val Ser Ile Thr Glu
625                 630                 635                 640

Asn Arg Gly Asn Gln Phe Asp Gln Leu Ser Tyr Glu Gly Leu Ala Tyr
                645                 650                 655

Pro Gln Tyr Ala Asp Trp Arg Lys Lys Ala Ser Lys Phe Val Ser Leu
            660                 665                 670

Trp Gln Ile Thr Lys Lys Asn Lys Lys Lys Glu Ile Val Thr Val Glu
        675                 680                 685

Ala Lys Glu Lys Phe Asp Ala Ile Cys Lys Tyr Gln Pro Arg Leu Tyr
    690                 695                 700

Lys Phe Asn Lys Glu Tyr Ala Tyr Leu Leu Arg Asp Ile Val Arg Gly
705                 710                 715                 720

Lys Ser Leu Val Glu Leu Gln Gln Ile Arg Gln Glu Ile Phe Arg Phe
                725                 730                 735

Ile Glu Gln Asp Cys Gly Val Thr Arg Leu Gly Ser Leu Ser Leu Ser
            740                 745                 750
```

Thr Leu Glu Thr Val Lys Ala Val Lys Gly Ile Ile Tyr Ser Tyr Phe
755 760 765

Ser Thr Ala Leu Asn Ala Ser Lys Asn Asn Pro Ile Ser Asp Glu Gln
770 775 780

Arg Lys Glu Phe Asp Pro Glu Leu Phe Ala Leu Leu Glu Lys Leu Glu
785 790 795 800

Leu Ile Arg Thr Arg Lys Lys Lys Gln Lys Val Glu Arg Ile Ala Asn
805 810 815

Ser Leu Ile Gln Thr Cys Leu Glu Asn Asn Ile Lys Phe Ile Arg Gly
820 825 830

Glu Gly Asp Leu Ser Thr Thr Asn Asn Ala Thr Lys Lys Lys Ala Asn
835 840 845

Ser Arg Ser Met Asp Trp Leu Ala Arg Gly Val Phe Asn Lys Ile Arg
850 855 860

Gln Leu Ala Pro Met His Asn Ile Thr Leu Phe Gly Cys Gly Ser Leu
865 870 875 880

Tyr Thr Ser His Gln Asp Pro Leu Val His Arg Asn Pro Asp Lys Ala
885 890 895

Met Lys Cys Arg Trp Ala Ala Ile Pro Val Lys Asp Ile Gly Asp Trp
900 905 910

Val Leu Arg Lys Leu Ser Gln Asn Leu Arg Ala Lys Asn Ile Gly Thr
915 920 925

Gly Glu Tyr Tyr His Gln Gly Val Lys Glu Phe Leu Ser His Tyr Glu
930 935 940

Leu Gln Asp Leu Glu Glu Glu Leu Leu Lys Trp Arg Ser Asp Arg Lys
945 950 955 960

Ser Asn Ile Pro Cys Trp Val Leu Gln Asn Arg Leu Ala Glu Lys Leu
965 970 975

Gly Asn Lys Glu Ala Val Val Tyr Ile Pro Val Arg Gly Gly Arg Ile
980 985 990

Tyr Phe Ala Thr His Lys Val Ala Thr Gly Ala Val Ser Ile Val Phe
995 1000 1005

Asp Gln Lys Gln Val Trp Val Cys Asn Ala Asp His Val Ala Ala
1010 1015 1020

Ala Asn Ile Ala Leu Thr Val Lys Gly Ile Gly Glu Gln Ser Ser
1025 1030 1035

Asp Glu Glu Asn Pro Asp Gly Ser Arg Ile Lys Leu Gln Leu Thr
1040 1045 1050

Ser

<210> SEQ ID NO 923
<211> LENGTH: 1054
<212> TYPE: PRT
<213> ORGANISM: Artificial Sequence
<220> FEATURE:
<223> OTHER INFORMATION: Synthetic

<400> SEQUENCE: 923

Met Ser Ser Ala Ile Lys Ser Tyr Lys Ser Val Leu Arg Pro Asn Glu
1 5 10 15

Arg Lys Asn Gln Leu Leu Lys Ser Thr Ile Gln Cys Leu Glu Asp Gly
20 25 30

Ser Ala Phe Phe Phe Lys Met Leu Gln Gly Leu Phe Gly Gly Ile Thr
35 40 45

```
Pro Glu Ile Val Arg Phe Ser Thr Glu Gln Glu Lys Gln Gln Gln Asp
    50                  55                  60

Ile Ala Leu Trp Cys Ala Val Asn Trp Phe Arg Pro Val Ser Gln Asp
65                  70                  75                  80

Ser Leu Thr His Thr Ile Ala Ser Asp Asn Leu Val Glu Lys Phe Glu
                85                  90                  95

Glu Tyr Tyr Gly Gly Thr Ala Ser Asp Ala Ile Lys Gln Tyr Phe Ser
            100                 105                 110

Ala Ser Ile Gly Glu Ser Tyr Tyr Trp Asn Asp Cys Arg Gln Gln Tyr
        115                 120                 125

Tyr Asp Leu Cys Arg Glu Leu Gly Val Glu Val Ser Asp Leu Thr His
    130                 135                 140

Asp Leu Glu Ile Leu Cys Arg Glu Lys Cys Leu Ala Val Ala Thr Glu
145                 150                 155                 160

Ser Asn Gln Asn Asn Ser Ile Ile Ser Val Leu Phe Gly Thr Gly Glu
                165                 170                 175

Lys Glu Asp Arg Ser Val Lys Leu Arg Ile Thr Lys Lys Ile Leu Glu
            180                 185                 190

Ala Ile Ser Asn Leu Lys Glu Ile Pro Lys Asn Val Ala Pro Ile Gln
        195                 200                 205

Glu Ile Ile Leu Asn Val Ala Lys Ala Thr Lys Glu Thr Phe Arg Gln
    210                 215                 220

Val Tyr Ala Gly Asn Leu Gly Ala Pro Ser Thr Leu Glu Lys Phe Ile
225                 230                 235                 240

Ala Lys Asp Gly Gln Lys Glu Phe Asp Leu Lys Lys Leu Gln Thr Asp
                245                 250                 255

Leu Lys Lys Val Ile Arg Gly Lys Ser Lys Glu Arg Asp Trp Cys Cys
            260                 265                 270

Gln Glu Glu Leu Arg Ser Tyr Val Glu Gln Asn Thr Ile Gln Tyr Asp
        275                 280                 285

Leu Trp Ala Trp Gly Glu Met Phe Asn Lys Ala His Thr Ala Leu Lys
    290                 295                 300

Ile Lys Ser Thr Arg Asn Tyr Asn Phe Ala Lys Gln Arg Leu Glu Gln
305                 310                 315                 320

Phe Lys Glu Ile Gln Ser Leu Asn Asn Leu Leu Val Val Lys Lys Leu
                325                 330                 335

Asn Asp Phe Phe Asp Ser Glu Phe Phe Ser Gly Glu Glu Thr Tyr Thr
            340                 345                 350

Ile Cys Val His His Leu Gly Gly Lys Asp Leu Ser Lys Leu Tyr Lys
        355                 360                 365

Ala Trp Glu Asp Asp Pro Ala Asp Pro Glu Asn Ala Ile Val Val Leu
    370                 375                 380

Cys Asp Asp Leu Lys Asn Asn Phe Lys Lys Glu Pro Ile Arg Asn Ile
385                 390                 395                 400

Leu Arg Tyr Ile Phe Thr Ile Arg Gln Glu Cys Ser Ala Gln Asp Ile
                405                 410                 415

Leu Ala Ala Ala Lys Tyr Asn Gln Gln Leu Asp Arg Tyr Lys Ser Gln
            420                 425                 430

Lys Ala Asn Pro Ser Val Leu Gly Asn Gln Gly Phe Thr Trp Thr Asn
        435                 440                 445

Ala Val Ile Leu Pro Glu Lys Ala Gln Arg Asn Asp Arg Pro Asn Ser
    450                 455                 460

Leu Asp Leu Arg Ile Trp Leu Tyr Leu Lys Leu Arg His Pro Asp Gly
```

```
465                 470                 475                 480

Arg Trp Lys Lys His His Ile Pro Phe Tyr Asp Thr Arg Phe Phe Gln
                485                 490                 495

Glu Ile Tyr Ala Ala Gly Asn Ser Pro Val Asp Thr Cys Gln Phe Arg
            500                 505                 510

Thr Pro Arg Phe Gly Tyr His Leu Pro Lys Leu Thr Asp Gln Thr Ala
        515                 520                 525

Ile Arg Val Asn Lys Lys His Val Lys Ala Ala Lys Thr Glu Ala Arg
    530                 535                 540

Ile Arg Leu Ala Ile Gln Gln Gly Thr Leu Pro Val Ser Asn Leu Lys
545                 550                 555                 560

Ile Thr Glu Ile Ser Ala Thr Ile Asn Ser Lys Gly Gln Val Arg Ile
                565                 570                 575

Pro Val Lys Phe Arg Val Gly Arg Gln Lys Gly Thr Leu Gln Ile Gly
            580                 585                 590

Asp Arg Phe Cys Gly Tyr Asp Gln Asn Gln Thr Ala Ser His Ala Tyr
        595                 600                 605

Ser Leu Trp Glu Val Val Lys Glu Gly Gln Tyr His Lys Glu Leu Gly
    610                 615                 620

Cys Phe Val Arg Phe Ile Ser Ser Gly Asp Ile Val Ser Ile Thr Glu
625                 630                 635                 640

Asn Arg Gly Asn Gln Phe Asp Gln Leu Ser Tyr Glu Gly Leu Ala Tyr
                645                 650                 655

Pro Gln Tyr Ala Asp Trp Arg Lys Lys Ala Ser Lys Phe Val Ser Leu
            660                 665                 670

Trp Gln Ile Thr Lys Lys Asn Lys Lys Lys Glu Ile Val Thr Val Glu
        675                 680                 685

Ala Lys Glu Lys Phe Asp Ala Ile Cys Lys Tyr Gln Pro Arg Leu Tyr
    690                 695                 700

Lys Phe Asn Lys Glu Tyr Ala Tyr Leu Leu Arg Asp Ile Val Arg Gly
705                 710                 715                 720

Lys Ser Leu Val Glu Leu Gln Gln Ile Arg Gln Glu Ile Phe Arg Phe
                725                 730                 735

Ile Glu Gln Asp Cys Gly Val Thr Arg Leu Gly Ser Leu Ser Leu Ser
            740                 745                 750

Thr Leu Glu Thr Val Lys Ala Val Lys Gly Ile Ile Tyr Ser Tyr Phe
        755                 760                 765

Ser Thr Ala Leu Asn Ala Ser Lys Asn Asn Pro Ile Ser Asp Glu Gln
    770                 775                 780

Arg Lys Glu Phe Asp Pro Glu Leu Phe Ala Leu Leu Glu Lys Leu Glu
785                 790                 795                 800

Leu Ile Arg Thr Arg Lys Lys Lys Gln Lys Val Glu Arg Ile Ala Asn
                805                 810                 815

Ser Leu Ile Gln Thr Cys Leu Glu Asn Asn Ile Lys Phe Ile Arg Gly
            820                 825                 830

Glu Gly Asp Leu Ser Thr Thr Asn Asn Ala Thr Lys Lys Lys Ala Asn
        835                 840                 845

Ser Arg Ser Met Asp Trp Leu Ala Arg Gly Val Phe Asn Lys Ile Arg
    850                 855                 860

Gln Leu Ala Pro Met His Asn Ile Thr Leu Phe Gly Cys Gly Ser Leu
865                 870                 875                 880

Tyr Thr Ser His Gln Asp Pro Leu Val His Arg Asn Pro Asp Lys Ala
                885                 890                 895
```

Met Lys Cys Arg Trp Ala Ala Ile Pro Val Lys Asp Ile Gly Arg Trp
900 905 910

Val Leu Arg Lys Leu Ser Gln Asn Leu Arg Ala Lys Asn Arg Gly Thr
915 920 925

Gly Glu Tyr Tyr His Gln Gly Val Lys Glu Phe Leu Ser His Tyr Glu
930 935 940

Leu Gln Asp Leu Glu Glu Glu Leu Leu Lys Trp Arg Ser Asp Arg Lys
945 950 955 960

Ser Asn Ile Pro Cys Trp Val Leu Gln Asn Arg Leu Ala Glu Lys Leu
965 970 975

Gly Asn Lys Glu Ala Val Val Tyr Ile Pro Val Arg Gly Gly Arg Ile
980 985 990

Tyr Phe Ala Thr His Lys Val Ala Thr Gly Ala Val Ser Ile Val Phe
995 1000 1005

Asp Gln Lys Gln Val Trp Val Cys Asn Ala Asp His Val Ala Ala
1010 1015 1020

Ala Asn Ile Ala Leu Thr Gly Lys Gly Ile Gly Glu Gln Ser Ser
1025 1030 1035

Asp Glu Glu Asn Pro Asp Gly Ser Arg Ile Lys Leu Gln Leu Thr
1040 1045 1050

Ser

<210> SEQ ID NO 924
<211> LENGTH: 1054
<212> TYPE: PRT
<213> ORGANISM: Artificial Sequence
<220> FEATURE:
<223> OTHER INFORMATION: Synthetic

<400> SEQUENCE: 924

Met Ser Ser Ala Ile Lys Ser Tyr Lys Ser Val Leu Arg Pro Asn Glu
1 5 10 15

Arg Lys Asn Gln Leu Leu Lys Ser Thr Ile Gln Cys Leu Glu Asp Gly
20 25 30

Ser Ala Phe Phe Phe Lys Met Leu Gln Gly Leu Phe Gly Gly Ile Thr
35 40 45

Pro Glu Ile Val Arg Phe Ser Thr Glu Gln Glu Lys Gln Gln Gln Asp
50 55 60

Ile Ala Leu Trp Cys Ala Val Asn Trp Phe Arg Pro Val Ser Gln Asp
65 70 75 80

Ser Leu Thr His Thr Ile Ala Ser Asp Asn Leu Val Glu Lys Phe Glu
85 90 95

Glu Tyr Tyr Gly Gly Thr Ala Ser Asp Ala Ile Lys Gln Tyr Phe Ser
100 105 110

Ala Ser Ile Gly Glu Ser Tyr Tyr Trp Asn Asp Cys Arg Gln Gln Tyr
115 120 125

Tyr Asp Leu Cys Arg Glu Leu Gly Val Glu Val Ser Asp Leu Thr His
130 135 140

Asp Leu Glu Ile Leu Cys Arg Glu Lys Cys Leu Ala Val Ala Thr Glu
145 150 155 160

Ser Asn Gln Asn Asn Ser Ile Ile Ser Val Leu Phe Gly Thr Gly Glu
165 170 175

Lys Glu Asp Arg Ser Val Lys Leu Arg Ile Thr Lys Lys Ile Leu Glu
180 185 190

```
Ala Ile Ser Asn Leu Lys Glu Ile Pro Lys Asn Val Ala Pro Ile Gln
        195                 200                 205

Glu Ile Ile Leu Asn Val Ala Lys Ala Thr Lys Glu Thr Phe Arg Gln
    210                 215                 220

Val Tyr Ala Gly Asn Leu Gly Ala Pro Ser Thr Leu Glu Lys Phe Ile
225                 230                 235                 240

Ala Lys Asp Gly Gln Lys Glu Phe Asp Leu Lys Lys Leu Gln Thr Asp
                245                 250                 255

Leu Lys Lys Val Ile Arg Gly Lys Ser Lys Glu Arg Asp Trp Cys Cys
            260                 265                 270

Gln Glu Glu Leu Arg Ser Tyr Val Glu Gln Asn Thr Ile Gln Tyr Asp
        275                 280                 285

Leu Trp Ala Trp Gly Glu Met Phe Asn Lys Ala His Thr Ala Leu Lys
    290                 295                 300

Ile Lys Ser Thr Arg Asn Tyr Asn Phe Ala Lys Gln Arg Leu Glu Gln
305                 310                 315                 320

Phe Lys Glu Ile Gln Ser Leu Asn Asn Leu Leu Val Val Lys Lys Leu
                325                 330                 335

Asn Asp Phe Phe Asp Ser Glu Phe Phe Ser Gly Glu Glu Thr Tyr Thr
            340                 345                 350

Ile Cys Val His His Leu Gly Gly Lys Asp Leu Ser Lys Leu Tyr Lys
        355                 360                 365

Ala Trp Glu Asp Asp Pro Ala Asp Pro Glu Asn Ala Ile Val Val Leu
    370                 375                 380

Cys Asp Asp Leu Lys Asn Asn Phe Lys Lys Glu Pro Ile Arg Asn Ile
385                 390                 395                 400

Leu Arg Tyr Ile Phe Thr Ile Arg Gln Glu Cys Ser Ala Gln Asp Ile
                405                 410                 415

Leu Ala Ala Ala Lys Tyr Asn Gln Gln Leu Asp Arg Tyr Lys Ser Gln
            420                 425                 430

Lys Ala Asn Pro Ser Val Leu Gly Asn Gln Gly Phe Thr Trp Thr Asn
        435                 440                 445

Ala Val Ile Leu Pro Glu Lys Ala Gln Arg Asn Asp Arg Pro Asn Ser
    450                 455                 460

Leu Asp Leu Arg Ile Trp Leu Tyr Leu Lys Leu Arg His Pro Asp Gly
465                 470                 475                 480

Arg Trp Lys Lys His His Ile Pro Phe Tyr Asp Thr Arg Phe Phe Gln
                485                 490                 495

Glu Ile Tyr Ala Ala Gly Asn Ser Pro Val Asp Thr Cys Gln Phe Arg
            500                 505                 510

Thr Pro Arg Phe Gly Tyr His Leu Pro Lys Leu Thr Asp Gln Thr Ala
        515                 520                 525

Ile Arg Val Asn Lys Lys His Val Lys Ala Ala Lys Thr Glu Ala Arg
    530                 535                 540

Ile Arg Leu Ala Ile Gln Gln Gly Thr Leu Pro Val Ser Asn Leu Lys
545                 550                 555                 560

Ile Thr Glu Ile Ser Ala Thr Ile Asn Ser Lys Gly Gln Val Arg Ile
                565                 570                 575

Pro Val Lys Phe Arg Val Gly Arg Gln Lys Gly Thr Leu Gln Ile Gly
            580                 585                 590

Asp Arg Phe Cys Gly Tyr Asp Gln Asn Gln Thr Ala Ser His Ala Tyr
        595                 600                 605

Ser Leu Trp Glu Val Val Lys Glu Gly Gln Tyr His Lys Glu Leu Gly
```

```
    610                 615                 620

Cys Phe Val Arg Phe Ile Ser Ser Gly Asp Ile Val Ser Ile Thr Glu
625                 630                 635                 640

Asn Arg Gly Asn Gln Phe Asp Gln Leu Ser Tyr Glu Gly Leu Ala Tyr
                645                 650                 655

Pro Gln Tyr Ala Asp Trp Arg Lys Lys Ala Ser Lys Phe Val Ser Leu
            660                 665                 670

Trp Gln Ile Thr Lys Lys Asn Lys Lys Lys Glu Ile Val Thr Val Glu
        675                 680                 685

Ala Lys Glu Lys Phe Asp Ala Ile Cys Lys Tyr Gln Pro Arg Leu Tyr
    690                 695                 700

Lys Phe Asn Lys Glu Tyr Ala Tyr Leu Leu Arg Asp Ile Val Arg Gly
705                 710                 715                 720

Lys Ser Leu Val Glu Leu Gln Gln Ile Arg Gln Glu Ile Phe Arg Phe
                725                 730                 735

Ile Glu Gln Asp Cys Gly Val Thr Arg Leu Gly Ser Leu Ser Leu Ser
            740                 745                 750

Thr Leu Glu Thr Val Lys Ala Val Lys Gly Ile Ile Tyr Ser Tyr Phe
        755                 760                 765

Ser Thr Ala Leu Asn Ala Ser Lys Asn Asn Pro Ile Ser Asp Glu Gln
    770                 775                 780

Arg Lys Glu Phe Asp Pro Glu Leu Phe Ala Leu Leu Glu Lys Leu Glu
785                 790                 795                 800

Leu Ile Arg Thr Arg Lys Lys Lys Gln Lys Val Glu Arg Ile Ala Asn
                805                 810                 815

Ser Leu Ile Gln Thr Cys Leu Glu Asn Asn Ile Lys Phe Ile Arg Gly
            820                 825                 830

Glu Gly Asp Leu Ser Thr Thr Asn Asn Ala Thr Lys Lys Lys Ala Asn
        835                 840                 845

Ser Arg Ser Met Asp Trp Leu Ala Arg Gly Val Phe Asn Lys Ile Arg
    850                 855                 860

Gln Leu Ala Pro Met His Asn Ile Thr Leu Phe Gly Cys Gly Ser Leu
865                 870                 875                 880

Tyr Thr Ser His Gln Asp Pro Leu Val His Arg Asn Pro Asp Lys Ala
                885                 890                 895

Met Lys Cys Arg Trp Ala Ala Ile Pro Val Lys Asp Ile Gly Asp Trp
            900                 905                 910

Val Leu Arg Lys Leu Ser Gln Asn Leu Arg Ala Lys Asn Arg Gly Thr
        915                 920                 925

Gly Glu Tyr Tyr His Gln Gly Val Lys Glu Phe Leu Ser His Tyr Glu
    930                 935                 940

Leu Gln Asp Leu Glu Glu Glu Leu Leu Lys Trp Arg Ser Asp Arg Lys
945                 950                 955                 960

Ser Asn Ile Pro Cys Trp Val Leu Gln Asn Arg Leu Ala Glu Lys Leu
                965                 970                 975

Gly Asn Lys Glu Ala Val Val Tyr Ile Pro Val Arg Gly Gly Arg Ile
            980                 985                 990

Tyr Phe Ala Thr His Lys Val Ala  Thr Gly Ala Val Ser  Ile Val Phe
        995                 1000                1005

Asp Gln  Lys Gln Val Trp Val  Cys Asn Ala Asp His  Val Ala Ala
    1010                1015                1020

Ala Asn  Ile Ala Leu Thr Gly  Lys Gly Ile Gly Glu  Gln Ser Ser
    1025                1030                1035
```

Asp Glu Glu Asn Pro Asp Gly Ser Arg Ile Lys Leu Gln Leu Thr
1040 1045 1050

Ser

<210> SEQ ID NO 925
<211> LENGTH: 1054
<212> TYPE: PRT
<213> ORGANISM: Artificial Sequence
<220> FEATURE:
<223> OTHER INFORMATION: Synthetic

<400> SEQUENCE: 925

Met Ser Ser Ala Ile Lys Ser Tyr Lys Ser Val Leu Arg Pro Asn Glu
1 5 10 15

Arg Lys Asn Gln Leu Leu Lys Ser Thr Ile Gln Cys Leu Glu Asp Gly
20 25 30

Ser Ala Phe Phe Phe Lys Met Leu Gln Gly Leu Phe Gly Gly Ile Thr
35 40 45

Pro Glu Ile Val Arg Phe Ser Thr Glu Gln Glu Lys Gln Gln Gln Asp
50 55 60

Ile Ala Leu Trp Cys Ala Val Asn Trp Phe Arg Pro Val Ser Gln Asp
65 70 75 80

Ser Leu Thr His Thr Ile Ala Ser Asp Asn Leu Val Glu Lys Phe Glu
85 90 95

Glu Tyr Tyr Gly Gly Thr Ala Ser Asp Ala Ile Lys Gln Tyr Phe Ser
100 105 110

Ala Ser Ile Gly Glu Ser Tyr Tyr Trp Asn Asp Cys Arg Gln Gln Tyr
115 120 125

Tyr Asp Leu Cys Arg Glu Leu Gly Val Glu Val Ser Asp Leu Thr His
130 135 140

Asp Leu Glu Ile Leu Cys Arg Glu Lys Cys Leu Ala Val Ala Thr Glu
145 150 155 160

Ser Asn Gln Asn Asn Ser Ile Ile Ser Val Leu Phe Gly Thr Gly Glu
165 170 175

Lys Glu Asp Arg Ser Val Lys Leu Arg Ile Thr Lys Lys Ile Leu Glu
180 185 190

Ala Ile Ser Asn Leu Lys Glu Ile Pro Lys Asn Val Ala Pro Ile Gln
195 200 205

Glu Ile Ile Leu Asn Val Ala Lys Ala Thr Lys Glu Thr Phe Arg Gln
210 215 220

Val Tyr Ala Gly Asn Leu Gly Ala Pro Ser Thr Leu Glu Lys Phe Ile
225 230 235 240

Ala Lys Asp Gly Gln Lys Glu Phe Asp Leu Lys Lys Leu Gln Thr Asp
245 250 255

Leu Lys Lys Val Ile Arg Gly Lys Ser Lys Glu Arg Asp Trp Cys Cys
260 265 270

Gln Glu Glu Leu Arg Ser Tyr Val Glu Gln Asn Thr Ile Gln Tyr Asp
275 280 285

Leu Trp Ala Trp Gly Glu Met Phe Asn Lys Ala His Thr Ala Leu Lys
290 295 300

Ile Lys Ser Thr Arg Asn Tyr Asn Phe Ala Lys Gln Arg Leu Glu Gln
305 310 315 320

Phe Lys Glu Ile Gln Ser Leu Asn Asn Leu Leu Val Val Lys Lys Leu
325 330 335

```
Asn Asp Phe Phe Asp Ser Glu Phe Phe Ser Gly Glu Glu Thr Tyr Thr
            340                 345                 350

Ile Cys Val His His Leu Gly Gly Lys Asp Leu Ser Lys Leu Tyr Lys
        355                 360                 365

Ala Trp Glu Asp Asp Pro Ala Asp Pro Glu Asn Ala Ile Val Val Leu
    370                 375                 380

Cys Asp Asp Leu Lys Asn Asn Phe Lys Lys Glu Pro Ile Arg Asn Ile
385                 390                 395                 400

Leu Arg Tyr Ile Phe Thr Ile Arg Gln Glu Cys Ser Ala Gln Asp Ile
                405                 410                 415

Leu Ala Ala Ala Lys Tyr Asn Gln Gln Leu Asp Arg Tyr Lys Ser Gln
            420                 425                 430

Lys Ala Asn Pro Ser Val Leu Gly Asn Gln Gly Phe Thr Trp Thr Asn
        435                 440                 445

Ala Val Ile Leu Pro Glu Lys Ala Gln Arg Asn Asp Arg Pro Asn Ser
    450                 455                 460

Leu Asp Leu Arg Ile Trp Leu Tyr Leu Lys Leu Arg His Pro Asp Gly
465                 470                 475                 480

Arg Trp Lys Lys His His Ile Pro Phe Tyr Asp Thr Arg Phe Phe Gln
                485                 490                 495

Glu Ile Tyr Ala Ala Gly Asn Ser Pro Val Asp Thr Cys Gln Phe Arg
            500                 505                 510

Thr Pro Arg Phe Gly Tyr His Leu Pro Lys Leu Thr Asp Gln Thr Ala
        515                 520                 525

Ile Arg Val Asn Lys Lys His Val Lys Ala Ala Lys Thr Glu Ala Arg
    530                 535                 540

Ile Arg Leu Ala Ile Gln Gln Gly Thr Leu Pro Val Ser Asn Leu Lys
545                 550                 555                 560

Ile Thr Glu Ile Ser Ala Thr Ile Asn Ser Lys Gly Gln Val Arg Ile
                565                 570                 575

Pro Val Lys Phe Arg Val Gly Arg Gln Lys Gly Thr Leu Gln Ile Gly
            580                 585                 590

Asp Arg Phe Cys Gly Tyr Asp Gln Asn Gln Thr Ala Ser His Ala Tyr
        595                 600                 605

Ser Leu Trp Glu Val Val Lys Glu Gly Gln Tyr His Lys Glu Leu Gly
    610                 615                 620

Cys Phe Val Arg Phe Ile Ser Ser Gly Asp Ile Val Ser Ile Thr Glu
625                 630                 635                 640

Asn Arg Gly Asn Gln Phe Asp Gln Leu Ser Tyr Glu Gly Leu Ala Tyr
                645                 650                 655

Pro Gln Tyr Ala Asp Trp Arg Lys Lys Ala Ser Lys Phe Val Ser Leu
            660                 665                 670

Trp Gln Ile Thr Lys Lys Asn Lys Lys Lys Glu Ile Val Thr Val Glu
        675                 680                 685

Ala Lys Glu Lys Phe Asp Ala Ile Cys Lys Tyr Gln Pro Arg Leu Tyr
    690                 695                 700

Lys Phe Asn Lys Glu Tyr Ala Tyr Leu Leu Arg Asp Ile Val Arg Gly
705                 710                 715                 720

Lys Ser Leu Val Glu Leu Gln Gln Ile Arg Gln Glu Ile Phe Arg Phe
                725                 730                 735

Ile Glu Gln Asp Cys Gly Val Thr Arg Leu Gly Ser Leu Ser Leu Ser
            740                 745                 750

Thr Leu Glu Thr Val Lys Ala Val Lys Gly Ile Ile Tyr Ser Tyr Phe
```

755 760 765

Ser Thr Ala Leu Asn Ala Ser Lys Asn Asn Pro Ile Ser Asp Glu Gln
770 775 780

Arg Lys Glu Phe Asp Pro Glu Leu Phe Ala Leu Leu Glu Lys Leu Glu
785 790 795 800

Leu Ile Arg Thr Arg Lys Lys Lys Gln Lys Val Glu Arg Ile Ala Asn
805 810 815

Ser Leu Ile Gln Thr Cys Leu Glu Asn Asn Ile Lys Phe Ile Arg Gly
820 825 830

Glu Gly Asp Leu Ser Thr Thr Asn Asn Ala Thr Lys Lys Lys Ala Asn
835 840 845

Ser Arg Ser Met Asp Trp Leu Ala Arg Gly Val Phe Asn Lys Ile Arg
850 855 860

Gln Leu Ala Pro Met His Asn Ile Thr Leu Phe Gly Cys Gly Ser Leu
865 870 875 880

Tyr Thr Ser His Gln Asp Pro Leu Val His Arg Asn Pro Asp Lys Ala
885 890 895

Met Lys Cys Arg Trp Ala Ala Ile Pro Val Lys Asp Ile Gly Asp Trp
900 905 910

Val Leu Arg Lys Leu Ser Gln Asn Leu Arg Ala Lys Asn Arg Gly Thr
915 920 925

Gly Glu Tyr Tyr His Gln Gly Val Lys Glu Phe Leu Ser His Tyr Glu
930 935 940

Leu Gln Asp Leu Glu Glu Glu Leu Leu Lys Trp Arg Ser Asp Arg Lys
945 950 955 960

Ser Asn Ile Pro Cys Trp Val Leu Gln Asn Arg Leu Ala Glu Lys Leu
965 970 975

Gly Asn Lys Glu Ala Val Val Tyr Ile Pro Val Arg Gly Gly Arg Ile
980 985 990

Tyr Phe Ala Thr His Lys Val Ala Thr Gly Ala Val Ser Ile Val Phe
995 1000 1005

Asp Gln Lys Gln Val Trp Val Cys Asn Ala Asp His Val Ala Ala
1010 1015 1020

Ala Asn Ile Ala Leu Thr Gly Lys Gly Ile Gly Glu Gln Ser Ser
1025 1030 1035

Asp Glu Glu Asn Pro Asp Gly Gly Arg Ile Lys Leu Gln Leu Thr
1040 1045 1050

Ser

<210> SEQ ID NO 926
<211> LENGTH: 1054
<212> TYPE: PRT
<213> ORGANISM: Artificial Sequence
<220> FEATURE:
<223> OTHER INFORMATION: Synthetic

<400> SEQUENCE: 926

Met Ser Ser Ala Ile Lys Ser Tyr Lys Ser Val Leu Arg Pro Asn Glu
1 5 10 15

Arg Lys Asn Gln Leu Leu Lys Ser Thr Ile Gln Cys Leu Glu Asp Gly
20 25 30

Ser Ala Phe Phe Phe Lys Met Leu Gln Gly Leu Phe Gly Gly Ile Thr
35 40 45

Pro Glu Ile Val Arg Phe Ser Thr Glu Gln Glu Lys Gln Gln Gln Asp
50 55 60

```
Ile Ala Leu Trp Cys Ala Val Asn Trp Phe Arg Pro Val Ser Gln Asp
65                  70                  75                  80

Ser Leu Thr His Thr Ile Ala Ser Asp Asn Leu Val Glu Lys Phe Glu
                85                  90                  95

Glu Tyr Tyr Gly Gly Thr Ala Ser Asp Ala Ile Lys Gln Tyr Phe Ser
            100                 105                 110

Ala Ser Ile Gly Glu Ser Tyr Tyr Trp Asn Asp Cys Arg Gln Gln Tyr
        115                 120                 125

Tyr Asp Leu Cys Arg Glu Leu Gly Val Glu Val Ser Asp Leu Thr His
    130                 135                 140

Asp Leu Glu Ile Leu Cys Arg Glu Lys Cys Leu Ala Val Ala Thr Glu
145                 150                 155                 160

Ser Asn Gln Asn Asn Ser Ile Ile Ser Val Leu Phe Gly Thr Gly Glu
                165                 170                 175

Lys Glu Asp Arg Ser Val Lys Leu Arg Ile Thr Lys Lys Ile Leu Glu
            180                 185                 190

Ala Ile Ser Asn Leu Lys Glu Ile Pro Lys Asn Val Ala Pro Ile Gln
        195                 200                 205

Glu Ile Ile Leu Asn Val Ala Lys Ala Thr Lys Glu Thr Phe Arg Gln
    210                 215                 220

Val Tyr Ala Gly Asn Leu Gly Ala Pro Ser Thr Leu Glu Lys Phe Ile
225                 230                 235                 240

Ala Lys Asp Gly Gln Lys Glu Phe Asp Leu Lys Lys Leu Gln Thr Asp
                245                 250                 255

Leu Lys Lys Val Ile Arg Gly Lys Ser Lys Glu Arg Asp Trp Cys Cys
            260                 265                 270

Gln Glu Glu Leu Arg Ser Tyr Val Glu Gln Asn Thr Ile Gln Tyr Asp
        275                 280                 285

Leu Trp Ala Trp Gly Glu Met Phe Asn Lys Ala His Thr Ala Leu Lys
    290                 295                 300

Ile Lys Ser Thr Arg Asn Tyr Asn Phe Ala Lys Gln Arg Leu Glu Gln
305                 310                 315                 320

Phe Lys Glu Ile Gln Ser Leu Asn Asn Leu Leu Val Val Lys Lys Leu
                325                 330                 335

Asn Asp Phe Phe Asp Ser Glu Phe Phe Ser Gly Glu Glu Thr Tyr Thr
            340                 345                 350

Ile Cys Val His His Leu Gly Gly Lys Asp Leu Ser Lys Leu Tyr Lys
        355                 360                 365

Ala Trp Glu Asp Asp Pro Ala Asp Pro Glu Asn Ala Ile Val Val Leu
    370                 375                 380

Cys Asp Asp Leu Lys Asn Asn Phe Lys Lys Glu Pro Ile Arg Asn Ile
385                 390                 395                 400

Leu Arg Tyr Ile Phe Thr Ile Arg Gln Glu Cys Ser Ala Gln Asp Ile
                405                 410                 415

Leu Ala Ala Ala Lys Tyr Asn Gln Gln Leu Asp Arg Tyr Lys Ser Gln
            420                 425                 430

Lys Ala Asn Pro Ser Val Leu Gly Asn Gln Gly Phe Thr Trp Thr Asn
        435                 440                 445

Ala Val Ile Leu Pro Glu Lys Ala Gln Arg Asn Asp Arg Pro Asn Ser
    450                 455                 460

Leu Asp Leu Arg Ile Trp Leu Tyr Leu Lys Leu Arg His Pro Asp Gly
465                 470                 475                 480
```

```
Arg Trp Lys Lys His His Ile Pro Phe Tyr Asp Thr Arg Phe Phe Gln
                485                 490                 495

Glu Ile Tyr Ala Ala Gly Asn Ser Pro Val Asp Thr Cys Gln Phe Arg
            500                 505                 510

Thr Pro Arg Phe Gly Tyr His Leu Pro Lys Leu Thr Asp Gln Thr Ala
        515                 520                 525

Ile Arg Val Asn Lys Lys His Val Lys Ala Ala Lys Thr Glu Ala Arg
    530                 535                 540

Ile Arg Leu Ala Ile Gln Gln Gly Thr Leu Pro Val Ser Asn Leu Lys
545                 550                 555                 560

Ile Thr Glu Ile Ser Ala Thr Ile Asn Ser Lys Gly Gln Val Arg Ile
                565                 570                 575

Pro Val Lys Phe Arg Val Gly Arg Gln Lys Gly Thr Leu Gln Ile Gly
            580                 585                 590

Asp Arg Phe Cys Gly Tyr Asp Gln Asn Gln Thr Ala Ser His Ala Tyr
        595                 600                 605

Ser Leu Trp Glu Val Val Lys Glu Gly Gln Tyr His Lys Glu Leu Arg
    610                 615                 620

Cys Arg Val Arg Phe Ile Ser Ser Gly Asp Ile Val Ser Ile Thr Glu
625                 630                 635                 640

Asn Arg Gly Asn Gln Phe Asp Gln Leu Ser Tyr Glu Gly Leu Ala Tyr
                645                 650                 655

Pro Gln Tyr Ala Asp Trp Arg Lys Lys Ala Ser Lys Phe Val Ser Leu
            660                 665                 670

Trp Gln Ile Thr Lys Lys Asn Lys Lys Lys Glu Ile Val Thr Val Glu
        675                 680                 685

Ala Lys Glu Lys Phe Asp Ala Ile Cys Lys Tyr Gln Pro Arg Leu Tyr
    690                 695                 700

Lys Phe Asn Lys Glu Tyr Ala Tyr Leu Leu Arg Asp Ile Val Arg Gly
705                 710                 715                 720

Lys Ser Leu Val Glu Leu Gln Gln Ile Arg Gln Glu Ile Phe Arg Phe
                725                 730                 735

Ile Glu Gln Asp Cys Gly Val Thr Arg Leu Gly Ser Leu Ser Leu Ser
            740                 745                 750

Thr Leu Glu Thr Val Lys Ala Val Lys Gly Ile Ile Tyr Ser Tyr Phe
        755                 760                 765

Ser Thr Ala Leu Asn Ala Ser Lys Asn Asn Pro Ile Ser Asp Glu Gln
    770                 775                 780

Arg Lys Glu Phe Asp Pro Glu Leu Phe Ala Leu Leu Glu Lys Leu Glu
785                 790                 795                 800

Leu Ile Arg Thr Arg Lys Lys Lys Gln Lys Val Glu Arg Ile Ala Asn
                805                 810                 815

Ser Leu Ile Gln Thr Cys Leu Glu Asn Asn Ile Lys Phe Ile Arg Gly
            820                 825                 830

Glu Gly Asp Leu Ser Thr Thr Asn Asn Ala Thr Lys Lys Lys Ala Asn
        835                 840                 845

Ser Arg Ser Met Asp Trp Leu Ala Arg Gly Val Phe Asn Lys Ile Arg
    850                 855                 860

Gln Leu Ala Pro Met His Asn Ile Thr Leu Phe Gly Cys Gly Ser Leu
865                 870                 875                 880

Tyr Thr Ser His Gln Asp Pro Leu Val His Arg Asn Pro Asp Lys Ala
                885                 890                 895

Met Lys Cys Arg Trp Ala Ala Ile Pro Val Lys Asp Ile Gly Asp Trp
```

900 905 910

Val Leu Arg Lys Leu Ser Gln Asn Leu Arg Ala Lys Asn Arg Gly Thr
915 920 925

Gly Glu Tyr Tyr His Gln Gly Val Lys Glu Phe Leu Ser His Tyr Glu
930 935 940

Leu Gln Asp Leu Glu Glu Glu Leu Leu Lys Trp Arg Ser Asp Arg Lys
945 950 955 960

Ser Asn Ile Pro Cys Trp Val Leu Gln Asn Arg Leu Ala Glu Lys Leu
965 970 975

Gly Asn Lys Glu Ala Val Val Tyr Ile Pro Val Arg Gly Gly Arg Ile
980 985 990

Tyr Phe Ala Thr His Lys Val Ala Thr Gly Ala Val Ser Ile Val Phe
995 1000 1005

Asp Gln Lys Gln Val Trp Val Cys Asn Ala Asp His Val Ala Ala
1010 1015 1020

Ala Asn Ile Ala Leu Thr Gly Lys Gly Ile Gly Arg Gln Ser Ser
1025 1030 1035

Asp Glu Glu Asn Pro Asp Gly Gly Arg Ile Lys Leu Gln Leu Thr
1040 1045 1050

Ser

<210> SEQ ID NO 927
<211> LENGTH: 1054
<212> TYPE: PRT
<213> ORGANISM: Artificial Sequence
<220> FEATURE:
<223> OTHER INFORMATION: Synthetic

<400> SEQUENCE: 927

Met Ser Ser Ala Ile Lys Ser Tyr Lys Ser Val Leu Arg Pro Asn Glu
1 5 10 15

Arg Lys Asn Gln Leu Leu Lys Ser Thr Ile Gln Cys Leu Glu Asp Gly
20 25 30

Ser Ala Phe Phe Phe Lys Met Leu Gln Gly Leu Phe Gly Gly Ile Thr
35 40 45

Pro Glu Ile Val Arg Phe Ser Thr Glu Gln Glu Lys Gln Gln Gln Asp
50 55 60

Ile Ala Leu Trp Cys Ala Val Asn Trp Phe Arg Pro Val Ser Gln Asp
65 70 75 80

Ser Leu Thr His Thr Ile Ala Ser Asp Asn Leu Val Glu Lys Phe Glu
85 90 95

Glu Tyr Tyr Gly Gly Thr Ala Ser Asp Ala Ile Lys Gln Tyr Phe Ser
100 105 110

Ala Ser Ile Gly Glu Ser Tyr Tyr Trp Asn Asp Cys Arg Gln Gln Tyr
115 120 125

Tyr Asp Leu Cys Arg Glu Leu Gly Val Glu Val Ser Asp Leu Thr His
130 135 140

Asp Leu Glu Ile Leu Cys Arg Glu Lys Cys Leu Ala Val Ala Thr Glu
145 150 155 160

Ser Asn Gln Asn Asn Ser Ile Ile Ser Val Leu Phe Gly Thr Gly Glu
165 170 175

Lys Glu Asp Arg Ser Val Lys Leu Arg Ile Thr Lys Lys Ile Leu Glu
180 185 190

Ala Ile Ser Asn Leu Lys Glu Ile Pro Lys Asn Val Ala Pro Ile Gln
195 200 205

```
Glu Ile Ile Leu Asn Val Ala Lys Ala Thr Lys Glu Thr Phe Arg Gln
    210                 215                 220

Val Tyr Ala Gly Asn Leu Gly Ala Pro Ser Thr Leu Glu Lys Phe Ile
225                 230                 235                 240

Ala Lys Asp Gly Gln Lys Glu Phe Asp Leu Lys Lys Leu Gln Thr Asp
                245                 250                 255

Leu Lys Lys Val Ile Arg Gly Lys Ser Lys Glu Arg Asp Trp Cys Cys
            260                 265                 270

Gln Glu Glu Leu Arg Ser Tyr Val Glu Gln Asn Thr Ile Gln Tyr Asp
        275                 280                 285

Leu Trp Ala Trp Gly Glu Met Phe Asn Lys Ala His Thr Ala Leu Lys
    290                 295                 300

Ile Lys Ser Thr Arg Asn Tyr Asn Phe Ala Lys Gln Arg Leu Glu Gln
305                 310                 315                 320

Phe Lys Glu Ile Gln Ser Leu Asn Asn Leu Leu Val Val Lys Lys Leu
                325                 330                 335

Asn Asp Phe Phe Asp Ser Glu Phe Phe Ser Gly Glu Glu Thr Tyr Thr
            340                 345                 350

Ile Cys Val His His Leu Gly Gly Lys Asp Leu Ser Lys Leu Tyr Lys
        355                 360                 365

Ala Trp Glu Asp Asp Pro Ala Asp Pro Glu Asn Ala Ile Val Val Leu
    370                 375                 380

Cys Asp Asp Leu Lys Asn Asn Phe Lys Lys Glu Pro Ile Arg Asn Ile
385                 390                 395                 400

Leu Arg Tyr Ile Phe Thr Ile Arg Gln Glu Cys Ser Ala Gln Asp Ile
                405                 410                 415

Leu Ala Ala Ala Lys Tyr Asn Gln Gln Leu Asp Arg Tyr Lys Ser Gln
            420                 425                 430

Lys Ala Asn Pro Ser Val Leu Gly Asn Gln Gly Phe Thr Trp Thr Asn
        435                 440                 445

Ala Val Ile Leu Pro Glu Lys Ala Gln Arg Asn Asp Arg Pro Asn Ser
    450                 455                 460

Leu Asp Leu Arg Ile Trp Leu Tyr Leu Lys Leu Arg His Pro Asp Gly
465                 470                 475                 480

Arg Trp Lys Lys His His Ile Pro Phe Tyr Asp Thr Arg Phe Phe Gln
                485                 490                 495

Glu Ile Tyr Ala Ala Gly Asn Ser Pro Val Asp Thr Cys Gln Phe Arg
            500                 505                 510

Thr Pro Arg Phe Gly Tyr His Leu Pro Lys Leu Thr Asp Gln Thr Ala
        515                 520                 525

Ile Arg Val Asn Lys Lys His Val Lys Ala Ala Lys Thr Glu Ala Arg
    530                 535                 540

Ile Arg Leu Ala Ile Gln Gln Gly Thr Leu Pro Val Ser Asn Leu Lys
545                 550                 555                 560

Ile Thr Glu Ile Ser Ala Thr Ile Asn Ser Lys Gly Gln Val Arg Ile
                565                 570                 575

Pro Val Lys Phe Arg Val Gly Arg Gln Lys Gly Thr Leu Gln Ile Gly
            580                 585                 590

Asp Arg Phe Cys Gly Tyr Asp Gln Asn Gln Thr Ala Ser His Ala Tyr
        595                 600                 605

Ser Leu Trp Glu Val Val Lys Glu Gly Gln Tyr His Lys Glu Leu Arg
    610                 615                 620
```

Cys Arg Val Arg Phe Ile Ser Ser Gly Asp Ile Val Ser Ile Thr Glu
625 630 635 640

Asn Arg Gly Asn Gln Phe Asp Gln Leu Ser Tyr Glu Gly Leu Ala Tyr
645 650 655

Pro Gln Tyr Ala Asp Trp Arg Lys Lys Ala Ser Lys Phe Val Ser Leu
660 665 670

Trp Gln Ile Thr Lys Lys Asn Lys Lys Lys Glu Ile Val Thr Val Glu
675 680 685

Ala Lys Glu Lys Phe Asp Ala Ile Cys Lys Tyr Gln Pro Arg Leu Tyr
690 695 700

Lys Phe Asn Lys Glu Tyr Ala Tyr Leu Leu Arg Asp Ile Val Arg Gly
705 710 715 720

Lys Ser Leu Val Glu Leu Gln Gln Ile Arg Gln Glu Ile Phe Arg Phe
725 730 735

Ile Glu Gln Asp Cys Gly Val Thr Arg Leu Gly Ser Leu Ser Leu Ser
740 745 750

Thr Leu Glu Thr Val Lys Ala Val Lys Gly Ile Ile Tyr Ser Tyr Phe
755 760 765

Ser Thr Ala Leu Asn Ala Ser Lys Asn Asn Pro Ile Ser Asp Glu Gln
770 775 780

Arg Lys Glu Phe Asp Pro Glu Leu Phe Ala Leu Leu Glu Lys Leu Glu
785 790 795 800

Leu Ile Arg Thr Arg Lys Lys Lys Gln Lys Val Glu Arg Ile Ala Asn
805 810 815

Ser Leu Ile Gln Thr Cys Leu Glu Asn Asn Ile Lys Phe Ile Arg Gly
820 825 830

Glu Gly Asp Leu Ser Thr Thr Asn Asn Ala Thr Lys Lys Lys Ala Asn
835 840 845

Ser Arg Ser Met Asp Trp Leu Ala Arg Gly Val Phe Asn Lys Ile Arg
850 855 860

Gln Leu Ala Thr Met His Asn Ile Thr Leu Phe Gly Cys Gly Ser Leu
865 870 875 880

Tyr Thr Ser His Gln Asp Pro Leu Val His Arg Asn Pro Asp Lys Ala
885 890 895

Met Lys Cys Arg Trp Ala Ala Ile Pro Val Lys Asp Ile Gly Asp Trp
900 905 910

Val Leu Arg Lys Leu Ser Gln Asn Leu Arg Ala Lys Asn Arg Gly Thr
915 920 925

Gly Glu Tyr Tyr His Gln Gly Val Lys Glu Phe Leu Ser His Tyr Glu
930 935 940

Leu Gln Asp Leu Glu Glu Glu Leu Leu Lys Trp Arg Ser Asp Arg Lys
945 950 955 960

Ser Asn Ile Pro Cys Trp Val Leu Gln Asn Arg Leu Ala Glu Lys Leu
965 970 975

Gly Asn Lys Glu Ala Val Val Tyr Ile Pro Val Arg Gly Gly Arg Ile
980 985 990

Tyr Phe Ala Thr His Lys Val Ala Thr Gly Ala Val Ser Ile Val Phe
995 1000 1005

Asp Gln Lys Gln Val Trp Val Cys Asn Ala Asp His Val Ala Ala
1010 1015 1020

Ala Asn Ile Ala Leu Thr Gly Lys Gly Ile Gly Arg Gln Ser Ser
1025 1030 1035

Asp Glu Glu Asn Pro Asp Gly Gly Arg Ile Lys Leu Gln Leu Thr 1040 1045 1050

Ser

<210> SEQ ID NO 928
<211> LENGTH: 32767
<212> TYPE: DNA
<213> ORGANISM: Artificial Sequence
<220> FEATURE:
<223> OTHER INFORMATION: Synthetic

<400> SEQUENCE: 928
aacgaactcc atctgggata gcaataacct gtgaaaatgc tcccccggct aatttgtatc 60
aatgattatg aacaacatgc taaatcagta cttccaaagt ctatatatga ctattacagg 120
tctggggcaa atgatgaaga aactttggct gataatattg cagcattttc caggtaagaa 180
aatttatttt ttaaaatcat gttttaaaat tacacaaaga ccgtaccaaa ataagatctc 240
ctagttttac gttggtggtg tgtaattatt tgttcagatt tgtgcttagt agagagggaa 300
aagttcttgg ggctgtaaga aatcttgggc ctttaaattg ttaaaaaata ttccaagcct 360
gtgaatcttg aggaactgac tgcaaaagcc aaacctatgt tacttcactt ggaaatatga 420
caacaattaa tttaactaca tgtaaaaata gcgataaatt cggatgactt ttcttttttct 480 tagtatgaca gtaaatgctt atgttcatgg tgtaggaaac agcattaaat gccagataac 540
catcttatcc ggatgaacca gactggattg ttggctcaaa tgttttcttc ctgctggctt 600
ttcgtgttat cattcatttt gattactgtt gtctaaactt tcactttaga tttcaatttg 660
tctatgcagc attaatcttt caactttgct gtttcatctc tccttcaaag cacttcatct 720
ctcttcccaa attagttttc ctttgacttt catatttcaa agcacaagat ggtgggtgac 780
atggtttatg ttttctgttt gtaataaaaa caagaaataa aatcatttca aagggttttt 840
ttttatagca gttacaaaaa tggtttattt gctggagcaa gagaggagtg ccttcactac 900
actacactca gtctcatcca tctaacatta tggctgttag taaaggcaat cggtattgtg 960
ggtactcatt gatggtgata aagacaaaaa ggcagaaaat atgcaggggg agagaattag 1020
ccttcctccc tgatttcttc tttagtctac aacaaaatca ctcaaaatca gttttccata 1080
tttaaattag gagaaataaa attatcctgg ccaaggtggt ctctggtagg cagcactgat 1140
tcacccacaa atccatgtag aagactgaaa atggcaatgg ggtgaaggat acggcctctc 1200
cccaaccctt tcaagccttg actttgtctc aggttttgcc tggaacccaa atgagctcaa 1260
caaatgccag ggaagtcatg ggaagggaag ttgactgaga gtagaggggc ttaaaattct 1320
gcatcattat ttactatttt ggactcattt aaaagtttct gctcttggaa gatgcccctt 1380
cttgggccga tattaacttt gtccaccaaa atttgcctat gagtggtctc ttgaaaacac 1440
tttaacccaa ataggttatt acaaccaagg aaatttcaga cccttgacag atttatagag 1500
ttagtgtctc agcattgcta gacctccaat gctcaagtga ttatttattt catttgtata 1560
cagctttcct tacttcttaa ttccctttgt cgcatgctag ctaattaact agagctaatt 1620
aggagtctcc atgagctaca ctgtgtacta catgctgagg acaaagcagt gagccagaca 1680
aagttcctgt ccctaggaac ttacattccc ctggatgcat atcagcctcc ataatgctgt 1740
tgggttgaat tgatgcaaaa tgggcccaaa atagttggcc aagtggaggt ctcagagagg 1800
atgcaaaggg gcgccccaaa gcagatggat cacctatgca accctttaaa atgtagaaac 1860
tttgggagac atagaaggct tggtgacttc taagttatga actggaaaag tgcctcatgc 1920
cttatgtgaa ttacatggta ttcaagtgag tattcccatc ctatgtgtgt accgagtaac 1980
ttagggatag gacacagata atgaaaatga atttgcagtg tcaccttttc catgaacctt 2040
gatcattctc ttttgttcag ctttaaatta aaaaaaaaaa tcaatcaact ttctttggag 2100
gacagctgat gctattttat tatcaactag ttgagttttt attgcaatac attttgcaat 2160
gtgtcctctt ttgctgtatg actcgctagg tgaaccttga ttcctcacac tgcatcatgt 2220
agctggtcac gtgaaactaa gaatagaaat tctgccaggg ttgtggagac tttgggttga 2280
tggcatgaag gaaatcaacc tgaaatttca cattctgatt ctaatgaaaa gtgcaaaaca 2340
atcaaacctc agataaccca ttgtgataca aagccagagt atttcaaaca catttatgaa 2400
atttatacac ctccccatct cgcaagtaca acaaaaggtc attcaccgtg acagctttta 2460
tttctctgta ctcagctctg ataatcacat tttggagttc tggggacatg gaccactcat 2520
gtgacccagc agttgcttgg agatattttt gggtaagact tcagactaat attactgtgg 2580
cagtagaaaa aaatgtttaa aaggacaagt aaatggaacc acccagaaca aaatttctta 2640
cggtggttat aacaaaacag ggtaaatgtc aacttgctac attttgcatg gctggaattg 2700
attgggatta attcaacgaa gaacagtaat ttgtttctct tacacattta ttcaaagtag 2760
ccttctcaac tatggtcttc acgttgttgt agcttttttt tctgaaatta tcaatgatgg 2820
aagatgatta aacaatttcg acacttagaa gccctcatga tttcagaaaa ggaaactctt 2880
ttctgctgcg ttacctattg agactgaaga tggcatcatt ttcttttaaa taacagatgg 2940
gtaaaagtga tgtcattctt tcactttaat atttgagaag tgatatgaag ttaccagtga 3000
cattgtgttc tcataggcat aaatgtcaca aaataattta tctagtatcc acaataggtg 3060
aataaggtgt ttttgcttta tatattttaa ctgtttagag taaaaaatta atgtggagaa 3120
aattggaatg cagtattata ggattacaca acttacaaaa catgaatcca ctatgtccag 3180
ttagtgtgat tcagaaacag catgcagtta taaagctggg tgaggcatgg gtgtcttcct 3240
tcaacagggc agctactttg tgaggagtgt atatatcatt tgattttttt ataagttaaa 3300
tttgaggccc ctgttagatg tgagggtggg ccaaaattcc tgtgaacaga ttctccccgt 3360
taccccgctt cctttactct ggcatctcat tttctatcct ttgaaaacgg tttattattc 3420
aattggttca actgtttgcc agttgaacca attctttttc caaagtggag gcccaggaaa 3480
gcacagtccg agaatatagt gaggtgctat tttatgtatg attgtgggaa atttacttaa 3540
atttggagtg gggttgggca aggcttggaa agctagtgag ctatctgaca tagttgttac 3600
tactatttga aaaatatcaa aacatggagg actctttaga taacatgcct gttcccattc 3660
cattgatttt atctaatttt acgtagcaat tacgttttgt gcattggttg acaagcctct 3720
gtattatcct cagaacagaa aatactgttt aagggaaatt aagagcccgc agttactaaa 3780
gtgactgcgc caccaagtgg acaagtgtaa agccactgtc tggagatgga aggattcagc 3840
tttgctttat aaatgggaat ttgaccttta aaaatgtccc ttttggcacg cacgcgcgcg 3900
cgcgcgcgcg aacacacaca cacacacaca cacacacaca cacacacaca cacacggctg 3960
ctgccctgca gatttgcttg ttcttgtcat aaagctttca ttgtttctct agctctaagt 4020
aaatattaat gccttccaag gctggcatgc caatggctgc tattaagatc gttttctctc 4080
attctaataa cacacttaga gatgattggt aataaaaact ctcttcaagg cttctgcttc 4140
tccccccttca aaatggagat caaagaatca tgctgtgagg gtccgtcaag aagaaaagac 4200
tttcagcaac agagcatgtg gtgtggcata aaataatgac aattataatg ttcaaaggaa 4260
tagcatagaa atcacacagt aaaacttctt tattatgctt ttcagggact ggatgttttt 4320
actttattat gtgaggaagg gttagattac agacccttag ctattccaca aagcaataga 4380
aggcagaatt tcttcttccg ctacaggaag cacgcttcga ttaagggctt tttctttttc 4440
ttcttttttt ttctttaagt tactgcatta ctatatcata cttcactata tttactaaaa 4500
agtcatgctg tttctggaag tagagttaca tctaggaaat actaggtgaa tgctggttag 4560
atatgcatgt gtgcctaaac aacacgttta ttatactcat gcatactaga aatagggctg 4620
tattttcttc aattttaatc agtactaatg agaataataa atcaaaacaa ataggagaga 4680
tatattttgc caggaggaaa gagaactagt tcttctgtaa attttactgg tgaatttttg 4740
gttgctggtt tattggtaat tttcattcca acacagaaga atcacagaaa cattcattta 4800
aaataatttt ccggagtcaa aaacttttta acacccaaat ttcagttttt gtcaaataac 4860
atttttgaga aaagtgttaa attaaactaa taaaaaacct tccctcatca ttagacttta 4920
atgaatatgg catataacta aataattttg aagaaaccaa attataattt taaaagtaat 4980
tgcctgaagc tgctgtttat cacataaaaa gaagacaaac tagacatagc atatcttctt 5040
aaactctaat ctaaactcta tgcatttgta taccatcttg attttcaaga ttggggaagt 5100
gaaacgaaaa ctatgttcac acaagaacct gtacgtgaat gtttgtagtg gctttattta 5160
gaatttcccc ccaaactgta agtattcaaa atgtctttta gcttgggaat gactggacaa 5220
atgatagtac ccctgtatga tggaatatta ttcatcaacc aaaaggaaca aactattgac 5280
acgtacaaca acatgagaaa atctctaatg cgttatgtta agtgaaagaa gccaaactca 5340
aaaggctaca tactgaatga ttttgtttac atgatattct tgcaaagcaa aattatcagg 5400
acaaagaaaa aatgcatcag tggttgtcag gggattgaac tggggagagt ttctctgcaa 5460
aagaaaatgg ggactttttt gggaatgatt gaactttttc tagatcttga ttgtcatggc 5520
agttacacca ctgtatgcat ttgtcaaaat tcacaaaact gcagactaaa atgagtgaat 5580
actattatgt attagttata ctttaataaa taattgcttg ggaaattcat tatcctctaa 5640
ttgttaactt tctaaccaaa caaacagtaa aattgcctct tttccattag ctttatgaag 5700
tcatttgctt gtttggaaaa aatccaatta tatttttttct tttaactaaa atgtaatgtc 5760
aaagttttgg ttatgattct gaaactctaa agccttttat tttattttat tttttaattc 5820
tagatggaag ctgtatccaa ggatgctccg gaatgttgct gaaacagatc tgtcgacttc 5880
tgttttagga cagagggtca gcatgccaat atgtgtgggg gctacggcca tgcagcgcat 5940
ggctcatgtg gacggcgagc ttgccactgt gagaggtagg aggaagattg tcaccacagg 6000
gacagaagga ggctaacgtt tatcgacctc cttctctgaa tgcaccaagc aaatatgttc 6060
cttgatgttt ttacactcag aaacattaag ctcatggact ctatcatcaa aatacttgtt 6120
cttgcatgtc ctgctcctct tctttccagc tgtgtgactg ggcaagatat cctctctctg 6180
cattggtttc cttggctgta aaatagggac aaaaattgta cctgcctcat tgggttatgg 6240
tgagaattga atgagttcag gtatacaaag ttcatggcag agagtagggg ctcagtaact 6300
gttggttata ttatgggtat taatagtact gtctcaggaa atggatctct gacaggtaga 6360
cttgcccaaa gtcacagcta ggtagttaca gaattggaat tcagccctgt ggctacctta 6420
tctcaaaacc ctcctgcttc ccccaaacca aagtggttct cacagccaaa ttgcaaatgg 6480
agcaacgtgg ttggttgtgt tttcttccgt ggttttgggt catgattctt ttttatggat 6540
gagttatatt cccaatagag cagttccagc tgtcttagga gggagtgatg agaaaatcaa 6600
atatgatgta aagaaatctc ttattagggc taatttatta actttccagt tctctagcaa 6660
ctgtgaacat ttgaaaggct gtgcagagta aaaaatctcc ccaaattgtg ctccagaaac 6720

```
taatataaaa gttggaaatg aattattttg atgctaagca gagcagaaaa agaacacgac   6780
tatataatat tttaaaacat tttagtttta agaattaagg atcttgtgaa ttcacttccc   6840
ttcttgaaat gtctgacata aaattctgtc agggatatca gaatggcaca atgaggtttt   6900
gctggacaga cttagcagct tccttaattc taggaccaca tacaaataag tggctttggg   6960
gcctcagcct tttgtctatg gtaatcctga aacataagta gagagaagaa aaaaaaaggg   7020
aaatactaaa tgggtaaata tctatacaaa atcaagataa taaaggccct ttcaggcttg   7080
aaactatagg caacaacctt agaacaaaag aaaacaaatg aacatcaaaa aactaaaact   7140
ttagtgctct taaatctcaa tgaaaataaa aagtaaatgg taaactgaaa gaaatggaaa   7200
aaaaatatga gactgtgaag ggttaatgtc ctttccacgt aaaaagccct tatatttgaa   7260
gaagaaaata atatattgct caaagggaaa aagagaaata agtgaacaaa agatataaat   7320
aggaaattta caaatggaga cataaaagtg accaataaac atatgaaaaa tattcaattt   7380
cattaataag caaagacatg gaaattatga ccatctattt tattttccgt atatcgaatt   7440
tttattttaa gatcaggcag tatgattagg ttagggagaa aatgtgcatt tcaaacagtg   7500
ttgagaaaag tataaagtgg aataatcttc ctagaaaata atctggcact gtatatcaaa   7560
gctctaaaaa tgtaaattcc atgtgatgtt aaaaattctc ttctaggaat tccaaggaaa   7620
taattatgat ttttgaggaa aaaaatcatt tctgcaagga ttttcatgct tcttattttt   7680
agcaggaaaa taatttgaaa aaaataccca aacatcttat aattggagat agtttgcaaa   7740
aaatatgatg cataaaaatg acatcaaatt taaaaattat actataggaa gagtgcaata   7800
atgtagaatg atattttaat ttaaaattgt gagaaatcag ttgcaaacaa tagtcaggtc   7860
ctaaaataca tttagtttca aagatcacaa tttacaaatg tttatttata agtgatgaga   7920
ttactcctga ctttatactc ttctgatttt tggctcaacc ttataaactc ttctttgaat   7980
tattttgtaa ggaggaaatg ataacaatta gatttaaaag agtagagata aagggacaag   8040
ggaccatgaa gagaatggaa ataaagaaag gaagcagaga aagcaaaaag cagagctcac   8100
ttggtaaggc accctggagc cagcaaatta tttttaccac atgtattagt tccttctcac   8160
actgatttaa agatactctt cgagactggg taatttatta aggaaagagg tttaactgac   8220
tcacagttct acatggctgg ggaggcctca ggaaacttac aatcatggtg gaaggcaaag   8280
gggaaggaac gaccttcttc ccatggtggc aggagagaga agtgcaagca gggaaatgcc   8340
agatacttat aaaaccatct gatctcatga gaactcaccc actatcatga gaacagcatg   8400
ggggaaacca cccccatgat ccaatcacct cccactaggt ctttccctca acacctggga   8460
ttataattca agatgagatt tggatggaga aacaaagcct aaccatacca acacatattg   8520
ctttatttga tatttgacag gtgtttctgt ccctgttttg tgggcaagta gctaaagttc   8580
cagagaaaac agtttttcat agctcgtcaa tgacagactt attctccaag tcacatttga   8640
tggttccaag accagtcttt attcttggtg gagttgggct gagaagaaag aggagaagaa   8700
agaagaaaag aaagcttcct tagaaactat gatttgacag tgtaagtagg actatttcct   8760
ccagaagtaa ccataagaag atattaaatg cctattacag tcttatcccc ttagatttat   8820
ttaacactta taaagcaatt atcatgttcc agacactatt ttaagtatat tacgagtatt   8880
atagcattga aggctcagag cggcccaaat aaatcgatca tattattaaa cctattttac   8940
acaggagaaa ctgaggtaca cgccaggtga ataaccttgc ctagggatgc acaattcata   9000
agtgatagag atgggattca gacagaggta ttctgtctcc agaatctggg ctcctcacca   9060
```

```
ctttgcaaga gctttaattt cagaaactcc tatgaagtgt catgaggaga agcccattat   9120
gatcccctag aagtaattat agttttagga gcatgcaaag cagacccctc aggaagataa   9180
gttacacaat agacatttgg ataaggtgga tccagcagaa caaagagagg gtggtgacat   9240
cgagattgca gaggaattgg agaaggcaat ggaagtgtac acatgttgcc ctcaaaaaca   9300
tagggtcctc cattgggttc ctatcagggc agcaacatca gagtttctat tctgtattta   9360
tactagaaac ctctctccag ggtttctaag ttttcaccta tgttttaaag actatctata   9420
ggttattagt ctatttaata tttaggtgta tccagaaagc tgatggtcat cagctcatag   9480
caggtgttct ttggctggtg tgtttatgtt gtgggacagt gggttacttg caaggaaagg   9540
atgaatggct ggagtagatg gtgcttgtgc tctgcatgta ttcccttctt acttcccatt   9600
tccatcagac ctaccacttt ttgcctgaca ttatctgttg caacatgagc ccatggatag   9660
gtgtgtttga agtaggggaa tgggagagag ggttccctag ctaatgatgt acagcagtag   9720
gtggataaat acctcagctc tctttgctca ggtaactgaa gcattttcta atatggtcac   9780
ccagtgttcc ttggaaggat tgagtcccag ttgccccctg aggttgcctg cccatgaaca   9840
caccctcttt tattggcttc cttcccattc ttttctcact tccccattcc ttcaattcat   9900
tgagattgtt tccaaataag atgacttgct ctcacatctc tgtgtcattt ttggcttctt   9960
gaagtatgca aaccaggata atagctaact gaaggctata gatagccaca ggcaaattta  10020
agtaacagtg taagaatatt catacttggc agagatttat ttataaaaac tcagaaaatt  10080
cacatggaat tatgaagtta ttattgtatt tattccatca ttcccagaaa gaatatggaa  10140
atcctctcaa gcaagccagt ccttgggaat attgggaaat ctatgcaatt tgttgtggag  10200
tatttttttt tttgttaccc tcctaaatat ctggccgcta agcattcctg tctccaggga  10260
cttagaccct agcaaggaag agaagttggg gccaggttca gaaaacgggt tagttatcaa  10320
tctccctgga gaagtgtccc cctcagcagg gtcagtgaga gtaagtgaaa cccattggtg  10380
cccacaggca atggtctggc ctgagtaatt agaatgggcc tccagaaagt tctgggaatt  10440
gctatggtgc catagtctca ttttccccgt tgactctcca gatttattca gagtccaact  10500
tcaagggcct ttctgccctt cctctcacaa ctgtggaata ataataatcc accttattaa  10560
ctgggaccga gaactgagct cgactcttat ttttttgaga cagagtcttg ctctgtcacc  10620
agactggagt gcagtggcac tatctcagct cactgcaacc tctgcctccc aggttcaagc  10680
gattcccctg cctcagcctc ctgggtagct aggactatag gcacgcaccg cgacggctgg  10740
ctaatttttt gtattttagt atagacaggg tttcaccatg ttggccagga tggtcttgat  10800
ctcctgacct catgatctgc ctgccttggc ctcccaaagt gctgggatta catgcgtgag  10860
ccaccgcgcc ctgtctgaac tctacttttt tacactgctg catgtttgta gagtgaccaa  10920
tgaagctata ctttttttcat tttcaaaatg atgatgaata caaggttatc aaataaaaca  10980
cagagggccc attatgtttg aatttcagat aaacaacaaa tcataggtgt cctgtatgtt  11040
tgctcaatct ggcaaccctg gatgaataag agctctcacc tgaggatttc ttgtgaggat  11100
tcatgaaata aatgctagaa atgcttacac actatcttta tttgcccctc agagcccaaa  11160
gtctctgaaa tctttatctt tcacacacaa aaactcactt tcagaaaagt atattccatt  11220
tacatctagt ggaaataaaa attgttcttt ttctttgtga aaaatatttt tattttaagc  11280
tttatgcaga aacctcaggg aaaaaaaggt acttttagga gccaggcttg taatgtaaat  11340
gtccaaaaaa gatgaaattg aaacaaacaa acaaacaaac aaacaaacaa acaaacaaaa  11400
aacagtgcaa gctcctgtgt ggagactgca gtgagtctga gattgcatgt tccatcagaa  11460
```

gggggcagcc acatcttagc tcttgatgac ccaagggagc agggatgtgg ggttgccaaa 11520
tcttccaaaa ttttaagaag ccagaaatct tgatttctat gtacaatctc ctggttttta 11580
aatgtgggca aataaatcaa aattccctaa aacactgttt ggggcaacaa tgtgtgggcc 11640
aaagtaaata cttttgtggg ctacaagtgt cccctaggct gtacatctgg gacatctgat 11700
ttatgtggaa atttaccgag aactagtttt atttctgtgg caggtcattt tcactttcta 11760
ggattatgtt tcttcattga taaagtgagc tacttgagca agaccagtgg attgaatgcc 11820
acgtcccaag gaggctgggg ttgtttccag ggatcttaca gaacttaggt gtgatactga 11880
gcatgagcta cttgtgttgc attttggtgt tcaaaagaaa agttctttaa atagttctgc 11940
tggaaagaca aaaaaaaaaa aaagaaaaaa ctttcacaac aaaaatctcc aaaaacaaaa 12000
acccagaaaa ctggcataga agtggatgat ctttgcaatt tttttcagta tataaataaa 12060
tgattttgat cccatttaaa attttatcaa atgcaaaaag aaacaattca aagtatagag 12120
ctaccttttc ttactctact gaaatctaca ctttatgtca gccctggagg gtttagacgc 12180
actttatgtc agcccacttc tttcgactgc actatgtcag ccttggaggg tttagatgag 12240
gcagtgagca tttgaatgct tttaatttcc atttttcaaa gtacattctt ggtctatagg 12300
agaggaacaa gatatgtaac tatctctgac tattgctaaa aacacaaacg tctttaataa 12360
atgttgcata aactcagaaa gtgatacttc aaagtcttgt gaaaaatgat gatcaccagc 12420
atttatacag caattagtat gtgccacgca atttgacttt attatttatt catctatctt 12480
taccaccatc ttaaaatatg tgagtgcaaa accctgagaa actttctcca actcctgtgg 12540
gtgtggaaat cgaggcttag agaggttaat gctttgctca gattattaat cacttaggca 12600
gtgctaccta taatatcctg ctctgttact ggtatttcca aacgtcatta actgtagcaa 12660
gaatcctaag gcaagcacta tgctatcatc ttaaaatatt tattgcaaac atcctatgtt 12720
ttattgtttt atctttttaa ctttgagaag ataaaataag ccacagaagt gaaattaatt 12780
gggaaatcat tcgctttttg caaaatttgg gagcataaac aatgggtcat gaattacaat 12840
caaacaaaag ataaaattct aagaagtctt ttaaagtgga aaaaaataac tgaaaaatac 12900
tgaatggagg gcagtttttc atgcactgtg ttacgaataa aaaatttgat tcaatggatt 12960
acttaatcaa cattttaata gttgtaaatc ttataatatt taagctgttt tataagtgcc 13020
tctacttata atggcacatc cgtttgaaac tctagcagat catttttatt tatttttttg 13080
aatttttttc tttatattct ttaaagaagg atacaaaatt atttctatga atatttaaca 13140
tatggaagga aatagcaata ataaacataa atgctaacac atataaaata ggtggtatca 13200
ttaggctaaa ttttagtctt ccaggataag tagaacatct ctgacttctc aaatatccaa 13260
ttaataaaat gcttactata ccatttggtg ctttaagaac attgccatgg aaacctctca 13320
ggttttatgc acagtagcta taataaaatt ttccttcatc tttcatggag ctacttgaga 13380
tttttttttct ccctttaaac atgagaaatc aaaaagaaag agaaaagaag gattaaatat 13440
tcatttatcc ttttgcttct gacttgttat gtgggcaagt gccacatgag ggagtgctgg 13500
gacctcatat caagaaaaat taaaacctac ctaatgcgtt ccaggaatgt tcagcatatt 13560
agcaaattct tattaaactg tcaaaaaaaa aaaaagtttt aaaagaaatt ccagcccctg 13620
gatgcaatta gaggctacca cactggattt gatgggccat aaaaccatta aatctaaaca 13680
ctttcttttt gagcctaaaa ggccagaaca ttccaaagtg aagttttggg actcagctat 13740
gacttgacca cctattaaga tgcaggtgga acagattgca gagtaacaca aagagccaca 13800
cagaccccag atgactgcat tagggtgtag gtgagagttt tagctgttga attttctgga 13860
ttttccaaga ttaagtgatc aaccttaaca atgagtgaaa gaccattcaa caggaagaat 13920
tgtcatttcc tttgctctaa acccaaacga tgtatttttt gaaagcttta ttgatttata 13980
tatttatgtg ttgtgctagg cgaccgacta gatatatgtt tcagcatacc tactaggaaa 14040
atatccccat tattctcaat tttacctaat ccaggcaaag cactggactt gctttaagga 14100
acatttttac tctttctgaa gtggagtgcc tgtcatgtat caggtgcaat gcttggactt 14160
tacgttcttg tgattaatcc ttacaatagg cctgtgaagt aattctcatt ctgtttgaca 14220
gtagagaaga aggaagccct tgaccaaggt ctagtgccag taatggtggt gatggggttt 14280
gaacctaagt ctgtttcact ctaaagtgta accaaatttt atgttttaga cttgcttttc 14340
taacaataaa aagtcagtga catgctcttt ctgtgtgtaa gcactcacac acacacacac 14400
aaacacacat ccgtattaca tatgcttata tatgtattaa aagattatgg acatttgata 14460
tatatacata tactaaaatg tataattcat tgctaaagta ttttcatata aatagtggct 14520
tcagtgttaa aatcactttg caatgaaaca agattgttga ttaaaacacc tattaaaaaa 14580
ttagaatcta gccatattaa agacagtcat cgaatggagt gatttctacg attttgcacc 14640
aaaatttaag ctattgggtg gctttcttga gagcatgaga ttgcttcttc tcagaattat 14700
taatgtgcct gatgacatta aaatgtgaca gtgaaaaaag tcagaggctc acatgtgtat 14760
cccaacactg aagttgttaa acactgggag gttggttgaa gttgttgtgt gcaaactcaa 14820
tactccttaa aaccattatt taaaggccta tcactgtgtt atggtctcca tatgatctgc 14880
catttatgcc aggacttgac aattcagtaa aatgacagaa taataacaca ggaatcactg 14940
cagtagagct aatgttttag tctgttgcag agttctgccc tagaaataca gtgaaaacaa 15000
ggaagggaga gctaagatgt ccctgagact aattgttcct tgaaaatatt ttcataagta 15060
aaaaagaggt ctagaggtgt agtggcagtg tgatcactca agattatata gctccggatt 15120
cgttcaatgg gccatgatga aagcacggca acgattaaat ctggtttctt ggtctttctt 15180
ggcagtgttt aaattggttc agttccataa attgtaaatt aagatctgtt tgacaacttt 15240
taagtatttc aagcataatt gtagttgaag gtttgttctt ttagatcact gacttcagaa 15300
ctttattttt ctggttaatc tcaattgtaa ttttagacat tcataaaaca atgttgactg 15360
cgtctatgtg atggtagatc ctctgtgaag acctttatga tggtagttcc cctgtgaaga 15420
taggatgaca cactcaatgg acattatggt gcacagttat acaaacactt cactatgaca 15480
ggccctgagt ttagaaccac acaactgctt ggtacttggt catcgcatat tttccccatt 15540
acgtaatgac ttcctgtgca gatgacaaaa tgcgttttct caacaaaatt attttcagtg 15600
cagctgtttt gatgactaag ttttgtagga gctttttaat caaatgcacc taagaaaacc 15660
ccaacacttt aggccctttg aacatattac actttttgc ttcctctttc ctctttttcc 15720
ttaaaaccat aatttggaaa tttgattctg ccttcccata aaagagaatt attttcaaag 15780
aaattatttg ggtctaaatt aacatgttac ttaattgttc tgcttgaatc taggtatatg 15840
attagtccca tatgaattga tgttccaaat aatttactct cattgataac taatattttc 15900
tatttccctc tattgttttg tggtggtggt ggtggctgtg gatgaacatc attctcaaat 15960
atattataat tcccttcctc atcaagccca gcatgataaa cttcagtttt gcctgatggt 16020
tcatcatctt atttctgtgt gtaagattgt tggatttgac attaaacatt tggaaactat 16080
tttataattg ataacttgtg ctttctcagc tttgagtaag cgctctcttc ttcatcttat 16140
accattttat ttttatttat tattcacttc tgcttctgat ctgagatcta ggaagctgga 16200

```
caaatcccag ataagcaagc taaacaaaca aacaacaaca acaacaacaa caacaacaac  16260
aacacaaccc aaactaaacc aaaccaaaat catgggataa tggttaagtg tactgagggg  16320
ccattatgcg aacacagttt aattccttgg ctttaaaact aataagagaa gaatacataa  16380
acaaatgtgg caaatgtacc tgtgaccctc tccagagggt gccaggctag aagaaaggca  16440
gatttatcag caaggcatgg cgggccattg gcaaaccatg ggacaaccac taccaacttc  16500
actgccattg ctccatattt ccctcccgtt ttcaatgagc cccaactttg ctcaggacat  16560
cacacatatt ctactaattt ggatgagtcc ttttgaaaga aaatatctac ctcatggttc  16620
tcaaagtatg gtccttggaa catcagcgtc agcaggactc tggagcttgt tagaaatgca  16680
gatcttaggt cgcactacag acctactgag tcagaatctg aattttgtta acatacccat  16740
gtgattcctc aaagattgag aagccctgat cagagcctgg gatgaaagtt cctgttggtt  16800
ccaagccaaa ggcatagttc aggtcttcac acatgacact attagatgta gatggatatt  16860
gttcccttct gaagaccctc aaggtcttct gagagcctat taagttcaga atgactgcct  16920
gaaatgagtg agaagtcaca aggagactct agataattaa gagatgtgtt cacagtagtc  16980
tttgataaaa acctgggaca ggcaggctta gtatgcaggc ccctaaaatt tatgtacaca  17040
atggatttcc tatttttgct tcttcacatc cagattacct ggatcagaaa taaatgtttt  17100
cattaagact tgatgtgaca aacaaacaaa acaaaactct gccaagctct agaagaacaa  17160
ttgcatttcc cagccagagg gagaacactg ccagtttttg ctgttttcca aagctgttta  17220
cctgtcctag ctcatttaaa tcactgtact ttggagttcc ggattagcgt ccccagaggt  17280
agctgcattc atacttgatg agttctttta aatctcagcc attgattgta ggttccatag  17340
tataggaaat ttagccaacc ctctattgaa tggcagttta gaaaggtcga gctacactta  17400
ccttatgtca ggttattgca gacccttgtg gcattttttcc accctaggac atgtgattta  17460
actctaatag aaatctttat tatgggtggg tctgagatta acttttattc tataaaacag  17520
aaatcatgcc actggccgta gcccattttt tgagatggag tggggggaat ggatgatagt  17580
aaacaaggat attaatctca tttattttta tatcattata tttatagtta cattgcaaat  17640
ggaagagtag agaaaccaaa aacttacact gggaacttta caatttttct tccaagtatt  17700
actgattgat gtttggacta tgcaagtgct gccagcccct tagactcact ctgcagctcc  17760
ccccatggaa atttgtgaac aggttagggt ggggataggg aaaagcatgt tcttgtttca  17820
cttcttggat tatttgttcc aggctctcca aagtaatgtg taccttggga atgcagaaat  17880
tatctcctta gatattctct ccctatatat gtcctcacag ggaattcttg gaattggaga  17940
agattccact ctcctttagg agctttctcc ataaaggtat tgagcattgg acactatatt  18000
tgcaagggaa aagaggaatg ggtctcttga gcatcaaaat cattgtagaa gaatctccaa  18060
actgtttttc aaaatgtctg tactaactta cattcctgac atcaatgggt tccctttttct  18120
ccacaagggt tccctttttct ttgcatcttc accaacactt gttatcattg gtgtttttga  18180
taataaccat tctaacagtt ggaggtgata cttcattatg attttaattt aaatttccct  18240
gataattagt gatactgagc ttctttcata tatctattgg ccatttatat ctcttctttt  18300
gagaaatgtc tgttcagatc ctttgccaat ttttttttctt ttttcaactt ttattttaga  18360
atcagggagc catgtgcagg tttgttacaa aggtatattg catgatgctg aggtttggag  18420
tgcaaatgaa tccatcacct aggtagtgac cacaattcca aacaggtagt ttttttcagc  18480
ccttttcccc ctcccaaccc cactgttgta ttccccagca tctattgtta ccattttttt  18540
```

```
gaccatgtgt atccaatatt cagcttccat ttataagtga caacatgtgg tatttggttt  18600
ttggttacta cattaattca cttaggttat tgatttccag ctgcatccat gttggtgcaa  18660
aggacattat tttgttattt tttatggcta catagtattc catggtggat atgtaccaca  18720
ttttaaaaat tcaatccacc attggtgggc acctggattg attccatgtc tttgctattg  18780
tgaatagtgc tgtgatgaac atgcaggtgc acgtgtctct ttggtagaat gacttattgt  18840
cctttgggaa tatacccagt tagtgggatt gctggatcga atggtagaaa aactctcagg  18900
tctttgagaa atctccaaac tgctctctat agtggcttat ttaatttaca ttccctacag  18960
cagtgtatca gccttctctt ttctccacag actcaccaac atagtatttt ttgacttttt  19020
aacaaaagta attctgactg gtatgagatg gtatatcatt gtggttttga tttgcatttc  19080
tttgatgatt agagatgatg agcatcattt tcatatattt atcagcctct tttatgcctt  19140
tgtttgagaa gtatctgcaa atgtcctttg cccacttttt aatggggtta tctgttttgt  19200
catgttgatt tgtttaagtt tcttaaagat tctggatatt agacctttgt tggatgcata  19260
gtatgcaaat attttctcca attttgtagg ttgcctgttt actcctttga ttgtttctct  19320
tgctgtcctt tgcctatttt ttaattgggt tatttgtttt ctggctattg agttgtttga  19380
gttccttatt tttttttttg gatattagca ctcattagat atacacttta caaatatttt  19440
ctcccaatac ctgtgttgtc tcttgattct gttaattgtt ttctttgctg tgcagaaaca  19500
ttttagtttc acacaattcc ttaaaaaact aaaaatagaa ttgccatatg atccagaaat  19560
tctacttctg gatatttatt gagaggaatt gaaatcagca tgttgaagag atatctgcac  19620
ttctatgttc gttatagcat tattcataat agtcatgata tgccatcaac ctaagtatcc  19680
attgacagat gaatggataa agaatgaggt gtatgtacac aaaggaatac tattcagcct  19740
ttaaaaagtg ggaaattctg taacaacatg gatagacaga tactatatga tcttacttat  19800
atgtggaatc taaaaaggta ggtctcacag aaacagatca taaaaaggtg gctaccagag  19860
gctgggagag gaaggaaaag aatgaggaaa gtgacatatt gatcaaagtt gtacaaagtt  19920
tcagtgcgac tggagtaata ggttttagtg atctattgta ctgcatggtg tccacagtta  19980
atagtaatgt attgtatatc ttaaaattac taaacgatta ggtatttaat gttctcccta  20040
caaaaaaatg gtaagttggt gtattagtcc actttcacac tgctataagg aactgcccga  20100
gactaagtaa tttataaaga aaagaggttt actggctcac agttctgtat ggctggggag  20160
gcctcaggaa gcttacaatc atggtgaaag ggaaagcagg tatgtcttac atggtggcag  20220
gtaagagatc ctgtgtgtga agtgaagggg gaagagtccc ttataaaacc atcagatctc  20280
gtgtgagctc actcactagc atgaaaacag catggaggaa atcaccccta tgatccaatc  20340
acctctttcc ctcaacacat ggggattaca gttccctgcc ttgatgcgtg ggattaaaat  20400
ttgagataag atttgggtgg ggacacaaag ccaaacctta tcagttggtg aggtgatgaa  20460
tatggtcatt agcttgtcta aatttgtctg caatgtatac atagatcaaa acatcacttt  20520
gtaccccata aacatgtgca attactattt tccaattaaa aataaatata aataaattaa  20580
aaataattgc aaaggaaagc tggctgtgga gaagattaac aaataatgac attaagaaat  20640
tcaggtcctt ggcaaaatta gaaatacata caaagctatc cagaacttat ttttccaaat  20700
gcattaggcg tcctctcacc ttacccttta caattgcatg gcttcagaga ttacacagaa  20760
aacgttcaga aacattgccc cagtagatga tcttgcaatg ctatgaagta ggcagaacag  20820
ctgtggctat agcaattgtg cagatagaac gtacttcatg gatggcaaga ctgggactct  20880
aggacaggct ttcaatccat tctaccctgt tgttgttctg aaatgaaagt tttatctccc  20940
```

agtttatata ggtagcctta tctttgatgc ttcaatacct gagacctggc cagtgtccct 21000
tttagtgatt gtatgtgtgt gtgtgtgtgt catatgcaat ttccttatag caatggcaca 21060
gtgtatcact gtttaattaa agaagagaaa gaaatgccaa acatacgaat aaagtctgaa 21120
tatatctgta acattaaaag tgtaggtgtc tatctttgaa gatatgtctt aaggacaatg 21180
aaagagtcag tgagtaagag aagagagtcc tgggatttca tacaagatca gtgttacttg 21240
atggtgtagg ctcctaggta tttcatcttt aggatatacc gtctattaca aaagccaaga 21300
tttttagatt tggatcaaca ttagggaact tcattctagg caagagccag gttttgcctt 21360
tatgttaata tgacctcagc tgtgagctcc attttgccag gcatcttaaa actgcaacac 21420
atatcattgg aatcttccgt tacagtctaa tacatagcca cacattggga gcaagaatga 21480
aatccaaccc ctgtcctttg caaaatgcaa tgagacagtg tctgctttgg gagcagggag 21540
tcagaatttc attgtggaca atggataagg tgagtaaaag ggcttaaaac atttgtgctt 21600
tcaagccata ggctaggata acgatagtca gaactttttg atgaagtctg accatgctac 21660
gccatttata aaattttgaa gcttgtaagt attaccccaa aatgagcagt gtgaactcaa 21720
agggtttatc attgtctctc aggcaaaggt aatatttgaa ttatttagca aaggactttg 21780
agcaattgga agagatactc agctgctggt ctctagcgct ctaacagggt ggatgccccc 21840
cgctctgccg gcactgatgt ttaagttgct ggattatgag gaagtctggg gattccttgg 21900
ggagaaaagg aagtgatgac atattgaagc acaacgacat attgaagaga ctcgggggct 21960
ggggtgataa acttcagagc cgtggctatt taccaattgg agtgtaagta ttttaatatt 22020
ttaacaaaca taattgccat tctggtatgt accaacttca tctcagatct gtccttaaga 22080
aataggcaaa ttctttattg cctctctgaa tggttcatat aaattcccag gctcccttag 22140
ctcattctaa cataaaactg tattaaaaat aatgaatgta attcatcaat aattttcctt 22200
tgtcatagca aatagtcaca agtggattga gatcagagtg atcactcata tttgttctgg 22260
ggagaaggga gcctgctgtt ttgctcctgt tttctcctag gactagtatt ttagcttcaa 22320
atgataatac cttagcacag actctgatat tcctcctaca tgcaggagca ttctcttgga 22380
ataattttgg ggatgccaat tcaaaatttc agccatgtat gatttactta ttggaaaata 22440
atcactgagc agcaataact ccagcagtta cttgtatcaa ggtagaatca agaaatagat 22500
ggtatggacc aaacttgctt ctctctaaat atgcataccc aagtgatttg ggtaaaatgt 22560
ttgtgaaggg cttacatttc ctgcaagtca gatggtttaa gagaagtaga aattatgtgt 22620
gttttgcagc attttggtaa tctgtgtgga gtgtctgtag atatttctca tgagttcaag 22680
ggaatccttt tgtggatttt gatgttccta ttggcagagc tgctgcttga ctacatgatg 22740
tctttgtatt aactacaaaa acatgcccta tcatctgagt gattttctct gccagacccc 22800
tttgtgcatc cacactctgc acctccagtg tacggaggac cttcccactg gattctaaga 22860
ttccatgcct tcccaatgca tggcagtgtc tctcatgcac atggcaaacc tactctcttg 22920
gatgtcactg ccctgaaata ttgagggagt acatttatct aggcatggta ccagggagtc 22980
atttagacat gtagggagtc tagaaagatc attgccctgg gagagtgctc agccatgctg 23040
agttctccta ctttgttgct catttctgtg tgaccttagg taacatcctc ttcaggactt 23100
ttttttttt ttttttttg acagggagtc tcattctgtc atccaggctg gagtacagtg 23160
gtgtgatctc agctcactgc aatctccgcc tcctgggttc aagcaatcct agtgcttcag 23220
tcgcctgagt agctgggatt acaggcatgc gccactacgc ccagctaata tttgtatttt 23280
cagtagagat agggttttat catgttgatc aggctggtct tgaactcctg acctcaaggg 23340
atctgcctac cttggcctcc caaagtgctg ggattacaga tgagagccac caaccctggc 23400
caggacataa tttatttcag gtgaattgat tgttggagga ttttgatcca agcaatcaat 23460
gtcccttggt gttcctttca aacagcagta agtgacctga atttattttc cacatttcca 23520
aatcttaatg aaaatcagac aatggtctat atgttcattt gtgttcttac ttaataaaat 23580
gtgggtttta gacaatattt tgccagtcat gaattcctat agaaggaact ctttgggaga 23640
acagactagt gatctataga catgatgacc tccaactcag atcttctgta gctaaccact 23700
gaccgggaga acatgtatga aaaacatctt caaaggcatt gaaaaattaa catttatcaa 23760
aaacaaaata cattttattt catttgaact tagaccttta ctatctaatg gctatggtac 23820
tatttaaatg tcaaagtgtg atctagcatc agcctaatct ggttagaaat gcaaactctt 23880
gggccacatc tcagacttac tggaccagaa gctctgtggg tgggacccag aaatctgtgt 23940
ttcattcaca tgccctccag ggattgtcc tgctaaagtt tgagaatcat ggaagctttt 24000
taacctctca ttatagcttt ataagcagca actcactgga ttcctatcaa catcctgtga 24060
gtgtcatttg gacaagtata tttataccca tttgatgcat ggtaggcaca cagatgagtc 24120
aaatgacttg aaggaataga gttttacata atatactttt atatatttat acttctaata 24180
tatttatact ttataacaga tttgactgtt ttatatattg catataaaca ttatatcagt 24240
ttctcctcca ctaaggctga ctccaatttt actccaattt tactaccaat ttttggaaga 24300
aagcctacct atcactcatg ttctctcaag taccctctaa aactattagt tagatgactc 24360
tatttaattt tccatttatt tgcccgtttc ttgctacctt tccccccaaa atgtaactgc 24420
taccttgctc aaaaggatgt gtctacttgg gatatctagc acacacattt tatgagattt 24480
taaaagacaa cataaatggt aaactatata tttaatacaa ttttgaaaga caaaatttta 24540
aaattaaaaa ggaagaaaaa aattaaacta accccataat tctcccaccc atcattagca 24600
tgtagtttgt ttagattcat ctaccaataa gtagaattgt acaaatttga tatcatgtaa 24660
tacatgtcat tttgtaaact tttttctttc cttaatatat ctatatatca taaacatttt 24720
tctatgtcta tattatttta aaattgtaat acccagagtt ctccagagaa acagaattaa 24780
taggatctcc cccttggaga tttctcatct ttttctctct cgatagatac agatagatac 24840
atacataagt ctatctctct atctctatct ttatctctaa aacacctatc catagataga 24900
catttttagg aattggctca tgtgtttgtg gaagcttgca agttcaaatg tgcagagtag 24960
gtgggcaagc taccagggaa atgttgatgt tgcagttcca gtctgaaggc aggctccttg 25020
cagaattctt ctttttctta gcagtcttac ttccccttcc tcttcccctt ctccttcccc 25080
tttcccttct tcttctcctt cccccttcttc ttattctcct tcacagactt atttttaagg 25140
ccttgagctg attagataag acccactcac attatgaggg ataatctgct ttacctgtag 25200
tctactaatt aaaatgttaa tctcatctaa aaaacacctt catagcagca ttcagacatg 25260
tttcaccaaa tatctgggca ccatggttta gcatattgat gcagaaaatt gattatcata 25320
ataatattat tttttttga gatgtagttt cactcttgtc acccaggcta gagcgcaatg 25380
ctgcaatctc agctcacttc aacctcttcc tcctaggttc aagcgattct cctgcctcag 25440
cctcctgagt agctgggact acaggcgccc atgaccacgc ccggttaatt ttgtgttttt 25500
ttagtagaga tggggtttca ccacgttggt caggctggtc tcgaactcct gacctcaggt 25560
gatccacccg cctcagcctc ccaaagtgct gggattacag gcgtgagcca ctgtgcccag 25620
caataatatt aattttaatg ggtgtgttca tttcatttta tatatgacct acaatttaac 25680 caatcccta aggctggatg ttcaggttct taatattttt tgcccgtatt tacagacacc 25740
tttgactatt ggatttattt tgttcttcag gaacaatata caaagtgtgg aaagaaatgt 25800
atatttctaa tcattggaaa ataaacactg agcagaaata actccagtag ccatttgtat 25860
cagaggaggt agaatcagga aatagatggt atgggccaga ctttcttctc tctttaagag 25920
atttgacttc atattgccaa attgcccttc tagatgtctt tactcatcca actacaattc 25980
aaaggtttgg gagggtaagc aatgccaggc ccatcttgat catccccttt ctttctcagc 26040
ctgtcagtcc ctgggaacgg gcatgatgtt gagttcctgg gccacctcct caattgaaga 26100
agtggcggaa gctggtcctg aggcacttcg ttggctgcaa ctgtatatct acaaggaccg 26160
agaagtcacc aagaagctag tgcggcaggc agagaagatg ggctacaagg ccatatttgt 26220
gacagtggac acaccttacc tgggcaaccg tctggatgat gtgcgtaaca gattcaaact 26280
gccgccacaa ctcaggtaac catgatcatg tgggccccga gctgaggcga aagggatctt 26340
gactgggaat gttagggtct gggttctact gatagcaacg ttgctaaaca tctagttaat 26400
cttcagctaa tcacatccct tttgtagaca tcactttttt tgagatacac aatagaaaca 26460
gaaatggcct ctataaaagt ccaataaatt ttcagaccag agtgcattaa gggctttggc 26520
tttgggaagt atgaattgct atacagatgg aagatactga attttgccca agcagcagtt 26580
tattattatc atcctggtgc cctatttctt tgttaaagtc aaagagccac ctttaccttt 26640
tatttttaat ggtacatggg acagctaagg ctaagaagat tgaagaaaga aaataatgaa 26700
ggtttaaaaa agccacatct ttgatccctc actgtctact tcttctttca gcaatattcc 26760
tttcactgtg gttcatccat gggtcaagat tcattgattc attcactcaa atcattcatc 26820
ttagcaaaaa caatatatca cataatctga tgttgaacta taaaggtttc atcaggtcat 26880
tcattcaccc tgtccacaag ctgtgaatta ttatctcttt cctggttgta ttttgggatt 26940
acaatcatct tgagtcaaag ctggaaactg agtggaagtc tctgggaaag actcaaacct 27000
ccttaagcta tacacctctt ttccccatca gatttccctt ccttcagttt ccaccaaaat 27060
gtgctcttgg atttttcata tgaatgtata atgtacctca ggcctataag tattttaaaa 27120
gggatcaaaa tcttagtttt aatggaggac atttttatga tggactccta cagcatccat 27180
cagaatatgt aagatgatga ggaatgtctt cctgtgttcc cagatctcat gccacagagg 27240
cccttgctta ctctatgttt gaattgtatt tggaaaaaaa aaaaaaaaca aaaaactagg 27300
gctagcaaaa ttgaaaaaag ataaaagacg aaagaagcca catgtaaaca tactgtgttt 27360
actcttctaa aatattaaaa aatgaaaaga tccaaaatca aattaatatt cccctggaat 27420
ttcatatcta tttcagtgac tgtggagtga atctcaccac gaaagttgct gcagtcttgt 27480
ataagtttca catagtttta ctgtgtttgt gcctatgtga gaataaacta ctgtgcataa 27540
aatcttgctg ttgagccatg tgtgaattag ctgtgtgatg ttacctccct gttactacca 27600
ggctggttta ggatatcatt tctgtatgtg gcaccaggat tagaccaatg acagaaaaag 27660
aaagtgctct ccctgccaaa ctggccaata aaactgttcc acatatccca gactcagggt 27720
tacctaaaca acctgtgttt aaagagaaca aaaacaaaag cctctgacat agtcttactc 27780
cttgccaaat tcgtcagaaa gctgatggat tcaaattccc ccaatatgaa tcccgtattt 27840
acattatttc tctattttga ctactttttt tttttttaa agactttcta aatagtttcc 27900
cactatcgag gcttcttaga ggaaacattt ctcattattt ccccttggct atttgaaaag 27960
gaatttgttc ttccttttcc tccatctctt aacactacta ctactaacaa tagtaacaac 28020
aatagtaagt acagtagggt tttttgtttt gtttttaact taagacatac tttcttgttc 28080
tggataccaa aatatgtttc acagaggcat ctacttagat ggggtgcaga tgacacagtt 28140
gttaattctg gcaggtacct cttgcttctt cactgctggg gctactcagt gagtggcagg 28200
aaggttgatt tgctttcccc ccttttcttt tgctcctggg ctccttccca gatgatgtga 28260
cgggccatga aacaaagact cttttcagct gtcggtgtgc atagaactgg ctgcggcttc 28320
ctagcttgtc acatctccgg tctgaagatg atcaaataat gagcaacaca tccaggttat 28380
agggaacacg ggaaacaccc cgcagctggg tgtaccccag cccctcagag tgcacattgg 28440
tgttgtttgt cctagtggac ttcggagtag gccagtgcct tctggtcagt tcctcagtgg 28500
cccacattca gctcttaaag gcagagcatg ctaacgggag gtccaggctt ccgcctgagg 28560
ccaaatacac cccaaaagct catctgttat agcctgatat gaaatcggtt tctttctgca 28620
actgacctga ctcatagaaa gtgaagcctg gcttttcata agtgaagttt ggcaggcaag 28680
ggaggcagga aatccagagg agaatgagcc tgtaaagcat ggctccttcc agcccttgtt 28740
acttcctctg cccaagtgtg ggggagggtc ctgtctcttg gcatctgggc ccagcaagag 28800
ttcagaggtt tggtagtctc tgcttggtcc atatgcaaaa cacatgtatg tgtatacatt 28860
attaatggca agggggttcc tgaaactgag agggagtaag gagacttctc atctgctctt 28920
ggaagaagca aggaatgaag ccagttcagt agactgattc ctgaggcttt ggggcaggaa 28980
ctttttcttt ctccatatcc ccatggagat ggttcattta ccctgaatta agatttggcc 29040
cttcggtgca gtgccaaggc agtttaaaga gaagaaaagt aatttctgat cattgactaa 29100
gatcaaggta aatcatgaca cttatccttt ctatgatttg ccagtgacat gttttcttaa 29160
gcccagaaat gatttattga tcgcagcagc cagaatatat cacactaaaa cagatcagcc 29220
tgccactgtc ttctcaggtc tctcatgatt aaagtggcct gctttaaagt agactcaatg 29280
tgaataggtc tccatgacct ctgcctcact gcgtagcact cacatcctca cccactcttg 29340
cactctggct tccctgcggt tctttcaata tgccaggcat gctggaaccc cggagccttt 29400
gcactggctg ttccctctgt ctgtaacagt cattcgcaga atcaacgcat gactaatagc 29460
ctcacttcca ttgagtcttg acattaggaa tggatataca tgtctatatt gggaaaccac 29520
aataaaaatt gatggtagag atgcaaatat gagcaagata acagggtggg ggcaggggag 29580
agaggtcagt ggaggacttg gcacagtagc ctcttaaatg gcacaatagc ctcttaaatt 29640
tttggttaag aaatcattca cattgataag tatggcagga taaaggtgtc catgagtgaa 29700
tcccgggaac ctgttacttt atgtggcaaa agggactttg cagatgtgat taacttaagg 29760
ggcttgagat gggaagattt ttcctgtttt tatcagtagg cttgatataa ttaaaagggt 29820
ccttataaga gggaagcaag agtgtcagag tcagagaaag agatgaaatg acagatgtag 29880
aggttggaat gatgtggtca ggaaccaggg aaagcagggg gtatctagaa gctggaaaag 29940
acaagggaat agggcttccc ctagattctc cagaaataca gccctattga tatcttgagt 30000
ttagtccagt gagacttatt ttagacttct gacatttgga actgtaatat aataccttca 30060
tgttattttt attgctgttg taacaaataa ccacaaacac agttctacta atttctttct 30120
caaggtagct tctcaatttt gccaacgctg gttaccatac atacttaaag tttcattttg 30180
agtctctgaa aactcacatc tctcttaatc tgctctactt ttttcttggc tttgtatagt 30240
gcttatgttc tgctacactt tgtaatttat tgattatgct taccatgggc agggattctt 30300
aactgtttta tttatttata tatcttaaac attgaaaaca ctggcatgta gtagatgctt 30360
aataagtaat tgttgactca atcgataaaa tatactagaa catacaagat tttcccaatg 30420
taacataact agtaagaggc tgaaccggga tttgaactca aaattcattc cctgaacctt 30480
cttctagcag ccacattgag gaagaaatta ccagggctgt gttctcaaca caagtgtttt 30540
ccgaaccaca gaattaaagg ctggtggccc atgtatcagt gtctgtattt atgagcccct 30600
ctttcaatct ctttcttttc atattgtgtt gatgctgtag cttctactgg tcatgttatt 30660
tttttgtttc ccaagacgga attatgtggc tttatcttta atgttgcatt atcaatactt 30720
ataataaata atattatgta ttactcaata ttcatgatta atagtgttac tattggttat 30780
ttaataatgt ttaacttaca ttagcagttg ttactatttt tatgatgcta aattactaac 30840
agctaaaaca acttctatat taaaaagtat atttgagtgc cactcaagag ataatgagta 30900
ccttacaaag aagaaatctt gtttctcacc tttgcgtcat taaacagatc aggatttgga 30960
gaattaagcc ctaagtaata gtgttattat tttgatctca cccctttttt tcttatgaaa 31020
tggaatactt tggttatcag aagccacttt aagcatatat atatatatat atatatatac 31080
atatatatat atatatatgt cataatccga ataaaaatag cattcatgga ggtttctttt 31140
ggagcctttg gtaaaacact ccatcgtggg tctctgtcaa gatatctgaa aactttttct 31200
tggcttctgg ctttgaacaa agtttcagag taacaacaag gcttcattgt gcactgaaat 31260
ttctgtaagg caacattcat tcaagtgttg attcgcattt caccatccaa gaataacaac 31320
agttatttat ataattttat ccacgtttct gttttttcct atccatttca ccctttcacc 31380
ccacccctgc tgaaacactg gagcttgttt gggatggggg tggggtgcca tgcagactac 31440
atacacatac agatgttttt ctttttcttt tcccggtctt gctatgggat agacagactg 31500
gactttttct tattaacaat attatttaaa agcttggaat ttattatcat ttaatcattt 31560
gtatgtaatg aaataggtct ccatggtaaa gatgtgttta ttgaccagcg gttagcttta 31620
ttcaaattag ggtgaccata gaagaccaag gactatgata taatgtacaa tcctaagtgg 31680
tttgatttaa ataaaaagaa agaccaggca tttcagctaa aatccccacc aaagcccaat 31740
gactagatgg gcatccatat gactcaatga aattttctat gatcttaaat ggccatctga 31800
gtccgtgaaa ctataggact aactattcaa tccttattga gaaagccttg ttaatagctt 31860
gaattgagtt atatgggata ggaatgttca tatctttatg acaatatatg ccacctaagc 31920
tacataacca gctgtgttag ctaaaatact ctaaagtgta aaaaatcata gttttctatt 31980
aaaggaagtc atgattgtta aaaataattt ttaaatagtg tgcctagatt cttctagtat 32040
aatatataat tttttttttt tttttatttt gagacagagt cttgctctgt cacccaggct 32100
ggagtgcagt ggctggagtt gctcactgca acctcgcctc ccgggttcaa gcgattctcg 32160
tgcctcagcc tcccaagtag ctgagattac acgtgcccac cactatgtcc ggctaatttt 32220
tttgaatttt tagtagagac tgggtttcat catgctggcc agactggtct tgaactcctg 32280
acctcaggtg atctgcccac ctcggcctcc caaagtgctg ggattacagg catgagccat 32340
tgcgcccagc cgatatataa atttttatat ggctccatga tcttctctac atttaatgac 32400
agaactggtg gaggggaaga aagagatggg actaagccag agatcaatat acatacaact 32460
atactttgac caaaaaaagg gagattgact ggcaggggaa ttaatagtat gcagaagagc 32520
aaggtgagtc cagtcactgt cattattcaa aaacagcctt tcaggagaag tttgcaactg 32580
aatttgggac tgtgggcaga taagtcacag gaatgattct attgtgtatc ctgaagtcat 32640
ccatccagct aggagtcaga ggtgcaggct gaaaagacat tgcccctaga gtggggaact 32700
gccaaaatct agccaggata ttaggccaag agaaaagacc tcaggcacag gggaagccag 32760
cttcaga 32767

<210> SEQ ID NO 929
<211> LENGTH: 223
<212> TYPE: DNA
<213> ORGANISM: Artificial Sequence
<220> FEATURE:
<223> OTHER INFORMATION: Synthetic

<400> SEQUENCE: 929
aacgaactcc atctgggata gcaataacct gtgaaaatgc tcccccggct aatttgtatc 60
aatgattatg aacaacatgc taaatcagta cttccaaagt ctatatatga ctattacagg 120
tctggggcaa atgatgaaga aactttggct gataatattg cagcattttc caggtaagaa 180
aatttatttt ttaaaatcat gttttaaaat tacacaaaga ccg 223

<210> SEQ ID NO 930
<211> LENGTH: 252
<212> TYPE: DNA
<213> ORGANISM: Artificial Sequence
<220> FEATURE:
<223> OTHER INFORMATION: Synthetic

<400> SEQUENCE: 930
tgattctgaa actctaaagc cttttatttt attttatttt ttaattctag atggaagctg 60
tatccaagga tgctccggaa tgttgctgaa acagatctgt cgacttctgt tttaggacag 120
agggtcagca tgccaatatg tgtgggggct acggccatgc agcgcatggc tcatgtggac 180
ggcgagcttg ccactgtgag aggtaggagg aagattgtca ccacagggac agaaggaggc 240
taacgtttat cg 252

<210> SEQ ID NO 931
<211> LENGTH: 356
<212> TYPE: DNA
<213> ORGANISM: Artificial Sequence
<220> FEATURE:
<223> OTHER INFORMATION: Synthetic

<400> SEQUENCE: 931
ggagggtaag caatgccagg cccatcttga tcatcccctt tctttctcag cctgtcagtc 60
cctgggaacg ggcatgatgt tgagttcctg ggccacctcc tcaattgaag aagtggcgga 120
agctggtcct gaggcacttc gttggctgca actgtatatc tacaaggacc gagaagtcac 180
caagaagcta gtgcggcagg cagagaagat gggctacaag gccatatttg tgacagtgga 240
cacaccttac ctgggcaacc gtctggatga tgtgcgtaac agattcaaac tgccgccaca 300
actcaggtaa ccatgatcat gtgggccccg agctgaggcg aaagggatct tgactg 356

<210> SEQ ID NO 932
<211> LENGTH: 276
<212> TYPE: DNA
<213> ORGANISM: Artificial Sequence
<220> FEATURE:
<223> OTHER INFORMATION: Synthetic

<400> SEQUENCE: 932
acgtatttct aatttggcaa atttctcatt ttatgcattt cttattttag gatgaaaaat 60
tttgaaacca gtactttatc attttctcct gaggaaaatt ttggagacga cagtggactt 120
gctgcatatg tggctaaagc aatagaccca tctatcagct gggaagatat caaatggctg 180
agaagactga catcattgcc aattgttgca aagggcattt tgagaggttc gtttatttct 240
ctacttgaat tcatactgac tttgtgatcc tttgtg 276

<210> SEQ ID NO 933
<211> LENGTH: 192
<212> TYPE: DNA
<213> ORGANISM: Artificial Sequence
<220> FEATURE:
<223> OTHER INFORMATION: Synthetic

<400> SEQUENCE: 933
ctgcctgtta agttacagtt tccctaaggt gcttgtttta ctctctccag gtgatgatgc 60
cagggaggct gttaaacatg gcttgaatgg gatcttggtg tcgaatcatg ggctcgaca 120 actcgatggg gtgccagcca ctgtgagttt tggcagacgc taagatttcc ttttggagtt 180
cccatttcca tc 192

<210> SEQ ID NO 934
<211> LENGTH: 444
<212> TYPE: DNA
<213> ORGANISM: Artificial Sequence
<220> FEATURE:
<223> OTHER INFORMATION: Synthetic

<400> SEQUENCE: 934
taacaattca gtgttaatag agtcacatta ttgaactttt ctttccccag attgatgttc 60
tgccagaaat tgtggaggct gtggaaggga aggtggaagt cttcctggac gggggtgtgc 120
ggaaaggcac tgatgttctg aaagctctgg ctcttggcgc caaggctgtg tttgtgggga 180
gaccaatcgt ttggggctta gctttccagg taactggaca aagaaatgaa tatataaaat 240
agacaacttg acagtaaaac aaatgaataa aacaagtcag actgatttag ttctgaatca 300
ctctgtatct tttcacttgg ttagggggag aaaggtgttc aagatgtcct cgagatacta 360
aaggaagaat tccggttggc catggctctg agtggtaaga ctcattcttg tttacaactt 420
tcttttcttt tatgatcttt aagt 444

<210> SEQ ID NO 935
<211> LENGTH: 729
<212> TYPE: DNA
<213> ORGANISM: Artificial Sequence
<220> FEATURE:
<223> OTHER INFORMATION: Synthetic

<400> SEQUENCE: 935
tgattattat tgcattcagt tcatattaaa tgtatgcatt attttttcag ggtgccagaa 60
tgtgaaagtc atcgacaaga cattggtgag gaaaaatcct ttggccgttt ccaagatctg 120
acagtgcaca atattttccc atctgtatta ttttttttca gcatgtatta cttgacaaag 180
agacactgtg cagagggtga ccacagtctg taattcccca cttcaataca aagggtgtcg 240
ttcttttcca acaaaatagc aatccctttt atttcattgc ttttgacttt tcaatgggtg 300
tcctaggaac cttttagaaa gaaatggact ttcatcctgg aaatatatta actgttaaaa 360
agaaaacatt gaaaatgtgt ttagacaacg tcatcccctg gcaggctaaa gtgctgtatc 420
ctttagtaaa attggaggta gcaaacacta aggtgaaaag ataatgatct cattgtttat 480
taacctgtat tctgtttaca tgtctttaaa acagtggttc ttaaattgta agctcaggtt 540
caaagtgttg gtaatgcctg attcacaact ttgagaaggt agcactggag agaattggaa 600
tgggtggcgg taattggtga tacttctttg aatgtagatt tccaatcaca tctttagtgt 660
ctgaatatat ccaaatgttt taggatgtat gttacttctt agagagaaat aaagcatttt 720
tgggaagaa 729

<210> SEQ ID NO 936
<211> LENGTH: 36
<212> TYPE: RNA
<213> ORGANISM: Artificial Sequence
<220> FEATURE:
<223> OTHER INFORMATION: Synthetic

<400> SEQUENCE: 936
ucucaacgau agucagacau guguccucag ugacac 36

<210> SEQ ID NO 937
<211> LENGTH: 36
<212> TYPE: RNA
<213> ORGANISM: Artificial Sequence
<220> FEATURE:
<223> OTHER INFORMATION: Synthetic

<400> SEQUENCE: 937
uuuuaacaac acucaggcau guguccacag ugacac 36

<210> SEQ ID NO 938
<211> LENGTH: 36
<212> TYPE: RNA
<213> ORGANISM: Artificial Sequence
<220> FEATURE:
<223> OTHER INFORMATION: Synthetic

<400> SEQUENCE: 938
uugaacggau acucagacau guguuuccag ugacac 36

<210> SEQ ID NO 939
<211> LENGTH: 36
<212> TYPE: RNA
<213> ORGANISM: Artificial Sequence
<220> FEATURE:
<223> OTHER INFORMATION: Synthetic

<400> SEQUENCE: 939
ugcccucaau agucagaugu guguccacag ugacac 36

<210> SEQ ID NO 940
<211> LENGTH: 36
<212> TYPE: RNA
<213> ORGANISM: Artificial Sequence
<220> FEATURE:
<223> OTHER INFORMATION: Synthetic

<400> SEQUENCE: 940
ucucaaugau acuuagauac guguccucag ugacac 36

<210> SEQ ID NO 941
<211> LENGTH: 36
<212> TYPE: RNA
<213> ORGANISM: Artificial Sequence
<220> FEATURE:
<223> OTHER INFORMATION: Synthetic

<400> SEQUENCE: 941
ucucaaugau acucagacau guguccccag ugacac 36

<210> SEQ ID NO 942
<211> LENGTH: 36

<212> TYPE: RNA
<213> ORGANISM: Artificial Sequence
<220> FEATURE:
<223> OTHER INFORMATION: Synthetic

<400> SEQUENCE: 942
ucucaaugau acuaagacau guguccucag ugacac 36

<210> SEQ ID NO 943
<211> LENGTH: 36
<212> TYPE: RNA
<213> ORGANISM: Artificial Sequence
<220> FEATURE:
<223> OTHER INFORMATION: Synthetic

<400> SEQUENCE: 943
ucucaacuau acucagacau guguccucag ugacac 36

<210> SEQ ID NO 944
<211> LENGTH: 36
<212> TYPE: RNA
<213> ORGANISM: Artificial Sequence
<220> FEATURE:
<223> OTHER INFORMATION: Synthetic

<400> SEQUENCE: 944
ucucaacgau acucagacau guguccucag ugacac 36

<210> SEQ ID NO 945
<211> LENGTH: 36
<212> TYPE: RNA
<213> ORGANISM: Artificial Sequence
<220> FEATURE:
<223> OTHER INFORMATION: Synthetic

<400> SEQUENCE: 945
ucucaacgau acuaagauau guguccucag cgacac 36

<210> SEQ ID NO 946
<211> LENGTH: 36
<212> TYPE: RNA
<213> ORGANISM: Artificial Sequence
<220> FEATURE:
<223> OTHER INFORMATION: Synthetic

<400> SEQUENCE: 946
ucucaacgau acuaagauau guguccccag ugacac 36

<210> SEQ ID NO 947
<211> LENGTH: 36
<212> TYPE: RNA
<213> ORGANISM: Artificial Sequence
<220> FEATURE:
<223> OTHER INFORMATION: Synthetic

<400> SEQUENCE: 947
ucucaacgau acuaagauau guguccacag ugacac 36

<210> SEQ ID NO 948
<211> LENGTH: 36
<212> TYPE: RNA
<213> ORGANISM: Artificial Sequence
<220> FEATURE:
<223> OTHER INFORMATION: Synthetic

<400> SEQUENCE: 948
ucucaacaau acucagacau guguccccag ugacac 36

<210> SEQ ID NO 949
<211> LENGTH: 36
<212> TYPE: RNA
<213> ORGANISM: Artificial Sequence
<220> FEATURE:
<223> OTHER INFORMATION: Synthetic

<400> SEQUENCE: 949
ucucaacaau acuaaggcau guguccccag ugaccc 36

<210> SEQ ID NO 950
<211> LENGTH: 36
<212> TYPE: RNA
<213> ORGANISM: Artificial Sequence
<220> FEATURE:
<223> OTHER INFORMATION: Synthetic

<400> SEQUENCE: 950
ucucaaagau acucagacac guguccccag ugacac 36

<210> SEQ ID NO 951
<211> LENGTH: 36
<212> TYPE: RNA
<213> ORGANISM: Artificial Sequence
<220> FEATURE:
<223> OTHER INFORMATION: Synthetic

<400> SEQUENCE: 951
ucucaaaaau acucagacau guguccucag ugacac 36

<210> SEQ ID NO 952
<211> LENGTH: 36
<212> TYPE: RNA
<213> ORGANISM: Artificial Sequence
<220> FEATURE:
<223> OTHER INFORMATION: Synthetic

<400> SEQUENCE: 952
gcgaaacaac agucagacau guguccccag ugacac 36

<210> SEQ ID NO 953
<211> LENGTH: 36
<212> TYPE: RNA
<213> ORGANISM: Artificial Sequence
<220> FEATURE:
<223> OTHER INFORMATION: Synthetic

<400> SEQUENCE: 953
ccucaacgau auuaagacau guguccgcag ugacac 36

<210> SEQ ID NO 954
<211> LENGTH: 22
<212> TYPE: RNA
<213> ORGANISM: Artificial Sequence
<220> FEATURE:
<223> OTHER INFORMATION: Synthetic

<400> SEQUENCE: 954
agacaugugu ccucagugac ac 22

<210> SEQ ID NO 955
<211> LENGTH: 3222
<212> TYPE: DNA
<213> ORGANISM: Artificial Sequence
<220> FEATURE:
<223> OTHER INFORMATION: Synthetic

<400> SEQUENCE: 955

```
atggcttcca tctctaggcc atacggcacc aagctgcgac cggacgcacg gaagaaggag     60
atgctcgata agttctttaa tacactgact aagggtcagc gcgtgttcgc agacctggcc    120
ctgtgcatct atggctccct gaccctggag atggccaagt ctctggagcc agaaagtgat    180
tcagaactgg tgtgcgctat tgggtggttt cggctggtgg acaagaccat ctggtccaag    240
gatggcatca agcaggagaa tctggtgaaa cagtacgaag cctattccgg aaaggaggct    300
tctgaagtgg tcaaaacata cctgaacagc cccagctccg acaagtacgt gtggatcgat    360
tgcaggcaga aattcctgag gtttcagcgc gagctcggca ctcgcaacct gtccgaggac    420
ttcgaatgta tgctctttga acagtacatt agactgacca agggcgagat cgaagggtat    480
gccgctattt caaatatgtt cggaaacggc gagaaggaag accggagcaa gaaaagaatg    540
tacgctacac ggatgaaaga ttggctggag gcaaacgaaa atatcacttg ggagcagtat    600
agagaggccc tgaagaacca gctgaatgct aaaaacctgg agcaggttgt ggccaattac    660
aaggggaacg ctggcggggc agaccccttc tttaagtata gcttctccaa agagggaatg    720
gtgagcaaga aagaacatgc acagcagctc gacaagttca aaccgtcct gaagaacaaa     780
gcccgggacc tgaattttcc aaacaaggag aagctgaagc agtacctgga ggccgaaatc    840
ggcattccgg tcgacgctaa cgtgtactcc cagatgttct ctaacggggt gagtgaggtc    900
cagcctaaga ccacacggaa tatgtctttt agtaacgaga aactggatct gctcactgaa    960
ctgaaggacc tgaacaaggg cgatgggttc gagtacgcca gagaagtgct gaacgggttc   1020
tttgactccg agctccacac taccgaggat aagtttaata tcacctctag gtacctggga   1080
ggcgacaaat caaaccgcct gagcaaactc tataagatct ggaagaaaga gggtgtggac   1140
tgcgaggaag gcattcagca gttctgtgaa gccgtcaaag ataagatggg ccagatcccc   1200
attcgaaatg tgctgaagta cctgtggcag ttccgggaga cagtcagtgc cgaggatttt   1260
gaagcagccg ctaaggctaa ccatctggag gaaaagatca gccgggtgaa agcccaccca   1320
atcgtgatta gcaataggta ctgggctttt gggacttccg cactggtggg aaacattatg   1380
cccgcagaca agaggcatca gggagagtat gccggtcaga atttcaaaat gtggctggag   1440
gctgaactgc actacgatgg caagaaagca aagcaccatc tgcctttttta taacgcccgc   1500
ttctttgagg aagtgtactg ctatcacccc tctgtcgccg agatcactcc tttcaaaacc   1560
aagcagtttg gctgtgaaat cgggaaggac attccagatt acgtgagcgt cgctctgaag   1620
gacaatccgt ataagaaagc aaccaaacga atcctgcgtg caatctacaa tcccgtcgcc   1680
aacacaactg gcgttgataa gaccacaaac tgcagcttca tgatcaaacg cgagaatgac   1740
gaatataagc tggtcatcaa ccgaaaaatt tccgtggatc ggcctaagag aatcgaagtg   1800
ggcaggacaa ttatggggta cgaccgcaat cagacagcta gcgatactta ttggattggc   1860
cggctggtgc cacctggaac ccggggcgca taccgcatcg gagagtggag cgtccagtat   1920
attaagtccg ggcctgtcct gtctagtact cagggagtta acaattccac taccgaccag   1980
ctggtgtaca acggcatgcc atcaagctcc gagcggttca aggcctggaa gaaagccaga   2040
atggctttta tccgaaaact cattcgtcag ctgaatgacg agggactgga atctaagggt   2100
caggattata tccccgagaa cccttctagt ttcgatgtgc ggggcgaaac cctgtacgtc   2160
tttaacagta attatctgaa ggccctggtg agcaaacaca gaaaggccaa gaaacctgtt   2220
```

```
gaggggatcc tggacgagat tgaagcctgg acatctaaag acaaggattc atgcagcctg   2280
atgcggctga gcagcctgag cgatgcttcc atgcagggaa tcgccagcct gaagagtctg   2340
attaacagct acttcaacaa gaatggctgt aaaaccatcg aggacaaaga aaagtttaat   2400
cccgtgctgt atgccaagct ggttgaggtg gaacagcgga gaacaaacaa gcggtctgag   2460
aaagtgggaa gaatcgcagg tagtctggag cagctggccc tgctgaacgg ggttgaggtg   2520
gtcatcggcg aagctgacct gggggaggtc gaaaaaggaa agagtaagaa acagaattca   2580
cggaacatgg attggtgcgc aaagcaggtg gcacagcggc tggagtacaa actggccttc   2640
catggaatcg gttactttgg agtgaacccc atgtatacca gccaccagga ccctttcgaa   2700
cataggcgcg tggctgatca catcgtcatg cgagcacgtt ttgaggaagt caacgtggag   2760
aacattgccg aatggcacgt gcgaaatttc tcaaactacc tgcgtgcaga cagcggcact   2820
gggctgtact ataagcaggc caccatggac ttcctgaaac attacggtct ggaggaacac   2880
gctgagggcc tggaaaataa gaaaatcaag ttctatgact ttagaaagat cctggaggat   2940
aaaaacctga caagcgtgat cattccaaag aggggcgggc gcatctacat ggccaccaac   3000
ccagtgacat ccgactctac cccgattaca tacgccggca agacttataa taggtgtaac   3060
gctgatgagg tggcagccgc taatatcgtt atttctgtgc tggctccccg cagtaagaaa   3120
aacgaggaac aggacgatat ccctctgatt accaagaaag ccgagagtaa gtcaccaccg   3180
aaagaccgga agagatcaaa aacaagccag ctgcctcaga aa                      3222
```

```
<210> SEQ ID NO 956
<211> LENGTH: 1074
<212> TYPE: PRT
<213> ORGANISM: Artificial Sequence
<220> FEATURE:
<223> OTHER INFORMATION: Synthetic

<400> SEQUENCE: 956

Met Ala Ser Ile Ser Arg Pro Tyr Gly Thr Lys Leu Arg Pro Asp Ala
1               5                   10                  15

Arg Lys Lys Glu Met Leu Asp Lys Phe Phe Asn Thr Leu Thr Lys Gly
            20                  25                  30

Gln Arg Val Phe Ala Asp Leu Ala Leu Cys Ile Tyr Gly Ser Leu Thr
        35                  40                  45

Leu Glu Met Ala Lys Ser Leu Glu Pro Glu Ser Asp Ser Glu Leu Val
    50                  55                  60

Cys Ala Ile Gly Trp Phe Arg Leu Val Asp Lys Thr Ile Trp Ser Lys
65                  70                  75                  80

Asp Gly Ile Lys Gln Glu Asn Leu Val Lys Gln Tyr Glu Ala Tyr Ser
                85                  90                  95

Gly Lys Glu Ala Ser Glu Val Val Lys Thr Tyr Leu Asn Ser Pro Ser
            100                 105                 110

Ser Asp Lys Tyr Val Trp Ile Asp Cys Arg Gln Lys Phe Leu Arg Phe
        115                 120                 125

Gln Arg Glu Leu Gly Thr Arg Asn Leu Ser Glu Asp Phe Glu Cys Met
    130                 135                 140

Leu Phe Glu Gln Tyr Ile Arg Leu Thr Lys Gly Glu Ile Glu Gly Tyr
145                 150                 155                 160

Ala Ala Ile Ser Asn Met Phe Gly Asn Gly Glu Lys Glu Asp Arg Ser
                165                 170                 175

Lys Lys Arg Met Tyr Ala Thr Arg Met Lys Asp Trp Leu Glu Ala Asn
            180                 185                 190
```

Glu Asn Ile Thr Trp Glu Gln Tyr Arg Glu Ala Leu Lys Asn Gln Leu
195 200 205

Asn Ala Lys Asn Leu Glu Gln Val Val Ala Asn Tyr Lys Gly Asn Ala
210 215 220

Gly Gly Ala Asp Pro Phe Phe Lys Tyr Ser Phe Ser Lys Glu Gly Met
225 230 235 240

Val Ser Lys Lys Glu His Ala Gln Gln Leu Asp Lys Phe Lys Thr Val
245 250 255

Leu Lys Asn Lys Ala Arg Asp Leu Asn Phe Pro Asn Lys Glu Lys Leu
260 265 270

Lys Gln Tyr Leu Glu Ala Glu Ile Gly Ile Pro Val Asp Ala Asn Val
275 280 285

Tyr Ser Gln Met Phe Ser Asn Gly Val Ser Glu Val Gln Pro Lys Thr
290 295 300

Thr Arg Asn Met Ser Phe Ser Asn Glu Lys Leu Asp Leu Leu Thr Glu
305 310 315 320

Leu Lys Asp Leu Asn Lys Gly Asp Gly Phe Glu Tyr Ala Arg Glu Val
325 330 335

Leu Asn Gly Phe Phe Asp Ser Glu Leu His Thr Thr Glu Asp Lys Phe
340 345 350

Asn Ile Thr Ser Arg Tyr Leu Gly Gly Asp Lys Ser Asn Arg Leu Ser
355 360 365

Lys Leu Tyr Lys Ile Trp Lys Lys Glu Gly Val Asp Cys Glu Glu Gly
370 375 380

Ile Gln Gln Phe Cys Glu Ala Val Lys Asp Lys Met Gly Gln Ile Pro
385 390 395 400

Ile Arg Asn Val Leu Lys Tyr Leu Trp Gln Phe Arg Glu Thr Val Ser
405 410 415

Ala Glu Asp Phe Glu Ala Ala Ala Lys Ala Asn His Leu Glu Glu Lys
420 425 430

Ile Ser Arg Val Lys Ala His Pro Ile Val Ile Ser Asn Arg Tyr Trp
435 440 445

Ala Phe Gly Thr Ser Ala Leu Val Gly Asn Ile Met Pro Ala Asp Lys
450 455 460

Arg His Gln Gly Glu Tyr Ala Gly Gln Asn Phe Lys Met Trp Leu Glu
465 470 475 480

Ala Glu Leu His Tyr Asp Gly Lys Lys Ala Lys His His Leu Pro Phe
485 490 495

Tyr Asn Ala Arg Phe Phe Glu Glu Val Tyr Cys Tyr His Pro Ser Val
500 505 510

Ala Glu Ile Thr Pro Phe Lys Thr Lys Gln Phe Gly Cys Glu Ile Gly
515 520 525

Lys Asp Ile Pro Asp Tyr Val Ser Val Ala Leu Lys Asp Asn Pro Tyr
530 535 540

Lys Lys Ala Thr Lys Arg Ile Leu Arg Ala Ile Tyr Asn Pro Val Ala
545 550 555 560

Asn Thr Thr Gly Val Asp Lys Thr Thr Asn Cys Ser Phe Met Ile Lys
565 570 575

Arg Glu Asn Asp Glu Tyr Lys Leu Val Ile Asn Arg Lys Ile Ser Val
580 585 590

Asp Arg Pro Lys Arg Ile Glu Val Gly Arg Thr Ile Met Gly Tyr Asp
595 600 605

```
Arg Asn Gln Thr Ala Ser Asp Thr Tyr Trp Ile Gly Arg Leu Val Pro
    610                 615                 620

Pro Gly Thr Arg Gly Ala Tyr Arg Ile Gly Glu Trp Ser Val Gln Tyr
625                 630                 635                 640

Ile Lys Ser Gly Pro Val Leu Ser Ser Thr Gln Gly Val Asn Asn Ser
                645                 650                 655

Thr Thr Asp Gln Leu Val Tyr Asn Gly Met Pro Ser Ser Ser Glu Arg
            660                 665                 670

Phe Lys Ala Trp Lys Lys Ala Arg Met Ala Phe Ile Arg Lys Leu Ile
        675                 680                 685

Arg Gln Leu Asn Asp Glu Gly Leu Glu Ser Lys Gly Gln Asp Tyr Ile
    690                 695                 700

Pro Glu Asn Pro Ser Ser Phe Asp Val Arg Gly Glu Thr Leu Tyr Val
705                 710                 715                 720

Phe Asn Ser Asn Tyr Leu Lys Ala Leu Val Ser Lys His Arg Lys Ala
                725                 730                 735

Lys Lys Pro Val Glu Gly Ile Leu Asp Glu Ile Glu Ala Trp Thr Ser
            740                 745                 750

Lys Asp Lys Asp Ser Cys Ser Leu Met Arg Leu Ser Ser Leu Ser Asp
        755                 760                 765

Ala Ser Met Gln Gly Ile Ala Ser Leu Lys Ser Leu Ile Asn Ser Tyr
    770                 775                 780

Phe Asn Lys Asn Gly Cys Lys Thr Ile Glu Asp Lys Glu Lys Phe Asn
785                 790                 795                 800

Pro Val Leu Tyr Ala Lys Leu Val Glu Val Glu Gln Arg Arg Thr Asn
                805                 810                 815

Lys Arg Ser Glu Lys Val Gly Arg Ile Ala Gly Ser Leu Glu Gln Leu
            820                 825                 830

Ala Leu Leu Asn Gly Val Glu Val Val Ile Gly Glu Ala Asp Leu Gly
        835                 840                 845

Glu Val Glu Lys Gly Lys Ser Lys Lys Gln Asn Ser Arg Asn Met Asp
    850                 855                 860

Trp Cys Ala Lys Gln Val Ala Gln Arg Leu Glu Tyr Lys Leu Ala Phe
865                 870                 875                 880

His Gly Ile Gly Tyr Phe Gly Val Asn Pro Met Tyr Thr Ser His Gln
                885                 890                 895

Asp Pro Phe Glu His Arg Arg Val Ala Asp His Ile Val Met Arg Ala
            900                 905                 910

Arg Phe Glu Glu Val Asn Val Glu Asn Ile Ala Glu Trp His Val Arg
        915                 920                 925

Asn Phe Ser Asn Tyr Leu Arg Ala Asp Ser Gly Thr Gly Leu Tyr Tyr
    930                 935                 940

Lys Gln Ala Thr Met Asp Phe Leu Lys His Tyr Gly Leu Glu Glu His
945                 950                 955                 960

Ala Glu Gly Leu Glu Asn Lys Lys Ile Lys Phe Tyr Asp Phe Arg Lys
                965                 970                 975

Ile Leu Glu Asp Lys Asn Leu Thr Ser Val Ile Ile Pro Lys Arg Gly
            980                 985                 990

Gly Arg Ile Tyr Met Ala Thr Asn  Pro Val Thr Ser Asp  Ser Thr Pro
        995                 1000                1005

Ile Thr  Tyr Ala Gly Lys Thr  Tyr Asn Arg Cys Asn  Ala Asp Glu
    1010                 1015                 1020

Val Ala  Ala Ala Asn Ile Val  Ile Ser Val Leu Ala  Pro Arg Ser
```

```
    1025                1030                1035

Lys Lys  Asn Glu Glu Gln Asp  Asp Ile Pro Leu Ile  Thr Lys Lys
    1040                1045                1050

Ala Glu  Ser Lys Ser Pro Pro  Lys Asp Arg Lys Arg  Ser Lys Thr
    1055                1060                1065

Ser Gln  Leu Pro Gln Lys
    1070


<210> SEQ ID NO 957
<211> LENGTH: 1074
<212> TYPE: PRT
<213> ORGANISM: Artificial Sequence
<220> FEATURE:
<223> OTHER INFORMATION: Synthetic

<400> SEQUENCE: 957

Met Ala Ser Ile Ser Arg Pro Tyr Gly Thr Lys Leu Arg Pro Asp Ala
1               5                   10                  15

Arg Lys Lys Glu Met Leu Asp Lys Phe Phe Asn Thr Leu Thr Lys Gly
            20                  25                  30

Gln Arg Val Phe Ala Asp Leu Ala Leu Cys Ile Tyr Gly Ser Leu Thr
        35                  40                  45

Leu Glu Met Ala Lys Ser Leu Glu Pro Glu Ser Asp Ser Glu Leu Val
    50                  55                  60

Cys Ala Ile Gly Trp Phe Arg Leu Val Asp Lys Thr Ile Trp Ser Lys
65                  70                  75                  80

Asp Gly Ile Lys Gln Glu Asn Leu Val Lys Gln Tyr Glu Ala Tyr Ser
                85                  90                  95

Gly Lys Glu Ala Ser Glu Val Val Lys Thr Tyr Leu Asn Ser Pro Ser
            100                 105                 110

Ser Asp Lys Tyr Val Trp Ile Asp Cys Arg Gln Lys Phe Leu Arg Phe
        115                 120                 125

Gln Arg Glu Leu Gly Thr Arg Asn Leu Ser Glu Asp Phe Glu Cys Met
    130                 135                 140

Leu Phe Glu Gln Tyr Ile Arg Leu Thr Lys Gly Glu Ile Glu Gly Tyr
145                 150                 155                 160

Ala Ala Ile Ser Asn Met Phe Gly Asn Gly Glu Lys Glu Asp Arg Ser
                165                 170                 175

Lys Lys Arg Met Tyr Ala Thr Arg Met Lys Asp Trp Leu Glu Ala Asn
            180                 185                 190

Glu Asn Ile Thr Trp Glu Gln Tyr Arg Glu Ala Leu Lys Asn Gln Leu
        195                 200                 205

Asn Ala Lys Asn Leu Glu Gln Val Val Ala Asn Tyr Lys Gly Asn Ala
    210                 215                 220

Gly Gly Ala Asp Pro Phe Phe Lys Tyr Ser Phe Ser Lys Glu Gly Met
225                 230                 235                 240

Val Ser Lys Lys Glu His Ala Gln Gln Leu Asp Lys Phe Lys Thr Val
                245                 250                 255

Leu Lys Asn Lys Ala Arg Asp Leu Asn Phe Pro Asn Lys Glu Lys Leu
            260                 265                 270

Lys Gln Tyr Leu Glu Ala Glu Ile Gly Ile Pro Val Asp Ala Asn Val
        275                 280                 285

Tyr Ser Gln Met Phe Ser Asn Gly Val Ser Glu Val Gln Pro Lys Thr
    290                 295                 300

Thr Arg Asn Met Ser Phe Ser Asn Glu Lys Leu Asp Leu Leu Thr Glu
```

-continued

```
305                 310                 315                 320

Leu Lys Asp Leu Asn Lys Gly Asp Gly Phe Glu Tyr Ala Arg Glu Val
                325                 330                 335

Leu Asn Gly Phe Phe Asp Ser Glu Leu His Thr Thr Glu Asp Lys Phe
            340                 345                 350

Asn Ile Thr Ser Arg Tyr Leu Gly Gly Asp Lys Ser Asn Arg Leu Ser
        355                 360                 365

Lys Leu Tyr Lys Ile Trp Lys Lys Glu Gly Val Asp Cys Glu Glu Gly
    370                 375                 380

Ile Gln Gln Phe Cys Glu Ala Val Lys Asp Lys Met Gly Gln Ile Pro
385                 390                 395                 400

Ile Arg Asn Val Leu Lys Tyr Leu Trp Gln Phe Arg Glu Thr Val Ser
                405                 410                 415

Ala Glu Asp Phe Glu Ala Ala Ala Lys Ala Asn His Leu Glu Glu Lys
            420                 425                 430

Ile Ser Arg Val Lys Ala His Pro Ile Val Ile Ser Asn Arg Tyr Trp
        435                 440                 445

Ala Phe Gly Thr Ser Ala Leu Val Gly Asn Ile Met Pro Ala Asp Lys
    450                 455                 460

Arg His Gln Gly Glu Tyr Ala Gly Gln Asn Phe Lys Met Trp Leu Glu
465                 470                 475                 480

Ala Glu Leu His Tyr Asp Gly Lys Lys Ala Lys His His Leu Pro Phe
                485                 490                 495

Tyr Asn Ala Arg Phe Phe Glu Glu Val Tyr Cys Tyr His Pro Ser Val
            500                 505                 510

Ala Glu Ile Thr Pro Phe Lys Thr Lys Gln Phe Gly Cys Glu Ile Gly
        515                 520                 525

Lys Asp Ile Pro Asp Tyr Val Ser Val Ala Leu Lys Asp Asn Pro Tyr
    530                 535                 540

Lys Lys Ala Thr Lys Arg Ile Leu Arg Ala Ile Tyr Asn Pro Val Ala
545                 550                 555                 560

Asn Thr Thr Gly Val Asp Lys Thr Thr Asn Cys Ser Phe Met Ile Lys
                565                 570                 575

Arg Glu Asn Asp Glu Tyr Lys Leu Val Ile Asn Arg Lys Ile Ser Arg
            580                 585                 590

Asp Arg Pro Lys Arg Ile Glu Val Gly Arg Thr Ile Met Gly Tyr Asp
        595                 600                 605

Arg Asn Gln Thr Ala Ser Asp Thr Tyr Trp Ile Gly Arg Leu Val Pro
    610                 615                 620

Pro Gly Thr Arg Gly Ala Tyr Arg Ile Gly Glu Trp Ser Val Gln Tyr
625                 630                 635                 640

Ile Lys Ser Gly Pro Val Leu Ser Ser Thr Gln Gly Val Asn Asn Ser
                645                 650                 655

Thr Thr Asp Gln Leu Val Tyr Asn Gly Met Pro Ser Ser Ser Glu Arg
            660                 665                 670

Phe Lys Ala Trp Lys Lys Ala Arg Met Ala Phe Ile Arg Lys Leu Ile
        675                 680                 685

Arg Gln Leu Asn Asp Glu Gly Leu Glu Ser Lys Gly Gln Asp Tyr Ile
    690                 695                 700

Pro Glu Asn Pro Ser Ser Phe Asp Val Arg Gly Glu Thr Leu Tyr Val
705                 710                 715                 720

Phe Asn Ser Asn Tyr Leu Lys Ala Leu Val Ser Lys His Arg Lys Ala
                725                 730                 735
```

Lys Lys Pro Val Glu Gly Ile Leu Asp Glu Ile Glu Ala Trp Thr Ser
740 745 750

Lys Asp Lys Asp Ser Cys Ser Leu Met Arg Leu Ser Ser Leu Ser Asp
755 760 765

Ala Ser Met Gln Gly Ile Ala Ser Leu Lys Ser Leu Ile Asn Ser Tyr
770 775 780

Phe Asn Lys Asn Gly Cys Lys Thr Ile Glu Asp Lys Glu Lys Phe Asn
785 790 795 800

Pro Val Leu Tyr Ala Lys Leu Val Glu Val Glu Gln Arg Arg Thr Asn
805 810 815

Lys Arg Ser Glu Lys Val Gly Arg Ile Ala Gly Ser Leu Glu Gln Leu
820 825 830

Ala Leu Leu Asn Gly Val Glu Val Val Ile Gly Glu Ala Asp Leu Gly
835 840 845

Glu Val Glu Lys Gly Lys Ser Lys Lys Gln Asn Ser Arg Asn Met Asp
850 855 860

Trp Cys Ala Lys Gln Val Ala Gln Arg Leu Glu Tyr Lys Leu Ala Phe
865 870 875 880

His Gly Ile Gly Tyr Phe Gly Val Asn Pro Met Tyr Thr Ser His Gln
885 890 895

Asp Pro Phe Glu His Arg Arg Val Ala Asp His Ile Val Met Arg Ala
900 905 910

Arg Phe Glu Glu Val Asn Val Glu Asn Ile Ala Glu Trp His Val Arg
915 920 925

Asn Phe Ser Asn Tyr Leu Arg Ala Asp Ser Gly Thr Gly Leu Tyr Tyr
930 935 940

Lys Gln Ala Thr Met Asp Phe Leu Lys His Tyr Gly Leu Glu Glu His
945 950 955 960

Ala Glu Gly Leu Glu Asn Lys Lys Ile Lys Phe Tyr Asp Phe Arg Lys
965 970 975

Ile Leu Glu Asp Lys Asn Leu Thr Ser Val Ile Ile Pro Lys Arg Gly
980 985 990

Gly Arg Ile Tyr Met Ala Thr Asn Pro Val Thr Ser Asp Ser Thr Pro
995 1000 1005

Ile Thr Tyr Ala Gly Lys Thr Tyr Asn Arg Cys Asn Ala Asp Glu
1010 1015 1020

Val Ala Ala Ala Asn Ile Val Ile Ser Val Leu Ala Pro Arg Ser
1025 1030 1035

Lys Lys Asn Arg Glu Gln Asp Asp Ile Pro Leu Ile Thr Lys Lys
1040 1045 1050

Ala Glu Ser Lys Ser Pro Pro Lys Asp Arg Lys Arg Ser Lys Thr
1055 1060 1065

Ser Gln Leu Pro Gln Lys
1070

<210> SEQ ID NO 958
<211> LENGTH: 1074
<212> TYPE: PRT
<213> ORGANISM: Artificial Sequence
<220> FEATURE:
<223> OTHER INFORMATION: Synthetic

<400> SEQUENCE: 958

Met Ala Ser Ile Ser Arg Pro Tyr Gly Thr Lys Leu Arg Pro Asp Ala
1 5 10 15

```
Arg Lys Lys Glu Met Leu Asp Lys Phe Phe Asn Thr Leu Thr Lys Gly
            20                  25                  30

Gln Arg Val Phe Ala Asp Leu Ala Leu Cys Ile Tyr Gly Ser Leu Thr
        35                  40                  45

Leu Glu Met Ala Lys Ser Leu Glu Pro Glu Ser Asp Ser Glu Leu Val
    50                  55                  60

Cys Ala Ile Gly Trp Phe Arg Leu Val Asp Lys Thr Ile Trp Ser Lys
65                  70                  75                  80

Asp Gly Ile Lys Gln Glu Asn Leu Val Lys Gln Tyr Glu Ala Tyr Ser
                85                  90                  95

Gly Lys Glu Ala Ser Glu Val Val Lys Thr Tyr Leu Asn Ser Pro Ser
            100                 105                 110

Ser Asp Lys Tyr Val Trp Ile Asp Cys Arg Gln Lys Phe Leu Arg Phe
        115                 120                 125

Gln Arg Glu Leu Gly Thr Arg Asn Leu Ser Glu Asp Phe Glu Cys Met
    130                 135                 140

Leu Phe Glu Gln Tyr Ile Arg Leu Thr Lys Gly Glu Ile Glu Gly Tyr
145                 150                 155                 160

Ala Ala Ile Ser Asn Met Phe Gly Asn Gly Glu Lys Glu Asp Arg Ser
                165                 170                 175

Lys Lys Arg Met Tyr Ala Thr Arg Met Lys Asp Trp Leu Glu Ala Asn
            180                 185                 190

Glu Asn Ile Thr Trp Glu Gln Tyr Arg Glu Ala Leu Lys Asn Gln Leu
        195                 200                 205

Asn Ala Lys Asn Leu Glu Gln Val Val Ala Asn Tyr Lys Gly Asn Ala
    210                 215                 220

Gly Gly Ala Asp Pro Phe Phe Lys Tyr Ser Phe Ser Lys Glu Gly Met
225                 230                 235                 240

Val Ser Lys Lys Glu His Ala Gln Gln Leu Asp Lys Phe Lys Thr Val
                245                 250                 255

Leu Lys Asn Lys Ala Arg Asp Leu Asn Phe Pro Asn Lys Glu Lys Leu
            260                 265                 270

Lys Gln Tyr Leu Glu Ala Glu Ile Gly Ile Pro Val Asp Ala Asn Val
        275                 280                 285

Tyr Ser Gln Met Phe Ser Asn Gly Val Ser Glu Val Gln Pro Lys Thr
    290                 295                 300

Thr Arg Asn Met Ser Phe Ser Asn Glu Lys Leu Asp Leu Leu Thr Glu
305                 310                 315                 320

Leu Lys Asp Leu Asn Lys Gly Asp Gly Phe Glu Tyr Ala Arg Glu Val
                325                 330                 335

Leu Asn Gly Phe Phe Asp Ser Glu Leu His Thr Thr Glu Asp Lys Phe
            340                 345                 350

Asn Ile Thr Ser Arg Tyr Leu Gly Gly Asp Lys Ser Asn Arg Leu Ser
        355                 360                 365

Lys Leu Tyr Lys Ile Trp Lys Lys Glu Gly Val Asp Cys Glu Glu Gly
    370                 375                 380

Ile Gln Gln Phe Cys Glu Ala Val Lys Asp Lys Met Gly Gln Ile Pro
385                 390                 395                 400

Ile Arg Asn Val Leu Lys Tyr Leu Trp Gln Phe Arg Glu Thr Val Ser
                405                 410                 415

Ala Glu Asp Phe Glu Ala Ala Ala Lys Ala Asn His Leu Glu Glu Lys
            420                 425                 430
```

-continued

```
Ile Ser Arg Val Lys Ala His Pro Ile Val Ile Ser Asn Arg Tyr Trp
        435                 440                 445

Ala Phe Gly Thr Ser Ala Leu Val Gly Asn Ile Met Pro Ala Asp Lys
    450                 455                 460

Arg His Gln Gly Glu Tyr Ala Gly Gln Asn Phe Lys Met Trp Leu Arg
465                 470                 475                 480

Ala Glu Leu His Tyr Asp Gly Lys Lys Ala Lys His His Leu Pro Phe
                485                 490                 495

Tyr Asn Ala Arg Phe Phe Glu Glu Val Tyr Cys Tyr His Pro Ser Val
            500                 505                 510

Ala Glu Ile Thr Pro Phe Lys Thr Lys Gln Phe Gly Cys Glu Ile Gly
        515                 520                 525

Lys Asp Ile Pro Asp Tyr Val Ser Val Ala Leu Lys Asp Asn Pro Tyr
    530                 535                 540

Lys Lys Ala Thr Lys Arg Ile Leu Arg Ala Ile Tyr Asn Pro Val Ala
545                 550                 555                 560

Asn Thr Thr Arg Val Asp Lys Thr Thr Asn Cys Ser Phe Met Ile Lys
                565                 570                 575

Arg Glu Asn Asp Glu Tyr Lys Leu Val Ile Asn Arg Lys Ile Ser Arg
            580                 585                 590

Asp Arg Pro Lys Arg Ile Glu Val Gly Arg Thr Ile Met Gly Tyr Asp
        595                 600                 605

Arg Asn Gln Thr Ala Ser Asp Thr Tyr Trp Ile Gly Arg Leu Val Pro
    610                 615                 620

Pro Gly Thr Arg Gly Ala Tyr Arg Ile Gly Glu Trp Ser Val Gln Tyr
625                 630                 635                 640

Ile Lys Ser Gly Pro Val Leu Ser Ser Thr Gln Gly Val Asn Asn Ser
                645                 650                 655

Thr Thr Asp Gln Leu Val Tyr Asn Gly Met Pro Ser Ser Ser Glu Arg
            660                 665                 670

Phe Lys Ala Trp Lys Lys Ala Arg Met Ala Phe Ile Arg Lys Leu Ile
        675                 680                 685

Arg Gln Leu Asn Asp Glu Gly Leu Glu Ser Lys Gly Gln Asp Tyr Ile
    690                 695                 700

Pro Glu Asn Pro Ser Ser Phe Asp Val Arg Gly Glu Thr Leu Tyr Val
705                 710                 715                 720

Phe Asn Ser Asn Tyr Leu Lys Ala Leu Val Ser Lys His Arg Lys Ala
                725                 730                 735

Lys Lys Pro Val Glu Gly Ile Leu Asp Glu Ile Glu Ala Trp Thr Ser
            740                 745                 750

Lys Asp Lys Asp Ser Cys Ser Leu Met Arg Leu Ser Ser Leu Ser Asp
        755                 760                 765

Ala Ser Met Gln Gly Ile Ala Ser Leu Lys Ser Leu Ile Asn Ser Tyr
    770                 775                 780

Phe Asn Lys Asn Gly Cys Lys Thr Ile Glu Asp Lys Glu Lys Phe Asn
785                 790                 795                 800

Pro Val Leu Tyr Ala Lys Leu Val Glu Val Glu Gln Arg Arg Thr Asn
                805                 810                 815

Lys Arg Ser Glu Lys Val Gly Arg Ile Ala Gly Ser Leu Glu Gln Leu
            820                 825                 830

Ala Leu Leu Asn Gly Val Glu Val Val Ile Gly Glu Ala Asp Leu Gly
        835                 840                 845

Glu Val Glu Lys Gly Lys Ser Lys Lys Gln Asn Ser Arg Asn Met Asp
```

```
    850                 855                 860

Trp Cys Ala Lys Gln Val Ala Gln Arg Leu Glu Tyr Lys Leu Ala Phe
865                 870                 875                 880

His Gly Ile Gly Tyr Phe Gly Val Asn Pro Met Tyr Thr Ser His Gln
                885                 890                 895

Asp Pro Phe Glu His Arg Arg Val Ala Asp His Ile Val Met Arg Ala
            900                 905                 910

Arg Phe Glu Glu Val Asn Val Glu Asn Ile Ala Glu Trp His Val Arg
        915                 920                 925

Asn Phe Ser Asn Tyr Leu Arg Ala Asp Ser Gly Thr Gly Leu Tyr Tyr
    930                 935                 940

Lys Gln Ala Thr Met Asp Phe Leu Lys His Tyr Gly Leu Glu Glu His
945                 950                 955                 960

Ala Glu Gly Leu Glu Asn Lys Lys Ile Lys Phe Tyr Asp Phe Arg Lys
                965                 970                 975

Ile Leu Glu Asp Lys Asn Leu Thr Ser Val Ile Ile Pro Lys Arg Gly
            980                 985                 990

Gly Arg Ile Tyr Met Ala Thr Asn  Pro Val Thr Ser Asp  Ser Thr Pro
        995                 1000                1005

Ile Thr  Tyr Ala Gly Lys Thr  Tyr Asn Arg Cys Asn  Ala Asp Glu
    1010                1015                1020

Val Ala  Ala Ala Asn Ile Val  Ile Ser Val Leu Ala  Pro Arg Ser
    1025                1030                1035

Lys Lys  Asn Arg Glu Gln Asp  Asp Ile Pro Leu Ile  Thr Lys Lys
    1040                1045                1050

Ala Glu  Ser Lys Ser Pro Pro  Lys Asp Arg Lys Arg  Ser Lys Thr
    1055                1060                1065

Ser Gln  Leu Pro Gln Lys
    1070
```

<210> SEQ ID NO 959
<211> LENGTH: 36
<212> TYPE: RNA
<213> ORGANISM: Artificial Sequence
<220> FEATURE:
<223> OTHER INFORMATION: Synthetic

<400> SEQUENCE: 959
guuggaauga cuaauuuuug ugcccaccgu uggcac 36

<210> SEQ ID NO 960
<211> LENGTH: 24
<212> TYPE: RNA
<213> ORGANISM: Artificial Sequence
<220> FEATURE:
<223> OTHER INFORMATION: Synthetic

<400> SEQUENCE: 960
aauuuuugug cccaucguug gcac 24

<210> SEQ ID NO 961
<211> LENGTH: 23
<212> TYPE: RNA
<213> ORGANISM: Artificial Sequence
<220> FEATURE:
<223> OTHER INFORMATION: Synthetic

<400> SEQUENCE: 961
auuuuugugc ccaucguugg cac 23

<210> SEQ ID NO 962
<211> LENGTH: 36
<212> TYPE: RNA
<213> ORGANISM: Artificial Sequence
<220> FEATURE:
<223> OTHER INFORMATION: Synthetic

<400> SEQUENCE: 962
cuagcaauga ccuaauagug uguccuuagu ugacau 36

<210> SEQ ID NO 963
<211> LENGTH: 36
<212> TYPE: RNA
<213> ORGANISM: Artificial Sequence
<220> FEATURE:
<223> OTHER INFORMATION: Synthetic

<400> SEQUENCE: 963
ccuacaauac cuaagaaauc cguccuaagu ugacgg 36

<210> SEQ ID NO 964
<211> LENGTH: 22
<212> TYPE: RNA
<213> ORGANISM: Artificial Sequence
<220> FEATURE:
<223> OTHER INFORMATION: Synthetic

<400> SEQUENCE: 964 auagugugucc cuuaguugac au 22

<210> SEQ ID NO 965
<211> LENGTH: 1093
<212> TYPE: PRT
<213> ORGANISM: Artificial Sequence
<220> FEATURE:
<223> OTHER INFORMATION: Synthetic

<400> SEQUENCE: 965

```
Met Ser Asn Lys Glu Lys Asn Ala Ser Glu Thr Arg Lys Ala Tyr Thr
1               5                   10                  15

Thr Lys Met Ile Pro Arg Ser His Asp Arg Met Lys Leu Leu Gly Asn
            20                  25                  30

Phe Met Asp Tyr Leu Met Asp Gly Thr Pro Ile Phe Phe Glu Leu Trp
        35                  40                  45

Asn Gln Phe Gly Gly Gly Ile Asp Arg Asp Ile Ile Ser Gly Thr Ala
    50                  55                  60

Asn Lys Asp Lys Ile Ser Asp Asp Leu Leu Leu Ala Val Asn Trp Phe
65                  70                  75                  80

Lys Val Met Pro Ile Asn Ser Lys Pro Gln Gly Val Ser Pro Ser Asn
                85                  90                  95

Leu Ala Asn Leu Phe Gln Gln Tyr Ser Gly Ser Glu Pro Asp Ile Gln
            100                 105                 110

Ala Gln Glu Tyr Phe Ala Ser Asn Phe Asp Thr Glu Lys His Gln Trp
        115                 120                 125

Lys Asp Met Arg Val Glu Tyr Glu Arg Leu Leu Ala Glu Leu Gln Leu
    130                 135                 140

Ser Arg Ser Asp Met His His Asp Leu Lys Leu Met Tyr Lys Glu Lys
145                 150                 155                 160

Cys Ile Gly Leu Ser Leu Ser Thr Ala His Tyr Ile Thr Ser Val Met
                165                 170                 175
```

```
Phe Gly Thr Gly Ala Lys Asn Asn Arg Gln Thr Lys His Gln Phe Tyr
            180                 185                 190

Ser Lys Val Ile Gln Leu Leu Glu Glu Ser Thr Gln Ile Asn Ser Val
        195                 200                 205

Glu Gln Leu Ala Ser Ile Ile Leu Lys Ala Gly Asp Cys Asp Ser Tyr
    210                 215                 220

Arg Lys Leu Arg Ile Arg Cys Ser Arg Lys Gly Ala Thr Pro Ser Ile
225                 230                 235                 240

Leu Lys Ile Val Gln Asp Tyr Glu Leu Gly Thr Asn His Asp Asp Glu
                245                 250                 255

Val Asn Val Pro Ser Leu Ile Ala Asn Leu Lys Glu Lys Leu Gly Arg
            260                 265                 270

Phe Glu Tyr Glu Cys Glu Trp Lys Cys Met Glu Lys Ile Lys Ala Phe
        275                 280                 285

Leu Ala Ser Lys Val Gly Pro Tyr Tyr Leu Gly Ser Tyr Ser Ala Met
    290                 295                 300

Leu Glu Asn Ala Leu Ser Pro Ile Lys Gly Met Thr Thr Lys Asn Cys
305                 310                 315                 320

Lys Phe Val Leu Lys Gln Ile Asp Ala Lys Asn Asp Ile Lys Tyr Glu
                325                 330                 335

Asn Glu Pro Phe Gly Lys Ile Val Glu Gly Phe Phe Asp Ser Pro Tyr
            340                 345                 350

Phe Glu Ser Asp Thr Asn Val Lys Trp Val Leu His Pro His His Ile
        355                 360                 365

Gly Glu Ser Asn Ile Lys Thr Leu Trp Glu Asp Leu Asn Ala Ile His
    370                 375                 380

Ser Lys Tyr Glu Glu Asp Ile Ala Ser Leu Ser Glu Asp Lys Lys Glu
385                 390                 395                 400

Lys Arg Ile Lys Val Tyr Gln Gly Asp Val Cys Gln Thr Ile Asn Thr
                405                 410                 415

Tyr Cys Glu Glu Val Gly Lys Glu Ala Lys Thr Pro Leu Val Gln Leu
            420                 425                 430

Leu Arg Tyr Leu Tyr Ser Arg Lys Asp Asp Ile Ala Val Asp Lys Ile
        435                 440                 445

Ile Asp Gly Ile Thr Phe Leu Ser Lys Lys His Lys Val Glu Lys Gln
    450                 455                 460

Lys Ile Asn Pro Val Ile Gln Lys Tyr Pro Ser Phe Asn Phe Gly Asn
465                 470                 475                 480

Asn Ser Lys Leu Leu Gly Lys Ile Ile Ser Pro Lys Asp Lys Leu Lys
                485                 490                 495

His Asn Leu Lys Cys Asn Arg Asn Gln Val Asp Asn Tyr Ile Trp Ile
            500                 505                 510

Glu Ile Lys Val Leu Asn Thr Lys Thr Met Arg Trp Glu Lys His His
        515                 520                 525

Tyr Ala Leu Ser Ser Thr Arg Phe Leu Glu Glu Val Tyr Tyr Pro Ala
    530                 535                 540

Thr Ser Glu Asn Pro Pro Asp Ala Leu Ala Ala Arg Phe Arg Thr Lys
545                 550                 555                 560

Thr Asn Gly Tyr Glu Gly Lys Pro Ala Leu Ser Ala Glu Gln Ile Glu
                565                 570                 575

Gln Ile Arg Ser Ala Pro Val Gly Leu Arg Lys Val Lys Lys Arg Gln
            580                 585                 590
```

```
Met Arg Leu Glu Ala Ala Arg Gln Gln Asn Leu Leu Pro Arg Tyr Thr
        595                 600                 605

Trp Gly Lys Asp Phe Asn Ile Asn Ile Cys Lys Arg Gly Asn Asn Phe
    610                 615                 620

Glu Val Thr Leu Ala Thr Lys Val Lys Lys Lys Lys Glu Lys Asn Tyr
625                 630                 635                 640

Lys Val Val Leu Gly Tyr Asp Ala Asn Ile Val Arg Lys Asn Thr Tyr
                645                 650                 655

Ala Ala Ile Glu Ala His Ala Asn Gly Asp Gly Val Ile Asp Tyr Asn
            660                 665                 670

Asp Leu Pro Val Lys Pro Ile Glu Ser Gly Phe Val Thr Val Glu Ser
        675                 680                 685

Gln Val Arg Asp Lys Ser Tyr Asp Gln Leu Ser Tyr Asn Gly Val Lys
    690                 695                 700

Leu Leu Tyr Cys Lys Pro His Val Glu Ser Arg Arg Ser Phe Leu Glu
705                 710                 715                 720

Lys Tyr Arg Asn Gly Thr Met Lys Asp Asn Arg Gly Asn Asn Ile Gln
                725                 730                 735

Ile Asp Phe Met Lys Asp Phe Glu Ala Ile Ala Asp Asp Glu Thr Ser
            740                 745                 750

Leu Tyr Tyr Phe Asn Met Lys Tyr Cys Lys Leu Leu Gln Ser Ser Ile
        755                 760                 765

Arg Asn His Ser Ser Gln Ala Lys Glu Tyr Arg Glu Glu Ile Phe Glu
    770                 775                 780

Leu Leu Arg Asp Gly Lys Leu Ser Val Leu Lys Leu Ser Ser Leu Ser
785                 790                 795                 800

Asn Leu Ser Phe Val Met Phe Lys Val Ala Lys Ser Leu Ile Gly Thr
                805                 810                 815

Tyr Phe Gly His Leu Leu Lys Lys Pro Lys Asn Ser Lys Ser Asp Val
            820                 825                 830

Lys Ala Pro Pro Ile Thr Asp Glu Asp Lys Gln Lys Ala Asp Pro Glu
        835                 840                 845

Met Phe Ala Leu Arg Leu Ala Leu Glu Glu Lys Arg Leu Asn Lys Val
    850                 855                 860

Lys Ser Lys Lys Glu Val Ile Ala Asn Lys Ile Val Ala Lys Ala Leu
865                 870                 875                 880

Glu Leu Arg Asp Lys Tyr Gly Pro Val Leu Ile Lys Gly Glu Asn Ile
                885                 890                 895

Ser Asp Thr Thr Lys Lys Gly Lys Lys Ser Ser Thr Asn Ser Phe Leu
            900                 905                 910

Met Asp Trp Leu Ala Arg Gly Val Ala Asn Lys Val Lys Glu Met Val
        915                 920                 925

Met Met His Gln Gly Leu Glu Phe Val Glu Val Asn Pro Asn Phe Thr
    930                 935                 940

Ser His Gln Asp Pro Phe Val His Lys Asn Pro Glu Asn Thr Phe Arg
945                 950                 955                 960

Ala Arg Tyr Ser Arg Cys Thr Pro Ser Glu Leu Thr Glu Lys Asn Arg
                965                 970                 975

Lys Glu Ile Leu Ser Phe Leu Ser Asp Lys Pro Ser Lys Arg Pro Thr
            980                 985                 990

Asn Ala Tyr Tyr Asn Glu Gly Ala  Met Ala Phe Leu Ala  Thr Tyr Gly
        995                 1000                1005

Leu Lys  Lys Asn Asp Val Leu  Gly Val Ser Leu Glu  Lys Phe Lys
```

1010 1015 1020

Gln Ile Met Ala Asn Ile Leu His Gln Arg Ser Glu Asp Gln Leu
1025 1030 1035

Leu Phe Pro Ser Arg Gly Gly Met Phe Tyr Leu Ala Thr Tyr Lys
1040 1045 1050

Leu Asp Ala Asp Ala Thr Ser Val Asn Trp Asn Gly Lys Gln Phe
1055 1060 1065

Trp Val Cys Asn Ala Asp Leu Val Ala Ala Tyr Asn Val Gly Leu
1070 1075 1080

Val Asp Ile Gln Lys Asp Phe Lys Lys Lys
1085 1090

<210> SEQ ID NO 966
<211> LENGTH: 1098
<212> TYPE: PRT
<213> ORGANISM: Artificial Sequence
<220> FEATURE:
<223> OTHER INFORMATION: Synthetic

<400> SEQUENCE: 966

Met Ser Ile Ser Asn Asn Asn Ile Leu Pro Tyr Asn Pro Lys Leu Leu
1 5 10 15

Pro Asp Asp Arg Lys His Lys Met Leu Val Asp Thr Phe Asn Gln Leu
20 25 30

Asp Leu Ile Arg Asn Asn Leu His Asp Met Ile Ile Ala Leu Tyr Gly
35 40 45

Ala Leu Lys Tyr Asp Asn Ile Lys Gln Phe Ala Ser Lys Glu Lys Pro
50 55 60

His Ile Ser Ala Asp Ala Leu Cys Ser Ile Asn Trp Phe Arg Leu Val
65 70 75 80

Lys Thr Asn Glu Arg Lys Pro Ala Ile Glu Ser Asn Gln Ile Ile Ser
85 90 95

Lys Phe Ile Gln Tyr Ser Gly His Thr Pro Asp Lys Tyr Ala Leu Ser
100 105 110

His Ile Thr Gly Asn His Glu Pro Ser His Lys Trp Ile Asp Cys Arg
115 120 125

Glu Tyr Ala Ile Asn Tyr Ala Arg Ile Met His Leu Ser Phe Ser Gln
130 135 140

Phe Gln Asp Leu Ala Thr Ala Cys Leu Asn Cys Lys Ile Leu Ile Leu
145 150 155 160

Asn Gly Thr Leu Thr Ser Ser Trp Ala Trp Gly Ala Asn Ser Ala Leu
165 170 175

Phe Gly Gly Ser Asp Lys Glu Asn Phe Ser Val Lys Ala Lys Ile Leu
180 185 190

Asn Ser Phe Ile Glu Asn Leu Lys Asp Glu Met Asn Thr Thr Lys Phe
195 200 205

Gln Val Val Glu Lys Val Cys Gln Gln Ile Gly Ser Ser Asp Ala Ala
210 215 220

Asp Leu Phe Asp Leu Tyr Arg Ser Thr Val Lys Asp Gly Asn Arg Gly
225 230 235 240

Pro Ala Thr Gly Arg Asn Pro Lys Val Met Asn Leu Phe Ser Gln Asp
245 250 255

Gly Glu Ile Ser Ser Glu Gln Arg Glu Asp Phe Ile Glu Ser Phe Gln
260 265 270

Lys Val Met Gln Glu Lys Asn Ser Lys Gln Ile Ile Pro His Leu Asp

-continued

```
        275                 280                 285

Lys Leu Lys Tyr His Leu Val Lys Gln Ser Gly Leu Tyr Asp Ile Tyr
    290                 295                 300

Ser Trp Ala Ala Ala Ile Lys Asn Ala Asn Ser Thr Ile Val Ala Ser
305                 310                 315                 320

Asn Ser Ser Asn Leu Asn Thr Ile Leu Asn Lys Thr Glu Lys Gln Gln
                325                 330                 335

Thr Phe Glu Glu Leu Arg Lys Asp Glu Lys Ile Val Ala Cys Ser Lys
            340                 345                 350

Ile Leu Leu Ser Val Asn Asp Thr Leu Pro Glu Asp Leu His Tyr Asn
        355                 360                 365

Pro Ser Thr Ser Asn Leu Gly Lys Asn Leu Asp Val Phe Phe Asp Leu
    370                 375                 380

Leu Asn Glu Asn Ser Val His Thr Ile Glu Asn Lys Glu Glu Lys Asn
385                 390                 395                 400

Lys Ile Val Lys Glu Cys Val Asn Gln Tyr Met Glu Glu Cys Lys Gly
                405                 410                 415

Leu Asn Lys Pro Pro Met Pro Val Leu Leu Thr Phe Ile Ser Asp Tyr
            420                 425                 430

Ala His Lys His Gln Ala Gln Asp Phe Leu Ser Ala Ala Lys Met Asn
        435                 440                 445

Phe Ile Asp Leu Lys Ile Lys Ser Ile Lys Val Val Pro Thr Val His
    450                 455                 460

Gly Ser Ser Pro Tyr Thr Trp Ile Ser Asn Leu Ser Lys Lys Asn Lys
465                 470                 475                 480

Asp Gly Lys Met Ile Arg Thr Pro Asn Ser Ser Leu Ile Gly Trp Ile
                485                 490                 495

Ile Pro Pro Glu Glu Ile His Asp Gln Lys Phe Ala Gly Gln Asn Pro
            500                 505                 510

Ile Ile Trp Ala Val Leu Arg Val Tyr Cys Asn Asn Lys Trp Glu Met
        515                 520                 525

His His Phe Pro Phe Ser Asp Ser Arg Phe Phe Thr Glu Val Tyr Ala
    530                 535                 540

Tyr Lys Pro Asn Leu Pro Tyr Leu Pro Gly Gly Glu Asn Arg Ser Lys
545                 550                 555                 560

Arg Phe Gly Tyr Arg His Ser Thr Asn Leu Ser Asn Glu Ser Arg Gln
                565                 570                 575

Ile Leu Leu Asp Lys Ser Lys Tyr Ala Lys Ala Asn Lys Ser Val Leu
            580                 585                 590

Arg Cys Met Glu Asn Met Thr His Asn Val Val Phe Asp Pro Lys Thr
        595                 600                 605

Ser Leu Asn Ile Arg Ile Lys Thr Asp Lys Asn Asn Ser Pro Val Leu
    610                 615                 620

Asp Asp Lys Gly Arg Ile Thr Phe Val Met Gln Ile Asn His Arg Ile
625                 630                 635                 640

Leu Glu Lys Tyr Asn Asn Thr Lys Ile Glu Ile Gly Asp Arg Ile Leu
                645                 650                 655

Ala Tyr Asp Gln Asn Gln Ser Glu Asn His Thr Tyr Ala Ile Leu Gln
            660                 665                 670

Arg Thr Glu Glu Gly Ser His Ala His Gln Phe Asn Gly Trp Tyr Val
        675                 680                 685

Arg Val Leu Glu Thr Gly Lys Val Thr Ser Ile Val Gln Gly Leu Ser
    690                 695                 700
```

Gly Pro Ile Asp Gln Leu Asn Tyr Asp Gly Met Pro Val Thr Ser His
705 710 715 720

Lys Phe Asn Cys Trp Gln Ala Asp Arg Ser Ala Phe Val Ser Gln Phe
725 730 735

Ala Ser Leu Lys Ile Ser Glu Thr Glu Thr Phe Asp Glu Ala Tyr Gln
740 745 750

Ala Ile Asn Ala Gln Gly Ala Tyr Thr Trp Asn Leu Phe Tyr Leu Arg
755 760 765

Ile Leu Arg Lys Ala Leu Arg Val Cys His Met Glu Asn Ile Asn Gln
770 775 780

Phe Arg Glu Glu Ile Leu Ala Ile Ser Lys Asn Arg Leu Ser Pro Met
785 790 795 800

Ser Leu Gly Ser Leu Ser Gln Asn Ser Leu Lys Met Ile Arg Ala Phe
805 810 815

Lys Ser Ile Ile Asn Cys Tyr Met Ser Arg Met Ser Phe Val Asp Glu
820 825 830

Leu Gln Lys Lys Glu Gly Asp Leu Glu Leu His Thr Ile Met Arg Leu
835 840 845

Thr Asp Asn Lys Leu Asn Asp Lys Arg Val Glu Lys Ile Asn Arg Ala
850 855 860

Ser Ser Phe Leu Thr Asn Lys Ala His Ser Met Gly Cys Lys Met Ile
865 870 875 880

Val Gly Glu Ser Asp Leu Pro Val Ala Asp Ser Lys Thr Ser Lys Lys
885 890 895

Gln Asn Val Asp Arg Met Asp Trp Cys Ala Arg Ala Leu Ser His Lys
900 905 910

Val Glu Tyr Ala Cys Lys Leu Met Gly Leu Ala Tyr Arg Gly Ile Pro
915 920 925

Ala Tyr Met Ser Ser His Gln Asp Pro Leu Val His Leu Val Glu Ser
930 935 940

Lys Arg Ser Val Leu Arg Pro Arg Phe Val Val Ala Asp Lys Ser Asp
945 950 955 960

Val Lys Gln His His Leu Asp Asn Leu Arg Arg Met Leu Asn Ser Lys
965 970 975

Thr Lys Val Gly Thr Ala Val Tyr Tyr Arg Glu Ala Val Glu Leu Met
980 985 990

Cys Glu Glu Leu Gly Ile His Lys Thr Asp Met Ala Lys Gly Lys Val
995 1000 1005

Ser Leu Ser Asp Phe Val Asp Lys Phe Ile Gly Glu Lys Ala Ile
1010 1015 1020

Phe Pro Gln Arg Gly Gly Arg Phe Tyr Met Ser Thr Lys Arg Leu
1025 1030 1035

Thr Thr Gly Ala Lys Leu Ile Cys Tyr Ser Gly Ser Asp Val Trp
1040 1045 1050

Leu Ser Asp Ala Asp Glu Ile Ala Ala Ile Asn Ile Gly Met Phe
1055 1060 1065

Val Val Cys Asp Gln Thr Gly Ala Phe Lys Lys Lys Lys Lys Glu
1070 1075 1080

Lys Leu Asp Asp Glu Glu Cys Asp Ile Leu Pro Phe Arg Pro Met
1085 1090 1095

<210> SEQ ID NO 967
<211> LENGTH: 43

<212> TYPE: RNA
<213> ORGANISM: Artificial Sequence
<220> FEATURE:
<223> OTHER INFORMATION: Synthetic

<400> SEQUENCE: 967
agaaauccgu cuuucauuga cggcaaaguc uauauaugac uau 43

<210> SEQ ID NO 968
<211> LENGTH: 43
<212> TYPE: RNA
<213> ORGANISM: Artificial Sequence
<220> FEATURE:
<223> OTHER INFORMATION: Synthetic

<400> SEQUENCE: 968
agaaauccgu cuuucauuga cggggaagua cugauuuagc aug 43

<210> SEQ ID NO 969
<211> LENGTH: 43
<212> TYPE: RNA
<213> ORGANISM: Artificial Sequence
<220> FEATURE:
<223> OTHER INFORMATION: Synthetic

<400> SEQUENCE: 969
agaaauccgu cuuucauuga cggaucauuu gccccagacc ugu 43

<210> SEQ ID NO 970
<211> LENGTH: 43
<212> TYPE: RNA
<213> ORGANISM: Artificial Sequence
<220> FEATURE:
<223> OTHER INFORMATION: Synthetic

<400> SEQUENCE: 970
agaaauccgu cuuucauuga cggggcugau aauauugcag cau 43

<210> SEQ ID NO 971
<211> LENGTH: 43
<212> TYPE: RNA
<213> ORGANISM: Artificial Sequence
<220> FEATURE:
<223> OTHER INFORMATION: Synthetic

<400> SEQUENCE: 971
agaaauccgu cuuucauuga cggguaucaa ugauuaugaa caa 43

<210> SEQ ID NO 972
<211> LENGTH: 43
<212> TYPE: RNA
<213> ORGANISM: Artificial Sequence
<220> FEATURE:
<223> OTHER INFORMATION: Synthetic

<400> SEQUENCE: 972
agaaauccgu cuuucauuga cgguaucaau gauuaugaac aac 43

<210> SEQ ID NO 973
<211> LENGTH: 43
<212> TYPE: RNA
<213> ORGANISM: Artificial Sequence
<220> FEATURE:
<223> OTHER INFORMATION: Synthetic

<400> SEQUENCE: 973
agaaauccgu cuuucauuga cggugaacaa caugcuaaau cag 43

<210> SEQ ID NO 974
<211> LENGTH: 43
<212> TYPE: RNA
<213> ORGANISM: Artificial Sequence
<220> FEATURE:
<223> OTHER INFORMATION: Synthetic

<400> SEQUENCE: 974
agaaauccgu cuuucauuga cgggcauguu guucauaauc auu 43

<210> SEQ ID NO 975
<211> LENGTH: 43
<212> TYPE: RNA
<213> ORGANISM: Artificial Sequence
<220> FEATURE:
<223> OTHER INFORMATION: Synthetic

<400> SEQUENCE: 975
agaaauccgu cuuucauuga cggagcaugu uguucauaau cau 43

<210> SEQ ID NO 976
<211> LENGTH: 43
<212> TYPE: RNA
<213> ORGANISM: Artificial Sequence
<220> FEATURE:
<223> OTHER INFORMATION: Synthetic

<400> SEQUENCE: 976
agaaauccgu cuuucauuga cgggaaguac ugauuuagca ugu 43

<210> SEQ ID NO 977
<211> LENGTH: 43
<212> TYPE: RNA
<213> ORGANISM: Artificial Sequence
<220> FEATURE:
<223> OTHER INFORMATION: Synthetic

<400> SEQUENCE: 977
agaaauccgu cuuucauuga cggcaggucu ggggcaaaug aug 43

<210> SEQ ID NO 978
<211> LENGTH: 43
<212> TYPE: RNA
<213> ORGANISM: Artificial Sequence
<220> FEATURE:
<223> OTHER INFORMATION: Synthetic

<400> SEQUENCE: 978
agaaauccgu cuuucauuga cggccccaga ccuguaauag uca 43

<210> SEQ ID NO 979
<211> LENGTH: 43
<212> TYPE: RNA
<213> ORGANISM: Artificial Sequence
<220> FEATURE:
<223> OTHER INFORMATION: Synthetic

<400> SEQUENCE: 979
agaaauccgu cuuucauuga cgggccccag accuguaaua guc 43

<210> SEQ ID NO 980
<211> LENGTH: 43
<212> TYPE: RNA
<213> ORGANISM: Artificial Sequence
<220> FEATURE:
<223> OTHER INFORMATION: Synthetic

<400> SEQUENCE: 980
agaaauccgu cuuucauuga cgguucauca uuugccccag acc 43

<210> SEQ ID NO 981
<211> LENGTH: 43
<212> TYPE: RNA
<213> ORGANISM: Artificial Sequence
<220> FEATURE:
<223> OTHER INFORMATION: Synthetic

<400> SEQUENCE: 981
agaaauccgu cuuucauuga cggcuucauc auuugcccca gac 43

<210> SEQ ID NO 982
<211> LENGTH: 43
<212> TYPE: RNA
<213> ORGANISM: Artificial Sequence
<220> FEATURE:
<223> OTHER INFORMATION: Synthetic

<400> SEQUENCE: 982
agaaauccgu cuuucauuga cggaaugcug caauauuauc agc 43

<210> SEQ ID NO 983
<211> LENGTH: 43
<212> TYPE: RNA
<213> ORGANISM: Artificial Sequence
<220> FEATURE:
<223> OTHER INFORMATION: Synthetic

<400> SEQUENCE: 983
agaaauccgu cuuucauuga cggcuuaccu ggaaaaugcu gca 43

<210> SEQ ID NO 984
<211> LENGTH: 43
<212> TYPE: RNA
<213> ORGANISM: Artificial Sequence
<220> FEATURE:
<223> OTHER INFORMATION: Synthetic

<400> SEQUENCE: 984
agaaauccgu cuuucauuga cggucuuacc uggaaaaugc ugc 43

<210> SEQ ID NO 985
<211> LENGTH: 43
<212> TYPE: RNA
<213> ORGANISM: Artificial Sequence
<220> FEATURE:
<223> OTHER INFORMATION: Synthetic

<400> SEQUENCE: 985
agaaauccgu cuuucauuga cgguguuuua ggacagaggg uca 43

<210> SEQ ID NO 986
<211> LENGTH: 43
<212> TYPE: RNA
<213> ORGANISM: Artificial Sequence
<220> FEATURE:
<223> OTHER INFORMATION: Synthetic

<400> SEQUENCE: 986
agaaauccgu cuuucauuga cggcuccuac cucucacagu ggc 43

<210> SEQ ID NO 987
<211> LENGTH: 43
<212> TYPE: RNA
<213> ORGANISM: Artificial Sequence
<220> FEATURE:
<223> OTHER INFORMATION: Synthetic

<400> SEQUENCE: 987
agaaauccgu cuuucauuga cggauucuag auggaagcug uau 43

<210> SEQ ID NO 988
<211> LENGTH: 43
<212> TYPE: RNA
<213> ORGANISM: Artificial Sequence
<220> FEATURE:
<223> OTHER INFORMATION: Synthetic

<400> SEQUENCE: 988
agaaauccgu cuuucauuga cgguagaugg aagcuguauc caa 43

<210> SEQ ID NO 989
<211> LENGTH: 43
<212> TYPE: RNA
<213> ORGANISM: Artificial Sequence
<220> FEATURE:
<223> OTHER INFORMATION: Synthetic

<400> SEQUENCE: 989
agaaauccgu cuuucauuga cggcggagca uccuuggaua cag 43

<210> SEQ ID NO 990
<211> LENGTH: 43
<212> TYPE: RNA
<213> ORGANISM: Artificial Sequence
<220> FEATURE:
<223> OTHER INFORMATION: Synthetic

<400> SEQUENCE: 990
agaaauccgu cuuucauuga cggcugaaac agaucugucg acu 43

<210> SEQ ID NO 991
<211> LENGTH: 43
<212> TYPE: RNA
<213> ORGANISM: Artificial Sequence
<220> FEATURE:
<223> OTHER INFORMATION: Synthetic

<400> SEQUENCE: 991
agaaauccgu cuuucauuga cggagcaaca uuccggagca ucc 43

<210> SEQ ID NO 992
<211> LENGTH: 43
<212> TYPE: RNA
<213> ORGANISM: Artificial Sequence
<220> FEATURE:
<223> OTHER INFORMATION: Synthetic

<400> SEQUENCE: 992
agaaauccgu cuuucauuga cggcagcaac auuccggagc auc 43

<210> SEQ ID NO 993
<211> LENGTH: 43
<212> TYPE: RNA
<213> ORGANISM: Artificial Sequence
<220> FEATURE:
<223> OTHER INFORMATION: Synthetic

<400> SEQUENCE: 993
agaaauccgu cuuucauuga cgguaggaca gagggucagc aug 43

<210> SEQ ID NO 994
<211> LENGTH: 43
<212> TYPE: RNA
<213> ORGANISM: Artificial Sequence
<220> FEATURE:
<223> OTHER INFORMATION: Synthetic

<400> SEQUENCE: 994
agaaauccgu cuuucauuga cggaggacag agggucagca ugc 43

<210> SEQ ID NO 995
<211> LENGTH: 43
<212> TYPE: RNA
<213> ORGANISM: Artificial Sequence
<220> FEATURE:
<223> OTHER INFORMATION: Synthetic

<400> SEQUENCE: 995
agaaauccgu cuuucauuga cggggacaga gggucagcau gcc 43

<210> SEQ ID NO 996
<211> LENGTH: 43
<212> TYPE: RNA
<213> ORGANISM: Artificial Sequence
<220> FEATURE:
<223> OTHER INFORMATION: Synthetic

<400> SEQUENCE: 996
agaaauccgu cuuucauuga cggcuuucuc agccugucag ucc 43

<210> SEQ ID NO 997
<211> LENGTH: 43
<212> TYPE: RNA
<213> ORGANISM: Artificial Sequence
<220> FEATURE:
<223> OTHER INFORMATION: Synthetic

<400> SEQUENCE: 997
agaaauccgu cuuucauuga cggcucagcc ugucaguccc ugg 43

<210> SEQ ID NO 998
<211> LENGTH: 43
<212> TYPE: RNA
<213> ORGANISM: Artificial Sequence
<220> FEATURE:
<223> OTHER INFORMATION: Synthetic

<400> SEQUENCE: 998
agaaauccgu cuuucauuga cggccaggga cugacaggcu gag 43

<210> SEQ ID NO 999
<211> LENGTH: 43
<212> TYPE: RNA
<213> ORGANISM: Artificial Sequence
<220> FEATURE:
<223> OTHER INFORMATION: Synthetic

<400> SEQUENCE: 999
agaaauccgu cuuucauuga cggcugggcc accuccucaa uug 43

<210> SEQ ID NO 1000

<211> LENGTH: 43
<212> TYPE: RNA
<213> ORGANISM: Artificial Sequence
<220> FEATURE:
<223> OTHER INFORMATION: Synthetic

<400> SEQUENCE: 1000
agaaauccgu cuuucauuga cggaauugag gagguggccc agg 43

<210> SEQ ID NO 1001
<211> LENGTH: 43
<212> TYPE: RNA
<213> ORGANISM: Artificial Sequence
<220> FEATURE:
<223> OTHER INFORMATION: Synthetic

<400> SEQUENCE: 1001
agaaauccgu cuuucauuga cgguucaauu gaggaggugg ccc 43

<210> SEQ ID NO 1002
<211> LENGTH: 43
<212> TYPE: RNA
<213> ORGANISM: Artificial Sequence
<220> FEATURE:
<223> OTHER INFORMATION: Synthetic

<400> SEQUENCE: 1002
agaaauccgu cuuucauuga cggcgccacu ucuucaauug agg 43

<210> SEQ ID NO 1003
<211> LENGTH: 43
<212> TYPE: RNA
<213> ORGANISM: Artificial Sequence
<220> FEATURE:
<223> OTHER INFORMATION: Synthetic

<400> SEQUENCE: 1003
agaaauccgu cuuucauuga cggguuggcu gcaacuguau auc 43

<210> SEQ ID NO 1004
<211> LENGTH: 43
<212> TYPE: RNA
<213> ORGANISM: Artificial Sequence
<220> FEATURE:
<223> OTHER INFORMATION: Synthetic

<400> SEQUENCE: 1004
agaaauccgu cuuucauuga cggucggucc uuguagauau aca 43

<210> SEQ ID NO 1005
<211> LENGTH: 43
<212> TYPE: RNA
<213> ORGANISM: Artificial Sequence
<220> FEATURE:
<223> OTHER INFORMATION: Synthetic

<400> SEQUENCE: 1005
agaaauccgu cuuucauuga cggucugccu gccgcacuag cuu 43

<210> SEQ ID NO 1006
<211> LENGTH: 43
<212> TYPE: RNA
<213> ORGANISM: Artificial Sequence
<220> FEATURE:
<223> OTHER INFORMATION: Synthetic

<400> SEQUENCE: 1006
agaaauccgu cuuucauuga cgguuucuca gccugucagu ccc 43

<210> SEQ ID NO 1007
<211> LENGTH: 43
<212> TYPE: RNA
<213> ORGANISM: Artificial Sequence
<220> FEATURE:
<223> OTHER INFORMATION: Synthetic

<400> SEQUENCE: 1007
agaaauccgu cuuucauuga cggucagccu gucagucccu ggg 43

<210> SEQ ID NO 1008
<211> LENGTH: 43
<212> TYPE: RNA
<213> ORGANISM: Artificial Sequence
<220> FEATURE:
<223> OTHER INFORMATION: Synthetic

<400> SEQUENCE: 1008
agaaauccgu cuuucauuga cggaguuccu gggccaccuc cuc 43

<210> SEQ ID NO 1009
<211> LENGTH: 43
<212> TYPE: RNA
<213> ORGANISM: Artificial Sequence
<220> FEATURE:
<223> OTHER INFORMATION: Synthetic

<400> SEQUENCE: 1009
agaaauccgu cuuucauuga cggaggaggu ggcccaggaa cuc 43

<210> SEQ ID NO 1010
<211> LENGTH: 43
<212> TYPE: RNA
<213> ORGANISM: Artificial Sequence
<220> FEATURE:
<223> OTHER INFORMATION: Synthetic

<400> SEQUENCE: 1010
agaaauccgu cuuucauuga cggaagaagu ggcggaagcu ggu 43

<210> SEQ ID NO 1011
<211> LENGTH: 43
<212> TYPE: RNA
<213> ORGANISM: Artificial Sequence
<220> FEATURE:
<223> OTHER INFORMATION: Synthetic

<400> SEQUENCE: 1011
agaaauccgu cuuucauuga cgggcugcaa cuguauaucu aca 43

<210> SEQ ID NO 1012
<211> LENGTH: 43
<212> TYPE: RNA
<213> ORGANISM: Artificial Sequence
<220> FEATURE:
<223> OTHER INFORMATION: Synthetic

<400> SEQUENCE: 1012
agaaauccgu cuuucauuga cggcagccaa cgaagugccu cag 43

<210> SEQ ID NO 1013
<211> LENGTH: 43
<212> TYPE: RNA

<213> ORGANISM: Artificial Sequence
<220> FEATURE:
<223> OTHER INFORMATION: Synthetic

<400> SEQUENCE: 1013
agaaauccgu cuuucauuga cgguagauau acaguugcag cca 43

<210> SEQ ID NO 1014
<211> LENGTH: 43
<212> TYPE: RNA
<213> ORGANISM: Artificial Sequence
<220> FEATURE:
<223> OTHER INFORMATION: Synthetic

<400> SEQUENCE: 1014
agaaauccgu cuuucauuga cgggugacuu cucgguccuu gua 43

<210> SEQ ID NO 1015
<211> LENGTH: 43
<212> TYPE: RNA
<213> ORGANISM: Artificial Sequence
<220> FEATURE:
<223> OTHER INFORMATION: Synthetic

<400> SEQUENCE: 1015
agaaauccgu cuuucauuga cgggugacag uggacacacc uua 43

<210> SEQ ID NO 1016
<211> LENGTH: 43
<212> TYPE: RNA
<213> ORGANISM: Artificial Sequence
<220> FEATURE:
<223> OTHER INFORMATION: Synthetic

<400> SEQUENCE: 1016
agaaauccgu cuuucauuga cggugacagu ggacacaccu uac 43

<210> SEQ ID NO 1017
<211> LENGTH: 43
<212> TYPE: RNA
<213> ORGANISM: Artificial Sequence
<220> FEATURE:
<223> OTHER INFORMATION: Synthetic

<400> SEQUENCE: 1017
agaaauccgu cuuucauuga cggccugggc aaccgucugg aug 43

<210> SEQ ID NO 1018
<211> LENGTH: 43
<212> TYPE: RNA
<213> ORGANISM: Artificial Sequence
<220> FEATURE:
<223> OTHER INFORMATION: Synthetic

<400> SEQUENCE: 1018
agaaauccgu cuuucauuga cggcccaggu aaggugugug cac 43

<210> SEQ ID NO 1019
<211> LENGTH: 43
<212> TYPE: RNA
<213> ORGANISM: Artificial Sequence
<220> FEATURE:
<223> OTHER INFORMATION: Synthetic

<400> SEQUENCE: 1019
agaaauccgu cuuucauuga cggcgcacau cauccagacg guu 43

<210> SEQ ID NO 1020
<211> LENGTH: 43
<212> TYPE: RNA
<213> ORGANISM: Artificial Sequence
<220> FEATURE:
<223> OTHER INFORMATION: Synthetic

<400> SEQUENCE: 1020
agaaauccgu cuuucauuga cggaaucugu uacgcacauc auc 43

<210> SEQ ID NO 1021
<211> LENGTH: 43
<212> TYPE: RNA
<213> ORGANISM: Artificial Sequence
<220> FEATURE:
<223> OTHER INFORMATION: Synthetic

<400> SEQUENCE: 1021
agaaauccgu cuuucauuga cgggaaucug uuacgcacau cau 43

<210> SEQ ID NO 1022
<211> LENGTH: 43
<212> TYPE: RNA
<213> ORGANISM: Artificial Sequence
<220> FEATURE:
<223> OTHER INFORMATION: Synthetic

<400> SEQUENCE: 1022
agaaauccgu cuuucauuga cgguggcggc aguuugaauc ugu 43

<210> SEQ ID NO 1023
<211> LENGTH: 43
<212> TYPE: RNA
<213> ORGANISM: Artificial Sequence
<220> FEATURE:
<223> OTHER INFORMATION: Synthetic

<400> SEQUENCE: 1023
agaaauccgu cuuucauuga cggccugagu uguggcggca guu 43

<210> SEQ ID NO 1024
<211> LENGTH: 1113
<212> TYPE: DNA
<213> ORGANISM: Artificial Sequence
<220> FEATURE:
<223> OTHER INFORMATION: Synthetic

<400> SEQUENCE: 1024
atgctccccc ggctaatttg tatcaatgat tatgaacaac atgctaaatc agtacttcca 60
aagtctatat atgactatta caggtctggg gcaaatgatg aagaaacttt ggctgataat 120
attgcagcat tttccagatg gaagctgtat ccaaggatgc tccggaatgt tgctgaaaca 180
gatctgtcga cttctgtttt aggacagagg gtcagcatgc caatatgtgt gggggctacg 240
gccatgcagc gcatggctca tgtggacggc gagcttgcca ctgtgagagc ctgtcagtcc 300
ctgggaacgg gcatgatgtt gagttcctgg gccacctcct caattgaaga agtggcggaa 360
gctggtcctg aggcacttcg ttggctgcaa ctgtatatct acaaggaccg agaagtcacc 420
aagaagctag tgcggcaggc agagaagatg ggctacaagg ccatatttgt gacagtggac 480
acaccttacc tgggcaaccg tctggatgat gtgcgtaaca gattcaaact gccgccacaa 540
ctcaggatga aaaattttga aaccagtact ttatcatttt ctcctgagga aaattttgga 600
gacgacagtg gacttgctgc atatgtggct aaagcaatag acccatctat cagctgggaa 660
gatatcaaat ggctgagaag actgacatca ttgccaattg ttgcaaaggg cattttgaga 720
ggtgatgatg ccagggaggc tgttaaacat ggcttgaatg ggatcttggt gtcgaatcat 780
ggggctcgac aactcgatgg ggtgccagcc actattgatg ttctgccaga aattgtggag 840
gctgtggaag ggaaggtgga agtcttcctg gacgggggtg tgcggaaagg cactgatgtt 900
ctgaaagctc tggctcttgg cgccaaggct gtgtttgtgg ggagaccaat cgtttggggc 960
ttagctttcc agggggagaa aggtgttcaa gatgtcctcg agatactaaa ggaagaattc 1020
cggttggcca tggctctgag tgggtgccag aatgtgaaag tcatcgacaa gacattggtg 1080
aggaaaaatc ctttggccgt ttccaagatc tga 1113

<210> SEQ ID NO 1025
<211> LENGTH: 20
<212> TYPE: DNA
<213> ORGANISM: Artificial Sequence
<220> FEATURE:
<223> OTHER INFORMATION: Synthetic

<400> SEQUENCE: 1025
caaagtctat atatgactat 20

<210> SEQ ID NO 1026
<211> LENGTH: 20
<212> TYPE: DNA
<213> ORGANISM: Artificial Sequence
<220> FEATURE:
<223> OTHER INFORMATION: Synthetic

<400> SEQUENCE: 1026
ggaagtactg atttagcatg 20

<210> SEQ ID NO 1027
<211> LENGTH: 20
<212> TYPE: DNA
<213> ORGANISM: Artificial Sequence
<220> FEATURE:
<223> OTHER INFORMATION: Synthetic

<400> SEQUENCE: 1027
atcatttgcc ccagacctgt 20

<210> SEQ ID NO 1028
<211> LENGTH: 20
<212> TYPE: DNA
<213> ORGANISM: Artificial Sequence
<220> FEATURE:
<223> OTHER INFORMATION: Synthetic

<400> SEQUENCE: 1028
ggctgataat attgcagcat 20

<210> SEQ ID NO 1029
<211> LENGTH: 20
<212> TYPE: DNA
<213> ORGANISM: Artificial Sequence
<220> FEATURE:
<223> OTHER INFORMATION: Synthetic

<400> SEQUENCE: 1029
gtatcaatga ttatgaacaa 20

<210> SEQ ID NO 1030
<211> LENGTH: 20
<212> TYPE: DNA
<213> ORGANISM: Artificial Sequence
<220> FEATURE:
<223> OTHER INFORMATION: Synthetic

<400> SEQUENCE: 1030
tatcaatgat tatgaacaac 20

<210> SEQ ID NO 1031
<211> LENGTH: 20
<212> TYPE: DNA
<213> ORGANISM: Artificial Sequence
<220> FEATURE:
<223> OTHER INFORMATION: Synthetic

<400> SEQUENCE: 1031
tgaacaacat gctaaatcag 20

<210> SEQ ID NO 1032
<211> LENGTH: 20
<212> TYPE: DNA
<213> ORGANISM: Artificial Sequence
<220> FEATURE:
<223> OTHER INFORMATION: Synthetic

<400> SEQUENCE: 1032
gcatgttgtt cataatcatt 20

<210> SEQ ID NO 1033
<211> LENGTH: 20
<212> TYPE: DNA
<213> ORGANISM: Artificial Sequence
<220> FEATURE:
<223> OTHER INFORMATION: Synthetic

<400> SEQUENCE: 1033
agcatgttgt tcataatcat 20

<210> SEQ ID NO 1034
<211> LENGTH: 20
<212> TYPE: DNA
<213> ORGANISM: Artificial Sequence
<220> FEATURE:
<223> OTHER INFORMATION: Synthetic

<400> SEQUENCE: 1034
gaagtactga tttagcatgt 20

<210> SEQ ID NO 1035
<211> LENGTH: 20
<212> TYPE: DNA
<213> ORGANISM: Artificial Sequence
<220> FEATURE:
<223> OTHER INFORMATION: Synthetic

<400> SEQUENCE: 1035
caggtctggg gcaaatgatg 20

<210> SEQ ID NO 1036
<211> LENGTH: 20
<212> TYPE: DNA
<213> ORGANISM: Artificial Sequence
<220> FEATURE:
<223> OTHER INFORMATION: Synthetic

<400> SEQUENCE: 1036
ccccagacct gtaatagtca 20

<210> SEQ ID NO 1037
<211> LENGTH: 20
<212> TYPE: DNA
<213> ORGANISM: Artificial Sequence
<220> FEATURE:
<223> OTHER INFORMATION: Synthetic

<400> SEQUENCE: 1037
gccccagacc tgtaatagtc 20

<210> SEQ ID NO 1038
<211> LENGTH: 20
<212> TYPE: DNA
<213> ORGANISM: Artificial Sequence
<220> FEATURE:
<223> OTHER INFORMATION: Synthetic

<400> SEQUENCE: 1038
ttcatcattt gccccagacc 20

<210> SEQ ID NO 1039
<211> LENGTH: 20
<212> TYPE: DNA
<213> ORGANISM: Artificial Sequence
<220> FEATURE:
<223> OTHER INFORMATION: Synthetic

<400> SEQUENCE: 1039
cttcatcatt tgccccagac 20

<210> SEQ ID NO 1040
<211> LENGTH: 20
<212> TYPE: DNA
<213> ORGANISM: Artificial Sequence
<220> FEATURE:
<223> OTHER INFORMATION: Synthetic

<400> SEQUENCE: 1040
aatgctgcaa tattatcagc 20

<210> SEQ ID NO 1041
<211> LENGTH: 20
<212> TYPE: DNA
<213> ORGANISM: Artificial Sequence
<220> FEATURE:
<223> OTHER INFORMATION: Synthetic

<400> SEQUENCE: 1041
cttacctgga aaatgctgca 20

<210> SEQ ID NO 1042
<211> LENGTH: 20
<212> TYPE: DNA
<213> ORGANISM: Artificial Sequence
<220> FEATURE:
<223> OTHER INFORMATION: Synthetic

<400> SEQUENCE: 1042
tcttacctgg aaaatgctgc 20

<210> SEQ ID NO 1043
<211> LENGTH: 20

<212> TYPE: DNA
<213> ORGANISM: Artificial Sequence
<220> FEATURE:
<223> OTHER INFORMATION: Synthetic

<400> SEQUENCE: 1043
tgttttagga cagagggtca 20

<210> SEQ ID NO 1044
<211> LENGTH: 20
<212> TYPE: DNA
<213> ORGANISM: Artificial Sequence
<220> FEATURE:
<223> OTHER INFORMATION: Synthetic

<400> SEQUENCE: 1044
ctcctacctc tcacagtggc 20

<210> SEQ ID NO 1045
<211> LENGTH: 20
<212> TYPE: DNA
<213> ORGANISM: Artificial Sequence
<220> FEATURE:
<223> OTHER INFORMATION: Synthetic

<400> SEQUENCE: 1045
attctagatg gaagctgtat 20

<210> SEQ ID NO 1046
<211> LENGTH: 20
<212> TYPE: DNA
<213> ORGANISM: Artificial Sequence
<220> FEATURE:
<223> OTHER INFORMATION: Synthetic

<400> SEQUENCE: 1046
tagatggaag ctgtatccaa 20

<210> SEQ ID NO 1047
<211> LENGTH: 20
<212> TYPE: DNA
<213> ORGANISM: Artificial Sequence
<220> FEATURE:
<223> OTHER INFORMATION: Synthetic

<400> SEQUENCE: 1047
cggagcatcc ttggatacag 20

<210> SEQ ID NO 1048
<211> LENGTH: 20
<212> TYPE: DNA
<213> ORGANISM: Artificial Sequence
<220> FEATURE:
<223> OTHER INFORMATION: Synthetic

<400> SEQUENCE: 1048
ctgaaacaga tctgtcgact 20

<210> SEQ ID NO 1049
<211> LENGTH: 20
<212> TYPE: DNA
<213> ORGANISM: Artificial Sequence
<220> FEATURE:
<223> OTHER INFORMATION: Synthetic

<400> SEQUENCE: 1049
agcaacattc cggagcatcc 20

<210> SEQ ID NO 1050
<211> LENGTH: 20
<212> TYPE: DNA
<213> ORGANISM: Artificial Sequence
<220> FEATURE:
<223> OTHER INFORMATION: Synthetic

<400> SEQUENCE: 1050
cagcaacatt ccggagcatc 20

<210> SEQ ID NO 1051
<211> LENGTH: 20
<212> TYPE: DNA
<213> ORGANISM: Artificial Sequence
<220> FEATURE:
<223> OTHER INFORMATION: Synthetic

<400> SEQUENCE: 1051
taggacagag ggtcagcatg 20

<210> SEQ ID NO 1052
<211> LENGTH: 20
<212> TYPE: DNA
<213> ORGANISM: Artificial Sequence
<220> FEATURE:
<223> OTHER INFORMATION: Synthetic

<400> SEQUENCE: 1052
aggacagagg gtcagcatgc 20

<210> SEQ ID NO 1053
<211> LENGTH: 20
<212> TYPE: DNA
<213> ORGANISM: Artificial Sequence
<220> FEATURE:
<223> OTHER INFORMATION: Synthetic

<400> SEQUENCE: 1053
ggacagaggg tcagcatgcc 20

<210> SEQ ID NO 1054
<211> LENGTH: 20
<212> TYPE: DNA
<213> ORGANISM: Artificial Sequence
<220> FEATURE:
<223> OTHER INFORMATION: Synthetic

<400> SEQUENCE: 1054
ctttctcagc ctgtcagtcc 20

<210> SEQ ID NO 1055
<211> LENGTH: 20
<212> TYPE: DNA
<213> ORGANISM: Artificial Sequence
<220> FEATURE:
<223> OTHER INFORMATION: Synthetic

<400> SEQUENCE: 1055
ctcagcctgt cagtccctgg 20

<210> SEQ ID NO 1056
<211> LENGTH: 20
<212> TYPE: DNA
<213> ORGANISM: Artificial Sequence
<220> FEATURE:
<223> OTHER INFORMATION: Synthetic

<400> SEQUENCE: 1056
ccagggactg acaggctgag 20

<210> SEQ ID NO 1057
<211> LENGTH: 20
<212> TYPE: DNA
<213> ORGANISM: Artificial Sequence
<220> FEATURE:
<223> OTHER INFORMATION: Synthetic

<400> SEQUENCE: 1057
ctgggccacc tcctcaattg 20

<210> SEQ ID NO 1058
<211> LENGTH: 20
<212> TYPE: DNA
<213> ORGANISM: Artificial Sequence
<220> FEATURE:
<223> OTHER INFORMATION: Synthetic

<400> SEQUENCE: 1058
aattgaggag gtggcccagg 20

<210> SEQ ID NO 1059
<211> LENGTH: 20
<212> TYPE: DNA
<213> ORGANISM: Artificial Sequence
<220> FEATURE:
<223> OTHER INFORMATION: Synthetic

<400> SEQUENCE: 1059
ttcaattgag gaggtggccc 20

<210> SEQ ID NO 1060
<211> LENGTH: 20
<212> TYPE: DNA
<213> ORGANISM: Artificial Sequence
<220> FEATURE:
<223> OTHER INFORMATION: Synthetic

<400> SEQUENCE: 1060
cgccacttct tcaattgagg 20

<210> SEQ ID NO 1061
<211> LENGTH: 20
<212> TYPE: DNA
<213> ORGANISM: Artificial Sequence
<220> FEATURE:
<223> OTHER INFORMATION: Synthetic

<400> SEQUENCE: 1061
gttggctgca actgtatatc 20

<210> SEQ ID NO 1062
<211> LENGTH: 20
<212> TYPE: DNA
<213> ORGANISM: Artificial Sequence
<220> FEATURE:
<223> OTHER INFORMATION: Synthetic

<400> SEQUENCE: 1062
tcggtccttg tagatataca 20

<210> SEQ ID NO 1063
<211> LENGTH: 20
<212> TYPE: DNA
<213> ORGANISM: Artificial Sequence
<220> FEATURE:
<223> OTHER INFORMATION: Synthetic

<400> SEQUENCE: 1063
tctgcctgcc gcactagctt 20

<210> SEQ ID NO 1064
<211> LENGTH: 20
<212> TYPE: DNA
<213> ORGANISM: Artificial Sequence
<220> FEATURE:
<223> OTHER INFORMATION: Synthetic

<400> SEQUENCE: 1064
tttctcagcc tgtcagtccc 20

<210> SEQ ID NO 1065
<211> LENGTH: 20
<212> TYPE: DNA
<213> ORGANISM: Artificial Sequence
<220> FEATURE:
<223> OTHER INFORMATION: Synthetic

<400> SEQUENCE: 1065
tcagcctgtc agtccctggg 20

<210> SEQ ID NO 1066
<211> LENGTH: 20
<212> TYPE: DNA
<213> ORGANISM: Artificial Sequence
<220> FEATURE:
<223> OTHER INFORMATION: Synthetic

<400> SEQUENCE: 1066
agttcctggg ccacctcctc 20

<210> SEQ ID NO 1067
<211> LENGTH: 20
<212> TYPE: DNA
<213> ORGANISM: Artificial Sequence
<220> FEATURE:
<223> OTHER INFORMATION: Synthetic

<400> SEQUENCE: 1067
aggaggtggc ccaggaactc 20

<210> SEQ ID NO 1068
<211> LENGTH: 20
<212> TYPE: DNA
<213> ORGANISM: Artificial Sequence
<220> FEATURE:
<223> OTHER INFORMATION: Synthetic

<400> SEQUENCE: 1068
aagaagtggc ggaagctggt 20

<210> SEQ ID NO 1069
<211> LENGTH: 20
<212> TYPE: DNA
<213> ORGANISM: Artificial Sequence
<220> FEATURE:
<223> OTHER INFORMATION: Synthetic

<400> SEQUENCE: 1069
gctgcaactg tatatctaca 20

<210> SEQ ID NO 1070
<211> LENGTH: 20
<212> TYPE: DNA
<213> ORGANISM: Artificial Sequence
<220> FEATURE:
<223> OTHER INFORMATION: Synthetic

<400> SEQUENCE: 1070
cagccaacga agtgcctcag 20

<210> SEQ ID NO 1071
<211> LENGTH: 20
<212> TYPE: DNA
<213> ORGANISM: Artificial Sequence
<220> FEATURE:
<223> OTHER INFORMATION: Synthetic

<400> SEQUENCE: 1071
tagatataca gttgcagcca 20

<210> SEQ ID NO 1072
<211> LENGTH: 20
<212> TYPE: DNA
<213> ORGANISM: Artificial Sequence
<220> FEATURE:
<223> OTHER INFORMATION: Synthetic

<400> SEQUENCE: 1072
gtgacttctc ggtccttgta 20

<210> SEQ ID NO 1073
<211> LENGTH: 20
<212> TYPE: DNA
<213> ORGANISM: Artificial Sequence
<220> FEATURE:
<223> OTHER INFORMATION: Synthetic

<400> SEQUENCE: 1073
gtgacagtgg acacacctta 20

<210> SEQ ID NO 1074
<211> LENGTH: 20
<212> TYPE: DNA
<213> ORGANISM: Artificial Sequence
<220> FEATURE:
<223> OTHER INFORMATION: Synthetic

<400> SEQUENCE: 1074
tgacagtgga cacaccttac 20

<210> SEQ ID NO 1075
<211> LENGTH: 20
<212> TYPE: DNA
<213> ORGANISM: Artificial Sequence
<220> FEATURE:
<223> OTHER INFORMATION: Synthetic

<400> SEQUENCE: 1075
cctgggcaac cgtctggatg 20

<210> SEQ ID NO 1076

<211> LENGTH: 20
<212> TYPE: DNA
<213> ORGANISM: Artificial Sequence
<220> FEATURE:
<223> OTHER INFORMATION: Synthetic

<400> SEQUENCE: 1076
cccaggtaag gtgtgtccac 20

<210> SEQ ID NO 1077
<211> LENGTH: 20
<212> TYPE: DNA
<213> ORGANISM: Artificial Sequence
<220> FEATURE:
<223> OTHER INFORMATION: Synthetic

<400> SEQUENCE: 1077
cgcacatcat ccagacggtt 20

<210> SEQ ID NO 1078
<211> LENGTH: 20
<212> TYPE: DNA
<213> ORGANISM: Artificial Sequence
<220> FEATURE:
<223> OTHER INFORMATION: Synthetic

<400> SEQUENCE: 1078
aatctgttac gcacatcatc 20

<210> SEQ ID NO 1079
<211> LENGTH: 20
<212> TYPE: DNA
<213> ORGANISM: Artificial Sequence
<220> FEATURE:
<223> OTHER INFORMATION: Synthetic

<400> SEQUENCE: 1079
gaatctgtta cgcacatcat 20

<210> SEQ ID NO 1080
<211> LENGTH: 20
<212> TYPE: DNA
<213> ORGANISM: Artificial Sequence
<220> FEATURE:
<223> OTHER INFORMATION: Synthetic

<400> SEQUENCE: 1080
tggcggcagt ttgaatctgt 20

<210> SEQ ID NO 1081
<211> LENGTH: 20
<212> TYPE: DNA
<213> ORGANISM: Artificial Sequence
<220> FEATURE:
<223> OTHER INFORMATION: Synthetic

<400> SEQUENCE: 1081
cctgagttgt ggcggcagtt 20

<210> SEQ ID NO 1082
<211> LENGTH: 43
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (40)..(43)
<223> OTHER INFORMATION: modified with phosphorothioate
<220> FEATURE:
<221> NAME/KEY: misc_feature
<222> LOCATION: (40)..(42)
<223> OTHER INFORMATION: modified with 2'-O-methlyation

<400> SEQUENCE: 1082
agaaauccgu cuuucauuga cggcggagca uccuuggaua cag 43

<210> SEQ ID NO 1083
<211> LENGTH: 43
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with phosphorothioate
<220> FEATURE:
<221> NAME/KEY: misc_feature
<222> LOCATION: (1)..(3)
<223> OTHER INFORMATION: modified with 2'-O-methlyation
<220> FEATURE:
<221> NAME/KEY: misc_feature
<222> LOCATION: (40)..(42)
<223> OTHER INFORMATION: modified with 2'-O-methlyation
<220> FEATURE:
<221> NAME/KEY: misc_feature
<222> LOCATION: (40)..(43)
<223> OTHER INFORMATION: modified with phosphorothioate

<400> SEQUENCE: 1083
agaaauccgu cuuucauuga cggcggagca uccuuggaua cag 43

<210> SEQ ID NO 1084
<211> LENGTH: 43
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (40)..(43)
<223> OTHER INFORMATION: modified with phosphorothioate
<220> FEATURE:
<221> NAME/KEY: misc_feature
<222> LOCATION: (40)..(42)
<223> OTHER INFORMATION: modified with 2'-O-methlyation

<400> SEQUENCE: 1084
agaaauccgu cuuucauuga cggggaagua cugauuuagc aug 43

<210> SEQ ID NO 1085
<211> LENGTH: 43
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with phosphorothioate
<220> FEATURE:
<221> NAME/KEY: misc_feature
<222> LOCATION: (1)..(3)
<223> OTHER INFORMATION: modified with 2'-O-methlyation
<220> FEATURE:
<221> NAME/KEY: misc_feature
<222> LOCATION: (40)..(42)
<223> OTHER INFORMATION: modified with 2'-O-methlyation
<220> FEATURE:

<221> NAME/KEY: misc_feature
<222> LOCATION: (40)..(43)
<223> OTHER INFORMATION: modified with phosphorothioate

<400> SEQUENCE: 1085
agaaauccgu cuuucauuga cggggaagua cugauuuagc aug 43

<210> SEQ ID NO 1086
<211> LENGTH: 43
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (40)..(43)
<223> OTHER INFORMATION: modified with phosphorothioate
<220> FEATURE:
<221> NAME/KEY: misc_feature
<222> LOCATION: (40)..(42)
<223> OTHER INFORMATION: modified with 2'-O-methlyation

<400> SEQUENCE: 1086
agaaauccgu cuuucauuga cggcaaaguc uauauaugac uau 43

<210> SEQ ID NO 1087
<211> LENGTH: 43
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with phosphorothioate
<220> FEATURE:
<221> NAME/KEY: misc_feature
<222> LOCATION: (1)..(3)
<223> OTHER INFORMATION: modified with 2'-O-methlyation
<220> FEATURE:
<221> NAME/KEY: misc_feature
<222> LOCATION: (40)..(42)
<223> OTHER INFORMATION: modified with 2'-O-methlyation
<220> FEATURE:
<221> NAME/KEY: misc_feature
<222> LOCATION: (40)..(43)
<223> OTHER INFORMATION: modified with phosphorothioate

<400> SEQUENCE: 1087
agaaauccgu cuuucauuga cggcaaaguc uauauaugac uau 43

<210> SEQ ID NO 1088
<211> LENGTH: 122
<212> TYPE: DNA
<213> ORGANISM: Artificial Sequence
<220> FEATURE:
<223> OTHER INFORMATION: Synthetic

<400> SEQUENCE: 1088
attgtgcact gtcagatctt ggaaacggcc aaaggatttt tcctcaccaa tgtcttgtcg 60
atgactttca cattctggca cccactcaga gccatggcca accggaattc ttcctttagt 120
at 122

<210> SEQ ID NO 1089
<211> LENGTH: 3213
<212> TYPE: RNA
<213> ORGANISM: Artificial Sequence
<220> FEATURE:
<223> OTHER INFORMATION: Synthetic

<400> SEQUENCE: 1089
augagcuccg ccaucaaguc cuacaagucu gugcugcggc caaacgagag aaagaaucag 60
cugcugaagu ccaccaucca gugccuggag gacggcuccg ccuucuuuuu caagaugcug 120
cagggccugu uuggcggcau cacccccgag aucgugagau ucagcacaga gcaggagaag 180
cagcagcagg auaucgcccu guggugugcc gugaauuggu ucaggccugu gagccaggac 240
ucccugaccc acacaaucgc cuccgauaac cugguggaga aguuugagga guacuauggc 300
ggcacagcca gcgacgccau caagcaguac uucagcgccu ccaucggcga guccuacuau 360
uggaaugacu gccgccagca guacuaugau cugugucggg agcugggcgu ggaggugucu 420
gaccugaccc acgaucugga gauccugugc cgggagaagu gucuggccgu ggccacagag 480
agcaaccaga acaauucuau caucagcgug cuguuuggca ccggcgagaa ggaggauagg 540
ucugugaagc ugcgcaucac aaagaagauc cuggaggcca ucagcaaccu gaaggagauc 600
ccaaagaaug uggcccccau ccaggagauc auccugaaug uggccaaggc caccaaggag 660
acauucagac agguguacgc aggaaaccug ggagcaccau ccacccugga gaaguuuauc 720
gccaaggacg gccagaagga guucgaucug aagaagcugc agacagaccu gaagaaagug 780
auccggggca agucuaagga gagagauugg ugcugucagg aggagcugag gagcuacgug 840
gagcagaaua ccauccagua ugaccugugg gccuggggcg agauguucaa caaggcccac 900
accgcccuga agaucaaguc cacaagaaac uacaauuuug ccaagcagag gcuggagcag 960
uucaaggaga uccagucucu gaacaaucug cugguggyga agaagcugaa cgacuuuuuc 1020
gauagcgagu uuuucuccgg cgaggagacc uacacaaucu gcgugcacca ccugggcggc 1080
aaggaccugu ccaagcugua uaaggccugg gaggacgauc ccgccgaucc ugagaaugcc 1140
aucgguggugc ugugcgacga ucugaagaac aauuuuaaga aggagccuau caggaacauc 1200
cugcgcuaca ucuucaccau ccgccaggag uguagcgcac aggacauccu ggcagcagca 1260
aaguacaauc agcagcugga ucgguauaag agccagaagg ccaacccauc cgugcugggc 1320
aaucagggcu uuaccuggac aaacgccgug auccugccag agaaggccca gcggaacgac 1380
agacccaauu cucuggaucu gcgcaucugg cuguaccuga agcugcggca cccugacggc 1440
agauggaaga agcaccacau cccauucuac gauacccggu uuuuccagga gaucuaugcc 1500
gccggcaaua gcccugugga caccugucag uuuaggacac cccgcuucgg cuaucaccug 1560
ccuaagcuga ccgaucagac agccauccgc gugaacaaga agcacgugaa ggcagcaaag 1620
accgaggcac ggaucagacu ggccauccag cagggcacac ugccaguguc caaucugaag 1680
aucaccgaga ucuccgccac aaucaacucu aagggccagg ugcgcauccc cgugaaguuu 1740
cggguggggaa ggcagaaggg aacccugcag aucggcgacc gguucugcgg cuacgaucag 1800
aaccagacag ccucucacgc cuauagccug ugggaggugg ugaaggaggg ccaguaccac 1860
aaggagcugg gcuguuuugu gcgcuucauc ucuagcggcg acaucguguc caucaccgag 1920
aaccggggca aucaguuuga ucagcugucu uaugagggcc uggccuaccc ccaguaugcc 1980
gacuggagaa agaaggccuc caaguucgug ucucuguggc agaucaccaa gaagaacaag 2040
aagaaggaga ucgugacagu ggaggccaag gagaaguuug acgccaucug caaguaccag 2100
ccuaggcugu auaaguucaa caaggaguac gccuaucugc ugcgggauau cgugagaggc 2160
aagagccugg uggagcugca gcagaucagg caggagaucu uucgcuucau cgagcaggac 2220
uguggaguga cccgccuggg aucucugagc cuguccaccc uggagacagu gaaggccgug 2280

```
aagggcauca ucuacuccua uuuuucuaca gcccugaaug ccucuaagaa caaucccauc   2340

agcgacgagc agcggaagga guuugauccu gagcuguucg cccugcugga gaagcuggag   2400

cugaucagga cucggaagaa gaagcagaag guggagagaa ucgccaauag ccugauccag   2460

acaugccugg agaacaauau caaguucauc aggggcgagg gcgaccuguc caccacaaac   2520

aaugccacca agaagaaggc caacucuagg agcauggauu ggcuggccag aggcguguuu   2580

aauaagaucc ggcagcuggc cccaaugcac aacaucaccc uguucggcug cggcagccug   2640

uacacauccc accaggaccc ucuggugcac agaaacccag auaaggccau gaaguguaga   2700

ugggcagcaa ucccagugaa ggacaucggc gauugggugc ugagaaagcu gucccagaac   2760

cugagggcca agaaucgggg caccggcgag uacuaucacc agggcgugaa ggaguuccug   2820

ucucacuaug agcugcagga ccuggaggag gagcugcuga aguggcgguc ugauagaaag   2880

agcaacaucc cuugcugggu gcugcagaau agacuggccg agaagcuggg caacaaggag   2940

gccguggugu acaucccagu gaggggcggc cgcaucuauu uugcaaccca caagguggca   3000

acaggagccg ugagcaucgu guucgaccag aagcaagugu gggugugua ugcagaucac   3060

guggcagcag caaacaucgc acugaccggc aagggcaucg gcgagcaguc cucugacgag   3120

gagaaccccg auggcuccag gaucaagcug cagcugacau cuaaaaggcc ggcggccacg   3180

aaaaaggccg gccaggcaaa aaagaaaaag uaa                                 3213
```

<210> SEQ ID NO 1090
<211> LENGTH: 3213
<212> TYPE: RNA
<213> ORGANISM: Artificial Sequence
<220> FEATURE:
<223> OTHER INFORMATION: Synthetic

<400> SEQUENCE: 1090

```
augagcuccg ccaucaaguc cuacaagucu gugcugcggc caaacgagag aaagaaucag     60

cugcugaagu ccaccaucca gugccuggag gacggcuccg ccuucuuuuu caagaugcug    120

cagggccugu uuggcggcau cacccccgag aucgugagau ucagcacaga gcaggagaag    180

cagcagcagg auaucgcccu gugguguggcc gugaauuggu ucaggccugu gagccaggac    240

ucccugaccc acacaaucgc cuccgauaac cugguggaga aguuugagga guacuauggc    300

ggcacagcca gcgacgccau caagcaguac uucagcgccu ccaucggcga guccuacuau    360

uggaaugacu gccgccagca guacuaugau cugugucggg agcugggcgu ggaggugucu    420

gaccugaccc acgaucugga gauccugugc cgggagaagu gucuggccgu ggccacagag    480

agcaaccaga acaauucuau caucagcgug cuguuuggca ccggcgagaa ggaggauagg    540

ucugugaagc ugcgcaucac aaagaagauc cuggaggcca ucagcaaccu gaaggagauc    600

ccaaagaaug uggcccccau ccaggagauc auccugaaug uggccaaggc caccaaggag    660

acauucagac agguguacgc aggaaaccug ggagcaccau ccacccugga gaaguuuauc    720

gccaaggacg gccagaagga guucgaucug aagaagcugc agacagaccu gaagaaagug    780

auccggggca agucuaagga gagagauugg ugcugucagg aggagcugag gagcuacgug    840

gagcagaaua ccauccagua ugaccugugg gccuggggcg agauguucaa caaggcccac    900

accgcccuga agaucaaguc cacaagaaac uacaauuuug ccaagcagag gcuggagcag    960

uucaaggaga uccagucucu gaacaaucug cugguggugua agaagcugaa cgacuuuuuc   1020

gauagcgagu uuuucuccgg cgaggagacc uacacaaucu gcgugcacca ccugggcggc   1080

aaggaccugu ccaagcugua uaaggccugg gaggacgauc ccgccgaucc ugagaaugcc   1140
```

```
aucguggugc ugugcgacga ucugaagaac aauuuuaaga aggagccuau caggaacauc   1200
cugcgcuaca ucuucaccau ccgccaggag uguagcgcac aggacauccu ggcagcagca   1260
aaguacaauc agcagcugga ucgguauaag agccagaagg ccaacccauc cgugcugggc   1320
aaucagggcu uuaccuggac aaacgccgug auccugccag agaaggccca gcggaacgac   1380
agacccaauu cucuggaucu gcgcaucugg cuguaccuga agcugcggca cccugacggc   1440
agauggaaga agcaccacau cccauucuac gauacccggu uuuuccagga gaucuaugcc   1500
gccggcaaua gcccugugga caccugucag uuuaggacac cccgcuucgg cuaucaccug   1560
ccuaagcuga ccgaucagac agccauccgc gugaacaaga agcacgugaa ggcagcaaag   1620
accgaggcac ggaucagacu ggccauccag cagggcacac ugccagugac caaucugaag   1680
aucaccgaga ucuccgccac aaucaacucu aagggccagg ugcgcauccc cgugaaguuu   1740
cgggugggaa ggcagaaggg aacccugcag aucggcgacc gguucugcgg cuacgaucag   1800
aaccagacag ccucucacgc cuauagccug ugggaggugg ugaaggaggg ccaguaccac   1860
aaggagcugc ggugucgggu gcgcuucauc ucuagcggcg acaucgugac caucaccgag   1920
aaccggggca aucaguuuga ucagcugucu uaugagggcc uggccuaccc ccaguaugcc   1980
gacuggagaa agaaggccuc caaguucgug ucucuguggc agaucaccaa gaagaacaag   2040
aagaaggaga ucgugacagu ggaggccaag gagaaguuug acgccaucug caaguaccag   2100
ccuaggcugu auaaguucaa caaggaguac gccuaucugc ugcgggauau cgugagaggc   2160
aagagccugg uggagcugca gcagaucagg caggagaucu uucgcuucau cgagcaggac   2220
uguggaguga cccgccuggg aucucugagc cuguccaccc uggagacagu gaaggccgug   2280
aagggcauca ucuacuccua uuuuucuaca gcccugaaug ccucuaagaa caaucccauc   2340
agcgacgagc agcggaagga guuugauccu gagcuguucg cccugcugga gaagcuggag   2400
cugaucagga cucggaagaa gaagcagaag guggagagaa ucgccaauag ccugauccag   2460
acaugccugg agaacaauau caaguucauc aggggcgagg gcgaccuguc caccacaaac   2520
aaugccacca agaagaaggc caacucuagg agcauggauu ggcuggccag aggcguguuu   2580
aauaagaucc ggcagcuggc caccaugcac aacaucaccc uguucggcug cggcagccug   2640
uacacauccc accaggaccc ucuggugcac agaaacccag auaaggccau gaaguguaga   2700
ugggcagcaa ucccagugaa ggacaucggc gauugggugc ugagaaagcu gucccagaac   2760
cugagggcca agaaucgggg caccggcgag uacuaucacc agggcgugaa ggaguuccug   2820
ucucacuaug agcugcagga ccuggaggag gagcugcuga aguggcgguc ugauagaaag   2880
agcaacaucc cuugcugggu gcugcagaau agacuggccg agaagcuggg caacaaggag   2940
gccgugguga acaucccagu gaggggcggc cgcaucuauu uugcaaccca caagguggca   3000
acaggagccg ugagcaucgu guucgaccag aagcaagugu gggugaguaa ugcagaucac   3060
guggcagcag caaacaucgc acugaccggc aagggcaucg gccggcaguc cucugacgag   3120
gagaaccccg auggcggcag gaucaagcug cagcugacau cuaaaaggcc ggcggccacg   3180
aaaaaggccg gccaggcaaa aaagaaaaag uaa                                3213
```

<210> SEQ ID NO 1091
<211> LENGTH: 43
<212> TYPE: RNA
<213> ORGANISM: Artificial Sequence
<220> FEATURE:
<223> OTHER INFORMATION: Synthetic
<220> FEATURE:

<221> NAME/KEY: misc_feature
<222> LOCATION: (40)..(43)
<223> OTHER INFORMATION: modified with phosphorothioate
<220> FEATURE:
<221> NAME/KEY: misc_feature
<222> LOCATION: (40)..(42)
<223> OTHER INFORMATION: modified with 2'-O-methlyation

<400> SEQUENCE: 1091
agaaauccgu cuuucauuga cggcggagca uccuuggaua cag 43

<210> SEQ ID NO 1092
<211> LENGTH: 43
<212> TYPE: RNA
<213> ORGANISM: Artificial Sequence
<220> FEATURE:
<223> OTHER INFORMATION: Synthetic
<220> FEATURE:
<221> NAME/KEY: misc_feature
<222> LOCATION: (1)..(4)
<223> OTHER INFORMATION: modified with phosphorothioate
<220> FEATURE:
<221> NAME/KEY: misc_feature
<222> LOCATION: (1)..(3)
<223> OTHER INFORMATION: modified with 2'-O-methlyation
<220> FEATURE:
<221> NAME/KEY: misc_feature
<222> LOCATION: (40)..(42)
<223> OTHER INFORMATION: modified with 2'-O-methlyation
<220> FEATURE:
<221> NAME/KEY: misc_feature
<222> LOCATION: (40)..(43)
<223> OTHER INFORMATION: modified with phosphorothioate

<400> SEQUENCE: 1092
agaaauccgu cuuucauuga cggcggagca uccuuggaua cag 43

<210> SEQ ID NO 1093
<211> LENGTH: 20
<212> TYPE: RNA
<213> ORGANISM: Artificial Sequence
<220> FEATURE:
<223> OTHER INFORMATION: Synthetic

<400> SEQUENCE: 1093
caaagucuau auaugacuau 20

<210> SEQ ID NO 1094
<211> LENGTH: 20
<212> TYPE: RNA
<213> ORGANISM: Artificial Sequence
<220> FEATURE:
<223> OTHER INFORMATION: Synthetic

<400> SEQUENCE: 1094
ggaaguacug auuuagcaug 20

<210> SEQ ID NO 1095
<211> LENGTH: 20
<212> TYPE: RNA
<213> ORGANISM: Artificial Sequence
<220> FEATURE:
<223> OTHER INFORMATION: Synthetic

<400> SEQUENCE: 1095
uagauggaag cuguauccaa 20

<210> SEQ ID NO 1096
<211> LENGTH: 20

```
<212> TYPE: RNA
<213> ORGANISM: Artificial Sequence
<220> FEATURE:
<223> OTHER INFORMATION: Synthetic

<400> SEQUENCE: 1096

cggagcaucc uuggauacag                                         20


<210> SEQ ID NO 1097
<211> LENGTH: 20
<212> TYPE: RNA
<213> ORGANISM: Artificial Sequence
<220> FEATURE:
<223> OTHER INFORMATION: Synthetic

<400> SEQUENCE: 1097

aggacagagg gucagcaugc                                         20
```

GENE EDITING SYSTEMS COMPRISING AN RNA GUIDE TARGETING HYDROXYACID OXIDASE 1 (HAO1) AND USES THEREOF

CROSS REFERENCE TO RELATED APPLICATIONS

This application claims the benefit under 35 U.S.C. § 119(e) of U.S. Provisional Application No. 63/197,073, filed Jun. 4, 2021, U.S. Provisional Application No. 63/225,046, filed Jul. 23, 2021, U.S. Provisional Application No. 63/292,889, filed Dec. 22, 2021, and U.S. Provisional Application No. 63/300,727, filed Jan. 19, 2022, the contents of each of which are incorporated by reference herein in their entirety.

SEQUENCE LISTING

The instant application contains a Sequence Listing which has been filed electronically in ASCII format and is hereby incorporated by reference in its entirety. Said ASCII copy, created on Jun. 3, 2022, is named 116928-0039-0004US00_SEQ.txt and is 367,354 bytes in size.

BACKGROUND

Clustered Regularly Interspaced Short Palindromic Repeats (CRISPR) and CRISPR-associated (Cas) genes, collectively known as CRISPR-Cas or CRISPR/Cas systems, are adaptive immune systems in archaea and bacteria that defend particular species against foreign genetic elements.

SUMMARY OF THE INVENTION

The present disclosure is based, at least in part, on the development of a system for genetic editing of a hydroxyacid oxidase 1 (HAO1) gene. The system involves a Cas12i CRISPR nuclease polypeptide (e.g., a Cas12i2 polypeptide) and an RNA guide mediating cleavage at a genetic site within the HAO1 gene by the CRISPR nuclease polypeptide. As reported herein, the gene editing system disclosed herein has achieved successful editing of HAO1 gene with high editing efficiency and accuracy.

Without being bound by theory, the gene editing system disclosed herein may further exhibit one or more of the following advantageous features. Compared to SpCas9 and Cas12a, Cas12i effectors are smaller (1033 to 1093aa), which, in conjunction with their short mature crRNA (40-43 nt), is preferable in terms of delivery and cost of synthesis. Cas12i cleavage results in larger deletions compared to the small deletions and +1 insertions induced by Cas9 cleavage. Cas12i PAM sequences also differ from those of Cas9. Therefore, larger and different portions of genetic sites of interest can be disrupted with a Cas12i polypeptide and RNA guide compared to Cas9. Using an unbiased approach of tagmentation-based tag integration site sequencing (TTISS), more potential off-target sites with a higher number of unique integration events were identified for SpCas9 compared to Cas12i2. See WO/2021/202800. Therefore, Cas12i such as Cas12i2 may be more specific than Cas9.

Accordingly, provided herein are gene editing systems for editing HAO1 gene, pharmaceutical compositions or kits comprising such, methods of using the gene editing systems to produce genetically modified cells, and the resultant cells thus produced. Also provided herein are uses of the gene editing systems disclosed herein, the pharmaceutical compositions and kits comprising such, and/or the genetically modified cells thus produced for treating primary hyperoxaluria (PH) in a subject.

In some aspects, the present disclosure features system for genetic editing of a hydroxyacid oxidase 1 (HAO1) gene, comprising (i) a Cas12i polypeptide or a first nucleic acid encoding the Cas12i polypeptide, and (ii) an RNA guide or a second nucleic acid encoding the RNA guide. The RNA guide comprises a spacer sequence specific to a target sequence within an HAO1 gene, the target sequence being adjacent to a protospacer adjacent motif (PAM) comprising the motif of 5'-TTN-3', which is located 5' to the target sequence.

In some embodiments, the Cas12i polypeptide can be a Cas12i2 polypeptide. In other embodiments, the Cas12i polypeptide can be a Cas12i4 polypeptide.

In some embodiments, the Cas12i polypeptide is a Cas12i2 polypeptide, which comprises an amino acid sequence at least 95% identical to SEQ ID NO: 922 and comprises one or more mutations relative to SEQ ID NO: 922. In some embodiments, the one or more mutations in the Cas12i2 polypeptide are at positions D581, G624, F626, P868, I926, V1030, E1035, and/or S1046 of SEQ ID NO: 922. In some examples, the one or more mutations are amino acid substitutions, which optionally is D581R, G624R, F626R, P868T, I926R, V1030G, E1035R, S1046G, or a combination thereof.

In one example, the Cas12i2 polypeptide comprises mutations at positions D581, D911, 1926, and V1030 (e.g., amino acid substitutions of D581R, D911R, I926R, and V1030G). In another example, the Cas12i2 polypeptide comprises mutations at positions D581, I926, and V1030 (e.g., amino acid substitutions of D581R, I926R, and V1030G). In yet another example, the Cas12i2 polypeptide comprises mutations at positions D581, I926, V1030, and S1046 (e.g., amino acid substitutions of D581R, I926R, V1030G, and S1046G). In still another example, the Cas12i2 polypeptide comprises mutations at positions D581, G624, F626, I926, V1030, E1035, and S1046 (e.g., amino acid substitutions of D581R, G624R, F626R, I926R, V1030G, E1035R, and S1046G). In another example, the Cas12i2 polypeptide comprises mutations at positions D581, G624, F626, P868, I926, V1030, E1035, and S1046 (e.g., amino acid substitutions of D581R, G624R, F626R, P868T, I926R, V1030G, E1035R, and 51046G).

Exemplary Cas12i2 polypeptides for use in any of the gene editing systems disclosed herein may comprise the amino acid sequence of any one of SEQ ID NOs: 923-927. In one example, the exemplary Cas12i2 polypeptide for use in any of the gene editing systems disclosed herein comprises the amino acid sequence of SEQ ID NO: 924. In another example, the exemplary Cas12i2 polypeptide for use in any of the gene editing systems disclosed herein comprises the amino acid sequence of SEQ ID NO: 927.

In some embodiments, the gene editing system may comprise the first nucleic acid encoding the Cas12i polypeptide (e.g., the Cas12i2 polypeptide as disclosed herein). In some instances, the first nucleic acid is located in a first vector (e.g., a viral vector such as an adeno-associated viral vector or AAV vector). In some instances, the first nucleic acid is a messenger RNA (mRNA). In some instances, the nucleic acid encoding the Cas12i polypeptide (e.g., the Cas12i2 polypeptide as disclosed herein) is codon-optimized.

In some embodiments, the target sequence may be within exon 1 or exon 2 of the HAO1 gene. In some examples, the target sequence comprises 5'-CAAAGTCTATATATGAC- TAT-3' (SEQ ID NO: 1025), 5'-GGAAGTACTGATTTAG-CATG-3' (SEQ ID NO: 1026), 5'-TAGATG-GAAGCTGTATCCAA-3' (SEQ ID NO: 1046), 5'-CGGAGCATCCTTGGATACAG-3' (SEQ ID NO: 1047), or 5'-AGGACAGAGGGTCAGCATGC-3' (SEQ ID NO: 1052). In specific examples, the target sequence can be the nucleotide sequence of SEQ ID NO: 1047.

In some embodiments, the spacer sequence may be 20-30-nucleotide in length. In some examples, the spacer sequence is 20-nucleotide in length. In some examples, the spacer sequence comprises 5'-CAAAGUCUAUAUAUGACUAU-3' (SEQ ID NO: 1093); 5'-GGAAGUACUGAUUUAG-CAUG-3' (SEQ ID NO: 1094); 5'-UAGAUGGAAGCU-GUAUCCAA-3' (SEQ ID NO: 1095); 5'-CGGAGCAUCCUUGGAUACAG-3' (SEQ ID NO: 1096); or 5'-AGGACAGAGGGUCAGCAUGC-3 (SEQ ID NO: 1097). In specific examples, the spacer sequence may comprise SEQ ID NO: 1096.

In some embodiments, the RNA guide comprises the spacer and a direct repeat sequence. In some examples, the direct repeat sequence is 23-36-nucleotide in length. In one example, the direct repeat sequence is at least 90% identical to any one of SEQ ID NOs: 1-10 or a fragment thereof that is at least 23-nucleotide in length. In some specific examples, the direct repeat sequence is any one of SEQ ID NOs: 1-10, or a fragment thereof that is at least 23-nucleotide in length. By way of non-limiting example, the direct repeat sequence is 5'-AGAAAUCCGUCUUU-CAUUGACGG-3' (SEQ ID NO: 10).

In specific examples, the RNA guide may comprise the nucleotide sequence of 5'-AGAAAUCCGUCUUU-CAUUGACGGCAAAGUCUAUAUAUGACUAU-3' (SEQ ID NO: 967), 5'-AGAAAUCCGUCUUU-CAUUGACGGGGAAGUACUGAUUUAGCAUG-3' (SEQ ID NO: 968), 5'-AGAAAUCCGUCUUU-CAUUGACGGUAGAUGGAAGCUGUAUCCAA-3' (SEQ ID NO: 988), 5'-AGAAAUCCGUCUUU-CAUUGACGGCGGAGCAUCCUUGGAUACAG-3' (SEQ ID NO: 989), or 5'-AGAAAUCCGUCUUUCAUUGACG-GAGGACAGAGGGUCAGCAUGC-3' (SEQ ID NO: 994). In specific examples, the RNA guide may comprise SEQ ID NO: 989.

In some embodiments, the system may comprise the second nucleic acid encoding the RNA guide. In some examples, the nucleic acid encoding the RNA guide may be located in a viral vector. In some examples, the viral vector comprises the both the first nucleic acid encoding the Cas12i2 polypeptide and the second nucleic acid encoding the RNA guide.

In some embodiments, any of the systems described herein may comprise the first nucleic acid encoding the Cas12i2 polypeptide, which is located in a first vector, and the second nucleic acid encoding the RNA guide, which is located on a second vector. In some examples, the first and/or second vector is a viral vector. In some specific examples, the first and second vectors are the same vector. In other examples, the first and second vectors are different vectors.

In some embodiments, any of the systems described herein may comprise one or more lipid nanoparticles (LNPs), which encompass the Cas12i2 polypeptide or the first nucleic acid encoding the Cas12i2 polypeptide, the RNA guide or the second nucleic acid encoding the RNA guide, or both.

In some embodiments, the system described herein may comprise a LNP, which encompass the Cas12i2 polypeptide or the first nucleic acid encoding the Cas12i2 polypeptide, and a viral vector comprising the second nucleic acid encoding the RNA guide. In some examples, the viral vector is an AAV vector. In other embodiments, the system described herein may comprise a LNP, which encompass the RNA guide or the second nucleic acid encoding the RNA guide, and a viral vector comprising the first nucleic acid encoding the Cas12i2 polypeptide. In some examples, the viral vector is an AAV vector.

In some aspects, the present disclosure also provides a pharmaceutical composition comprising any of the gene editing systems disclosed herein, or a kit comprising the components of the gene editing system.

In other aspects, the present disclosure also features a method for editing a hydroxyacid oxidase 1 (HAO1) gene in a cell, the method comprising contacting a host cell with any of the systems disclosed herein to genetically edit the HAO1 gene in the host cell. In some examples, the host cell is cultured in vitro. In other examples, the contacting step is performed by administering the system for editing the HAO1 gene to a subject comprising the host cell.

Also within the scope of the present disclosure is a cell comprising a disrupted a hydroxyacid oxidase 1 (HAO1) gene, which can be produced by contacting a host cell with the system disclosed herein genetically edit the HAO1 gene in the host cell.

Still in other aspects, the present disclosure provides a method for treating primary hyperoxaluria (PH) in a subject. The method may comprise administering to a subject in need thereof any of the systems for editing a hydroxyacid oxidase 1 (HAO1) gene or any of the modified cells disclosed herein. In some embodiments, the subject may be a human patient having the PH. In some examples, the PH is PH1, PH2, or PH3. In a specific example, the PH is PH1.

Also provided herein is an RNA guide, comprising (i) a spacer sequence as disclosed herein that is specific to a target sequence in a hydroxyacid oxidase 1 (HAO1) gene, wherein the target sequence is adjacent to a protospacer adjacent motif (PAM) comprising the motif of 5'-TTN-3', which is located 5' to the target sequence; and (ii) a direct repeat sequence.

In some embodiments, the spacer may be 20-30-nucleotide in length. In some examples, the spacer is 20-nucleotide in length.

In some embodiments, the direct repeat sequence may be 23-36-nucleotide in length. In some examples, the direct repeat sequence is 23-nucleotide in length.

In some embodiments, the target sequence may be within exon 1 or exon 2 of the HAO1 gene. In some examples, the target sequence comprises 5'-CAAAGTCTATATATGAC-TAT-3' (SEQ ID NO: 1025), 5'-GGAAGTACTGATTTAG-CATG-3' (SEQ ID NO: 1026), 5'-TAGATG-GAAGCTGTATCCAA-3' (SEQ ID NO: 1046), 5'-CGGAGCATCCTTGGATACAG- 3' (SEQ ID NO: 1047), or 5'-AGGACAGAGGGTCAGCATGC-3' (SEQ ID NO: 1052). In specific examples, the target sequence may comprise SEQ ID NO: 1047.

In some embodiments, the spacer sequence may be set forth as 5'-CAAAGUCUAUAUAUGACUAU-3' (SEQ ID NO: 1093); 5'-GGAAGUACUGAUUUAGCAUG-3' (SEQ ID NO:1094); 5'-UAGAUGGAAGCUGUAUCCAA-3' (SEQ ID NO: 1095); 5'-CGGAGCAUCCUUGGAUACAG-3' (SEQ ID NO: 1096); or 5'-AGGACAGAGGGUCAG-CAUGC-3 (SEQ ID NO: 1097). In specific examples, the spacer sequence may comprise SEQ ID NO: 1096.

In some embodiments, the direct repeat sequence may be at least 90% identical to any one of SEQ ID NOs: 1-10 or a fragment thereof that is at least 23-nucleotide in length. In some examples, the direct repeat sequence is any one of SEQ ID NOs: 1-10, or a fragment thereof that is at least 23-nucleotide in length. By way of non-limiting example, the direct repeat sequence is 5'-AGAAAUCCGUCUUUCAUUGACGG-3' (SEQ ID NO: 10).

In some embodiments, the RNA guide may comprise the nucleotide sequence of 5'-AGAAAUCCGUCUUUCAUUGACGGCAAAGUCUAUAUAUGACUAU-3' (SEQ ID NO: 967), 5'-AGAAAUCCGUCUUUCAUUGACGGGGAAGUACUGAUUUAGCAUG-3' (SEQ ID NO: 968), 5'-AGAAAUCCGUCUUUCAUUGACGGUAGAUGGAAGCUGUAUCCAA-3' (SEQ ID NO: 988), 5'-AGAAAUCCGUCUUUCAUUGACGGCGGAGCAUCCUUGGAUACAG-3' (SEQ ID NO: 989), or 5'-AGAAAUCCGUCUUUCAUUGACGGAGGACAGAGGGUCAGCAUGC-3' (SEQ ID NO: 994). In specific examples, the RNA guide may comprise SEQ ID NO: 989.

Also provided herein are any of the gene editing systems disclosed herein, pharmaceutical compositions or kits comprising such, or genetically modified cells generated by the gene editing system for use in treating PH in a subject, as well as uses of the gene editing systems disclosed herein, pharmaceutical compositions or kits comprising such, or genetically modified cells generated by the gene editing system for manufacturing a medicament for treatment of PH in a subject.

The details of one or more embodiments of the invention are set forth in the description below. Other features or advantages of the present invention will be apparent from the following drawings and detailed description of several embodiments, and also from the appended claims.

BRIEF DESCRIPTION OF THE DRAWINGS

The following drawings form part of the present specification and are included to further demonstrate certain aspects of the present disclosure, which can be better understood by reference to the drawing in combination with the detailed description of specific embodiments presented herein.

DETAILED DESCRIPTION

Figure 1:
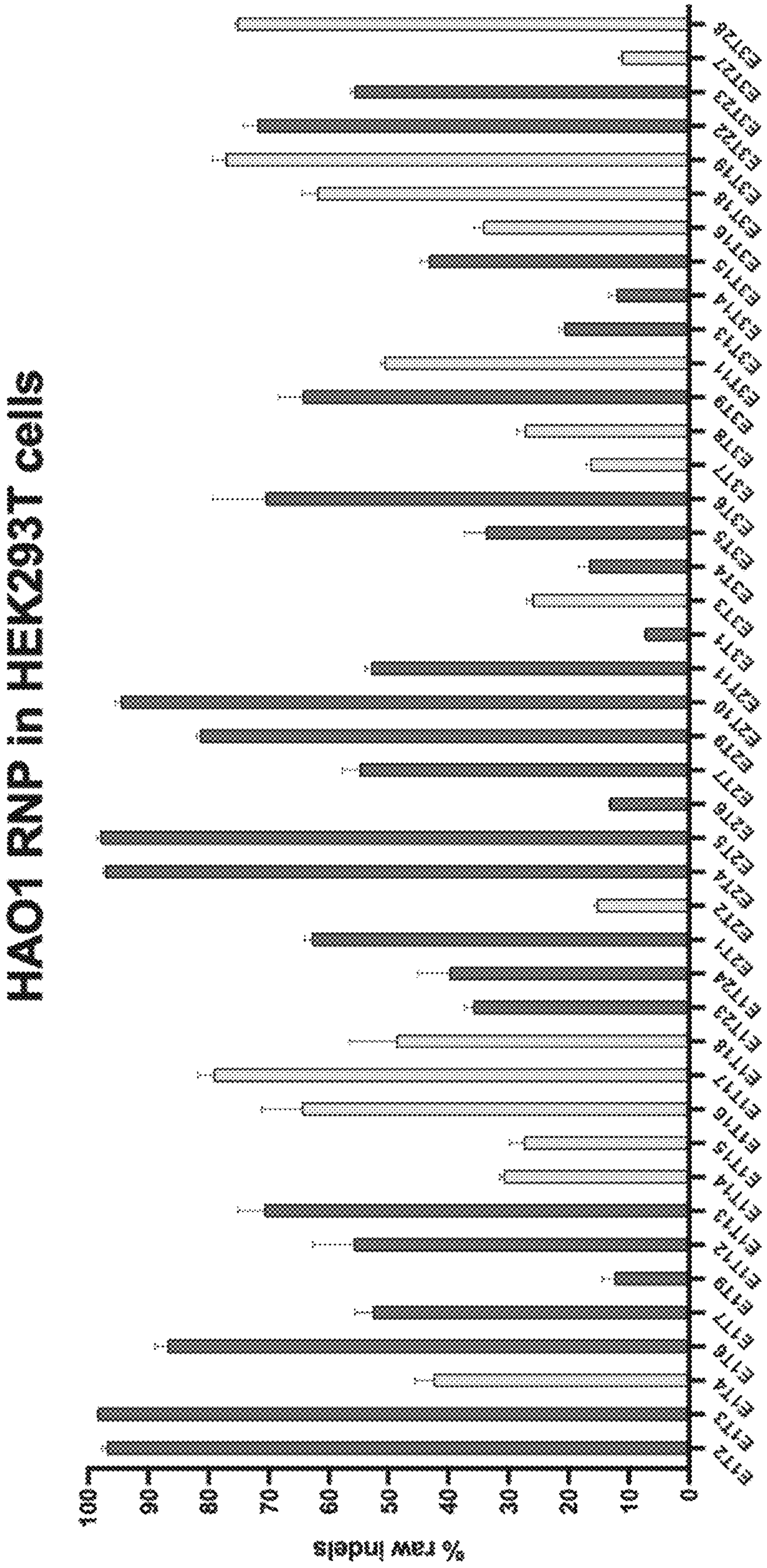
FIG. 1 is a graph showing the ability of RNPs prepared with a Cas12i2 polypeptide and a crRNA to edit the HAO1 gene in HEK293 cells. The darker grey bars represent target sequences with perfect homology to both rhesus macaque (*Macaca mulatta*) and crab-eating macaque (*Macaca fascicularis*) sequences.

The present disclosure relates to a system for genetic editing of a hydroxyacid oxidase 1 (HAO1) gene (a.k.a., glycolate oxidase gene), which comprises (i) a Cas12i polypeptide or a first nucleic acid encoding the Cas12i polypeptide, and (ii) an RNA guide or a second nucleic acid encoding the RNA guide, wherein the RNA guide comprises a spacer sequence specific to a target sequence within an HAO1 gene, the target sequence being adjacent to a protospacer adjacent motif (PAM) comprising the motif of 5'-TTN-3', which is located 5' to the target sequence. Also provided in the present disclosure are a pharmaceutical composition or a kit comprising such system as well as uses thereof. Further disclosed herein are a method for editing a HAO1 gene in a cell, a cell so produced that comprises a disrupted a HAO1 gene, a method of treating primary hyperoxaluria (PH) in a subject, and an RNA guide that comprises (i) a spacer that is specific to a target sequence in a HAO1 gene, wherein the target sequence is adjacent to a protospacer adjacent motif (PAM) comprising the motif of 5'-TTN-3', which is located 5' to the target sequence; and (ii) a direct repeat sequence as well as uses thereof.

The Cas12i polypeptide for use in the gene editing system disclosed herein may be a Cas12i2 polypeptide, e.g., a wild-type Cas12i polypeptide or a variant thereof as those disclosed herein. In some examples, the Cas12i2 polypeptide comprises an amino acid sequence at least 95% identical to SEQ ID NO: 922 and comprises one or more mutations relative to SEQ ID NO: 922. In other examples, the Cas12i polypeptide may be a Cas12i4 polypeptide, which is also disclosed herein.

Definitions

The present disclosure will be described with respect to particular embodiments and with reference to certain Figures, but the disclosure is not limited thereto but only by the claims. Terms as set forth hereinafter are generally to be understood in their common sense unless indicated otherwise.

As used herein, the term "activity" refers to a biological activity. In some embodiments, activity includes enzymatic activity, e.g., catalytic ability of a Cas12i polypeptide. For example, activity can include nuclease activity.

As used herein the term "HAO1" refers to "glycolate oxidase 1," which is also known as "hydroxyacid oxidase." HAO1 is a peroxisome protein expressed primarily in the liver and pancreas, and its activities include oxidation of glycolate and 2-hydroxy fatty acids. SEQ ID NO: 928 as set forth herein provides an example of an HAO1 gene sequence.

As used herein, the term "Cas12i polypeptide" (also referred to herein as Cas12i) refers to a polypeptide that binds to a target sequence on a target nucleic acid specified by an RNA guide, wherein the polypeptide has at least some amino acid sequence homology to a wild-type Cas12i polypeptide. In some embodiments, the Cas12i polypeptide comprises at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99% or 100% sequence identity with any one of SEQ ID NOs: 1-5 and 11-18 of U.S. Pat. No. 10,808,245, which is incorporated by reference for the subject matter and purpose referenced herein. In some embodiments, a Cas12i polypeptide comprises at least 75%, at least 80%, at least 81%, at least 82%, at least 83%, at least 84%, at least 85%, at least 90%, at least 91%, at least 92%, at least 93%, at least 94%, at least 95%, at least 96%, at least 97%, at least 98%, at least 99% or 100% sequence identity with any one of SEQ ID NOs: 8, 2, 11, and 9 of the present application. In some embodiments, a Cas12i polypeptide of the disclosure is a Cas12i2 polypeptide as described in WO/2021/202800, the relevant disclosures of which are incorporated by reference for the subject matter and purpose referenced herein. In some embodiments, the Cas12i polypeptide cleaves a target nucleic acid (e.g., as a nick or a double strand break).

As used herein, the term "adjacent to" refers to a nucleotide or amino acid sequence in close proximity to another nucleotide or amino acid sequence. In some embodiments, a nucleotide sequence is adjacent to another nucleotide sequence if no nucleotides separate the two sequences (i.e., immediately adjacent). In some embodiments, a nucleotide sequence is adjacent to another nucleotide sequence if a small number of nucleotides separate the two sequences (e.g., about 1, 2, 3, 4, 5, 6, 7, 8, 9, 10, 11, 12, 13, 14, 15, 16, 17, 18, 19, or 20 nucleotides). In some embodiments, a first sequence is adjacent to a second sequence if the two sequences are separated by about 5, 6, 7, 8, 9, 10, 11, 12, 13, 14, or 15 nucleotides. In some embodiments, a first sequence is adjacent to a second sequence if the two sequences are separated by up to 2 nucleotides, up to 5 nucleotides, up to 8 nucleotides, up to 10 nucleotides, up to 12 nucleotides, or up to 15 nucleotides. In some embodiments, a first sequence is adjacent to a second sequence if the two sequences are separated by 2-5 nucleotides, 4-6 nucleotides, 4-8 nucleotides, 4-10 nucleotides, 6-8 nucleotides, 6-10 nucleotides, 6-12 nucleotides, 8-10 nucleotides, 8-12 nucleotides, 10-12 nucleotides, 10-15 nucleotides, or 12-15 nucleotides.

As used herein, the term "complex" refers to a grouping of two or more molecules. In some embodiments, the complex comprises a polypeptide and a nucleic acid molecule interacting with (e.g., binding to, coming into contact with, adhering to) one another. For example, the term "complex" can refer to a grouping of an RNA guide and a polypeptide (e.g., a Cas12i polypeptide). Alternatively, the term "complex" can refer to a grouping of an RNA guide, a polypeptide, and the complementary region of a target sequence. In another example, the term "complex" can refer to a grouping of an HAO1-targeting RNA guide and a Cas12i polypeptide.

As used herein, the term "protospacer adjacent motif" or "PAM" refers to a DNA sequence adjacent to a target sequence (e.g., an HAO1 target sequence) to which a complex comprising an RNA guide (e.g., an HAO1-targeting RNA guide) and a Cas12i polypeptide binds. In a double-stranded DNA molecule, the strand containing the PAM motif is called the "PAM-strand" and the complementary strand is called the "non-PAM strand." The RNA guide binds to a site in the non-PAM strand that is complementary to a target sequence disclosed herein.

In some embodiments, the PAM strand is a coding (e.g., sense) strand. In other embodiments, the PAM strand is a non-coding (e.g., antisense strand). Since an RNA guide binds the non-PAM strand via base-pairing, the non-PAM strand is also known as the target strand, while the PAM strand is also known as the non-target strand.

As used herein, the term "target sequence" refers to a DNA fragment adjacent to a PAM motif (on the PAM strand). The complementary region of the target sequence is on the non-PAM strand. A target sequence may be immediately adjacent to the PAM motif. Alternatively, the target sequence and the PAM may be separately by a small sequence segment (e.g., up to 5 nucleotides, for example, up to 4, 3, 2, or 1 nucleotide). A target sequence may be located at the 3' end of the PAM motif or at the 5' end of the PAM motif, depending upon the CRISPR nuclease that recognizes the PAM motif, which is known in the art. For example, a target sequence is located at the 3' end of a PAM motif for a Cas12i polypeptide (e.g., a Cas12i2 polypeptide such as those disclosed herein). In some embodiments, the target sequence is a sequence within an HAO1 gene sequence, including, but not limited, to the sequence set forth in SEQ ID NO: 928.

As used herein, the term "adjacent to" refers to a nucleotide or amino acid sequence in close proximity to another nucleotide or amino acid sequence. In some embodiments, a nucleotide sequence is adjacent to another nucleotide sequence if no nucleotides separate the two sequences (i.e., immediately adjacent). In some embodiments, a nucleotide sequence is adjacent to another nucleotide sequence if a small number of nucleotides separate the two sequences (e.g., about 1, 2, 3, 4, 5, 6, 7, 8, 9, 10, 11, 12, 13, 14, 15, 16, 17, 18, 19, or 20 nucleotides). In some embodiments, a first sequence is adjacent to a second sequence if the two sequences are separated by about 5, 6, 7, 8, 9, 10, 11, 12, 13, 14, or 15 nucleotides. In some embodiments, a first sequence is adjacent to a second sequence if the two sequences are separated by up to 2 nucleotides, up to 5 nucleotides, up to 8 nucleotides, up to 10 nucleotides, up to 12 nucleotides, or up to 15 nucleotides. In some embodiments, a first sequence is adjacent to a second sequence if the two sequences are separated by 2-5 nucleotides, 4-6 nucleotides, 4-8 nucleotides, 4-10 nucleotides, 6-8 nucleotides, 6-10 nucleotides, 6-12 nucleotides, 8-10 nucleotides, 8-12 nucleotides, 10-12 nucleotides, 10-15 nucleotides, or 12-15 nucleotides.

As used herein, the term "spacer" or "spacer sequence" is a portion in an RNA guide that is the RNA equivalent of the target sequence (a DNA sequence). The spacer contains a sequence capable of binding to the non-PAM strand via base-pairing at the site complementary to the target sequence (in the PAM strand). Such a spacer is also known as specific to the target sequence. In some instances, the spacer may be at least 75% identical to the target sequence (e.g., at least 80%, at least 85%, at least 90%, at least 95%, at least 98%, or at least 99%), except for the RNA-DNA sequence difference. In some instances, the spacer may be 100% identical to the target sequence except for the RNA-DNA sequence difference.

As used herein, the term "RNA guide" or "RNA guide sequence" refers to any RNA molecule or a modified RNA molecule that facilitates the targeting of a polypeptide (e.g., a Cas12i polypeptide) described herein to a target sequence (e.g., a sequence of an HAO1 gene). For example, an RNA guide can be a molecule that is designed to be complementary to a specific nucleic acid sequence (a target sequence such as a target sequence with an HAO1 gene). An RNA guide may comprise a spacer sequence and a direct repeat (DR) sequence. In some instances, the RNA guide can be a modified RNA molecule comprising one or more deoxyribonucleotides, for example, in a DNA-binding sequence contained in the RNA guide, which binds a sequence complementary to the target sequence. In some examples, the DNA-binding sequence may contain a DNA sequence or a DNA/RNA hybrid sequence. The terms CRISPR RNA (crRNA), pre-crRNA and mature crRNA are also used herein to refer to an RNA guide.

As used herein, the term "complementary" refers to a first polynucleotide (e.g., a spacer sequence of an RNA guide) that has a certain level of complementarity to a second polynucleotide (e.g., the complementary sequence of a target sequence) such that the first and second polynucleotides can form a double-stranded complex via base-pairing to permit an effector polypeptide that is complexed with the first polynucleotide to act on (e.g., cleave) the second polynucleotide. In some embodiments, the first polynucleotide may be substantially complementary to the second polynucleotide, i.e., having at least about 80%, 81%, 82%, 83%, 84%, 85%, 86%, 87%, 88%, 89%, 90%, 91%, 92%, 93%, 94%, 95%, 96%, 97%, 98%, or 99% complementarity to the second polynucleotide. In some embodiments, the first polynucleotide is completely complementary to the second polynucleotide, i.e., having 100% complementarity to the second polynucleotide.

The "percent identity" (a.k.a., sequence identity) of two nucleic acids or of two amino acid sequences is determined using the algorithm of Karlin and Altschul *Proc. Natl. Acad. Sci.* USA 87:2264-68, 1990, modified as in Karlin and Altschul *Proc. Natl. Acad. Sci.* USA 90:5873-77, 1993. Such an algorithm is incorporated into the NBLAST and XBLAST programs (version 2.0) of Altschul, et al. *J. Mol. Biol.* 215:403-10, 1990. BLAST nucleotide searches can be performed with the NBLAST program, score=100, wordlength-12 to obtain nucleotide sequences homologous to the nucleic acid molecules of the invention. BLAST protein searches can be performed with the XBLAST program, score=50, word length=3 to obtain amino acid sequences homologous to the protein molecules of the invention. Where gaps exist between two sequences, Gapped BLAST can be utilized as described in Altschul et al., *Nucleic Acids Res.* 25(17):3389-3402, 1997. When utilizing BLAST and Gapped BLAST programs, the default parameters of the respective programs (e.g., XBLAST and NBLAST) can be used.

As used herein, the term "edit" refers to one or more modifications introduced into a target nucleic acid, e.g., within the HAO1 gene. The edit can be one or more substitutions, one or more insertions, one or more deletions, or a combination thereof. As used herein, the term "substitution" refers to a replacement of a nucleotide or nucleotides with a different nucleotide or nucleotides, relative to a reference sequence. As used herein, the term "insertion" refers to a gain of a nucleotide or nucleotides in a nucleic acid sequence, relative to a reference sequence. As used herein, the term "deletion" refers to a loss of a nucleotide or nucleotides in a nucleic acid sequence, relative to a reference sequence.

No particular process is implied in how to make a sequence comprising a deletion. For instance, a sequence comprising a deletion can be synthesized directly from individual nucleotides. In other embodiments, a deletion is made by providing and then altering a reference sequence. The nucleic acid sequence can be in a genome of an organism. The nucleic acid sequence can be in a cell. The nucleic acid sequence can be a DNA sequence. The deletion can be a frameshift mutation or a non-frameshift mutation. A deletion described herein refers to a deletion of up to several kilobases.

As used herein, the terms "upstream" and "downstream" refer to relative positions within a single nucleic acid (e.g., DNA) sequence in a nucleic acid molecule. "Upstream" and "downstream" relate to the 5' to 3' direction, respectively, in which RNA transcription occurs. A first sequence is upstream of a second sequence when the 3' end of the first sequence occurs before the 5' end of the second sequence. A first sequence is downstream of a second sequence when the 5' end of the first sequence occurs after the 3' end of the second sequence. In some embodiments, the 5'-NTTN-3' or 5'-TTN-3' sequence is upstream of an indel described herein, and a Cas12i-induced indel is downstream of the 5'-NTTN-3' or 5'-TTN-3' sequence.

I. Gene Editing Systems

In some aspects, the present disclosure provides gene editing systems comprising an RNA guide targeting an HAO1 gene. Such a gene editing system can be used to edit the HAO1 target gene, e.g., to disrupt the HAO1 gene.

Hydroxyacid oxidase 1 (HAO1, also known as glycolate oxidase [GOX or GO]), converts glycolate into glyoxylate. It has been proposed that inhibition of HAO1 in individuals with PH1 would block formation of glyoxylate, and excess glycolate would be excreted through the urine. The idea of treating PH1 by inhibition of HAO1 is further supported that some individuals with abnormal splice variants of HAO1 are asymptomatic for glycolic aciduria, whereby there was increased urinary glycolic acid excretion without apparent kidney pathology. Thus, inhibition of HAO1 expression would block production of glyoxylate, and in turn block production of its metabolite, oxalate. Accordingly, the gene editing systems disclosed here, targeting the HAO1 gene, could be used to treat primary hyperoxaluria (PH) in a subject in need of the treatment.

In some embodiments, the RNA guide is comprised of a direct repeat component and a spacer component. In some embodiments, the RNA guide binds a Cas12i polypeptide. In some embodiments, the spacer component is specific to an HAO1 target sequence, wherein the HAO1 target sequence is adjacent to a 5'-NTTN-3' or 5'-TTN-3' PAM sequence as described herein. In the case of a double-stranded target, the RNA guide binds to a first strand of the target (i.e., the non-PAM strand) and a PAM sequence as described herein is present in the second, complementary strand (i.e., the PAM strand).

In some embodiments, the present disclosure provides compositions comprising a complex, wherein the complex comprises an RNA guide targeting HAO1. In some embodiments, the present disclosure comprises a complex comprising an RNA guide and a Cas12i polypeptide. In some embodiments, the RNA guide and the Cas12i polypeptide bind to each other in a molar ratio of about 1:1. In some embodiments, a complex comprising an RNA guide and a Cas12i polypeptide binds to the complementary region of a target sequence within an HAO1 gene. In some embodiments, a complex comprising an RNA guide targeting HAO1 and a Cas12i polypeptide binds to the complementary region of a target sequence within an HAO1 gene at a molar ratio of about 1:1. In some embodiments, the complex comprises enzymatic activity, such as nuclease activity, that can cleave the HAO1 target sequence and/or the complementary sequence. The RNA guide, the Cas12i polypeptide, and the complementary region of the HAO1 target sequence, either alone or together, do not naturally occur. In some embodiments, the RNA guide in the complex comprises a direct repeat and/or a spacer sequence described herein. In some embodiments, the sequence of the RNA guide has at least 90% identity (e.g., at least 90%, 91%, 92%, 93%, 94%, 95%, 96%, 97%, 98%, or 99% identity) to a sequence of any one of SEQ ID NOs: 967-1023. In some embodiments, the RNA guide has a sequence of any one of SEQ ID NOs: 967-1023.

In some embodiments, the present disclosure described herein comprises compositions comprising an RNA guide as described herein and/or an RNA encoding a Cas12i polypeptide as described herein. In some embodiments, the RNA guide and the RNA encoding a Cas12i polypeptide are comprised together within the same composition. In some embodiments, the RNA guide and the RNA encoding a Cas12i polypeptide are comprised within separate compositions. In some embodiments, the RNA guide comprises a direct repeat and/or a spacer sequence described herein. In some embodiments, the sequence of the RNA guide has at least 90% identity (e.g., at least 90%, 91%, 92%, 93%, 94%, 95%, 96%, 97%, 98%, or 99% identity) to a sequence of any one of SEQ ID NOs: 967-1023. In some embodiments, the RNA guide has a sequence of any one of SEQ ID NOs: 967-1023.

Use of the gene editing systems disclosed herein has advantages over those of other known nuclease systems. Cas12i polypeptides are smaller than other nucleases. For example, Cas12i2 is 1,054 amino acids in length, whereas *S. pyogenes* Cas9 (SpCas9) is 1,368 amino acids in length, *S. thermophilus* Cas9 (StCas9) is 1,128 amino acids in length, FnCpf1 is 1,300 amino acids in length, AsCpf1 is 1,307 amino acids in length, and LbCpf1 is 1,246 amino acids in length. Cas12i RNA guides, which do not require a trans-activating CRISPR RNA (tracrRNA), are also smaller than Cas9 RNA guides. The smaller Cas12i polypeptide and RNA guide sizes are beneficial for delivery. Compositions comprising a Cas12i polypeptide also demonstrate decreased off-target activity compared to compositions comprising an SpCas9 polypeptide. See PCT/US2021/025257, which is incorporated by reference in its entirety. Furthermore, indels induced by compositions comprising a Cas12i polypeptide differ from indels induced by compositions comprising an SpCas9 polypeptide. For example, SpCas9 polypeptides primarily induce insertions and deletions of 1 nucleotide in length. However, Cas12i polypeptides induce larger deletions, which can be beneficial in disrupting a larger portion of a gene such as HAO1.

Also provided herein is a system for genetic editing of a hydroxyacid oxidase 1 (HAO1) gene, which comprises (i) a Cas12i polypeptide (e.g., a Cas12i2 polypeptide) or a first nucleic acid encoding the Cas12i polypeptide (e.g., a Cas12i2 polypeptide comprises an amino acid sequence at least 95% identical to SEQ ID NO: 922, which may and comprises one or more mutations relative to SEQ ID NO: 922); and (ii) an RNA guide or a second nucleic acid encoding the RNA guide, wherein the RNA guide comprises a spacer sequence specific to a target sequence within an HAO1 gene (e.g., within exon 1 or exon 2 of the HAO1 gene), the target sequence being adjacent to a protospacer adjacent motif (PAM) comprising the motif of 5'-TTN-3' (5'-NTTN-3'), which is located 5' to the target sequence.

A. RNA Guides

In some embodiments, the gene editing system described herein comprises an RNA guide targeting a HAO1 gene, for example, targeting exon 1 or exon 2 of the HAO1 gene. In some embodiments, the gene editing system described herein may comprise two or more (e.g., 2, 3, 4, 5, 6, 7, 8, 9, or more) RNA guides targeting HAO1.

The RNA guide may direct the Cas12i polypeptide contained in the gene editing system as described herein to an HAO1 target sequence. Two or more RNA guides may direct two or more separate Cas12i polypeptides (e.g., Cas12i polypeptides having the same or different sequence) as described herein to two or more (e.g., 2, 3, 4, 5, 6, 7, 8, 9, or more) HAO1 target sequences.

Those skilled in the art reading the below examples of particular kinds of RNA guides will understand that, in some embodiments, an RNA guide is HAO1 target-specific. That is, in some embodiments, an RNA guide binds specifically to one or more HAO1 target sequences (e.g., within a cell) and not to non-targeted sequences (e.g., non-specific DNA or random sequences within the same cell).

In some embodiments, the RNA guide comprises a spacer sequence followed by a direct repeat sequence, referring to the sequences in the 5' to 3' direction. In some embodiments, the RNA guide comprises a first direct repeat sequence followed by a spacer sequence and a second direct repeat sequence, referring to the sequences in the 5' to 3' direction. In some embodiments, the first and second direct repeats of such an RNA guide are identical. In some embodiments, the first and second direct repeats of such an RNA guide are different.

In some embodiments, the spacer sequence and the direct repeat sequence(s) of the RNA guide are present within the same RNA molecule. In some embodiments, the spacer and direct repeat sequences are linked directly to one another. In some embodiments, a short linker is present between the spacer and direct repeat sequences, e.g., an RNA linker of 1, 2, or 3 nucleotides in length. In some embodiments, the spacer sequence and the direct repeat sequence(s) of the RNA guide are present in separate molecules, which are joined to one another by base pairing interactions.

Additional information regarding exemplary direct repeat and spacer components of RNA guides is provided as follows.

(i). Direct Repeat

In some embodiments, the RNA guide comprises a direct repeat sequence. In some embodiments, the direct repeat sequence of the RNA guide has a length of between 12-100, 13- 75, 14-50, or 15-40 nucleotides (e.g., 15, 16, 17, 18, 19, 20, 21, 22, 23, 24, 25, 26, 27, 28, 29, 30, 31, 32, 33, 34, 35, 36, 37, 38, 39, or 40 nucleotides).

In some embodiments, the direct repeat sequence is a sequence of Table 1 or a portion of a sequence of Table 1. The direct repeat sequence can comprise nucleotide 1 through nucleotide 36 of any one of SEQ ID NOs: 1, 2, 3, 4, 5, 6, 7, or 8. The direct repeat sequence can comprise nucleotide 2 through nucleotide 36 of any one of SEQ ID NOs: 1, 2, 3, 4, 5, 6, 7, or 8. The direct repeat sequence can comprise nucleotide 3 through nucleotide 36 of any one of SEQ ID NOs: 1, 2, 3, 4, 5, 6, 7, or 8. The direct repeat sequence can comprise nucleotide 4 through nucleotide 36 of any one of SEQ ID NOs: 1, 2, 3, 4, 5, 6, 7, or 8. The direct repeat sequence can comprise nucleotide 5 through nucleotide 36 of any one of SEQ ID NOs: 1, 2, 3, 4, 5, 6, 7, or 8. The direct repeat sequence can comprise nucleotide 6 through nucleotide 36 of any one of SEQ ID NOs: 1, 2, 3, 4, 5, 6, 7, or 8. The direct repeat sequence can comprise nucleotide 7 through nucleotide 36 of any one of SEQ ID NOs: 1, 2, 3, 4, 5, 6, 7, or 8. The direct repeat sequence can comprise nucleotide 8 through nucleotide 36 of any one of SEQ ID NOs: 1, 2, 3, 4, 5, 6, 7, or 8. The direct repeat sequence can comprise nucleotide 9 through nucleotide 36 of any one of SEQ ID NOs: 1, 2, 3, 4, 5, 6, 7, or 8. The direct repeat sequence can comprise nucleotide 10 through nucleotide 36 of any one of SEQ ID NOs: 1, 2, 3, 4, 5, 6, 7, or 8. The direct repeat sequence can comprise nucleotide 11 through nucleotide 36 of any one of SEQ ID NOs: 1, 2, 3, 4, 5, 6, 7, or 8. The direct repeat sequence can comprise nucleotide 12 through nucleotide 36 of any one of SEQ ID NOs: 1, 2, 3, 4, 5, 6, 7, or 8. The direct repeat sequence can comprise nucleotide 13 through nucleotide 36 of any one of SEQ ID NOs: 1, 2, 3, 4, 5, 6, 7, or 8. The direct repeat sequence can comprise nucleotide 14 through nucleotide 36 of any one of SEQ ID NOs: 1, 2, 3, 4, 5, 6, 7, or 8.

The direct repeat sequence can comprise nucleotide 1 through nucleotide 34 of SEQ ID NO: 9. The direct repeat sequence can comprise nucleotide 2 through nucleotide 34 of SEQ ID NO: 9. The direct repeat sequence can comprise nucleotide 3 through nucleotide 34 of SEQ ID NO: 9. The direct repeat sequence can comprise nucleotide 4 through nucleotide 34 of SEQ ID NO: 9. The direct repeat sequence can comprise nucleotide 5 through nucleotide 34 of SEQ ID NO: 9. The direct repeat sequence can comprise nucleotide 6 through nucleotide 34 of SEQ ID NO: 9. The direct repeat sequence can comprise nucleotide 7 through nucleotide 34 of SEQ ID NO: 9. The direct repeat sequence can comprise nucleotide 8 through nucleotide 34 of SEQ ID NO: 9. The direct repeat sequence can comprise nucleotide 9 through nucleotide 34 of SEQ ID NO: 9. The direct repeat sequence can comprise nucleotide 10 through nucleotide 34 of SEQ ID NO: 9. The direct repeat sequence can comprise nucleotide 11 through nucleotide 34 of SEQ ID NO: 9. The direct repeat sequence can comprise nucleotide 12 through nucleotide 34 of SEQ ID NO: 9. In some embodiments, the direct repeat sequence is set forth in SEQ ID NO: 10. In some embodiments, the direct repeat sequence comprises a portion of the sequence set forth in SEQ ID NO: 10.

In some embodiments, the direct repeat sequence has at least 90% identity (e.g., at least 90%, 91%, 92%, 93%, 94%, 95%, 96%, 97%, 98% or 99% identity) to a sequence of Table 1 or a portion of a sequence of Table 1. The direct repeat sequence can have at least 90% identity to a sequence comprising nucleotide 1 through nucleotide 36 of any one of SEQ ID NOs: 1, 2, 3, 4, 5, 6, 7, or 8. The direct repeat sequence can have at least 90% identity to a sequence comprising 2 through nucleotide 36 of any one of SEQ ID NOs: 1, 2, 3, 4, 5, 6, 7, or 8. The direct repeat sequence can have at least 90% identity to a sequence comprising 3 through nucleotide 36 of any one of SEQ ID NOs: 1, 2, 3, 4, 5, 6, 7, or 8. The direct repeat sequence can have at least 90% identity to a sequence comprising 4 through nucleotide 36 of any one of SEQ ID NOs: 1, 2, 3, 4, 5, 6, 7, or 8. The direct repeat sequence can have at least 90% identity to a sequence comprising 5 through nucleotide 36 of any one of SEQ ID NOs: 1, 2, 3, 4, 5, 6, 7, or 8. The direct repeat sequence can have at least 90% identity to a sequence comprising 6 through nucleotide 36 of any one of SEQ ID NOs: 1, 2, 3, 4, 5, 6, 7, or 8. The direct repeat sequence can have at least 90% identity to a sequence comprising 7 through nucleotide 36 of any one of SEQ ID NOs: 1, 2, 3, 4, 5, 6, 7, or 8. The direct repeat sequence can have at least 90% identity to a sequence comprising 8 through nucleotide 36 of any one of SEQ ID NOs: 1, 2, 3, 4, 5, 6, 7, or 8. The direct repeat sequence can have at least 90% identity to a sequence comprising 9 through nucleotide 36 of any one of SEQ ID NOs: 1, 2, 3, 4, 5, 6, 7, or 8. The direct repeat sequence can have at least 90% identity to a sequence comprising 10 through nucleotide 36 of any one of SEQ ID NOs: 1, 2, 3, 4, 5, 6, 7, or 8. The direct repeat sequence can have at least 90% identity to a sequence comprising 11 through nucleotide 36 of any one of SEQ ID NOs: 1, 2, 3, 4, 5, 6, 7, or 8. The direct repeat sequence can have at least 90% identity to a sequence comprising 12 through nucleotide 36 of any one of SEQ ID NOs: 1, 2, 3, 4, 5, 6, 7, or 8. The direct repeat sequence can have at least 90% identity to a sequence comprising 13 through nucleotide 36 of any one of SEQ ID NOs: 1, 2, 3, 4, 5, 6, 7, or 8. The direct repeat sequence can have at least 90% identity to a sequence comprising 14 through nucleotide 36 of any one of SEQ ID NOs: 1, 2, 3, 4, 5, 6, 7, or 8. The direct repeat sequence can have at least 90% identity to a sequence comprising 1 through nucleotide 34 of SEQ ID NO: 9. The direct repeat sequence can have at least 90% identity to a sequence comprising 2 through nucleotide 34 of SEQ ID NO: 9. The direct repeat sequence can have at least 90% identity to a sequence comprising 3 through nucleotide 34 of SEQ ID NO: 9.

The direct repeat sequence can have at least 90% identity to a sequence comprising 4 through nucleotide 34 of SEQ ID NO: 9. The direct repeat sequence can have at least 90% identity to a sequence comprising 5 through nucleotide 34 of SEQ ID NO: 9. The direct repeat sequence can have at least 90% identity to a sequence comprising 6 through nucleotide 34 of SEQ ID NO: 9. The direct repeat sequence can have at least 90% identity to a sequence comprising 7 through nucleotide 34 of SEQ ID NO: 9. The direct repeat sequence can have at least 90% identity to a sequence comprising 8 through nucleotide 34 of SEQ ID NO: 9. The direct repeat sequence can have at least 90% identity to a sequence comprising 9 through nucleotide 34 of SEQ ID NO: 9. The direct repeat sequence can have at least 90% identity to a sequence comprising 10 through nucleotide 34 of SEQ ID NO: 9. The direct repeat sequence can have at least 90% identity to a sequence comprising 11 through nucleotide 34 of SEQ ID NO: 9.

The direct repeat sequence can have at least 90% identity to a sequence comprising 12 through nucleotide 34 of SEQ ID NO: 9. In some embodiments, the direct repeat sequence has at least 90% identity (e.g., at least 90%, 91%, 92%, 93%, 94%, 95%, 96%, 97%, 98% or 99% identity) to SEQ ID NO: 10. In some embodiments, the direct repeat sequence has at least 90% identity to a portion of the sequence set forth in SEQ ID NO: 10.

In some embodiments, compositions comprising a Cas12i2 polypeptide and an RNA guide comprising the direct repeat of SEQ ID NO: 10 and a spacer length of 20 nucleotides are capable of introducing indels into an HAO1 target sequence. See, e.g., Example 1, where indels were measured at forty-four HAO1 target sequences following delivery of an RNA guide and a Cas12i2 polypeptide of SEQ ID NO: 924 to HEK293T cells by RNP; Example 2, where indels were measured at eleven HAO1 target sequences following delivery of an RNA guide and a Cas12i2 polypeptide of SEQ ID NO: 924 to HepG2 cells by RNP; and Example 3, where indels were measured at five HAO1 target sequences following delivery of an RNA guide and a Cas12i2 polypeptide of SEQ ID NO: 924 to primary hepatocytes by RNP.

In some embodiments, the direct repeat sequence is at least 90% identical to the reverse complement of any one of SEQ ID NOs: 1-10 (see, Table 1). In some embodiments, the direct repeat sequence is the reverse complement of any one of SEQ ID NOs: 1-10.

TABLE 1

Cas12i2 Direct Repeat Sequences

| Sequence identifier | Direct Repeat Sequence |
|---|---|
| SEQ ID NO: 1 | GUUGCAAAACCCAAGAAAUCCGUCUUUCAUUGACGG |
| SEQ ID NO: 2 | AAUAGCGGCCCUAAGAAAUCCGUCUUUCAUUGACGG |
| SEQ ID NO: 3 | AUUGGAACUGGCGAGAAAUCCGUCUUUCAUUGACGG |
| SEQ ID NO: 4 | CCAGCAACACCUAAGAAAUCCGUCUUUCAUUGACGG |
| SEQ ID NO: 5 | CGGCGCUCGAAUAGGAAAUCCGUCUUUCAUUGACGG |
| SEQ ID NO: 6 | GUGGCAACACCUAAGAAAUCCGUCUUUCAUUGACGG |
| SEQ ID NO: 7 | GUUGCAACACCUAAGAAAUCCGUCUUUCAUUGACGG |
| SEQ ID NO: 8 | GUUGCAAUGCCUAAGAAAUCCGUCUUUCAUUGACGG |
| SEQ ID NO: 9 | GCAACACCUAAGAAAUCCGUCUUUCAUUGACGGG |
| SEQ ID NO: 10 | AGAAAUCCGUCUUUCAUUGACGG |

In some embodiments, the direct repeat sequence is a sequence of Table 2 or a portion of a sequence of Table 2. The direct repeat sequence can comprise nucleotide 1 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 2 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 3 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 4 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 5 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 6 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 7 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 8 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 9 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 10 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 11 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 12 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 13 through nucleotide 36 of any one of SEQ ID NOs: 936, 937, 938, 939, 940, 941, 942, 943, 944, 945, 946, 947, 948, 949, 950, 951, 952, or 953. The direct repeat sequence can comprise nucleotide 14 through nucleotide 36 of any one of SEQ ID NOs: 936, 937, 938, 939, 940, 941, 942, 943, 944, 945, 946, 947, 948, 949, 950, 951, 952, or 953.

In some embodiments, the direct repeat sequence has at least 95% identity (e.g., at least 95%, 96%, 97%, 98% or 99% identity) to a sequence of Table 2 or a portion of a sequence of Table 2. The direct repeat sequence can have at least 95% identity to a sequence comprising nucleotide 1 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 2 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 3 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 4 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 5 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 6 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 7 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 8 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 9 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 10 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 11 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 12 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 95% identity to a sequence comprising 13 through nucleotide 36 of any one of SEQ ID NOs: 936, 937, 938, 939, 940, 941, 942, 943, 944, 945, 946, 947, 948, 949, 950, 951, 952, or 953.

In some embodiments, the direct repeat sequence has at least 90% identity (e.g., at least 90%, 91%, 92%, 93%, 94%, 95%, 96%, 97%, 98% or 99% identity) to a sequence of Table 2 or a portion of a sequence of Table 2. The direct repeat sequence can have at least 90% identity to a sequence comprising nucleotide 1 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 2 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 3 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 4 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 5 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 6 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 7 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 8 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 9 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 10 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 11 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 12 through nucleotide 36 of any one of SEQ ID NOs: 936, 937, 938, 939, 940, 941, 942, 943, 944, 945, 946, 947, 948, 949, 950, 951, 952, or 953. The direct repeat sequence can have at least 90% identity to a sequence comprising 13 through nucleotide 36 of any one of SEQ ID NOs: 936, 937, 938, 939, 940, 941, 942, 943, 944, 945, 946, 947, 948, 949, 950, 951, 952, or 953.

In some embodiments, the direct repeat sequence is at least 90% identical to the reverse complement of any one of SEQ ID NOs: 936, 937, 938, 939, 940, 941, 942, 943, 944, 945, 946, 947, 948, 949, 950, 951, 952, or 953. In some embodiments, the direct repeat sequence is at least 95% identical to the reverse complement of any one of SEQ ID NOs: 936, 937, 938, 939, 940, 941, 942, 943, 944, 945, 946, 947, 948, 949, 950, 951, 952, or 953. In some embodiments, the direct repeat sequence is the reverse complement of any one of SEQ ID NOs: 936, 937, 938, 939, 940, 941, 942, 943, 944, 945, 946, 947, 948, 949, 950, 951, 952, or 953.

In some embodiments, the direct repeat sequence is at least 90% identical to SEQ ID NO: 954 or a portion of SEQ ID NO: 954. In some embodiments, the direct repeat sequence is at least 95% identical to SEQ ID NO: 954 or a portion of SEQ ID NO: 954. In some embodiments, the direct repeat sequence is 100% identical to SEQ ID NO: 954 or a portion of SEQ ID NO: 954.

TABLE 2

Cas12i4 Direct Repeat Sequences

| Sequence identifier | Direct Repeat Sequence |
|---|---|
| SEQ ID NO: 936 | UCUCAACGAUAGUCAGACAUGUGUCCUCAGUGACAC |
| SEQ ID NO: 937 | UUUUAACAACACUCAGGCAUGUGUCCACAGUGACAC |
| SEQ ID NO: 938 | UUGAACGGAUACUCAGACAUGUGUUUCCAGUGACAC |
| SEQ ID NO: 939 | UGCCCUCAAUAGUCAGAUGUGUGUCCACAGUGACAC |
| SEQ ID NO: 940 | UCUCAAUGAUACUUAGAUACGUGUCCUCAGUGACAC |
| SEQ ID NO: 941 | UCUCAAUGAUACUCAGACAUGUGUCCCCAGUGACAC |
| SEQ ID NO: 942 | UCUCAAUGAUACUAAGACAUGUGUCCUCAGUGACAC |
| SEQ ID NO: 943 | UCUCAACUAUACUCAGACAUGUGUCCUCAGUGACAC |
| SEQ ID NO: 944 | UCUCAACGAUACUCAGACAUGUGUCCUCAGUGACAC |
| SEQ ID NO: 945 | UCUCAACGAUACUAAGAUAUGUGUCCUCAGCGACAC |
| SEQ ID NO: 946 | UCUCAACGAUACUAAGAUAUGUGUCCCCAGUGACAC |
| SEQ ID NO: 947 | UCUCAACGAUACUAAGAUAUGUGUCCACAGUGACAC |
| SEQ ID NO: 948 | UCUCAACAAUACUCAGACAUGUGUCCCCAGUGACAC |
| SEQ ID NO: 949 | UCUCAACAAUACUAAGGCAUGUGUCCCCAGUGACCC |
| SEQ ID NO: 950 | UCUCAAAGAUACUCAGACACGUGUCCCCAGUGACAC |
| SEQ ID NO: 951 | UCUCAAAAAUACUCAGACAUGUGUCCUCAGUGACAC |
| SEQ ID NO: 952 | GCGAAACAACAGUCAGACAUGUGUCCCCAGUGACAC |
| SEQ ID NO: 953 | CCUCAACGAUAUUAAGACAUGUGUCCGCAGUGACAC |
| SEQ ID NO: 954 | AGACAUGUGUCCUCAGUGACAC |

In some embodiments, the direct repeat sequence is a sequence of Table 3 or a portion of a sequence of Table 3. In some embodiments, the direct repeat sequence has at least 95% identity (e.g., at least 95%, 96%, 97%, 98% or 99% identity) to a sequence of Table 3 or a portion of a sequence of Table 3. In some embodiments, the direct repeat sequence has at least 90% identity (e.g., at least 90%, 91%, 92%, 93%, 94%, 95%, 96%, 97%, 98% or 99% identity) to a sequence of Table 3 or a portion of a sequence of Table 3. In some embodiments, the direct repeat sequence is at least 90% identical to the reverse complement of any one of SEQ ID NOs: 959-961. In some embodiments, the direct repeat sequence is at least 95% identical to the reverse complement of any one of SEQ ID NOs: 959-961. In some embodiments, the direct repeat sequence is the reverse complement of any one of SEQ ID NOs: 959-961.

TABLE 3

| Cas12i1 Direct Repeat Sequences | |
|---|---|
| Sequence identifier | Direct Repeat Sequence |
| SEQ ID NO: 959 | GUUGGAAUGACUAAUUUUUGUGCCCACCGUUGGCAC |
| SEQ ID NO: 960 | AAUUUUUGUGCCCAUCGUUGGCAC |
| SEQ ID NO: 961 | AUUUUUGUGCCCAUCGUUGGCAC |

In some embodiments, the direct repeat sequence is a sequence of Table 4 or a portion of a sequence of Table 4. In some embodiments, the direct repeat sequence has at least 95% identity (e.g., at least 95%, 96%, 97%, 98% or 99% identity) to a sequence of Table 4 or a portion of a sequence of Table 4. In some embodiments, the direct repeat sequence has at least 90% identity (e.g., at least 90%, 91%, 92%, 93%, 94%, 95%, 96%, 97%, 98% or 99% identity) to a sequence of Table 4 or a portion of a sequence of Table 4. In some embodiments, the direct repeat sequence is at least 90% identical to the reverse complement of any one of SEQ ID NOs: 962-964. In some embodiments, the direct repeat sequence is at least 95% identical to the reverse complement of any one of SEQ ID NOs: 962-964. In some embodiments, the direct repeat sequence is the reverse complement of any one of SEQ ID NOs: 962-964.

TABLE 4

| Cas12i3 Direct Repeat Sequences | |
|---|---|
| Sequence identifier | Direct Repeat Sequence |
| SEQ ID NO: 962 | CUAGCAAUGACCUAAUAGUGUGUCCUUAGUUGACAU |
| SEQ ID NO: 963 | CCUACAAUACCUAAGAAAUCCGUCCUAAGUUGACGG |
| SEQ ID NO: 964 | AUAGUGUGUCCUUAGUUGACAU |

In some embodiments, a direct repeat sequence described herein comprises an uracil (U). In some embodiments, a direct repeat sequence described herein comprises a thymine (T). In some embodiments, a direct repeat sequence according to Tables 1~4 comprises a sequence comprising a thymine in one or more places indicated as uracil in Tables 1-4.

(ii). Spacer Sequence

In some embodiments, the RNA guide comprises a DNA targeting or spacer sequence. In some embodiments, the spacer sequence of the RNA guide has a length of between 12-100, 13-75, 14-50, or 15-30 nucleotides (e.g., 15, 16, 17, 18, 19, 20, 21, 22, 23, 24, 25, 26, 27, 28, 29, or 30 nucleotides) and is complementary to a non-PAM strand sequence. In some embodiments, the spacer sequence is designed to be complementary to a specific DNA strand, e.g., of a genomic locus.

In some embodiments, the RNA guide spacer sequence is substantially identical to a complementary strand of a target sequence. In some embodiments, the RNA guide comprises a sequence (e.g., a spacer sequence) having at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to a complementary strand of a reference nucleic acid sequence, e.g., a target sequence. The percent identity between two such nucleic acids can be determined manually by inspection of the two optimally aligned nucleic acid sequences or by using software programs or algorithms (e.g., BLAST, ALIGN, CLUSTAL) using standard parameters.

In some embodiments, the RNA guide comprises a spacer sequence that has a length of between 12-100, 13-75, 14-50, or 15-30 nucleotides (e.g., 15, 16, 17, 18, 19, 20, 21, 22, 23, 24, 25, 26, 27, 28, 29, or 30 nucleotides) and at least 80%, at least 90%, at least 95%, at least 96%, at least 97%, at least 98%, at least 99% complementary to a region on the non-PAM strand that is complementary to the target sequence. In some embodiments, the RNA guide comprises a sequence at least 80%, at least 90%, at least 95%, at least 96%, at least 97%, at least 98%, at least 99% complementary to a target DNA sequence. In some embodiments, the RNA guide comprises a sequence at least 80%, at least 90%, at least 95%, at least 96%, at least 97%, at least 98%, at least 99% complementary to a target genomic sequence. In some embodiments, the RNA guide comprises a sequence, e.g., RNA sequence, that is a length of up to 50 and at least 80%, at least 90%, at least 95%, at least 96%, at least 97%, at least 98%, at least 99% complementary to a region on the non-PAM strand that is complementary to the target sequence. In some embodiments, the RNA guide comprises a sequence at least 80%, at least 90%, at least 95%, at least 96%, at least 97%, at least 98%, at least 99% complementary to a target DNA sequence. In some embodiments, the RNA guide comprises a sequence at least 80%, at least 90%, at least 95%, at least 96%, at least 97%, at least 98%, at least 99% complementary to a target genomic sequence.

In some embodiments, the spacer sequence is a sequence of Table 5 or a portion of a sequence of Table 5. It should be understood that an indication of SEQ ID NOs: 466-920 should be considered as equivalent to a listing of SEQ ID NOs: 466-920, with each of the intervening numbers present in the listing, i.e., 466, 467, 468, 469, 470, 471, 472, 473, 474, 475, 476, 477, 478, 479, 480, 481, 482, 483, 484, 485, 486, 487, 488, 489, 490, 491, 492, 493, 494, 495, 496, 497, 498, 499, 500, 501, 502, 503, 504, 505, 506, 507, 508, 509, 510, 511, 512, 513, 514, 515, 516, 517, 518, 519, 520, 521, 522, 523, 524, 525, 526, 527, 528, 529, 530, 531, 532, 533, 534, 535, 536, 537, 538, 539, 540, 541, 542, 543, 544, 545, 546, 547, 548, 549, 550, 551, 552, 553, 554, 555, 556, 557, 558, 559, 560, 561, 562, 563, 564, 565, 566, 567, 568, 569, 570, 571, 572, 573, 574, 575, 576, 577, 578, 579, 580, 581, 582, 583, 584, 585, 586, 587, 588, 589, 590, 591, 592, 593, 594, 595, 596, 597, 598, 599, 600, 601, 602, 603, 604, 605, 606, 607, 608, 609, 610, 611, 612, 613, 614, 615, 616, 617, 618, 619, 620, 621, 622, 623, 624, 625, 626, 627, 628, 629, 630, 631, 632, 633, 634, 635, 636, 637, 638, 639, 640, 641, 642, 643, 644, 645, 646, 647, 648, 649, 650, 651, 652, 653, 654, 655, 656, 657, 658, 659, 660, 661, 662, 663, 664, 665, 666, 667, 668, 669, 670, 671, 672, 673, 674, 675, 676, 677, 678, 679, 680, 681, 682, 683, 684, 685, 686, 687, 688, 689, 690, 691, 692, 693, 694, 695, 696, 697, 698, 699, 700, 701, 702, 703, 704, 705, 706, 707, 708, 709, 710, 711, 712, 713, 714, 715, 716, 717, 718, 719, 720, 721, 722, 723, 724, 725, 726, 727, 728, 729, 730, 731, 732, 733, 734, 735, 736, 737, 738, 739, 740, 741, 742, 743, 744, 745, 746, 747, 748, 749, 750, 751, 752, 753, 754, 755, 756, 757, 758, 759, 760, 761, 762, 763, 764, 765, 766, 767, 768, 769, 770, 771, 772, 773, 774, 775, 776, 777, 778, 779, 780, 781, 782, 783, 784, 785, 786, 787, 788, 789, 790, 791, 792, 793, 794, 795, 796, 797, 798, 799, 800, 801, 802, 803, 804, 805, 806, 807, 808, 809, 810, 811, 812, 813, 814, 815, 816, 817, 818, 819, 820, 821, 822, 823, 824, 825, 826, 827, 828, 829, 830, 831, 832, 833, 834, 835, 836, 837, 838, 839, 840, 841, 842, 843, 844, 845, 846, 847, 848, 849, 850, 851, 852, 853, 854, 855, 856, 857, 858, 859, 860, 861, 862, 863, 864, 865, 866, 867, 868, 869, 870, 871, 872, 873, 874, 875, 876, 877, 878, 879, 880, 881, 882, 883, 884, 885, 886, 887, 888, 889, 890, 891, 892, 893, 894, 895, 896, 897, 898, 899, 900, 901, 902, 903, 904, 905, 906, 907, 908, 909, 910, 911, 912, 913, 914, 915, 916, 917, 918, 919, and 920.

The spacer sequence can comprise nucleotide 1 through nucleotide 16 of any one of SEQ ID NOs: 466-920. The spacer sequence can comprise nucleotide 1 through nucleotide 17 of any one of SEQ ID NOs: 466-920. The spacer sequence can comprise nucleotide 1 through nucleotide 18 of any one of SEQ ID NOs: 466-920. The spacer sequence can comprise nucleotide 1 through nucleotide 19 of any one of SEQ ID NOs: 466-920. The spacer sequence can comprise nucleotide 1 through nucleotide 20 of any one of SEQ ID NOs: 466-920. The spacer sequence can comprise nucleotide 1 through nucleotide 21 of any one of SEQ ID NOs: 466-920. The spacer sequence can comprise nucleotide 1 through nucleotide 22 of any one of SEQ ID NOs: 466-920. The spacer sequence can comprise nucleotide 1 through nucleotide 23 of any one of SEQ ID NOs: 466-920. The spacer sequence can comprise nucleotide 1 through nucleotide 24 of any one of SEQ ID NOs: 466-920. The spacer sequence can comprise nucleotide 1 through nucleotide 25 of any one of SEQ ID NOs: 466-920. The spacer sequence can comprise nucleotide 1 through nucleotide 26 of any one of SEQ ID NOs: 466-920. The spacer sequence can comprise nucleotide 1 through nucleotide 27 of any one of SEQ ID NOs: 466-920. The spacer sequence can comprise nucleotide 1 through nucleotide 28 of any one of SEQ ID NOs: 466-920. The spacer sequence can comprise nucleotide 1 through nucleotide 29 of any one of SEQ ID NOs: 466-920. The spacer sequence can comprise nucleotide 1 through nucleotide 30 of any one of SEQ ID NOs: 466-920.

In some embodiments, the spacer sequence has at least 90% identity (e.g., at least 90%, 91%, 92%, 93%, 94%, 95%, 96%, 97%, 98% or 99% identity) to a sequence of Table 5 or a portion of a sequence of Table 5. The spacer sequence can have at least 90% identity to a sequence comprising nucleotide 1 through nucleotide 16 of any one of SEQ ID NOs: 466-920. The spacer sequence can have at least 90% identity to a sequence comprising nucleotide 1 through nucleotide 17 of any one of SEQ ID NOs: 466-920. The spacer sequence can have at least 90% identity to a sequence comprising nucleotide 1 through nucleotide 18 of any one of SEQ ID NOs: 466-920. The spacer sequence can have at least 90% identity to a sequence comprising nucleotide 1 through nucleotide 19 of any one of SEQ ID NOs: 466-920. The spacer sequence can have at least 90% identity to a sequence comprising nucleotide 1 through nucleotide 20 of any one of SEQ ID NOs: 466-920. The spacer sequence can have at least 90% identity to a sequence comprising nucleotide 1 through nucleotide 21 of any one of SEQ ID NOs: 466-920. The spacer sequence can have at least 90% identity to a sequence comprising nucleotide 1 through nucleotide 22 of any one of SEQ ID NOs: 466-920. The spacer sequence can have at least 90% identity to a sequence comprising nucleotide 1 through nucleotide 23 of any one of SEQ ID NOs: 466-920. The spacer sequence can have at least 90% identity to a sequence comprising nucleotide 1 through nucleotide 24 of any one of SEQ ID NOs: 466-920.

The spacer sequence can have at least 90% identity to a sequence comprising nucleotide 1 through nucleotide 25 of any one of SEQ ID NOs: 466-920. The spacer sequence can have at least 90% identity to a sequence comprising nucleotide 1 through nucleotide 26 of any one of SEQ ID NOs: 466-920. The spacer sequence can have at least 90% identity to a sequence comprising nucleotide 1 through nucleotide 27 of any one of SEQ ID NOs: 466-920. The spacer sequence can have at least 90% identity to a sequence comprising nucleotide 1 through nucleotide 28 of any one of SEQ ID NOs: 466-920. The spacer sequence can have at least 90% identity to a sequence comprising nucleotide 1 through nucleotide 29 of any one of SEQ ID NOs: 466-920. The spacer sequence can have at least 90% identity to a sequence comprising nucleotide 1 through nucleotide 30 of any one of 466-920.

TABLE 5

Target and Spacer Sequences

| HAO1 | Strand | PAM* | SEQ ID NO | Target Sequence | SEQ ID NO | Spacer Sequence |
|---|---|---|---|---|---|---|
| HAO1_exon1 | + | **CTTA** | 11 | CCTGGAAAATGCTGCAA TATTATCAGGCAA | 466 | CCUGGAAAAUGCUGCAAUA UUAUCAGCCAA |
| HAO1_exon1 | + | **ATTT** | 12 | TCTTACCTGGAAAATGC TGCAATATTATCA | 467 | UCUUACCUGGAAAAUGCUG CAAUAUUAUCA |
| HAO1_exon1 | + | **TTTT** | 13 | CTTACCTGGAAAATGCT GCAATATTATCAG | 468 | CUUACCUGGAAAAUGCUGC AAUAUUAUCAG |
| HAO1_exon1 | + | **TTTC** | 14 | TTACCTGGAAAATGCTG CAATATTATCAGC | 469 | UUACCUGGAAAAUGCUGCA AUAUUAUCAGC |
| HAO1_exon1 | + | **ATTA** | 15 | TCAGCCAAAGTTTCTTC ATCATTTGCCCCA | 470 | UCAGCCAAAGUUUCUUCAU CAUUUGCCCCA |
| HAO1_exon1 | + | **GTTT** | 16 | CTTCATCATTTGCCCCA GACCTGTAATAGT | 471 | CUUCAUCAUUUGCCCCAGA CCUGUAAUAGU |
| HAO1_exon1 | + | **TTTC** | 17 | TTCATCATTTGCCCCAG ACCTGTAATAGTC | 472 | UUCAUCAUUUGCCCCAGAC CUGUAAUAGUC |
| HAO1_exon1 | + | **CTTC** | 18 | ATCATTTGCCCCAGACC TGTAATAGTCATA | 473 | AUCAUUUGCCCCAGACCUG UAAUAGUCAUA |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon1 | + | **ATTT** | 19 | GCCCCAGACCTGTAATAGTCATATATAGAC | 474 | GCCCCAGACCUGUAAUAGUCAUAUAUAGAC |
| HAO1_exon1 | + | **TTTG** | 20 | CCCCAGACCTGTAATAGTCATATATAGACT | 475 | CCCCAGACCUGUAAUAGUCAUAUAUAGACU |
| HAO1_exon1 | + | **TTTT** | 21 | AAAAAATAAATTTTCTTACCTGGAAAATGC | 476 | AAAAAAUAAAUUUUCUUACCUGGAAAAUGC |
| HAO1_exon1 | + | C**TTT** | 22 | GGAAGTACTGATTTAGCATGTTGTTCATAA | 477 | GGAAGUACUGAUUUAGCAUGUUGUUCAUAA |
| HAO1_exon1 | + | **ATTT** | 23 | AGCATGTTGTTCATAATCATTGATACAAAT | 478 | AGCAUGUUGUUCAUAAUCAUUGAUACAAAU |
| HAO1_exon1 | + | **TTTA** | 24 | GCATGTTGTTCATAATCATTGATACAAATT | 479 | GCAUGUUGUUCAUAAUCAUUGAUACAAAUU |
| HAO1_exon1 | + | **GTTG** | 25 | TTCATAATCATTGATACAAATTAGCCGGGG | 480 | UUCAUAAUCAUUGAUACAAAUUAGCCGGGG |
| HAO1_exon1 | + | **GTTC** | 26 | ATAATCATTGATACAAATTAGCCGGGGGAG | 481 | AUAAUCAUUGAUACAAAUUAGCCGGGGGAG |
| HAO1_exon1 | + | **ATTG** | 27 | ATACAAATTAGCCGGGGGAGCATTTTCACA | 482 | AUACAAAUUAGCCGGGGGAGCAUUUUCACA |
| HAO1_exon1 | + | **ATTA** | 28 | GCCGGGGGAGCATTTTCACAGGTTATTGCT | 483 | GCCGGGGGAGCAUUUUCACAGGUUAUUGCU |
| HAO1_exon1 | + | **ATTT** | 29 | TCACAGGTTATTGCTATCCCAGATGGAGTT | 484 | UCACAGGUUAUUGCUAUCCCAGAUGGAGUU |
| HAO1_exon1 | + | **TTTT** | 30 | CACAGGTTATTGCTATCCCAGATGGAGTTC | 485 | CACAGGUUAUUGCUAUCCCAGAUGGAGUUC |
| HAO1_exon1 | + | **TTTC** | 31 | ACAGGTTATTGCTATCCCAGATGGAGTTCG | 486 | ACAGGUUAUUGCUAUCCCAGAUGGAGUUCG |
| HAO1_exon1 | + | **TTTG** | 32 | GAAGTACTGATTTAGCATGTTGTTCATAAT | 487 | GAAGUACUGAUUUAGCAUGUUGUUCAUAAU |
| HAO1_exon1 | + | **ATTT** | 33 | TAAAAAATAAATTTTCTTACCTGGAAAATG | 488 | UAAAAAAUAAAUUUUCUUACCUGGAAAAUG |
| HAO1_exon1 | + | **TTTA** | 34 | AAAAATAAATTTTCTTACCTGGAAAATGCT | 489 | AAAAAUAAAUUUUCUUACCUGGAAAAUGCU |
| HAO1_exon1 | + | **TTTT** | 35 | AAAACATGATTTTAAAAAATAAATTTTCTT | 490 | AAAACAUGAUUUUAAAAAAUAAAUUUUCUU |
| HAO1_exon1 | - | **TTTG** | 36 | TATCAATGATTATGAACAACATGCTAAATC | 491 | UAUCAAUGAUUAUGAACAACAUGCUAAAUC |
| HAO1_exon1 | - | **ATTA** | 37 | TGAACAACATGCTAAATCAGTACTTCCAAA | 492 | UGAACAACAUGCUAAAUCAGUACUUCCAAA |
| HAO1_exon1 | - | C**TTC** | 38 | CAAAGTCTATATATGACTATTACAGGTCTG | 493 | CAAAGUCUAUAUAUGACUAUUACAGGUCUG |
| HAO1_exon1 | - | **ATTA** | 39 | CAGGTCTGGGGCAAATGATGAAGAAACTTT | 494 | CAGGUCUGGGGCAAAUGAUGAAGAAACUUU |
| HAO1_exon1 | - | C**TTT** | 40 | GGCTGATAATATTGCAGCATTTTCCAGGTA | 495 | GGCUGAUAAUAUUGCAGCAUUUUCCAGGUA |
| HAO1_exon1 | - | **TTTG** | 41 | GCTGATAATATTGCAGCATTTTCCAGGTAA | 496 | GCUGAUAAUAUUGCAGCAUUUUCCAGGUAA |
| HAO1_exon1 | - | **ATTG** | 42 | CAGCATTTTCCAGGTAAGAAAATTTATTTT | 497 | CAGCAUUUUCCAGGUAAGAAAAUUUAUUUU |
| HAO1_exon1 | - | **ATTT** | 43 | TCCAGGTAAGAAAATTTATTTTTAAAATC | 498 | UCCAGGUAAGAAAAUUUAUUUUUUAAAAUC |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon1 | - | **TTTT** | 44 | CCAGGTAAGAAAATTTATTTTTTAAAATCA | 499 | CCAGGUAAGAAAAUUUAUUUUUUAAAAUCA |
| HAO1_exon1 | + | **TTTA** | 45 | AAACATGATTTTAAAAAATAAATTTTCTTA | 500 | AAACAUGAUUUUAAAAAAUAAAUUUUCUUA |
| HAO1_exon1 | - | **ATTT** | 46 | ATTTTTTAAAATCATGTTTTAAAATTACAC | 501 | AUUUUUUAAAAUCAUGUUUUAAAAUUACAC |
| HAO1_exon1 | - | **TTTC** | 47 | CAGGTAAGAAAATTTATTTTTTAAAATCAT | 502 | CAGGUAAGAAAAUUUAUUUUUUAAAAUCAU |
| HAO1_exon1 | - | **ATTT** | 48 | TTTAAAATCATGTTTTAAAATTACACAAAG | 503 | UUUAAAAUCAUGUUUUAAAAUUACACAAAG |
| HAO1_exon1 | - | **TTTT** | 49 | TTAAAATCATGTTTTAAAATTACACAAAGA | 504 | UUAAAAUCAUGUUUUAAAAUUACACAAAGA |
| HAO1_exon1 | - | **TTTT** | 50 | TAAAATCATGTTTTAAAATTACACAAAGAC | 505 | UAAAAUCAUGUUUUAAAAUUACACAAAGAC |
| HAO1_exon1 | - | **TTTT** | 51 | AAAATCATGTTTTAAAATTACACAAAGACC | 506 | AAAAUCAUGUUUUAAAAUUACACAAAGACC |
| HAO1_exon1 | - | **TTTA** | 52 | AAATCATGTTTTAAAATTACACAAAGACCG | 507 | AAAUCAUGUUUUAAAAUUACACAAAGACCG |
| HAO1_exon1 | + | C**TTT** | 53 | GTGTAATTTTAAAACATGATTTTAAAAAAT | 508 | GUGUAAUUUUAAAACAUGAUUUUAAAAAAU |
| HAO1_exon1 | + | **TTTG** | 54 | TGTAATTTTAAAACATGATTTTAAAAAATA | 509 | UGUAAUUUUAAAACAUGAUUUUAAAAAAUA |
| HAO1_exon1 | + | **ATTT** | 55 | TAAAACATGATTTTAAAAAATAAATTTTCT | 510 | UAAAACAUGAUUUUAAAAAAUAAAUUUUCU |
| HAO1_exon1 | - | **TTTA** | 56 | TTTTTTAAAATCATGTTTTAAAATTACACA | 511 | UUUUUUAAAAUCAUGUUUUAAAAUUACACA |
| HAO1_exon1 | - | **ATTT** | 57 | GTATCAATGATTATGAACAACATGCTAAAT | 512 | GUAUCAAUGAUUAUGAACAACAUGCUAAAU |
| HAO1_exon1 | + | **GTTA** | 58 | TTGCTATCCCAGATGGAGTTCGTT | 513 | UUGCUAUCCCAGAUGGAGUUCGUU |
| HAO1_exon1 | + | **ATTG** | 59 | CTATCCCAGATGGAGTTCGTT | 514 | CUAUCCCAGAUGGAGUUCGUU |
| HAO1_exon2 | - | **TTTA** | 60 | TTTTTTAATTCTAGATGGAAGCTGTATCCA | 515 | UUUUUUAAUUCUAGAUGGAAGCUGUAUCCA |
| HAO1_exon2 | - | **TTTT** | 61 | ATTTTATTTTTTAATTCTAGATGGAAGCTG | 516 | AUUUUAUUUUUUAAUUCUAGAUGGAAGCUG |
| HAO1_exon2 | - | **TTTT** | 62 | ATTTTTTAATTCTAGATGGAAGCTGTATCC | 517 | AUUUUUUAAUUCUAGAUGGAAGCUGUAUCC |
| HAO1_exon2 | - | **ATTT** | 63 | TATTTTTTAATTCTAGATGGAAGCTGTATC | 518 | UAUUUUUUAAUUCUAGAUGGAAGCUGUAUC |
| HAO1_exon2 | - | **TTTA** | 64 | TTTTATTTTTTAATTCTAGATGGAAGCTGT | 519 | UUUUAUUUUUUAAUUCUAGAUGGAAGCUGU |
| HAO1_exon2 | + | **ATTA** | 65 | AAAAATAAAATAAAATAAAGGCTTTAGAG | 520 | AAAAAUAAAAUAAAAUAAAGGCUUUAGAG |
| HAO1_exon2 | - | **TTTT** | 66 | ATTTTATTTTATTTTTTAATTCTAGATGGA | 521 | AUUUUAUUUUAUUUUUUAAUUCUAGAUGGA |
| HAO1_exon2 | - | C**TTT** | 67 | TATTTTATTTTATTTTTTAATTCTAGATGG | 522 | UAUUUUAUUUUAUUUUUUAAUUCUAGAUGG |
| HAO1_exon2 | - | **ATTC** | 68 | TGAAACTCTAAAGCCTTTTATTTTATTTTA | 523 | UGAAACUCUAAAGCCUUUUAUUUUAUUUUA |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon2 | - | **ATTT** | 69 | TTTAATTCTAGATGGAA GCTGTATCCAAGG | 524 | UUUAAUUCUAGAUGGAAGC UGUAUCCAAGG |
| HAO1_exon2 | - | **TTTA** | 70 | TTTTATTTTATTTTTTA ATTCTAGATGGAA | 525 | UUUUAUUUUAUUUUUUAAU UCUAGAUGGAA |
| HAO1_exon2 | - | **TTTT** | 71 | TTAATTCTAGATGGAAG CTGTATCCAAGGA | 526 | UUAAUUCUAGAUGGAAGCU GUAUCCAAGGA |
| HAO1_exon2 | - | **ATTT** | 72 | TATTTTATTTTTTAATT CTAGATGGAAGCT | 527 | UAUUUUAUUUUUUAAUUCU AGAUGGAAGCU |
| HAO1_exon2 | + | **CTTC** | 73 | CATCTAGAATTAAAAAA TAAAATAAAATAA | 528 | CAUCUAGAAUUAAAAAAUA AAAUAAAAUAA |
| HAO1_exon2 | - | **TTTT** | 74 | TAATTCTAGATGGAAGC TGTATCCAAGGAT | 529 | UAAUUCUAGAUGGAAGCUG UAUCCAAGGAU |
| HAO1_exon2 | - | **TTTT** | 75 | AATTCTAGATGGAAGCT GTATCCAAGGATG | 530 | AAUUCUAGAUGGAAGCUGU AUCCAAGGAUG |
| HAO1_exon2 | - | **TTTA** | 76 | ATTCTAGATGGAAGCTG TATCCAAGGATGC | 531 | AUUCUAGAUGGAAGCUGUA UCCAAGGAUGC |
| HAO1_exon2 | - | **ATTC** | 77 | TAGATGGAAGCTGTATC CAAGGATGCTCCG | 532 | UAGAUGGAAGCUGUAUCCA AGGAUGCUCCG |
| HAO1_exon2 | - | **GTTG** | 78 | CTGAAACAGATCTGTCG ACTTCTGTTTTAG | 533 | CUGAAACAGAUCUGUCGAC UUCUGUUUUAG |
| HAO1_exon2 | - | **GTTT** | 79 | TAGGACAGAGGGTCAGC ATGCCAATATGTG | 534 | UAGGACAGAGGGUCAGCAU GCCAAUAUGUG |
| HAO1_exon2 | - | **TTTT** | 80 | AGGACAGAGGGTCAGCA TGCCAATATGTGT | 535 | AGGACAGAGGGUCAGCAUG CCAAUAUGUGU |
| HAO1_exon2 | - | **TTTA** | 81 | GGACAGAGGGTCAGCAT GCCAATATGTGTG | 536 | GGACAGAGGGUCAGCAUGC CAAUAUGUGUG |
| HAO1_exon2 | - | **GTTG** | 82 | CCACTGTGAGAGGTAGG AGGAAGATTGTCA | 537 | CCACUGUGAGAGGUAGGAG GAAGAUUGUCA |
| HAO1_exon2 | - | **CTTC** | 83 | TGTTTTAGGACAGAGGG TCAGCATGCCAAT | 538 | UGUUUUAGGACAGAGGGUC AGCAUGCCAAU |
| HAO1_exon2 | + | **GTTA** | 84 | GCCTCCTTCTGTCCCTG TGGTGACAATCTT | 539 | GCCUCCUUCUGUCCCUGUG GUGACAAUCUU |
| HAO1_exon2 | - | **ATTG** | 85 | TCACCACAGGGACAGAA GGAGGCTAACGTT | 540 | UCACCACAGGGACAGAAGG AGGCUAACGUU |
| HAO1_exon2 | + | **ATTC** | 86 | CGGAGCATCCTTGGATA CAGCTTCCATCTA | 541 | CGGAGCAUCCUUGGAUACA GCUUCCAUCUA |
| HAO1_exon2 | + | **TTTC** | 87 | AGCAACATTCCGGAGCA TCCTTGGATACAG | 542 | AGCAACAUUCCGGAGCAUC CUUGGAUACAG |
| HAO1_exon2 | + | **GTTT** | 88 | CAGCAACATTCCGGAGC ATCCTTGGATACA | 543 | CAGCAACAUUCCGGAGCAU CCUUGGAUACA |
| HAO1_exon2 | + | **GTTG** | 89 | GATACAGCTTCCATCTA GAATTAAAAAATA | 544 | GAUACAGCUUCCAUCUAGA AUUAAAAAAUA |
| HAO1_exon2 | + | **CTTC** | 90 | CTCCTACCTCTCACAGT GGCAAGCTCGCCG | 545 | CUCCUACCUCUCACAGUGG CAAGCUCGCCG |
| HAO1_exon2 | + | **CTTC** | 91 | TGTCCCTGTGGTGACAA TCTTCCTCCTACC | 546 | UGUCCCUGUGGUGACAAUC UUCCUCCUACC |
| HAO1_exon2 | + | **ATTG** | 92 | GCATGCTGACCCTCTGT CCTAAAACAGAAG | 547 | GCAUGCUGACCCUCUGUCC UAAAACAGAAG |
| HAO1_exon3 | - | **CTTA** | 93 | CCTGGGCAACCGTCTGG ATGATGTGCGTAA | 548 | CCUGGGCAACCGUCUGGAU GAUGUGCGUAA |

TABLE 5-continued

| Target and Spacer Sequences | | | | | | |
|---|---|---|---|---|---|---|
| HAO1 | Strand | PAM* | SEQ ID NO | Target Sequence | SEQ ID NO | Spacer Sequence |
| HAO1_exon3 | + | **TTTG** | 94 | AATCTGTTACGCACATC ATCCAGACGGTTG | 549 | AAUCUGUUACGCACAUCAU CCAGACGGUUG |
| HAO1_exon3 | + | **GTTT** | 95 | GAATCTGTTACGCACAT CATCCAGACGGTT | 550 | GAAUCUGUUACGCACAUCA UCCAGACGGUU |
| HAO1_exon3 | + | **GTTG** | 96 | TGGCGGCAGTTTGAATC TGTTACGCACATC | 551 | UGGCGGCAGUUUGAAUCUG UUACGCACAUC |
| HAO1_exon3 | + | **GTTA** | 97 | CCTGAGTTGTGGCGGCA GTTTGAATCTGTT | 552 | CCUGAGUUGUGGCGGCAGU UUGAAUCUGUU |
| HAO1_exon3 | + | **TTTC** | 98 | GCCTCAGCTCGGGGCCC ACATGATCATGGT | 553 | GCCUCAGCUCGGGGCCCAC AUGAUCAUGGU |
| HAO1_exon3 | + | C**TTT** | 99 | CGCCTCAGCTCGGGGCC CACATGATCATGG | 554 | CGCCUCAGCUCGGGGCCCA CAUGAUCAUGG |
| HAO1_exon3 | - | **ATTC** | 100 | AAACTGCCGCCACAACT CAGGTAACCATGA | 555 | AAACUGCCGCCACAACUCA GGUAACCAUGA |
| HAO1_exon3 | - | **TTTG** | 101 | TGACAGTGGACACACCT TACCTGGGCAACC | 556 | UGACAGUGGACACACCUUA CCUGGGCAACC |
| HAO1_exon3 | - | C**TTG** | 102 | ATCATCCCCTTTCTTTC TCAGCCTGTCAGT | 557 | AUCAUCCCCUUUCUUUCUC AGCCUGUCAGU |
| HAO1_exon3 | - | **GTTG** | 103 | GCTGCAACTGTATATCT ACAAGGACCGAGA | 558 | GCUGCAACUGUAUAUCUAC AAGGACCGAGA |
| HAO1_exon3 | - | **ATTG** | 104 | AAGAAGTGGCGGAAGCT GGTCCTGAGGCAC | 559 | AAGAAGUGGCGGAAGCUGG UCCUGAGGCAC |
| HAO1_exon3 | - | **GTTC** | 105 | CTGGGCCACCTCCTCAA TTGAAGAAGTGGC | 560 | CUGGGCCACCUCCUCAAUU GAAGAAGUGGC |
| HAO1_exon3 | - | **GTTG** | 106 | AGTTCCTGGGCCACCTC CTCAATTGAAGAA | 561 | AGUUCCUGGGCCACCUCCU CAAUUGAAGAA |
| HAO1_exon3 | - | **TTTC** | 107 | TCAGCCTGTCAGTCCCT GGGAACGGGCATG | 562 | UCAGCCUGUCAGUCCCUGG GAACGGGCAUG |
| HAO1_exon3 | - | C**TTT** | 108 | CTCAGCCTGTCAGTCCC TGGGAACGGGCAT | 563 | CUCAGCCUGUCAGUCCCUG GGAACGGGCAU |
| HAO1_exon3 | - | **TTTC** | 109 | TTTCTCAGCCTGTCAGT CCCTGGGAACGGG | 564 | UUUCUCAGCCUGUCAGUCC CUGGGAACGGG |
| HAO1_exon3 | - | C**TTT** | 110 | CTTTCTCAGCCTGTCAG TCCCTGGGAACGG | 565 | CUUUCUCAGCCUGUCAGUC CCUGGGAACGG |
| HAO1_exon3 | + | **GTTA** | 111 | CGCACATCATCCAGACG GTTGCCCAGGTAA | 566 | CGCACAUCAUCCAGACGGU UGCCCAGGUAA |
| HAO1_exon3 | - | **ATTT** | 112 | GTGACAGTGGACACACC TTACCTGGGCAAC | 567 | GUGACAGUGGACACACCUU ACCUGGGCAAC |
| HAO1_exon3 | + | **GTTG** | 113 | CCCAGGTAAGGTGTGTC CACTGTCACAAAT | 568 | CCCAGGUAAGGUGUGUCCA CUGUCACAAAU |
| HAO1_exon3 | - | C**TTC** | 114 | GTTGGCTGCAACTGTAT ATCTACAAGGACC | 569 | GUUGGCUGCAACUGUAUAU CUACAAGGACC |
| HAO1_exon3 | + | C**TTC** | 115 | TCTGCCTGCCGCACTAG CTTCTTGGTGACT | 570 | UCUGCCUGCCGCACUAGCU UCUUGGUGACU |
| HAO1_exon3 | + | C**TTG** | 116 | TAGCCCATCTTCTCTGC CTGCCGCACTAGC | 571 | UAGCCCAUCUUCUCUGCCU GCCGCACUAGC |
| HAO1_exon3 | + | **GTTC** | 117 | CCAGGGACTGACAGGCT GAGAAAGAAAGGG | 572 | CCAGGGACUGACAGGCUGA GAAAGAAAGGG |
| HAO1_exon3 | + | **ATTG** | 118 | AGGAGGTGGCCCAGGAA CTCAACATCATGC | 573 | AGGAGGUGGCCCAGGAACU CAACAUCAUGC |

TABLE 5-continued

| Target and Spacer Sequences | | | | | | |
|---|---|---|---|---|---|---|
| HAO1 | Strand | PAM* | SEQ ID NO | Target Sequence | SEQ ID NO | Spacer Sequence |
| HAO1_exon3 | + | **CTTC** | 119 | TTCAATTGAGGAGGTGGCCCAGGAACTCAA | 574 | UUCAAUUGAGGAGGUGGCCCAGGAACUCAA |
| HAO1_exon3 | + | **CTTC** | 120 | CGCCACTTCTTCAATTGAGGAGGTGGCCCA | 575 | CGCCACUUCUUCAAUUGAGGAGGUGGCCCA |
| HAO1_exon3 | + | **CTTC** | 121 | AATTGAGGAGGTGGCCCAGGAACTCAACAT | 576 | AAUUGAGGAGGUGGCCCAGGAACUCAACAU |
| HAO1_exon3 | + | **CTTG** | 122 | TAGATATACAGTTGCAGCCAACGAAGTGCC | 577 | UAGAUAUACAGUUGCAGCCAACGAAGUGCC |
| HAO1_exon3 | + | **CTTC** | 123 | TCGGTCCTTGTAGATATACAGTTGCAGCCA | 578 | UCGGUCCUUGUAGAUAUACAGUUGCAGCCA |
| HAO1_exon3 | + | **CTTG** | 124 | GTGACTTCTCGGTCCTTGTAGATATACAGT | 579 | GUGACUUCUCGGUCCUUGUAGAUAUACAGU |
| HAO1_exon3 | + | **CTTC** | 125 | TTGGTGACTTCTCGGTCCTTGTAGATATAC | 580 | UUGGUGACUUCUCGGUCCUUGUAGAUAUAC |
| HAO1_exon3 | + | **GTTG** | 126 | CAGCCAACGAAGTGCCTCAGGACCAGCTTC | 581 | CAGCCAACGAAGUGCCUCAGGACCAGCUUC |
| HAO1_exon4 | - | **ATTT** | 127 | CTAATTTGGCAAATTTCTCATTTTATGCAT | 582 | CUAAUUUGGCAAAUUUCUCAUUUUAUGCAU |
| HAO1_exon4 | + | **TTTC** | 128 | ATCCTAAAATAAGAAATGCATAAAATGAGA | 583 | AUCCUAAAAUAAGAAAUGCAUAAAAUGAGA |
| HAO1_exon4 | + | **ATTC** | 129 | AAGTAGAGAAATAAACGAACCTCTCAAAAT | 584 | AAGUAGAGAAAUAAACGAACCUCUCAAAAU |
| HAO1_exon4 | - | **TTTC** | 130 | TCTACTTGAATTCATACTGACTTTGTGATC | 585 | UCUACUUGAAUUCAUACUGACUUUGUGAUC |
| HAO1_exon4 | - | **TTTC** | 131 | TAATTTGGCAAATTTCTCATTTTATGCATT | 586 | UAAUUUGGCAAAUUUCUCAUUUUAUGCAUU |
| HAO1_exon4 | - | **ATTT** | 132 | TATGCATTTCTTATTTTAGGATGAAAAATT | 587 | UAUGCAUUUCUUAUUUUAGGAUGAAAAAUU |
| HAO1_exon4 | - | **TTTG** | 133 | GCAAATTTCTCATTTTATGCATTTCTTATT | 588 | GCAAAUUUCUCAUUUUAUGCAUUUCUUAUU |
| HAO1_exon4 | - | **ATTT** | 134 | CTCATTTTATGCATTTCTTATTTTAGGATG | 589 | CUCAUUUUAUGCAUUUCUUAUUUUAGGAUG |
| HAO1_exon4 | - | **TTTC** | 135 | TCATTTTATGCATTTCTTATTTTAGGATGA | 590 | UCAUUUUAUGCAUUUCUUAUUUUAGGAUGA |
| HAO1_exon4 | + | **TTTT** | 136 | CATCCTAAAATAAGAAATGCATAAAATGAG | 591 | CAUCCUAAAAUAAGAAAUGCAUAAAAUGAG |
| HAO1_exon4 | - | **ATTT** | 137 | GGCAAATTTCTCATTTTATGCATTTCTTAT | 592 | GGCAAAUUUCUCAUUUUAUGCAUUUCUUAU |
| HAO1_exon4 | + | **TTTT** | 138 | TCATCCTAAAATAAGAAATGCATAAAATGA | 593 | UCAUCCUAAAAUAAGAAAUGCAUAAAAUGA |
| HAO1_exon4 | + | **ATTT** | 139 | TCCTCAGGAGAAAATGATAAAGTACTGGTT | 594 | UCCUCAGGAGAAAAUGAUAAAGUACUGGUU |
| HAO1_exon4 | + | **TTTC** | 140 | AAAATTTTTCATCCTAAAATAAGAAATGCA | 595 | AAAAUUUUUCAUCCUAAAAUAAGAAAUGCA |
| HAO1_exon4 | + | **GTTT** | 141 | CAAAATTTTTCATCCTAAAATAAGAAATGC | 596 | CAAAAUUUUUCAUCCUAAAAUAAGAAAUGC |
| HAO1_exon4 | + | **TTTC** | 142 | CTCAGGAGAAAATGATAAAGTACTGGTTTC | 597 | CUCAGGAGAAAAUGAUAAAGUACUGGUUUC |
| HAO1_exon4 | + | **TTTT** | 143 | CCTCAGGAGAAAATGATAAAGTACTGGTTT | 598 | CCUCAGGAGAAAAUGAUAAAGUACUGGUUU |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon4 | - | **TTTT** | 144 | ATGCATTTCTTATTTTA GGATGAAAAATTT | 599 | AUGCAUUUCUUAUUUUAGG AUGAAAAAUUU |
| HAO1_exon4 | + | **TTTA** | 145 | GCCACATATGCAGCAAG TCCACTGTCGTCT | 600 | GCCACAUAUGCAGCAAGUC CACUGUCGUCU |
| HAO1_exon4 | + | **CTTT** | 146 | AGCCACATATGCAGCAA GTCCACTGTCGTC | 601 | AGCCACAUAUGCAGCAAGU CCACUGUCGUC |
| HAO1_exon4 | + | **ATTG** | 147 | CTTTAGCCACATATGCA GCAAGTCCACTGT | 602 | CUUUAGCCACAUAUGCAGC AAGUCCACUGU |
| HAO1_exon4 | + | **CTTC** | 148 | CCAGCTGATAGATGGGT CTATTGCTTTAGC | 603 | CCAGCUGAUAGAUGGGUCU AUUGCUUUAGC |
| HAO1_exon4 | + | **TTTG** | 149 | ATATCTTCCCAGCTGAT AGATGGGTCTATT | 604 | AUAUCUUCCCAGCUGAUAG AUGGGUCUAUU |
| HAO1_exon4 | + | **ATTT** | 150 | GATATCTTCCCAGCTGA TAGATGGGTCTAT | 605 | GAUAUCUUCCCAGCUGAUA GAUGGGUCUAU |
| HAO1_exon4 | + | **CTTC** | 151 | TCAGCCATTTGATATCT TCCCAGCTGATAG | 606 | UCAGCCAUUUGAUAUCUUC CCAGCUGAUAG |
| HAO1_exon4 | + | **ATTG** | 152 | GCAATGATGTCAGTCTT CTCAGCCATTTGA | 607 | GCAAUGAUGUCAGUCUUCU CAGCCAUUUGA |
| HAO1_exon4 | + | **ATTT** | 153 | TTCATCCTAAAATAAGA AATGCATAAAATG | 608 | UUCAUCCUAAAAUAAGAAA UGCAUAAAAUG |
| HAO1_exon4 | - | **TTTA** | 154 | TGCATTTCTTATTTTAG GATGAAAAATTTT | 609 | UGCAUUUCUUAUUUUAGGA UGAAAAAUUUU |
| HAO1_exon4 | - | **TTTA** | 155 | GGATGAAAAATTTTGAA ACCAGTACTTTAT | 610 | GGAUGAAAAAUUUUGAAAC CAGUACUUUAU |
| HAO1_exon4 | - | **TTTC** | 156 | TTATTTTAGGATGAAAA ATTTTGAAACCAG | 611 | UUAUUUUAGGAUGAAAAAU UUUGAAACCAG |
| HAO1_exon4 | - | **ATTG** | 157 | CCAATTGTTGCAAAGGG CATTTTGAGAGGT | 612 | CCAAUUGUUGCAAAGGGCA UUUUGAGAGGU |
| HAO1_exon4 | - | **ATTG** | 158 | TTGCAAAGGGCATTTTG AGAGGTTCGTTTA | 613 | UUGCAAAGGGCAUUUUGAG AGGUUCGUUUA |
| HAO1_exon4 | + | **CTTT** | 159 | GCAACAATTGGCAATGA TGTCAGTCTTCTC | 614 | GCAACAAUUGGCAAUGAUG UCAGUCUUCUC |
| HAO1_exon4 | - | **GTTG** | 160 | CAAAGGGCATTTTGAGA GGTTCGTTTATTT | 615 | CAAAGGGCAUUUUGAGAGG UUCGUUUAUUU |
| HAO1_exon4 | - | **ATTT** | 161 | TGAGAGGTTCGTTTATT TCTCTACTTGAAT | 616 | UGAGAGGUUCGUUUAUUUC UCUACUUGAAU |
| HAO1_exon4 | - | **TTTT** | 162 | GAGAGGTTCGTTTATTT CTCTACTTGAATT | 617 | GAGAGGUUCGUUUAUUUCU CUACUUGAAUU |
| HAO1_exon4 | - | **TTTG** | 163 | AGAGGTTCGTTTATTTC TCTACTTGAATTC | 618 | AGAGGUUCGUUUAUUUCUC UACUUGAAUUC |
| HAO1_exon4 | - | **GTTC** | 164 | GTTTATTTCTCTACTTG AATTCATACTGAC | 619 | GUUUAUUUCUCUACUUGAA UUCAUACUGAC |
| HAO1_exon4 | - | **GTTT** | 165 | ATTTCTCTACTTGAATT CATACTGACTTTG | 620 | AUUUCUCUACUUGAAUUCA UACUGACUUUG |
| HAO1_exon4 | - | **TTTA** | 166 | TTTCTCTACTTGAATTC ATACTGACTTTGT | 621 | UUUCUCUACUUGAAUUCAU ACUGACUUUGU |
| HAO1_exon4 | - | **ATTT** | 167 | CTCTACTTGAATTCATA CTGACTTTGTGAT | 622 | CUCUACUUGAAUUCAUACU GACUUUGUGAU |
| HAO1_exon4 | - | **GTTG** | 168 | CTGCATATGTGGCTAAA GCAATAGACCCAT | 623 | CUGCAUAUGUGGCUAAAGC AAUAGACCCAU |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon4 | - | **ATTT** | 169 | CTTATTTTAGGATGAAAAATTTTGAAACCA | 624 | CUUAUUUUAGGAUGAAAAAUUUUGAAACCA |
| HAO1_exon4 | - | **TTTG** | 170 | GAGACGACAGTGGACTTGCTGCATATGTGG | 625 | GAGACGACAGUGGACUUGCUGCAUAUGUGG |
| HAO1_exon4 | - | **ATTT** | 171 | TGGAGACGACAGTGGACTTGCTGCATATGT | 626 | UGGAGACGACAGUGGACUUGCUGCAUAUGU |
| HAO1_exon4 | - | **TTTC** | 172 | TCCTGAGGAAAATTTTGGAGACGACAGTGG | 627 | UCCUGAGGAAAAUUUUGGAGACGACAGUGG |
| HAO1_exon4 | - | **TTTT** | 173 | CTCCTGAGGAAAATTTTGGAGACGACAGTG | 628 | CUCCUGAGGAAAAUUUUGGAGACGACAGUG |
| HAO1_exon4 | - | **ATTT** | 174 | TCTCCTGAGGAAAATTTTGGAGACGACAGT | 629 | UCUCCUGAGGAAAAUUUUGGAGACGACAGU |
| HAO1_exon4 | - | **TTTA** | 175 | TCATTTTCTCCTGAGGAAAATTTTGGAGAC | 630 | UCAUUUUCUCCUGAGGAAAAUUUUGGAGAC |
| HAO1_exon4 | - | **CTTT** | 176 | ATCATTTTCTCCTGAGGAAAATTTTGGAGA | 631 | AUCAUUUUCUCCUGAGGAAAAUUUUGGAGA |
| HAO1_exon4 | - | **TTTG** | 177 | AAACCAGTACTTTATCATTTTCTCCTGAGG | 632 | AAACCAGUACUUUAUCAUUUUCUCCUGAGG |
| HAO1_exon4 | - | **TTTT** | 178 | GAAACCAGTACTTTATCATTTTCTCCTGAG | 633 | GAAACCAGUACUUUAUCAUUUUCUCCUGAG |
| HAO1_exon4 | - | **ATTT** | 179 | TGAAACCAGTACTTTATCATTTTCTCCTGA | 634 | UGAAACCAGUACUUUAUCAUUUUCUCCUGA |
| HAO1_exon4 | - | **TTTT** | 180 | AGGATGAAAAATTTTGAAACCAGTACTTTA | 635 | AGGAUGAAAAAUUUUGAAACCAGUACUUUA |
| HAO1_exon4 | - | **ATTT** | 181 | TAGGATGAAAAATTTTGAAACCAGTACTTT | 636 | UAGGAUGAAAAAUUUUGAAACCAGUACUUU |
| HAO1_exon4 | - | **CTTA** | 182 | TTTTAGGATGAAAAATTTTGAAACCAGTAC | 637 | UUUUAGGAUGAAAAAUUUUGAAACCAGUAC |
| HAO1_exon4 | - | **TTTT** | 183 | GGAGACGACAGTGGACTTGCTGCATATGTG | 638 | GGAGACGACAGUGGACUUGCUGCAUAUGUG |
| HAO1_exon4 | + | **TTTG** | 184 | CAACAATTGGCAATGATGTCAGTCTTCTCA | 639 | CAACAAUUGGCAAUGAUGUCAGUCUUCUCA |
| HAO1_exon4 | - | **CTTG** | 185 | AATTCATACTGACTTTGTGATCCTTTGTG | 640 | AAUUCAUACUGACUUUGUGAUCCUUUGUG |
| HAO1_exon4 | - | **ATTC** | 186 | ATACTGACTTTGTGATCCTTTGTG | 641 | AUACUGACUUUGUGAUCCUUUGUG |
| HAO1_exon5 | - | **GTTA** | 187 | AGTTACAGTTTCCCTAAGGTGCTTGTTTTA | 642 | AGUUACAGUUUCCCUAAGGUGCUUGUUUUA |
| HAO1_exon5 | + | **ATTC** | 188 | AAGCCATGTTTAACAGCCTCCCTGGCATCA | 643 | AAGCCAUGUUUAACAGCCUCCCUGGCAUCA |
| HAO1_exon5 | + | **TTTA** | 189 | ACAGCCTCCCTGGCATCATCACCTGGAGAG | 644 | ACAGCCUCCCUGGCAUCAUCACCUGGAGAG |
| HAO1_exon5 | + | **GTTT** | 190 | AACAGCCTCCCTGGCATCATCACCTGGAGA | 645 | AACAGCCUCCCUGGCAUCAUCACCUGGAGA |
| HAO1_exon5 | + | **ATTC** | 191 | GACACCAAGATCCCATTCAAGCCATGTTTA | 646 | GACACCAAGAUCCCAUUCAAGCCAUGUUUA |
| HAO1_exon5 | + | **GTTG** | 192 | TCGAGCCCCATGATTCGACACCAAGATCCC | 647 | UCGAGCCCCAUGAUUCGACACCAAGAUCCC |
| HAO1_exon5 | + | **GTTA** | 193 | GCGTCTGCCAAAACTCACAGTGGCTGGCAC | 648 | GCGUCUGCCAAAACUCACAGUGGCUGGCAC |

TABLE 5-continued

| Target and Spacer Sequences | | | | | | |
|---|---|---|---|---|---|---|
| HAO1 | Strand | PAM* | SEQ ID NO | Target Sequence | SEQ ID NO | Spacer Sequence |
| HAO1_exon5 | - | **TTTG** | 194 | GCAGACGCTAAGATTTCCTTTTGGAGTTCC | 649 | GCAGACGCUAAGAUUUCCUUUUGGAGUUCC |
| HAO1_exon5 | - | **GTTT** | 195 | TGGCAGACGCTAAGATTTCCTTTTGGAGTT | 650 | UGGCAGACGCUAAGAUUUCCUUUUGGAGUU |
| HAO1_exon5 | - | **GTTG** | 196 | GTGTCGAATCATGGGGCTCGACAACTCGAT | 651 | GUGUCGAAUCAUGGGGCUCGACAACUCGAU |
| HAO1_exon5 | - | **TTTT** | 197 | GGCAGACGCTAAGATTTCCTTTTGGAGTTC | 652 | GGCAGACGCUAAGAUUUCCUUUUGGAGUUC |
| HAO1_exon5 | - | **GTTA** | 198 | AACATGGCTTGAATGGGATCTTGGTGTCGA | 653 | AACAUGGCUUGAAUGGGAUCUUGGUGUCGA |
| HAO1_exon5 | - | **TTTA** | 199 | CTCTCTCCAGGTGATGATGCCAGGGAGGCT | 654 | CUCUCUCCAGGUGAUGAUGCCAGGGAGGCU |
| HAO1_exon5 | - | **TTTT** | 200 | ACTCTCTCCAGGTGATGATGCCAGGGAGGC | 655 | ACUCUCUCCAGGUGAUGAUGCCAGGGAGGC |
| HAO1_exon5 | - | **GTTT** | 201 | TACTCTCTCCAGGTGATGATGCCAGGGAGG | 656 | UACUCUCUCCAGGUGAUGAUGCCAGGGAGG |
| HAO1_exon5 | - | **GTTG** | 202 | TTTTACTCTCTCCAGGTGATGATGCCAGGG | 657 | UUUUACUCUCUCCAGGUGAUGAUGCCAGGG |
| HAO1_exon5 | - | **TTTC** | 203 | CCTAAGGTGCTTGTTTTACTCTCTCCAGGT | 658 | CCUAAGGUGCUUGUUUUACUCUCUCCAGGU |
| HAO1_exon5 | - | **GTTT** | 204 | CCCTAAGGTGCTTGTTTTACTCTCTCCAGG | 659 | CCCUAAGGUGCUUGUUUUACUCUCUCCAGG |
| HAO1_exon5 | - | **GTTA** | 205 | CAGTTTCCCTAAGGTGCTTGTTTTACTCTC | 660 | CAGUUUCCCUAAGGUGCUUGUUUUACUCUC |
| HAO1_exon5 | - | **GTTG** | 206 | AATGGGATCTTGGTGTCGAATCATGGGGCT | 661 | AAUGGGAUCUUGGUGUCGAAUCAUGGGGCU |
| HAO1_exon5 | - | **ATTT** | 207 | CCTTTTGGAGTTCCCATTTCCATC | 662 | CCUUUUGGAGUUCCCAUUUCCAUC |
| HAO1_exon5 | - | **TTTC** | 208 | CTTTTGGAGTTCCCATTTCCATC | 663 | CUUUUGGAGUUCCCAUUUCCAUC |
| HAO1_exon5 | + | **GTTA** | 209 | GGGAAACTGTAACTTAACAGGCAG | 664 | GGGAAACUGUAACUUAACAGGCAG |
| HAO1_exon6 | - | **TTTA** | 210 | CAACTTTCTTTTCTTTTATGATCTTTAAGT | 665 | CAACUUUCUUUUCUUUUAUGAUCUUUAAGU |
| HAO1_exon6 | - | **ATTC** | 211 | CGGTTGGCCATGGCTCTGAGTGGTAAGACT | 666 | CGGUUGGCCAUGGCUCUGAGUGGUAAGACU |
| HAO1_exon6 | - | **GTTG** | 212 | GCCATGGCTCTGAGTGGTAAGACTCATTCT | 667 | GCCAUGGCUCUGAGUGGUAAGACUCAUUCU |
| HAO1_exon6 | - | **ATTC** | 213 | TTGTTTACAACTTTCTTTTCTTTTATGATC | 668 | UUGUUUACAACUUUCUUUUCUUUUAUGAUC |
| HAO1_exon6 | - | **CTTG** | 214 | TTTACAACTTTCTTTTCTTTTATGATCTTT | 669 | UUUACAACUUUCUUUUCUUUUAUGAUCUUU |
| HAO1_exon6 | - | **GTTT** | 215 | ACAACTTTCTTTTCTTTTATGATCTTTAAG | 670 | ACAACUUUCUUUUCUUUUAUGAUCUUUAAG |
| HAO1_exon6 | + | **CTTA** | 216 | AAGATCATAAAAGAAAAGAAAGTTGTAAAC | 671 | AAGAUCAUAAAAGAAAAGAAAGUUGUAAAC |
| HAO1_exon6 | + | **GTTG** | 217 | TCTATTTTATATATTCATTTCTTTGTCCAG | 672 | UCUAUUUUAUAUAUUCAUUUCUUUGUCCAG |
| HAO1_exon6 | + | **CTTA** | 218 | CCACTCAGAGCCATGGCCAACCGGAATTCT | 673 | CCACUCAGAGCCAUGGCCAACCGGAAUUCU |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon6 | + | **ATTC** | 219 | TTCCTTTAGTATCTCGA GGACATCTTGAAC | 674 | UUCCUUUAGUAUCUCGAGG ACAUCUUGAAC |
| HAO1_exon6 | + | **CTTC** | 220 | CTTTAGTATCTCGAGGA CATCTTGAACACC | 675 | CUUUAGUAUCUCGAGGACA UCUUGAACACC |
| HAO1_exon6 | + | **GTTT** | 221 | AGTATCTCGAGGACATC TTGAACACCTTTC | 676 | AGUAUCUCGAGGACAUCUU GAACACCUUUC |
| HAO1_exon6 | + | **TTTA** | 222 | GTATCTCGAGGACATCT TGAACACCTTTCT | 677 | GUAUCUCGAGGACAUCUUG AACACCUUUCU |
| HAO1_exon6 | - | **GTTC** | 223 | AAGATGTCCTCGAGATA CTAAAGGAAGAAT | 678 | AAGAUGUCCUCGAGAUACU AAAGGAAGAAU |
| HAO1_exon6 | + | **GTTG** | 224 | TAAACAAGAATGAGTCT TACCACTCAGAGC | 679 | UAAACAAGAAUGAGUCUUA CCACUCAGAGC |
| HAO1_exon6 | - | **GTTA** | 225 | GGGGGAGAAAGGTGTTC AAGATGTCCTCGA | 680 | GGGGGAGAAAGGUGUUCAA GAUGUCCUCGA |
| HAO1_exon6 | - | **GTTT** | 226 | CCAGGTAACTGGACAAA GAAATGAATATAT | 681 | CCAGGUAACUGGACAAAGA AAUGAAUAUAU |
| HAO1_exon6 | - | **TTTC** | 227 | ACTTGGTTAGGGGGAGA AAGGTGTTCAAGA | 682 | ACUUGGUUAGGGGGAGAAA GGUGUUCAAGA |
| HAO1_exon6 | - | **TTTT** | 228 | CACTTGGTTAGGGGGAG AAAGGTGTTCAAG | 683 | CACUUGGUUAGGGGGAGAA AGGUGUUCAAG |
| HAO1_exon6 | - | **GTTT** | 229 | TCACTTGGTTAGGGGGA GAAAGGTGTTCAA | 684 | UCACUUGGUUAGGGGGAGA AAGGUGUUCAA |
| HAO1_exon6 | - | **GTTC** | 230 | TGAATCACTCTGTATCT TTTCACTTGGTTA | 685 | UGAAUCACUCUGUAUCUUU UCACUUGGUUA |
| HAO1_exon6 | - | **TTTA** | 231 | GTTCTGAATCACTCTGT ATCTTTTCACTTG | 686 | GUUCUGAAUCACUCUGUAU CUUUUCACUUG |
| HAO1_exon6 | - | **ATTT** | 232 | AGTTCTGAATCACTCTG TATCTTTTCACTT | 687 | AGUUCUGAAUCACUCUGUA UCUUUUCACUU |
| HAO1_exon6 | - | **CTTG** | 233 | ACAGTAAAACAAATGAA TAAAACAAGTCAG | 688 | ACAGUAAAACAAAUGAAUA AAACAAGUCAG |
| HAO1_exon6 | - | **TTTC** | 234 | CAGGTAACTGGACAAAG AAATGAATATATA | 689 | CAGGUAACUGGACAAAGAA AUGAAUAUAUA |
| HAO1_exon6 | + | **CTTG** | 235 | AACACCTTTCTCCCCCT AACCAAGTGAAAA | 690 | AACACCUUUCUCCCCCUAA CCAAGUGAAAA |
| HAO1_exon6 | - | **CTTA** | 236 | GCTTTCCAGGTAACTGG ACAAAGAAATGAA | 691 | GCUUUCCAGGUAACUGGAC AAAGAAAUGAA |
| HAO1_exon6 | - | **TTTG** | 237 | GGGCTTAGCTTTCCAGG TAACTGGACAAAG | 692 | GGGCUUAGCUUUCCAGGUA ACUGGACAAAG |
| HAO1_exon6 | - | **GTTT** | 238 | GGGGCTTAGCTTTCCAG GTAACTGGACAAA | 693 | GGGGCUUAGCUUUCCAGGU AACUGGACAAA |
| HAO1_exon6 | - | **TTTG** | 239 | TGGGGAGACCAATCGTT TGGGGCTTAGCTT | 694 | UGGGGAGACCAAUCGUUUG GGGCUUAGCUU |
| HAO1_exon6 | - | **GTTT** | 240 | GTGGGGAGACCAATCGT TTGGGGCTTAGCT | 695 | GUGGGGAGACCAAUCGUUU GGGGCUUAGCU |
| HAO1_exon6 | - | **CTTG** | 241 | GTTAGGGGGAGAAAGGT GTTCAAGATGTCC | 696 | GUUAGGGGGAGAAAGGUGU UCAAGAUGUCC |
| HAO1_exon6 | + | **CTTT** | 242 | CTCCCCCTAACCAAGTG AAAAGATACAGAG | 697 | CUCCCCCUAACCAAGUGAA AAGAUACAGAG |
| HAO1_exon6 | + | **GTTT** | 243 | TACTGTCAAGTTGTCTA TTTTATATATTCA | 698 | UACUGUCAAGUUGUCUAUU UUAUAUAUUCA |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon6 | + | **ATTC** | 244 | AGAACTAAATCAGTCTG ACTTGTTTTATTC | 699 | AGAACUAAAUCAGUCUGAC UUGUUUUAUUC |
| HAO1_exon6 | + | **GTTC** | 245 | AATAATGTGACTCTATT AACACTGAATTGT | 700 | AAUAAUGUGACUCUAUUAA CACUGAAUUGU |
| HAO1_exon6 | + | **TTTC** | 246 | TGGCAGAACATCAATCT GGGGAAAGAAAAG | 701 | UGGCAGAACAUCAAUCUGG GGAAAGAAAAG |
| HAO1_exon6 | + | **ATTT** | 247 | CTGGCAGAACATCAATC TGGGGAAAGAAAA | 702 | CUGGCAGAACAUCAAUCUG GGGAAAGAAAA |
| HAO1_exon6 | + | **GTTC** | 248 | CACAGCCTCCACAATTT CTGGCAGAACATC | 703 | CACAGCCUCCACAAUUUCU GGCAGAACAUC |
| HAO1_exon6 | + | C**TTC** | 249 | CCTTCCACAGCCTCCAC AATTTCTGGCAGA | 704 | CCUUCCACAGCCUCCACAA UUUCUGGCAGA |
| HAO1_exon6 | + | **GTTC** | 250 | CACCTTCCCTTCCACAG CCTCCACAATTTC | 705 | CACCUUCCCUUCCACAGCC UCCACAAUUUC |
| HAO1_exon6 | + | **TTTC** | 251 | CGCACACCCCCGTCCAG GAAGACTTCCACC | 706 | CGCACACCCCCGUCCAGGA AGACUUCCACC |
| HAO1_exon6 | + | C**TTT** | 252 | CCGCACACCCCCGTCCA GGAAGACTTCCAC | 707 | CCGCACACCCCCGUCCAGG AAGACUUCCAC |
| HAO1_exon6 | + | **TTTC** | 253 | AGAACATCAGTGCCTTT CCGCACACCCCCG | 708 | AGAACAUCAGUGCCUUUCC GCACACCCCCG |
| HAO1_exon6 | + | C**TTT** | 254 | CAGAACATCAGTGCCTT TCCGCACACCCCC | 709 | CAGAACAUCAGUGCCUUUC CGCACACCCCC |
| HAO1_exon6 | + | **CTTG** | 255 | GCGCCAAGAGCCAGAGC TTTCAGAACATCA | 710 | GCGCCAAGAGCCAGAGCUU UCAGAACAUCA |
| HAO1_exon6 | + | **ATTG** | 256 | GTCTCCCCACAAACACA GCCTTGGCGCCAA | 711 | GUCUCCCCACAAACACAGC CUUGGCGCCAA |
| HAO1_exon6 | + | **GTTA** | 257 | CCTGGAAAGCTAAGCCC CAAACGATTGGTC | 712 | CCUGGAAAGCUAAGCCCCA AACGAUUGGUC |
| HAO1_exon6 | + | **TTTG** | 258 | TCCAGTTACCTGGAAAG CTAAGCCCCAAAC | 713 | UCCAGUUACCUGGAAAGCU AAGCCCCAAAC |
| HAO1_exon6 | + | C**TTT** | 259 | GTCCAGTTACCTGGAAA GCTAAGCCCCAAA | 714 | GUCCAGUUACCUGGAAAGC UAAGCCCCAAA |
| HAO1_exon6 | + | **TTTC** | 260 | TTTGTCCAGTTACCTGG AAAGCTAAGCCCC | 715 | UUUGUCCAGUUACCUGGAA AGCUAAGCCCC |
| HAO1_exon6 | + | **ATTT** | 261 | CTTTGTCCAGTTACCTG GAAAGCTAAGCCC | 716 | CUUUGUCCAGUUACCUGGA AAGCUAAGCCC |
| HAO1_exon6 | + | **CTTG** | 262 | TTTTATTCATTTGTTTT ACTGTCAAGTTGT | 717 | UUUUAUUCAUUUGUUUUAC UGUCAAGUUGU |
| HAO1_exon6 | + | **GTTT** | 263 | TATTCATTTGTTTTACT GTCAAGTTGTCTA | 718 | UAUUCAUUUGUUUUACUGU CAAGUUGUCUA |
| HAO1_exon6 | + | **TTTT** | 264 | ATTCATTTGTTTTACTG TCAAGTTGTCTAT | 719 | AUUCAUUUGUUUUACUGUC AAGUUGUCUAU |
| HAO1_exon6 | + | **TTTA** | 265 | TTCATTTGTTTTACTGT CAAGTTGTCTATT | 720 | UUCAUUUGUUUUACUGUCA AGUUGUCUAUU |
| HAO1_exon6 | + | **ATTC** | 266 | ATTTGTTTTACTGTCAA GTTGTCTATTTTA | 721 | AUUUGUUUUACUGUCAAGU UGUCUAUUUUA |
| HAO1_exon6 | + | **ATTT** | 267 | GTTTTACTGTCAAGTTG TCTATTTTATATA | 722 | GUUUUACUGUCAAGUUGUC UAUUUUAUAUA |
| HAO1_exon6 | + | **TTTC** | 268 | TCCCCCTAACCAAGTGA AAAGATACAGAGT | 723 | UCCCCCUAACCAAGUGAAA AGAUACAGAGU |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon6 | + | **TTTG** | 269 | TTTTACTGTCAAGTTGTCTATTTTATATAT | 724 | UUUUACUGUCAAGUUGUCUAUUUUAUAUAU |
| HAO1_exon6 | + | **TTTT** | 270 | ACTGTCAAGTTGTCTATTTTATATATTCAT | 725 | ACUGUCAAGUUGUCUAUUUUAUAUAUUCAU |
| HAO1_exon6 | + | **TTTA** | 271 | CTGTCAAGTTGTCTATTTTATATATTCATT | 726 | CUGUCAAGUUGUCUAUUUUAUAUAUUCAUU |
| HAO1_exon6 | + | **ATTT** | 272 | TATATATTCATTTCTTTGTCCAGTTACCTG | 727 | UAUAUAUUCAUUUCUUUGUCCAGUUACCUG |
| HAO1_exon6 | + | **TTTT** | 273 | ATATATTCATTTCTTTGTCCAGTTACCTGG | 728 | AUAUAUUCAUUUCUUUGUCCAGUUACCUGG |
| HAO1_exon6 | + | **TTTA** | 274 | TATATTCATTTCTTTGTCCAGTTACCTGGA | 729 | UAUAUUCAUUUCUUUGUCCAGUUACCUGGA |
| HAO1_exon6 | + | **ATTC** | 275 | ATTTCTTTGTCCAGTTACCTGGAAAGCTAA | 730 | AUUUCUUUGUCCAGUUACCUGGAAAGCUAA |
| HAO1_exon6 | - | **CTTG** | 276 | GCGCCAAGGCTGTGTTTGTGGGGAGACCAA | 731 | GCGCCAAGGCUGUGUUUGUGGGGAGACCAA |
| HAO1_exon6 | - | **GTTC** | 277 | TGAAAGCTCTGGCTCTTGGCGCCAAGGCTG | 732 | UGAAAGCUCUGGCUCUUGGCGCCAAGGCUG |
| HAO1_exon6 | - | **ATTG** | 278 | TGGAGGCTGTGGAAGGGAAGGTGGAAGTCT | 733 | UGGAGGCUGUGGAAGGGAAGGUGGAAGUCU |
| HAO1_exon6 | - | **ATTA** | 279 | TTGAACTTTTCTTTCCCCAGATTGATGTTC | 734 | UUGAACUUUUCUUUCCCCAGAUUGAUGUUC |
| HAO1_exon6 | - | **GTTC** | 280 | TGCCAGAAATTGTGGAGGCTGTGGAAGGGA | 735 | UGCCAGAAAUUGUGGAGGCUGUGGAAGGGA |
| HAO1_exon6 | - | **ATTG** | 281 | ATGTTCTGCCAGAAATTGTGGAGGCTGTGG | 736 | AUGUUCUGCCAGAAAUUGUGGAGGCUGUGG |
| HAO1_exon6 | - | **TTTC** | 282 | CCCAGATTGATGTTCTGCCAGAAATTGTGG | 737 | CCCAGAUUGAUGUUCUGCCAGAAAUUGUGG |
| HAO1_exon6 | - | **CTTT** | 283 | CCCCAGATTGATGTTCTGCCAGAAATTGTG | 738 | CCCCAGAUUGAUGUUCUGCCAGAAAUUGUG |
| HAO1_exon6 | - | **TTTC** | 284 | TTTCCCCAGATTGATGTTCTGCCAGAAATT | 739 | UUUCCCCAGAUUGAUGUUCUGCCAGAAAUU |
| HAO1_exon6 | - | **TTTT** | 285 | CTTTCCCCAGATTGATGTTCTGCCAGAAAT | 740 | CUUUCCCCAGAUUGAUGUUCUGCCAGAAAU |
| HAO1_exon6 | - | **CTTT** | 286 | TCTTTCCCCAGATTGATGTTCTGCCAGAAA | 741 | UCUUUCCCCAGAUUGAUGUUCUGCCAGAAA |
| HAO1_exon6 | - | **ATTG** | 287 | AACTTTTCTTTCCCCAGATTGATGTTCTGC | 742 | AACUUUUCUUUCCCCAGAUUGAUGUUCUGC |
| HAO1_exon6 | - | **GTTA** | 288 | ATAGAGTCACATTATTGAACTTTTCTTTCC | 743 | AUAGAGUCACAUUAUUGAACUUUUCUUUCC |
| HAO1_exon6 | - | **ATTC** | 289 | AGTGTTAATAGAGTCACATTATTGAACTTT | 744 | AGUGUUAAUAGAGUCACAUUAUUGAACUUU |
| HAO1_exon6 | - | **GTTC** | 290 | CTGGACGGGGGTGTGCGGAAAGGCACTGAT | 745 | CUGGACGGGGGUGUGCGGAAAGGCACUGAU |
| HAO1_exon6 | - | **CTTT** | 291 | CTTTTCTTTTATGATCTTTAAGT | 746 | CUUUUCUUUUAUGAUCUUUAAGU |
| HAO1_exon6 | - | **TTTC** | 292 | TTTTCTTTTATGATCTTTAAGT | 747 | UUUUCUUUUAUGAUCUUUAAGU |
| HAO1_exon7 | - | **ATTT** | 293 | TTTCAGGGTGCCAGAATGTGAAAGTCATCG | 748 | UUUCAGGGUGCCAGAAUGUGAAAGUCAUCG |

TABLE 5-continued

| Target and Spacer Sequences | | | | | | |
|---|---|---|---|---|---|---|
| HAO1 | Strand | PAM* | SEQ ID NO | Target Sequence | SEQ ID NO | Spacer Sequence |
| HAO1_exon7 | - | **ATTA** | 294 | TTTTTTCAGGGTGCCAGAATGTGAAAGTCA | 749 | UUUUUUCAGGGUGCCAGAAUGUGAAAGUCA |
| HAO1_exon7 | - | **ATTG** | 295 | TAAGCTCAGGTTCAAAGTGTTGGTAATGCC | 750 | UAAGCUCAGGUUCAAAGUGUUGGUAAUGCC |
| HAO1_exon7 | - | **GTTC** | 296 | ATATTAAATGTATGCATTATTTTTTCAGGG | 751 | AUAUUAAAUGUAUGCAUUAUUUUUUCAGGG |
| HAO1_exon7 | - | **ATTC** | 297 | AGTTCATATTAAATGTATGCATTATTTTTT | 752 | AGUUCAUAUUAAAUGUAUGCAUUAUUUUUU |
| HAO1_exon7 | - | **TTTT** | 298 | TTCAGGGTGCCAGAATGTGAAAGTCATCGA | 753 | UUCAGGGUGCCAGAAUGUGAAAGUCAUCGA |
| HAO1_exon7 | - | **ATTA** | 299 | AATGTATGCATTATTTTTTCAGGGTGCCAG | 754 | AAUGUAUGCAUUAUUUUUUCAGGGUGCCAG |
| HAO1_exon7 | - | **TTTT** | 300 | TCAGGGTGCCAGAATGTGAAAGTCATCGAC | 755 | UCAGGGUGCCAGAAUGUGAAAGUCAUCGAC |
| HAO1_exon7 | - | **TTTG** | 301 | GCCGTTTCCAAGATCTGACAGTGCACAATA | 756 | GCCGUUUCCAAGAUCUGACAGUGCACAAUA |
| HAO1_exon7 | - | **TTTC** | 302 | AGGGTGCCAGAATGTGAAAGTCATCGACAA | 757 | AGGGUGCCAGAAUGUGAAAGUCAUCGACAA |
| HAO1_exon7 | - | **ATTG** | 303 | GTGAGGAAAAATCCTTTGGCCGTTTCCAAG | 758 | GUGAGGAAAAAUCCUUUGGCCGUUUCCAAG |
| HAO1_exon7 | - | **CTTT** | 304 | GGCCGTTTCCAAGATCTGACAGTGGACAAT | 759 | GGCCGUUUCCAAGAUCUGACAGUGCACAAU |
| HAO1_exon7 | - | **ATTG** | 305 | CATTCAGTTCATATTAAATGTATGCATTAT | 760 | CAUUCAGUUCAUAUUAAAUGUAUGCAUUAU |
| HAO1_exon7 | - | **GTTT** | 306 | CCAAGATCTGACAGTGCACAATATTTTCCC | 761 | CCAAGAUCUGACAGUGCACAAUAUUUUCCC |
| HAO1_exon7 | - | **TTTC** | 307 | CAAGATCTGACAGTGCACAATATTTTCCCA | 762 | CAAGAUCUGACAGUGCACAAUAUUUUCCCA |
| HAO1_exon7 | - | **TTTT** | 308 | CAGGGTGCCAGAATGTGAAAGTCATCGACA | 763 | CAGGGUGCCAGAAUGUGAAAGUCAUCGACA |
| HAO1_exon7 | - | **ATTA** | 309 | TTGCATTCAGTTCATATTAAATGTATGCAT | 764 | UUGCAUUCAGUUCAUAUUAAAUGUAUGCAU |
| HAO1_exon7 | - | **ATTG** | 310 | GAGGTAGCAAACACTAAGGTGAAAAGATAA | 765 | GAGGUAGCAAACACUAAGGUGAAAAGAUAA |
| HAO1_exon7 | - | **GTTT** | 311 | AGACAACGTCATCCCCTGGCAGGCTAAAGT | 766 | AGACAACGUCAUCCCCUGGCAGGCUAAAGU |
| HAO1_exon7 | - | **CTTA** | 312 | AATTGTAAGCTCAGGTTCAAAGTGTTGGTA | 767 | AAUUGUAAGCUCAGGUUCAAAGUGUUGGUA |
| HAO1_exon7 | - | **GTTC** | 313 | TTAAATTGTAAGCTCAGGTTCAAAGTGTTG | 768 | UUAAAUUGUAAGCUCAGGUUCAAAGUGUUG |
| HAO1_exon7 | - | **TTTA** | 314 | AAACAGTGGTTCTTAAATTGTAAGCTCAGG | 769 | AAACAGUGGUUCUUAAAUUGUAAGCUCAGG |
| HAO1_exon7 | - | **GTTT** | 315 | AAAACAGTGGTTCTTAAATTGTAAGCTCAG | 770 | AAAACAGUGGUUCUUAAAUUGUAAGCUCAG |
| HAO1_exon7 | - | **TTTA** | 316 | CATGTCTTTAAAACAGTGGTTCTTAAATTG | 771 | CAUGUCUUUAAAACAGUGGUUCUUAAAUUG |
| HAO1_exon7 | - | **GTTT** | 317 | ACATGTCTTTAAAACAGTGGTTCTTAAATT | 772 | ACAUGUCUUUAAAACAGUGGUUCUUAAAUU |
| HAO1_exon7 | - | **ATTC** | 318 | TGTTTACATGTCTTTAAAACAGTGGTTCTT | 773 | UGUUUACAUGUCUUUAAAACAGUGGUUCUU |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon7 | - | **ATTA** | 319 | ACCTGTATTCTGTTTACATGTCTTTAAAAC | 774 | ACCUGUAUUCUGUUUACAUGUCUUUAAAAC |
| HAO1_exon7 | - | **TTTA** | 320 | TTAACCTGTATTCTGTTTACATGTCTTTAA | 775 | UUAACCUGUAUUCUGUUUACAUGUCUUUAA |
| HAO1_exon7 | - | **GTTT** | 321 | ATTAACCTGTATTCTGTTTACATGTCTTTA | 776 | AUUAACCUGUAUUCUGUUUACAUGUCUUUA |
| HAO1_exon7 | - | **ATTG** | 322 | TTTATTAACCTGTATTCTGTTTACATGTCT | 777 | UUUAUUAACCUGUAUUCUGUUUACAUGUCU |
| HAO1_exon7 | - | **ATTT** | 323 | TCCCATCTGTATTATTTTTTTTCAGCATGT | 778 | UCCCAUCUGUAUUAUUUUUUUUCAGCAUGU |
| HAO1_exon7 | - | **TTTA** | 324 | GTAAAATTGGAGGTAGCAAACACTAAGGTG | 779 | GUAAAAUUGGAGGUAGCAAACACUAAGGUG |
| HAO1_exon7 | - | **GTTT** | 325 | AGTAAAATTGGAGGTAGCAAACACTAAGGT | 780 | AGUAAAAUUGGAGGUAGCAAACACUAAGGU |
| HAO1_exon7 | - | **TTTA** | 326 | GACAACGTCATCCCCTGGCAGGCTAAAGTG | 781 | GACAACGUCAUCCCCUGGCAGGCUAAAGUG |
| HAO1_exon7 | - | **ATTA** | 327 | TTATTGCATTCAGTTCATATTAAATGTATG | 782 | UUAUUGCAUUCAGUUCAUAUUAAAUGUAUG |
| HAO1_exon7 | - | **TTTT** | 328 | CCCATCTGTATTATTTTTTTTCAGCATGTA | 783 | CCCAUCUGUAUUAUUUUUUUUCAGCAUGUA |
| HAO1_exon7 | - | **TTTT** | 329 | TTCAGCATGTATTACTTGACAAAGAGACAC | 784 | UUCAGCAUGUAUUACUUGACAAAGAGACAC |
| HAO1_exon7 | - | **ATTA** | 330 | TTTTTTTTCAGCATGTATTACTTGACAAAG | 785 | UUUUUUUUCAGCAUGUAUUACUUGACAAAG |
| HAO1_exon7 | - | **TTTC** | 331 | ATTGCTTTTGACTTTTCAATGGGTGTCCTA | 786 | AUUGCUUUUGACUUUUCAAUGGGUGUCCUA |
| HAO1_exon7 | - | **ATTG** | 332 | CTTTTGACTTTTCAATGGGTGTCCTAGGAA | 787 | CUUUUGACUUUUCAAUGGGUGUCCUAGGAA |
| HAO1_exon7 | - | **CTTT** | 333 | TGACTTTTCAATGGGTGTCCTAGGAACCTT | 788 | UGACUUUUCAAUGGGUGUCCUAGGAACCUU |
| HAO1_exon7 | - | **TTTT** | 334 | GACTTTTCAATGGGTGTCCTAGGAACCTTT | 789 | GACUUUUCAAUGGGUGUCCUAGGAACCUUU |
| HAO1_exon7 | - | **TTTG** | 335 | ACTTTTCAATGGGTGTCCTAGGAACCTTTT | 790 | ACUUUUCAAUGGGUGUCCUAGGAACCUUUU |
| HAO1_exon7 | - | **CTTT** | 336 | TCAATGGGTGTCCTAGGAACCTTTTAGAAA | 791 | UCAAUGGGUGUCCUAGGAACCUUUUAGAAA |
| HAO1_exon7 | - | **TTTT** | 337 | CAATGGGTGTCCTAGGAACCTTTTAGAAAG | 792 | CAAUGGGUGUCCUAGGAACCUUUUAGAAAG |
| HAO1_exon7 | - | **TTTC** | 338 | AATGGGTGTCCTAGGAACCTTTTAGAAAGA | 793 | AAUGGGUGUCCUAGGAACCUUUUAGAAAGA |
| HAO1_exon7 | - | **CTTT** | 339 | TAGAAAGAAATGGACTTTTCATCCTGGAAAT | 794 | UAGAAAGAAAUGGACUUUCAUCCUGGAAAU |
| HAO1_exon7 | - | **TTTT** | 340 | AGAAAGAAATGGACTTTCATCCTGGAAATA | 795 | AGAAAGAAAUGGACUUUCAUCCUGGAAAUA |
| HAO1_exon7 | - | **TTTA** | 341 | GAAAGAAATGGACTTTCATCCTGGAAATAT | 796 | GAAAGAAAUGGACUUUCAUCCUGGAAAUAU |
| HAO1_exon7 | - | **CTTT** | 342 | CATCCTGGAAATATATTAACTGTTAAAAAG | 797 | CAUCCUGGAAAUAUAUUAACUGUUAAAAAG |
| HAO1_exon7 | - | **TTTC** | 343 | ATCCTGGAAATATATTAACTGTTAAAAAGA | 798 | AUCCUGGAAAUAUAUUAACUGUUAAAAAGA |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon7 | - | **ATTA** | 344 | ACTGTTAAAAAGAAAAC ATTGAAAATGTGT | 799 | ACUGUUAAAAAGAAAACAU UGAAAAUGUGU |
| HAO1_exon7 | - | **GTTA** | 345 | AAAAGAAAACATTGAAA ATGTGTTTAGACA | 800 | AAAAGAAAACAUUGAAAAU GUGUUUAGACA |
| HAO1_exon7 | - | **ATTT** | 346 | CATTGCTTTTGACTTTT CAATGGGTGTCCT | 801 | CAUUGCUUUUGACUUUUCA AUGGGUGUCCU |
| HAO1_exon7 | - | **TTTC** | 347 | CCATCTGTATTATTTTT TTTCAGCATGTAT | 802 | CCAUCUGUAUUAUUUUUUU UCAGCAUGUAU |
| HAO1_exon7 | - | **TTTA** | 348 | TTTCATTGCTTTTGACT TTTCAATGGGTGT | 803 | UUUCAUUGCUUUUGACUUU UCAAUGGGUGU |
| HAO1_exon7 | - | C**TTT** | 349 | TATTTCATTGCTTTTGA CTTTTCAATGGGT | 804 | UAUUUCAUUGCUUUUGACU UUUCAAUGGGU |
| HAO1_exon7 | - | **ATTG** | 350 | AAAATGTGTTTAGACAA CGTCATCCCCTGG | 805 | AAAAUGUGUUUAGACAACG UCAUCCCCUGG |
| HAO1_exon7 | - | **ATTT** | 351 | TTTTTCAGCATGTATTA CTTGACAAAGAGA | 806 | UUUUUCAGCAUGUAUUACU UGACAAAGAGA |
| HAO1_exon7 | - | **TTTT** | 352 | TTTTCAGCATGTATTAC TTGACAAAGAGAC | 807 | UUUUCAGCAUGUAUUACUU GACAAAGAGAC |
| HAO1_exon7 | - | **TTTT** | 353 | TTTCAGCATGTATTACT TGACAAAGAGACA | 808 | UUUCAGCAUGUAUUACUUG ACAAAGAGACA |
| HAO1_exon7 | - | **TTTT** | 354 | TCAGCATGTATTACTTG ACAAAGAGACACT | 809 | UCAGCAUGUAUUACUUGAC AAAGAGACACU |
| HAO1_exon7 | - | **TTTT** | 355 | CAGCATGTATTACTTGA CAAAGAGACACTG | 810 | CAGCAUGUAUUACUUGACA AAGAGACACUG |
| HAO1_exon7 | - | **TTTC** | 356 | AGCATGTATTACTTGAC AAAGAGACACTGT | 811 | AGCAUGUAUUACUUGACAA AGAGACACUGU |
| HAO1_exon7 | - | **ATTA** | 357 | CTTGACAAAGAGACACT GTGCAGAGGGTGA | 812 | CUUGACAAAGAGACACUGU GCAGAGGGUGA |
| HAO1_exon7 | - | C**TTG** | 358 | ACAAAGAGACACTGTGC AGAGGGTGACCAC | 813 | ACAAAGAGACACUGUGCAG AGGGUGACCAC |
| HAO1_exon7 | - | **ATTC** | 359 | CCCACTTCAATACAAAG GGTGTCGTTCTTT | 814 | CCCACUUCAAUACAAAGGG UGUCGUUCUUU |
| HAO1_exon7 | - | C**TTC** | 360 | AATACAAAGGGTGTCGT TCTTTTCCAACAA | 815 | AAUACAAAGGGUGUCGUUC UUUUCCAACAA |
| HAO1_exon7 | - | **GTTC** | 361 | TTTTCCAACAAAATAGC AATCCCTTTTATT | 816 | UUUUCCAACAAAAUAGCAA UCCCUUUUAUU |
| HAO1_exon7 | - | C**TTT** | 362 | TCCAACAAAATAGCAAT CCCTTTTATTTCA | 817 | UCCAACAAAAUAGCAAUCC CUUUUAUUUCA |
| HAO1_exon7 | - | **TTTT** | 363 | CCAACAAAATAGCAATC CCTTTTATTTCAT | 818 | CCAACAAAAUAGCAAUCCC UUUUAUUUCAU |
| HAO1_exon7 | - | **TTTC** | 364 | CAACAAAATAGCAATCC CTTTTATTTCATT | 819 | CAACAAAAUAGCAAUCCCU UUUAUUUCAUU |
| HAO1_exon7 | - | **TTTT** | 365 | ATTTCATTGCTTTTGAC TTTTCAATGGGTG | 820 | AUUUCAUUGCUUUUGACUU UUCAAUGGGUG |
| HAO1_exon7 | - | **GTTC** | 366 | AAAGTGTTGGTAATGCC TGATTCACAACTT | 821 | AAAGUGUUGGUAAUGCCUG AUUCACAACUU |
| HAO1_exon7 | + | **ATTT** | 367 | CTCTCTAAGAAGTAACA TACATCCTAAAAC | 822 | CUCUCUAAGAAGUAACAUA CAUCCUAAAAC |
| HAO1_exon7 | - | **ATTC** | 368 | ACAACTTTGAGAAGGTA GCACTGGAGAGAA | 823 | ACAACUUUGAGAAGGUAGC ACUGGAGAGAA |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon7 | + | **TTTC** | 369 | ACCTTAGTGTTTGCTAC CTCCAATTTTACT | 824 | ACCUUAGUGUUUGCUACCU CCAAUUUUACU |
| HAO1_exon7 | + | **CTTA** | 370 | GTGTTTGCTACCTCCAA TTTTACTAAAGGA | 825 | GUGUUUGCUACCUCCAAUU UUACUAAAGGA |
| HAO1_exon7 | + | **GTTT** | 371 | GCTACCTCCAATTTTAC TAAAGGATACAGC | 826 | GCUACCUCCAAUUUUACUA AAGGAUACAGC |
| HAO1_exon7 | + | **TTTG** | 372 | CTACCTCCAATTTTACT AAAGGATACAGCA | 827 | CUACCUCCAAUUUUACUAA AGGAUACAGCA |
| HAO1_exon7 | + | **ATTT** | 373 | TACTAAAGGATACAGCA CTTTAGCCTGCCA | 828 | UACUAAAGGAUACAGCACU UUAGCCUGCCA |
| HAO1_exon7 | + | **TTTT** | 374 | ACTAAAGGATACAGCAC TTTAGCCTGCCAG | 829 | ACUAAAGGAUACAGCACUU UAGCCUGCCAG |
| HAO1_exon7 | + | **TTTA** | 375 | CTAAAGGATACAGCACT TTAGCCTGCCAGG | 830 | CUAAAGGAUACAGCACUUU AGCCUGCCAGG |
| HAO1_exon7 | + | **CTTT** | 376 | AGCCTGCCAGGGGATGA CGTTGTCTAAACA | 831 | AGCCUGCCAGGGGAUGACG UUGUCUAAACA |
| HAO1_exon7 | + | **TTTA** | 377 | GCCTGCCAGGGGATGAC GTTGTCTAAACAC | 832 | GCCUGCCAGGGGAUGACGU UGUCUAAACAC |
| HAO1_exon7 | + | **TTTT** | 378 | CACCTTAGTGTTTGCTA CCTCCAATTTTAC | 833 | CACCUUAGUGUUUGCUACC UCCAAUUUUAC |
| HAO1_exon7 | + | **GTTG** | 379 | TCTAAACACATTTTCAA TGTTTTCTTTTTA | 834 | UCUAAACACAUUUUCAAUG UUUUCUUUUUA |
| HAO1_exon7 | + | **TTTT** | 380 | CAATGTTTTCTTTTTAA CAGTTAATATATT | 835 | CAAUGUUUUCUUUUUAACA GUUAAUAUAUU |
| HAO1_exon7 | + | **TTTC** | 381 | AATGTTTTCTTTTTAAC AGTTAATATATTT | 836 | AAUGUUUUCUUUUUAACAG UUAAUAUAUUU |
| HAO1_exon7 | + | **GTTT** | 382 | TCTTTTTAACAGTTAAT ATATTTCCAGGAT | 837 | UCUUUUUAACAGUUAAUAU AUUUCCAGGAU |
| HAO1_exon7 | + | **TTTT** | 383 | CTTTTTAACAGTTAATA TATTTCCAGGATG | 838 | CUUUUUAACAGUUAAUAUA UUUCCAGGAUG |
| HAO1_exon7 | + | **TTTC** | 384 | TTTTTAACAGTTAATAT ATTTCCAGGATGA | 839 | UUUUUAACAGUUAAUAUAU UUCCAGGAUGA |
| HAO1_exon7 | + | **CTTT** | 385 | TTAACAGTTAATATATT TCCAGGATGAAAG | 840 | UUAACAGUUAAUAUAUUUC CAGGAUGAAAG |
| HAO1_exon7 | + | **TTTT** | 386 | TAACAGTTAATATATTT CCAGGATGAAAGT | 841 | UAACAGUUAAUAUAUUUCC AGGAUGAAAGU |
| HAO1_exon7 | + | **TTTT** | 387 | AACAGTTAATATATTTC CAGGATGAAAGTC | 842 | AACAGUUAAUAUAUUUCCA GGAUGAAAGUC |
| HAO1_exon7 | + | **TTTA** | 388 | ACAGTTAATATATTTCC AGGATGAAAGTCC | 843 | ACAGUUAAUAUAUUUCCAG GAUGAAAGUCC |
| HAO1_exon7 | + | **ATTT** | 389 | TCAATGTTTTCTTTTTA ACAGTTAATATAT | 844 | UCAAUGUUUUCUUUUUAAC AGUUAAUAUAU |
| HAO1_exon7 | + | **GTTA** | 390 | ATATATTTCCAGGATGA AAGTCCATTTCTT | 845 | AUAUAUUUCCAGGAUGAAA GUCCAUUUCUU |
| HAO1_exon7 | + | **CTTT** | 391 | TCACCTTAGTGTTTGCT ACCTCCAATTTTA | 846 | UCACCUUAGUGUUUGCUAC CUCCAAUUUUA |
| HAO1_exon7 | + | **GTTA** | 392 | ATAAACAATGAGATCAT TATCTTTTCACCT | 847 | AUAAACAAUGAGAUCAUUA UCUUUUCACCU |
| HAO1_exon7 | + | **TTTC** | 393 | TCTCTAAGAAGTAACAT ACATCCTAAAACA | 848 | UCUCUAAGAAGUAACAUAC AUCCUAAAACA |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon7 | + | **ATTT** | 394 | GGATATATTCAGACACT AAAGATGTGATTG | 849 | GGAUAUAUUCAGACACUAA AGAUGUGAUUG |
| HAO1_exon7 | + | **TTTG** | 395 | GATATATTCAGACACTA AAGATGTGATTGG | 850 | GAUAUAUUCAGACACUAAA GAUGUGAUUGG |
| HAO1_exon7 | + | **ATTC** | 396 | AGACACTAAAGATGTGA TTGGAAATCTACA | 851 | AGACACUAAAGAUGUGAUU GGAAAUCUACA |
| HAO1_exon7 | + | **ATTG** | 397 | GAAATCTACATTCAAAG AAGTATCACCAAT | 852 | GAAAUCUACAUUCAAAGAA GUAUCACCAAU |
| HAO1_exon7 | + | **ATTC** | 398 | AAAGAAGTATCACCAAT TACCGCCACCCAT | 853 | AAAGAAGUAUCACCAAUUA CCGCCACCCAU |
| HAO1_exon7 | + | **ATTA** | 399 | CCGCCACCCATTCCAAT TCTCTCCAGTGCT | 854 | CCGCCACCCAUUCCAAUUC UCUCCAGUGCU |
| HAO1_exon7 | + | **ATTC** | 400 | CAATTCTCTCCAGTGCT ACCTTCTCAAAGT | 855 | CAAUUCUCUCCAGUGCUAC CUUCUCAAAGU |
| HAO1_exon7 | + | **ATTC** | 401 | TCTCCAGTGCTACCTTC TCAAAGTTGTGAA | 856 | UCUCCAGUGCUACCUUCUC AAAGUUGUGAA |
| HAO1_exon7 | + | **ATTA** | 402 | TCTTTTCACCTTAGTGT TTGCTACCTCCAA | 857 | UCUUUUCACCUUAGUGUUU GCUACCUCCAA |
| HAO1_exon7 | + | **CTTC** | 403 | TCAAAGTTGTGAATCAG GCATTACCAACAC | 858 | UCAAAGUUGUGAAUCAGGC AUUACCAACAC |
| HAO1_exon7 | + | **ATTA** | 404 | CCAACACTTTGAACCTG AGCTTACAATTTA | 859 | CCAACACUUUGAACCUGAG CUUACAAUUUA |
| HAO1_exon7 | + | **CTTT** | 405 | GAACCTGAGCTTACAAT TTAAGAACCACTG | 860 | GAACCUGAGCUUACAAUUU AAGAACCACUG |
| HAO1_exon7 | + | **TTTG** | 406 | AACCTGAGCTTACAATT TAAGAACCACTGT | 861 | AACCUGAGCUUACAAUUUA AGAACCACUGU |
| HAO1_exon7 | + | **CTTA** | 407 | CAATTTAAGAACCACTG TTTTAAAGACATG | 862 | CAAUUUAAGAACCACUGUU UUAAAGACAUG |
| HAO1_exon7 | + | **ATTT** | 408 | AAGAACCACTGTTTTAA AGACATGTAAACA | 863 | AAGAACCACUGUUUUAAAG ACAUGUAAACA |
| HAO1_exon7 | + | **TTTA** | 409 | AGAACCACTGTTTTAAA GACATGTAAACAG | 864 | AGAACCACUGUUUUAAAGA CAUGUAAACAG |
| HAO1_exon7 | + | **GTTT** | 410 | TAAAGACATGTAAACAG AATACAGGTTAAT | 865 | UAAAGACAUGUAAACAGAA UACAGGUUAAU |
| HAO1_exon7 | + | **TTTT** | 411 | AAAGACATGTAAACAGA ATACAGGTTAATA | 866 | AAAGACAUGUAAACAGAAU ACAGGUUAAUA |
| HAO1_exon7 | + | **TTTA** | 412 | AAGACATGTAAACAGAA TACAGGTTAATAA | 867 | AAGACAUGUAAACAGAAUA CAGGUUAAUAA |
| HAO1_exon7 | + | **GTTG** | 413 | TGAATCAGGCATTACCA ACACTTTGAACCT | 868 | UGAAUCAGGCAUUACCAAC ACUUUGAACCU |
| HAO1_exon7 | - | **GTTG** | 414 | GTAATGCCTGATTCACA ACTTTGAGAAGGT | 869 | GUAAUGCCUGAUUCACAAC UUUGAGAAGGU |
| HAO1_exon7 | + | **ATTT** | 415 | CCAGGATGAAAGTCCAT TTCTTTCTAAAAG | 870 | CCAGGAUGAAAGUCCAUUU CUUUCUAAAAG |
| HAO1_exon7 | + | **GTTT** | 416 | ATTTCTCTCTAAGAAGT AACATACATCCTA | 871 | AUUUCUCUCUAAGAAGUAA CAUACAUCCUA |
| HAO1_exon7 | + | **TTTC** | 417 | ACATTCTGGCACCCTGA AAAAATAATGCAT | 872 | ACAUUCUGGCACCCUGAAA AAAUAAUGCAU |
| HAO1_exon7 | + | **ATTC** | 418 | TGGCACCCT GAAAAAAT AATGCATACATTT | 873 | UGGCACCCUGAAAAAAUAA UGCAUACAUUU |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon7 | + | **TTTA** | 419 | TTTCTCTCTAAGAAGTA ACATACATCCTAA | 874 | UUUCUCUCUAAGAAGUAAC AUACAUCCUAA |
| HAO1_exon7 | + | **CTTC** | 420 | CCAAAAATGCTTTATTT CTCTCTAAGAAGT | 875 | CCAAAAAUGCUUUAUUUCU CUCUAAGAAGU |
| HAO1_exon7 | - | **CTTC** | 421 | TTAGAGAGAAATAAAGC ATTTTTGGGAAGA | 876 | UUAGAGAGAAAUAAAGCAU UUUUGGGAAGA |
| HAO1_exon7 | - | **GTTA** | 422 | CTTCTTAGAGAGAAATA AAGCATTTTTGGG | 877 | CUUCUUAGAGAGAAAUAAA GCAUUUUUGGG |
| HAO1_exon7 | - | **TTTA** | 423 | GGATGTATGTTACTTCT TAGAGAGAAATAA | 878 | GGAUGUAUGUUACUUCUUA GAGAGAAAUAA |
| HAO1_exon7 | - | **TTTT** | 424 | AGGATGTATGTTACTTC TTAGAGAGAAATA | 879 | AGGAUGUAUGUUACUUCUU AGAGAGAAAUA |
| HAO1_exon7 | - | **GTTT** | 425 | TAGGATGTATGTTACTT CTTAGAGAGAAAT | 880 | UAGGAUGUAUGUUACUUCU UAGAGAGAAAU |
| HAO1_exon7 | + | **GTTT** | 426 | CACATTCTGGCACCCTG AAAAAATAATGCA | 881 | CACAUUCUGGCACCCUGAA AAAAUAAUGCA |
| HAO1_exon7 | - | **TTTA** | 427 | GTGTCTGAATATATCCA AATGTTTTAGGAT | 882 | GUGUCUGAAUAUAUCCAAA UGUUUUAGGAU |
| HAO1_exon7 | - | **TTTC** | 428 | CAATCACATCTTTAGTG TCTGAATATATCC | 883 | CAAUCACAUCUUUAGUGUC UGAAUAUAUCC |
| HAO1_exon7 | - | **ATTT** | 429 | CCAATCACATCTTTAGT GTCTGAATATATC | 884 | CCAAUCACAUCUUUAGUGU CUGAAUAUAUC |
| HAO1_exon7 | - | **TTTG** | 430 | AATGTAGATTTCCAATC ACATCTTTAGTGT | 885 | AAUGUAGAUUUCCAAUCAC AUCUUUAGUGU |
| HAO1_exon7 | - | **GTTT** | 431 | GAATGTAGATTTCCAAT CACATCTTTAGTG | 886 | GAAUGUAGAUUUCCAAUCA CAUCUUUAGUG |
| HAO1_exon7 | - | **CTTC** | 432 | TTTGAATGTAGATTTCC AATCACATCTTTA | 887 | UUUGAAUGUAGAUUUCCAA UCACAUCUUUA |
| HAO1_exon7 | - | **ATTG** | 433 | GTGATACTTCTTTGAAT GTAGATTTCCAAT | 888 | GUGAUACUUCUUUGAAUGU AGAUUUCCAAU |
| HAO1_exon7 | - | **ATTG** | 434 | GAATGGGTGGCGGTAAT TGGTGATACTTCT | 889 | GAAUGGGUGGCGGUAAUUG GUGAUACUUCU |
| HAO1_exon7 | - | **TTTG** | 435 | AGAAGGTAGCACTGGAG AGAATTGGAATGG | 890 | AGAAGGUAGCACUGGAGAG AAUUGGAAUGG |
| HAO1_exon7 | - | **GTTT** | 436 | GAGAAGGTAGCACTGGA GAGAATTGGAATG | 891 | GAGAAGGUAGCACUGGAGA GAAUUGGAAUG |
| HAO1_exon7 | - | **GTTT** | 437 | AGTGTCTGAATATATCC AAATGTTTTAGGA | 892 | AGUGUCUGAAUAUAUCCAA AUGUUUUAGGA |
| HAO1_exon7 | + | **TTTC** | 438 | CAGGATGAAAGTCCATT TCTTTCTAAAAGG | 893 | CAGGAUGAAAGUCCAUUUC UUUCUAAAAGG |
| HAO1_exon7 | + | **CTTG** | 439 | TCGATGACTTTCACATT CTGGCACCCTGAA | 894 | UCGAUGACUUUCACAUUCU GGCACCCUGAA |
| HAO1_exon7 | + | **TTTT** | 440 | CCTCACCAATGTCTTGT CGATGACTTTCAC | 895 | CCUCACCAAUGUCUUGUCG AUGACUUUCAC |
| HAO1_exon7 | + | **TTTC** | 441 | TTTCTAAAAGGTTCCTA GGACACCCATTGA | 896 | UUUCUAAAAGGUUCCUAGG ACACCCAUUGA |
| HAO1_exon7 | + | **CTTT** | 442 | CTAAAAGGTTCCTAGGA CACCCATTGAAAA | 897 | CUAAAAGGUUCCUAGGACA CCCAUUGAAAA |
| HAO1_exon7 | + | **TTTC** | 443 | TAAAAGGTTCCTAGGAC ACCCATTGAAAAG | 898 | UAAAAGGUUCCUAGGACAC CCAUUGAAAAG |

TABLE 5-continued

Target and Spacer Sequences

| HAO1 | Strand | PAM* | SEQ ID NO | Target Sequence | SEQ ID NO | Spacer Sequence |
|---|---|---|---|---|---|---|
| HAO1_exon7 | + | **GTT**C | 444 | CTAGGACACCCATTGAA AAGTCAAAAGCAA | 899 | CUAGGACACCCAUUGAAAA GUCAAAAGCAA |
| HAO1_exon7 | + | A**TTG** | 445 | AAAAGTCAAAAGCAATG AAATAAAAGGGAT | 900 | AAAAGUCAAAAGCAAUGAA AUAAAAGGGAU |
| HAO1_exon7 | + | A**TTG** | 446 | CTATTTTGTTGGAAAAG AACGACACCCTTT | 901 | CUAUUUUGUUGGAAAAGAA CGACACCCUUU |
| HAO1_exon7 | + | A**TTT** | 447 | TGTTGGAAAAGAACGAC ACCCTTTGTATTG | 902 | UGUUGGAAAAGAACGACAC CCUUUGUAUUG |
| HAO1_exon7 | + | **TTTT** | 448 | GTTGGAAAAGAACGACA CCCTTTGTATTGA | 903 | GUUGGAAAAGAACGACACC CUUUGUAUUGA |
| HAO1_exon7 | + | **TTTG** | 449 | TTGGAAAAGAACGACAC CCTTTGTATTGAA | 904 | UUGGAAAAGAACGACACCC UUUGUAUUGAA |
| HAO1_exon7 | + | **TTTC** | 450 | CTCACCAATGTCTTGTC GATGACTTTCACA | 905 | CUCACCAAUGUCUUGUCGA UGACUUUCACA |
| HAO1_exon7 | + | G**TTG** | 451 | GAAAAGAACGACACCCT TTGTATTGAAGTG | 906 | GAAAAGAACGACACCCUUU GUAUUGAAGUG |
| HAO1_exon7 | + | **TTTG** | 452 | TATTGAAGTGGGGAATT ACAGACTGTGGTC | 907 | UAUUGAAGUGGGGAAUUAC AGACUGUGGUC |
| HAO1_exon7 | + | A**TTG** | 453 | AAGTGGGGAATTACAGA CTGTGGTCACCCT | 908 | AAGUGGGGAAUUACAGACU GUGGUCACCCU |
| HAO1_exon7 | + | A**TTA** | 454 | CAGACTGTGGTCACCCT CTGCACAGTGTCT | 909 | CAGACUGUGGUCACCCUCU GCACAGUGUCU |
| HAO1_exon7 | + | C**TTT** | 455 | GTCAAGTAATACATGCT GAAAAAAAATAAT | 910 | GUCAAGUAAUACAUGCUGA AAAAAAAUAAU |
| HAO1_exon7 | + | **TTTG** | 456 | TCAAGTAATACATGCTG AAAAAAAATAATA | 911 | UCAAGUAAUACAUGCUGAA AAAAAAUAAUA |
| HAO1_exon7 | + | A**TTG** | 457 | TGCACTGTCAGATCTTG GAAACGGCCAAAG | 912 | UGCACUGUCAGAUCUUGGA AACGGCCAAAG |
| HAO1_exon7 | + | C**TTG** | 458 | GAAACGGCCAAAGGATT TTTCCTCACCAAT | 913 | GAAACGGCCAAAGGAUUUU UCCUCACCAAU |
| HAO1_exon7 | + | A**TTT** | 459 | TTCCTCACCAATGTCTT GTCGATGACTTTC | 914 | UUCCUCACCAAUGUCUUGU CGAUGACUUUC |
| HAO1_exon7 | + | **TTTT** | 460 | TCCTCACCAATGTCTTG TCGATGACTTTCA | 915 | UCCUCACCAAUGUCUUGUC GAUGACUUUCA |
| HAO1_exon7 | + | C**TTT** | 461 | GTATTGAAGTGGGGAAT TACAGACTGTGGT | 916 | GUAUUGAAGUGGGGAAUUA CAGACUGUGGU |
| HAO1_exon7 | + | A**TTT** | 462 | CTTTCTAAAAGGTTCCT AGGACACCCATTG | 917 | CUUUCUAAAAGGUUCCUAG GACACCCAUUG |
| HAO1_exon7 | - | C**TTA** | 463 | GAGAGAAATAAAGCATT TTTGGGAAGAA | 918 | GAGAGAAAUAAAGCAUUUU UGGGAAGAA |
| HAO1_exon7 | + | A**TTT** | 464 | AATATGAACTGAATGCA ATAATAATCA | 919 | AAUAUGAACUGAAUGCAAU AAUAAUCA |
| HAO1_exon7 | + | **TTTA** | 465 | ATATGAACTGAATGCAA TAATAATCA | 920 | AUAUGAACUGAAUGCAAUA AUAAUCA |

*The 5'-TTN-3' 3-nucleotide PAM motif is in boldface.

The present disclosure includes all combinations of the direct repeats and spacers listed above, consistent with the disclosure herein.

In some embodiments, a spacer sequence described herein comprises an uracil (U). In some embodiments, a spacer sequence described herein comprises a thymine (T). In some embodiments, a spacer sequence according to Table 5 comprises a sequence comprising a thymine in one or more places indicated as uracil in Table 5.

(iii). Exemplary RNA Guides

The present disclosure provides RNA guides that comprise any and all combinations of the direct repeats and spacers described herein (e.g., as set forth in Table 5, above). In some embodiments, the sequence of an RNA guide has at least 90% identity (e.g., at least 90%, 91%, 92%, 93%, 94%, 95%, 96%, 97%, 98%, or 99% identity) to a sequence of any one of SEQ ID NOs: 967-1023. In some embodiments, an RNA guide has a sequence of any one of SEQ ID NOs: 967-1023.

In some embodiments, exemplary RNA guides provided herein may comprise a spacer sequence of any one of SEQ ID NOs: 1093-1097. In one example, the RNA guide may comprise a spacer of SEQ ID NO: 1096.

Any of the exemplary RNA guides disclosed herein may comprise a direct sequence of any one of SEQ ID NOs:1-10 or a fragment thereof that is at least 23-nucleotide in length. In one example, the direct sequence may comprise SEQ ID NO: 10.

In specific examples, the RNA guides provide herein may comprise the nucleotide sequence of SEQ ID NOs: 967, 968, 988, 989, or 994. In one example, the RNA guide provided herein comprise the nucleotide sequence of SEQ ID NO: 989.

(iv). Modifications

The RNA guide may include one or more covalent modifications with respect to a reference sequence, in particular the parent polyribonucleotide, which are included within the scope of the present disclosure.

Exemplary modifications can include any modification to the sugar, the nucleobase, the internucleoside linkage (e.g., to a linking phosphate/to a phosphodiester linkage/to the phosphodiester backbone), and any combination thereof. Some of the exemplary modifications provided herein are described in detail below.

The RNA guide may include any useful modification, such as to the sugar, the nucleobase, or the internucleoside linkage (e.g., to a linking phosphate/to a phosphodiester linkage/to the phosphodiester backbone). One or more atoms of a pyrimidine nucleobase may be replaced or substituted with optionally substituted amino, optionally substituted thiol, optionally substituted alkyl (e.g., methyl or ethyl), or halo (e.g., chloro or fluoro). In certain embodiments, modifications (e.g., one or more modifications) are present in each of the sugar and the internucleoside linkage. Modifications may be modifications of ribonucleic acids (RNAs) to deoxyribonucleic acids (DNAs), threose nucleic acids (TNAs), glycol nucleic acids (GNAs), peptide nucleic acids (PNAs), locked nucleic acids (LNAs) or hybrids thereof). Additional modifications are described herein.

In some embodiments, the modification may include a chemical or cellular induced modification. For example, some nonlimiting examples of intracellular RNA modifications are described by Lewis and Pan in "RNA modifications and structures cooperate to RNA guide-protein interactions" from Nat Reviews Mol Cell Biol, 2017, 18:202-210.

Different sugar modifications, nucleotide modifications, and/or internucleoside linkages (e.g., backbone structures) may exist at various positions in the sequence. One of ordinary skill in the art will appreciate that the nucleotide analogs or other modification(s) may be located at any position(s) of the sequence, such that the function of the sequence is not substantially decreased. The sequence may include from about 1% to about 100% modified nucleotides (either in relation to overall nucleotide content, or in relation to one or more types of nucleotide, i.e., any one or more of A, G, U or C) or any intervening percentage (e.g., from 1% to 20%>, from 1% to 25%, from 1% to 50%, from 1% to 60%, from 1% to 70%, from 1% to 80%, from 1% to 90%, from 1% to 95%, from 10% to 20%, from 10% to 25%, from 10% to 50%, from 10% to 60%, from 10% to 70%, from 10% to 80%, from 10% to 90%, from 10% to 95%, from 10% to 100%, from 20% to 25%, from 20% to 50%, from 20% to 60%, from 20% to 70%, from 20% to 80%, from 20% to 90%, from 20% to 95%, from 20% to 100%, from 50% to 60%, from 50% to 70%, from 50% to 80%, from 50% to 90%, from 50% to 95%, from 50% to 100%, from 70% to 80%, from 70% to 90%, from 70% to 95%, from 70% to 100%, from 80% to 90%, from 80% to 95%, from 80% to 100%, from 90% to 95%, from 90% to 100%, and from 95% to 100%).

In some embodiments, sugar modifications (e.g., at the 2' position or 4' position) or replacement of the sugar at one or more ribonucleotides of the sequence may, as well as backbone modifications, include modification or replacement of the phosphodiester linkages. Specific examples of a sequence include, but are not limited to, sequences including modified backbones or no natural internucleoside linkages such as internucleoside modifications, including modification or replacement of the phosphodiester linkages. Sequences having modified backbones include, among others, those that do not have a phosphorus atom in the backbone. For the purposes of this application, and as sometimes referenced in the art, modified RNAs that do not have a phosphorus atom in their internucleoside backbone can also be considered to be oligonucleosides. In particular embodiments, a sequence will include ribonucleotides with a phosphorus atom in its internucleoside backbone.

Modified sequence backbones may include, for example, phosphorothioates, chiral phosphorothioates, phosphorodithioates, phosphotriesters, aminoalkylphosphotriesters, methyl and other alkyl phosphonates such as 3'-alkylene phosphonates and chiral phosphonates, phosphinates, phosphoramidates such as 3'-amino phosphoramidate and aminoalkylphosphoramidates, thionophosphoramidates, thionoalkylphosphonates, thionoalkylphosphotriesters, and boranophosphates having normal 3'-5' linkages, 2'-5' linked analogs of these, and those having inverted polarity wherein the adjacent pairs of nucleoside units are linked 3'-5' to 5'-3' or 2'-5' to 5'-2'. Various salts, mixed salts and free acid forms are also included. In some embodiments, the sequence may be negatively or positively charged.

The modified nucleotides, which may be incorporated into the sequence, can be modified on the internucleoside linkage (e.g., phosphate backbone). Herein, in the context of the polynucleotide backbone, the phrases "phosphate" and "phosphodiester" are used interchangeably. Backbone phosphate groups can be modified by replacing one or more of the oxygen atoms with a different substituent. Further, the modified nucleosides and nucleotides can include the wholesale replacement of an unmodified phosphate moiety with another internucleoside linkage as described herein. Examples of modified phosphate groups include, but are not limited to, phosphorothioate, phosphoroselenates, boranophosphates, boranophosphate esters, hydrogen phosphonates, phosphoramidates, phosphorodiamidates, alkyl or aryl phosphonates, and phosphotriesters. Phosphorodithioates have both non-linking oxygens replaced by sulfur. The phosphate linker can also be modified by the replacement of a linking oxygen with nitrogen (bridged phosphoramidates), sulfur (bridged phosphorothioates), and carbon (bridged methylene-phosphonates).

The α-thio substituted phosphate moiety is provided to confer stability to RNA and DNA polymers through the unnatural phosphorothioate backbone linkages. Phosphorothioate DNA and RNA have increased nuclease resistance and subsequently a longer half-life in a cellular environment.

In specific embodiments, a modified nucleoside includes an alpha-thio-nucleoside (e.g., 5'-O-(1-thiophosphate)-adenosine, 5'-O-(1-thiophosphate)-cytidine (α-thio-cytidine), 5'-O-(1-thiophosphate)-guanosine, 5'-O-(1-thiophosphate)-uridine, or 5'-O-(1-thiophosphate)-pseudouridine).

Other internucleoside linkages that may be employed according to the present disclosure, including internucleoside linkages which do not contain a phosphorous atom, are described herein.

In some embodiments, the sequence may include one or more cytotoxic nucleosides. For example, cytotoxic nucleosides may be incorporated into sequence, such as bifunctional modification. Cytotoxic nucleoside may include, but are not limited to, adenosine arabinoside, 5-azacytidine, 4'-thio-aracytidine, cyclopentenylcytosine, cladribine, clofarabine, cytarabine, cytosine arabinoside, 1-(2-C-cyano-2-deoxy-beta-D-arabino-pentofuranosyl)-cytosine, decitabine, 5-fluorouracil, fludarabine, floxuridine, gemcitabine, a combination of tegafur and uracil, tegafur ((RS)-5-fluoro-1-(tetrahydrofuran-2-yl)pyrimidine-2,4(1H,3H)-dione), troxacitabine, tezacitabine, 2'-deoxy-2'-methylidenecytidine (DMDC), and 6-mercaptopurine. Additional examples include fludarabine phosphate, N4-behenoyl-1-beta-D-arabinofuranosylcytosine, N4-octadecyl-1-beta-D-arabinofuranosylcytosine, N4-palmitoyl-1-(2-C-cyano-2-deoxy-beta-D-arabino-pentofuranosyl) cytosine, and P-4055 (cytarabine 5'-elaidic acid ester).

In some embodiments, the sequence includes one or more post-transcriptional modifications (e.g., capping, cleavage, polyadenylation, splicing, poly-A sequence, methylation, acylation, phosphorylation, methylation of lysine and arginine residues, acetylation, and nitrosylation of thiol groups and tyrosine residues, etc). The one or more post-transcriptional modifications can be any post-transcriptional modification, such as any of the more than one hundred different nucleoside modifications that have been identified in RNA (Rozenski, J, Crain, P, and McCloskey, J. (1999). The RNA Modification Database: 1999 update. Nucl Acids Res 27: 196-197) In some embodiments, the first isolated nucleic acid comprises messenger RNA (mRNA). In some embodiments, the mRNA comprises at least one nucleoside selected from the group consisting of pyridin-4-one ribonucleoside, 5-aza-uridine, 2-thio-5-aza-uridine, 2-thiouridine, 4-thio-pseudouridine, 2-thio-pseudouridine, 5-hydroxyuridine, 3-methyluridine, 5-carboxymethyl-uridine, 1-carboxymethyl-pseudouridine, 5-propynyl-uridine, 1-propynyl-pseudouridine, 5-taurinomethyluridine, 1-taurinomethyl-pseudouridine, 5-taurinomethyl-2-thio-uridine, 1-taurinomethyl-4-thio-uridine, 5-methyl-uridine, 1-methyl-pseudouridine, 4-thio-1-methyl-pseudouridine, 2-thio-1-methyl-pseudouridine, 1-methyl-1-deaza-pseudouridine, 2-thio-1-methyl-1-deaza-pseudouridine, dihydrouridine, dihydropseudouridine, 2-thio-dihydrouridine, 2-thio-dihydropseudouridine, 2-methoxyuridine, 2-methoxy-4-thio-uridine, 4-methoxy-pseudouridine, and 4-methoxy-2-thio-pseudouridine. In some embodiments, the mRNA comprises at least one nucleoside selected from the group consisting of 5-aza-cytidine, pseudoisocytidine, 3-methyl-cytidine, N4-acetylcytidine, 5-formylcytidine, N4-methylcytidine, 5-hydroxymethylcytidine, 1-methyl-pseudoisocytidine, pyrrolo-cytidine, pyrrolo-pseudoisocytidine, 2-thio-cytidine, 2-thio-5-methyl-cytidine, 4-thio-pseudoisocytidine, 4-thio-1-methyl-pseudoisocytidine, 4-thio-1-methyl-1-deaza-pseudoisocytidine, 1-methyl-1-deaza-pseudoisocytidine, zebularine, 5-aza-zebularine, 5-methyl-zebularine, 5-aza-2-thio-zebularine, 2-thio-zebularine, 2-methoxy-cytidine, 2-methoxy-5-methyl-cytidine, 4-methoxy-pseudoisocytidine, and 4-methoxy-1-methyl-pseudoisocytidine. In some embodiments, the mRNA comprises at least one nucleoside selected from the group consisting of 2-aminopurine, 2,6-diaminopurine, 7-deaza-adenine, 7-deaza-8-aza-adenine, 7-deaza-2-aminopurine, 7-deaza-8-aza-2-aminopurine, 7-deaza-2,6-diaminopurine, 7-deaza-8-aza-2,6-diaminopurine, 1-methyladenosine, N6-methyladenosine, N6-isopentenyladenosine, N6-(cis-hydroxyisopentenyl)adenosine, 2-methylthio-N6-(cis-hydroxyisopentenyl) adenosine, N6-glycinylcarbamoyladenosine, N6-threonylcarbamoyladenosine, 2-methylthio-N6-threonyl carbamoyladenosine, N6,N6-dimethyladenosine, 7-methyladenine, 2-methylthio-adenine, and 2-methoxy-adenine. In some embodiments, mRNA comprises at least one nucleoside selected from the group consisting of inosine, 1-methyl-inosine, wyosine, wybutosine, 7-deaza-guanosine, 7-deaza-8-aza-guanosine, 6-thio-guanosine, 6-thio-7-deaza-guanosine, 6-thio-7-deaza-8-aza-guanosine, 7-methyl-guanosine, 6-thio-7-methyl-guanosine, 7-methylinosine, 6-methoxy-guanosine, 1-methylguanosine, N2-methylguanosine, N2,N2-dimethylguanosine, 8-oxo-guanosine, 7-methyl-8-oxo-guanosine, 1-methyl-6-thio-guanosine, N2-methyl-6-thio-guanosine, and N2,N2-dimethyl-6-thio-guanosine.

The sequence may or may not be uniformly modified along the entire length of the molecule. For example, one or more or all types of nucleotides (e.g., naturally-occurring nucleotides, purine or pyrimidine, or any one or more or all of A, G, U, C, I, pU) may or may not be uniformly modified in the sequence, or in a given predetermined sequence region thereof. In some embodiments, the sequence includes a pseudouridine. In some embodiments, the sequence includes an inosine, which may aid in the immune system characterizing the sequence as endogenous versus viral RNAs. The incorporation of inosine may also mediate improved RNA stability/reduced degradation. See for example, Yu, Z. et al. (2015) RNA editing by ADAR1 marks dsRNA as "self". Cell Res. 25, 1283-1284, which is incorporated by reference in its entirety.

In some embodiments, one or more of the nucleotides of an RNA guide comprises a 2'-O-methyl phosphorothioate modification. In some embodiments, each of the first three nucleotides of the RNA guide comprises a 2'-O-methyl phosphorothioate modification. In some embodiments, each of the last four nucleotides of the RNA guide comprises a 2'-O-methyl phosphorothioate modification. In some embodiments, each of the first to last, second to last, and third to last nucleotides of the RNA guide comprises a 2'-O-methyl phosphorothioate modification, and wherein the last nucleotide of the RNA guide is unmodified. In some embodiments, each of the first three nucleotides of the RNA guide comprises a 2'-O-methyl phosphorothioate modification, and each of the first to last, second to last, and third to last nucleotides of the RNA guide comprises a 2'-O-methyl phosphorothioate modification.

When a gene editing system disclosed herein comprises nucleic acids encoding the Cas12i polypeptide disclosed herein, e.g., mRNA molecules, such nucleic acid molecules may contain any of the modifications disclosed herein, where applicable.

B. Cas12i Polypeptides

In some embodiments, the composition or system of the present disclosure includes a Cas12i polypeptide as described in WO/2019/178427, the relevant disclosures of which are incorporated by reference for the subject matter and purpose referenced herein.

In some embodiments, the genetic editing system disclosed herein includes a Cas12i2 polypeptide described herein (e.g., a polypeptide comprising SEQ ID NO: 922 and/or encoded by SEQ ID NO: 921). In some embodiments, the Cas12i2 polypeptide comprises at least one RuvC domain.

A nucleic acid sequence encoding the Cas12i2 polypeptide described herein may be substantially identical to a reference nucleic acid sequence, e.g., SEQ ID NO: 921. In some embodiments, the Cas12i2 polypeptide is encoded by a nucleic acid comprising a sequence having least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the reference nucleic acid sequence, e.g., SEQ ID NO: 921. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the nucleic acid molecules hybridize to the complementary sequence of the other under stringent conditions of temperature and ionic strength (e.g., within a range of medium to high stringency). See, e.g., Tijssen, "Hybridization with Nucleic Acid Probes. Part I. Theory and Nucleic Acid Preparation" (Laboratory Techniques in Biochemistry and Molecular Biology, Vol 24).

In some embodiments, the Cas12i2 polypeptide is encoded by a nucleic acid sequence having at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more sequence identity, but not 100% sequence identity, to a reference nucleic acid sequence, e.g., SEQ ID NO: 921.

In some embodiments, the Cas12i2 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 922.

In some embodiments, the present disclosure describes a Cas12i2 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 922. Homology or identity can be determined by amino acid sequence alignment, e.g., using a program such as BLAST, ALIGN, or CLUSTAL, as described herein.

Also provided is a Cas12i2 polypeptide of the present disclosure having enzymatic activity, e.g., nuclease or endonuclease activity, and comprising an amino acid sequence which differs from the amino acid sequences of SEQ ID NO: 922 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

In some examples, the Cas12i2 polypeptide may contain one or more mutations relative to SEQ ID NO: 922, for example, at position D581, G624, F626, P868, I926, V1030, E1035, S1046, or any combination thereof. In some instances, the one or more mutations are amino acid substitutions, for example, D581R, G624R, F626R, P868T, I926R, V1030G, E1035R, 51046G, or a combination thereof.

In some examples, the Cas12i2 polypeptide contains mutations at positions D581, D911, 1926, and V1030. Such a Cas12i2 polypeptide may contain amino acid substitutions of D581R, D911R, I926R, and V1030G (e.g., SEQ ID NO: 923). In some examples, the Cas12i2 polypeptide contains mutations at positions D581, I926, and V1030. Such a Cas12i2 polypeptide may contain amino acid substitutions of D581R, I926R, and V1030G (e.g., SEQ ID NO: 924). In some examples, the Cas12i2 polypeptide may contain mutations at positions D581, I926, V1030, and S1046. Such a Cas12i2 polypeptide may contain amino acid substitutions of D581R, I926R, V1030G, and 51046G (e.g., SEQ ID NO: 925). In some examples, the Cas12i2 polypeptide may contain mutations at positions D581, G624, F626, I926, V1030, E1035, and S1046. Such a Cas12i2 polypeptide may contain amino acid substitutions of D581R, G624R, F626R, I926R, V1030G, E1035R, and 51046G (e.g., SEQ ID NO: 926). In some examples, the Cas12i2 polypeptide may contain mutations at positions D581, G624, F626, P868, I926, V1030, E1035, and S1046. Such a Cas12i2 polypeptide may contain amino acid substitutions of D581R, G624R, F626R, P868T, I926R, V1030G, E1035R, and 51046G (e.g., SEQ ID NO: 927).

In some embodiments, the Cas12i2 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 923, SEQ ID NO: 924, SEQ ID NO: 925, SEQ ID NO: 926, or SEQ ID NO: 927. In some embodiments, a Cas12i2 polypeptide having at least 50%, 60%, 65%, 70%, 75%, 80%, 85%, 90%, 91%, 92%, 93%, 94%, 95%, 96%, 97%, 98%, 99%, or 100% identity to SEQ ID NO: 923, SEQ ID NO: 924, SEQ ID NO: 925, SEQ ID NO: 926, or SEQ ID NO: 927 maintains the amino acid changes (or at least 1, 2, 3 etc. of these changes) that differentiate the polypeptide from its respective parent/reference sequence.

In some embodiments, the present disclosure describes a Cas12i2 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 923, SEQ ID NO: 924, SEQ ID NO: 925, SEQ ID NO: 926, or SEQ ID NO: 927. Homology or identity can be determined by amino acid sequence alignment, e.g., using a program such as BLAST, ALIGN, or CLUSTAL, as described herein.

Also provided is a Cas12i2 polypeptide of the present disclosure having enzymatic activity, e.g., nuclease or endonuclease activity, and comprising an amino acid sequence which differs from the amino acid sequences of SEQ ID NO: 923, SEQ ID NO: 924, SEQ ID NO: 925, SEQ ID NO: 926, or SEQ ID NO: 927 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

In some embodiments, the composition of the present disclosure includes a Cas12i4 polypeptide described herein (e.g., a polypeptide comprising SEQ ID NO: 956 and/or encoded by SEQ ID NO: 955). In some embodiments, the Cas12i4 polypeptide comprises at least one RuvC domain.

A nucleic acid sequence encoding the Cas12i4 polypeptide described herein may be substantially identical to a reference nucleic acid sequence, e.g., SEQ ID NO: 955. In some embodiments, the Cas12i4 polypeptide is encoded by a nucleic acid comprising a sequence having least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or at least about 99.5% sequence identity to the reference nucleic acid sequence, e.g., SEQ ID NO: 955. The percent identity between two such nucleic acids can be determined manually by inspection of the two optimally aligned nucleic acid sequences or by using software programs or algorithms (e.g., BLAST, ALIGN, CLUSTAL) using standard parameters. One indication that two nucleic acid sequences are substantially identical is that the nucleic acid molecules hybridize to the complementary sequence of the other under stringent conditions of temperature and ionic strength (e.g., within a range of medium to high stringency).

In some embodiments, the Cas12i4 polypeptide is encoded by a nucleic acid sequence having at least about 60%, at least about 65%, at least about 70%, at least about 75%, at least about 80%, at least about 85%, at least about 90%, at least about 91%, at least about 92%, at least about 93%, at least about 94%, at least about 95%, at least about 96%, at least about 97%, at least about 98%, at least about 99%, or more sequence identity, but not 100% sequence identity, to a reference nucleic acid sequence, e.g., SEQ ID NO: 955.

In some embodiments, the Cas12i4 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 956.

In some embodiments, the present disclosure describes a Cas12i4 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 956. Homology or identity can be determined by amino acid sequence alignment, e.g., using a program such as BLAST, ALIGN, or CLUSTAL, as described herein.

Also provided is a Cas12i4 polypeptide of the present disclosure having enzymatic activity, e.g., nuclease or endonuclease activity, and comprising an amino acid sequence which differs from the amino acid sequences of SEQ ID NO: 956 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

In some embodiments, the Cas12i4 polypeptide comprises a polypeptide having a sequence of SEQ ID NO: 957 or SEQ ID NO: 958.

In some embodiments, the Cas12i4 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 957 or SEQ ID NO: 958. In some embodiments, a Cas12i4 polypeptide having at least 50%, 60%, 65%, 70%, 75%, 80%, 85%, 90%, 91%, 92%, 93%, 94%, 95%, 96%, 97%, 98%, 99%, or 100% identity to SEQ ID NO: 957 or SEQ ID NO: 958 maintains the amino acid changes (or at least 1, 2, 3 etc. of these changes) that differentiate it from its respective parent/reference sequence.

In some embodiments, the present disclosure describes a Cas12i4 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 957 or SEQ ID NO: 958. Homology or identity can be determined by amino acid sequence alignment, e.g., using a program such as BLAST, ALIGN, or CLUSTAL, as described herein.

Also provided is a Cas12i4 polypeptide of the present disclosure having enzymatic activity, e.g., nuclease or endonuclease activity, and comprising an amino acid sequence which differs from the amino acid sequences of SEQ ID NO: 957 or SEQ ID NO: 958 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

In some embodiments, the composition of the present disclosure includes a Cas12i1 polypeptide described herein (e.g., a polypeptide comprising SEQ ID NO: 965). In some embodiments, the Cas12i4 polypeptide comprises at least one RuvC domain.

In some embodiments, the Cas12i1 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 965.

In some embodiments, the present disclosure describes a Cas12i1 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 965. Homology or identity can be determined by amino acid sequence alignment, e.g., using a program such as BLAST, ALIGN, or CLUSTAL, as described herein.

Also provided is a Cas12i1 polypeptide of the present disclosure having enzymatic activity, e.g., nuclease or endonuclease activity, and comprising an amino acid sequence which differs from the amino acid sequences of SEQ ID NO: 965 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

In some embodiments, the composition of the present disclosure includes a Cas12i3 polypeptide described herein (e.g., a polypeptide comprising SEQ ID NO: 966). In some embodiments, the Cas12i4 polypeptide comprises at least one RuvC domain.

In some embodiments, the Cas12i3 polypeptide of the present disclosure comprises a polypeptide sequence having at least 50%, 60%, 65%, 70%, 75%, 80%, 85%, 90%, 91%, 92%, 93%, 94%, 95%, 96%, 97%, 98%, 99%, or 100% identity to SEQ ID NO: 966.

In some embodiments, the present disclosure describes a Cas12i3 polypeptide having a specified degree of amino acid sequence identity to one or more reference polypeptides, e.g., at least 60%, at least 65%, at least 70%, at least 75%, at least 80%, at least 85%, at least 90%, at least 91%, at least 92%, at least 93%, at least 94%, at least 95%, at least 96%, at least 97%, at least 98%, or even at least 99%, but not 100%, sequence identity to the amino acid sequence of SEQ ID NO: 966. Homology or identity can be determined by amino acid sequence alignment, e.g., using a program such as BLAST, ALIGN, or CLUSTAL, as described herein.

Also provided is a Cas12i3 polypeptide of the present disclosure having enzymatic activity, e.g., nuclease or endonuclease activity, and comprising an amino acid sequence which differs from the amino acid sequences of SEQ ID NO: 966 by 50, 40, 35, 30, 25, 20, 19, 18, 17, 16, 15, 14, 13, 12, 11, 10, 9, 8, 7, 6, 5, 4, 3, 2, 1, or 0 amino acid residue(s), when aligned using any of the previously described alignment methods.

Although the changes described herein may be one or more amino acid changes, changes to the Cas12i polypeptide may also be of a substantive nature, such as fusion of polypeptides as amino- and/or carboxyl-terminal extensions. For example, the Cas12i polypeptide may contain additional peptides, e.g., one or more peptides. Examples of additional peptides may include epitope peptides for labelling, such as a polyhistidine tag (His-tag), Myc, and FLAG. In some embodiments, the Cas12i polypeptide described herein can be fused to a detectable moiety such as a fluorescent protein (e.g., green fluorescent protein (GFP) or yellow fluorescent protein (YFP)).

In some embodiments, the Cas12i polypeptide comprises at least one (e.g., two, three, four, five, six, or more) nuclear localization signal (NLS). In some embodiments, the Cas12i polypeptide comprises at least one (e.g., two, three, four, five, six, or more) nuclear export signal (NES). In some embodiments, the Cas12i polypeptide comprises at least one (e.g., two, three, four, five, six, or more) NLS and at least one (e.g., two, three, four, five, six, or more) NES.

In some embodiments, the Cas12i polypeptide described herein can be self-inactivating. See, Epstein et al., "Engineering a Self-Inactivating CRISPR System for AAV Vectors," Mol. Ther., 24 (2016): S50, which is incorporated by reference in its entirety.

In some embodiments, the nucleotide sequence encoding the Cas12i polypeptide described herein can be codon-optimized for use in a particular host cell or organism. For example, the nucleic acid can be codon-optimized for any non-human eukaryote including mice, rats, rabbits, dogs, livestock, or non-human primates. Codon usage tables are readily available, for example, at the "Codon Usage Database" available at www.kazusa.orjp/codon/ and these tables can be adapted in a number of ways. See Nakamura et al. *Nucl. Acids Res.* 28:292 (2000), which is incorporated herein by reference in its entirety. Computer algorithms for codon optimizing a particular sequence for expression in a particular host cell are also available, such as Gene Forge (Aptagen; Jacobus, PA). In some examples, the nucleic acid encoding the Cas12i polypeptides such as Cas12i2 polypeptides as disclosed herein can be an mRNA molecule, which can be codon optimized.

Exemplary Cas12i polypeptide sequences and corresponding nucleotide sequences are listed in Table 6.

TABLE 6

Cas12i and HAO1 Sequences

| SEQ ID NO | Sequence | Description |
|---|---|---|
| 921 | ATGAGCAGCGCGATCAAAAGCTACAAGAGCGTTCTGCGTCCGAACGAGCGTAAGAA<br>CCAACTGCTGAAAAGCACCATTCAGTGCCTGGAAGACGGTAGCGCGTTCTTTTTCA<br>AGATGCTGCAAGGCCTGTTTGGTGGCATCACCCCGGAGATTGTTCGTTTCAGCACC<br>GAACAGGAGAAACAGCAACAGGATATCGCGCTGTGGTGCGCGGTTAACTGGTTCCG<br>TCCGGTGAGCCAAGACAGCCTGACCCACACCATTGCGAGCGATAACCTGGTGGAGA<br>AGTTTGAGGAATACTATGGTGGCACCGCGAGCGACGCGATCAAACAGTACTTCAGC<br>GCGAGCATTGGCGAAAGCTACTATTGGAACGACTGCCGTCAACAGTACTATGATCT<br>GTGCCGTGAGCTGGGTGTTGAGGTGAGCGACCTGACCCATGATCTGGAGATCCTGT<br>GCCGTGAAAAGTGCCTGGCGGTTGCGACCGAGAGCAACCAGAACAACAGCATCATT<br>AGCGTTCTGTTTGGCACCGGCGAAAAAGAGGACCGTAGCGTGAAACTGCGTATCAC<br>CAAGAAAATTCTGGAGGCGATCAGCAACCTGAAAGAAATCCCGAAGAACGTTGCGC<br>CGATTCAAGAGATCATTCTGAACGTGGCGAAAGCGACCAAGGAAACCTTCCGTCAG<br>GTGTATGCGGGTAACCTGGGTGCGCCGAGCACCCTGGAGAAATTTATCGCGAAGGA<br>CGGCCAAAAAGAGTTCGATCTGAAGAAACTGCAGACCGACCTGAAGAAAGTTATTC<br>GTGGTAAAAGCAAGGAGCGTGATTGGTGCTGCCAGGAAGAGCTGCGTAGCTACGTG<br>GAGCAAAACACCATCCAGTATGACCTGTGGGCGTGGGGCGAAATGTTCAACAAAGC<br>GCACACCGCGCTGAAAATCAAGAGCACCCGTAACTACAACTTTGCGAAGCAACGTC<br>TGGAACAGTTCAAAGAGATTCAGAGCCTGAACAACCTGCTGGTTGTGAAGAAGCTG<br>AACGACTTTTTCGATAGCGAATTTTTCAGCGGCGAGGAAACCTACACCATCTGCGT<br>TCACCATCTGGGTGGCAAGGACCTGAGCAAACTGTATAAGGCGTGGGAGGATGATC<br>CGGCGGACCCGGAAAACGCGATTGTGGTTCTGTGCGACGATCTGAAAAACAACTTT<br>AAGAAAGAGCCGATCCGTAACATTCTGCGTTACATCTTCACCATTCGTCAAGAATG<br>CAGCGCGCAGGACATCCTGGCGGCGGCGAAGTACAACCAACAGCTGGATCGTTATA<br>AAAGCCAAAAGGCGAACCCGAGCGTTCTGGGTAACCAGGGCTTTACCTGGACCAAC<br>GCGGTGATCCTGCCGGAGAAGGCGCAGCGTAACGACCGTCCGAACAGCCTGGATCT<br>GCGTATTTGGCTGTACCTGAAACTGCGTCACCCGGACGGTCGTTGGAAGAAACACC<br>ATATCCCGTTCTACGATACCCGTTTCTTCCAAGAAATTTATGCGGCGGGCAACAGC<br>CCGGTTGACACCTGCCAGTTTCGTACCCCGCGTTTCGGTTATCACCTGCCGAAACT | Nucleotide sequence encoding parent Cas12i2 |

TABLE 6-continued

Cas12i and HAO1 Sequences

| SEQ ID NO | Sequence | Description |
|---|---|---|
| | GACCGATCAGACCGCGATCCGTGTTAACAAGAAACATGTGAAAGCGGCGAAGACCG<br>AGGCGCGTATTCGTCTGGCGATCCAACAGGGCACCCTGCCGGTGAGCAACCTGAAG<br>ATCACCGAAATTAGCGCGACCATCAACAGCAAAGGTCAAGTGCGTATTCCGGTTAA<br>GTTTGACGTGGGTCGTCAAAAAGGCACCCTGCAGATCGGTGACCGTTTCTGCGGCT<br>ACGATCAAAACCAGACCGCGAGCCACGCGTATAGCCTGTGGGAAGTGGTTAAAGAG<br>GGTCAATACCATAAAGAGCTGGGCTGCTTTGTTCGTTTCATCAGCAGCGGTGACAT<br>CGTGAGCATTACCGAGAACCGTGGCAACCAATTTGATCAGCTGAGCTATGAAGGTC<br>TGGCGTACCCGCAATATGCGGACTGGCGTAAGAAAGCGAGCAAGTTCGTGAGCCTG<br>TGGCAGATCACCAAGAAAAACAAGAAAAAGGAAATCGTGACCGTTGAAGCGAAAGA<br>GAAGTTTGACGCGATCTGCAAGTACCAGCCGCGTCTGTATAAATTCAACAAGGAGT<br>ACGCGTATCTGCTGCGTGATATTGTTCGTGGCAAAAGCCTGGTGGAACTGCAACAG<br>ATTCGTCAAGAGATCTTTCGTTTCATTGAACAGGACTGCGGTGTTACCCGTCTGGG<br>CAGCCTGAGCCTGAGCACCCTGGAAACCGTGAAAGCGGTTAAGGGTATCATTTACA<br>GCTATTTTAGCACCGCGCTGAACGCGAGCAAGAACAACCCGATCAGCGACGAACAG<br>CGTAAAGAGTTTGATCCGGAACTGTTCGCGCTGCTGGAAAAGCTGGAGCTGATTCG<br>TACCCGTAAAAAGAAACAAAAAGTGGAACGTATCGCGAACAGCCTGATTCAGACCT<br>GCCTGGAGAACAACATCAAGTTCATTCGTGGTGAAGGCGACCTGAGCACCACCAAC<br>AACGCGACCAAGAAAAAGGCGAACAGCCGTAGCATGGATTGGTTGGCGCGTGGTGT<br>TTTTAACAAAATCCGTCAACTGGCGCCGATGCACAACATTACCCTGTTCGGTTGCG<br>GCAGCCTGTACACCAGCCACCAGGACCCGCTGGTGCATCGTAACCCGGATAAAGCG<br>ATGAAGTGCCGTTGGGCGGCGATCCCGGTTAAGGACATTGGCGATTGGGTGCTGCG<br>TAAGCTGAGCCAAAACCTGCGTGCGAAAAACATCGGCACCGGCGAGTACTATCACC<br>AAGGTGTTAAAGAGTTCCTGAGCCATTATGAACTGCAGGACCTGGAGGAAGAGCTG<br>CTGAAGTGGCGTAGCGATCGTAAAAGCAACATTCCGTGCTGGGTGCTGCAGAACCG<br>TCTGGCGGAGAAGCTGGGCAACAAAGAAGCGGTGGTTTACATCCCGGTTCGTGGTG<br>GCCGTATTTATTTTGCGACCCACAAGGTGGCGACCGGTGCGGTGAGCATCGTTTTC<br>GACCAAAAACAAGTGTGGGTTTGCAACGCGGATCATGTTGCGGCGGCGAACATCGC<br>GCTGACCGTGAAGGGTATTGGCGAACAAAGCAGCGACGAAGAGAACCCGGATGGTA<br>GCCGTATCAAACTGCAGCTGACCAGC | |
| 922 | MSSAIKSYKSVLRPNERKNQLLKSTIQCLEDGSAFFFKMLQGLFGGITPEIVRFST<br>EQEKQQQDIALWCAVNWFRPVSQDSLTHTIASDNLVEKFEEYYGGTASDAIKQYFS<br>ASIGESYYWNDCRQQYYDLCRELGVEVSDLTHDLEILCREKCLAVATESNQNNSII<br>SVLFGTGEKEDRSVKLRITKKILEAISNLKEIPKNVAPIQEIILNVAKATKETFRQ<br>VYAGNLGAPSTLEKFIAKDGQKEFDLKKLQTDLKKVIRGKSKERDWCCQEELRSYV<br>EQNTIQYDLWAWGEMFNKAHTALKIKSTRNYNFAKQRLEQFKEIQSLNNLLVVKKL<br>NDFFDSEFFSGEETYTICVHHLGGKDLSKLYKAWEDDPADPENAIVVLCDDLKNNF<br>KKEPIRNILRYIFTIRQECSAQDILAAAKYNQQLDRYKSQKANPSVLGNQGFTWTN<br>AVILPEKAQRNDRPNSLDLRIWLYLKLRHPDGRWKKHHIPFYDTRFFQEIYAAGNS<br>PVDTCQFRTPRFGYHLPKLTDQTAIRVNKKHVKAAKTEARIRLAIQQGTLPVSNLK<br>ITEISATINSKGQVRIPVKFDVGRQKGTLQIGDRFCGYDQNQTASHAYSLWEVVKE<br>GQYHKELGCFVRFISSGDIVSITENRGNQFDQLSYEGLAYPQYADWRKKASKFVSL<br>WQITKKNKKKEIVTVEAKEKFDAICKYQPRLYKFNKEYAYLLRDIVRGKSLVELQQ<br>IRQEIFRFIEQDCGVTRLGSLSLSTLETVKAVKGIIYSYFSTALNASKNNPISDEQ<br>RKEFDPELFALLEKLELIRTRKKKQKVERIANSLIQTCLENNIKFIRGEGDLSTTN<br>NATKKKANSRSMDWLARGVFNKIRQLAPMHNITLFGCGSLYTSHQDPLVHRNPDKA<br>MKCRWAAIPVKDIGDWVLRKLSQNLRAKNIGTGEYYHQGVKEFLSHYELQDLEEEL<br>LKWRSDRKSNIPCWVLQNRLAEKLGNKEAVVYIPVRGGRIYFATHKVATGAVSIVF<br>DQKQVWVCNADHVAAANIALTVKGIGEQSSDEENPDGSRIKLQLTS | Parent Cas12i2 amino acid sequence |
| 923 | MSSAIKSYKS VLRPNERKNQ LLKSTIQCLE DGSAFFFKML QGLFGGITPE<br>IVRFSTEQEK QQQDIALWCA VNWFRPVSQD SLTHTIASDN LVEKFEEYYG<br>GTASDAIKQY FSASIGESYY WNDCRQQYYD LCRELGVEVS DLTHDLEILC<br>REKCLAVATE SNQNNSIISV LFGTGEKEDR SVKLRITKKI LEAISNLKEI<br>PKNVAPIQEI ILNVAKATKE TFRQVYAGNL GAPSTLEKFI AKDGQKEFDL<br>KKLQTDLKKV IRGKSKERDW CCQEELRSYV EQNTIQYDLW AWGEMFNKAH<br>TALKIKSTRN YNFAKQRLEQ FKEIQSLNNL LVVKKLNDFF DSEFFSGEET<br>YTICVHHLGG KDLSKLYKAW EDDPADPENA IVVLCDDLKN NFKKEPIRNI<br>LRYIFTIRQE CSAQDILAAA KYNQQLDRYK SQKANPSVLG NQGFTWTNAV<br>ILPEKAQRND RPNSLDLRIW LYLKLRHPDG RWKKHHIPFY DTRFFQEIYA<br>AGNSPVDTCQ FRTPRFGYHL PKLTDQTAIR VNKKHVKAAK TEARIRLAIQ<br>QGTLPVSNLK ITEISATINS KGQVRIPVKF RVGRQKGTLQ IGDRFCGYDQ<br>NQTASHAYSL WEVVKEGQYH KELGCFVRFI SSGDIVSITE NRGNQFDQLS<br>YEGLAYPQYA DWRKKASKFV SLWQITKKNK KKEIVTVEAK EKFDAICKYQ<br>PRLYKFNKEY AYLLRDIVRG KSLVELQQIR QEIFRFIEQD CGVTRLGSLS<br>LSTLETVKAV KGIIYSYFST ALNASKNNPI SDEQRKEFDP ELFALLEKLE<br>LIRTRKKKQK VERIANSLIQ TCLENNIKFI RGEGDLSTTN NATKKKANSR<br>SMDWLARGVF NKIRQLAPMH NITLFGCGSL YTSHQDPLVH RNPDKAMKCR<br>WAAIPVKDIG RWVLRKLSQN LRAKNRGTGE YYHQGVKEFL SHYELQDLEE<br>ELLKWRSDRK SNIPCWVLQN RLAEKLGNKE AVVYIPVRGG RIYFATHKVA<br>TGAVSIVFDQ KQVWVCNADH VAAANIALTG KGIGEQSSDE ENPDGSRIKL<br>QLTS | Variant Cas12i2 of SEQ ID NO: 3 of PCT/US2021/025257 |

TABLE 6-continued

| Cas12i and HAO1 Sequences | | |
|---|---|---|
| SEQ ID NO | Sequence | Description |
| 924 | MSSAIKSYKS VLRPNERKNQ LLKSTIQCLE DGSAFFFKML QGLFGGITPE<br>IVRFSTEQEK QQQDIALWCA VNWFRPVSQD SLTHTIASDN LVEKFEEYYG<br>GTASDAIKQY FSASIGESYY WNDCRQQYYD LCRELGVEVS DLTHDLEILC<br>REKCLAVATE SNQNNSIISV LFGTGEKEDR SVKLRITKKI LEAISNLKEI<br>PKNVAPIQEI ILNVAKATKE TFRQVYAGNL GAPSTLEKFI AKDGQKEFDL<br>KKLQTDLKKV IRGKSKERDW CCQEELRSYV EQNTIQYDLW AWGEMFNKAH<br>TALKIKSTRN YNFAKQRLEQ FKEIQSLNNL LVVKKLNDFF DSEFFSGEET<br>YTICVHHLGG KDLSKLYKAW EDDPADPENA IVVLCDDLKN NFKKEPIRNI<br>LRYIFTIRQE CSAQDILAAA KYNQQLDRYK SQKANPSVLG NQGFTWTNAV<br>ILPEKAQRND RPNSLDLRIW LYLKLRHPDG RWKKHHIPFY DTRFFQEIYA<br>AGNSPVDTCQ FRTPRFGYHL PKLTDQTAIR VNKKHVKAAK TEARIRLAIQ<br>QGTLPVSNLK ITEISATINS KGQVRIPVKF RVGRQKGTLQ IGDRFCGYDQ<br>NQTASHAYSL WEVVKEGQYH KELGCFVRFI SSGDIVSITE NRGNQFDQLS<br>YEGLAYPQYA DWRKKASKFV SLWQITKKNK KKEIVTVEAK EKFDAICKYQ<br>PRLYKFNKEY AYLLRDIVRG KSLVELQQIR QEIFRFIEQD CGVTRLGSLS<br>LSTLETVKAV KGIIYSYFST ALNASKNNPI SDEQRKEFDP ELFALLEKLE<br>LIRTRKKKQK VERIANSLIQ TCLENNIKFI RGEGDLSTTN NATKKKANSR<br>SMDWLARGVF NKIRQLAPMH NITLFGCGSL YTSHQDPLVH RNPDKAMKCR<br>WAAIPVKDIG DWVLRKLSQN LRAKNRGTGE YYHQGVKEFL SHYELQDLEE<br>ELLKWRSDRK SNIPCWVLQN RLAEKLGNKE AVVYIPVRGG RIYFATHKVA<br>TGAVSIVFDQ KQVWVCNADH VAAANIALTG KGIGEQSSDE ENPDGSRIKL<br>QLTS | Variant Cas12i2 of SEQ ID NO: 4 of PCT/US2021/ 025257 |
| 925 | MSSAIKSYKS VLRPNERKNQ LLKSTIQCLE DGSAFFFKML QGLFGGITPE<br>IVRFSTEQEK QQQDIALWCA VNWFRPVSQD SLTHTIASDN LVEKFEEYYG<br>GTASDAIKQY FSASIGESYY WNDCRQQYYD LCRELGVEVS DLTHDLEILC<br>REKCLAVATE SNQNNSIISV LFGTGEKEDR SVKLRITKKI LEAISNLKEI<br>PKNVAPIQEI ILNVAKATKE TFRQVYAGNL GAPSTLEKFI AKDGQKEFDL<br>KKLQTDLKKV IRGKSKERDW CCQEELRSYV EQNTIQYDLW AWGEMFNKAH<br>TALKIKSTRN YNFAKQRLEQ FKEIQSLNNL LVVKKLNDFF DSEFFSGEET<br>YTICVHHLGG KDLSKLYKAW EDDPADPENA IVVLCDDLKN NFKKEPIRNI<br>LRYIFTIRQE CSAQDILAAA KYNQQLDRYK SQKANPSVLG NQGFTWTNAV<br>ILPEKAQRND RPNSLDLRIW LYLKLRHPDG RWKKHHIPFY DTRFFQEIYA<br>AGNSPVDTCQ FRTPRFGYHL PKLTDQTAIR VNKKHVKAAK TEARIRLAIQ<br>QGTLPVSNLK ITEISATINS KGQVRIPVKF RVGRQKGTLQ IGDRFCGYDQ<br>NQTASHAYSL WEVVKEGQYH KELGCFVRFI SSGDIVSITE NRGNQFDQLS<br>YEGLAYPQYA DWRKKASKFV SLWQITKKNK KKEIVTVEAK EKFDAICKYQ<br>PRLYKFNKEY AYLLRDIVRG KSLVELQQIR QEIFRFIEQD CGVTRLGSLS<br>LSTLETVKAV KGIIYSYFST ALNASKNNPI SDEQRKEFDP ELFALLEKLE<br>LIRTRKKKQK VERIANSLIQ TCLENNIKFI RGEGDLSTTN NATKKKANSR<br>SMDWLARGVF NKIRQLAPMH NITLFGCGSL YTSHQDPLVH RNPDKAMKCR<br>WAAIPVKDIG DWVLRKLSQN LRAKNRGTGE YYHQGVKEFL SHYELQDLEE<br>ELLKWRSDRK SNIPCWVLQN RLAEKLGNKE AVVYIPVRGG RIYFATHKVA<br>TGAVSIVFDQ KQVWVCNADH VAAANIALTG KGIGEQSSDE ENPDGGRIKL<br>QLTS | Variant Cas12i2 of SEQ ID NO: 5 of PCT/US2021/ 025257 |
| 926 | MSSAIKSYKS VLRPNERKNQ LLKSTIQCLE DGSAFFFKML QGLFGGITPE<br>IVRFSTEQEK QQQDIALWCA VNWFRPVSQD SLTHTIASDN LVEKFEEYYG<br>GTASDAIKQY FSASIGESYY WNDCRQQYYD LCRELGVEVS DLTHDLEILC<br>REKCLAVATE SNQNNSIISV LFGTGEKEDR SVKLRITKKI LEAISNLKEI<br>PKNVAPIQEI ILNVAKATKE TFRQVYAGNL GAPSTLEKFI AKDGQKEFDL<br>KKLQTDLKKV IRGKSKERDW CCQEELRSYV EQNTIQYDLW AWGEMFNKAH<br>TALKIKSTRN YNFAKQRLEQ FKEIQSLNNL LVVKKLNDFF DSEFFSGEET<br>YTICVHHLGG KDLSKLYKAW EDDPADPENA IVVLCDDLKN NFKKEPIRNI<br>LRYIFTIRQE CSAQDILAAA KYNQQLDRYK SQKANPSVLG NQGFTWTNAV<br>ILPEKAQRND RPNSLDLRIW LYLKLRHPDG RWKKHHIPFY DTRFFQEIYA<br>AGNSPVDTCQ FRTPRFGYHL PKLTDQTAIR VNKKHVKAAK TEARIRLAIQ<br>QGTLPVSNLK ITEISATINS KGQVRIPVKF RVGRQKGTLQ IGDRFCGYDQ<br>NQTASHAYSL WEVVKEGQYH KELRCRVRFI SSGDIVSITE NRGNQFDQLS<br>YEGLAYPQYA DWRKKASKFV SLWQITKKNK KKEIVTVEAK EKFDAICKYQ<br>PRLYKFNKEY AYLLRDIVRG KSLVELQQIR QEIFRFIEQD CGVTRLGSLS<br>LSTLETVKAV KGIIYSYFST ALNASKNNPI SDEQRKEFDP ELFALLEKLE<br>LIRTRKKKQK VERIANSLIQ TCLENNIKFI RGEGDLSTTN NATKKKANSR<br>SMDWLARGVF NKIRQLAPMH NITLFGCGSL YTSHQDPLVH RNPDKAMKCR<br>WAAIPVKDIG DWVLRKLSQN LRAKNRGTGE YYHQGVKEFL SHYELQDLEE<br>ELLKWRSDRK SNIPCWVLQN RLAEKLGNKE AVVYIPVRGG RIYFATHKVA<br>TGAVSIVFDQ KQVWVCNADH VAAANIALTG KGIGRQSSDE ENPDGGRIKL<br>QLTS | Variant Cas12i2 of SEQ ID NO: 495 of PCT/US2021/ 025257 |
| 927 | MSSAIKSYKS VLRPNERKNQ LLKSTIQCLE DGSAFFFKML QGLFGGITPE<br>IVRFSTEQEK QQQDIALWCA VNWFRPVSQD SLTHTIASDN LVEKFEEYYG<br>GTASDAIKQY FSASIGESYY WNDCRQQYYD LCRELGVEVS DLTHDLEILC<br>REKCLAVATE SNQNNSIISV LFGTGEKEDR SVKLRITKKI LEAISNLKEI<br>PKNVAPIQEI ILNVAKATKE TFRQVYAGNL GAPSTLEKFI AKDGQKEFDL<br>KKLQTDLKKV IRGKSKERDW CCQEELRSYV EQNTIQYDLW AWGEMFNKAH | Variant Cas12i2 of SEQ ID NO: 496 of PCT/US2021/ 025257 |

TABLE 6-continued

Cas12i and HAO1 Sequences

| SEQ ID NO | Sequence | Description |
|---|---|---|
| | TALKIKSTRN YNFAKQRLEQ FKEIQSLNNL LVVKKLNDFF DSEFFSGEET<br>YTICVHHLGG KDLSKLYKAW EDDPADPENA IVVLCDDLKN NFKKEPIRNI<br>LRYIFTIRQE CSAQDILAAA KYNQQLDRYK SQKANPSVLG NQGFTWTNAV<br>ILPEKAQRND RPNSLDLRIW LYLKLRHPDG RWKKHHIPFY DTRFFQEIYA<br>AGNSPVDTCQ FRTPRFGYHL PKLTDQTAIR VNKKHVKAAK TEARIRLAIQ<br>QGTLPVSNLK ITEISATINS KGQVRIPVKF RVGRQKGTLQ IGDRFCGYDQ<br>NQTASHAYSL WEVVKEGQYH KELRCRVRFI SSGDIVSITE NRGNQFDQLS<br>YEGLAYPQYA DWRKKASKFV SLWQITKKNK KKEIVTVEAK EKFDAICKYQ<br>PRLYKFNKEY AYLLRDIVRG KSLVELQQIR QEIFRFIEQD CGVTRLGSLS<br>LSTLETVKAV KGIIYSYFST ALNASKNNPI SDEQRKEFDP ELFALLEKLE<br>LIRTRKKKQK VERIANSLIQ TCLENNIKFI RGEGDLSTTN NATKKKANSR<br>SMDWLARGVF NKIRQLATMH NITLFGCGSL YTSHQDPLVH RNPDKAMKCR<br>WAAIPVKDIG DWVLRKLSQN LRAKNRGTGE YYHQGVKEFL SHYELQDLEE<br>ELLKWRSDRK SNIPCWVLQN RLAEKLGNKE AVVYIPVRGG RIYFATHKVA<br>TGAVSIVFDQ KQVWVCNADH VAAANIALTG KGIGRQSSDE ENPDGGRIKL<br>QLTS | |
| 955 | ATGGCTTCCATCTCTAGGCCATACGGCACCAAGCTGCGACCGGACGCACGGAAGAA<br>GGAGATGCTCGATAAGTTCTTTAATACACTGACTAAGGGTCAGCGCGTGTTCGCAG<br>ACCTGGCCCTGTGCATCTATGGCTCCCTGACCCTGGAGATGGCCAAGTCTCTGGAG<br>CCAGAAAGTGATTCAGAACTGGTGTGCGCTATTGGGTGGTTTCGGCTGGTGGACAA<br>GACCATCTGGTCCAAGGATGGCATCAAGCAGGAGAATCTGGTGAAACAGTACGAAG<br>CCTATTCCGGAAAGGAGGCTTCTGAAGTGGTCAAAACATACCTGAACAGCCCCAGC<br>TCCGACAAGTACGTGTGGATCGATTGCAGGCAGAAATTCCTGAGGTTTCAGCGCGA<br>GCTCGGCACTCGCAACCTGTCCGAGGACTTCGAATGTATGCTCTTTGAACAGTACA<br>TTAGACTGACCAAGGGCGAGATCGAAGGGTATGCCGCTATTTCAAATATGTTCGGA<br>AACGGCGAGAAGGAAGACCGGAGCAAGAAAAGAATGTACGCTACACGGATGAAAGA<br>TTGGCTGGAGGCAAACGAAAATATCACTTGGGAGCAGTATAGAGAGGCCCTGAAGA<br>ACCAGCTGAATGCTAAAAACCTGGAGCAGGTTGTGGCCAATTACAAGGGGAACGCT<br>GGCGGGGCAGACCCCTTCTTTAAGTATAGCTTCTCCAAAGAGGGAATGGTGAGCAA<br>GAAAGAACATGCACAGCAGCTCGACAAGTTCAAAACCGTCCTGAAGAACAAAGCCC<br>GGGACCTGAATTTTCCAAACAAGGAGAAGCTGAAGCAGTACCTGGAGGCCGAAATC<br>GGCATTCCGGTCGACGCTAACGTGTACTCCCAGATGTTCTCTAACGGGGTGAGTGA<br>GGTCCAGCCTAAGACCACACGGAATATGTCTTTTAGTAACGAGAAACTGGATCTGC<br>TCACTGAACTGAAGGACCTGAACAAGGGCGATGGGTTCGAGTACGCCAGAGAAGTG<br>CTGAACGGGTTCTTTGACTCCGAGCTCCACACTACCGAGGATAAGTTTAATATCAC<br>CTCTAGGTACCTGGGAGGCGACAAATCAAACCGCCTGAGCAAACTCTATAAGATCT<br>GGAAGAAAGAGGGTGTGGACTGCGAGGAAGGCATTCAGCAGTTCTGTGAAGCCGTC<br>AAAGATAAGATGGGCCAGATCCCCATTCGAAATGTGCTGAAGTACCTGTGGCAGTT<br>CCGGGAGACAGTCAGTGCCGAGGATTTTGAAGCAGCCGCTAAGGCTAACCATCTGG<br>AGGAAAAGATCAGCCGGGTGAAAGCCCACCCAATCGTGATTAGCAATAGGTACTGG<br>GCTTTTGGGACTTCCGCACTGGTGGGAAACATTATGCCCGCAGACAAGAGGCATCA<br>GGGAGAGTATGCCGGTCAGAATTTCAAAATGTGGCTGGAGGCTGAACTGCACTACG<br>ATGGCAAGAAAGCAAAGCACCATCTGCCTTTTTATAACGCCCGCTTCTTTGAGGAA<br>GTGTACTGCTATCACCCCTCTGTCGCCGAGATCACTCCTTTCAAAACCAAGCAGTT<br>TGGCTGTGAAATCGGGAAGGACATTCCAGATTACGTGAGCGTCGCTCTGAAGGACA<br>ATCCGTATAAGAAAGCAACCAAACGAATCCTGCGTGCAATCTACAATCCCGTCGCC<br>AACACAACTGGCGTTGATAAGACCACAAACTGCAGCTTCATGATCAAACGCGAGAA<br>TGACGAATATAAGCTGGTCATCAACCGAAAAATTTCCGTGGATCGGCCTAAGAGAA<br>TCGAAGTGGGCAGGACAATTATGGGGTACGACCGCAATCAGACAGCTAGCGATACT<br>TATTGGATTGGCCGGCTGGTGCCACCTGGAACCCGGGGCGCATACCGCATCGGAGA<br>GTGGAGCGTCCAGTATATTAAGTCCGGGCCTGTCCTGTCTAGTACTCAGGGAGTTA<br>ACAATTCCACTACCGACCAGCTGGTGTACAACGGCATGCCATCAAGCTCCGAGCGG<br>TTCAAGGCCTGGAAGAAAGCCAGAATGGCTTTTATCCGAAAACTCATTCGTCAGCT<br>GAATGACGAGGGACTGGAATCTAAGGGTCAGGATTATATCCCCGAGAACCCTTCTA<br>GTTTCGATGTGCGGGGCGAAACCCTGTACGTCTTTAACAGTAATTATCTGAAGGCC<br>CTGGTGAGCAAACACAGAAAGGCCAAGAAACCTGTTGAGGGGATCCTGGACGAGAT<br>TGAAGCCTGGACATCTAAAGACAAGGATTCATGCAGCCTGATGCGGCTGAGCAGCC<br>TGAGCGATGCTTCCATGCAGGGAATCGCCAGCCTGAAGAGTCTGATTAACAGCTAC<br>TTCAACAAGAATGGCTGTAAAACCATCGAGGACAAAGAAAAGTTTAATCCCGTGCT<br>GTATGCCAAGCTGGTTGAGGTGGAACAGCGGAGAACAAACAAGCGGTCTGAGAAAG<br>TGGGAAGAATCGCAGGTAGTCTGGAGCAGCTGGCCCTGCTGAACGGGGTTGAGGTG<br>GTCATCGGCGAAGCTGACCTGGGGGAGGTCGAAAAAGGAAAGAGTAAGAAACAGAA<br>TTCACGGAACATGGATTGGTGCGCAAAGCAGGTGGCACAGCGGCTGGAGTACAAAC<br>TGGCCTTCCATGGAATCGGTTACTTTGGAGTGAACCCCATGTATACCAGCCACCAG<br>GACCCTTTCGAACATAGGCGCGTGGCTGATCACATCGTCATGCGAGCACGTTTTGA<br>GGAAGTCAACGTGGAGAACATTGCCGAATGGCACGTGCGAAATTTCTCAAACTACC<br>TGCGTGCAGACAGCGGCACTGGGCTGTACTATAAGCAGGCCACCATGGACTTCCTG<br>AAACATTACGGTCTGGAGGAACACGCTGAGGGCCTGGAAAATAAGAAAATCAAGTT<br>CTATGACTTTAGAAAGATCCTGGAGGATAAAAACCTGACAAGCGTGATCATTCCAA<br>AGAGGGGCGGGCGCATCTACATGGCCACCAACCCAGTGACATCCGACTCTACCCCG<br>ATTACATACGCCGGCAAGACTTATAATAGGTGTAACGCTGATGAGGTGGCAGCCGC<br>TAATATCGTTATTTCTGTGCTGGCTCCCCGCAGTAAGAAAAACGAGGAACAGGACG<br>ATATCCCTCTGATTACCAAGAAAGCCGAGAGTAAGTCACCACCGAAAGACCGGAAG<br>AGATCAAAAACAAGCCAGCTGCCTCAGAAA | Nucleotide sequence encoding parent Cas12i4 |

TABLE 6-continued

Cas12i and HAO1 Sequences

| SEQ ID NO | Sequence | Description |
|---|---|---|
| 956 | MASISRPYGTKLRPDARKKEMLDKFFNTLTKGQRVFADLALCIYGSLTLEMAKSLE<br>PESDSELVCAIGWFRLVDKTIWSKDGIKQENLVKQYEAYSGKEASEVVKTYLNSPS<br>SDKYVWIDCRQKFLRFQRELGTRNLSEDFECMLFEQYIRLTKGEIEGYAAISNMFG<br>NGEKEDRSKKRMYATRMKDWLEANENITWEQYREALKNQLNAKNLEQVVANYKGNA<br>GGADPFFKYSFSKEGMVSKKEHAQQLDKFKTVLKNKARDLNFPNKEKLKQYLEAEI<br>GIPVDANVYSQMFSNGVSEVQPKTTRNMSFSNEKLDLLTELKDLNKGDGFEYAREV<br>LNGFFDSELHTTEDKFNITSRYLGGDKSNRLSKLYKIWKKEGVDCEEGIQQFCEAV<br>KDKMGQIPIRNVLKYLWQFRETVSAEDFEAAAKANHLEEKISRVKAHPIVISNRYW<br>AFGTSALVGNIMPADKRHQGEYAGQNFKMWLEAELHYDGKKAKHHLPFYNARFFEE<br>VYCYHPSVAEITPFKTKQFGCEIGKDIPDYVSVALKDNPYKKATKRILRAIYNPVA<br>NTTGVDKTTNCSFMIKRENDEYKLVINRKISVDRPKRIEVGRTIMGYDRNQTASDT<br>YWIGRLVPPGTRGAYRIGEWSVQYIKSGPVLSSTOGVNNSTTDQLVYNGMPSSSER<br>FKAWKKARMAFIRKLIRQLNDEGLESKGQDYIPENPSSFDVRGETLYVFNSNYLKA<br>LVSKHRKAKKPVEGILDEIEAWTSKDKDSCSLMRLSSLSDASMQGIASLKSLINSY<br>FNKNGCKTIEDKEKFNPVLYAKLVEVEQRRTNKRSEKVGRIAGSLEQLALLNGVEV<br>VIGEADLGEVEKGKSKKQNSRNMDWCAKQVAQRLEYKLAFHGIGYFGVNPMYTSHQ<br>DPFEHRRVADHIVMRARFEEVNVENIAEWHVRNFSNYLRADSGTGLYYKQATMDFL<br>KHYGLEEHAEGLENKKIKFYDFRKILEDKNLTSVIIPKRGGRIYMATNPVTSDSTP<br>ITYAGKTYNRCNADEVAAANIVISVLAPRSKKNEEQDDIPLITKKAESKSPPKDRK<br>RSKTSQLPQK | Parent Cas12i4 amino acid sequence |
| 957 | MASISRPYGT KLRPDARKKE MLDKFFNTLT KGQRVFADLA LCIYGSLTLE<br>MAKSLEPESD SELVCAIGWF RLVDKTIWSK DGIKQENLVK QYEAYSGKEA<br>SEVVKTYLNS PSSDKYVWID CRQKFLRFQR ELGTRNLSED FECMLFEQYI<br>RLTKGEIEGY AAISNMFGNG EKEDRSKKRM YATRMKDWLE ANENITWEQY<br>REALKNQLNA KNLEQVVANY KGNAGGADPF FKYSFSKEGM VSKKEHAQQL<br>DKFKTVLKNK ARDLNFPNKE KLKQYLEAEI GIPVDANVYS QMFSNGVSEV<br>QPKTTRNMSF SNEKLDLLTE LKDLNKGDGF EYAREVLNGF FDSELHTTED<br>KFNITSRYLG GDKSNRLSKL YKIWKKEGVD CEEGIQQFCE AVKDKMGQIP<br>IRNVLKYLWQ FRETVSAEDF EAAAKANHLE EKISRVKAHP IVISNRYWAF<br>GTSALVGNIM PADKRHQGEY AGQNFKMWLE AELHYDGKKA KHHLPFYNAR<br>FFEEVYCYHP SVAEITPFKT KQFGCEIGKD IPDYVSVALK DNPYKKATKR<br>ILRAIYNPVA NTTGVDKTTN CSFMIKREND EYKLVINRKI SRDRPKRIEV<br>GRTIMGYDRN QTASDTYWIG RLVPPGTRGA YRIGEWSVQY IKSGPVLSST<br>QGVNNSTTDQ LVYNGMPSSS ERFKAWKKAR MAFIRKLIRQ LNDEGLESKG<br>QDYIPENPSS FDVRGETLYV FNSNYLKALV SKHRKAKKPV EGILDEIEAW<br>TSKDKDSCSL MRLSSLSDAS MQGIASLKSL INSYFNKNGC KTIEDKEKFN<br>PVLYAKLVEV EQRRTNKRSE KVGRIAGSLE QLALLNGVEV VIGEADLGEV<br>EKGKSKKQNS RNMDWCAKQV AQRLEYKLAF HGIGYFGVNP MYTSHQDPFE<br>HRRVADHIVM RARFEEVNVE NIAEWHVRNF SNYLRADSGT GLYYKQATMD<br>FLKHYGLEEH AEGLENKKIK FYDFRKILED KNLTSVIIPK RGGRIYMATN<br>PVTSDSTPIT YAGKTYNRCN ADEVAAANIV ISVLAPRSKK NREQDDIPLI<br>TKKAESKSPP KDRKRSKTSQ LPQK | Variant Cas12i4 A |
| 958 | MASISRPYGT KLRPDARKKE MLDKFFNTLT KGQRVFADLA LCIYGSLTLE<br>MAKSLEPESD SELVCAIGWF RLVDKTIWSK DGIKQENLVK QYEAYSGKEA<br>SEVVKTYLNS PSSDKYVWID CRQKFLRFQR ELGTRNLSED FECMLFEQYI<br>RLTKGEIEGY AAISNMFGNG EKEDRSKKRM YATRMKDWLE ANENITWEQY<br>REALKNQLNA KNLEQVVANY KGNAGGADPF FKYSFSKEGM VSKKEHAQQL<br>DKFKTVLKNK ARDLNFPNKE KLKQYLEAEI GIPVDANVYS QMFSNGVSEV<br>QPKTTRNMSF SNEKLDLLTE LKDLNKGDGF EYAREVLNGF FDSELHTTED<br>KFNITSRYLG GDKSNRLSKL YKIWKKEGVD CEEGIQQFCE AVKDKMGQIP<br>IRNVLKYLWQ FRETVSAEDF EAAAKANHLE EKISRVKAHP IVISNRYWAF<br>GTSALVGNIM PADKRHQGEY AGQNFKMWLR AELHYDGKKA KHHLPFYNAR<br>FFEEVYCYHP SVAEITPFKT KQFGCEIGKD IPDYVSVALK DNPYKKATKR<br>ILRAIYNPVA NTTRVDKTTN CSFMIKREND EYKLVINRKI SRDRPKRIEV<br>GRTIMGYDRN QTASDTYWIG RLVPPGTRGA YRIGEWSVQY IKSGPVLSST<br>QGVNNSTTDQ LVYNGMPSSS ERFKAWKKAR MAFIRKLIRQ LNDEGLESKG<br>QDYIPENPSS FDVRGETLYV FNSNYLKALV SKHRKAKKPV EGILDEIEAW<br>TSKDKDSCSL MRLSSLSDAS MQGIASLKSL INSYFNKNGC KTIEDKEKFN<br>PVLYAKLVEV EQRRTNKRSE KVGRIAGSLE QLALLNGVEV VIGEADLGEV<br>EKGKSKKQNS RNMDWCAKQV AQRLEYKLAF HGIGYFGVNP MYTSHQDPFE<br>HRRVADHIVM RARFEEVNVE NIAEWHVRNF SNYLRADSGT GLYYKQATMD<br>FLKHYGLEEH AEGLENKKIK FYDFRKILED KNLTSVIIPK RGGRIYMATN<br>PVTSDSTPIT YAGKTYNRCN ADEVAAANIV ISVLAPRSKK NREQDDIPLI<br>TKKAESKSPP KDRKRSKTSQ LPQK | Variant Cas12i4 B |
| 928 | AACGAACTCCATCTGGGATAGCAATAACCTGTGAAAATGCTCCCCCGGCTAATTTG<br>TATCAATGATTATGAACAACATGCTAAATCAGTACTTCCAAAGTCTATATATGACT<br>ATTACAGGTCTGGGGCAAATGATGAAGAAACTTTGGCTGATAATATTGCAGCATTT<br>TCCAGGTAAGAAAATTTATTTTTTAAAATCATGTTTTAAAATTACACAAAGACCGT<br>ACCAAAATAAGATCTCCTAGTTTTACGTTGGTGGTGTGTAATTATTTGTTCAGATT<br>TGTGCTTAGTAGAGAGGGAAAAGTTCTTGGGGCTGTAAGAAATCTTGGGCCTTTAA<br>ATTGTTAAAAAATATTCCAAGCCTGTGAATCTTGAGGAACTGACTGCAAAAGCCAA | HAO1 |

TABLE 6-continued

Cas12i and HAO1 Sequences

| SEQ ID NO | Sequence | Description |
|---|---|---|
| | ACCTATGTTACTTCACTTGGAAATATGACAACAATTAATTTAACTACATGTAAAAA | |
| | TAGCGATAAATTCGGATGACTTTTCTTTTTCTTAGTATGACAGTAAATGCTTATGT | |
| | TCATGGTGTAGGAAACAGCATTAAATGCCAGATAACCATCTTATCCGGATGAACCA | |
| | GACTGGATTGTTGGCTCAAATGTTTTCTTCCTGCTGGCTTTTCGTGTTATCATTCA | |
| | TTTTGATTACTGTTGTCTAAACTTTCACTTTAGATTTCAATTTGTCTATGCAGCAT | |
| | TAATCTTTCAACTTTGCTGTTTCATCTCTCCTTCAAAGCACTTCATCTCTCTTCCC | |
| | AAATTAGTTTTCCTTTGACTTTCATATTTCAAAGCACAAGATGGTGGGTGACATGG | |
| | TTTATGTTTTCTGTTTGTAATAAAAACAAGAAATAAAATCATTTCAAAGGGTTTTT | |
| | TTTTATAGCAGTTACAAAAATGGTTTATTTGCTGGAGCAAGAGAGGAGTGCCTTCA | |
| | CTACACTACACTCAGTCTCATCCATCTAACATTATGGCTGTTAGTAAAGGCAATCG | |
| | GTATTGTGGGTACTCATTGATGGTGATAAAGACAAAAAGGCAGAAAATATGCAGGG | |
| | GGAGAGAATTAGCCTTCCTCCCTGATTTCTTCTTTAGTCTACAACAAAATCACTCA | |
| | AAATCAGTTTTCCATATTTAAATTAGGAGAAATAAAATTATCCTGGCCAAGGTGGT | |
| | CTCTGGTAGGCAGCACTGATTCACCCACAAATCCATGTAGAAGACTGAAAATGGCA | |
| | ATGGGGTGAAGGATACGGCCTCTCCCCAACCCTTTCAAGCCTTGACTTTGTCTCAG | |
| | GTTTTGCCTGGAACCCAAATGAGCTCAACAAATGCCAGGGAAGTCATGGGAAGGGA | |
| | AGTTGACTGAGAGTAGAGGGGCTTAAAATTCTGCATCATTATTTACTATTTTGGAC | |
| | TCATTTAAAAGTTTCTGCTCTTGGAAGATGCCCCTTCTTGGGCCGATATTAACTTT | |
| | GTCCACCAAAATTTGCCTATGAGTGGTCTCTTGAAAACACTTTAACCCAAATAGGT | |
| | TATTACAACCAAGGAAATTTCAGACCCTTGACAGATTTATAGAGTTAGTGTCTCAG | |
| | CATTGCTAGACCTCCAATGCTCAAGTGATTATTTATTTCATTTGTATACAGCTTTC | |
| | CTTACTTCTTAATTCCCTTTGTCGCATGCTAGCTAATTAACTAGAGCTAATTAGGA | |
| | GTCTCCATGAGCTACACTGTGTACTACATGCTGAGGACAAAGCAGTGAGCCAGACA | |
| | AAGTTCCTGTCCCTAGGAACTTACATTCCCCTGGATGCATATCAGCCTCCATAATG | |
| | CTGTTGGGTTGAATTGATGCAAAATGGGCCCAAAATAGTTGGCCAAGTGGAGGTCT | |
| | CAGAGAGGATGCAAAGGGGCGCCCCAAAGCAGATGGATCACCTATGCAACCCTTTA | |
| | AAATGTAGAAACTTTGGGAGACATAGAAGGCTTGGTGACTTCTAAGTTATGAACTG | |
| | GAAAAGTGCCTCATGCCTTATGTGAATTACATGGTATTCAAGTGAGTATTCCCATC | |
| | CTATGTGTGTACCGAGTAACTTAGGGATAGGACACAGATAATGAAAATGAATTTGC | |
| | AGTGTCACCTTTTCCATGAACCTTGATCATTCTCTTTTGTTCAGCTTTAAATTAAA | |
| | AAAAAAAATCAATCAACTTTCTTTGGAGGACAGCTGATGCTATTTTATTATCAACT | |
| | AGTTGAGTTTTTATTGCAATACATTTTGCAATGTGTCCTCTTTTGCTGTATGACTC | |
| | GCTAGGTGAACCTTGATTCCTCACACTGCATCATGTAGCTGGTCACGTGAAACTAA | |
| | GAATAGAAATTCTGCCAGGGTTGTGGAGACTTTGGGTTGATGGCATGAAGGAAATC | |
| | AACCTGAAATTTCACATTCTGATTCTAATGAAAAGTGCAAAACAATCAAACCTCAG | |
| | ATAACCCATTGTGATACAAAGCCAGAGTATTTCAAACACATTTATGAAATTTATAC | |
| | ACCTCCCCATCTCGCAAGTACAACAAAAGGTCATTCACCGTGACAGCTTTTATTTC | |
| | TCTGTACTCAGCTCTGATAATCACATTTTGGAGTTCTGGGGACATGGACCACTCAT | |
| | GTGACCCAGCAGTTGCTTGGAGATATTTTTGGGTAAGACTTCAGACTAATATTACT | |
| | GTGGCAGTAGAAAAAAATGTTTAAAAGGACAAGTAAATGGAACCACCCAGAACAAA | |
| | ATTTCTTACGGTGGTTATAACAAAACAGGGTAAATGTCAACTTGCTACATTTTGCA | |
| | TGGCTGGAATTGATTGGGATTAATTCAACGAAGAACAGTAATTTGTTTCTCTTACA | |
| | CATTTATTCAAAGTAGCCTTCTCAACTATGGTCTTCACGTTGTTGTAGCTTTTTTT | |
| | TCTGAAATTATCAATGATGGAAGATGATTAAACAATTTCGACACTTAGAAGCCCTC | |
| | ATGATTTCAGAAAAGGAAACTCTTTTCTGCTGCGTTACCTATTGAGACTGAAGATG | |
| | GCATCATTTTCTTTTAAATAACAGATGGGTAAAAGTGATGTCATTCTTTCACTTTA | |
| | ATATTTGAGAAGTGATATGAAGTTACCAGTGACATTGTGTTCTCATAGGCATAAAT | |
| | GTCACAAAATAATTTATCTAGTATCCACAATAGGTGAATAAGGTGTTTTTGCTTTA | |
| | TATATTTTAACTGTTTAGAGTAAAAAATTAATGTGGAGAAAATTGGAATGCAGTAT | |
| | TATAGGATTACACAACTTACAAAACATGAATCCACTATGTCCAGTTAGTGTGATTC | |
| | AGAAACAGCATGCAGTTATAAAGCTGGGTGAGGCATGGGTGTCTTCCTTCAACAGG | |
| | GCAGCTACTTTGTGAGGAGTGTATATATCATTTGATTTTTTTATAAGTTAAATTTG | |
| | AGGCCCCTGTTAGATGTGAGGGTGGGCCAAAATTCCTGTGAACAGATTCTCCCCGT | |
| | TACCCCGCTTCCTTTACTCTGGCATCTCATTTTCTATCCTTTGAAAACGGTTTATT | |
| | ATTCAATTGGTTCAACTGTTTGCCAGTTGAACCAATTCTTTTTCCAAAGTGGAGGC | |
| | CCAGGAAAGCACAGTCCGAGAATATAGTGAGGTGCTATTTTATGTATGATTGTGGG | |
| | AAATTTACTTAAATTTGGAGTGGGGTTGGGCAAGGCTTGGAAAGCTAGTGAGCTAT | |
| | CTGACATAGTTGTTACTACTATTTGAAAAATATCAAAACATGGAGGACTCTTTAGA | |
| | TAACATGCCTGTTCCCATTCCATTGATTTTATCTAATTTTACGTAGCAATTACGTT | |
| | TTGTGCATTGGTTGACAAGCCTCTGTATTATCCTCAGAACAGAAAATACTGTTTAA | |
| | GGGAAATTAAGAGCCCGCAGTTACTAAAGTGACTGCGCCACCAAGTGGACAAGTGT | |
| | AAAGCCACTGTCTGGAGATGGAAGGATTCAGCTTTGCTTTATAAATGGGAATTTGA | |
| | CCTTTAAAAATGTCCCTTTTGGCACGCACGCGCGCGCGCGCGCGCGAACACACACA | |
| | CACACACACACACACACACACACACACACACACACGGCTGCTGCCCTGCAGATTTG | |
| | CTTGTTCTTGTCATAAAGCTTTCATTGTTTCTCTAGCTCTAAGTAAATATTAATGC | |
| | CTTCCAAGGCTGGCATGCCAATGGCTGCTATTAAGATCGTTTTCTCTCATTCTAAT | |
| | AACACACTTAGAGATGATTGGTAATAAAAACTCTCTTCAAGGCTTCTGCTTCTCCC | |
| | CCTTCAAAATGGAGATCAAAGAATCATGCTGTGAGGGTCCGTCAAGAAGAAAAGAC | |
| | TTTCAGCAACAGAGCATGTGGTGTGGCATAAAATAATGACAATTATAATGTTCAAA | |
| | GGAATAGCATAGAAATCACACAGTAAAACTTCTTTATTATGCTTTTCAGGGACTGG | |
| | ATGTTTTTACTTTATTATGTGAGGAAGGGTTAGATTACAGACCCTTAGCTATTCCA | |
| | CAAAGCAATAGAAGGCAGAATTTCTTCTTCCGCTACAGGAAGCACGCTTCGATTAA | |
| | GGGCTTTTTCTTTTTCTTCTTTTTTTTTCTTTAAGTTACTGCATTACTATATCATA | |
| | CTTCACTATATTTACTAAAAAGTCATGCTGTTTCTGGAAGTAGAGTTACATCTAGG | |
| | AAATACTAGGTGAATGCTGGTTAGATATGCATGTGTGCCTAAACAACACGTTTATT | |

TABLE 6-continued

Cas12i and HAO1 Sequences

| SEQ ID NO | Sequence | Description |
|---|---|---|
| | ATACTCATGCATACTAGAAATAGGGCTGTATTTTCTTCAATTTTAATCAGTACTAA<br>TGAGAATAATAAATCAAAACAAATAGGAGAGATATATTTTGCCAGGAGGAAAGAGA<br>ACTAGTTCTTCTGTAAATTTTACTGGTGAATTTTTGGTTGCTGGTTTATTGGTAAT<br>TTTCATTCCAACACAGAAGAATCACAGAAACATTCATTTAAAATAATTTTCCGGAG<br>TCAAAAACTTTTTAACACCCAAATTTCAGTTTTTGTCAAATAACATTTTTGAGAAA<br>AGTGTTAAATTAAACTAATAAAAAACCTTCCCTCATCATTAGACTTTAATGAATAT<br>GGCATATAACTAAATAATTTTGAAGAAACCAAATTATAATTTTAAAAGTAATTGCC<br>TGAAGCTGCTGTTTATCACATAAAAAGAAGACAAACTAGACATAGCATATCTTCTT<br>AAACTCTAATCTAAACTCTATGCATTTGTATACCATCTTGATTTTCAAGATTGGGG<br>AAGTGAAACGAAAACTATGTTCACACAAGAACCTGTACGTGAATGTTTGTAGTGGC<br>TTTATTTAGAATTTCCCCCCAAACTGTAAGTATTCAAAATGTCTTTTAGCTTGGGA<br>ATGACTGGACAAATGATAGTACCCCTGTATGATGGAATATTATTCATCAACCAAAA<br>GGAACAAACTATTGACACGTACAACAACATGAGAAAATCTCTAATGCGTTATGTTA<br>AGTGAAAGAAGCCAAACTCAAAAGGCTACATACTGAATGATTTTGTTTACATGATA<br>TTCTTGCAAAGCAAAATTATCAGGACAAAGAAAAAATGCATCAGTGGTTGTCAGGG<br>GATTGAACTGGGGAGAGTTTCTCTGCAAAAGAAAATGGGGACTTTTTTGGGAATGA<br>TTGAACTTTTTCTAGATCTTGATTGTCATGGCAGTTACACCACTGTATGCATTTGT<br>CAAAATTCACAAAACTGCAGACTAAAATGAGTGAATACTATTATGTATTAGTTATA<br>CTTTAATAAATAATTGCTTGGGAAATTCATTATCCTCTAATTGTTAACTTTCTAAC<br>CAAACAAACAGTAAAATTGCCTCTTTTCCATTAGCTTTATGAAGTCATTTGCTTGT<br>TTGGAAAAAATCCAATTATATTTTTTCTTTTAACTAAAATGTAATGTCAAAGTTTT<br>GGTTATGATTCTGAAACTCTAAAGCCTTTTATTTTATTTTATTTTTTAATTCTAGA<br>TGGAAGCTGTATCCAAGGATGCTCCGGAATGTTGCTGAAACAGATCTGTCGACTTC<br>TGTTTTAGGACAGAGGGTCAGCATGCCAATATGTGTGGGGGCTACGGCCATGCAGC<br>GCATGGCTCATGTGGACGGCGAGCTTGCCACTGTGAGAGGTAGGAGGAAGATTGTC<br>ACCACAGGGACAGAAGGAGGCTAACGTTTATCGACCTCCTTCTCTGAATGCACCAA<br>GCAAATATGTTCCTTGATGTTTTTACACTCAGAAACATTAAGCTCATGGACTCTAT<br>CATCAAAATACTTGTTCTTGCATGTCCTGCTCCTCTTCTTTCCAGCTGTGTGACTG<br>GGCAAGATATCCTCTCTCTGCATTGGTTTCCTTGGCTGTAAAATAGGGACAAAAAT<br>TGTACCTGCCTCATTGGGTTATGGTGAGAATTGAATGAGTTCAGGTATACAAAGTT<br>CATGGCAGAGAGTAGGGGCTCAGTAACTGTTGGTTATATTATGGGTATTAATAGTA<br>CTGTCTCAGGAAATGGATCTCTGACAGGTAGACTTGCCCAAAGTCACAGCTAGGTA<br>GTTACAGAATTGGAATTCAGCCCTGTGGCTACCTTATCTCAAAACCCTCCTGCTTC<br>CCCCAAACCAAAGTGGTTCTCACAGCCAAATTGCAAATGGAGCAACGTGGTTGGTT<br>GTGTTTTCTTCCGTGGTTTTGGGTCATGATTCTTTTTTATGGATGAGTTATATTCC<br>CAATAGAGCAGTTCCAGCTGTCTTAGGAGGGAGTGATGAGAAAATCAAATATGATG<br>TAAAGAAATCTCTTATTAGGGCTAATTTATTAACTTTCCAGTTCTCTAGCAACTGT<br>GAACATTTGAAAGGCTGTGCAGAGTAAAAAATCTCCCCAAATTGTGCTCCAGAAAC<br>TAATATAAAAGTTGGAAATGAATTATTTTGATGCTAAGCAGAGCAGAAAAAGAACA<br>CGACTATATAATATTTTAAAACATTTTAGTTTTAAGAATTAAGGATCTTGTGAATT<br>CACTTCCCTTCTTGAAATGTCTGACATAAAATTCTGTCAGGGATATCAGAATGGCA<br>CAATGAGGTTTTGCTGGACAGACTTAGCAGCTTCCTTAATTCTAGGACCACATACA<br>AATAAGTGGCTTTGGGGCCTCAGCCTTTTGTCTATGGTAATCCTGAAACATAAGTA<br>GAGAGAAGAAAAAAAAAGGGAAATACTAAATGGGTAAATATCTATACAAAATCAAG<br>ATAATAAAGGCCCTTTCAGGCTTGAAACTATAGGCAACAACCTTAGAACAAAAGAA<br>AACAAATGAACATCAAAAAACTAAAACTTTAGTGCTCTTAAATCTCAATGAAAATA<br>AAAAGTAAATGGTAAACTGAAAGAAATGGAAAAAAAATATGAGACTGTGAAGGGTT<br>AATGTCCTTTCCACGTAAAAAGCCCTTATATTTGAAGAAGAAAATAATATATTGCT<br>CAAAGGGAAAAAGAGAAATAAGTGAACAAAAGATATAAATAGGAAATTTACAAATG<br>GAGACATAAAAGTGACCAATAAACATATGAAAAATATTCAATTTCATTAATAAGCA<br>AAGACATGGAAATTATGACCATCTATTTTATTTTCCGTATATCGAATTTTTATTTT<br>AAGATCAGGCAGTATGATTAGGTTAGGGAGAAAATGTGCATTTCAAACAGTGTTGA<br>GAAAAGTATAAAGTGGAATAATCTTCCTAGAAAATAATCTGGCACTGTATATCAAA<br>GCTCTAAAAATGTAAATTCCATGTGATGTTAAAAATTCTCTTCTAGGAATTCCAAG<br>GAAATAATTATGATTTTTGAGGAAAAAAATCATTTCTGCAAGGATTTTCATGCTTC<br>TTATTTTTAGCAGGAAAATAATTTGAAAAAAATACCCAAACATCTTATAATTGGAG<br>ATAGTTTGCAAAAAATATGATGCATAAAAATGACATCAAATTTAAAAATTATACTA<br>TAGGAAGAGTGCAATAATGTAGAATGATATTTTAATTTAAAATTGTGAGAAATCAG<br>TTGCAAACAATAGTCAGGTCCTAAAATACATTTAGTTTCAAAGATCACAATTTACA<br>AATGTTTATTTATAAGTGATGAGATTACTCCTGACTTTATACTCTTCTGATTTTTG<br>GCTCAACCTTATAAACTCTTCTTTGAATTATTTTGTAAGGAGGAAATGATAACAAT<br>TAGATTTAAAAGAGTAGAGATAAAGGGACAAGGGACCATGAAGAGAATGGAAATAA<br>AGAAAGGAAGCAGAGAAAGCAAAAAGCAGAGCTCACTTGGTAAGGCACCCTGGAGC<br>CAGCAAATTATTTTTACCACATGTATTAGTTCCTTCTCACACTGATTTAAAGATAC<br>TCTTCGAGACTGGGTAATTTATTAAGGAAAGAGGTTTAACTGACTCACAGTTCTAC<br>ATGGCTGGGGAGGCCTCAGGAAACTTACAATCATGGTGGAAGGCAAAGGGGAAGGA<br>ACGACCTTCTTCCCATGGTGGCAGGAGAGAGAAGTGCAAGCAGGGAAATGCCAGAT<br>ACTTATAAAACCATCTGATCTCATGAGAACTCACCCACTATCATGAGAACAGCATG<br>GGGGAAACCACCCCCATGATCCAATCACCTCCCACTAGGTCTTTCCCTCAACACCT<br>GGGATTATAATTCAAGATGAGATTTGGATGGAGAAACAAAGCCTAACCATACCAAC<br>ACATATTGCTTTATTTGATATTTGACAGGTGTTTCTGTCCCTGTTTTGTGGGCAAG<br>TAGCTAAAGTTCCAGAGAAAACAGTTTTTCATAGCTCGTCAATGACAGACTTATTC<br>TCCAAGTCACATTTGATGGTTCCAAGACCAGTCTTTATTCTTGGTGGAGTTGGGCT<br>GAGAAGAAAGAGGAGAAGAAAGAAGAAAAGAAAGCTTCCTTAGAAACTATGATTTG<br>ACAGTGTAAGTAGGACTATTTCCTCCAGAAGTAACCATAAGAAGATATTAAATGCC | |

TABLE 6-continued

| Cas12i and HAO1 Sequences | | |
|---|---|---|
| SEQ ID NO | Sequence | Description |
| | TATTACAGTCTTATCCCCTTAGATTTATTTAACACTTATAAAGCAATTATCATGTT<br>CCAGACACTATTTTAAGTATATTACGAGTATTATAGCATTGAAGGCTCAGAGCGGC<br>CCAAATAAATCGATCATATTATTAAACCTATTTTACACAGGAGAAACTGAGGTACA<br>CGCCAGGTGAATAACCTTGCCTAGGGATGCACAATTCATAAGTGATAGAGATGGGA<br>TTCAGACAGAGGTATTCTGTCTCCAGAATCTGGGCTCCTCACCACTTTGCAAGAGC<br>TTTAATTTCAGAAACTCCTATGAAGTGTCATGAGGAGAAGCCCATTATGATCCCCT<br>AGAAGTAATTATAGTTTTAGGAGCATGCAAAGCAGACCCCTCAGGAAGATAAGTTA<br>CACAATAGACATTTGGATAAGGTGGATCCAGCAGAACAAAGAGAGGGTGGTGACAT<br>CGAGATTGCAGAGGAATTGGAGAAGGCAATGGAAGTGTACACATGTTGCCCTCAAA<br>AACATAGGGTCCTCCATTGGGTTCCTATCAGGGCAGCAACATCAGAGTTTCTATTC<br>TGTATTTATACTAGAAACCTCTCTCCAGGGTTTCTAAGTTTTCACCTATGTTTTAA<br>AGACTATCTATAGGTTATTAGTCTATTTAATATTTAGGTGTATCCAGAAAGCTGAT<br>GGTCATCAGCTCATAGCAGGTGTTCTTTGGCTGGTGTGTTTATGTTGTGGGACAGT<br>GGGTTACTTGCAAGGAAAGGATGAATGGCTGGAGTAGATGGTGCTTGTGCTCTGCA<br>TGTATTCCCTTCTTACTTCCCATTTCCATCAGACCTACCACTTTTTGCCTGACATT<br>ATCTGTTGCAACATGAGCCCATGGATAGGTGTGTTTGAAGTAGGGGAATGGGAGAG<br>AGGGTTCCCTAGCTAATGATGTACAGCAGTAGGTGGATAAATACCTCAGCTCTCTT<br>TGCTCAGGTAACTGAAGCATTTTCTAATATGGTCACCCAGTGTTCCTTGGAAGGAT<br>TGAGTCCCAGTTGCCCCCTGAGGTTGCCTGCCCATGAACACACCCTCTTTTATTGG<br>CTTCCTTCCCATTCTTTTCTCACTTCCCCATTCCTTCAATTCATTGAGATTGTTTC<br>CAAATAAGATGACTTGCTCTCACATCTCTGTGTCATTTTTGGCTTCTTGAAGTATG<br>CAAACCAGGATAATAGCTAACTGAAGGCTATAGATAGCCACAGGCAAATTTAAGTA<br>ACAGTGTAAGAATATTCATACTTGGCAGAGATTTATTTATAAAAACTCAGAAAATT<br>CACATGGAATTATGAAGTTATTATTGTATTTATTCCATCATTCCCAGAAAGAATAT<br>GGAAATCCTCTCAAGCAAGCCAGTCCTTGGGAATATTGGGAAATCTATGCAATTTG<br>TTGTGGAGTATTTTTTTTTTTGTTACCCTCCTAAATATCTGGCCGCTAAGCATTCC<br>TGTCTCCAGGGACTTAGACCCTAGCAAGGAAGAGAAGTTGGGGCCAGGTTCAGAAA<br>ACGGGTTAGTTATCAATCTCCCTGGAGAAGTGTCCCCCTCAGCAGGGTCAGTGAGA<br>GTAAGTGAAACCCATTGGTGCCCACAGGCAATGGTCTGGCCTGAGTAATTAGAATG<br>GGCCTCCAGAAAGTTCTGGGAATTGCTATGGTGCCATAGTCTCATTTTCCCCGTTG<br>ACTCTCCAGATTTATTCAGAGTCCAACTTCAAGGGCCTTTCTGCCCTTCCTCTCAC<br>AACTGTGGAATAATAATAATCCACCTTATTAACTGGGACCGAGAACTGAGCTCGAC<br>TCTTATTTTTTTGAGACAGAGTCTTGCTCTGTCACCAGACTGGAGTGCAGTGGCAC<br>TATCTCAGCTCACTGCAACCTCTGCCTCCCAGGTTCAAGCGATTCCCCTGCCTCAG<br>CCTCCTGGGTAGCTAGGACTATAGGCACGCACCGCGACGGCTGGCTAATTTTTTGT<br>ATTTTAGTATAGACAGGGTTTCACCATGTTGGCCAGGATGGTCTTGATCTCCTGAC<br>CTCATGATCTGCCTGCCTTGGCCTCCCAAAGTGCTGGGATTACATGCGTGAGCCAC<br>CGCGCCCTGTCTGAACTCTACTTTTTTACACTGCTGCATGTTTGTAGAGTGACCAA<br>TGAAGCTATACTTTTTTCATTTTCAAAATGATGATGAATACAAGGTTATCAAATAA<br>AACACAGAGGGCCCATTATGTTTGAATTTCAGATAAACAACAAATCATAGGTGTCC<br>TGTATGTTTGCTCAATCTGGCAACCCTGGATGAATAAGAGCTCTCACCTGAGGATT<br>TCTTGTGAGGATTCATGAAATAAATGCTAGAAATGCTTACACACTATCTTTATTTG<br>CCCCTCAGAGCCCAAAGTCTCTGAAATCTTTATCTTTCACACACAAAAACTCACTT<br>TCAGAAAAGTATATTCCATTTACATCTAGTGGAAATAAAAATTGTTCTTTTTCTTT<br>GTGAAAAATATTTTTATTTTAAGCTTTATGCAGAAACCTCAGGGAAAAAAAGGTAC<br>TTTTAGGAGCCAGGCTTGTAATGTAAATGTCCAAAAAAGATGAAATTGAAACAAAC<br>AAACAAACAAACAAACAAACAAACAAACAAAAAACAGTGCAAGCTCCTGTGTGGAG<br>ACTGCAGTGAGTCTGAGATTGCATGTTCCATCAGAAGGGGGCAGCCACATCTTAGC<br>TCTTGATGACCCAAGGGAGCAGGGATGTGGGGTTGCCAAATCTTCCAAAATTTTAA<br>GAAGCCAGAAATCTTGATTTCTATGTACAATCTCCTGGTTTTTAAATGTGGGCAAA<br>TAAATCAAAATTCCCTAAAACACTGTTTGGGGCAACAATGTGTGGGCCAAAGTAAA<br>TACTTTTGTGGGCTACAAGTGTCCCCTAGGCTGTACATCTGGGACATCTGATTTAT<br>GTGGAAATTTACCGAGAACTAGTTTTATTTCTGTGGCAGGTCATTTTCACTTTCTA<br>GGATTATGTTTCTTCATTGATAAAGTGAGCTACTTGAGCAAGACCAGTGGATTGAA<br>TGCCACGTCCCAAGGAGGCTGGGGTTGTTTCCAGGGATCTTACAGAACTTAGGTGT<br>GATACTGAGCATGAGCTACTTGTGTTGCATTTTGGTGTTCAAAAGAAAAGTTCTTT<br>AAATAGTTCTGCTGGAAAGACAAAAAAAAAAAAAAAGAAAAAACTTTCACAACAAAA<br>ATCTCCAAAAACAAAAACCCAGAAAACTGGCATAGAAGTGGATGATCTTTGCAATT<br>TTTTTCAGTATATAAATAAATGATTTTGATCCCATTTAAAATTTTATCAAATGCAA<br>AAAGAAACAATTCAAAGTATAGAGCTACCTTTTCTTACTCTACTGAAATCTACACT<br>TTATGTCAGCCCTGGAGGGTTTAGACGCACTTTATGTCAGCCCACTTCTTTCGACT<br>GCACTATGTCAGCCTTGGAGGGTTTAGATGAGGCAGTGAGCATTTGAATGCTTTTA<br>ATTTCCATTTTTCAAAGTACATTCTTGGTCTATAGGAGAGGAACAAGATATGTAAC<br>TATCTCTGACTATTGCTAAAAACACAAACGTCTTTAATAAATGTTGCATAAACTCA<br>GAAAGTGATACTTCAAAGTCTTGTGAAAAATGATGATCACCAGCATTTATACAGCA<br>ATTAGTATGTGCCACGCAATTTGACTTTATTATTTATTCATCTATCTTTACCACCA<br>TCTTAAAATATGTGAGTGCAAAACCCTGAGAAACTTTCTCCAACTCCTGTGGGTGT<br>GGAAATCGAGGCTTAGAGAGGTTAATGCTTTGCTCAGATTATTAATCACTTAGGCA<br>GTGCTACCTATAATATCCTGCTCTGTTACTGGTATTTCCAAACGTCATTAACTGTA<br>GCAAGAATCCTAAGGCAAGCACTATGCTATCATCTTAAAATATTTATTGCAAACAT<br>CCTATGTTTTATTGTTTTATCTTTTTAACTTTGAGAAGATAAAATAAGCCACAGAA<br>GTGAAATTAATTGGGAAATCATTCGCTTTTTGCAAAATTTGGGAGCATAAACAATG<br>GGTCATGAATTACAATCAAACAAAAGATAAAATTCTAAGAAGTCTTTTAAAGTGGA<br>AAAAAATAACTGAAAAATACTGAATGGAGGGCAGTTTTTCATGCACTGTGTTACGA<br>ATAAAAAATTTGATTCAATGGATTACTTAATCAACATTTTAATAGTTGTAAATCTT | |

TABLE 6-continued

Cas12i and HAO1 Sequences

| SEQ ID NO | Sequence | Description |
|---|---|---|
| | ATAATATTTAAGCTGTTTTATAAGTGCCTCTACTTATAATGGCACATCCGTTTGAA | |
| | ACTCTAGCAGATCATTTTTATTTATTTTTTTGAATTTTTTTCTTTATATTCTTTAA | |
| | AGAAGGATACAAAATTATTTCTATGAATATTTAACATATGGAAGGAAATAGCAATA | |
| | ATAAACATAAATGCTAACACATATAAAATAGGTGGTATCATTAGGCTAAATTTTAG | |
| | TCTTCCAGGATAAGTAGAACATCTCTGACTTCTCAAATATCCAATTAATAAAATGC | |
| | TTACTATACCATTTGGTGCTTTAAGAACATTGCCATGGAAACCTCTCAGGTTTTAT | |
| | GCACAGTAGCTATAATAAAATTTTCCTTCATCTTTCATGGAGCTACTTGAGATTTT | |
| | TTTTCTCCCTTTAAACATGAGAAATCAAAAAGAAAGAGAAAAGAAGGATTAAATAT | |
| | TCATTTATCCTTTTGCTTCTGACTTGTTATGTGGGCAAGTGCCACATGAGGGAGTG | |
| | CTGGGACCTCATATCAAGAAAAATTAAAACCTACCTAATGCGTTCCAGGAATGTTC | |
| | AGCATATTAGCAAATTCTTATTAAACTGTCAAAAAAAAAAAAAGTTTTAAAAGAAA | |
| | TTCCAGCCCCTGGATGCAATTAGAGGCTACCACACTGGATTTGATGGGCCATAAAA | |
| | CCATTAAATCTAAACACTTTCTTTTTGAGCCTAAAAGGCCAGAACATTCCAAAGTG | |
| | AAGTTTTGGGACTCAGCTATGACTTGACCACCTATTAAGATGCAGGTGGAACAGAT | |
| | TGCAGAGTAACACAAAGAGCCACACAGACCCCAGATGACTGCATTAGGGTGTAGGT | |
| | GAGAGTTTTAGCTGTTGAATTTTCTGGATTTTCCAAGATTAAGTGATCAACCTTAA | |
| | CAATGAGTGAAAGACCATTCAACAGGAAGAATTGTCATTTCCTTTGCTCTAAACCC | |
| | AAACGATGTATTTTTTGAAAGCTTTATTGATTTATATATTTATGTGTTGTGCTAGG | |
| | CGACCGACTAGATATATGTTTCAGCATACCTACTAGGAAAATATCCCCATTATTCT | |
| | CAATTTTACCTAATCCAGGCAAAGCACTGGACTTGCTTTAAGGAACATTTTTACTC | |
| | TTTCTGAAGTGGAGTGCCTGTCATGTATCAGGTGCAATGCTTGGACTTTACGTTCT | |
| | TGTGATTAATCCTTACAATAGGCCTGTGAAGTAATTCTCATTCTGTTTGACAGTAG | |
| | AGAAGAAGGAAGCCCTTGACCAAGGTCTAGTGCCAGTAATGGTGGTGATGGGGTTT | |
| | GAACCTAAGTCTGTTTCACTCTAAAGTGTAACCAAATTTTATGTTTTAGACTTGCT | |
| | TTTCTAACAATAAAAAGTCAGTGACATGCTCTTTCTGTGTGTAAGCACTCACACAC | |
| | ACACACACAAACACACATCCGTATTACATATGCTTATATATGTATTAAAAGATTAT | |
| | GGACATTTGATATATATACATATACTAAAATGTATAATTCATTGCTAAAGTATTTT | |
| | CATATAAATAGTGGCTTCAGTGTTAAAATCACTTTGCAATGAAACAAGATTGTTGA | |
| | TTAAAACACCTATTAAAAAATTAGAATCTAGCCATATTAAAGACAGTCATCGAATG | |
| | GAGTGATTTCTACGATTTTGCACCAAAATTTAAGCTATTGGGTGGCTTTCTTGAGA | |
| | GCATGAGATTGCTTCTTCTCAGAATTATTAATGTGCCTGATGACATTAAAATGTGA | |
| | CAGTGAAAAAAGTCAGAGGCTCACATGTGTATCCCAACACTGAAGTTGTTAAACAC | |
| | TGGGAGGTTGGTTGAAGTTGTTGTGTGCAAACTCAATACTCCTTAAAACCATTATT | |
| | TAAAGGCCTATCACTGTGTTATGGTCTCCATATGATCTGCCATTTATGCCAGGACT | |
| | TGACAATTCAGTAAAATGACAGAATAATAACACAGGAATCACTGCAGTAGAGCTAA | |
| | TGTTTTAGTCTGTTGCAGAGTTCTGCCCTAGAAATACAGTGAAAACAAGGAAGGGA | |
| | GAGCTAAGATGTCCCTGAGACTAATTGTTCCTTGAAAATATTTTCATAAGTAAAAA | |
| | AGAGGTCTAGAGGTGTAGTGGCAGTGTGATCACTCAAGATTATATAGCTCCGGATT | |
| | CGTTCAATGGGCCATGATGAAAGCACGGCAACGATTAAATCTGGTTTCTTGGTCTT | |
| | TCTTGGCAGTGTTTAAATTGGTTCAGTTCCATAAATTGTAAATTAAGATCTGTTTG | |
| | ACAACTTTTAAGTATTTCAAGCATAATTGTAGTTGAAGGTTTGTTCTTTTAGATCA | |
| | CTGACTTCAGAACTTTATTTTTCTGGTTAATCTCAATTGTAATTTTAGACATTCAT | |
| | AAAACAATGTTGACTGCGTCTATGTGATGGTAGATCCTCTGTGAAGACCTTTATGA | |
| | TGGTAGTTCCCCTGTGAAGATAGGATGACACACTCAATGGACATTATGGTGCACAG | |
| | TTATACAAACACTTCACTATGACAGGCCCTGAGTTTAGAACCACACAACTGCTTGG | |
| | TACTTGGTCATCGCATATTTTCCCCATTACGTAATGACTTCCTGTGCAGATGACAA | |
| | AATGCGTTTTCTCAACAAAATTATTTTCAGTGCAGCTGTTTTGATGACTAAGTTTT | |
| | GTAGGAGCTTTTTAATCAAATGCACCTAAGAAAACCCCAACACTTTAGGCCCTTTG | |
| | AACATATTACACTTTTTTGCTTCCTCTTTCCTCTTTTTCCTTAAAACCATAATTTG | |
| | GAAATTTGATTCTGCCTTCCCATAAAAGAGAATTATTTTCAAAGAAATTATTTGGG | |
| | TCTAAATTAACATGTTACTTAATTGTTCTGCTTGAATCTAGGTATATGATTAGTCC | |
| | CATATGAATTGATGTTCCAAATAATTTACTCTCATTGATAACTAATATTTTCTATT | |
| | TCCCTCTATTGTTTTGTGGTGGTGGTGGTGGCTGTGGATGAACATCATTCTCAAAT | |
| | ATATTATAATTCCCTTCCTCATCAAGCCCAGCATGATAAACTTCAGTTTTGCCTGA | |
| | TGGTTCATCATCTTATTTCTGTGTGTAAGATTGTTGGATTTGACATTAAACATTTG | |
| | GAAACTATTTTATAATTGATAACTTGTGCTTTCTCAGCTTTGAGTAAGCGCTCTCT | |
| | TCTTCATCTTATACCATTTTATTTTTATTTATTATTCACTTCTGCTTCTGATCTGA | |
| | GATCTAGGAAGCTGGACAAATCCCAGATAAGCAAGCTAAACAAACAAACAACAACA | |
| | ACAACAACAACAACAACAACAACACAACCCAAACTAAACCAAACCAAAATCATGGG | |
| | ATAATGGTTAAGTGTACTGAGGGGCCATTATGCGAACACAGTTTAATTCCTTGGCT | |
| | TTAAAACTAATAAGAGAAGAATACATAAACAAATGTGGCAAATGTACCTGTGACCC | |
| | TCTCCAGAGGGTGCCAGGCTAGAAGAAAGGCAGATTTATCAGCAAGGCATGGCGGG | |
| | CCATTGGCAAACCATGGGACAACCACTACCAACTTCACTGCCATTGCTCCATATTT | |
| | CCCTCCCGTTTTCAATGAGCCCCAACTTTGCTCAGGACATCACACATATTCTACTA | |
| | ATTTGGATGAGTCCTTTTGAAAGAAAATATCTACCTCATGGTTCTCAAAGTATGGT | |
| | CCTTGGAACATCAGCGTCAGCAGGACTCTGGAGCTTGTTAGAAATGCAGATCTTAG | |
| | GTCGCACTACAGACCTACTGAGTCAGAATCTGAATTTTGTTAACATACCCATGTGA | |
| | TTCCTCAAAGATTGAGAAGCCCTGATCAGAGCCTGGGATGAAAGTTCCTGTTGGTT | |
| | CCAAGCCAAAGGCATAGTTCAGGTCTTCACACATGACACTATTAGATGTAGATGGA | |
| | TATTGTTCCCTTCTGAAGACCCTCAAGGTCTTCTGAGAGCCTATTAAGTTCAGAAT | |
| | GACTGCCTGAAATGAGTGAGAAGTCACAAGGAGACTCTAGATAATTAAGAGATGTG | |
| | TTCACAGTAGTCTTTGATAAAAACCTGGGACAGGCAGGCTTAGTATGCAGGCCCCT | |
| | AAAATTTATGTACACAATGGATTTCCTATTTTTGCTTCTTCACATCCAGATTACCT | |
| | GGATCAGAAATAAATGTTTTCATTAAGACTTGATGTGACAAACAAACAAAACAAAA | |
| | CTCTGCCAAGCTCTAGAAGAACAATTGCATTTCCCAGCCAGAGGGAGAACACTGCC | |

TABLE 6-continued

Cas12i and HAO1 Sequences

| SEQ ID NO | Sequence | Description |
|---|---|---|
| | AGTTTTTGCTGTTTTCCAAAGCTGTTTACCTGTCCTAGCTCATTTAAATCACTGTA | |
| | CTTTGGAGTTCCGGATTAGCGTCCCCAGAGGTAGCTGCATTCATACTTGATGAGTT | |
| | CTTTTAAATCTCAGCCATTGATTGTAGGTTCCATAGTATAGGAAATTTAGCCAACC | |
| | CTCTATTGAATGGCAGTTTAGAAAGGTCGAGCTACACTTACCTTATGTCAGGTTAT | |
| | TGCAGACCCTTGTGGCATTTTTCCACCCTAGGACATGTGATTTAACTCTAATAGAA | |
| | ATCTTTATTATGGGTGGGTCTGAGATTAACTTTTATTCTATAAAACAGAAATCATG | |
| | CCACTGGCCGTAGCCCATTTTTTGAGATGGAGTGGGGGGAATGGATGATAGTAAAC | |
| | AAGGATATTAATCTCATTTATTTTTATATCATTATATTTATAGTTACATTGCAAAT | |
| | GGAAGAGTAGAGAAACCAAAAACTTACACTGGGAACTTTACAATTTTTCTTCCAAG | |
| | TATTACTGATTGATGTTTGGACTATGCAAGTGCTGCCAGCCCCTTAGACTCACTCT | |
| | GCAGCTCCCCCCATGGAAATTTGTGAACAGGTTAGGGTGGGGATAGGGAAAAGCAT | |
| | GTTCTTGTTTCACTTCTTGGATTATTTGTTCCAGGCTCTCCAAAGTAATGTGTACC | |
| | TTGGGAATGCAGAAATTATCTCCTTAGATATTCTCTCCCTATATATGTCCTCACAG | |
| | GGAATTCTTGGAATTGGAGAAGATTCCACTCTCCTTTAGGAGCTTTCTCCATAAAG | |
| | GTATTGAGCATTGGACACTATATTTGCAAGGGAAAAGAGGAATGGGTCTCTTGAGC | |
| | ATCAAAATCATTGTAGAAGAATCTCCAAACTGTTTTTCAAAATGTCTGTACTAACT | |
| | TACATTCCTGACATCAATGGGTTCCCTTTTCTCCACAAGGGTTCCCTTTTCTTTGC | |
| | ATCTTCACCAACACTTGTTATCATTGGTGTTTTTGATAATAACCATTCTAACAGTT | |
| | GGAGGTGATACTTCATTATGATTTTAATTTAAATTTCCCTGATAATTAGTGATACT | |
| | GAGCTTCTTTCATATATCTATTGGCCATTTATATCTCTTCTTTTGAGAAATGTCTG | |
| | TTCAGATCCTTTGCCAATTTTTTTTCTTTTTTCAACTTTTATTTTAGAATCAGGGA | |
| | GCCATGTGCAGGTTTGTTACAAAGGTATATTGCATGATGCTGAGGTTTGGAGTGCA | |
| | AATGAATCCATCACCTAGGTAGTGACCACAATTCCAAACAGGTAGTTTTTTTCAGC | |
| | CCTTTTCCCCCTCCCAACCCCACTGTTGTATTCCCCAGCATCTATTGTTACCATTT | |
| | TTTTGACCATGTGTATCCAATATTCAGCTTCCATTTATAAGTGACAACATGTGGTA | |
| | TTTGGTTTTTGGTTACTACATTAATTCACTTAGGTTATTGATTTCCAGCTGCATCC | |
| | ATGTTGGTGCAAAGGACATTATTTTGTTATTTTTTATGGCTACATAGTATTCCATG | |
| | GTGGATATGTACCACATTTTAAAAATTCAATCCACCATTGGTGGGCACCTGGATTG | |
| | ATTCCATGTCTTTGCTATTGTGAATAGTGCTGTGATGAACATGCAGGTGCACGTGT | |
| | CTCTTTGGTAGAATGACTTATTGTCCTTTGGGAATATACCCAGTTAGTGGGATTGC | |
| | TGGATCGAATGGTAGAAAAACTCTCAGGTCTTTGAGAAATCTCCAAACTGCTCTCT | |
| | ATAGTGGCTTATTTAATTTACATTCCCTACAGCAGTGTATCAGCCTTCTCTTTTCT | |
| | CCACAGACTCACCAACATAGTATTTTTTGACTTTTTAACAAAAGTAATTCTGACTG | |
| | GTATGAGATGGTATATCATTGTGGTTTTGATTTGCATTTCTTTGATGATTAGAGAT | |
| | GATGAGCATCATTTTCATATATTTATCAGCCTCTTTTATGCCTTTGTTTGAGAAGT | |
| | ATCTGCAAATGTCCTTTGCCCACTTTTTAATGGGGTTATCTGTTTTGTCATGTTGA | |
| | TTTGTTTAAGTTTCTTAAAGATTCTGGATATTAGACCTTTGTTGGATGCATAGTAT | |
| | GCAAATATTTTCTCCAATTTTGTAGGTTGCCTGTTTACTCCTTTGATTGTTTCTCT | |
| | TGCTGTCCTTTGCCTATTTTTTAATTGGGTTATTTGTTTTCTGGCTATTGAGTTGT | |
| | TTGAGTTCCTTATTTTTTTTTTTGGATATTAGCACTCATTAGATATACACTTTACA | |
| | AATATTTTCTCCCAATACCTGTGTTGTCTCTTGATTCTGTTAATTGTTTTCTTTGC | |
| | TGTGCAGAAACATTTTAGTTTCACACAATTCCTTAAAAAACTAAAAATAGAATTGC | |
| | CATATGATCCAGAAATTCTACTTCTGGATATTTATTGAGAGGAATTGAAATCAGCA | |
| | TGTTGAAGAGATATCTGCACTTCTATGTTCGTTATAGCATTATTCATAATAGTCAT | |
| | GATATGCCATCAACCTAAGTATCCATTGACAGATGAATGGATAAAGAATGAGGTGT | |
| | ATGTACACAAAGGAATACTATTCAGCCTTTAAAAAGTGGGAAATTCTGTAACAACA | |
| | TGGATAGACAGATACTATATGATCTTACTTATATGTGGAATCTAAAAAGGTAGGTC | |
| | TCACAGAAACAGATCATAAAAAGGTGGCTACCAGAGGCTGGGAGAGGAAGGAAAAG | |
| | AATGAGGAAAGTGACATATTGATCAAAGTTGTACAAAGTTTCAGTGCGACTGGAGT | |
| | AATAGGTTTTAGTGATCTATTGTACTGCATGGTGTCCACAGTTAATAGTAATGTAT | |
| | TGTATATCTTAAAATTACTAAACGATTAGGTATTTAATGTTCTCCCTACAAAAAAA | |
| | TGGTAAGTTGGTGTATTAGTCCACTTTCACACTGCTATAAGGAACTGCCCGAGACT | |
| | AAGTAATTTATAAAGAAAAGAGGTTTACTGGCTCACAGTTCTGTATGGCTGGGGAG | |
| | GCCTCAGGAAGCTTACAATCATGGTGAAAGGGAAAGCAGGTATGTCTTACATGGTG | |
| | GCAGGTAAGAGATCCTGTGTGTGAAGTGAAGGGGGAAGAGTCCCTTATAAAACCAT | |
| | CAGATCTCGTGTGAGCTCACTCACTAGCATGAAAACAGCATGGAGGAAATCACCCC | |
| | TATGATCCAATCACCTCTTTCCCTCAACACATGGGGATTACAGTTCCCTGCCTTGA | |
| | TGCGTGGGATTAAAATTTGAGATAAGATTTGGGTGGGGACACAAAGCCAAACCTTA | |
| | TCAGTTGGTGAGGTGATGAATATGGTCATTAGCTTGTCTAAATTTGTCTGCAATGT | |
| | ATACATAGATCAAAACATCACTTTGTACCCCATAAACATGTGCAATTACTATTTTC | |
| | CAATTAAAAATAAATATAAATAAATTAAAAATAATTGCAAAGGAAAGCTGGCTGTG | |
| | GAGAAGATTAACAAATAATGACATTAAGAAATTCAGGTCCTTGGCAAAATTAGAAA | |
| | TACATACAAAGCTATCCAGAACTTATTTTTCCAAATGCATTAGGCGTCCTCTCACC | |
| | TTACCCTTTACAATTGCATGGCTTCAGAGATTACACAGAAAACGTTCAGAAACATT | |
| | GCCCCAGTAGATGATCTTGCAATGCTATGAAGTAGGCAGAACAGCTGTGGCTATAG | |
| | CAATTGTGCAGATAGAACGTACTTCATGGATGGCAAGACTGGGACTCTAGGACAGG | |
| | CTTTCAATCCATTCTACCCTGTTGTTGTTCTGAAATGAAAGTTTTATCTCCCAGTT | |
| | TATATAGGTAGCCTTATCTTTGATGCTTCAATACCTGAGACCTGGCCAGTGTCCCT | |
| | TTTAGTGATTGTATGTGTGTGTGTGTGTGTCATATGCAATTTCCTTATAGCAATGG | |
| | CACAGTGTATCACTGTTTAATTAAAGAAGAGAAAGAAATGCCAAACATACGAATAA | |
| | AGTCTGAATATATCTGTAACATTAAAAGTGTAGGTGTCTATCTTTGAAGATATGTC | |
| | TTAAGGACAATGAAAGAGTCAGTGAGTAAGAGAAGAGAGTCCTGGGATTTCATACA | |
| | AGATCAGTGTTACTTGATGGTGTAGGCTCCTAGGTATTTCATCTTTAGGATATACC | |
| | GTCTATTACAAAAGCCAAGATTTTTAGATTTGGATCAACATTAGGGAACTTCATTC | |
| | TAGGCAAGAGCCAGGTTTTGCCTTTATGTTAATATGACCTCAGCTGTGAGCTCCAT | |

TABLE 6-continued

Cas12i and HAO1 Sequences

| SEQ ID NO | Sequence | Description |
|---|---|---|
| | TTTGCCAGGCATCTTAAAACTGCAACACATATCATTGGAATCTTCCGTTACAGTCT | |
| | AATACATAGCCACACATTGGGAGCAAGAATGAAATCCAACCCCTGTCCTTTGCAAA | |
| | ATGCAATGAGACAGTGTCTGCTTTGGGAGCAGGGAGTCAGAATTTCATTGTGGACA | |
| | ATGGATAAGGTGAGTAAAAGGGCTTAAAACATTTGTGCTTTCAAGCCATAGGCTAG | |
| | GATAACGATAGTCAGAACTTTTTGATGAAGTCTGACCATGCTACGCCATTTATAAA | |
| | ATTTTGAAGCTTGTAAGTATTACCCCAAAATGAGCAGTGTGAACTCAAAGGGTTTA | |
| | TCATTGTCTCTCAGGCAAAGGTAATATTTGAATTATTTAGCAAAGGACTTTGAGCA | |
| | ATTGGAAGAGATACTCAGCTGCTGGTCTCTAGCGCTCTAACAGGGTGGATGCCCCC | |
| | CGCTCTGCCGGCACTGATGTTTAAGTTGCTGGATTATGAGGAAGTCTGGGGATTCC | |
| | TTGGGGAGAAAAGGAAGTGATGACATATTGAAGCACAACGACATATTGAAGAGACT | |
| | CGGGGGCTGGGGTGATAAACTTCAGAGCCGTGGCTATTTACCAATTGGAGTGTAAG | |
| | TATTTTAATATTTTAACAAACATAATTGCCATTCTGGTATGTACCAACTTCATCTC | |
| | AGATCTGTCCTTAAGAAATAGGCAAATTCTTTATTGCCTCTCTGAATGGTTCATAT | |
| | AAATTCCCAGGCTCCCTTAGCTCATTCTAACATAAAACTGTATTAAAAATAATGAA | |
| | TGTAATTCATCAATAATTTTCCTTTGTCATAGCAAATAGTCACAAGTGGATTGAGA | |
| | TCAGAGTGATCACTCATATTTGTTCTGGGGAGAAGGGAGCCTGCTGTTTTGCTCCT | |
| | GTTTTCTCCTAGGACTAGTATTTTAGCTTCAAATGATAATACCTTAGCACAGACTC | |
| | TGATATTCCTCCTACATGCAGGAGCATTCTCTTGGAATAATTTTGGGGATGCCAAT | |
| | TCAAAATTTCAGCCATGTATGATTTACTTATTGGAAAATAATCACTGAGCAGCAAT | |
| | AACTCCAGCAGTTACTTGTATCAAGGTAGAATCAAGAAATAGATGGTATGGACCAA | |
| | ACTTGCTTCTCTCTAAATATGCATACCCAAGTGATTTGGGTAAAATGTTTGTGAAG | |
| | GGCTTACATTTCCTGCAAGTCAGATGGTTTAAGAGAAGTAGAAATTATGTGTGTTT | |
| | TGCAGCATTTTGGTAATCTGTGTGGAGTGTCTGTAGATATTTCTCATGAGTTCAAG | |
| | GGAATCCTTTTGTGGATTTTGATGTTCCTATTGGCAGAGCTGCTGCTTGACTACAT | |
| | GATGTCTTTGTATTAACTACAAAAACATGCCCTATCATCTGAGTGATTTTCTCTGC | |
| | CAGACCCCTTTGTGCATCCACACTCTGCACCTCCAGTGTACGGAGGACCTTCCCAC | |
| | TGGATTCTAAGATTCCATGCCTTCCCAATGCATGGCAGTGTCTCTCATGCACATGG | |
| | CAAACCTACTCTCTTGGATGTCACTGCCCTGAAATATTGAGGGAGTACATTTATCT | |
| | AGGCATGGTACCAGGGAGTCATTTAGACATGTAGGGAGTCTAGAAAGATCATTGCC | |
| | CTGGGAGAGTGCTCAGCCATGCTGAGTTCTCCTACTTTGTTGCTCATTTCTGTGTG | |
| | ACCTTAGGTAACATCCTCTTCAGGACTTTTTTTTTTTTTTTTTTTTTGACAGGGAG | |
| | TCTCATTCTGTCATCCAGGCTGGAGTACAGTGGTGTGATCTCAGCTCACTGCAATC | |
| | TCCGCCTCCTGGGTTCAAGCAATCCTAGTGCTTCAGTCGCCTGAGTAGCTGGGATT | |
| | ACAGGCATGCGCCACTACGCCCAGCTAATATTTGTATTTTCAGTAGAGATAGGGTT | |
| | TTATCATGTTGATCAGGCTGGTCTTGAACTCCTGACCTCAAGGGATCTGCCTACCT | |
| | TGGCCTCCCAAAGTGCTGGGATTACAGATGAGAGCCACCAACCCTGGCCAGGACAT | |
| | AATTTATTTCAGGTGAATTGATTGTTGGAGGATTTTGATCCAAGCAATCAATGTCC | |
| | CTTGGTGTTCCTTTCAAACAGCAGTAAGTGACCTGAATTTATTTTCCACATTTCCA | |
| | AATCTTAATGAAAATCAGACAATGGTCTATATGTTCATTTGTGTTCTTACTTAATA | |
| | AAATGTGGGTTTTAGACAATATTTTGCCAGTCATGAATTCCTATAGAAGGAACTCT | |
| | TTGGGAGAACAGACTAGTGATCTATAGACATGATGACCTCCAACTCAGATCTTCTG | |
| | TAGCTAACCACTGACCGGGAGAACATGTATGAAAAACATCTTCAAAGGCATTGAAA | |
| | AATTAACATTTATCAAAAACAAAATACATTTTATTTCATTTGAACTTAGACCTTTA | |
| | CTATCTAATGGCTATGGTACTATTTAAATGTCAAAGTGTGATCTAGCATCAGCCTA | |
| | ATCTGGTTAGAAATGCAAACTCTTGGGCCACATCTCAGACTTACTGGACCAGAAGC | |
| | TCTGTGGGTGGGACCCAGAAATCTGTGTTTCATTCACATGCCCTCCAGGGGATTGT | |
| | CCTGCTAAAGTTTGAGAATCATGGAAGCTTTTTAACCTCTCATTATAGCTTTATAA | |
| | GCAGCAACTCACTGGATTCCTATCAACATCCTGTGAGTGTCATTTGGACAAGTATA | |
| | TTTATACCCATTTGATGCATGGTAGGCACACAGATGAGTCAAATGACTTGAAGGAA | |
| | TAGAGTTTTACATAATATACTTTTATATATTTATACTTCTAATATATTTATACTTT | |
| | ATAACAGATTTGACTGTTTTATATATTGCATATAAACATTATATCAGTTTCTCCTC | |
| | CACTAAGGCTGACTCCAATTTTACTCCAATTTTACTACCAATTTTTGGAAGAAAGC | |
| | CTACCTATCACTCATGTTCTCTCAAGTACCCTCTAAAACTATTAGTTAGATGACTC | |
| | TATTTAATTTTCCATTTATTTGCCCGTTTCTTGCTACCTTTCCCCCCAAAATGTAA | |
| | CTGCTACCTTGCTCAAAAGGATGTGTCTACTTGGGATATCTAGCACACACATTTTA | |
| | TGAGATTTTAAAAGACAACATAAATGGTAAACTATATATTTAATACAATTTTGAAA | |
| | GACAAAATTTTAAAATTAAAAAGGAAGAAAAAAATTAAACTAACCCCATAATTCTC | |
| | CCACCCATCATTAGCATGTAGTTTGTTTAGATTCATCTACCAATAAGTAGAATTGT | |
| | ACAAATTTGATATCATGTAATACATGTCATTTTGTAAACTTTTTTCTTTCCTTAAT | |
| | ATATCTATATATCATAAACATTTTTCTATGTCTATATTATTTTAAAATTGTAATAC | |
| | CCAGAGTTCTCCAGAGAAACAGAATTAATAGGATCTCCCCCTTGGAGATTTCTCAT | |
| | CTTTTTCTCTCTCGATAGATACAGATAGATACATACATAAGTCTATCTCTCTATCT | |
| | CTATCTTTATCTCTAAAACACCTATCCATAGATAGACATTTTTAGGAATTGGCTCA | |
| | TGTGTTTGTGGAAGCTTGCAAGTTCAAATGTGCAGAGTAGGTGGGCAAGCTACCAG | |
| | GGAAATGTTGATGTTGCAGTTCCAGTCTGAAGGCAGGCTCCTTGCAGAATTCTTCT | |
| | TTTTCTTAGCAGTCTTACTTCCCCTTCCTCTTCCCCTTCTCCTTCCCCTTTCCCTT | |
| | CTTCTTCTCCTTCCCCTTCTTCTTATTCTCCTTCACAGACTTATTTTTAAGGCCTT | |
| | GAGCTGATTAGATAAGACCCACTCACATTATGAGGGATAATCTGCTTTACCTGTAG | |
| | TCTACTAATTAAAATGTTAATCTCATCTAAAAAACACCTTCATAGCAGCATTCAGA | |
| | CATGTTTCACCAAATATCTGGGCACCATGGTTTAGCATATTGATGCAGAAAATTGA | |
| | TTATCATAATAATATTATTTTTTTTTGAGATGTAGTTTCACTCTTGTCACCCAGGC | |
| | TAGAGCGCAATGCTGCAATCTCAGCTCACTTCAACCTCTTCCTCCTAGGTTCAAGC | |
| | GATTCTCCTGCCTCAGCCTCCTGAGTAGCTGGGACTACAGGCGCCCATGACCACGC | |
| | CCGGTTAATTTTGTGTTTTTTTAGTAGAGATGGGGTTTCACCACGTTGGTCAGGCT | |
| | GGTCTCGAACTCCTGACCTCAGGTGATCCACCCGCCTCAGCCTCCCAAAGTGCTGG | |

TABLE 6-continued

| SEQ ID NO | Sequence | Description |
|---|---|---|
| | Cas12i and HAO1 Sequences | |
| | GATTACAGGCGTGAGCCACTGTGCCCAGCAATAATATTAATTTTAATGGGTGTGTT | |
| | CATTTCATTTTATATATGACCTACAATTTAACCAATCCCCTAAGGCTGGATGTTCA | |
| | GGTTCTTAATATTTTTTGCCCGTATTTACAGACACCTTTGACTATTGGATTTATTT | |
| | TGTTCTTCAGGAACAATATACAAAGTGTGGAAAGAAATGTATATTTCTAATCATTG | |
| | GAAAATAAACACTGAGCAGAAATAACTCCAGTAGCCATTTGTATCAGAGGAGGTAG | |
| | AATCAGGAAATAGATGGTATGGGCCAGACTTTCTTCTCTCTTTAAGAGATTTGACT | |
| | TCATATTGCCAAATTGCCCTTCTAGATGTCTTTACTCATCCAACTACAATTCAAAG | |
| | GTTTGGGAGGGTAAGCAATGCCAGGCCCATCTTGATCATCCCCTTTCTTTCTCAGC | |
| | CTGTCAGTCCCTGGGAACGGGCATGATGTTGAGTTCCTGGGCCACCTCCTCAATTG | |
| | AAGAAGTGGCGGAAGCTGGTCCTGAGGCACTTCGTTGGCTGCAACTGTATATCTAC | |
| | AAGGACCGAGAAGTCACCAAGAAGCTAGTGCGGCAGGCAGAGAAGATGGGCTACAA | |
| | GGCCATATTTGTGACAGTGGACACACCTTACCTGGGCAACCGTCTGGATGATGTGC | |
| | GTAACAGATTCAAACTGCCGCCACAACTCAGGTAACCATGATCATGTGGGCCCCGA | |
| | GCTGAGGCGAAAGGGATCTTGACTGGGAATGTTAGGGTCTGGGTTCTACTGATAGC | |
| | AACGTTGCTAAACATCTAGTTAATCTTCAGCTAATCACATCCCTTTTGTAGACATC | |
| | ACTTTTTTTGAGATACACAATAGAAACAGAAATGGCCTCTATAAAAGTCCAATAAA | |
| | TTTTCAGACCAGAGTGCATTAAGGGCTTTGGCTTTGGGAAGTATGAATTGCTATAC | |
| | AGATGGAAGATACTGAATTTTGCCCAAGCAGCAGTTTATTATTATCATCCTGGTGC | |
| | CCTATTTCTTTGTTAAAGTCAAAGAGCCACCTTTACCTTTTATTTTTAATGGTACA | |
| | TGGGACAGCTAAGGCTAAGAAGATTGAAGAAAGAAAATAATGAAGGTTTAAAAAAG | |
| | CCACATCTTTGATCCCTCACTGTCTACTTCTTCTTTCAGCAATATTCCTTTCACTG | |
| | TGGTTCATCCATGGGTCAAGATTCATTGATTCATTCACTCAAATCATTCATCTTAG | |
| | CAAAAACAATATATCACATAATCTGATGTTGAACTATAAAGGTTTCATCAGGTCAT | |
| | TCATTCACCCTGTCCACAAGCTGTGAATTATTATCTCTTTCCTGGTTGTATTTTGG | |
| | GATTACAATCATCTTGAGTCAAAGCTGGAAACTGAGTGGAAGTCTCTGGGAAAGAC | |
| | TCAAACCTCCTTAAGCTATACACCTCTTTTCCCCATCAGATTTTCCTTCCTTCAGT | |
| | TTCCACCAAAATGTGCTCTTGGATTTTTCATATGAATGTATAATGTACCTCAGGCC | |
| | TATAAGTATTTTAAAAGGGATCAAAATCTTAGTTTTAATGGAGGACATTTTTATGA | |
| | TGGACTCCTACAGCATCCATCAGAATATGTAAGATGATGAGGAATGTCTTCCTGTG | |
| | TTCCCAGATCTCATGCCACAGAGGCCCTTGCTTACTCTATGTTTGAATTGTATTTG | |
| | GAAAAAAAAAAAAAAACAAAAAACTAGGGCTAGCAAAATTGAAAAAAGATAAAAGA | |
| | CGAAAGAAGCCACATGTAAACATACTGTGTTTACTCTTCTAAAATATTAAAAAATG | |
| | AAAAGATCCAAAATCAAATTAATATTCCCCTGGAATTTCATATCTATTTCAGTGAC | |
| | TGTGGAGTGAATCTCACCACGAAAGTTGCTGCAGTCTTGTATAAGTTTCACATAGT | |
| | TTTACTGTGTTTGTGCCTATGTGAGAATAAACTACTGTGCATAAAATCTTGCTGTT | |
| | GAGCCATGTGTGAATTAGCTGTGTGATGTTACCTCCCTGTTACTACCAGGCTGGTT | |
| | TAGGATATCATTTCTGTATGTGGCACCAGGATTAGACCAATGACAGAAAAAGAAAG | |
| | TGCTCTCCCTGCCAAACTGGCCAATAAAACTGTTCCACATATCCCAGACTCAGGGT | |
| | TACCTAAACAACCTGTGTTTAAAGAGAACAAAAACAAAAGCCTCTGACATAGTCTT | |
| | ACTCCTTGCCAAATTCGTCAGAAAGCTGATGGATTCAAATTCCCCCAATATGAATC | |
| | CCGTATTTACATTATTTCTCTATTTTGACTACTTTTTTTTTTTTTAAAGACTTTC | |
| | TAAATAGTTTCCCACTATCGAGGCTTCTTAGAGGAAACATTTCTCATTATTTCCCC | |
| | TTGGCTATTTGAAAAGGAATTTGTTCTTCCTTTTCCTCCATCTCTTAACACTACTA | |
| | CTACTAACAATAGTAACAACAATAGTAAGTACAGTAGGGTTTTTTGTTTTGTTTTT | |
| | AACTTAAGACATACTTTCTTGTTCTGGATACCAAAATATGTTTCACAGAGGCATCT | |
| | ACTTAGATGGGGTGCAGATGACACAGTTGTTAATTCTGGCAGGTACCTCTTGCTTC | |
| | TTCACTGCTGGGGCTACTCAGTGAGTGGCAGGAAGGTTGATTTGCTTTCCCCCCTT | |
| | TTCTTTTGCTCCTGGGCTCCTTCCCAGATGATGTGACGGGCCATGAAACAAAGACT | |
| | CTTTTCAGCTGTCGGTGTGCATAGAACTGGCTGCGGCTTCCTAGCTTGTCACATCT | |
| | CCGGTCTGAAGATGATCAAATAATGAGCAACACATCCAGGTTATAGGGAACACGGG | |
| | AAACACCCCGCAGCTGGGTGTACCCCAGCCCCTCAGAGTGCACATTGGTGTTGTTT | |
| | GTCCTAGTGGACTTCGGAGTAGGCCAGTGCCTTCTGGTCAGTTCCTCAGTGGCCCA | |
| | CATTCAGCTCTTAAAGGCAGAGCATGCTAACGGGAGGTCCAGGCTTCCGCCTGAGG | |
| | CCAAATACACCCCAAAAGCTCATCTGTTATAGCCTGATATGAAATCGGTTTCTTTC | |
| | TGCAACTGACCTGACTCATAGAAAGTGAAGCCTGGCTTTTCATAAGTGAAGTTTGG | |
| | CAGGCAAGGGAGGCAGGAAATCCAGAGGAGAATGAGCCTGTAAAGCATGGCTCCTT | |
| | CCAGCCCTTGTTACTTCCTCTGCCCAAGTGTGGGGGAGGGTCCTGTCTCTTGGCAT | |
| | CTGGGCCCAGCAAGAGTTCAGAGGTTTGGTAGTCTCTGCTTGGTCCATATGCAAAA | |
| | CACATGTATGTGTATACATTATTAATGGCAAGGGGGTTCCTGAAACTGAGAGGGAG | |
| | TAAGGAGACTTCTCATCTGCTCTTGGAAGAAGCAAGGAATGAAGCCAGTTCAGTAG | |
| | ACTGATTCCTGAGGCTTTGGGGCAGGAACTTTTTCTTTCTCCATATCCCCATGGAG | |
| | ATGGTTCATTTACCCTGAATTAAGATTTGGCCCTTCGGTGCAGTGCCAAGGCAGTT | |
| | TAAAGAGAAGAAAAGTAATTTCTGATCATTGACTAAGATCAAGGTAAATCATGACA | |
| | CTTATCCTTTCTATGATTTGCCAGTGACATGTTTTCTTAAGCCCAGAAATGATTTA | |
| | TTGATCGCAGCAGCCAGAATATATCACACTAAAACAGATCAGCCTGCCACTGTCTT | |
| | CTCAGGTCTCTCATGATTAAAGTGGCCTGCTTTAAAGTAGACTCAATGTGAATAGG | |
| | TCTCCATGACCTCTGCCTCACTGCGTAGCACTCACATCCTCACCCACTCTTGCACT | |
| | CTGGCTTCCCTGCGGTTCTTTCAATATGCCAGGCATGCTGGAACCCCGGAGCCTTT | |
| | GCACTGGCTGTTCCCTCTGTCTGTAACAGTCATTCGCAGAATCAACGCATGACTAA | |
| | TAGCCTCACTTCCATTGAGTCTTGACATTAGGAATGGATATACATGTCTATATTGG | |
| | GAAACCACAATAAAAATTGATGGTAGAGATGCAAATATGAGCAAGATAACAGGGTG | |
| | GGGGCAGGGGAGAGAGGTCAGTGGAGGACTTGGCACAGTAGCCTCTTAAATGGCAC | |
| | AATAGCCTCTTAAATTTTTGGTTAAGAAATCATTCACATTGATAAGTATGGCAGGA | |
| | TAAAGGTGTCCATGAGTGAATCCCGGGAACCTGTTACTTTATGTGGCAAAAGGGAC | |
| | TTTGCAGATGTGATTAACTTAAGGGGCTTGAGATGGGAAGATTTTTCCTGTTTTTA | |

TABLE 6-continued

| SEQ ID NO | Sequence | Description |
|---|---|---|
| | TCAGTAGGCTTGATATAATTAAAAGGGTCCTTATAAGAGGGAAGCAAGAGTGTCAG<br>AGTCAGAGAAAGAGATGAAATGACAGATGTAGAGGTTGGAATGATGTGGTCAGGAA<br>CCAGGGAAAGCAGGGGGTATCTAGAAGCTGGAAAAGACAAGGGAATAGGGCTTCCC<br>CTAGATTCTCCAGAAATACAGCCCTATTGATATCTTGAGTTTAGTCCAGTGAGACT<br>TATTTTAGACTTCTGACATTTGGAACTGTAATATAATACCTTCATGTTATTTTTAT<br>TGCTGTTGTAACAAATAACCACAAACACAGTTCTACTAATTTCTTTCTCAAGGTAG<br>CTTCTCAATTTTGCCAACGCTGGTTACCATACATACTTAAAGTTTCATTTTGAGTC<br>TCTGAAAACTCACATCTCTCTTAATCTGCTCTACTTTTTTCTTGGCTTTGTATAGT<br>GCTTATGTTCTGCTACACTTTGTAATTTATTGATTATGCTTACCATGGGCAGGGAT<br>TCTTAACTGTTTTATTTATTTATATATCTTAAACATTGAAAACACTGGCATGTAGT<br>AGATGCTTAATAAGTAATTGTTGACTCAATCGATAAAATATACTAGAACATACAAG<br>ATTTTCCCAATGTAACATAACTAGTAAGAGGCTGAACCGGGATTTGAACTCAAAAT<br>TCATTCCCTGAACCTTCTTCTAGCAGCCACATTGAGGAAGAAATTACCAGGGCTGT<br>GTTCTCAACACAAGTGTTTTCCGAACCACAGAATTAAAGGCTGGTGGCCCATGTAT<br>CAGTGTCTGTATTTATGAGCCCCTCTTTCAATCTCTTTCTTTTCATATTGTGTTGA<br>TGCTGTAGCTTCTACTGGTCATGTTATTTTTTTGTTTCCCAAGACGGAATTATGTG<br>GCTTTATCTTTAATGTTGCATTATCAATACTTATAATAAATAATATTATGTATTAC<br>TCAATATTCATGATTAATAGTGTTACTATTGGTTATTTAATAATGTTTAACTTACA<br>TTAGCAGTTGTTACTATTTTTATGATGCTAAATTACTAACAGCTAAAACAACTTCT<br>ATATTAAAAAGTATATTTGAGTGCCACTCAAGAGATAATGAGTACCTTACAAAGAA<br>GAAATCTTGTTTCTCACCTTTGCGTCATTAAACAGATCAGGATTTGGAGAATTAAG<br>CCCTAAGTAATAGTGTTATTATTTTGATCTCACCCCTTTTTTTCTTATGAAATGGA<br>ATACTTTGGTTATCAGAAGCCACTTTAAGCATATATATATATATATATATATATAC<br>ATATATATATATATATATGTCATAATCCGAATAAAAATAGCATTCATGGAGGTTTC<br>TTTTGGAGCCTTTGGTAAAACACTCCATCGTGGGTCTCTGTCAAGATATCTGAAAA<br>CTTTTTCTTGGCTTCTGGCTTTGAACAAAGTTTCAGAGTAACAACAAGGCTTCATT<br>GTGCACTGAAATTTCTGTAAGGCAACATTCATTCAAGTGTTGATTCGCATTTCACC<br>ATCCAAGAATAACAACAGTTATTTATATAATTTTATCCACGTTTCTGTTTTTTCCT<br>ATCCATTTCACCCTTTCACCCCACCCCTGCTGAAACACTGGAGCTTGTTTGGGATG<br>GGGGTGGGGTGCCATGCAGACTACATACACATACAGATGTTTTTCTTTTTCTTTTC<br>CCGGTCTTGCTATGGGATAGACAGACTGGACTTTTTCTTATTAACAATATTATTTA<br>AAAGCTTGGAATTTATTATCATTTAATCATTTGTATGTAATGAAATAGGTCTCCAT<br>GGTAAAGATGTGTTTATTGACCAGCGGTTAGCTTTATTCAAATTAGGGTGACCATA<br>GAAGACCAAGGACTATGATATAATGTACAATCCTAAGTGGTTTGATTTAAATAAAA<br>AGAAAGACCAGGCATTTCAGCTAAAATCCCCACCAAAGCCCAATGACTAGATGGGC<br>ATCCATATGACTCAATGAAATTTTCTATGATCTTAAATGGCCATCTGAGTCCGTGA<br>AACTATAGGACTAACTATTCAATCCTTATTGAGAAAGCCTTGTTAATAGCTTGAAT<br>TGAGTTATATGGGATAGGAATGTTCATATCTTTATGACAATATATGCCACCTAAGC<br>TACATAACCAGCTGTGTTAGCTAAAATACTCTAAAGTGTAAAAAATCATAGTTTTC<br>TATTAAAGGAAGTCATGATTGTTAAAAATAATTTTTAAATAGTGTGCCTAGATTCT<br>TCTAGTATAATATATAATTTTTTTTTTTTTTTATTTTGAGACAGAGTCTTGCTCT<br>GTCACCCAGGCTGGAGTGCAGTGGCTGGAGTTGCTCACTGCAACCTCGCCTCCCGG<br>GTTCAAGCGATTCTCGTGCCTCAGCCTCCCAAGTAGCTGAGATTACACGTGCCCAC<br>CACTATGTCCGGCTAATTTTTTTGAATTTTTAGTAGAGACTGGGTTTCATCATGCT<br>GGCCAGACTGGTCTTGAACTCCTGACCTCAGGTGATCTGCCCACCTCGGCCTCCCA<br>AAGTGCTGGGATTACAGGCATGAGCCATTGCGCCCAGCCGATATATAAATTTTTAT<br>ATGGCTCCATGATCTTCTCTACATTTAATGACAGAACTGGTGGAGGGGAAGAAAGA<br>GATGGGACTAAGCCAGAGATCAATATACATACAACTATACTTTGACCAAAAAAAGG<br>GAGATTGACTGGCAGGGGAATTAATAGTATGCAGAAGAGCAAGGTGAGTCCAGTCA<br>CTGTCATTATTCAAAAACAGCCTTTCAGGAGAAGTTTGCAACTGAATTTGGGACTG<br>TGGGCAGATAAGTCACAGGAATGATTCTATTGTGTATCCTGAAGTCATCCATCCAG<br>CTAGGAGTCAGAGGTGCAGGCTGAAAAGACATTGCCCCTAGAGTGGGGAACTGCCA<br>AAATCTAGCCAGGATATTAGGCCAAGAGAAAAGACCTCAGGCACAGGGGAAGCCAG<br>CTTCAGA | |
| 929 | AACGAACTCCATCTGGGATAGCAATAACCTGTGAAAATGCTCCCCCGGCTAATTTG<br>TATCAATGATTATGAACAACATGCTAAATCAGTACTTCCAAAGTCTATATATGACT<br>ATTACAGGTCTGGGGCAAATGATGAAGAAACTTTGGCTGATAATATTGCAGCATTT<br>TCCAGGTAAGAAAATTTATTTTTTAAAATCATGTTTTAAAATTACACAAAGACCG | HAO1 exon 1 |
| 930 | TGATTCTGAAACTCTAAAGCCTTTTATTTTATTTTATTTTTTAATTCTAGATGGAA<br>GCTGTATCCAAGGATGCTCCGGAATGTTGCTGAAACAGATCTGTCGACTTCTGTTT<br>TAGGACAGAGGGTCAGCATGCCAATATGTGTGGGGGCTACGGCCATGCAGCGCATG<br>GCTCATGTGGACGGCGAGCTTGCCACTGTGAGAGGTAGGAGGAAGATTGTCACCAC<br>AGGGACAGAAGGAGGCTAACGTTTATCG | HAO1 exon 2 |
| 931 | GGAGGGTAAGCAATGCCAGGCCCATCTTGATCATCCCCTTTCTTTCTCAGCCTGTC<br>AGTCCCTGGGAACGGGCATGATGTTGAGTTCCTGGGCCACCTCCTCAATTGAAGAA<br>GTGGCGGAAGCTGGTCCTGAGGCACTTCGTTGGCTGCAACTGTATATCTACAAGGA<br>CCGAGAAGTCACCAAGAAGCTAGTGCGGCAGGCAGAGAAGATGGGCTACAAGGCCA<br>TATTTGTGACAGTGGACACACCTTACCTGGGCAACCGTCTGGATGATGTGCGTAAC<br>AGATTCAAACTGCCGCCACAACTCAGGTAACCATGATCATGTGGGCCCCGAGCTGA<br>GGCGAAAGGATCTTGACTG | HAO1 exon 3 |

TABLE 6-continued

Cas12i and HAO1 Sequences

| SEQ ID NO | Sequence | Description |
|---|---|---|
| 932 | ACGTATTTCTAATTTGGCAAATTTCTCATTTTATGCATTTCTTATTTTAGGATGAA<br>AAATTTTGAAACCAGTACTTTATCATTTTCTCCTGAGGAAAATTTTGGAGACGACA<br>GTGGACTTGCTGCATATGTGGCTAAAGCAATAGACCCATCTATCAGCTGGGAAGAT<br>ATCAAATGGCTGAGAAGACTGACATCATTGCCAATTGTTGCAAAGGGCATTTTGAG<br>AGGTTCGTTTATTTCTCTACTTGAATTCATACTGACTTTGTGATCCTTTGTG | HAO1 exon 4 |
| 933 | CTGCCTGTTAAGTTACAGTTTCCCTAAGGTGCTTGTTTTACTCTCTCCAGGTGATG<br>ATGCCAGGGAGGCTGTTAAACATGGCTTGAATGGGATCTTGGTGTCGAATCATGGG<br>GCTCGACAACTCGATGGGGTGCCAGCCACTGTGAGTTTTGGCAGACGCTAAGATTT<br>CCTTTTGGAGTTCCCATTTCCATC | HAO1 exon 5 |
| 934 | TAACAATTCAGTGTTAATAGAGTCACATTATTGAACTTTTCTTTCCCCAGATTGAT<br>GTTCTGCCAGAAATTGTGGAGGCTGTGGAAGGGAAGGTGGAAGTCTTCCTGGACGG<br>GGGTGTGCGGAAAGGCACTGATGTTCTGAAAGCTCTGGCTCTTGGCGCCAAGGCTG<br>TGTTTGTGGGGAGACCAATCGTTTGGGGCTTAGCTTTCCAGGTAACTGGACAAAGA<br>AATGAATATATAAAATAGACAACTTGACAGTAAAACAAATGAATAAAACAAGTCAG<br>ACTGATTTAGTTCTGAATCACTCTGTATCTTTTCACTTGGTTAGGGGGAGAAAGGT<br>GTTCAAGATGTCCTCGAGATACTAAAGGAAGAATTCCGGTTGGCCATGGCTCTGAG<br>TGGTAAGACTCATTCTTGTTTACAACTTTCTTTTCTTTTATGATCTTTAAGT | HAO1 exon 6 |
| 935 | TGATTATTATTGCATTCAGTTCATATTAAATGTATGCATTATTTTTTCAGGGTGCC<br>AGAATGTGAAAGTCATCGACAAGACATTGGTGAGGAAAAATCCTTTGGCCGTTTCC<br>AAGATCTGACAGTGCACAATATTTTCCCATCTGTATTATTTTTTTTCAGCATGTAT<br>TACTTGACAAAGAGACACTGTGCAGAGGGTGACCACAGTCTGTAATTCCCCACTTC<br>AATACAAAGGGTGTCGTTCTTTTCCAACAAAATAGCAATCCCTTTTATTTCATTGC<br>TTTTGACTTTTCAATGGGTGTCCTAGGAACCTTTTAGAAAGAAATGGACTTTCATC<br>CTGGAAATATATTAACTGTTAAAAAGAAAACATTGAAAATGTGTTTAGACAACGTC<br>ATCCCCTGGCAGGCTAAAGTGCTGTATCCTTTAGTAAAATTGGAGGTAGCAAACAC<br>TAAGGTGAAAAGATAATGATCTCATTGTTTATTAACCTGTATTCTGTTTACATGTC<br>TTTAAAACAGTGGTTCTTAAATTGTAAGCTCAGGTTCAAAGTGTTGGTAATGCCTG<br>ATTCACAACTTTGAGAAGGTAGCACTGGAGAGAATTGGAATGGGTGGCGGTAATTG<br>GTGATACTTCTTTGAATGTAGATTTCCAATCACATCTTTAGTGTCTGAATATATCC<br>AAATGTTTTAGGATGTATGTTACTTCTTAGAGAGAAATAAAGCATTTTTGGGAAGA<br>A | HAO1 exon 7 |
| 965 | MSNKEKNASETRKAYTTKMIPRSHDRMKLLGNFMDYLMDGTPIFFELWNQFGGGID<br>RDIISGTANKDKISDDLLLAVNWFKVMPINSKPQGVSPSNLANLFQQYSGSEPDIQ<br>AQEYFASNFDTEKHQWKDMRVEYERLLAELQLSRSDMHHDLKLMYKEKCIGLSLST<br>AHYITSVMFGTGAKNNRQTKHQFYSKVIQLLEESTQINSVEQLASIILKAGDCDSY<br>RKLRIRCSRKGATPSILKIVQDYELGTNHDDEVNVPSLIANLKEKLGRFEYECEWK<br>CMEKIKAFLASKVGPYYLGSYSAMLENALSPIKGMTTKNCKFVLKQIDAKNDIKYE<br>NEPFGKIVEGFFDSPYFESDTNVKWVLHPHHIGESNIKTLWEDLNAIHSKYEEDIA<br>SLSEDKKEKRIKVYQGDVCQTINTYCEEVGKEAKTPLVQLLRYLYSRKDDIAVDKI<br>IDGITFLSKKHKVEKQKINPVIQKYPSFNFGNNSKLLGKIISPKDKLKHNLKCNRN<br>QVDNYIWIEIKVLNTKTMRWEKHHYALSSTRFLEEVYYPATSENPPDALAARFRTK<br>TNGYEGKPALSAEQIEQIRSAPVGLRKVKKRQMRLEAARQQNLLPRYTWGKDFNIN<br>ICKRGNNFEVTLATKVKKKKEKNYKVVLGYDANIVRKNTYAAIEAHANGDGVIDYN<br>DLPVKPIESGFVTVESQVRDKSYDQLSYNGVKLLYCKPHVESRRSFLEKYRNGTMK<br>DNRGNNIQIDFMKDFEAIADDETSLYYFNMKYCKLLQSSIRNHSSQAKEYREEIFE<br>LLRDGKLSVLKLSSLSNLSFVMFKVAKSLIGTYFGHLLKKPKNSKSDVKAPPITDE<br>DKQKADPEMFALRLALEEKRLNKVKSKKEVIANKIVAKALELRDKYGPVLIKGENI<br>SDTTKKGKKSSTNSFLMDWLARGVANKVKEMVMMHQGLEFVEVNPNFTSHQDPFVH<br>KNPENTFRARYSRCTPSELTEKNRKEILSFLSDKPSKRPTNAYYNEGAMAFLATYG<br>LKKNDVLGVSLEKFKQIMANILHQRSEDQLLFPSRGGMFYLATYKLDADATSVNWN<br>GKQFWVCNADLVAAYNVGLVDIQKDFKKK | (Cas12i1 of SEQ ID NO: 3 of U.S. Pat. No. 10,808,245) |
| 966 | MSISNNNILPYNPKLLPDDRKHKMLVDTFNQLDLIRNNLHDMIIALYGALKYDNIK<br>QFASKEKPHISADALCSINWFRLVKTNERKPAIESNQIISKFIQYSGHTPDKYALS<br>HITGNHEPSHKWIDCREYAINYARIMHLSFSQFQDLATACLNCKILILNGTLTSSW<br>AWGANSALFGGSDKENFSVKAKILNSFIENLKDEMNTTKFQVVEKVCQQIGSSDAA<br>DLFDLYRSTVKDGNRGPATGRNPKVMNLFSQDGEISSEQREDFIESF<br>QKVMQEKNSKQIIPHLDKLKYHLVKQSGLYDIYSWAAAIKNANSTIVASNSSNLNT<br>ILNKTEKQQTFEELRKDEKIVACSKILLSVNDTLPEDLHYNPSTSNLGKNLDVFFD<br>LLNENSVHTIENKEEKNKIVKECVNQYMEECKGLNKPPMPVLLTFISDYAHKHQAQ<br>DFLSAAKMNFIDLKIKSIKVVPTVHGSSPYTWISNLSKKNKDGKMIRTPNSSLIGW<br>IIPPEEIHDQKFAGQNPIIWAVLRVYCNNKWEMHHFPFSDSRFFTEVYAYKPNLPY<br>LPGGENRSKRFGYRHSTNLSNESRQILLDKSKYAKANKSVLRCMENMTHNVVFDPK<br>TSLNIRIKTDKNNSPVLDDKGRITFVMQINHRILEKYNNTKIEIGDRILAYDQNQS<br>ENHTYAILQRTEEGSHAHQFNGWYVRVLETGKVTSIVQGLSGPIDQLNYDGMPVTS<br>HKFNCWQADRSAFVSQFASLKISETETFDEAYQAINAQGAYTWNLFYLRILRKALR<br>VCHMENINQFREEILAISKNRLSPMSLGSLSQNSLKMIRAFKSIINCYMSRMSFVD<br>ELQKKEGDLELHTIMRLTDNKLNDKRVEKINRASSFLTNKAHSMGCKMIVGESDLP | (Cas12i3 of SEQ ID NO: 14 of U.S. Pat. No. 10,808,245) |

TABLE 6-continued

Cas12i and HAO1 Sequences

| SEQ ID NO | Sequence | Description |
|---|---|---|
| | VADSKTSKKQNVDRMDWCARALSHKVEYACKLMGLAYRGIPAYMSSHQDPLVHLVE SKRSVLRPRFVVADKSDVKQHHLDNLRRMLNSKTKVGTAVYYREAVELMCEELGIH KTDMAKGKVSLSDFVDKFIGEKAIFPQRGGRFYMSTKRLTTGAKLICYSGSDVWLS DADEIAAINIGMFVVCDQTGAFKKKKKEKLDDEECDILPFRPM | |
| 1024 | ATGCTCCCCCGGCTAATTTGTATCAATGATTATGAACAACATGCTAAATCAGTACT TCCAAAGTCTATATATGACTATTACAGGTCTGGGGCAAATGATGAAGAAACTTTGG CTGATAATATTGCAGCATTTTCCAGATGGAAGCTGTATCCAAGGATGCTCCGGAAT GTTGCTGAAACAGATCTGTCGACTTCTGTTTTAGGACAGAGGGTCAGCATGCCAAT ATGTGTGGGGGCTACGGCCATGCAGCGCATGGCTCATGTGGACGGCGAGCTTGCCA CTGTGAGAGCCTGTCAGTCCCTGGGAACGGGCATGATGTTGAGTTCCTGGGCCACC TCCTCAATTGAAGAAGTGGCGGAAGCTGGTCCTGAGGCACTTCGTTGGCTGCAACT GTATATCTACAAGGACCGAGAAGTCACCAAGAAGCTAGTGCGGCAGGCAGAGAAGA TGGGCTACAAGGCCATATTTGTGACAGTGGACACACCTTACCTGGGCAACCGTCTG GATGATGTGCGTAACAGATTCAAACTGCCGCCACAACTCAGGATGAAAAATTTTGA AACCAGTACTTTATCATTTTCTCCTGAGGAAAATTTTGGAGACGACAGTGGACTTG CTGCATATGTGGCTAAAGCAATAGACCCATCTATCAGCTGGGAAGATATCAAATGG CTGAGAAGACTGACATCATTGCCAATTGTTGCAAAGGGCATTTTGAGAGGTGATGA TGCCAGGGAGGCTGTTAAACATGGCTTGAATGGGATCTTGGTGTCGAATCATGGGG CTCGACAACTCGATGGGGTGCCAGCCACTATTGATGTTCTGCCAGAAATTGTGGAG GCTGTGGAAGGGAAGGTGGAAGTCTTCCTGGACGGGGGTGTGCGGAAAGGCACTGA TGTTCTGAAAGCTCTGGCTCTTGGCGCCAAGGCTGTGTTTGTGGGGAGACCAATCG TTTGGGGCTTAGCTTTCCAGGGGGAGAAAGGTGTTCAAGATGTCCTCGAGATACTA AAGGAAGAATTCCGGTTGGCCATGGCTCTGAGTGGGTGCCAGAATGTGAAAGTCAT CGACAAGACATTGGTGAGGAAAAATCCTTTGGCCGTTTCCAAGATCTGA | HAO1 cDNA |
| 1082 | rArGrArArArUrCrCrGrUrCrUrUrUrCrArUrUrGrArCrGrGrCrGrGrArG rCrArUrCrCrUrUrGrGrArUmA*mC*mA*rG | 3' end modified RNA guide targeting HAO1 sequence of SEQ ID NO: 1047 |
| 1083 | mA*mG*mA*rArArUrCrCrGrUrCrUrUrUrCrArUrUrGrArCrGrGrCrGrGr ArGrCrArUrCrCrUrUrGrGrArUrmA*mC*mA*rG | 5' and 3' end modified RNA guide targeting HAO1 sequence of SEQ ID NO: 1047 |
| 1084 | rArGrArArArUrCrCrGrUrCrUrUrUrCrArUrUrGrArCrGrGrGrGrArArG rUrArCrUrGrArUrUrUrArGmC*mA*mU*rG | 3' end modified RNA guide targeting HAO1 sequence of SEQ ID NO: 1026 |
| 1085 | mA*mG*mA*rArArUrCrCrGrUrCrUrUrUrCrArUrUrGrArCrGrGrGrGrAr ArGrUrArCrUrGrArUrUrUrArGmC*mA*mU*rG | 5' and 3' end modified RNA guide targeting HAO1 sequence of SEQ ID NO: 1026 |
| 1086 | rArGrArArArUrCrCrGrUrCrUrUrUrCrArUrUrGrArCrGrGrCrArArArG rUrCrUrArUrArUrArUrGrAmC*mU*mA*rU | 3' end modified RNA guide targeting HAO1 sequence of SEQ ID NO: 1025 |

TABLE 6-continued

| Cas12i and HAO1 Sequences | | |
|---|---|---|
| SEQ ID NO | Sequence | Description |
| 1087 | mA*mG*mA*rArArUrCrCrGrUrCrUrUrUrCrArUrUrGrArCrGrGrCrArAr ArGrUrCrUrArUrArUrArUrGrAmC*mU*mA*rU | 5' and 3' end modified RNA guide targeting HAO1 sequence of SEQ ID NO: 1025 |

In some embodiments, the gene editing system disclosed herein may comprise a Cas12i polypeptide as disclosed herein. In other embodiments, the gene editing system may comprise a nucleic acid encoding the Cas12i polypeptide. For example, the gene editing system may comprise a vector (e.g., a viral vector such as an AAV vector, such as AAV1, AAV2, AAV3, AAV4, AAV5, AAV6, AAV7, AAV8, AAV9, AAVrh10, AAV11 and AAV12) encoding the Cas12i polypeptide. Alternatively, the gene editing system may comprise a mRNA molecule encoding the Cas12i polypeptide. In some instances, the mRNA molecule may be codon-optimized.

II. Preparation of Gene Editing System Components

The present disclosure provides methods for production of components of the gene editing systems disclosed herein, e.g., the RNA guide, methods for production of the Cas12i polypeptide, and methods for complexing the RNA guide and Cas12i polypeptide.

A. RNA Guide

In some embodiments, the RNA guide is made by in vitro transcription of a DNA template. Thus, for example, in some embodiments, the RNA guide is generated by in vitro transcription of a DNA template encoding the RNA guide using an upstream promoter sequence (e.g., a T7 polymerase promoter sequence). In some embodiments, the DNA template encodes multiple RNA guides or the in vitro transcription reaction includes multiple different DNA templates, each encoding a different RNA guide. In some embodiments, the RNA guide is made using chemical synthetic methods. In some embodiments, the RNA guide is made by expressing the RNA guide sequence in cells transfected with a plasmid including sequences that encode the RNA guide. In some embodiments, the plasmid encodes multiple different RNA guides. In some embodiments, multiple different plasmids, each encoding a different RNA guide, are transfected into the cells. In some embodiments, the RNA guide is expressed from a plasmid that encodes the RNA guide and also encodes a Cas12i polypeptide. In some embodiments, the RNA guide is expressed from a plasmid that expresses the RNA guide but not a Cas12i polypeptide. In some embodiments, the RNA guide is purchased from a commercial vendor. In some embodiments, the RNA guide is synthesized using one or more modified nucleotide, e.g., as described above.

B. Cas12i Polypeptide

In some embodiments, the Cas12i polypeptide of the present disclosure can be prepared by (a) culturing bacteria which produce the Cas12i polypeptide of the present disclosure, isolating the Cas12i polypeptide, optionally, purifying the Cas12i polypeptide, and complexing the Cas12i polypeptide with an RNA guide. The Cas12i polypeptide can be also prepared by (b) a known genetic engineering technique, specifically, by isolating a gene encoding the Cas12i polypeptide of the present disclosure from bacteria, constructing a recombinant expression vector, and then transferring the vector into an appropriate host cell that expresses the RNA guide for expression of a recombinant protein that complexes with the RNA guide in the host cell. Alternatively, the Cas12i polypeptide can be prepared by (c) an in vitro coupled transcription-translation system and then complexing with an RNA guide.

In some embodiments, a host cell is used to express the Cas12i polypeptide. The host cell is not particularly limited, and various known cells can be preferably used. Specific examples of the host cell include bacteria such as *E. coli*, yeasts (budding yeast, *Saccharomyces cerevisiae*, and fission yeast, *Schizosaccharomyces pombe*), nematodes (*Caenorhabditis elegans*), *Xenopus laevis* oocytes, and animal cells (for example, CHO cells, COS cells and HEK293 cells). The method for transferring the expression vector described above into host cells, i.e., the transformation method, is not particularly limited, and known methods such as electroporation, the calcium phosphate method, the liposome method and the DEAE dextran method can be used.

After a host is transformed with the expression vector, the host cells may be cultured, cultivated or bred, for production of the Cas12i polypeptide. After expression of the Cas12i polypeptide, the host cells can be collected and Cas12i polypeptide purified from the cultures etc. according to conventional methods (for example, filtration, centrifugation, cell disruption, gel filtration chromatography, ion exchange chromatography, etc.).

In some embodiments, the methods for Cas12i polypeptide expression comprises translation of at least 5 amino acids, at least 10 amino acids, at least 15 amino acids, at least 20 amino acids, at least 50 amino acids, at least 100 amino acids, at least 150 amino acids, at least 200 amino acids, at least 250 amino acids, at least 300 amino acids, at least 400 amino acids, at least 500 amino acids, at least 600 amino acids, at least 700 amino acids, at least 800 amino acids, at least 900 amino acids, or at least 1000 amino acids of the Cas12i polypeptide. In some embodiments, the methods for protein expression comprises translation of about 5 amino acids, about 10 amino acids, about 15 amino acids, about 20 amino acids, about 50 amino acids, about 100 amino acids, about 150 amino acids, about 200 amino acids, about 250 amino acids, about 300 amino acids, about 400 amino acids, about 500 amino acids, about 600 amino acids, about 700 amino acids, about 800 amino acids, about 900 amino acids, about 1000 amino acids or more of the Cas12i polypeptide.

A variety of methods can be used to determine the level of production of a Cas12i polypeptide in a host cell. Such methods include, but are not limited to, for example, methods that utilize either polyclonal or monoclonal antibodies specific for the Cas12i polypeptide or a labeling tag as described elsewhere herein. Exemplary methods include, but are not limited to, enzyme-linked immunosorbent assays (ELISA), radioimmunoassays (MA), fluorescent immunoassays (FIA), and fluorescent activated cell sorting (FACS). These and other assays are well known in the art (See, e.g., Maddox et al., J. Exp. Med. 158:1211 [1983]).

The present disclosure provides methods of in vivo expression of the Cas12i polypeptide in a cell, comprising providing a polyribonucleotide encoding the Cas12i polypeptide to a host cell wherein the polyribonucleotide encodes the Cas12i polypeptide, expressing the Cas12i polypeptide in the cell, and obtaining the Cas12i polypeptide from the cell.

The present disclosure further provides methods of in vivo expression of a Cas12i polypeptide in a cell, comprising providing a polyribonucleotide encoding the Cas12i polypeptide to a host cell wherein the polyribonucleotide encodes the Cas12i polypeptide and expressing the Cas12i polypeptide in the cell. In some embodiments, the polyribonucleotide encoding the Cas12i polypeptide is delivered to the cell with an RNA guide and, once expressed in the cell, the Cas12i polypeptide and the RNA guide form a complex. In some embodiments, the polyribonucleotide encoding the Cas12i polypeptide and the RNA guide are delivered to the cell within a single composition. In some embodiments, the polyribonucleotide encoding the Cas12i polypeptide and the RNA guide are comprised within separate compositions. In some embodiments, the host cell is present in a subject, e.g., a human patient.

C. Complexes

In some embodiments, an RNA guide targeting HAO1 is complexed with a Cas12i polypeptide to form a ribonucleoprotein. In some embodiments, complexation of the RNA guide and Cas12i polypeptide occurs at a temperature lower than about any one of 20° C., 21° C., 22° C., 23° C., 24° C., 25° C., 26° C., 27° C., 28° C., 29° C., 30° C., 31° C., 32° C., 33° C., 34° C., 35° C., 36° C., 37° C., 38° C., 39° C., 40° C., 41° C., 42° C., 43° C., 44° C., 45° C., 50° C., or 55° C. In some embodiments, the RNA guide does not dissociate from the Cas12i polypeptide at about 37° C. over an incubation period of at least about any one of 10 mins, 15 mins, 20 mins, 25 mins, 30 mins, 35 mins, 40 mins, 45 mins, 50 mins, 55 mins, 1 hr, 2 hr, 3 hr, 4 hr, or more hours.

In some embodiments, the RNA guide and Cas12i polypeptide are complexed in a complexation buffer. In some embodiments, the Cas12i polypeptide is stored in a buffer that is replaced with a complexation buffer to form a complex with the RNA guide. In some embodiments, the Cas12i polypeptide is stored in a complexation buffer.

In some embodiments, the complexation buffer has a pH in a range of about 7.3 to 8.6. In one embodiment, the pH of the complexation buffer is about 7.3. In one embodiment, the pH of the complexation buffer is about 7.4. In one embodiment, the pH of the complexation buffer is about 7.5. In one embodiment, the pH of the complexation buffer is about 7.6. In one embodiment, the pH of the complexation buffer is about 7.7. In one embodiment, the pH of the complexation buffer is about 7.8. In one embodiment, the pH of the complexation buffer is about 7.9. In one embodiment, the pH of the complexation buffer is about 8.0. In one embodiment, the pH of the complexation buffer is about 8.1. In one embodiment, the pH of the complexation buffer is about 8.2. In one embodiment, the pH of the complexation buffer is about 8.3. In one embodiment, the pH of the complexation buffer is about 8.4. In one embodiment, the pH of the complexation buffer is about 8.5. In one embodiment, the pH of the complexation buffer is about 8.6.

In some embodiments, the Cas12i polypeptide can be overexpressed and complexed with the RNA guide in a host cell prior to purification as described herein. In some embodiments, mRNA or DNA encoding the Cas12i polypeptide is introduced into a cell so that the Cas12i polypeptide is expressed in the cell. In some embodiments, the RNA guide is also introduced into the cell, whether simultaneously, separately, or sequentially from a single mRNA or DNA construct, such that the ribonucleoprotein complex is formed in the cell.

III. Genetic Editing Methods

The disclosure also provides methods of modifying a target site within the HAO1 gene. In some embodiments, the methods comprise introducing an HAO1-targeting RNA guide and a Cas12i polypeptide into a cell. The HAO1-targeting RNA guide and Cas12i polypeptide can be introduced as a ribonucleoprotein complex into a cell. The HAO1-targeting RNA guide and Cas12i polypeptide can be introduced on a nucleic acid vector. The Cas12i polypeptide can be introduced as an mRNA. The RNA guide can be introduced directly into the cell. In some embodiments, the composition described herein is delivered to a cell/tissue/liver/person to reduce HAO1 in the cell/tissue/liver/person. In some embodiments, the composition described herein is delivered to a cell/tissue/liver/person to reduce oxalate production in the cell/tissue/liver/person. In some embodiments, the composition described herein is delivered to a cell/tissue/liver/person to correct calcium oxalate crystal deposition in the cell/tissue/liver/person. In some embodiments, the composition described herein is delivered to a person with primary hyperoxaluria.

Any of the gene editing systems disclosed herein may be used to genetically engineered an HAO1 gene. The gene editing system may comprise an RNA guide and a Cas12i2 polypeptide. The RNA guide comprises a spacer sequence specific to a target sequence in the HAO1 gene, e.g., specific to a region in exon1 or exon 2 of the HAO1 gene.

A. Target Sequence

In some embodiments, an RNA guide as disclosed herein is designed to be complementary to a target sequence that is adjacent to a 5'-TTN-3' PAM sequence or 5'-NTTN-3' PAM sequence.

In some embodiments, the target sequence is within an HAO1 gene or a locus of an HAO1 gene (e.g., in exon1 or exon 2), to which the RNA guide can bind via base pairing. In some embodiments, a cell has only one copy of the target sequence. In some embodiments, a cell has more than one copy, such as at least about any one of 2, 3, 4, 5, 10, 100, or more copies of the target sequence.

In some embodiments, the HAO1 gene is a mammalian gene. In some embodiments, the HAO1 gene is a human gene. For example, in some embodiments, the target sequence is within the sequence of SEQ ID NO: 928 (or the reverse complement thereof). In some embodiments, the target sequence is within an exon of the HAO1 gene set forth in SEQ ID NO: 928, e.g., within a sequence of SEQ ID NO: 929, 930, 931, 932, 933, 934, or 935 (or a reverse complement thereof). Target sequences within an exon region of the HAO1 gene of SEQ ID NO: 928 are set forth in Table 5. In some embodiments, the target sequence is within an intron of the HAO1 gene set forth in SEQ ID NO: 928 (or the reverse complement thereof). In some embodiments, the target sequence is within a variant (e.g., a polymorphic variant) of the HAO1 gene sequence set forth in SEQ ID NO: 928 (or the reverse complement thereof). In some embodiments, the HAO1 gene sequence is a homolog of the sequence set forth in SEQ ID NO: 928 (or the reverse complement thereof). For examples, in some embodiments, the HAO1 gene sequence is a non-human HAO1 sequence. In some embodiments, the HAO1 gene sequence is a coding sequence set forth in SEQ ID NO: 1024 (or the reverse complement thereof). In some embodiments, the HAO1 gene sequence is a homolog of a coding sequence set forth in SEQ ID NO: 1024 (or the reverse complement thereof).

In some embodiments, the target sequence is adjacent to a 5'-TTN-3' PAM sequence or a 5'-NTTN-3' PAM sequence, wherein N is any nucleotide. The 5'-NTTN-3' sequence may be immediately adjacent to the target sequence or, for example, within a small number (e.g., 1, 2, 3, 4, or 5) of nucleotides of the target sequence. In some embodiments the 5'-NTTN-3' sequence is 5'-NTTY-3', 5'-NTTC-3', 5'-NTTT-3', 5'-NTTA-3', 5'-NTTB-3', 5'-NTTG-3', 5'-CTTY-3', 5'-DTTR-3', 5'-CTTR-3', 5'-DTTT-3', 5'-ATTN-3', or 5'-GTTN-3', wherein Y is C or T, B is any nucleotide except for A, D is any nucleotide except for C, and R is A or G. In some embodiments, the 5'-NTTN-3' sequence is 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3'. The PAM sequence may be 5' to the target sequence.

The 5'-NTTN-3' sequence may be immediately adjacent to the target sequence or, for example, within a small number (e.g., 1, 2, 3, 4, or 5) of nucleotides of the target sequence. In some embodiments the 5'-NTTN-3' sequence is 5'-NTTY-3', 5'-NTTC-3', 5'-NTTT-3', 5' -NTTA-3', 5'-NTTB-3', 5'-NTTG-3', 5'-CTTY-3', 5'-DTTR-3', 5'-CTTR-3', 5'-DTTT-3', 5'-ATTN-3', or 5'-GTTN-3', wherein Y is C or T, B is any nucleotide except for A, D is any nucleotide except for C, and R is A or G. In some embodiments, the 5'-NTTN-3' sequence is 5'-*ATTA*-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3'. In some embodiments, the RNA guide is designed to bind to a first strand of a double-stranded target nucleic acid (i.e., the non-PAM strand), and the 5'-NTTN-3' PAM sequence is present in the second, complementary strand (i.e., the PAM strand). In some embodiments, the RNA guide binds to a region on the non-PAM strand that is complementary to a target sequence on the PAM strand, which is adjacent to a 5'-NAAN-3' sequence.

In some embodiments, the target sequence is present in a cell. In some embodiments, the target sequence is present in the nucleus of the cell. In some embodiments, the target sequence is endogenous to the cell. In some embodiments, the target sequence is a genomic DNA. In some embodiments, the target sequence is a chromosomal DNA. In some embodiments, the target sequence is a protein-coding gene or a functional region thereof, such as a coding region, or a regulatory element, such as a promoter, enhancer, a 5' or 3' untranslated region, etc.

In some embodiments, the target sequence is present in a readily accessible region of the target sequence. In some embodiments, the target sequence is in an exon of a target gene. In some embodiments, the target sequence is across an exon-intron junction of a target gene. In some embodiments, the target sequence is present in a non-coding region, such as a regulatory region of a gene.

B. Gene Editing

In some embodiments, the Cas12i polypeptide has enzymatic activity (e.g., nuclease activity). In some embodiments, the Cas12i polypeptide induces one or more DNA double-stranded breaks in the cell. In some embodiments, the Cas12i polypeptide induces one or more DNA single-stranded breaks in the cell. In some embodiments, the Cas12i polypeptide induces one or more DNA nicks in the cell. In some embodiments, DNA breaks and/or nicks result in formation of one or more indels (e.g., one or more deletions).

In some embodiments, an RNA guide disclosed herein forms a complex with the Cas12i polypeptide and directs the Cas12i polypeptide to a target sequence adjacent to a 5'-NTTN-3' sequence. In some embodiments, the complex induces a deletion (e.g., a nucleotide deletion or DNA deletion) adjacent to the 5'-NTTN-3' sequence. In some embodiments, the complex induces a deletion adjacent to a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the complex induces a deletion adjacent to a T/C-rich sequence.

In some embodiments, the deletion is downstream of a 5'-NTTN-3' sequence. In some embodiments, the deletion is downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion is downstream of a T/C-rich sequence.

In some embodiments, the deletion alters expression of the HAO1 gene. In some embodiments, the deletion alters function of the HAO1 gene. In some embodiments, the deletion inactivates the HAO1 gene. In some embodiments, the deletion is a frameshifting deletion. In some embodiments, the deletion is a non-frameshifting deletion. In some embodiments, the deletion leads to cell toxicity or cell death (e.g., apoptosis).

In some embodiments, the deletion starts within about 5 to about 15 nucleotides (e.g., about 3, 4, 5, 6, 7, 8, 9, 10, 11, 12, 13, 14, 15, 16, or 17 nucleotides) of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) of a T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a T/C-rich sequence.

In some embodiments, the deletion starts within about 5 to about 10 nucleotides (e.g., about 3, 4, 5, 6, 7, 8, 9, 10, 11, or 12 nucleotides) of the 5'-NTTN-3' sequence. In some embodiments, the deletion starts within about 5 to about 10 nucleotides (e.g., about 3, 4, 5, 6, 7, 8, 9, 10, 11, or 12 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) of a T/C-rich sequence.

In some embodiments, the deletion starts within about 5 to about 10 nucleotides (e.g., about 3, 4, 5, 6, 7, 8, 9, 10, 11, or 12 nucleotides) downstream of the 5'-NTTN-3' sequence. In some embodiments, the deletion starts within about 5 to about 10 nucleotides (e.g., about 3, 4, 5, 6, 7, 8, 9, 10, 11, or 12 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) downstream of a T/C-rich sequence.

In some embodiments, the deletion starts within about 10 to about 15 nucleotides (e.g., about 8, 9, 10, 11, 12, 13, 14, 15, 16, or 17 nucleotides) of the 5'-NTTN-3' sequence. In some embodiments, the deletion starts within about 10 to about 15 nucleotides (e.g., about 8, 9, 10, 11, 12, 13, 14, 15, 16, or 17 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) of a T/C-rich sequence.

In some embodiments, the deletion starts within about 10 to about 15 nucleotides (e.g., about 8, 9, 10, 11, 12, 13, 14, 15, 16, or 17 nucleotides) downstream of the 5'-NTTN-3' sequence. In some embodiments, the deletion starts within about 10 to about 15 nucleotides (e.g., about 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) downstream of a T/C-rich sequence.

In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) of the 5'-NTTN-3' sequence. In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) of a T/C-rich sequence.

In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-NTTN-3' sequence. In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 20 to about 30 nucleotides (e.g., about 17, 18, 19, 20, 21, 22, 23, 24, 25, 26, 27, 28, 29, 30, 31, 32, or 33 nucleotides) downstream of a T/C-rich sequence.

In some embodiments, the deletion ends within about 20 to about 25 nucleotides (e.g., about 17, 18, 19, 20, 21, 22, 23, 24, 25, 26, 27, or 28 nucleotides) of the 5'-NTTN-3' sequence. In some embodiments, the deletion ends within about 20 to about 25 nucleotides (e.g., about 17, 18, 19, 20, 21, 22, 23, 24, 25, 26, 27, or 28 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 20 to about 25 nucleotides (e.g., about 17, 18, 19, 20, 21, 22, 23, 24, 25, 26, 27, or 28 nucleotides) of a T/C-rich sequence.

In some embodiments, the deletion ends within about 20 to about 25 nucleotides (e.g., about 17, 18, 19, 20, 21, 22, 23, 24, 25, 26, 27, or 28 nucleotides) downstream of the 5'-NTTN-3' sequence. In some embodiments, the deletion ends within about 20 to about 25 nucleotides (e.g., about 17, 18, 19, 20, 21, 22, 23, 24, 25, 26, 27, or 28 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5' -CTTG-3', or 5'-CTTC-3' sequence. In some embodiments, the deletion ends within about 20 to about 25 nucleotides (e.g., about 17, 18, 19, 20, 21, 22, 23, 24, 25, 26, 27, or 28 nucleotides) downstream of a T/C-rich sequence.

In some embodiments, the deletion ends within about 25 to about 30 nucleotides (e.g., about 22, 23, 24, 25, 26, 27, 28, 29, 30, 31, 32, or 33 nucleotides) of the 5'-NTTN-3' sequence. In some embodiments, the deletion ends within about 25 to about 30 nucleotides (e.g., about 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 25 to about 30 nucleotides (e.g., about 22, 23, 24, 25, 26, 27, 28, 29, 30, 31, 32, or 33 nucleotides) of a T/C-rich sequence.

In some embodiments, the deletion ends within about 25 to about 30 nucleotides (e.g., about 22, 23, 24, 25, 26, 27, 28, 29, 30, 31, 32, or 33 nucleotides) downstream of the 5'-NTTN-3' sequence. In some embodiments, the deletion ends within about 25 to about 30 nucleotides (e.g., about 22, 23, 24, 25, 26, 27, 28, 29, 30, 31, 32, or 33 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion ends within about 25 to about 30 nucleotides (e.g., about 22, 23, 24, 25, 26, 27, 28, 29, 30, 31, 32, or 33 nucleotides) downstream of a T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of the 5'-NTTN-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a T/C-rich sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of a T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of the 5'-NTTN-3' sequence and ends within about 20 to about 25 nucleotides (e.g., about 17, 18, 19, 20, 21, 22, 23, 24, 25, 26, 27, or 28 nucleotides) downstream of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 25 nucleotides (e.g., about 17, 18, 19, 20, 21, 22, 23, 24, 25, 26, 27, or 28 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a T/C-rich sequence and ends within about 20 to about 25 nucleotides (e.g., about 17, 18, 19, 20, 21, 22, 23, 24, 25, 26, 27, or 28 nucleotides) downstream of the T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of a T/C-rich sequence.

In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of the 5'-NTTN-3' sequence and ends within about 25 to about 30 nucleotides (e.g., about 22, 23, 24, 25, 26, 27, 28, 29, 30, 31, 32, or 33 nucleotides) downstream of the 5'-NTTN-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 25 to about 30 nucleotides (e.g., about 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 15 nucleotides (e.g., about 3, 4, 5, 6, 7, 8, 9, 10, 11, 12, 13, 14, 15, 16, or 17 nucleotides) downstream of a T/C-rich sequence and ends within about 25 to about 30 nucleotides (e.g., about 22, 23, 24, 25, 26, 27, 28, 29, 30, 31, 32, or 33 nucleotides) downstream of the T/C-rich sequence.

In some embodiments, the deletion starts within about 5 to about 10 nucleotides (e.g., about 3, 4, 5, 6, 7, 8, 9, 10, 11, or 12 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of the 5'-NTTN-3' sequence. In some embodiments, the deletion starts within about 5 to about 10 nucleotides (e.g., about 3, 4, 5, 6, 7, 8, 9, 10, 11, or 12 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a T/C-rich sequence.

In some embodiments, the deletion starts within about 5 to about 10 nucleotides (e.g., about 3, 4, 5, 6, 7, 8, 9, 10, 11, or 12 nucleotides) downstream of the 5'-NTTN-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-NTTN-3' sequence. In some embodiments, the deletion starts within about 5 to about 10 nucleotides (e.g., about 3, 4, 5, 6, 7, 8, 9, 10, 11, or 12 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) downstream of a T/C-rich sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the T/C-rich sequence.

In some embodiments, the deletion starts within about 5 to about 10 nucleotides (e.g., about 3, 4, 5, 6, 7, 8, 9, 10, 11, or 12 nucleotides) and ends within about 20 to about 25 nucleotides (e.g., about 17, 18, 19, 20, 21, 22, 23, 24, 25, 26, 27, or 28 nucleotides) of the 5'-NTTN-3' sequence. In some embodiments, the deletion starts within about 5 to about 10 nucleotides (e.g., about 3, 4, 5, 6, 7, 8, 9, 10, 11, or 12 nucleotides) and ends within about 20 to about 25 nucleotides (e.g., about 17, 18, 19, 20, 21, 22, 23, 24, 25, 26, 27, or 28 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides and ends within about 20 to about 25 nucleotides (e.g., about 17, 18, 19, 20, 21, 22, 23, 24, 25, 26, 27, or 28 nucleotides) (e.g., about 3, 4, 5, 6, 7, 8, 9, 10, 11, or 12 nucleotides) of a T/C-rich sequence.

In some embodiments, the deletion starts within about 5 to about 10 nucleotides (e.g., about 3, 4, 5, 6, 7, 8, 9, 10, 11, or 12 nucleotides) downstream of the 5'-NTTN-3' sequence and ends within about 20 to about 25 nucleotides (e.g., about 17, 18, 19, 20, 21, 22, 23, 24, 25, 26, 27, or 28 nucleotides) downstream of the 5'-NTTN-3' sequence. In some embodiments, the deletion starts within about 5 to about 10 nucleotides (e.g., about 3, 4, 5, 6, 7, 8, 9, 10, 11, or 12 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 25 nucleotides (e.g., about 17, 18, 19, 20, 21, 22, 23, 24, 25, 26, 27, or 28 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) downstream of a T/C-rich sequence and ends within about 20 to about 25 nucleotides (e.g., about 17, 18, 19, 20, 21, 22, 23, 24, 25, 26, 27, or 28 nucleotides) downstream of the T/C-rich sequence.

In some embodiments, the deletion starts within about 5 to about 10 nucleotides (e.g., about 3, 4, 5, 6, 7, 8, 9, 10, 11, or 12 nucleotides) and ends within about 25 to about 30 nucleotides (e.g., about 22, 23, 24, 25, 26, 27, 28, 29, 30, 31, 32, or 33 nucleotides) of the 5'-NTTN-3' sequence. In some embodiments, the deletion starts within about 5 to about 10 nucleotides (e.g., about 3, 4, 5, 6, 7, 8, 9, 10, 11, or 12 nucleotides) and ends within about 25 to about 30 nucleotides (e.g., about 22, 23, 24, 25, 26, 27, 28, 29, 30, 31, 32, or 33 nucleotides) of a T/C-rich sequence.

In some embodiments, the deletion starts within about 5 to about 10 nucleotides (e.g., about 3, 4, 5, 6, 7, 8, 9, 10, 11, or 12 nucleotides) downstream of the 5'-NTTN-3' sequence and ends within about 25 to about 30 nucleotides (e.g., about 22, 23, 24, 25, 26, 27, 28, 29, 30, 31, 32, or 33 nucleotides) downstream of the 5'-NTTN-3' sequence. In some embodiments, the deletion starts within about 5 to about 10 nucleotides (e.g., about 3, 4, 5, 6, 7, 8, 9, 10, 11, or 12 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 25 to about 30 nucleotides (e.g., about 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 5 to about 10 nucleotides (e.g., about 3, 4, 5, 6, 7, 8, 9, 10, 11, or 12 nucleotides) downstream of a T/C-rich sequence and ends within about 25 to about 30 nucleotides (e.g., about 22, 23, 24, 25, 26, 27, 28, 29, 30, 31, 32, or 33 nucleotides) downstream of the T/C-rich sequence.

In some embodiments, the deletion starts within about 10 to about 15 nucleotides (e.g., about 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of the 5'-NTTN-3' sequence. In some embodiments, the deletion starts within about 10 to about 15 nucleotides (e.g., about 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) and ends within about 20 to about 30 nucleotides (e.g., about 17, 18, 19, 20, 21, 22, 23, 24, 25, 26, 27, 28, 29, 30, 31, 32, or 33 nucleotides) of a T/C-rich sequence.

In some embodiments, the deletion starts within about 10 to about 15 nucleotides (e.g., about 8, 9, 10, 11, 12, 13, 14, 15, 16, or 17 nucleotides) downstream of the 5'-NTTN-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-NTTN-3' sequence. In some embodiments, the deletion starts within about 10 to about 15 nucleotides (e.g., about 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) downstream of a T/C-rich sequence and ends within about 20 to about 30 nucleotides (e.g., about 17, 18, 19, 20, 21, 22, 23, 24, 25, 26, 27, 28, 29, 30, 31, 32, or 33 nucleotides) downstream of the T/C-rich sequence.

In some embodiments, the deletion starts within about 10 to about 15 nucleotides (e.g., about 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of the 5'-NTTN-3' sequence. In some embodiments, the deletion starts within about 10 to about 15 nucleotides (e.g., about 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA- 3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) and ends within about 20 to about 25 nucleotides (e.g., about 17, 18, 19, 20, 21, 22, 23, 24, 25, 26, 27, or 28 nucleotides) of a T/C-rich sequence.

In some embodiments, the deletion starts within about 10 to about 15 nucleotides (e.g., about 8, 9, 10, 11, 12, 13, 14, 15, 16, or 17 nucleotides) downstream of the 5'-NTTN-3' sequence and ends within about 20 to about 25 nucleotides (e.g., about 17, 18, 19, 20, 21, 22, 23, 24, 25, 26, 27, or 28 nucleotides) downstream of the 5'-NTTN-3' sequence. In some embodiments, the deletion starts within about 10 to about 15 nucleotides (e.g., about 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 20 to about 25 nucleotides (e.g., about 17, 18, 19, 20, 21, 22, 23, 24, 25, 26, 27, or 28 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) downstream of a T/C-rich sequence and ends within about 20 to about 25 nucleotides (e.g., about 17, 18, 19, 20, 21, 22, 23, 24, 25, 26, 27, or 28 nucleotides) downstream of the T/C-rich sequence.

In some embodiments, the deletion starts within about 10 to about 15 nucleotides (e.g., about 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of the 5'-NTTN-3' sequence. In some embodiments, the deletion starts within about 10 to about 15 nucleotides (e.g., about 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) and ends within about 25 to about 30 nucleotides (e.g., about 22, 23, 24, 25, 26, 27, 28, 29, 30, 31, 32, or 33 nucleotides) of a T/C-rich sequence.

In some embodiments, the deletion starts within about 10 to about 15 nucleotides (e.g., about 8, 9, 10, 11, 12, 13, 14, 15, 16, or 17 nucleotides) downstream of the 5'-NTTN-3' sequence and ends within about 25 to about 30 nucleotides (e.g., about 22, 23, 24, 25, 26, 27, 28, 29, 30, 31, 32, or 33 nucleotides) downstream of the 5'-NTTN-3' sequence. In some embodiments, the deletion starts within about 10 to about 15 nucleotides (e.g., about 8, 9, 10, 11, 12, 13, 14, 15, 16, or 17 nucleotides) downstream of a 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence and ends within about 25 to about 30 nucleotides (e.g., about 22, 23, 24, 25, 26, 27, 28, 29, 30, 31, 32, or 33 nucleotides) downstream of the 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3' sequence. In some embodiments, the deletion starts within about 10 to about 15 nucleotides (e.g., about 8, 9, 10, 11, 12, 13, 14, 15, 16, or 17 nucleotides) downstream of a T/C-rich sequence and ends within about 25 to about 30 nucleotides (e.g., about 22, 23, 24, 25, 26, 27, 28, 29, 30, 31, 32, or 33 nucleotides) downstream of the T/C-rich sequence.

In some embodiments, the deletion is up to about 40 nucleotides in length (e.g., about 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 nucleotides). In some embodiments, the deletion is between about 4 nucleotides and about 40 nucleotides in length (e.g., about 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 nucleotides). In some embodiments, the deletion is between about 4 nucleotides and about 25 nucleotides in length (e.g., about 3, 4, 5, 6, 7, 8, 9, 10, 11, 12, 13, 14, 15, 16, 17, 18, 19, 20, 21, 22, 23, 24, 25, 26, 27, or 28 nucleotides). In some embodiments, the deletion is between about 10 nucleotides and about 25 nucleotides in length (e.g., about 7, 8, 9, 10, 11, 12, 13, 14, 15, 16, 17, 18, 19, 20, 21, 22, 23, 24, 25, 26, 27, or 28 nucleotides). In some embodiments, the deletion is between about 10 nucleotides and about 15 nucleotides in length (e.g., about 7, 8, 9, 10, 11, 12, 13, 14, 15, 16, or 17 nucleotides).

In some embodiments, the methods described herein are used to engineer a cell comprising a deletion as described herein in an HAO1 gene. In some embodiments, the methods are carried out using a complex comprising a Cas12i enzyme as described herein and an RNA guide comprising a direct repeat and a spacer as described herein. In some embodiments, the sequence of the RNA guide has at least 90% identity (e.g., at least 90%, 91%, 92%, 93%, 94%, 95%, 96%, 97%, 98%, or 99% identity) to a sequence of any one of SEQ ID NOs: 967-1023. In some embodiments, an RNA guide has a sequence of any one of SEQ ID NOs: 967-1023.

In some embodiments, the RNA guide targeting HAO1 is encoded in a plasmid. In some embodiments, the RNA guide targeting HAO1 is synthetic or purified RNA. In some embodiments, the Cas12i polypeptide is encoded in a plasmid. In some embodiments, the Cas12i polypeptide is encoded by an RNA that is synthetic or purified.

C. Delivery

Components of any of the gene editing systems disclosed herein may be formulated, for example, including a carrier, such as a carrier and/or a polymeric carrier, e.g., a liposome, and delivered by known methods to a cell (e.g., a prokaryotic, eukaryotic, plant, mammalian, etc.). Such methods include, but not limited to, transfection (e.g., lipid-mediated, cationic polymers, calcium phosphate, dendrimers); electroporation or other methods of membrane disruption (e.g., nucleofection), viral delivery (e.g., lentivirus, retrovirus, adenovirus, adeno-associated virus (AAV)), microinjection, microprojectile bombardment ("gene gun"), fugene, direct sonic loading, cell squeezing, optical transfection, protoplast fusion, impalefection, magnetofection, exosome-mediated transfer, lipid nanoparticle-mediated transfer, and any combination thereof.

In some embodiments, the method comprises delivering one or more nucleic acids (e.g., nucleic acids encoding the Cas12i polypeptide, RNA guide, donor DNA, etc.), one or more transcripts thereof, and/or a pre-formed RNA guide/Cas12i polypeptide complex to a cell, where a ternary complex is formed. In some embodiments, an RNA guide and an RNA encoding a Cas12i polypeptide are delivered together in a single composition. In some embodiments, an RNA guide and an RNA encoding a Cas12i polypeptide are delivered in separate compositions. In some embodiments, an RNA guide and an RNA encoding a Cas12i polypeptide delivered in separate compositions are delivered using the same delivery technology. In some embodiments, an RNA guide and an RNA encoding a Cas12i polypeptide delivered in separate compositions are delivered using different delivery technologies. Exemplary intracellular delivery methods, include, but are not limited to: viruses, such as AAV, or virus-like agents; chemical-based transfection methods, such as those using calcium phosphate, dendrimers, liposomes, lipid nanoparticles, or cationic polymers (e.g., DEAE-dextran or polyethylenimine); non-chemical methods, such as microinjection, electroporation, cell squeezing, sonoporation, optical transfection, impalefection, protoplast fusion, bacterial conjugation, delivery of plasmids or transposons; particle-based methods, such as using a gene gun, magnectofection or magnet assisted transfection, particle bombardment; and hybrid methods, such as nucleofection. In some embodiments, a lipid nanoparticle comprises an mRNA encoding a Cas12i polypeptide, an RNA guide, or an mRNA encoding a Cas12i polypeptide and an RNA guide. In some embodiments, the mRNA encoding the Cas12i polypeptide is a transcript of the nucleotide sequence set forth in SEQ ID NO: 921 or SEQ ID NO: 955 or a variant thereof. In some embodiments, the present application further provides cells produced by such methods, and organisms (such as animals, plants, or fungi) comprising or produced from such cells.

D. Genetically Modified Cells

Any of the gene editing systems disclosed herein can be delivered to a variety of cells. In some embodiments, the cell is an isolated cell. In some embodiments, the cell is in cell culture or a co-culture of two or more cell types. In some embodiments, the cell is ex vivo. In some embodiments, the cell is obtained from a living organism and maintained in a cell culture. In some embodiments, the cell is a single-cellular organism.

In some embodiments, the cell is a prokaryotic cell. In some embodiments, the cell is a bacterial cell or derived from a bacterial cell. In some embodiments, the cell is an archaeal cell or derived from an archaeal cell.

In some embodiments, the cell is a eukaryotic cell. In some embodiments, the cell is a plant cell or derived from a plant cell. In some embodiments, the cell is a fungal cell or derived from a fungal cell. In some embodiments, the cell is an animal cell or derived from an animal cell. In some embodiments, the cell is an invertebrate cell or derived from an invertebrate cell. In some embodiments, the cell is a vertebrate cell or derived from a vertebrate cell. In some embodiments, the cell is a mammalian cell or derived from a mammalian cell. In some embodiments, the cell is a human cell. In some embodiments, the cell is a zebra fish cell. In some embodiments, the cell is a rodent cell. In some embodiments, the cell is synthetically made, sometimes termed an artificial cell.

In some embodiments, the cell is derived from a cell line. A wide variety of cell lines for tissue culture are known in the art. Examples of cell lines include, but are not limited to, 293T, MF7, K562, HeLa, CHO, and transgenic varieties thereof. Cell lines are available from a variety of sources known to those with skill in the art (see, e.g., the American Type Culture Collection (ATCC) (Manassas, Va.)). In some embodiments, the cell is an immortal or immortalized cell.

In some embodiments, the cell is a primary cell. In some embodiments, the cell is a stem cell such as a totipotent stem cell (e.g., omnipotent), a pluripotent stem cell, a multipotent stem cell, an oligopotent stem cell, or an unipotent stem cell. In some embodiments, the cell is an induced pluripotent stem cell (iPSC) or derived from an iPSC. In some embodiments, the cell is a differentiated cell. For example, in some embodiments, the differentiated cell is a liver cell (e.g., a hepatocyte), a biliary cell (e.g., a cholangiocyte), a stellate cell, a Kupffer cell, a liver sinusoidal endothelial cell, a muscle cell (e.g., a myocyte), a fat cell (e.g., an adipocyte), a bone cell (e.g., an osteoblast, osteocyte, osteoclast), a blood cell (e.g., a monocyte, a lymphocyte, a neutrophil, an eosinophil, a basophil, a macrophage, a erythrocyte, or a platelet), a nerve cell (e.g., a neuron), an epithelial cell, an immune cell (e.g., a lymphocyte, a neutrophil, a monocyte, or a macrophage), a fibroblast, or a sex cell. In some embodiments, the cell is a terminally differentiated cell. For example, in some embodiments, the terminally differentiated cell is a neuronal cell, an adipocyte, a cardiomyocyte, a skeletal muscle cell, an epidermal cell, or a gut cell. In some embodiments, the cell is an immune cell. In some embodiments, the immune cell is a T cell. In some embodiments, the immune cell is a B cell. In some embodiments, the immune cell is a Natural Killer (NK) cell. In some embodiments, the immune cell is a Tumor Infiltrating Lymphocyte (TIL). In some embodiments, the cell is a mammalian cell, e.g., a human cell or a murine cell. In some embodiments, the murine cell is derived from a wild-type mouse, an immunosuppressed mouse, or a disease-specific mouse model. In some embodiments, the cell is a cell within a living tissue, organ, or organism.

Any of the genetically modified cells produced using any of the gene editing system disclosed herein is also within the scope of the present disclosure. Such modified cells may comprise a disrupted HAO1 gene.

Compositions, vectors, nucleic acids, RNA guides and cells disclosed herein may be used in therapy. Compositions, vectors, nucleic acids, RNA guides and cells disclosed herein may be used in methods of treating a disease or condition in a subject. In some embodiments, the disease or condition is Any suitable delivery or administration method known in the art may be used to deliver compositions, vectors, nucleic acids, RNA guides and cells disclosed herein. Such methods may involve contacting a target sequence with a composition, vector, nucleic acid, or RNA guide disclosed herein. Such methods may involve a method of editing an HAO1 sequence as disclosed herein. In some embodiments, a cell engineered using an RNA guide disclosed herein is used for ex vivo gene therapy.

IV. Therapeutic Applications

Any of the gene editing systems or modified cells generated using such a gene editing system as disclosed herein may be used for treating a disease that is associated with the HAO1 gene, for example, primary hyperoxaluria (PH). In some embodiments, the PH is PH1, PH2, or PH3. In specific examples, the target disease is PH1.

The gene editing system, pharmaceutical composition or kit comprising such, and any of the RNA guides disclosed herein may be used for treating primary hyperoxaluria (PH) in a subject. PH is a rare genetic disorder effecting subjects of all ages from infants to elderly. PH includes three subtypes involving genetic defects that alter the expression of three distinct proteins. PH1 involves alanine-glyoxylate aminotransferase, or AGT/AGT1. PH2 involves glyoxylate/hydroxypyruvate reductase, or GR/HPR, and PH3 involves 4-hydroxy-2-oxoglutarate aldolase, or HOGA.

In PH1, excess oxalate can also combine with calcium to form calcium oxalate in the kidney and other organs. Deposits of calcium oxalate can produce widespread deposition of calcium oxalate (nephrocalcinosis) or formation of kidney and bladder stones (urolithiasis) and lead to kidney damage. Common kidney complications in PH1 include blood in the urine (hematuria), urinary tract infections, kidney damage, and end-stage renal disease (ESRD). Over time, kidneys in patients with PH1 may begin to fail, and levels of oxalate may rise in the blood. Deposition of oxalate in tissues throughout the body, e.g., systemic oxalosis, may occur due to high blood levels of oxalate and can lead to complications in bone, skin, and eye. Patients with PH1 normally have kidney failure at an early age, with renal dialysis or dual kidney/liver organ transplant as the only treatment options.

In some embodiments, provided herein is a method for treating a target disease as disclosed herein (e.g., PH such as PH1) comprising administering to a subject (e.g., a human patient) in need of the treatment any of the gene editing systems disclosed herein. The gene editing system may be delivered to a specific tissue or specific type of cells where the gene edit is needed. The gene editing system may comprise LNPs encompassing one or more of the components, one or more vectors (e.g., viral vectors) encoding one or more of the components, or a combination thereof. Components of the gene editing system may be formulated to form a pharmaceutical composition, which may further comprise one or more pharmaceutically acceptable carriers.

In some embodiments, modified cells produced using any of the gene editing systems disclosed herein may be administered to a subject (e.g., a human patient) in need of the treatment. The modified cells may comprise a substitution, insertion, and/or deletion described herein. In some examples, the modified cells may include a cell line modified by a CRISPR nuclease, reverse transcriptase polypeptide, and editing template RNA (e.g., RNA guide and RT donor RNA). In some instances, the modified cells may be a heterogenous population comprising cells with different types of gene edits. Alternatively, the modified cells may comprise a substantially homogenous cell population (e.g., at least 80% of the cells in the whole population) comprising one particular gene edit in the HAO1 gene. In some examples, the cells can be suspended in a suitable media.

In some embodiments, provided herein is a composition comprising the gene editing system or components thereof. Such a composition can be a pharmaceutical composition. A pharmaceutical composition that is useful may be prepared, packaged, or sold in a formulation suitable for oral, rectal, vaginal, parenteral, topical, pulmonary, intranasal, intralesional, buccal, ophthalmic, intravenous, intra-organ or another route of administration. A pharmaceutical composition of the disclosure may be prepared, packaged, or sold in bulk, as a single unit dose, or as a plurality of single unit doses. As used herein, a "unit dose" is discrete amount of the pharmaceutical composition (e.g., the gene editing system or components thereof), which would be administered to a subject or a convenient fraction of such a dosage such as, for example, one-half or one-third of such a dosage.

In some embodiments, a pharmaceutical composition comprising the gene editing system or components thereof as described herein may be administered to a subject in need thereof, e.g., one who suffers from a liver disease associated with the HAO1 gene. In some instances, the gene editing system or components thereof may be delivered to specific cells or tissue (e.g., to liver cells), where the gene editing system could function to genetically modify the HAO1 gene in such cells.

A formulation of a pharmaceutical composition suitable for parenteral administration may comprise the active agent (e.g., the gene editing system or components thereof or the modified cells) combined with a pharmaceutically acceptable carrier, such as sterile water or sterile isotonic saline. Such a formulation may be prepared, packaged, or sold in a form suitable for bolus administration or for continuous administration. Some injectable formulations may be prepared, packaged, or sold in unit dosage form, such as in ampules or in multi-dose containers containing a preservative. Some formulations for parenteral administration include, but are not limited to, suspensions, solutions, emulsions in oily or aqueous vehicles, pastes, and implantable sustained-release or biodegradable formulations. Some formulations may further comprise one or more additional ingredients including, but not limited to, suspending, stabilizing, or dispersing agents.

The pharmaceutical composition may be in the form of a sterile injectable aqueous or oily suspension or solution. This suspension or solution may be formulated according to the known art, and may comprise, in addition to the cells, additional ingredients such as the dispersing agents, wetting agents, or suspending agents described herein. Such sterile injectable formulation may be prepared using a non-toxic parenterally-acceptable diluent or solvent, such as water or saline. Other acceptable diluents and solvents include, but are not limited to, Ringer's solution, isotonic sodium chloride solution, and fixed oils such as synthetic mono- or di-glycerides. Other parentally-administrable formulations which that are useful include those which may comprise the cells in a packaged form, in a liposomal preparation, or as a component of a biodegradable polymer system. Some compositions for sustained release or implantation may comprise pharmaceutically acceptable polymeric or hydrophobic materials such as an emulsion, an ion exchange resin, a sparingly soluble polymer, or a sparingly soluble salt.

V. Kits and Uses Thereof

The present disclosure also provides kits that can be used, for example, to carry out a method described herein for genetical modification of the HAO1 gene. In some embodiments, the kits include an RNA guide and a Cas12i polypeptide. In some embodiments, the kits include a polynucleotide that encodes such a Cas12i polypeptide, and optionally the polynucleotide is comprised within a vector, e.g., as described herein. The Cas12i polypeptide and the RNA guide (e.g., as a ribonucleoprotein) can be packaged within the same or other vessel within a kit or system or can be packaged in separate vials or other vessels, the contents of which can be mixed prior to use. The kits can additionally include, optionally, a buffer and/or instructions for use of the RNA guide and Cas12i polypeptide.

In some embodiments, the kit may be useful for research purposes. For example, in some embodiments, the kit may be useful to study gene function.

All references and publications cited herein are hereby incorporated by reference.

ADDITIONAL EMBODIMENTS

Provided below are additional embodiments, which are also within the scope of the present disclosure.

Embodiment 1: A composition comprising an RNA guide, wherein the RNA guide comprises (i) a spacer sequence that is substantially complementary or completely complementary to a region on a non-PAM strand (the complementary sequence of a target sequence) within an HAO1 gene and (ii) a direct repeat sequence; wherein the target sequence is adjacent to a protospacer adjacent motif (PAM) comprising the sequence 5'-NTTN-3'.

In Embodiment 1, the target sequence may be within exon 1, exon 2, exon 3, exon 4, exon 5, exon 6, or exon 7 of the HAO1 gene. In some examples, the HAO1 gene comprises the sequence of SEQ ID NO: 928, the reverse complement of SEQ ID NO: 928, a variant of SEQ ID NO: 928, or the reverse complement of a variant of SEQ ID NO: 928.

In Embodiment 1, the spacer sequence may comprise: (a) nucleotide 1 through nucleotide 16 of a sequence that is at least 90% identical to a sequence of any one of SEQ ID NOs: 466-920; (b) nucleotide 1 through nucleotide 17 of a sequence that is at least 90% identical to a sequence of any one of SEQ ID NOs: 466-920; (c) nucleotide 1 through nucleotide 18 of a sequence that is at least 90% identical to a sequence of any one of SEQ ID NOs: 466-920; (d) nucleotide 1 through nucleotide 19 of a sequence that is at least 90% identical to a sequence of any one of SEQ ID NOs: 466-920; (e) nucleotide 1 through nucleotide 20 of a sequence that is at least 90% identical to a sequence of any one of SEQ ID NOs: 466-920; (f) nucleotide 1 through nucleotide 21 of a sequence that is at least 90% identical to a sequence of any one of SEQ ID NOs: 466-920; (g) nucleotide 1 through nucleotide 22 of a sequence that is at least 90% identical to a sequence of any one of SEQ ID NOs: 466-920; (h) nucleotide 1 through nucleotide 23 of a sequence that is at least 90% identical to a sequence of any one of SEQ ID NOs: 466-920; (i) nucleotide 1 through nucleotide 24 of a sequence that is at least 90% identical to a sequence of any one of SEQ ID NOs: 466-920; (j) nucleotide 1 through nucleotide 25 of a sequence that is at least 90% identical to a sequence of any one of SEQ ID NOs: 466-920; (k) nucleotide 1 through nucleotide 26 of a sequence that is at least 90% identical to a sequence of any one of SEQ ID NOs: 466-920; (l) nucleotide 1 through nucleotide 27 of a sequence that is at least 90% identical to a sequence of any one of SEQ ID NOs: 466-920; (m) nucleotide 1 through nucleotide 28 of a sequence that is at least 90% identical to a sequence of any one of SEQ ID NOs: 466-920; (n) nucleotide 1 through nucleotide 29 of a sequence that is at least 90% identical to a sequence of any one of SEQ ID NOs: 466-920; or (o) nucleotide 1 through nucleotide 30 of a sequence that is at least 90% identical to a sequence of any one of SEQ ID NOs: 466-920.

In any of the composition of Embodiment 1, the spacer sequence may comprise: (a) nucleotide 1 through nucleotide 16 of any one of SEQ ID NOs: 466-920; (b) nucleotide 1 through nucleotide 17 of any one of SEQ ID NOs: 466-920; (c) nucleotide 1 through nucleotide 18 of any one of SEQ ID NOs: 466-920; (d) nucleotide 1 through nucleotide 19 of any one of SEQ ID NOs: 466-920; (e) nucleotide 1 through nucleotide 20 of any one of SEQ ID NOs: 466-920; (f) nucleotide 1 through nucleotide 21 of any one of SEQ ID NOs: 466-920; (g) nucleotide 1 through nucleotide 22 of any one of SEQ ID NOs: 466-920; (h) nucleotide 1 through nucleotide 23 of any one of SEQ ID NOs: 466-920; (i) nucleotide 1 through nucleotide 24 of any one of SEQ ID NOs: 466-920; (j) nucleotide 1 through nucleotide 25 of any one of SEQ ID NOs: 466-920; (k) nucleotide 1 through nucleotide 26 of any one of SEQ ID NOs: 466-920; (l) nucleotide 1 through nucleotide 27 of any one of SEQ ID NOs: 466-920; (m) nucleotide 1 through nucleotide 28 of any one of SEQ ID NOs: 466-920; (n) nucleotide 1 through nucleotide 29 of any one of SEQ ID NOs: 466-920; or (o) nucleotide 1 through nucleotide 30 of any one of SEQ ID NOs: 466-920.

In any of the composition of Embodiment 1, the direct repeat sequence may comprises: (a) nucleotide 1 through nucleotide 36 of a sequence that is at least 90% identical to a sequence of any one of SEQ ID NOs: 1-8; (b) nucleotide 2 through nucleotide 36 of a sequence that is at least 90% identical to a sequence of any one of SEQ ID NOs: 1-8; (c) nucleotide 3 through nucleotide 36 of a sequence that is at least 90% identical to a sequence of any one of SEQ ID NOs: 1-8; (d) nucleotide 4 through nucleotide 36 of a sequence that is at least 90% identical to a sequence of any one of SEQ ID NOs: 1-8; (e) nucleotide 5 through nucleotide 36 of a sequence that is at least 90% identical to a sequence of any one of SEQ ID NOs: 1-8; (f) nucleotide 6 through nucleotide 36 of a sequence that is at least 90% identical to a sequence of any one of SEQ ID NOs: 1-8; (g) nucleotide 7 through nucleotide 36 of a sequence that is at least 90% identical to a sequence of any one of SEQ ID NOs: 1-8; (h) nucleotide 8 through nucleotide 36 of a sequence that is at least 90% identical to a sequence of any one of SEQ ID NOs: 1-8; (i) nucleotide 9 through nucleotide 36 of a sequence that is at least 90% identical to a sequence of any one of SEQ ID NOs: 1-8; (j) nucleotide 10 through nucleotide 36 of a sequence that is at least 90% identical to a sequence of any one of SEQ ID NOs: 1-8; (k) nucleotide 11 through nucleotide 36 of a sequence that is at least 90% identical to a sequence of any one of SEQ ID NOs: 1-8; (l) nucleotide 12 through nucleotide 36 of a sequence that is at least 90% identical to a sequence of any one of SEQ ID NOs: 1-8; (m) nucleotide 13 through nucleotide 36 of a sequence that is at least 90% identical to a sequence of any one of SEQ ID NOs: 1-8; (n) nucleotide 14 through nucleotide 36 of a sequence that is at least 90% identical to a sequence of any one of SEQ ID NOs: 1-8; (o) nucleotide 1 through nucleotide 34 of a sequence that is at least 90% identical to a sequence of SEQ ID NO: 9; (p) nucleotide 2 through nucleotide 34 of a sequence that is at least 90% identical to a sequence of SEQ ID NO: 9; (q) nucleotide 3 through nucleotide 34 of a sequence that is at least 90% identical to a sequence of SEQ ID NO: 9; (r) nucleotide 4 through nucleotide 34 of a sequence that is at least 90% identical to a sequence of SEQ ID NO: 9; (s) nucleotide 5 through nucleotide 34 of a sequence that is at least 90% identical to a sequence of SEQ ID NO: 9; (t) nucleotide 6 through nucleotide 34 of a sequence that is at least 90% identical to a sequence of SEQ ID NO: 9; (u) nucleotide 7 through nucleotide 34 of a sequence that is at least 90% identical to a sequence of SEQ ID NO: 9; (v) nucleotide 8 through nucleotide 34 of a sequence that is at least 90% identical to a sequence of SEQ ID NO: 9; (w) nucleotide 9 through nucleotide 34 of a sequence that is at least 90% identical to a sequence of SEQ ID NO: 9; (x) nucleotide 10 through nucleotide 34 of a sequence that is at least 90% identical to a sequence of SEQ ID NO: 9; (y) nucleotide 11 through nucleotide 34 of a sequence that is at least 90% identical to a sequence of SEQ ID NO: 9; (z) nucleotide 12 through nucleotide 34 of a sequence that is at least 90% identical to a sequence of SEQ ID NO: 9; or (aa) a sequence that is at least 90% identical to a sequence of SEQ ID NO: 10 or a portion thereof.

In some examples, the direct repeat sequence comprises: (a) nucleotide 1 through nucleotide 36 of any one of SEQ ID NOs: 1-8; (b) nucleotide 2 through nucleotide 36 of any one of SEQ ID NOs: 1-8; (c) nucleotide 3 through nucleotide 36 of any one of SEQ ID NOs: 1-8; (d) nucleotide 4 through nucleotide 36 of any one of SEQ ID NOs: 1-8; (e) nucleotide 5 through nucleotide 36 of any one of SEQ ID NOs: 1-8; (f) nucleotide 6 through nucleotide 36 of any one of SEQ ID NOs: 1-8; (g) nucleotide 7 through nucleotide 36 of any one of SEQ ID NOs: 1-8; (h) nucleotide 8 through nucleotide 36 of any one of SEQ ID NOs: 1-8; (i) nucleotide 9 through nucleotide 36 of any one of SEQ ID NOs: 1-8; (j) nucleotide 10 through nucleotide 36 of any one of SEQ ID NOs: 1-8; (k) nucleotide 11 through nucleotide 36 of any one of SEQ ID NOs: 1-8; (l) nucleotide 12 through nucleotide 36 of any one of SEQ ID NOs: 1-8; (m) nucleotide 13 through nucleotide 36 of any one of SEQ ID NOs: 1-8; (n) nucleotide 14 through nucleotide 36 of any one of SEQ ID NOs: 1-8; (o) nucleotide 1 through nucleotide 34 of SEQ ID NO: 9; (p) nucleotide 2 through nucleotide 34 of SEQ ID NO: 9; (q) nucleotide 3 through nucleotide 34 of SEQ ID NO: 9; (r) nucleotide 4 through nucleotide 34 of SEQ ID NO: 9; (s) nucleotide 5 through nucleotide 34 of SEQ ID NO: 9; (t) nucleotide 6 through nucleotide 34 of SEQ ID NO: 9; (u) nucleotide 7 through nucleotide 34 of SEQ ID NO: 9; (v) nucleotide 8 through nucleotide 34 of SEQ ID NO: 9; (w) nucleotide 9 through nucleotide 34 of SEQ ID NO: 9; (x) nucleotide 10 through nucleotide 34 of SEQ ID NO: 9; (y) nucleotide 11 through nucleotide 34 of SEQ ID NO: 9; (z) nucleotide 12 through nucleotide 34 of SEQ ID NO: 9; (or aa) SEQ ID NO: 10 or a portion thereof).

In some examples, the direct repeat sequence comprises: (a) nucleotide 1 through nucleotide 36 of a sequence that is at least 90% identical to a sequence of any one of SEQ ID NOs: 936-953; (b) nucleotide 2 through nucleotide 36 of a sequence that is at least 90% identical to a sequence of any one of SEQ ID NOs: 936-953; (c) nucleotide 3 through nucleotide 36 of a sequence that is at least 90% identical to a sequence of any one of SEQ ID NOs: 936-953; (d) nucleotide 4 through nucleotide 36 of a sequence that is at least 90% identical to a sequence of any one of SEQ ID NOs: 936-953; (e) nucleotide 5 through nucleotide 36 of a sequence that is at least 90% identical to a sequence of any one of SEQ ID NOs: 936-953; (f) nucleotide 6 through nucleotide 36 of a sequence that is at least 90% identical to a sequence of any one of SEQ ID NOs: 936-953; (g) nucleotide 7 through nucleotide 36 of a sequence that is at least 90% identical to a sequence of any one of SEQ ID NOs: 936-953; (h) nucleotide 8 through nucleotide 36 of a sequence that is at least 90% identical to a sequence of any one of SEQ ID NOs: 936-953; (i) nucleotide 9 through nucleotide 36 of a sequence that is at least 90% identical to a sequence of any one of SEQ ID NOs: 936-953; (j) nucleotide 10 through nucleotide 36 of a sequence that is at least 90% identical to a sequence of any one of SEQ ID NOs: 936-953; (k) nucleotide 11 through nucleotide 36 of a sequence that is at least 90% identical to a sequence of any one of SEQ ID NOs: 936-953; (l) nucleotide 12 through nucleotide 36 of a sequence that is at least 90% identical to a sequence of any one of SEQ ID NOs: 936-953; (m) nucleotide 13 through nucleotide 36 of a sequence that is at least 90% identical to a sequence of any one of SEQ ID NOs: 936-953; (n) nucleotide 14 through nucleotide 36 of a sequence that is at least 90% identical to a sequence of any one of SEQ ID NOs: 936-953; or (o) a sequence that is at least 90% identical to a sequence of SEQ ID NO: 954 or a portion thereof).

In some examples, the direct repeat sequence comprises: (a) nucleotide 1 through nucleotide 36 of any one of SEQ ID NOs: 936-953; (b) nucleotide 2 through nucleotide 36 of any one of SEQ ID NOs: 936-953; (c) nucleotide 3 through nucleotide 36 of any one of SEQ ID NOs: 936-953; (d) nucleotide 4 through nucleotide 36 of any one of SEQ ID NOs: 936-953; (e) nucleotide 5 through nucleotide 36 of any one of SEQ ID NOs: 936-953; (f) nucleotide 6 through nucleotide 36 of any one of SEQ ID NOs: 936-953; (g) nucleotide 7 through nucleotide 36 of any one of SEQ ID NOs: 936-953; (h) nucleotide 8 through nucleotide 36 of any one of SEQ ID NOs: 936-953; (i) nucleotide 9 through nucleotide 36 of any one of SEQ ID NOs: 936-953; (j) nucleotide 10 through nucleotide 36 of any one of SEQ ID NOs: 936-953; (k) nucleotide 11 through nucleotide 36 of any one of SEQ ID NOs: 936-953; (l) nucleotide 12 through nucleotide 36 of any one of SEQ ID NOs: 936-953; (m) nucleotide 13 through nucleotide 36 of any one of SEQ ID NOs: 936-953; (n) nucleotide 14 through nucleotide 36 of any one of SEQ ID NOs: 936-953; (or o) SEQ ID NO: 954 or a portion thereof.

In some examples, the direct repeat sequence comprises: (a) nucleotide 1 through nucleotide 36 of a sequence that is at least 90% identical to SEQ ID NO: 959; (b) nucleotide 2 through nucleotide 36 of a sequence that is at least 90% identical to SEQ ID NO: 959; (c) nucleotide 3 through nucleotide 36 of a sequence that is at least 90% identical to SEQ ID NO: 959; (d) nucleotide 4 through nucleotide 36 of a sequence that is at least 90% identical to SEQ ID NO: 959; (e) nucleotide 5 through nucleotide 36 of a sequence that is at least 90% identical to SEQ ID NO: 959; (f) nucleotide 6 through nucleotide 36 of a sequence that is at least 90% identical to SEQ ID NO: 959; (g) nucleotide 7 through nucleotide 36 of a sequence that is at least 90% identical to SEQ ID NO: 959; (h) nucleotide 8 through nucleotide 36 of a sequence that is at least 90% identical to SEQ ID NO: 959;

(i) nucleotide 9 through nucleotide 36 of a sequence that is at least 90% identical to SEQ ID NO: 959; (j) nucleotide 10 through nucleotide 36 of a sequence that is at least 90% identical to SEQ ID NO: 959; (k) nucleotide 11 through nucleotide 36 of a sequence that is at least 90% identical to SEQ ID NO: 959; (l) nucleotide 12 through nucleotide 36 of a sequence that is at least 90% identical to SEQ ID NO: 959; (m) nucleotide 13 through nucleotide 36 of a sequence that is at least 90% identical to SEQ ID NO: 959; (n) nucleotide 14 through nucleotide 36 of a sequence that is at least 90% identical to SEQ ID NO: 959; or (o) a sequence that is at least 90% identical to a sequence of SEQ ID NO: 960 or SEQ ID NO: 961 or a portion thereof).

In some examples, the direct repeat sequence comprises: (a) nucleotide 1 through nucleotide 36 of SEQ ID NO: 959; (b) nucleotide 2 through nucleotide 36 of SEQ ID NO: 959; (c) nucleotide 3 through nucleotide 36 of SEQ ID NO: 959; (d) nucleotide 4 through nucleotide 36 of SEQ ID NO: 959; (e) nucleotide 5 through nucleotide 36 of SEQ ID NO: 959; (f) nucleotide 6 through nucleotide 36 of SEQ ID NO: 959; (g) nucleotide 7 through nucleotide 36 of SEQ ID NO: 959; (h) nucleotide 8 through nucleotide 36 of SEQ ID NO: 959; (i) nucleotide 9 through nucleotide 36 of SEQ ID NO: 959; (j) nucleotide 10 through nucleotide 36 of SEQ ID NO: 959; (k) nucleotide 11 through nucleotide 36 of SEQ ID NO: 959; (l) nucleotide 12 through nucleotide 36 of SEQ ID NO: 959; (m) nucleotide 13 through nucleotide 36 of SEQ ID NO: 959; (n) nucleotide 14 through nucleotide 36 of SEQ ID NO: 959; or (o) SEQ ID NO: 960 or SEQ ID NO: 961 or a portion thereof).

In some examples, the direct repeat sequence comprises: (a) nucleotide 1 through nucleotide 36 of a sequence that is at least 90% identical to a sequence of SEQ ID NO: 962 or SEQ ID NO: 963; (b) nucleotide 2 through nucleotide 36 of a sequence that is at least 90% identical to a sequence of SEQ ID NO: 962 or SEQ ID NO: 963; (c) nucleotide 3 through nucleotide 36 of a sequence that is at least 90% identical to a sequence of SEQ ID NO: 962 or SEQ ID NO: 963; (d) nucleotide 4 through nucleotide 36 of a sequence that is at least 90% identical to a sequence of SEQ ID NO: 962 or SEQ ID NO: 963; (e) nucleotide 5 through nucleotide 36 of a sequence that is at least 90% identical to a sequence of SEQ ID NO: 962 or SEQ ID NO: 963; (f) nucleotide 6 through nucleotide 36 of a sequence that is at least 90% identical to a sequence of SEQ ID NO: 962 or SEQ ID NO: 963; (g) nucleotide 7 through nucleotide 36 of a sequence that is at least 90% identical to a sequence of SEQ ID NO: 962 or SEQ ID NO: 963; (h) nucleotide 8 through nucleotide 36 of a sequence that is at least 90% identical to a sequence of SEQ ID NO: 962 or SEQ ID NO: 963; (i) nucleotide 9 through nucleotide 36 of a sequence that is at least 90% identical to a sequence of SEQ ID NO: 962 or SEQ ID NO: 963; (j) nucleotide 10 through nucleotide 36 of a sequence that is at least 90% identical to a sequence of SEQ ID NO: 962 or SEQ ID NO: 963; (k) nucleotide 11 through nucleotide 36 of a sequence that is at least 90% identical to a sequence of SEQ ID NO: 962 or SEQ ID NO: 963; (l) nucleotide 12 through nucleotide 36 of a sequence that is at least 90% identical to a sequence of SEQ ID NO: 962 or SEQ ID NO: 963; (m) nucleotide 13 through nucleotide 36 of a sequence that is at least 90% identical to a sequence of SEQ ID NO: 962 or SEQ ID NO: 963; (n) nucleotide 14 through nucleotide 36 of a sequence that is at least 90% identical to a sequence of SEQ ID NO: 962 or SEQ ID NO: 963; (o) nucleotide 15 through nucleotide 36 of a sequence that is at least 90% identical to a sequence of SEQ ID NO: 962 or SEQ ID NO: 963; or (p) a sequence that is at least 90% identical to a sequence of SEQ ID NO: 964 or a portion thereof).

In some examples, the direct repeat sequence comprises: (a) nucleotide 1 through nucleotide 36 of SEQ ID NO: 962 or SEQ ID NO: 963; (b) nucleotide 2 through nucleotide 36 of SEQ ID NO: 962 or SEQ ID NO: 963; (c) nucleotide 3 through nucleotide 36 of SEQ ID NO: 962 or SEQ ID NO: 963; (d) nucleotide 4 through nucleotide 36 of SEQ ID NO: 962 or SEQ ID NO: 963; (e) nucleotide 5 through nucleotide 36 of SEQ ID NO: 962 or SEQ ID NO: 963; (f) nucleotide 6 through nucleotide 36 of SEQ ID NO: 962 or SEQ ID NO: 963; (g) nucleotide 7 through nucleotide 36 of SEQ ID NO: 962 or SEQ ID NO: 963; (h) nucleotide 8 through nucleotide 36 of SEQ ID NO: 962 or SEQ ID NO: 963; (i) nucleotide 9 through nucleotide 36 of SEQ ID NO: 962 or SEQ ID NO: 963; (j) nucleotide 10 through nucleotide 36 of SEQ ID NO: 962 or SEQ ID NO: 963; (k) nucleotide 11 through nucleotide 36 of SEQ ID NO: 962 or SEQ ID NO: 963; (l) nucleotide 12 through nucleotide 36 of SEQ ID NO: 962 or SEQ ID NO: 963; (m) nucleotide 13 through nucleotide 36 of SEQ ID NO: 962 or SEQ ID NO: 963; (n) nucleotide 14 through nucleotide 36 of SEQ ID NO: 962 or SEQ ID NO: 963; (o) nucleotide 15 through nucleotide 36 of SEQ ID NO: 962 or SEQ ID NO: 963; or (p) SEQ ID NO: 964 or a portion thereof).

In some examples, the spacer sequence is substantially complementary or completely complementary to the complement of a sequence of any one of SEQ ID NOs: 11-465.

In any of the composition of Embodiment 1, the PAM may comprise the sequence 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3'.

In some examples, the target sequence is immediately adjacent to the PAM sequence.

In some examples, the RNA guide has a sequence that is at least 90% identical to a sequence of any one of SEQ ID NOs: 967-1023.

In some examples, the RNA guide has the sequence of any one of SEQ ID NOs: 967-1023.

Embodiment 2: The composition of Embodiment 1 may further comprise a Cas12i polypeptide or a polyribonucleotide encoding a Cas12i polypeptide, which can be one of the following: (a) a Cas12i2 polypeptide comprising a sequence that is at least 90% identical to the sequence of SEQ ID NO: 922, SEQ ID NO: 923, SEQ ID NO: 924, SEQ ID NO: 925, SEQ ID NO: 926, or SEQ ID NO: 927; (b) a Cas12i4 polypeptide comprising a sequence that is at least 90% identical to the sequence of SEQ ID NO: 956, SEQ ID NO: 957, or SEQ ID NO: 958; (c) a Cas12i1 polypeptide comprising a sequence that is at least 90% identical to the sequence of SEQ ID NO: 965; or (d) a Cas12i3 polypeptide comprising a sequence that is at least 90% identical to the sequence of SEQ ID NO: 966.

In specific examples, the Cas12i polypeptide is: (a) a Cas12i2 polypeptide comprising a sequence of SEQ ID NO: 922, SEQ ID NO: 923, SEQ ID NO: 924, SEQ ID NO: 925, SEQ ID NO: 926, or SEQ ID NO: 927; (b) a Cas12i4 polypeptide comprising a sequence of SEQ ID NO: 956, SEQ ID NO: 957, or SEQ ID NO: 958; (c) a Cas12i1 polypeptide comprising a sequence of SEQ ID NO: 965; or (d) a Cas12i3 polypeptide comprising a sequence of SEQ ID NO: 966.

In any of the compositions of Embodiment 2, the RNA guide and the Cas12i polypeptide may form a ribonucleoprotein complex. In some examples, the ribonucleoprotein complex binds a target nucleic acid. In some examples, the composition is present within a cell.

In any of the compositions of Embodiment 2, the RNA guide and the Cas12i polypeptide may be encoded in a vector, e.g., expression vector. In some examples, the RNA guide and the Cas12i polypeptide are encoded in a single vector. In other examples, the RNA guide is encoded in a first vector and the Cas12i polypeptide is encoded in a second vector.

Embodiment 3: A vector system comprising one or more vectors encoding an RNA guide disclosed herein and a Cas12i polypeptide. In some examples, the vector system comprises a first vector encoding an RNA guide disclosed herein and a second vector encoding a Cas12i polypeptide. The vectors may be expression vectors.

Embodiment 4: A composition comprising an RNA guide and a Cas12i polypeptide, wherein the RNA guide comprises (i) a spacer sequence that is substantially complementary or completely complementary to a region on a non-PAM strand (the complementary sequence of a target sequence) within an HAO1 gene; and (ii) a direct repeat sequence.

In some examples, the target sequence is within exon 1, exon 2, exon 3, exon 4, exon 5, exon 6, or exon 7 of the HAO1 gene, which may comprise the sequence of SEQ ID NO: 928, the reverse complement of SEQ ID NO: 928, a variant of the sequence of SEQ ID NO: 928, or the reverse complement of a variant of SEQ ID NO: 928.

In some examples, the spacer sequence comprises: (a) nucleotide 1 through nucleotide 16 of a sequence that is at least 90% identical to a sequence of any one of SEQ ID NOs: 466-920; (b) nucleotide 1 through nucleotide 17 of a sequence that is at least 90% identical to a sequence of any one of SEQ ID NOs: 466-920; (c) nucleotide 1 through nucleotide 18 of a sequence that is at least 90% identical to a sequence of any one of SEQ ID NOs: 466-920; (d) nucleotide 1 through nucleotide 19 of a sequence that is at least 90% identical to a sequence of any one of SEQ ID NOs: 466-920; (e) nucleotide 1 through nucleotide 20 of a sequence that is at least 90% identical to a sequence of any one of SEQ ID NOs: 466-920; (f) nucleotide 1 through nucleotide 21 of a sequence that is at least 90% identical to a sequence of any one of SEQ ID NOs: 466-920; (g) nucleotide 1 through nucleotide 22 of a sequence that is at least 90% identical to a sequence of any one of SEQ ID NOs: 466-920; (h) nucleotide 1 through nucleotide 23 of a sequence that is at least 90% identical to a sequence of any one of SEQ ID NOs: 466-920; (i) nucleotide 1 through nucleotide 24 of a sequence that is at least 90% identical to a sequence of any one of SEQ ID NOs: 466-920; (j) nucleotide 1 through nucleotide 25 of a sequence that is at least 90% identical to a sequence of any one of SEQ ID NOs: 466-920; (k) nucleotide 1 through nucleotide 26 of a sequence that is at least 90% identical to a sequence of any one of SEQ ID NOs: 466-920; (l) nucleotide 1 through nucleotide 27 of a sequence that is at least 90% identical to a sequence of any one of SEQ ID NOs: 466-920; (m) nucleotide 1 through nucleotide 28 of a sequence that is at least 90% identical to a sequence of any one of SEQ ID NOs: 466-920; (n) nucleotide 1 through nucleotide 29 of a sequence that is at least 90% identical to a sequence of any one of SEQ ID NOs: 466-920; or (o) nucleotide 1 through nucleotide 30 of a sequence that is at least 90% identical to a sequence of any one of SEQ ID NOs: 466-920.

In some examples, the spacer sequence comprises: (a) nucleotide 1 through nucleotide 16 of any one of SEQ ID NOs: 466-920; (b) nucleotide 1 through nucleotide 17 of any one of SEQ ID NOs: 466-920; (c) nucleotide 1 through nucleotide 18 of any one of SEQ ID NOs: 466-920; (d) nucleotide 1 through nucleotide 19 of any one of SEQ ID NOs: 466-920; (e) nucleotide 1 through nucleotide 20 of any one of SEQ ID NOs: 466-920; (f) nucleotide 1 through nucleotide 21 of any one of SEQ ID NOs: 466-920; (g) nucleotide 1 through nucleotide 22 of any one of SEQ ID NOs: 466-920; (h) nucleotide 1 through nucleotide 23 of any one of SEQ ID NOs: 466-920; (i) nucleotide 1 through nucleotide 24 of any one of SEQ ID NOs: 466-920; (j) nucleotide 1 through nucleotide 25 of any one of SEQ ID NOs: 466-920; (k) nucleotide 1 through nucleotide 26 of any one of SEQ ID NOs: 466-920; (l) nucleotide 1 through nucleotide 27 of any one of SEQ ID NOs: 466-920; (m) nucleotide 1 through nucleotide 28 of any one of SEQ ID NOs: 466-920; (n) nucleotide 1 through nucleotide 29 of any one of SEQ ID NOs: 466-920; or (o) nucleotide 1 through nucleotide 30 of any one of SEQ ID NOs: 466-920.

In some examples, the direct repeat sequence comprises: (a) nucleotide 1 through nucleotide 36 of a sequence that is at least 90% identical to a sequence of any one of SEQ ID NOs: 1-8; (b) nucleotide 2 through nucleotide 36 of a sequence that is at least 90% identical to a sequence of any one of SEQ ID NOs: 1-8; (c) nucleotide 3 through nucleotide 36 of a sequence that is at least 90% identical to a sequence of any one of SEQ ID NOs: 1-8; (d) nucleotide 4 through nucleotide 36 of a sequence that is at least 90% identical to a sequence of any one of SEQ ID NOs: 1-8; (e) nucleotide 5 through nucleotide 36 of a sequence that is at least 90% identical to a sequence of any one of SEQ ID NOs: 1-8; (f) nucleotide 6 through nucleotide 36 of a sequence that is at least 90% identical to a sequence of any one of SEQ ID NOs: 1-8; (g) nucleotide 7 through nucleotide 36 of a sequence that is at least 90% identical to a sequence of any one of SEQ ID NOs: 1-8; (h) nucleotide 8 through nucleotide 36 of a sequence that is at least 90% identical to a sequence of any one of SEQ ID NOs: 1-8; (i) nucleotide 9 through nucleotide 36 of a sequence that is at least 90% identical to a sequence of any one of SEQ ID NOs: 1-8; (j) nucleotide 10 through nucleotide 36 of a sequence that is at least 90% identical to a sequence of any one of SEQ ID NOs: 1-8; (k) nucleotide 11 through nucleotide 36 of a sequence that is at least 90% identical to a sequence of any one of SEQ ID NOs: 1-8; (l) nucleotide 12 through nucleotide 36 of a sequence that is at least 90% identical to a sequence of any one of SEQ ID NOs: 1-8; (m) nucleotide 13 through nucleotide 36 of a sequence that is at least 90% identical to a sequence of any one of SEQ ID NOs: 1-8; (n) nucleotide 14 through nucleotide 36 of a sequence that is at least 90% identical to a sequence of any one of SEQ ID NOs: 1-8; (o) nucleotide 1 through nucleotide 34 of a sequence that is at least 90% identical to a sequence of SEQ ID NO: 9; (p) nucleotide 2 through nucleotide 34 of a sequence that is at least 90% identical to a sequence of SEQ ID NO: 9; (q) nucleotide 3 through nucleotide 34 of a sequence that is at least 90% identical to a sequence of SEQ ID NO: 9; (r) nucleotide 4 through nucleotide 34 of a sequence that is at least 90% identical to a sequence of SEQ ID NO: 9; (s) nucleotide 5 through nucleotide 34 of a sequence that is at least 90% identical to a sequence of SEQ ID NO: 9; (t) nucleotide 6 through nucleotide 34 of a sequence that is at least 90% identical to a sequence of SEQ ID NO: 9; (u) nucleotide 7 through nucleotide 34 of a sequence that is at least 90% identical to a sequence of SEQ ID NO: 9; (v) nucleotide 8 through nucleotide 34 of a sequence that is at least 90% identical to a sequence of SEQ ID NO: 9; (w) nucleotide 9 through nucleotide 34 of a sequence that is at least 90% identical to a sequence of SEQ ID NO: 9; (x) nucleotide 10 through nucleotide 34 of a sequence that is at least 90% identical to a sequence of SEQ ID NO: 9; (y) nucleotide 11 through nucleotide 34 of a sequence that is at least 90% identical to a sequence of SEQ ID NO: 9; (z) nucleotide 12 through nucleotide 34 of a sequence that is at least 90% identical to a sequence of SEQ ID NO: 9; or (aa) a sequence that is at least 90% identical to a sequence of SEQ ID NO: 10 or a portion thereof).

In some examples, the direct repeat sequence comprises: (a) nucleotide 1 through nucleotide 36 of any one of SEQ ID NOs: 1-8; (b) nucleotide 2 through nucleotide 36 of any one of SEQ ID NOs: 1-8; (c) nucleotide 3 through nucleotide 36 of any one of SEQ ID NOs: 1-8; (d) nucleotide 4 through nucleotide 36 of any one of SEQ ID NOs: 1-8; (e) nucleotide 5 through nucleotide 36 of any one of SEQ ID NOs: 1-8; (f) nucleotide 6 through nucleotide 36 of any one of SEQ ID NOs: 1-8; (g) nucleotide 7 through nucleotide 36 of any one of SEQ ID NOs: 1-8; (h) nucleotide 8 through nucleotide 36 of any one of SEQ ID NOs: 1-8; (i) nucleotide 9 through nucleotide 36 of any one of SEQ ID NOs: 1-8; (j) nucleotide 10 through nucleotide 36 of any one of SEQ ID NOs: 1-8; (k) nucleotide 11 through nucleotide 36 of any one of SEQ ID NOs: 1-8; (1) nucleotide 12 through nucleotide 36 of any one of SEQ ID NOs: 1-8; (m) nucleotide 13 through nucleotide 36 of any one of SEQ ID NOs: 1-8; (n) nucleotide 14 through nucleotide 36 of any one of SEQ ID NOs: 1-8; (o) nucleotide 1 through nucleotide 34 of SEQ ID NO: 9; (p) nucleotide 2 through nucleotide 34 of SEQ ID NO: 9; (q) nucleotide 3 through nucleotide 34 of SEQ ID NO: 9; (r) nucleotide 4 through nucleotide 34 of SEQ ID NO: 9; (s) nucleotide 5 through nucleotide 34 of SEQ ID NO: 9; (t) nucleotide 6 through nucleotide 34 of SEQ ID NO: 9; (u) nucleotide 7 through nucleotide 34 of SEQ ID NO: 9; (v) nucleotide 8 through nucleotide 34 of SEQ ID NO: 9; (w) nucleotide 9 through nucleotide 34 of SEQ ID NO: 9; (x) nucleotide 10 through nucleotide 34 of SEQ ID NO: 9; (y) nucleotide 11 through nucleotide 34 of SEQ ID NO: 9; (z) nucleotide 12 through nucleotide 34 of SEQ ID NO: 9; or (aa) SEQ ID NO: 10 or a portion thereof.

In some examples, the direct repeat sequence comprises: (a) nucleotide 1 through nucleotide 36 of a sequence that is at least 90% identical to a sequence of any one of SEQ ID NOs: 936-953; (b) nucleotide 2 through nucleotide 36 of a sequence that is at least 90% identical to a sequence of any one of SEQ ID NOs: 936-953; (c) nucleotide 3 through nucleotide 36 of a sequence that is at least 90% identical to a sequence of any one of SEQ ID NOs: 936-953; (d) nucleotide 4 through nucleotide 36 of a sequence that is at least 90% identical to a sequence of any one of SEQ ID NOs: 936-953; (e) nucleotide 5 through nucleotide 36 of a sequence that is at least 90% identical to a sequence of any one of SEQ ID NOs: 936-953; (f) nucleotide 6 through nucleotide 36 of a sequence that is at least 90% identical to a sequence of any one of SEQ ID NOs: 936-953; (g) nucleotide 7 through nucleotide 36 of a sequence that is at least 90% identical to a sequence of any one of SEQ ID NOs: 936-953; (h) nucleotide 8 through nucleotide 36 of a sequence that is at least 90% identical to a sequence of any one of SEQ ID NOs: 936-953; (i) nucleotide 9 through nucleotide 36 of a sequence that is at least 90% identical to a sequence of any one of SEQ ID NOs: 936-953; (j) nucleotide 10 through nucleotide 36 of a sequence that is at least 90% identical to a sequence of any one of SEQ ID NOs: 936-953; (k) nucleotide 11 through nucleotide 36 of a sequence that is at least 90% identical to a sequence of any one of SEQ ID NOs: 936-953; (l) nucleotide 12 through nucleotide 36 of a sequence that is at least 90% identical to a sequence of any one of SEQ ID NOs: 936-953; (m) nucleotide 13 through nucleotide 36 of a sequence that is at least 90% identical to a sequence of any one of SEQ ID NOs: 936-953; (n) nucleotide 14 through nucleotide 36 of a sequence that is at least 90% identical to a sequence of any one of SEQ ID NOs: 936-953; or (o) a sequence that is at least 90% identical to a sequence of SEQ ID NO: 954 or a portion thereof.

In some examples, the direct repeat sequence comprises: (a) nucleotide 1 through nucleotide 36 of any one of SEQ ID NOs: 936-953; (b) nucleotide 2 through nucleotide 36 of any one of SEQ ID NOs: 936-953; (c) nucleotide 3 through nucleotide 36 of any one of SEQ ID NOs: 936-953; (d) nucleotide 4 through nucleotide 36 of any one of SEQ ID NOs: 936-953; (e) nucleotide 5 through nucleotide 36 of any one of SEQ ID NOs: 936-953; (f) nucleotide 6 through nucleotide 36 of any one of SEQ ID NOs: 936-953; (g) nucleotide 7 through nucleotide 36 of any one of SEQ ID NOs: 936-953; (h) nucleotide 8 through nucleotide 36 of any one of SEQ ID NOs: 936-953; (i) nucleotide 9 through nucleotide 36 of any one of SEQ ID NOs: 936-953; (j) nucleotide 10 through nucleotide 36 of any one of SEQ ID NOs: 936-953; (k) nucleotide 11 through nucleotide 36 of any one of SEQ ID NOs: 936-953; (l) nucleotide 12 through nucleotide 36 of any one of SEQ ID NOs: 936-953; (m) nucleotide 13 through nucleotide 36 of any one of SEQ ID NOs: 936-953; (n) nucleotide 14 through nucleotide 36 of any one of SEQ ID NOs: 936-953; or (o) SEQ ID NO: 954 or a portion thereof.

In some embodiments, the direct repeat sequence comprises: (a) nucleotide 1 through nucleotide 36 of a sequence that is at least 90% identical to SEQ ID NO: 959; (b) nucleotide 2 through nucleotide 36 of a sequence that is at least 90% identical to SEQ ID NO: 959; (c) nucleotide 3 through nucleotide 36 of a sequence that is at least 90% identical to SEQ ID NO: 959; (d) nucleotide 4 through nucleotide 36 of a sequence that is at least 90% identical to SEQ ID NO: 959; (e) nucleotide 5 through nucleotide 36 of a sequence that is at least 90% identical to SEQ ID NO: 959; (f) nucleotide 6 through nucleotide 36 of a sequence that is at least 90% identical to SEQ ID NO: 959; (g) nucleotide 7 through nucleotide 36 of a sequence that is at least 90% identical to SEQ ID NO: 959; (h) nucleotide 8 through nucleotide 36 of a sequence that is at least 90% identical to SEQ ID NO: 959; (i) nucleotide 9 through nucleotide 36 of a sequence that is at least 90% identical to SEQ ID NO: 959; (j) nucleotide 10 through nucleotide 36 of a sequence that is at least 90% identical to SEQ ID NO: 959; (k) nucleotide 11 through nucleotide 36 of a sequence that is at least 90% identical to SEQ ID NO: 959; (l) nucleotide 12 through nucleotide 36 of a sequence that is at least 90% identical to SEQ ID NO: 959; (m) nucleotide 13 through nucleotide 36 of a sequence that is at least 90% identical to SEQ ID NO: 959; (n) nucleotide 14 through nucleotide 36 of a sequence that is at least 90% identical to SEQ ID NO: 959; or (o) a sequence that is at least 90% identical to a sequence of SEQ ID NO: 960 or SEQ ID NO: 961 or a portion thereof.

In some examples, the direct repeat sequence comprises: (a) nucleotide 1 through nucleotide 36 of SEQ ID NO: 959; (b) nucleotide 2 through nucleotide 36 of SEQ ID NO: 959; (c) nucleotide 3 through nucleotide 36 of SEQ ID NO: 959; (d) nucleotide 4 through nucleotide 36 of SEQ ID NO: 959; (e) nucleotide 5 through nucleotide 36 of SEQ ID NO: 959;

(f) nucleotide 6 through nucleotide 36 of SEQ ID NO: 959; (g) nucleotide 7 through nucleotide 36 of SEQ ID NO: 959; (h) nucleotide 8 through nucleotide 36 of SEQ ID NO: 959; (i) nucleotide 9 through nucleotide 36 of SEQ ID NO: 959; (j) nucleotide 10 through nucleotide 36 of SEQ ID NO: 959; (k) nucleotide 11 through nucleotide 36 of SEQ ID NO: 959; (l) nucleotide 12 through nucleotide 36 of SEQ ID NO: 959; (m) nucleotide 13 through nucleotide 36 of SEQ ID NO: 959; (n) nucleotide 14 through nucleotide 36 of SEQ ID NO: 959; or (o) SEQ ID NO: 960 or SEQ ID NO: 961 or a portion thereof.

In some examples, the direct repeat sequence comprises: (a) nucleotide 1 through nucleotide 36 of a sequence that is at least 90% identical to a sequence of SEQ ID NO: 962 or SEQ ID NO: 963; (b) nucleotide 2 through nucleotide 36 of a sequence that is at least 90% identical to a sequence of SEQ ID NO: 962 or SEQ ID NO: 963; (c) nucleotide 3 through nucleotide 36 of a sequence that is at least 90% identical to a sequence of SEQ ID NO: 962 or SEQ ID NO: 963; (d) nucleotide 4 through nucleotide 36 of a sequence that is at least 90% identical to a sequence of SEQ ID NO: 962 or SEQ ID NO: 963; (e) nucleotide 5 through nucleotide 36 of a sequence that is at least 90% identical to a sequence of SEQ ID NO: 962 or SEQ ID NO: 963; (f) nucleotide 6 through nucleotide 36 of a sequence that is at least 90% identical to a sequence of SEQ ID NO: 962 or SEQ ID NO: 963; (g) nucleotide 7 through nucleotide 36 of a sequence that is at least 90% identical to a sequence of SEQ ID NO: 962 or SEQ ID NO: 963; (h) nucleotide 8 through nucleotide 36 of a sequence that is at least 90% identical to a sequence of SEQ ID NO: 962 or SEQ ID NO: 963; (i) nucleotide 9 through nucleotide 36 of a sequence that is at least 90% identical to a sequence of SEQ ID NO: 962 or SEQ ID NO: 963; (j) nucleotide 10 through nucleotide 36 of a sequence that is at least 90% identical to a sequence of SEQ ID NO: 962 or SEQ ID NO: 963; (k) nucleotide 11 through nucleotide 36 of a sequence that is at least 90% identical to a sequence of SEQ ID NO: 962 or SEQ ID NO: 963; (l) nucleotide 12 through nucleotide 36 of a sequence that is at least 90% identical to a sequence of SEQ ID NO: 962 or SEQ ID NO: 963; (m) nucleotide 13 through nucleotide 36 of a sequence that is at least 90% identical to a sequence of SEQ ID NO: 962 or SEQ ID NO: 963; (n) nucleotide 14 through nucleotide 36 of a sequence that is at least 90% identical to a sequence of SEQ ID NO: 962 or SEQ ID NO: 963; (o) nucleotide 15 through nucleotide 36 of a sequence that is at least 90% identical to a sequence of SEQ ID NO: 962 or SEQ ID NO: 963; or (p) a sequence that is at least 90% identical to a sequence of SEQ ID NO: 964 or a portion thereof.

In some examples, the direct repeat sequence comprises: (a) nucleotide 1 through nucleotide 36 of SEQ ID NO: 962 or SEQ ID NO: 963; (b) nucleotide 2 through nucleotide 36 of SEQ ID NO: 962 or SEQ ID NO: 963; (c) nucleotide 3 through nucleotide 36 of SEQ ID NO: 962 or SEQ ID NO: 963; (d) nucleotide 4 through nucleotide 36 of SEQ ID NO: 962 or SEQ ID NO: 963; (e) nucleotide 5 through nucleotide 36 of SEQ ID NO: 962 or SEQ ID NO: 963; (f) nucleotide 6 through nucleotide 36 of SEQ ID NO: 962 or SEQ ID NO: 963; (g) nucleotide 7 through nucleotide 36 of SEQ ID NO: 962 or SEQ ID NO: 963; (h) nucleotide 8 through nucleotide 36 of SEQ ID NO: 962 or SEQ ID NO: 963; (i) nucleotide 9 through nucleotide 36 of SEQ ID NO: 962 or SEQ ID NO: 963; (j) nucleotide 10 through nucleotide 36 of SEQ ID NO: 962 or SEQ ID NO: 963; (k) nucleotide 11 through nucleotide 36 of SEQ ID NO: 962 or SEQ ID NO: 963; (l) nucleotide 12 through nucleotide 36 of SEQ ID NO: 962 or SEQ ID NO: 963; (m) nucleotide 13 through nucleotide 36 of SEQ ID NO: 962 or SEQ ID NO: 963; (n) nucleotide 14 through nucleotide 36 of SEQ ID NO: 962 or SEQ ID NO: 963; (o) nucleotide 15 through nucleotide 36 of SEQ ID NO: 962 or SEQ ID NO: 963; or (p) SEQ ID NO: 964 or a portion thereof.

In any of the compositions of Embodiment 4, the spacer sequence may be substantially complementary or completely complementary to the complement of a sequence of any one of SEQ ID NOs: 11-465.

In some examples, the target sequence is adjacent to a protospacer adjacent motif (PAM) comprising the sequence 5'-NTTN-3'. In some examples, the PAM comprises the sequence 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3'.

In some examples, the target sequence is immediately adjacent to the PAM sequence. In some examples, the target sequence is within 1, 2, 3, 4, or 5 nucleotides of the PAM sequence.

In any of the composition of Embodiment 4, the Cas12i polypeptide is: (a) a Cas12i2 polypeptide comprising a sequence that is at least 90% identical to the sequence of SEQ ID NO: 922, SEQ ID NO: 923, SEQ ID NO: 924, SEQ ID NO: 925, SEQ ID NO: 926, or SEQ ID NO: 927; (b) a Cas12i4 polypeptide comprising a sequence that is at least 90% identical to the sequence of SEQ ID NO: 956, SEQ ID NO: 957, or SEQ ID NO: 958; (c) a Cas12i1 polypeptide comprising a sequence that is at least 90% identical to the sequence of SEQ ID NO: 965; (or (d) a Cas12i3 polypeptide comprising a sequence that is at least 90% identical to the sequence of SEQ ID NO: 966.

In some examples, the Cas12i polypeptide is: (a) a Cas12i2 polypeptide comprising a sequence of SEQ ID NO: 922, SEQ ID NO: 923, SEQ ID NO: 924, SEQ ID NO: 925, SEQ ID NO: 926, or SEQ ID NO: 927; (b) a Cas12i4 polypeptide comprising a sequence of SEQ ID NO: 956, SEQ ID NO: 957, or SEQ ID NO: 958; (c) a Cas12i1 polypeptide comprising a sequence of SEQ ID NO: 965; or (d) a Cas12i3 polypeptide comprising a sequence of SEQ ID NO: 966.

In any of the composition of Embodiment 4, the RNA guide and the Cas12i polypeptide may form a ribonucleoprotein complex. In some examples, the ribonucleoprotein complex binds a target nucleic acid.

In any of the composition of Embodiment 4, the composition may be present within a cell.

In any of the composition of Embodiment 4, the RNA guide and the Cas12i polypeptide may be encoded in a vector, e.g., expression vector. In some examples, the RNA guide and the Cas12i polypeptide are encoded in a single vector. In other examples, the RNA guide is encoded in a first vector and the Cas12i polypeptide is encoded in a second vector.

Embodiment 5: A vector system comprising one or more vectors encoding an RNA guide disclosed herein and a Cas12i polypeptide. In some examples, the vector system comprises a first vector encoding an RNA guide disclosed herein and a second vector encoding a Cas12i polypeptide. In some examples, the vectors are expression vectors.

Embodiment 6: An RNA guide comprising (i) a spacer sequence that is substantially complementary or completely complementary to a region on a non-PAM strand (the complementary sequence of a target sequence) within an HAO1 gene, and (ii) a direct repeat sequence.

In some examples, the target sequence is within exon 1, exon 2, exon 3, exon 4, exon 5, exon 6, or exon 7 of the HAO1 gene, which may comprise the sequence of SEQ ID NO: 928, the reverse complement of SEQ ID NO: 928, a variant of the sequence of SEQ ID NO: 928, or the reverse complement of a variant of SEQ ID NO: 928.

In some examples, the spacer sequence comprises: (a) nucleotide 1 through nucleotide 16 of a sequence that is at least 90% identical to a sequence of any one of SEQ ID NOs: 466-920; (b) nucleotide 1 through nucleotide 17 of a sequence that is at least 90% identical to a sequence of any one of SEQ ID NOs: 466-920; (c) nucleotide 1 through nucleotide 18 of a sequence that is at least 90% identical to a sequence of any one of SEQ ID NOs: 466-920; (d) nucleotide 1 through nucleotide 19 of a sequence that is at least 90% identical to a sequence of any one of SEQ ID NOs: 466-920; (e) nucleotide 1 through nucleotide 20 of a sequence that is at least 90% identical to a sequence of any one of SEQ ID NOs: 466-920; (f) nucleotide 1 through nucleotide 21 of a sequence that is at least 90% identical to a sequence of any one of SEQ ID NOs: 466-920; (g) nucleotide 1 through nucleotide 22 of a sequence that is at least 90% identical to a sequence of any one of SEQ ID NOs: 466-920; (h) nucleotide 1 through nucleotide 23 of a sequence that is at least 90% identical to a sequence of any one of SEQ ID NOs: 466-920; (i) nucleotide 1 through nucleotide 24 of a sequence that is at least 90% identical to a sequence of any one of SEQ ID NOs: 466-920; (j) nucleotide 1 through nucleotide 25 of a sequence that is at least 90% identical to a sequence of any one of SEQ ID NOs: 466-920; (k) nucleotide 1 through nucleotide 26 of a sequence that is at least 90% identical to a sequence of any one of SEQ ID NOs: 466-920; (l) nucleotide 1 through nucleotide 27 of a sequence that is at least 90% identical to a sequence of any one of SEQ ID NOs: 466-920; (m) nucleotide 1 through nucleotide 28 of a sequence that is at least 90% identical to a sequence of any one of SEQ ID NOs: 466-920; (n) nucleotide 1 through nucleotide 29 of a sequence that is at least 90% identical to a sequence of any one of SEQ ID NOs: 466-920; or (o) nucleotide 1 through nucleotide 30 of a sequence that is at least 90% identical to a sequence of any one of SEQ ID NOs: 466-920.

In some examples, the spacer sequence comprises: (a) nucleotide 1 through nucleotide 16 of any one of SEQ ID NOs: 466-920; (b) nucleotide 1 through nucleotide 17 of any one of SEQ ID NOs: 466-920; (c) nucleotide 1 through nucleotide 18 of any one of SEQ ID NOs: 466-920; (d) nucleotide 1 through nucleotide 19 of any one of SEQ ID NOs: 466-920; (e) nucleotide 1 through nucleotide 20 of any one of SEQ ID NOs: 466-920; (f) nucleotide 1 through nucleotide 21 of any one of SEQ ID NOs: 466-920; (g) nucleotide 1 through nucleotide 22 of any one of SEQ ID NOs: 466-920; (h) nucleotide 1 through nucleotide 23 of any one of SEQ ID NOs: 466-920; (i) nucleotide 1 through nucleotide 24 of any one of SEQ ID NOs: 466-920; (j) nucleotide 1 through nucleotide 25 of any one of SEQ ID NOs: 466-920; (k) nucleotide 1 through nucleotide 26 of any one of SEQ ID NOs: 466-920; (l) nucleotide 1 through nucleotide 27 of any one of SEQ ID NOs: 466-920; (m) nucleotide 1 through nucleotide 28 of any one of SEQ ID NOs: 466-920; (n) nucleotide 1 through nucleotide 29 of any one of SEQ ID NOs: 466-920; or (o) nucleotide 1 through nucleotide 30 of any one of SEQ ID NOs: 466-920.

In some examples, the direct repeat sequence comprises: (a) nucleotide 1 through nucleotide 36 of a sequence that is at least 90% identical to a sequence of any one of SEQ ID NOs: 1-8; (b) nucleotide 2 through nucleotide 36 of a sequence that is at least 90% identical to a sequence of any one of SEQ ID NOs: 1-8; (c) nucleotide 3 through nucleotide 36 of a sequence that is at least 90% identical to a sequence of any one of SEQ ID NOs: 1-8; (d) nucleotide 4 through nucleotide 36 of a sequence that is at least 90% identical to a sequence of any one of SEQ ID NOs: 1-8; (e) nucleotide 5 through nucleotide 36 of a sequence that is at least 90% identical to a sequence of any one of SEQ ID NOs: 1-8; (f) nucleotide 6 through nucleotide 36 of a sequence that is at least 90% identical to a sequence of any one of SEQ ID NOs: 1-8; (g) nucleotide 7 through nucleotide 36 of a sequence that is at least 90% identical to a sequence of any one of SEQ ID NOs: 1-8; (h) nucleotide 8 through nucleotide 36 of a sequence that is at least 90% identical to a sequence of any one of SEQ ID NOs: 1-8; (i) nucleotide 9 through nucleotide 36 of a sequence that is at least 90% identical to a sequence of any one of SEQ ID NOs: 1-8; (j) nucleotide 10 through nucleotide 36 of a sequence that is at least 90% identical to a sequence of any one of SEQ ID NOs: 1-8; (k) nucleotide 11 through nucleotide 36 of a sequence that is at least 90% identical to a sequence of any one of SEQ ID NOs: 1-8; (l) nucleotide 12 through nucleotide 36 of a sequence that is at least 90% identical to a sequence of any one of SEQ ID NOs: 1-8; (m) nucleotide 13 through nucleotide 36 of a sequence that is at least 90% identical to a sequence of any one of SEQ ID NOs: 1-8; (n) nucleotide 14 through nucleotide 36 of a sequence that is at least 90% identical to a sequence of any one of SEQ ID NOs: 1-8; (o) nucleotide 1 through nucleotide 34 of a sequence that is at least 90% identical to a sequence of SEQ ID NO: 9; (p) nucleotide 2 through nucleotide 34 of a sequence that is at least 90% identical to a sequence of SEQ ID NO: 9; (q) nucleotide 3 through nucleotide 34 of a sequence that is at least 90% identical to a sequence of SEQ ID NO: 9; (r) nucleotide 4 through nucleotide 34 of a sequence that is at least 90% identical to a sequence of SEQ ID NO: 9; (s) nucleotide 5 through nucleotide 34 of a sequence that is at least 90% identical to a sequence of SEQ ID NO: 9; (t) nucleotide 6 through nucleotide 34 of a sequence that is at least 90% identical to a sequence of SEQ ID NO: 9; (u) nucleotide 7 through nucleotide 34 of a sequence that is at least 90% identical to a sequence of SEQ ID NO: 9; (v) nucleotide 8 through nucleotide 34 of a sequence that is at least 90% identical to a sequence of SEQ ID NO: 9; (w) nucleotide 9 through nucleotide 34 of a sequence that is at least 90% identical to a sequence of SEQ ID NO: 9; (x) nucleotide 10 through nucleotide 34 of a sequence that is at least 90% identical to a sequence of SEQ ID NO: 9; (y) nucleotide 11 through nucleotide 34 of a sequence that is at least 90% identical to a sequence of SEQ ID NO: 9; (z) nucleotide 12 through nucleotide 34 of a sequence that is at least 90% identical to a sequence of SEQ ID NO: 9; or (aa) a sequence that is at least 90% identical to a sequence of SEQ ID NO: 10 or a portion thereof.

In some examples, the direct repeat sequence comprises: (a) nucleotide 1 through nucleotide 36 of any one of SEQ ID NOs: 1-8; (b) nucleotide 2 through nucleotide 36 of any one of SEQ ID NOs: 1-8; (c) nucleotide 3 through nucleotide 36 of any one of SEQ ID NOs: 1-8; (d) nucleotide 4 through nucleotide 36 of any one of SEQ ID NOs: 1-8; (e) nucleotide 5 through nucleotide 36 of any one of SEQ ID NOs: 1-8; (f) nucleotide 6 through nucleotide 36 of any one of SEQ ID NOs: 1-8; (g) nucleotide 7 through nucleotide 36 of any one of SEQ ID NOs: 1-8; (h) nucleotide 8 through nucleotide 36 of any one of SEQ ID NOs: 1-8; (i) nucleotide 9 through nucleotide 36 of any one of SEQ ID NOs: 1-8; (j) nucleotide 10 through nucleotide 36 of any one of SEQ ID NOs: 1-8;

(k) nucleotide 11 through nucleotide 36 of any one of SEQ ID NOs: 1-8; (1) nucleotide 12 through nucleotide 36 of any one of SEQ ID NOs: 1-8; (m) nucleotide 13 through nucleotide 36 of any one of SEQ ID NOs: 1-8; (n) nucleotide 14 through nucleotide 36 of any one of SEQ ID NOs: 1-8; (o) nucleotide 1 through nucleotide 34 of SEQ ID NO: 9; (p) nucleotide 2 through nucleotide 34 of SEQ ID NO: 9; (q) nucleotide 3 through nucleotide 34 of SEQ ID NO: 9; (r) nucleotide 4 through nucleotide 34 of SEQ ID NO: 9; (s) nucleotide 5 through nucleotide 34 of SEQ ID NO: 9; (t) nucleotide 6 through nucleotide 34 of SEQ ID NO: 9; (u) nucleotide 7 through nucleotide 34 of SEQ ID NO: 9; (v) nucleotide 8 through nucleotide 34 of SEQ ID NO: 9; (w) nucleotide 9 through nucleotide 34 of SEQ ID NO: 9; (x) nucleotide 10 through nucleotide 34 of SEQ ID NO: 9; (y) nucleotide 11 through nucleotide 34 of SEQ ID NO: 9; (z) nucleotide 12 through nucleotide 34 of SEQ ID NO: 9; or (aa) SEQ ID NO: 10 or a portion thereof.

In some examples, the direct repeat sequence comprises: (a) nucleotide 1 through nucleotide 36 of a sequence that is at least 90% identical to a sequence of any one of SEQ ID NOs: 936-953; (b) nucleotide 2 through nucleotide 36 of a sequence that is at least 90% identical to a sequence of any one of SEQ ID NOs: 936-953; (c) nucleotide 3 through nucleotide 36 of a sequence that is at least 90% identical to a sequence of any one of SEQ ID NOs: 936-953; (d) nucleotide 4 through nucleotide 36 of a sequence that is at least 90% identical to a sequence of any one of SEQ ID NOs: 936-953; (e) nucleotide 5 through nucleotide 36 of a sequence that is at least 90% identical to a sequence of any one of SEQ ID NOs: 936-953; (f) nucleotide 6 through nucleotide 36 of a sequence that is at least 90% identical to a sequence of any one of SEQ ID NOs: 936-953; (g) nucleotide 7 through nucleotide 36 of a sequence that is at least 90% identical to a sequence of any one of SEQ ID NOs: 936-953; (h) nucleotide 8 through nucleotide 36 of a sequence that is at least 90% identical to a sequence of any one of SEQ ID NOs: 936-953; (i) nucleotide 9 through nucleotide 36 of a sequence that is at least 90% identical to a sequence of any one of SEQ ID NOs: 936-953; (j) nucleotide 10 through nucleotide 36 of a sequence that is at least 90% identical to a sequence of any one of SEQ ID NOs: 936-953; (k) nucleotide 11 through nucleotide 36 of a sequence that is at least 90% identical to a sequence of any one of SEQ ID NOs: 936-953; (l) nucleotide 12 through nucleotide 36 of a sequence that is at least 90% identical to a sequence of any one of SEQ ID NOs: 936-953; (m) nucleotide 13 through nucleotide 36 of a sequence that is at least 90% identical to a sequence of any one of SEQ ID NOs: 936-953; (n) nucleotide 14 through nucleotide 36 of a sequence that is at least 90% identical to a sequence of any one of SEQ ID NOs: 936-953; or (o) a sequence that is at least 90% identical to a sequence of SEQ ID NO: 954 or a portion thereof.

In some examples, the direct repeat sequence comprises: (a) nucleotide 1 through nucleotide 36 of any one of SEQ ID NOs: 936-953; (b) nucleotide 2 through nucleotide 36 of any one of SEQ ID NOs: 936-953; (c) nucleotide 3 through nucleotide 36 of any one of SEQ ID NOs: 936-953; (d) nucleotide 4 through nucleotide 36 of any one of SEQ ID NOs: 936-953; (e) nucleotide 5 through nucleotide 36 of any one of SEQ ID NOs: 936-953; (f) nucleotide 6 through nucleotide 36 of any one of SEQ ID NOs: 936-953; (g) nucleotide 7 through nucleotide 36 of any one of SEQ ID NOs: 936-953; (h) nucleotide 8 through nucleotide 36 of any one of SEQ ID NOs: 936-953; (i) nucleotide 9 through nucleotide 36 of any one of SEQ ID NOs: 936-953; (j) nucleotide 10 through nucleotide 36 of any one of SEQ ID NOs: 936-953; (k) nucleotide 11 through nucleotide 36 of any one of SEQ ID NOs: 936-953; (l) nucleotide 12 through nucleotide 36 of any one of SEQ ID NOs: 936-953; (m) nucleotide 13 through nucleotide 36 of any one of SEQ ID NOs: 936-953; (n) nucleotide 14 through nucleotide 36 of any one of SEQ ID NOs: 936-953; or (o) SEQ ID NO: 954 or a portion thereof.

In some examples, the direct repeat sequence comprises: (a) nucleotide 1 through nucleotide 36 of a sequence that is at least 90% identical to SEQ ID NO: 959; (b) nucleotide 2 through nucleotide 36 of a sequence that is at least 90% identical to SEQ ID NO: 959; (c) nucleotide 3 through nucleotide 36 of a sequence that is at least 90% identical to SEQ ID NO: 959; (d) nucleotide 4 through nucleotide 36 of a sequence that is at least 90% identical to SEQ ID NO: 959; (e) nucleotide 5 through nucleotide 36 of a sequence that is at least 90% identical to SEQ ID NO: 959; (f) nucleotide 6 through nucleotide 36 of a sequence that is at least 90% identical to SEQ ID NO: 959; (g) nucleotide 7 through nucleotide 36 of a sequence that is at least 90% identical to SEQ ID NO: 959; (h) nucleotide 8 through nucleotide 36 of a sequence that is at least 90% identical to SEQ ID NO: 959; (i) nucleotide 9 through nucleotide 36 of a sequence that is at least 90% identical to SEQ ID NO: 959; (j) nucleotide 10 through nucleotide 36 of a sequence that is at least 90% identical to SEQ ID NO: 959; (k) nucleotide 11 through nucleotide 36 of a sequence that is at least 90% identical to SEQ ID NO: 959; (l) nucleotide 12 through nucleotide 36 of a sequence that is at least 90% identical to SEQ ID NO: 959; (m) nucleotide 13 through nucleotide 36 of a sequence that is at least 90% identical to SEQ ID NO: 959; (n) nucleotide 14 through nucleotide 36 of a sequence that is at least 90% identical to SEQ ID NO: 959; or (o) a sequence that is at least 90% identical to a sequence of SEQ ID NO: 960 or SEQ ID NO: 961 or a portion thereof.

In some examples, the direct repeat sequence comprises: (a) nucleotide 1 through nucleotide 36 of SEQ ID NO: 959; (b) nucleotide 2 through nucleotide 36 of SEQ ID NO: 959; (c) nucleotide 3 through nucleotide 36 of SEQ ID NO: 959; (d) nucleotide 4 through nucleotide 36 of SEQ ID NO: 959; (e) nucleotide 5 through nucleotide 36 of SEQ ID NO: 959; (f) nucleotide 6 through nucleotide 36 of SEQ ID NO: 959; (g) nucleotide 7 through nucleotide 36 of SEQ ID NO: 959; (h) nucleotide 8 through nucleotide 36 of SEQ ID NO: 959; (i) nucleotide 9 through nucleotide 36 of SEQ ID NO: 959; (j) nucleotide 10 through nucleotide 36 of SEQ ID NO: 959; (k) nucleotide 11 through nucleotide 36 of SEQ ID NO: 959; (l) nucleotide 12 through nucleotide 36 of SEQ ID NO: 959; (m) nucleotide 13 through nucleotide 36 of SEQ ID NO: 959; (n) nucleotide 14 through nucleotide 36 of SEQ ID NO: 959; or (o) SEQ ID NO: 960 or SEQ ID NO: 961 or a portion thereof.

In some examples, the direct repeat sequence comprises: (a) nucleotide 1 through nucleotide 36 of a sequence that is at least 90% identical to a sequence of SEQ ID NO: 962 or SEQ ID NO: 963; (b) nucleotide 2 through nucleotide 36 of a sequence that is at least 90% identical to a sequence of SEQ ID NO: 962 or SEQ ID NO: 963; (c) nucleotide 3 through nucleotide 36 of a sequence that is at least 90% identical to a sequence of SEQ ID NO: 962 or SEQ ID NO: 963; (d) nucleotide 4 through nucleotide 36 of a sequence that is at least 90% identical to a sequence of SEQ ID NO: 962 or SEQ ID NO: 963; (e) nucleotide 5 through nucleotide 36 of a sequence that is at least 90% identical to a sequence of SEQ ID NO: 962 or SEQ ID NO: 963; (f) nucleotide 6 through nucleotide 36 of a sequence that is at least 90% identical to a sequence of SEQ ID NO: 962 or SEQ ID NO: 963; (g) nucleotide 7 through nucleotide 36 of a sequence that is at least 90% identical to a sequence of SEQ ID NO: 962 or SEQ ID NO: 963; (h) nucleotide 8 through nucleotide 36 of a sequence that is at least 90% identical to a sequence of SEQ ID NO: 962 or SEQ ID NO: 963; (i) nucleotide 9 through nucleotide 36 of a sequence that is at least 90% identical to a sequence of SEQ ID NO: 962 or SEQ ID NO: 963; (j) nucleotide 10 through nucleotide 36 of a sequence that is at least 90% identical to a sequence of SEQ ID NO: 962 or SEQ ID NO: 963; (k) nucleotide 11 through nucleotide 36 of a sequence that is at least 90% identical to a sequence of SEQ ID NO: 962 or SEQ ID NO: 963; (l) nucleotide 12 through nucleotide 36 of a sequence that is at least 90% identical to a sequence of SEQ ID NO: 962 or SEQ ID NO: 963; (m) nucleotide 13 through nucleotide 36 of a sequence that is at least 90% identical to a sequence of SEQ ID NO: 962 or SEQ ID NO: 963; (n) nucleotide 14 through nucleotide 36 of a sequence that is at least 90% identical to a sequence of SEQ ID NO: 962 or SEQ ID NO: 963; (o) nucleotide 15 through nucleotide 36 of a sequence that is at least 90% identical to a sequence of SEQ ID NO: 962 or SEQ ID NO: 963; or (p) a sequence that is at least 90% identical to a sequence of SEQ ID NO: 964 or a portion thereof.

In some examples, the direct repeat sequence comprises: (a) nucleotide 1 through nucleotide 36 of SEQ ID NO: 962 or SEQ ID NO: 963; (b) nucleotide 2 through nucleotide 36 of SEQ ID NO: 962 or SEQ ID NO: 963; (c) nucleotide 3 through nucleotide 36 of SEQ ID NO: 962 or SEQ ID NO: 963; (d) nucleotide 4 through nucleotide 36 of SEQ ID NO: 962 or SEQ ID NO: 963; (e) nucleotide 5 through nucleotide 36 of SEQ ID NO: 962 or SEQ ID NO: 963; (f) nucleotide 6 through nucleotide 36 of SEQ ID NO: 962 or SEQ ID NO: 963; (g) nucleotide 7 through nucleotide 36 of SEQ ID NO: 962 or SEQ ID NO: 963; (h) nucleotide 8 through nucleotide 36 of SEQ ID NO: 962 or SEQ ID NO: 963; (i) nucleotide 9 through nucleotide 36 of SEQ ID NO: 962 or SEQ ID NO: 963; (j) nucleotide 10 through nucleotide 36 of SEQ ID NO: 962 or SEQ ID NO: 963; (k) nucleotide 11 through nucleotide 36 of SEQ ID NO: 962 or SEQ ID NO: 963; (l) nucleotide 12 through nucleotide 36 of SEQ ID NO: 962 or SEQ ID NO: 963; (m) nucleotide 13 through nucleotide 36 of SEQ ID NO: 962 or SEQ ID NO: 963; (n) nucleotide 14 through nucleotide 36 of SEQ ID NO: 962 or SEQ ID NO: 963; (o) nucleotide 15 through nucleotide 36 of SEQ ID NO: 962 or SEQ ID NO: 963; or (p) SEQ ID NO: 964 or a portion thereof.

In any of the RNA guide of Embodiment 6, the spacer sequence may be substantially complementary or completely complementary to the complement of a sequence of any one of SEQ ID NOs: 11-465.

In any of the RNA guide of Embodiment 6, the target sequence may be adjacent to a protospacer adjacent motif (PAM) comprising the sequence 5'-NTTN-3', wherein N is any nucleotide. In some examples, the PAM comprises the sequence 5'-ATTA-3', 5'-ATTT-3', 5'-ATTG-3', 5'-ATTC-3', 5'-TTTA-3', 5'-TTTT-3', 5'-TTTG-3', 5'-TTTC-3', 5'-GTTA-3', 5'-GTTT-3', 5'-GTTG-3', 5'-GTTC-3', 5'-CTTA-3', 5'-CTTT-3', 5'-CTTG-3', or 5'-CTTC-3'.

In some examples, the target sequence is immediately adjacent to the PAM sequence. In other examples, the target sequence is within 1, 2, 3, 4, or 5 nucleotides of the PAM sequence.

In some examples, the RNA guide has a sequence that is at least 90% identical to a sequence of any one of SEQ ID NOs: 967-1023. In some specific examples, the RNA guide has the sequence of any one of SEQ ID NOs: 967-1023.

Embodiment 7: A nucleic acid encoding an RNA guide as described herein.

Embodiment 8: A vector comprising an RNA guide as described herein.

Embodiment 9: A cell comprising a composition, an RNA guide, a nucleic acid, or a vector as described herein. In some examples, the cell is a eukaryotic cell, an animal cell, a mammalian cell, a human cell, a primary cell, a cell line, a stem cell, or a hepatocyte.

Embodiment 10: A kit comprising a composition, an RNA guide, a nucleic acid, or a vector as described herein.

Embodiment 11: A method of editing an HAO1 sequence, the method comprising contacting an HAO1 sequence with a composition or an RNA guide as described herein. In some examples, the method is carried out in vitro. In other examples, the method is carried out ex vivo.

In some examples, the HAO1 sequence is in a cell.

In some examples, the composition or the RNA guide induces a deletion in the HAO1 sequence. In some examples, the deletion is adjacent to a 5'-NTTN-3' sequence, wherein N is any nucleotide. In some specific examples, the deletion is downstream of the 5'-NTTN-3' sequence. In some specific examples, the deletion is up to about 40 nucleotides in length. In some instances, the deletion is from about 4 nucleotides to 40 nucleotides, about 4 nucleotides to 25 nucleotides, about 10 nucleotides to 25 nucleotides, or about 10 nucleotides to 15 nucleotides in length.

In some examples, the deletion starts within about 5 nucleotides to about 15 nucleotides, about 5 nucleotides to about 10 nucleotides, or about 10 nucleotides to about 15 nucleotides of the 5'-NTTN-3' sequence.

In some examples, the deletion starts within about 5 nucleotides to about 15 nucleotides, about 5 nucleotides to about 10 nucleotides, or about 10 nucleotides to about 15 nucleotides downstream of the 5'-NTTN-3' sequence.

In some examples, the deletion ends within about 20 nucleotides to about 30 nucleotides, about 20 nucleotides to about 25 nucleotides, or about 25 nucleotides to about 30 nucleotides of the 5'-NTTN-3' sequence.

In some examples, the deletion ends within about 20 nucleotides to about 30 nucleotides, about 20 nucleotides to about 25 nucleotides, about 25 nucleotides to about 30 nucleotides downstream of the 5'-NTTN-3' sequence.

In some examples, the deletion starts within about 5 nucleotides to about 15 nucleotides downstream of the 5'-NTTN-3' sequence and ends within about 20 nucleotides to about 30 nucleotides downstream of the 5'-NTTN-3' sequence.

In some examples, the deletion starts within about 5 nucleotides to about 15 nucleotides downstream of the 5'-NTTN-3' sequence and ends within about 20 nucleotides to about 25 nucleotides downstream of the 5'-NTTN-3' sequence.

In some examples, the deletion starts within about 5 nucleotides to about 15 nucleotides downstream of the 5'-NTTN-3' sequence and ends within about 25 nucleotides to about 30 nucleotides downstream of the 5'-NTTN-3' sequence.

In some examples, the deletion starts within about 5 nucleotides to about 10 nucleotides downstream of the 5'-NTTN-3' sequence and ends within about 20 nucleotides to about 30 nucleotides downstream of the 5'-NTTN-3' sequence.

In some examples, the deletion starts within about 5 nucleotides to about 10 nucleotides downstream of the 5'-NTTN-3' sequence and ends within about 20 nucleotides to about 25 nucleotides downstream of the 5'-NTTN-3' sequence.

In some examples, the deletion starts within about 5 nucleotides to about 10 nucleotides downstream of the 5'-NTTN-3' sequence and ends within about 25 nucleotides to about 30 nucleotides downstream of the 5'-NTTN-3' sequence.

In some examples, the deletion starts within about 10 nucleotides to about 15 nucleotides downstream of the 5'-NTTN-3' sequence and ends within about 20 nucleotides to about 30 nucleotides downstream of the 5'-NTTN-3' sequence.

In some examples, the deletion starts within about 10 nucleotides to about 15 nucleotides downstream of the 5'-NTTN-3' sequence and ends within about 20 nucleotides to about 25 nucleotides downstream of the 5'-NTTN-3' sequence.

In some examples, the deletion starts within about 10 nucleotides to about 15 nucleotides downstream of the 5'-NTTN-3' sequence and ends within about 25 nucleotides to about 30 nucleotides downstream of the 5'-NTTN-3' sequence.

In some examples, the 5'-NTTN-3' sequence is 5'-CTTT-3', 5'-CTTC-3', 5'-GTTT-3', 5'-GTTC-3', 5'-TTTC-3', 5'-GTTA-3', or 5'-GTTG-3'.

In some examples, the deletion overlaps with a mutation in the HAO1 sequence. In some instances, the deletion overlaps with an insertion in the HAO1 sequence. In some instances, the deletion removes a repeat expansion of the HAO1 sequence or a portion thereof. In some instances, the deletion disrupts one or both alleles of the HAO1 sequence.

In any of the compositions, RNA guides, nucleic acids, vectors, cells, kits, or methods of Embodiments 1-10 described herein, the RNA guide may comprise the sequence of any one of SEQ ID NOs: 967-1023.

Embodiment 12: A method of treating primary hyperoxaluria (PH), which optionally is PH1, PH2, or PH3, in a subject, the method comprising administering any of the compositions, RNAs, or cells as described herein to the subject.

In any of the compositions, RNA guides, cells, kits, or methods described herein, the RNA guide and/or the polyribonucleotide encoding the Cas12i polypeptide may be comprised within a lipid nanoparticle. In some examples, the RNA guide and the polyribonucleotide encoding the Cas12i polypeptide are comprised within the same lipid nanoparticle. In other examples, the RNA guide and the polyribonucleotide encoding the Cas12i polypeptide are comprised within separate lipid nanoparticles.

Embodiment 13: An RNA guide comprising (i) a spacer sequence that is complementary to a target site within an HAO1 gene (the target site being on the non-PAM strand and complementary to a target sequence), and (ii) a direct repeat sequence, wherein the target sequence is any one of SEQ ID NOs: 1047, 1026, or 1025 or the reverse complement thereof.

In some examples, the direct repeat sequence comprises: (a) nucleotide 1 through nucleotide 36 of a sequence that is at least 90% identical to a sequence of any one of SEQ ID NOs: 1-8; (b) nucleotide 2 through nucleotide 36 of a sequence that is at least 90% identical to a sequence of any one of SEQ ID NOs: 1-8; (c) nucleotide 3 through nucleotide 36 of a sequence that is at least 90% identical to a sequence of any one of SEQ ID NOs: 1-8; (d) nucleotide 4 through nucleotide 36 of a sequence that is at least 90% identical to a sequence of any one of SEQ ID NOs: 1-8; (e) nucleotide 5 through nucleotide 36 of a sequence that is at least 90% identical to a sequence of any one of SEQ ID NOs: 1-8; (f) nucleotide 6 through nucleotide 36 of a sequence that is at least 90% identical to a sequence of any one of SEQ ID NOs: 1-8; (g) nucleotide 7 through nucleotide 36 of a sequence that is at least 90% identical to a sequence of any one of SEQ ID NOs: 1-8; (h) nucleotide 8 through nucleotide 36 of a sequence that is at least 90% identical to a sequence of any one of SEQ ID NOs: 1-8; (i) nucleotide 9 through nucleotide 36 of a sequence that is at least 90% identical to a sequence of any one of SEQ ID NOs: 1-8; (j) nucleotide 10 through nucleotide 36 of a sequence that is at least 90% identical to a sequence of any one of SEQ ID NOs: 1-8; (k) nucleotide 11 through nucleotide 36 of a sequence that is at least 90% identical to a sequence of any one of SEQ ID NOs: 1-8; (l) nucleotide 12 through nucleotide 36 of a sequence that is at least 90% identical to a sequence of any one of SEQ ID NOs: 1-8; (m) nucleotide 13 through nucleotide 36 of a sequence that is at least 90% identical to a sequence of any one of SEQ ID NOs: 1-8; (n) nucleotide 14 through nucleotide 36 of a sequence that is at least 90% identical to a sequence of any one of SEQ ID NOs: 1-8; (o) nucleotide 1 through nucleotide 34 of a sequence that is at least 90% identical to a sequence of SEQ ID NO: 9; (p) nucleotide 2 through nucleotide 34 of a sequence that is at least 90% identical to a sequence of SEQ ID NO: 9; (q) nucleotide 3 through nucleotide 34 of a sequence that is at least 90% identical to a sequence of SEQ ID NO: 9; (r) nucleotide 4 through nucleotide 34 of a sequence that is at least 90% identical to a sequence of SEQ ID NO: 9; (s) nucleotide 5 through nucleotide 34 of a sequence that is at least 90% identical to a sequence of SEQ ID NO: 9; (t) nucleotide 6 through nucleotide 34 of a sequence that is at least 90% identical to a sequence of SEQ ID NO: 9; (u) nucleotide 7 through nucleotide 34 of a sequence that is at least 90% identical to a sequence of SEQ ID NO: 9; (v) nucleotide 8 through nucleotide 34 of a sequence that is at least 90% identical to a sequence of SEQ ID NO: 9; (w) nucleotide 9 through nucleotide 34 of a sequence that is at least 90% identical to a sequence of SEQ ID NO: 9; (x) nucleotide 10 through nucleotide 34 of a sequence that is at least 90% identical to a sequence of SEQ ID NO: 9; (y) nucleotide 11 through nucleotide 34 of a sequence that is at least 90% identical to a sequence of SEQ ID NO: 9; (z) nucleotide 12 through nucleotide 34 of a sequence that is at least 90% identical to a sequence of SEQ ID NO: 9; or (aa) a sequence that is at least 90% identical to a sequence of SEQ ID NO: 10 or a portion thereof.

In some examples, the direct repeat sequence comprises: (a) nucleotide 1 through nucleotide 36 of any one of SEQ ID NOs: 1-8; (b) nucleotide 2 through nucleotide 36 of any one of SEQ ID NOs: 1-8; (c) nucleotide 3 through nucleotide 36 of any one of SEQ ID NOs: 1-8; (d) nucleotide 4 through nucleotide 36 of any one of SEQ ID NOs: 1-8; (e) nucleotide 5 through nucleotide 36 of any one of SEQ ID NOs: 1-8; (f) nucleotide 6 through nucleotide 36 of any one of SEQ ID NOs: 1-8; (g) nucleotide 7 through nucleotide 36 of any one of SEQ ID NOs: 1-8; (h) nucleotide 8 through nucleotide 36 of any one of SEQ ID NOs: 1-8; (i) nucleotide 9 through nucleotide 36 of any one of SEQ ID NOs: 1-8; (j) nucleotide 10 through nucleotide 36 of any one of SEQ ID NOs: 1-8; (k) nucleotide 11 through nucleotide 36 of any one of SEQ ID NOs: 1-8; (1) nucleotide 12 through nucleotide 36 of any one of SEQ ID NOs: 1-8; (m) nucleotide 13 through nucleotide 36 of any one of SEQ ID NOs: 1-8; (n) nucleotide 14 through nucleotide 36 of any one of SEQ ID NOs: 1-8; (o) nucleotide 1 through nucleotide 34 of SEQ ID NO: 9; (p)

nucleotide 2 through nucleotide 34 of SEQ ID NO: 9; (q) nucleotide 3 through nucleotide 34 of SEQ ID NO: 9; (r) nucleotide 4 through nucleotide 34 of SEQ ID NO: 9; (s) nucleotide 5 through nucleotide 34 of SEQ ID NO: 9; (t) nucleotide 6 through nucleotide 34 of SEQ ID NO: 9; (u) nucleotide 7 through nucleotide 34 of SEQ ID NO: 9; (v) nucleotide 8 through nucleotide 34 of SEQ ID NO: 9; (w) nucleotide 9 through nucleotide 34 of SEQ ID NO: 9; (x) nucleotide 10 through nucleotide 34 of SEQ ID NO: 9; (y) nucleotide 11 through nucleotide 34 of SEQ ID NO: 9; (z) nucleotide 12 through nucleotide 34 of SEQ ID NO: 9; or (aa) SEQ ID NO: 10 or a portion thereof.

In some examples, the direct repeat sequence comprises: (a) nucleotide 1 through nucleotide 36 of a sequence that is at least 90% identical to a sequence of any one of SEQ ID NOs: 936-953; (b) nucleotide 2 through nucleotide 36 of a sequence that is at least 90% identical to a sequence of any one of SEQ ID NOs: 936-953; (c) nucleotide 3 through nucleotide 36 of a sequence that is at least 90% identical to a sequence of any one of SEQ ID NOs: 936-953; (d) nucleotide 4 through nucleotide 36 of a sequence that is at least 90% identical to a sequence of any one of SEQ ID NOs: 936-953; (e) nucleotide 5 through nucleotide 36 of a sequence that is at least 90% identical to a sequence of any one of SEQ ID NOs: 936-953; (f) nucleotide 6 through nucleotide 36 of a sequence that is at least 90% identical to a sequence of any one of SEQ ID NOs: 936-953; (g) nucleotide 7 through nucleotide 36 of a sequence that is at least 90% identical to a sequence of any one of SEQ ID NOs: 936-953; (h) nucleotide 8 through nucleotide 36 of a sequence that is at least 90% identical to a sequence of any one of SEQ ID NOs: 936-953; (i) nucleotide 9 through nucleotide 36 of a sequence that is at least 90% identical to a sequence of any one of SEQ ID NOs: 936-953; (j) nucleotide 10 through nucleotide 36 of a sequence that is at least 90% identical to a sequence of any one of SEQ ID NOs: 936-953; (k) nucleotide 11 through nucleotide 36 of a sequence that is at least 90% identical to a sequence of any one of SEQ ID NOs: 936-953; (l) nucleotide 12 through nucleotide 36 of a sequence that is at least 90% identical to a sequence of any one of SEQ ID NOs: 936-953; (m) nucleotide 13 through nucleotide 36 of a sequence that is at least 90% identical to a sequence of any one of SEQ ID NOs: 936-953; (n) nucleotide 14 through nucleotide 36 of a sequence that is at least 90% identical to a sequence of any one of SEQ ID NOs: 936-953; or (o) a sequence that is at least 90% identical to a sequence of SEQ ID NO: 954 or a portion thereof.

In some examples, the direct repeat sequence comprises: (a) nucleotide 1 through nucleotide 36 of any one of SEQ ID NOs: 936-953; (b) nucleotide 2 through nucleotide 36 of any one of SEQ ID NOs: 936-953; (c) nucleotide 3 through nucleotide 36 of any one of SEQ ID NOs: 936-953; (d) nucleotide 4 through nucleotide 36 of any one of SEQ ID NOs: 936-953; (e) nucleotide 5 through nucleotide 36 of any one of SEQ ID NOs: 936-953; (f) nucleotide 6 through nucleotide 36 of any one of SEQ ID NOs: 936-953; (g) nucleotide 7 through nucleotide 36 of any one of SEQ ID NOs: 936-953; (h) nucleotide 8 through nucleotide 36 of any one of SEQ ID NOs: 936-953; (i) nucleotide 9 through nucleotide 36 of any one of SEQ ID NOs: 936-953; (j) nucleotide 10 through nucleotide 36 of any one of SEQ ID NOs: 936-953; (k) nucleotide 11 through nucleotide 36 of any one of SEQ ID NOs: 936-953; (l) nucleotide 12 through nucleotide 36 of any one of SEQ ID NOs: 936-953; (m) nucleotide 13 through nucleotide 36 of any one of SEQ ID NOs: 936-953; (n) nucleotide 14 through nucleotide 36 of any one of SEQ ID NOs: 936-953; or (o) SEQ ID NO: 954 or a portion thereof.

In some examples, the direct repeat sequence comprises: (a) nucleotide 1 through nucleotide 36 of a sequence that is at least 90% identical to SEQ ID NO: 959; (b) nucleotide 2 through nucleotide 36 of a sequence that is at least 90% identical to SEQ ID NO: 959; (c) nucleotide 3 through nucleotide 36 of a sequence that is at least 90% identical to SEQ ID NO: 959; (d) nucleotide 4 through nucleotide 36 of a sequence that is at least 90% identical to SEQ ID NO: 959; (e) nucleotide 5 through nucleotide 36 of a sequence that is at least 90% identical to SEQ ID NO: 959; (f) nucleotide 6 through nucleotide 36 of a sequence that is at least 90% identical to SEQ ID NO: 959; (g) nucleotide 7 through nucleotide 36 of a sequence that is at least 90% identical to SEQ ID NO: 959; (h) nucleotide 8 through nucleotide 36 of a sequence that is at least 90% identical to SEQ ID NO: 959; (i) nucleotide 9 through nucleotide 36 of a sequence that is at least 90% identical to SEQ ID NO: 959; (j) nucleotide 10 through nucleotide 36 of a sequence that is at least 90% identical to SEQ ID NO: 959; (k) nucleotide 11 through nucleotide 36 of a sequence that is at least 90% identical to SEQ ID NO: 959; (l) nucleotide 12 through nucleotide 36 of a sequence that is at least 90% identical to SEQ ID NO: 959; (m) nucleotide 13 through nucleotide 36 of a sequence that is at least 90% identical to SEQ ID NO: 959; (n) nucleotide 14 through nucleotide 36 of a sequence that is at least 90% identical to SEQ ID NO: 959; or (o) a sequence that is at least 90% identical to a sequence of SEQ ID NO: 960 or SEQ ID NO: 961 or a portion thereof.

In some examples, the direct repeat sequence comprises: (a) nucleotide 1 through nucleotide 36 of SEQ ID NO: 959; (b) nucleotide 2 through nucleotide 36 of SEQ ID NO: 959; (c) nucleotide 3 through nucleotide 36 of SEQ ID NO: 959; (d) nucleotide 4 through nucleotide 36 of SEQ ID NO: 959; (e) nucleotide 5 through nucleotide 36 of SEQ ID NO: 959; (f) nucleotide 6 through nucleotide 36 of SEQ ID NO: 959; (g) nucleotide 7 through nucleotide 36 of SEQ ID NO: 959; (h) nucleotide 8 through nucleotide 36 of SEQ ID NO: 959; (i) nucleotide 9 through nucleotide 36 of SEQ ID NO: 959; (j) nucleotide 10 through nucleotide 36 of SEQ ID NO: 959; (k) nucleotide 11 through nucleotide 36 of SEQ ID NO: 959; (l) nucleotide 12 through nucleotide 36 of SEQ ID NO: 959; (m) nucleotide 13 through nucleotide 36 of SEQ ID NO: 959; (n) nucleotide 14 through nucleotide 36 of SEQ ID NO: 959; or (o) SEQ ID NO: 960 or SEQ ID NO: 961 or a portion thereof.

In some examples, the direct repeat sequence comprises: (a) nucleotide 1 through nucleotide 36 of a sequence that is at least 90% identical to a sequence of SEQ ID NO: 962 or SEQ ID NO: 963; (b) nucleotide 2 through nucleotide 36 of a sequence that is at least 90% identical to a sequence of SEQ ID NO: 962 or SEQ ID NO: 963; (c) nucleotide 3 through nucleotide 36 of a sequence that is at least 90% identical to a sequence of SEQ ID NO: 962 or SEQ ID NO: 963; (d) nucleotide 4 through nucleotide 36 of a sequence that is at least 90% identical to a sequence of SEQ ID NO: 962 or SEQ ID NO: 963; (e) nucleotide 5 through nucleotide 36 of a sequence that is at least 90% identical to a sequence of SEQ ID NO: 962 or SEQ ID NO: 963; (f) nucleotide 6 through nucleotide 36 of a sequence that is at least 90% identical to a sequence of SEQ ID NO: 962 or SEQ ID NO: 963; (g) nucleotide 7 through nucleotide 36 of a sequence that is at least 90% identical to a sequence of SEQ ID NO: 962 or SEQ ID NO: 963; (h) nucleotide 8 through nucleotide 36 of a sequence that is at least 90% identical to a sequence of SEQ ID NO: 962 or SEQ ID NO: 963; (i) nucleotide 9 through nucleotide 36 of a sequence that is at least 90% identical to a sequence of SEQ ID NO: 962 or SEQ ID NO: 963; (j) nucleotide 10 through nucleotide 36 of a sequence that is at least 90% identical to a sequence of SEQ ID NO: 962 or SEQ ID NO: 963; (k) nucleotide 11 through nucleotide 36 of a sequence that is at least 90% identical to a sequence of SEQ ID NO: 962 or SEQ ID NO: 963; (l) nucleotide 12 through nucleotide 36 of a sequence that is at least 90% identical to a sequence of SEQ ID NO: 962 or SEQ ID NO: 963; (m) nucleotide 13 through nucleotide 36 of a sequence that is at least 90% identical to a sequence of SEQ ID NO: 962 or SEQ ID NO: 963; (n) nucleotide 14 through nucleotide 36 of a sequence that is at least 90% identical to a sequence of SEQ ID NO: 962 or SEQ ID NO: 963; (o) nucleotide 15 through nucleotide 36 of a sequence that is at least 90% identical to a sequence of SEQ ID NO: 962 or SEQ ID NO: 963; or (p) a sequence that is at least 90% identical to a sequence of SEQ ID NO: 964 or a portion thereof.

In some examples, the direct repeat sequence comprises: (a) nucleotide 1 through nucleotide 36 of SEQ ID NO: 962 or SEQ ID NO: 963; (b) nucleotide 2 through nucleotide 36 of SEQ ID NO: 962 or SEQ ID NO: 963; (c) nucleotide 3 through nucleotide 36 of SEQ ID NO: 962 or SEQ ID NO: 963; (d) nucleotide 4 through nucleotide 36 of SEQ ID NO: 962 or SEQ ID NO: 963; (e) nucleotide 5 through nucleotide 36 of SEQ ID NO: 962 or SEQ ID NO: 963; (f) nucleotide 6 through nucleotide 36 of SEQ ID NO: 962 or SEQ ID NO: 963; (g) nucleotide 7 through nucleotide 36 of SEQ ID NO: 962 or SEQ ID NO: 963; (h) nucleotide 8 through nucleotide 36 of SEQ ID NO: 962 or SEQ ID NO: 963; (i) nucleotide 9 through nucleotide 36 of SEQ ID NO: 962 or SEQ ID NO: 963; (j) nucleotide 10 through nucleotide 36 of SEQ ID NO: 962 or SEQ ID NO: 963; (k) nucleotide 11 through nucleotide 36 of SEQ ID NO: 962 or SEQ ID NO: 963; (l) nucleotide 12 through nucleotide 36 of SEQ ID NO: 962 or SEQ ID NO: 963; (m) nucleotide 13 through nucleotide 36 of SEQ ID NO: 962 or SEQ ID NO: 963; (n) nucleotide 14 through nucleotide 36 of SEQ ID NO: 962 or SEQ ID NO: 963; (o) nucleotide 15 through nucleotide 36 of SEQ ID NO: 962 or SEQ ID NO: 963; or (p) SEQ ID NO: 964 or a portion thereof.

In some examples, the RNA guide has a sequence that is at least 90% identical to a sequence of any one of SEQ ID NOs: 989, 968, or 967. In some specific examples, the RNA guide has the sequence of any one of SEQ ID NOs: 989, 968, or 967.

In some examples, each of the first three nucleotides of the RNA guide comprises a 2'-O-methyl phosphorothioate modification.

In some examples, each of the last four nucleotides of the RNA guide comprises a 2'-O-methyl phosphorothioate modification.

In some examples, each of the first to last, second to last, and third to last nucleotides of the RNA guide comprises a 2'-O-methyl phosphorothioate modification, and wherein the last nucleotide of the RNA guide is unmodified.

In some examples, the RNA guide has a sequence that is at least 90% identical to a sequence of any one of SEQ ID NOs: 1082-1087. In some specific examples, the RNA guide has a sequence of any one of SEQ ID NOs: 1082-1087.

In some embodiments, an HAO1-targeting RNA guide comprises at least 90% identity to any one of SEQ ID NOs: 1082-1087. In some embodiments, an HAO1-targeting RNA guide comprises any one of SEQ ID NOs: 1082-1087. In some embodiments, an HAO1-targeting RNA guide comprising at least 90% identity to SEQ ID NO: 1083 or SEQ ID NO: 1084 binds the complementary region of HAO1 target sequence of SEQ ID NO: 1047 via base-pairing. In some embodiments, the HAO1-targeting RNA guide of SEQ ID NO: 1083 or SEQ ID NO: 1084 binds the complementary region of HAO1 target sequence of SEQ ID NO: 1047 via base-pairing. In some embodiments, an HAO1-targeting RNA guide comprising at least 90% identity to SEQ ID NO: 1085 or SEQ ID NO: 1086 binds the complementary region of HAO1 target sequence of SEQ ID NO: 1026 via base-pairing. In some embodiments, the HAO1-targeting RNA guide of SEQ ID NO: 1085 or SEQ ID NO: 1086 binds the complementary region of HAO1 target sequence of SEQ ID NO: 1026 via base-pairing. In some embodiments, an HAO1-targeting RNA guide comprising at least 90% identity to SEQ ID NO: 1087 or SEQ ID NO: 2293 binds the complementary region of HAO1 target sequence of SEQ ID NO: 1025 via base-pairing. In some embodiments, the HAO1-targeting RNA guide of SEQ ID NO: 1087 or SEQ ID NO: 2293 binds the complementary region of HAO1 target sequence of SEQ ID NO: 1025 via base-pairing.

Embodiment 14: A nucleic acid encoding the RNA guide of Embodiment 13 as described herein.

Embodiment 15: A vector comprising the nucleic acid of Embodiment 14 as described herein.

Embodiment 16: A vector system comprising one or more vectors encoding (i) the RNA guide of Embodiment 13 as described herein, and (ii) a Cas12i polypeptide. In some examples, the vector system comprises a first vector encoding the RNA guide and a second vector encoding the Cas12i polypeptide.

Embodiment 17: A cell comprising the RNA guide, the nucleic acid, the vector, or the vector system of Embodiments 13-16 as described herein. In some examples, the cell is a eukaryotic cell, an animal cell, a mammalian cell, a human cell, a primary cell, a cell line, a stem cell, or a T cell.

Embodiment 18: A kit comprising the RNA guide, the nucleic acid, the vector, or the vector system of Embodiments 13-16 as described herein.

Embodiment 19: A method of editing an HAO1 sequence, the method comprising contacting an HAO1 sequence with the RNA guide of Embodiment 13 as described herein. In some examples, the HAO1 sequence is in a cell.

In some examples, the RNA guide induces an indel (e.g., an insertion or deletion) in the HAO1 sequence.

Embodiment 20: A method of treating primary hyperoxaluria (PH), which optionally is PH1, PH2, or PH3, in a subject, the method comprising administering the RNA guide of Embodiment 12 as described herein to the subject.

General Techniques

The practice of the present disclosure will employ, unless otherwise indicated, conventional techniques of molecular biology (including recombinant techniques), microbiology, cell biology, biochemistry, and immunology, which are within the skill of the art. Such techniques are explained fully in the literature, such as *Molecular Cloning: A Laboratory Manual*, second edition (Sambrook, et al., 1989) Cold Spring Harbor Press; *Oligonucleotide Synthesis* (M. J. Gait, ed. 1984); *Methods in Molecular Biology*, Humana Press; *Cell Biology: A Laboratory Notebook* (J. E. Cellis, ed., 1989) Academic Press; Animal Cell Culture (R. I. Freshney, ed. 1987); Introduction to Cell and Tissue Culture (J. P. Mather and P. E. Roberts, 1998) Plenum Press; Cell and Tissue Culture: Laboratory Procedures (A. Doyle, J. B. Griffiths, and D. G. Newell, eds. 1993-8) J. Wiley and Sons; Methods in Enzymology (Academic Press, Inc.); Handbook of Experimental Immunology (D. M. Weir and C. C. Black-well, eds.): Gene Transfer Vectors for Mammalian Cells (J. M. Miller and M. P. Calos, eds., 1987); Current Protocols in Molecular Biology (F. M. Ausubel, et al. eds. 1987); PCR: The Polymerase Chain Reaction, (Mullis, et al., eds. 1994); Current Protocols in Immunology (J. E. Coligan et al., eds., 1991); Short Protocols in Molecular Biology (Wiley and Sons, 1999); Immunobiology (C. A. Janeway and P. Travers, 1997); Antibodies (P. Finch, 1997); Antibodies: a practice approach (D. Catty., ed., IRL Press, 1988-1989); Monoclonal antibodies: a practical approach (P. Shepherd and C. Dean, eds., Oxford University Press, 2000); Using antibodies: a laboratory manual (E. Harlow and D. Lane (Cold Spring Harbor Laboratory Press, 1999); The Antibodies (M. Zanetti and J. D. Capra, eds. Harwood Academic Publishers, 1995); *DNA Cloning: A practical Approach*, Volumes I and II (D. N. Glover ed. 1985); *Nucleic Acid Hybridization* (B. D. Hames & S. J. Higgins eds. (1985*»; Transcription and Translation* (B. D. Hames & S. J. Higgins, eds. (1984*»; Animal Cell Culture* (R. I. Freshney, ed. (1986*»; Immobilized Cells and Enzymes* (IRL Press, (1986»; and B. Perbal, *A practical Guide To Molecular Cloning* (1984); F. M. Ausubel et al. (eds.).

Without further elaboration, it is believed that one skilled in the art can, based on the above description, utilize the present invention to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

The following examples are provided to further illustrate some embodiments of the present invention but are not intended to limit the scope of the invention; it will be understood by their exemplary nature that other procedures, methodologies, or techniques known to those skilled in the art may alternatively be used.

Example 1—Cas12i2-Mediated Editing of HAO1 Target Sites in HEK293T Cells

This Example describes the genomic editing of the HAO1 gene using Cas12i2 introduced into HEK293T cells.

Cas12i2 RNA guides (crRNAs) were designed and ordered from Integrated DNA Technologies (IDT). For initial guide screening in HEK293T cells, target sequences were designed by tiling the coding exons of HAO1 for 5'-NTTN-3' PAM sequences, and then spacer sequences were designed for the 20-bp target sequences downstream of the PAM sequence. The HAO1-targeting RNA guide sequences are shown in Table 7. In the figures, "E #T #" can also be represented as "exon # target #."

TABLE 7 crRNA Sequences for HAOI

| Guide Name | PAM* | Target strand (Non-PAM Strand) | crRNA Sequence | Target Sequences |
|---|---|---|---|---|
| HAO1_E1T2 | CTTC | BS | AGAAAUCCGUCUUUCAUUGACGGCAAAGUCUAUAUAUGACUAU (SEQ ID NO: 967) | CAAAGTCTATATATGACTAT (SEQ ID NO: 1025) |
| HAO1_E1T3 | CTTT | TS | AGAAAUCCGUCUUUCAUUGACGGGGAAGUACUGAUUUAGCAUG (SEQ ID NO: 968) | GGAAGTACTGATTTAGCATG (SEQ ID NO: 1026) |
| HAO1_E1T4 | CTTC | TS | AGAAAUCCGUCUUUCAUUGACGGAUCAUUUGCCCCAGACCUGU (SEQ ID NO: 969) | ATCATTTGCCCCAGACCTGT (SEQ ID NO: 1027) |
| HAO1_E1T5 | CTTT | BS | AGAAAUCCGUCUUUCAUUGACGGGGCUGAUAAUAUUGCAGCAU (SEQ ID NO: 970) | GGCTGATAATATTGCAGCAT (SEQ ID NO: 1028) |
| HAO1_E1T6 | ATTT | BS | AGAAAUCCGUCUUUCAUUGACGGGUAUCAAUGAUUAUGAACAA (SEQ ID NO: 971) | GTATCAATGATTATGAACAA (SEQ ID NO: 1029) |
| HAO1_E1T7 | TTTG | BS | AGAAAUCCGUCUUUCAUUGACGGUAUCAAUGAUUAUGAACAAC (SEQ ID NO: 972) | TATCAATGATTATGAACAAC (SEQ ID NO: 1030) |
| HAO1_E1T9 | ATTA | BS | AGAAAUCCGUCUUUCAUUGACGGUGAACAACAUGCUAAAUCAG (SEQ ID NO: 973) | TGAACAACATGCTAAATCAG (SEQ ID NO: 1031) |

TABLE 7-continued crRNA Sequences for HAOI

| Guide Name | PAM* | Target strand (Non-PAM Strand) | crRNA Sequence | Target Sequences |
|---|---|---|---|---|
| HAO1_E1T11 | TTTA | TS | AGAAAUCCGUCUUUCAU UGACGGGCAUGUUGUUC AUAAUCAUU (SEQ ID NO: 974) | GCATGTTGTTCATAAT CATT (SEQ ID NO: 1032) |
| HAO1_E1T12 | ATTT | TS | AGAAAUCCGUCUUUCAU UGACGGAGCAUGUUGUU CAUAAUCAU (SEQ ID NO: 975) | AGCATGTTGTTCATAA TCAT (SEQ ID NO: 1033) |
| HAO1_E1T13 | TTTG | TS | AGAAAUCCGUCUUUCAU UGACGGGAAGUACUGAU UUAGCAUGU (SEQ ID NO: 976) | GAAGTACTGATTTAGC ATGT (SEQ ID NO: 1034) |
| HAO1_E1T14 | ATTA | BS | AGAAAUCCGUCUUUCAU UGACGGCAGGUCUGGGG CAAAUGAUG (SEQ ID NO: 977) | CAGGTCTGGGGCAAAT GATG (SEQ ID NO: 1035) |
| HAO1_E1T15 | TTTG | TS | AGAAAUCCGUCUUUCAU UGACGGCCCCAGACCUG UAAUAGUCA (SEQ ID NO: 978) | CCCCAGACCTGTAATA GTCA (SEQ ID NO: 1036) |
| HAO1_E1T16 | ATTT | TS | AGAAAUCCGUCUUUCAU UGACGGGCCCCAGACCU GUAAUAGUC (SEQ ID NO: 979) | GCCCCAGACCTGTAAT AGTC (SEQ ID NO: 1037) |
| HAO1_E1T17 | TTTC | TS | AGAAAUCCGUCUUUCAU UGACGGUUCAUCAUUUG CCCCAGACC (SEQ ID NO: 980) | TTCATCATTTGCCCCAG ACC (SEQ ID NO: 1038) |
| HAO1_E1T18 | GTTT | TS | AGAAAUCCGUCUUUCAU UGACGGCUUCAUCAUUU GCCCCAGAC (SEQ ID NO: 981) | CTTCATCATTTGCCCCA GAC (SEQ ID NO: 1039) |
| HAO1_E1T19 | TTTG | BS | AGAAAUCCGUCUUUCAU UGACGGAAUGCUGCAAU AUUAUCAGC (SEQ ID NO: 982) | AATGCTGCAATATTAT CAGC (SEQ ID NO: 1040) |
| HAO1_E1T23 | TTTT | TS | AGAAAUCCGUCUUUCAU UGACGGCUUACCUGGAA AAUGCUGCA (SEQ ID NO: 983) | CTTACCTGGAAAATGC TGCA (SEQ ID NO: 1041) |
| HAO1_E1T24 | ATTT | TS | AGAAAUCCGUCUUUCAU UGACGGUCUUACCUGGA AAAUGCUGC (SEQ ID NO: 984) | TCTTACCTGGAAAATG CTGC (SEQ ID NO: 1042) |
| HAO1_E2T1 | CTTC | BS | AGAAAUCCGUCUUUCAU UGACGGUGUUUUAGGAC AGAGGGUCA (SEQ ID NO: 985) | TGTTTTAGGACAGAGG GTCA (SEQ ID NO: 1043) |
| HAO1_E2T2 | CTTC | TS | AGAAAUCCGUCUUUCAU UGACGGCUCCUACCUCU CACAGUGGC (SEQ ID NO: 986) | CTCCTACCTCTCACAGT GGC (SEQ ID NO: 1044) |
| HAO1_E2T3 | TTTA | BS | AGAAAUCCGUCUUUCAU UGACGGAUUCUAGAUGG AAGCUGUAU (SEQ ID NO: 987) | ATTCTAGATGGAAGCT GTAT (SEQ ID NO: 1045) |

TABLE 7-continued

| crRNA Sequences for HAOI | | | | |
|---|---|---|---|---|
| Guide Name | PAM* | Target strand (Non-PAM Strand) | crRNA Sequence | Target Sequences |
| HAO1_E2T4 | ATTC | BS | AGAAAUCCGUCUUUCAUUGACGGUAGAUGGAAGCUGUAUCCAA (SEQ ID NO: 988) | TAGATGGAAGCTGTATCCAA (SEQ ID NO: 1046) |
| HAO1_E2T5 | ATTC | TS | AGAAAUCCGUCUUUCAUUGACGGCGGAGCAUCCUUGGAUACAG (SEQ ID NO: 989) | CGGAGCATCCTTGGATACAG (SEQ ID NO: 1047) |
| HAO1_E2T6 | GTTG | BS | AGAAAUCCGUCUUUCAUUGACGGCUGAAACAGAUCUGUCGACU (SEQ ID NO: 990) | CTGAAACAGATCTGTCGACT (SEQ ID NO: 1048) |
| HAO1_E2T7 | TTTC | TS | AGAAAUCCGUCUUUCAUUGACGGAGCAACAUUCCGGAGCAUCC (SEQ ID NO: 991) | AGCAACATTCCGGAGCATCC (SEQ ID NO: 1049) |
| HAO1_E2T8 | GTTT | TS | AGAAAUCCGUCUUUCAUUGACGGCAGCAACAUUCCGGAGCAUC (SEQ ID NO: 992) | CAGCAACATTCCGGAGCATC (SEQ ID NO: 1050) |
| HAO1_E2T9 | GTTT | BS | AGAAAUCCGUCUUUCAUUGACGGUAGGACAGAGGGUCAGCAUG (SEQ ID NO: 993) | TAGGACAGAGGGTCAGCATG (SEQ ID NO: 1051) |
| HAO1_E2T10 | TTTT | BS | AGAAAUCCGUCUUUCAUUGACGGAGGACAGAGGGUCAGCAUGC (SEQ ID NO: 994) | AGGACAGAGGGTCAGCATGC (SEQ ID NO: 1052) |
| HAO1_E2T11 | TTTA | BS | AGAAAUCCGUCUUUCAUUGACGGGGACAGAGGGUCAGCAUGCC (SEQ ID NO: 995) | GGACAGAGGGTCAGCATGCC (SEQ ID NO: 1053) |
| HAO1_E3T1 | CTTT | BS | AGAAAUCCGUCUUUCAUUGACGGCUUUCUCAGCCUGUCAGUCC (SEQ ID NO: 996) | CTTTCTCAGCCTGTCAGTCC (SEQ ID NO: 1054) |
| HAO1_E3T2 | CTTT | BS | AGAAAUCCGUCUUUCAUUGACGGCUCAGCCUGUCAGUCCCUGG (SEQ ID NO: 997) | CTCAGCCTGTCAGTCCCTGG (SEQ ID NO: 1055) |
| HAO1_E3T3 | GTTC | TS | AGAAAUCCGUCUUUCAUUGACGGCCAGGGACUGACAGGCUGAG (SEQ ID NO: 998) | CCAGGGACTGACAGGCTGAG (SEQ ID NO: 1056) |
| HAO1_E3T4 | GTTC | BS | AGAAAUCCGUCUUUCAUUGACGGCUGGGCCACCUCCUCAAUUG (SEQ ID NO: 999) | CTGGGCCACCTCCTCAATTG (SEQ ID NO: 1057) |
| HAO1_E3T5 | CTTC | TS | AGAAAUCCGUCUUUCAUUGACGGAAUUGAGGAGGUGGCCCAGG (SEQ ID NO: 1000) | AATTGAGGAGGTGGCCCAGG (SEQ ID NO: 1058) |
| HAO1_E3T6 | CTTC | TS | AGAAAUCCGUCUUUCAUUGACGGUUCAAUUGAGGAGGUGGCCC (SEQ ID NO: 1001) | TTCAATTGAGGAGGTGGCCC (SEQ ID NO: 1059) |

TABLE 7-continued crRNA Sequences for HAOI

| Guide Name | PAM* | Target strand (Non-PAM Strand) | crRNA Sequence | Target Sequences |
|---|---|---|---|---|
| HAO1_E3T7 | CTTC | TS | AGAAAUCCGUCUUUCAUUGACGGCGCCACUUCUUCAAUUGAGG (SEQ ID NO: 1002) | CGCCACTTCTTCAATTGAGG (SEQ ID NO: 1060) |
| HAO1_E3T8 | CTTC | BS | AGAAAUCCGUCUUUCAUUGACGGGUUGGCUGCAACUGUAUAUC (SEQ ID NO: 1003) | GTTGGCTGCAACTGTATATC (SEQ ID NO: 1061) |
| HAO1_E3T9 | CTTC | TS | AGAAAUCCGUCUUUCAUUGACGGUCGGUCCUUGUAGAUAUACA (SEQ ID NO: 1004) | TCGGTCCTTGTAGATATACA (SEQ ID NO: 1062) |
| HAO1_E3T11 | CTTC | TS | AGAAAUCCGUCUUUCAUUGACGGUCUGCCUGCCGCACUAGCUU (SEQ ID NO: 1005) | TCTGCCTGCCGCACTAGCTT (SEQ ID NO: 1063) |
| HAO1_E3T12 | TTTC | BS | AGAAAUCCGUCUUUCAUUGACGGUUUCUCAGCCUGUCAGUCCC (SEQ ID NO: 1006) | TTTCTCAGCCTGTCAGTCCC (SEQ ID NO: 1064) |
| HAO1_E3T13 | TTTC | BS | AGAAAUCCGUCUUUCAUUGACGGUCAGCCUGUCAGUCCCUGGG (SEQ ID NO: 1007) | TCAGCCTGTCAGTCCCTGGG (SEQ ID NO: 1065) |
| HAO1_E3T14 | GTTG | BS | AGAAAUCCGUCUUUCAUUGACGGAGUUCCUGGGCCACCUCCUC (SEQ ID NO: 1008) | AGTTCCTGGGCCACCTCCTC (SEQ ID NO: 1066) |
| HAO1_E3T15 | ATTG | TS | AGAAAUCCGUCUUUCAUUGACGGAGGAGGUGGCCCAGGAACUC (SEQ ID NO: 1009) | AGGAGGTGGCCCAGGAACTC (SEQ ID NO: 1067) |
| HAO1_E3T16 | ATTG | BS | AGAAAUCCGUCUUUCAUUGACGGAAGAAGUGGCGGAAGCUGGU (SEQ ID NO: 1010) | AAGAAGTGGCGGAAGCTGGT (SEQ ID NO: 1068) |
| HAO1_E3T17 | GTTG | BS | AGAAAUCCGUCUUUCAUUGACGGGCUGCAACUGUAUAUCUACA (SEQ ID NO: 1011) | GCTGCAACTGTATATCTACA (SEQ ID NO: 1069) |
| HAO1_E3T18 | GTTG | TS | AGAAAUCCGUCUUUCAUUGACGGCAGCCAACGAAGUGCCUCAG (SEQ ID NO: 1012) | CAGCCAACGAAGTGCCTCAG (SEQ ID NO: 1070) |
| HAO1_E3T19 | CTTG | TS | AGAAAUCCGUCUUUCAUUGACGGUAGAUAUACAGUUGCAGCCA (SEQ ID NO: 1013) | TAGATATACAGTTGCAGCCA (SEQ ID NO: 1071) |
| HAO1_E3T20 | CTTG | TS | AGAAAUCCGUCUUUCAUUGACGGGUGACUUCUCGGUCCUUGUA (SEQ ID NO: 1014) | GTGACTTCTCGGTCCTTGTA (SEQ ID NO: 1072) |
| HAO1_E3T22 | ATTT | BS | AGAAAUCCGUCUUUCAUUGACGGGUGACAGUGGACACACCUUA (SEQ ID NO: 1015) | GTGACAGTGGACACACCTTA (SEQ ID NO: 1073) |

TABLE 7-continued crRNA Sequences for HAOI

| Guide Name | PAM* | Target strand (Non-PAM Strand) | crRNA Sequence | Target Sequences |
|---|---|---|---|---|
| HAO1_E3T23 | TTTG | BS | AGAAAUCCGUCUUUCAU UGACGGUGACAGUGGAC ACACCUUAC (SEQ ID NO: 1016) | TGACAGTGGACACACC TTAC (SEQ ID NO: 1074) |
| HAO1_E3T24 | CTTA | BS | AGAAAUCCGUCUUUCAU UGACGGCCUGGGCAACC GUCUGGAUG (SEQ ID NO: 1017) | CCTGGGCAACCGTCTG GATG (SEQ ID NO: 1075) |
| HAO1_E3T25 | GTTG | TS | AGAAAUCCGUCUUUCAU UGACGGCCCAGGUAAGG UGUGUCCAC (SEQ ID NO: 1018) | CCCAGGTAAGGTGTGT CCAC (SEQ ID NO: 1076) |
| HAO1_E3T26 | GTTA | TS | AGAAAUCCGUCUUUCAU UGACGGCGCACAUCAUC CAGACGGUU (SEQ ID NO: 1019) | CGCACATCATCCAGAC GGTT (SEQ ID NO: 1077) |
| HAO1_E3T27 | TTTG | TS | AGAAAUCCGUCUUUCAU UGACGGAAUCUGUUACG CACAUCAUC (SEQ ID NO: 1020) | AATCTGTTACGCACAT CATC (SEQ ID NO: 1078) |
| HAO1_E3T28 | GTTT | TS | AGAAAUCCGUCUUUCAU UGACGGGAAUCUGUUAC GCACAUCAU (SEQ ID NO: 1021) | GAATCTGTTACGCACA TCAT (SEQ ID NO: 1079) |
| HAO1_E3T29 | GTTG | TS | AGAAAUCCGUCUUUCAU UGACGGUGGCGGCAGUU UGAAUCUGU (SEQ ID NO: 1022) | TGGCGGCAGTTTGAAT CTGT (SEQ ID NO: 1080) |
| HAO1_E3T30 | GTTA | TS | AGAAAUCCGUCUUUCAU UGACGGCCUGAGUUGUG GCGGCAGUU (SEQ ID NO: 1023) | CCTGAGTTGTGGCGGC AGTT(SEQID NO: 1081) |

*The 3′ three nucleotides represent the 5′-TTN-3′ motif.

Cas12i2 RNP complexation reactions were made by mixing purified Cas12i2 polypeptide of SEQ ID NO: 924 (400 μM) with an HAO1-targeting crRNA (1 mM in 250 mM NaCl) at a 1:1 (Cas12i2:crRNA) volume ratio (2.5:1 crRNA: Cas12i2 molar ratio). Complexations were incubated on ice for 30-60 min.

HEK293T cells were harvested using TRYPLE™ (recombinant cell-dissociation enzymes; ThermoFisher) and counted. Cells were washed once with PBS and resuspended in SF buffer+supplement (SF CELL LINE 4D-NUCLEOFECTOR™ X KIT S; Lonza #V4XC-2032) at a concentration of 16,480 cells/μL. Resuspended cells were dispensed at $3\times10^5$ cells/reaction into Lonza 16-well NUCLEOCUVETTE® strips. Complexed Cas12i2 RNP was added to each reaction at a final concentration of 10 μM (Cas12i2), and transfection enhancer oligos were then added at a final concentration of 4 μM. The final volume of each electroporated reaction was 20 pt. Non-targeting guides were used as negative controls.

The strips were electroporated using an electroporation device (program CM-130, Lonza 4D-NUCLEOFECTOR™). Immediately following electroporation, 80 μL of pre-warmed DMEM+10% FBS was added to each well and mixed gently by pipetting. For each technical replicate plate, plated 10 μL (30,000 cells) of diluted nucleofected cells into pre-warmed 96-well plate with wells containing 100 μL DMEM+10% FBS. Editing plates were incubated for 3 days at 37° C. with 5% $CO_2$.

After 3 days, wells were harvested using TRYPLE™ (recombinant cell-dissociation enzymes; ThermoFisher) and transferred to 96-well TWIN.TEC® PCR plates (Eppendorf). Media was flicked off and cells were resuspended in 20 μL QUICKEXTRACT™ (DNA extraction buffer; Lucigen). Samples were then cycled in a PCR machine at 65° C. for 15 min, 68° C. for 15 min, 98° C. for 10 min. Samples were then frozen at −20° C.

Samples for Next Generation Sequencing (NGS) were prepared by rounds of PCR. The first round (PCR I) was used to amplify the genomic regions flanking the target site and add NGS adapters. The second round (PCR II) was used to add NGS indexes. Reactions were then pooled, purified by column purification, and quantified on a fluorometer (Qubit). Sequencing runs were done using a 150 cycle NGS instrument (NEXTSEQ™ v2.5) mid or high output kit (Illumina) and run on an NGS instrument (NEXTSEQ™ 550; Illumina).

For NGS analysis, the indel mapping function used a sample's fastq file, the amplicon reference sequence, and the forward primer sequence. For each read, a kmer-scanning algorithm was used to calculate the edit operations (match, mismatch, insertion, deletion) between the read and the reference sequence. In order to remove small amounts of primer dimer present in some samples, the first 30 nt of each read was required to match the reference and reads where over half of the mapping nucleotides are mismatches were filtered out as well. Up to 50,000 reads passing those filters were used for analysis, and reads were counted as an indel read if they contained an insertion or deletion. The % indels was calculated as the number of indel-containing reads divided by the number of reads analyzed (reads passing filters up to 50,000). The QC standard for the minimum number of reads passing filters was 10,000.

FIG. 1 shows HAO1 indels in HEK293T cells following RNP delivery. Error bars represent the average of three technical replicates across one biological replicate. Following delivery, indels were detected within and/or adjacent to each of the HAO1 target sites with each of the RNA guides. Delivery of E1T2, E1T3, E1T6, E1T7, E1T13, T1T17, E2T4, E2T5, E2T9, E2T10, E3T6, E3T19, E3T22, and E3T28 resulted in indels in over 70% of the NGS reads. Therefore, HAO1-targeting RNA guides induced indels in exon 1, exon 2, and exon 3 in HEK293T cells.

This Example thus shows that HAO1 can be individually targeted by Cas12i2 RNPs in mammalian cells such as HEK293T cells.

Example 2—Cas12i2-Mediated Editing of HAO1 Target Sites in HepG2 Cells

This Example describes the genomic editing of the HAO1 gene using Cas12i2 introduced into HepG2 cells by RNP.

RNP complexation reactions were performed as described in Example 1 with various RNA guides of Table 7. HepG2 cells were harvested using TRYPLE™ (recombinant cell-dissociation enzymes; ThermoFisher) and counted. Cells were washed once with PBS and resuspended in SF buffer+supplement (SF CELL LINE 4D-NUCLEOFECTOR™ X KIT S; Lonza #V4XC-2032) at a concentration of 13,889 cells/pt. Resuspended cells were dispensed at 2.5e5 cells/reaction into Lonza 16-well NUCLEOCUVETTE® strips. Complexed Cas12i2 RNP was added to each reaction at a final concentration of 20 μM (Cas12i2), with no transfection enhancer oligo. The final volume of each electroporated reaction was 20 pt. Non-targeting guides were used as negative controls.

The strips were electroporated using an electroporation device (program DJ-100, Lonza 4D-NUCLEOFECTOR™). Immediately following electroporation, 80 μL of pre-warmed EMEM+10% FBS was added to each well and mixed gently by pipetting. For each technical replicate plate, plated 10 μL (25,000 cells) of diluted nucleofected cells into pre-warmed 96-well plate with wells containing 100 μL EMEM+10% FBS. Editing plates were incubated for 3 days at 37° C. with 5% $CO_2$.

After 3 days, wells were harvested using TRYPLE™ (recombinant cell-dissociation enzymes; ThermoFisher) and transferred to 96-well TWIN.TEC® PCR plates (Eppendorf). Media was flicked off and cells were resuspended in 20 μL QUICKEXTRACT™ (DNA extraction buffer; Lucigen). Samples were then cycled in a PCR machine at 65° C. for 15 min, 68° C. for 15 min, 98° C. for 10 min. Samples were then frozen at −20° C. Samples were analyzed by NGS as described in Example 1.

Figure 2:
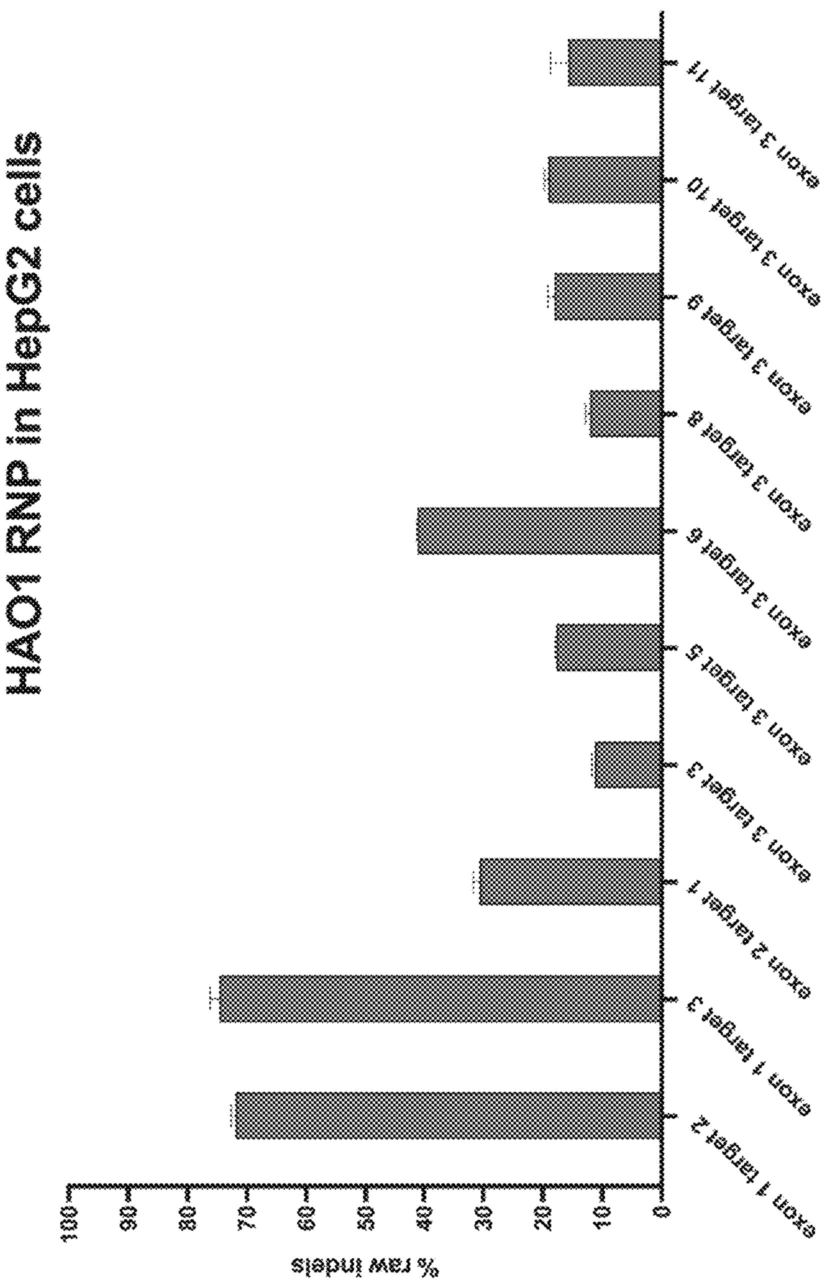
FIG. 2 is a graph showing the ability of RNPs prepared with a Cas12i2 polypeptide and a crRNA to edit the HAO1 gene in HepG2 cells.

FIG. 2 shows HAO1 indels in HepG2 cells following RNP delivery. Error bars represent the average of three technical replicates across one biological replicate. Following delivery, indels were detected within and/or adjacent to each of the HAO1 target sites with each of the RNA guides. Therefore, HAO1-targeting RNA guides induced indels in exon 1, exon 2, and exon 3 in HepG2 cells.

This Example thus shows that HAO1 can be targeted by Cas12i2 RNPs in mammalian cells such as HepG2 cells.

Example 3—Cas12i2-Mediated Editing of HAO1 Target Sites in Primary Hepatocytes This Example describes the genomic editing of the HAO1 using Cas12i2 introduced into primary hepatocytes cells by RNP.

RNP complexation reactions were performed as described in Example 1 with RNA guides of Table 7. Primary hepatocyte cells from human donors were thawed from liquid nitrogen very quickly in a 37° C. water bath. The cells were added to pre-warmed hepatocyte recovery media (Thermofisher, CM7000) and centrifuged at 100 g for 10 minutes. The cell pellet was resuspended in appropriate volume of hepatocyte plating Medium (Williams' Medium E, Thermofisher A1217601 supplemented with Hepatocyte Plating Supplement Pack (serum-containing), Thermofisher CM3000). The cells were subjected to trypan blue viability count with an INCUCYTE® disposable hemocytometer (Fisher scientific, 22-600-100). The cells were then washed in PBS and resuspended in P3 buffer+supplement (P3 PRIMARY CELL 4D-NUCLEOFECTOR™ X Kit; Lonza, VXP-3032) at a concentration of ~7,500 cells/μL. Resuspended cells were dispensed at 150,000 cells/reaction into the 16 well Lonza NUCLEOCUVETTE strips or 500,000 cells/reaction into the single Lonza NUCLEOCUVETTES® for the mRNA readout. Complexed Cas12i2 RNP was added to each reaction at a final concentration of 20 μM (Cas12i2), and transfection enhancer oligos were then added at a final concentration of 4 The final volume of each electroporated reaction was either 20 μL in the 16 well nucleocuvette strip format or 100 μL in the single nucleocuvette format. Non-targeting guides were used as negative controls.

The strips were electroporated using DS-150 program, while the single nucleocuvettes were electroporated using CA137 program (Lonza 4D-NUCLEOFECTOR™). Immediately following electroporation, pre-warmed Hepatocyte plating medium was added to each well and mixed very gently by pipetting. For each technical replicate plate, plated all the cell suspension of diluted nucleofected cells into a pre-warmed collagen-coated 96-well plate or 24-well plate (Thermofisher) with wells containing Hepatocyte plating medium. The cells were then incubated in a 37° C. incubator. The media was changed to hepatocyte maintenance media (Williams' Medium E, Thermofisher A1217601 supplemented with William's E medium Cell Maintenance Cocktail, Thermofisher CM 4000) after the cells attached after 4 hours. Fresh hepatocyte maintenance media was replaced after 2 days.

After 4-5 days post RNP electroporation, media was aspirated and the cells were harvested by shaking (500 rpm) in a 37° C. incubator with 2 mg/ml collagenase IV (Thermofisher, 17104019) dissolved in PBS containing Ca/Mg (Thermofisher). After cells were dissociated from the plate, they were transferred to 96-well TWIN.TEC® PCR plates (Eppendorf) and centrifuged. Media was flicked off and cell pellets for the NGS readout were resuspended in 20 μL QUICKEXTRACT™ (DNA extraction buffer; Lucigen). Samples were then cycled in a PCR machine at 65° C. for 15 min, 68° C. for 15 min, 98° C. for 10 min and analyzed by NGS as described in Example 1.

For the mRNA readout, cell pellets were frozen at −80° C. and subsequently resuspended in lysis buffer and DNA/RNA extracted with the RNeasy kit (Qiagen) following manufacturer's instructions. The DNA extracted from the samples were analyzed by NGS. The RNA isolated was checked for quantity and purity using nanodrop, and subsequently used for cDNA synthesis using 5× iScript reverse transcription reaction mix (Bio-Rad laboratories), following manufacturer's recommendations. cDNA templated was appropriately diluted to be in linear range of the subsequent analysis. Diluted cDNA was used to set up a 20 μL Digital Droplet PCR (ddPCR-BioRad laboratories) reaction using target-specific primer and probe for HAO1, ATTGTGCACTGTCAGATCTTGGAAACGGC-CAAAGGATTTTCCTCACCAATGTCTTG TCGATGACTTTCACATTCTGGCACCCACTCAGAGC-CATGGCCAACCGGAATTCTTCC TTTAGTAT (SEQ ID NO: 1088), and 2× ddPCR Supermix for Probes No dUTP (BioRad laboratories) following manufacturer's instructions. The reaction was used to generate droplets using Automated Droplet Generator (BioRad Laboratories), following manufacture's recommendations. The plate was sealed using PX1 PCR Plate Sealer (BioRad Laboratories) generated droplets were subjected to PCR amplification using C1000 Touch Thermal Cycler (BioRad Laboratories) using conditions recommended by the manufacturer. The PCR amplified droplets were read on QX200 Droplet Reader (BioRad Laboratories) and the acquired data was analyzed using QX Manager version 1.2 (BioRad Laboratories) to determine presence of absolute copy number of mRNA present in each reaction for the appropriate targets.

Figure 3:
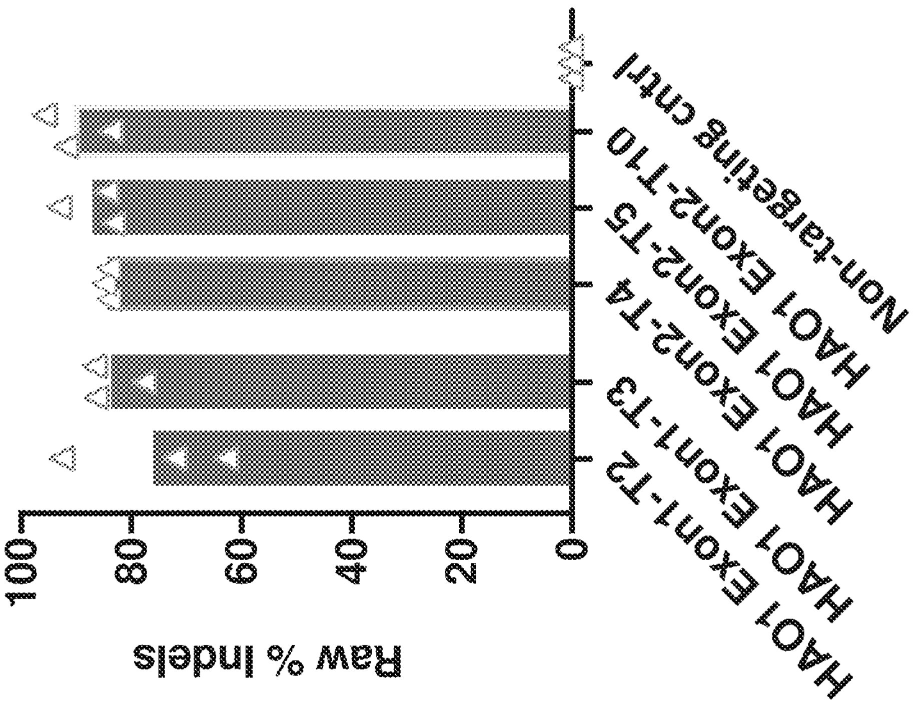
FIG. 3 is a graph showing the ability of RNPs prepared with a Cas12i2 polypeptide and a crRNA to edit the HAO1 gene in primary hepatocytes.
Figure 4:
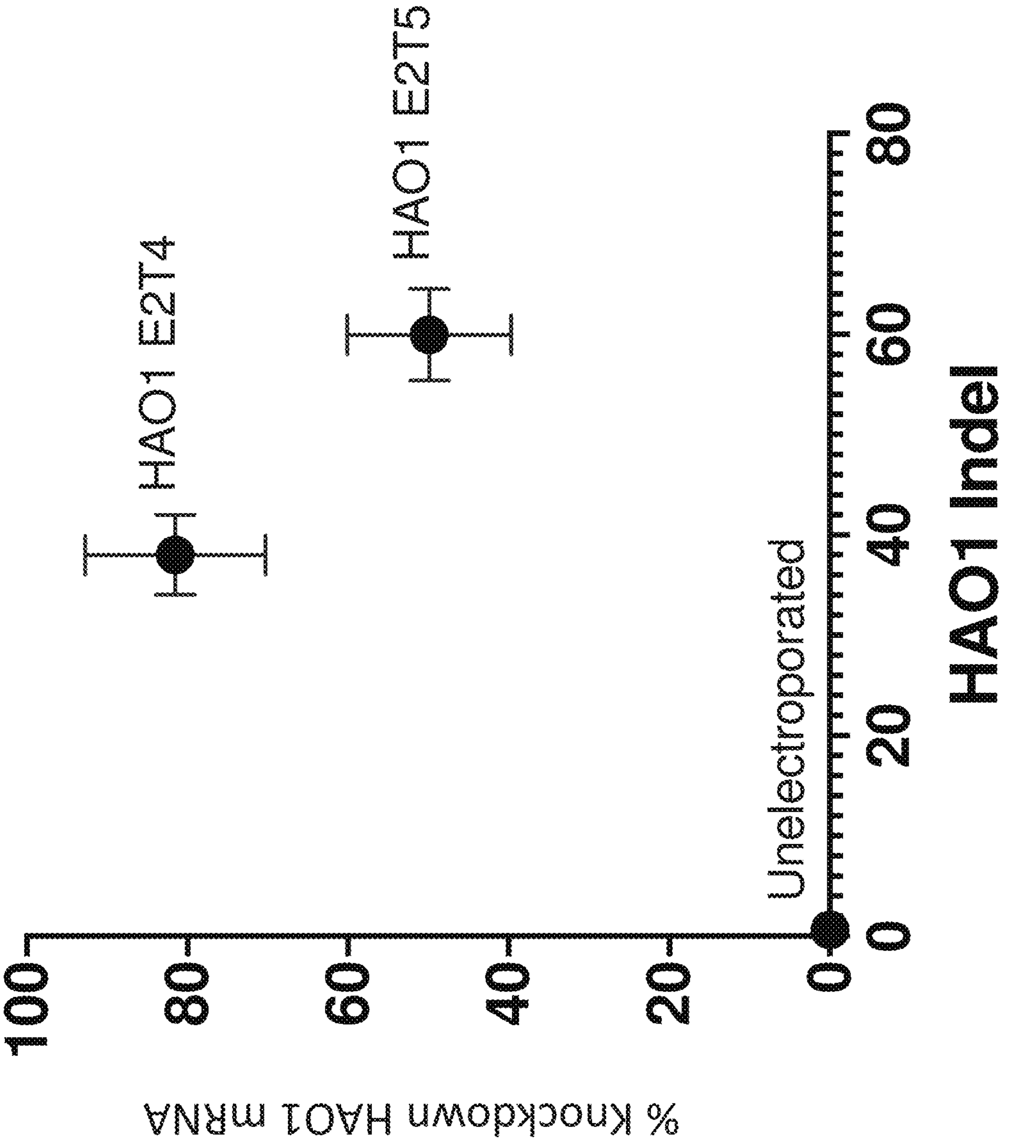
FIG. 4 is a graph showing knockdown of HAO1 mRNA in primary human hepatocytes with a Cas12i2 polypeptide and an HAO1-targeting crRNA.

As shown in FIG. 3, each RNA guide tested induced indels within and/or adjacent to the HAO1 target sites. Indels were not induced with the non-targeting control. Therefore, HAO1-targeting RNA guides induced indels in primary hepatocytes. Indels were then correlated with mRNA levels for each target to determine whether indels lead to mRNA knockdown and subsequent protein knockdown. FIG. 4 shows % mRNA knockdown of HAO1 in edited cells compared to unedited control cells. Although a higher percentage of NGS reads comprised indels using HAO1 E2T5 (SEQ ID NO: 989) compared to HAO1 E2T4 (SEQ ID NO: 988), HAO1 E2T4 resulted in a greater knockdown of HAO1 mRNA.

This Example thus shows that HAO1 can be targeted by Cas12i2 RNPs in mammalian cells such as primary human hepatocytes.

Example 4—Editing of HAO1 Target Sites in HepG2 Cells with Cas12i2 Variants

This Example describes indel assessment on HAO1 targets using variants introduced into HepG2 cells by transient transfection.

The Cas12i2 variants of SEQ ID NO: 924 and SEQ ID NO: 927 were individually cloned into a pcda3.1 backbone (Invitrogen). Nucleic acids encoding RNA guides E1T2 (SEQ ID NO: 967), E1T3 (SEQ ID NO: 968), E2T4 (SEQ ID NO: 988), E2T5 (SEQ ID NO: 989), E2T10 (SEQ ID NO: 994) were cloned into a pUC19 backbone (New England Biolabs). The plasmids were then maxi-prepped and diluted.

HepG2 cells were harvested using TRYPLE™ (recombinant cell-dissociation enzymes; ThermoFisher) and counted. Cells were washed once with PBS and resuspended in SF buffer+supplement (SF CELL LINE 4D-NUCLEOFECTOR™ X KIT S; Lonza #V4XC-2032).

Approximately 16 hours prior to transfection, 25,000 HepG2 cells in EMEM/10% FBS were plated into each well of a 96-well plate. On the day of transfection, the cells were 70-90% confluent. For each well to be transfected, a mixture of Lipofectamine™ 3000 and Opti-MEM® was prepared and then incubated at room temperature for 5 minutes (Solution 1). After incubation, the Lipofectamine™:OptiMEM® mixture was added to a separate mixture containing nuclease plasmid and RNA guide plasmid and P3000 reagent (Solution 2). In the case of negative controls, the crRNA was not included in Solution 2. The Solution 1 and Solution 2 were mixed by pipetting up and down and then incubated at room temperature for 15 minutes. Following incubation, the Solution 1 and Solution 2 mixture was added dropwise to each well of a 96 well plate containing the cells.

After 3 days, wells were harvested using TRYPLE™ (recombinant cell-dissociation enzymes; ThermoFisher) and transferred to 96-well TWIN.TEC® PCR plates (Eppendorf). Media was flicked off and cells were resuspended in 20 μL QUICKEXTRACT™ (DNA extraction buffer; Lucigen). Samples were then cycled in a PCR machine at 65° C. for 15 min, 68° C. for 15 min, 98° C. for 10 min. Samples were then frozen at −20° C. and analyzed by NGS as described in Example 1.

Figure 5A:
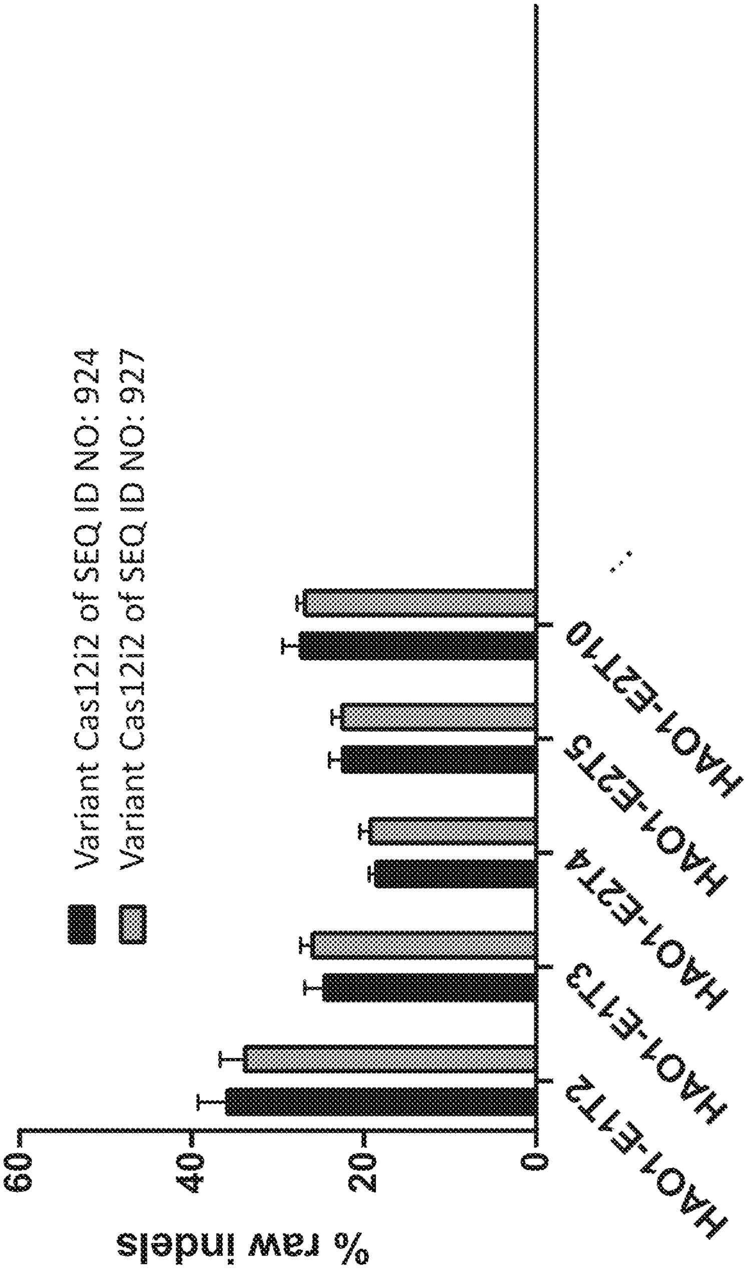
FIG. 5A is a graph showing % indels induced by an HAO1-targeting crRNA and the variant Cas12i2 polypeptide of SEQ ID NO: 924 or SEQ ID NO: 927 in HepG2 cells.
Figure 5B:
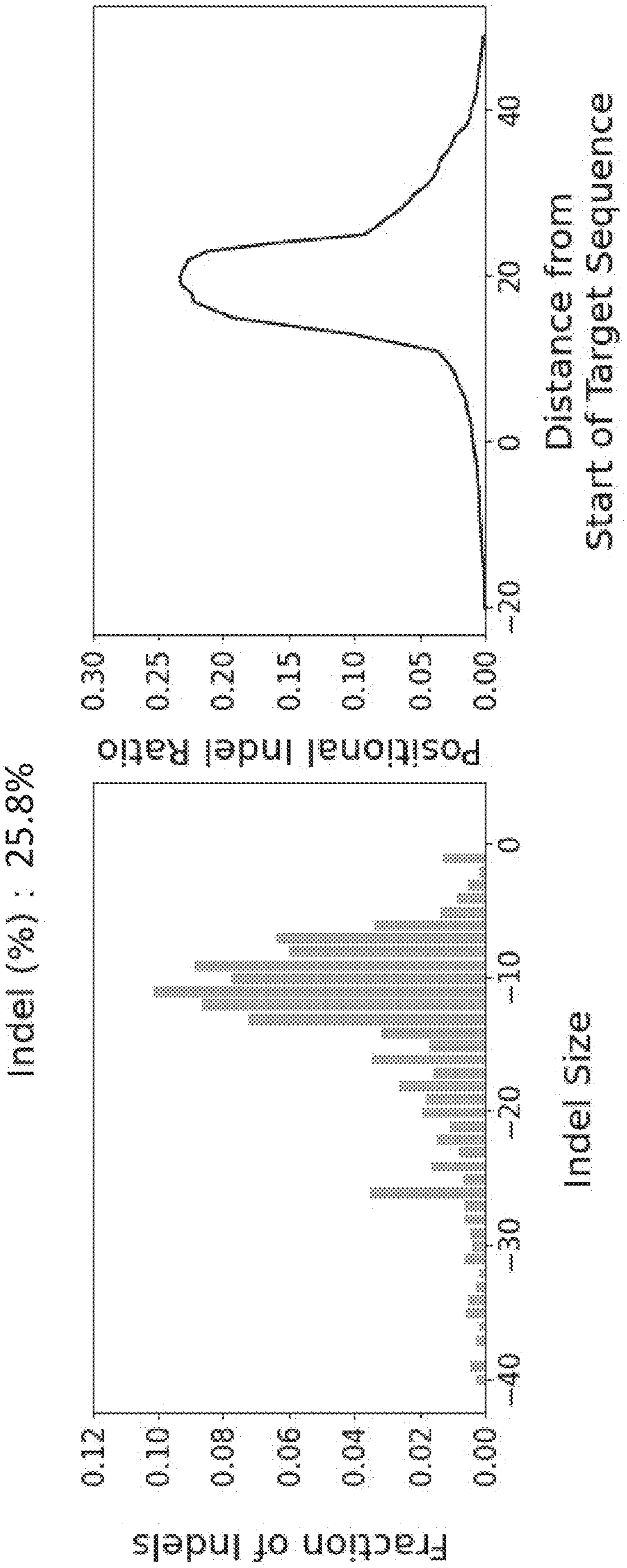
FIG. 5B shows the size (left) and start position (right) of indels induced in HepG2 cells by the variant Cas12i2 of SEQ ID NO: 924 and the HAO1-targeting RNA guide of E1T3 (SEQ ID NO: 968).

As shown in FIG. 5A, comparable indel activity with the two Cas12i2 variants was observed for E1T2, E1T3, E2T4, E2T5, E2T10. FIG. 5B shows the indel size frequency (left) and indel start position relative to the PAM for E1T3 and the variant Cas12i2 of SEQ ID NO: 924. As shown on the left, deletions ranged in size from 1 nucleotide to about 40 nucleotides. The majority of the deletions were about 6 nucleotides to about 27 nucleotides in length. As shown on the right, the target sequence is represented as starting at position 0 and ending at position 20. Indels started within about 10 nucleotides and about 35 nucleotides downstream of the PAM sequence. The majority of indels started near the end of the target sequence, e.g., about 18 nucleotides to about 25 nucleotides downstream of the PAM sequence.

Thus, this Example shows that HAO1 is capable of being targeted by multiple Cas12i2 polypeptides.

Example 5—Editing of HAO1 in Primary Human Hepatocytes Using Cas12i2 mRNA Constructs This Example describes indel assessment on HAO1 target sites via delivery of Cas12i2 mRNA and chemically modified HAO1-targeting RNA guides.

mRNA sequences corresponding to the variant Cas12i2 sequence of SEQ ID NO: 924 and the variant Cas12i2 sequence of SEQ ID NO: 927 were synthesized by Aldeveron with 1-pseudo-U modified nucleotides and using CleanCap® Reagent AG (TriLink Biotechnologies). The Cas12i2 mRNA sequences, shown in Table 8, further comprised a C-terminal NLS.

TABLE 8

| Cas12i2 mRNA Sequences | |
|---|---|
| Description | mRNA Sequence |
| mRNA corresponding to variant Cas12i2 of SEQ ID NO: 924 | AUGAGCUCCGCCAUCAAGUCCUACAAGUCUGUGCUGCGGCCAAACGAGAGAAAGAAUCAGC<br>UGCUGAAGUCCACCAUCCAGUGCCUGGAGGACGGCUCCGCCUUCUUUUUCAAGAUGCUGCA<br>GGGCCUGUUUGGCGGCAUCACCCCCGAGAUCGUGAGAUUCAGCACAGAGCAGGAGAAGCAG<br>CAGCAGGAUAUCGCCCUGUGGUGUGCCGUGAAUUGGUUCAGGCCUGUGAGCCAGGACUCCC<br>UGACCCACACAAUCGCCUCCGAUAACCUGGUGGAGAAGUUUGAGGAGUACUAUGGCGGCAC<br>AGCCAGCGACGCCAUCAAGCAGUACUUCAGCGCCUCCAUCGGCGAGUCCUACUAUUGGAAU<br>GACUGCCGCCAGCAGUACUAUGAUCUGUGUCGGGAGCUGGGCGUGGAGGUGUCUGACCUGA<br>CCCACGAUCUGGAGAUCCUGUGCCGGGAGAAGUGUCUGGCCGUGGCCACAGAGAGCAACCA<br>GAACAAUUCUAUCAUCAGCGUGCUGUUUGGCACCGGCGAGAAGGAGGAUAGGUCUGUGAAG<br>CUGCGCAUCACAAAGAAGAUCCUGGAGGCCAUCAGCAACCUGAAGGAGAUCCCAAAGAAUG<br>UGGCCCCCAUCCAGGAGAUCAUCCUGAAUGUGGCCAAGGCCACCAAGGAGACAUUCAGACA<br>GGUGUACGCAGGAAACCUGGGAGCACCAUCCACCCUGGAGAAGUUUAUCGCCAAGGACGGC<br>CAGAAGGAGUUCGAUCUGAAGAAGCUGCAGACAGACCUGAAGAAAGUGAUCCGGGGCAAGU<br>CUAAGGAGAGAGAUUGGUGCUGUCAGGAGGAGCUGAGGAGCUACGUGGAGCAGAAUACCAU<br>CCAGUAUGACCUGUGGGCCUGGGGCGAGAUGUUCAACAAGGCCCACACCGCCCUGAAGAUC<br>AAGUCCACAAGAAACUACAAUUUUGCCAAGCAGAGGCUGGAGCAGUUCAAGGAGAUCCAGU<br>CUCUGAACAAUCUGCUGGUGGUGAAGAAGCUGAACGACUUUUUCGAUAGCGAGUUUUUCUC<br>CGGCGAGGAGACCUACACAAUCUGCGUGCACCACCUGGGCGGCAAGGACCUGUCCAAGCUG<br>UAUAAGGCCUGGGAGGACGAUCCCGCCGAUCCUGAGAAUGCCAUCGUGGUGCUGUGCGACG<br>AUCUGAAGAACAAUUUUAAGAAGGAGCCUAUCAGGAACAUCCUGCGCUACAUCUUCACCAU<br>CCGCCAGGAGUGUAGCGCACAGGACAUCCUGGCAGCAGCAAAGUACAAUCAGCAGCUGGAU<br>CGGUAUAAGAGCCAGAAGGCCAACCCAUCCGUGCUGGGCAAUCAGGGCUUUACCUGGACAA<br>ACGCCGUGAUCCUGCCAGAGAAGGCCCAGCGGAACGACAGACCCAAUUCUCUGGAUCUGCG<br>CAUCUGGCUGUACCUGAAGCUGCGGCACCCUGACGGCAGAUGGAAGAAGCACCACAUCCCA<br>UUCUACGAUACCCGGUUUUUCCAGGAGAUCUAUGCCGCCGGCAAUAGCCCUGUGGACACCU<br>GUCAGUUUAGGACACCCCGCUUCGGCUAUCACCUGCCUAAGCUGACCGAUCAGACAGCCAU<br>CCGCGUGAACAAGAAGCACGUGAAGGCAGCAAAGACCGAGGCACGGAUCAGACUGGCCAUC<br>CAGCAGGGCACACUGCCAGUGUCCAAUCUGAAGAUCACCGAGAUCUCCGCCACAAUCAACU<br>CUAAGGGCCAGGUGCGCAUCCCCGUGAAGUUUCGGGUGGGAAGGCAGAAGGGAACCCUGCA<br>GAUCGGCGACCGGUUCUGCGGCUACGAUCAGAACCAGACAGCCUCUCACGCCUAUAGCCUG<br>UGGGAGGUGGUGAAGGAGGGCCAGUACCACAAGGAGCUGGGCUGUUUUGUGCGCUUCAUCU<br>CUAGCGGCGACAUCGUGUCCAUCACCGAGAACCGGGGCAAUCAGUUUGAUCAGCUGUCUUA<br>UGAGGGCCUGGCCUACCCCCAGUAUGCCGACUGGAGAAAGAAGGCCUCCAAGUUCGUGUCU<br>CUGUGGCAGAUCACCAAGAAGAACAAGAAGAAGGAGAUCGUGACAGUGGAGGCCAAGGAGA<br>AGUUUGACGCCAUCUGCAAGUACCAGCCUAGGCUGUAUAAGUUCAACAAGGAGUACGCCUA<br>UCUGCUGCGGGAUAUCGUGAGAGGCAAGAGCCUGGUGGAGCUGCAGCAGAUCAGGCAGGAG<br>AUCUUUCGCUUCAUCGAGCAGGACUGUGGAGUGACCCGCCUGGGAUCUCUGAGCCUGUCCA<br>CCCUGGAGACAGUGAAGGCCGUGAAGGGCAUCAUCUACUCCUAUUUUUCUACAGCCCUGAA<br>UGCCUCUAAGAACAAUCCCAUCAGCGACGAGCAGCGGAAGGAGUUUGAUCCUGAGCUGUUC<br>GCCCUGCUGGAGAAGCUGGAGCUGAUCAGGACUCGGAAGAAGAAGCAGAAGGUGGAGAGAA<br>UCGCCAAUAGCCUGAUCCAGACAUGCCUGGAGAACAAUAUCAAGUUCAUCAGGGGCGAGGG<br>CGACCUGUCCACCACAAACAAUGCCACCAAGAAGAAGGCCAACUCUAGGAGCAUGGAUUGG<br>CUGGCCAGAGGCGUGUUUAAUAAGAUCCGGCAGCUGGCCCCAAUGCACAACAUCACCCUGU<br>UCGGCUGCGGCAGCCUGUACACAUCCCACCAGGACCCUCUGGUGCACAGAAACCCAGAUAA<br>GGCCAUGAAGUGUAGAUGGGCAGCAAUCCCAGUGAAGGACAUCGGCGAUUGGGUGCUGAGA<br>AAGCUGUCCCAGAACCUGAGGGCCAAGAAUCGGGGCACCGGCGAGUACUAUCACCAGGGCG<br>UGAAGGAGUUCCUGUCUCACUAUGAGCUGCAGGACCUGGAGGAGGAGCUGCUGAAGUGGCG<br>GUCUGAUAGAAAGAGCAACAUCCCUUGCUGGGUGCUGCAGAAUAGACUGGCCGAGAAGCUG<br>GGCAACAAGGAGGCCGUGGUGUACAUCCCAGUGAGGGGCGGCCGCAUCUAUUUUGCAACCC<br>ACAAGGUGGCAACAGGAGCCGUGAGCAUCGUGUUCGACCAGAAGCAAGUGUGGGUGUGUAA<br>UGCAGAUCACGUGGCAGCAGCAAACAUCGCACUGACCGGCAAGGGCAUCGGCGAGCAGUCC<br>UCUGACGAGGAGAACCCCGAUGGCUCCAGGAUCAAGCUGCAGCUGACAUCUAAAAGGCCGG<br>CGGCCACGAAAAAGGCCGGCCAGGCAAAAAAGAAAAAGUAA (SEQ ID NO: 1089) |
| mRNA corresponding to variant Cas12i2 of SEQ ID NO: 927 | AUGAGCUCCGCCAUCAAGUCCUACAAGUCUGUGCUGCGGCCAAACGAGAGAAAGAAUCAGC<br>UGCUGAAGUCCACCAUCCAGUGCCUGGAGGACGGCUCCGCCUUCUUUUUCAAGAUGCUGCA<br>GGGCCUGUUUGGCGGCAUCACCCCCGAGAUCGUGAGAUUCAGCACAGAGCAGGAGAAGCAG<br>CAGCAGGAUAUCGCCCUGUGGUGUGCCGUGAAUUGGUUCAGGCCUGUGAGCCAGGACUCCC<br>UGACCCACACAAUCGCCUCCGAUAACCUGGUGGAGAAGUUUGAGGAGUACUAUGGCGGCAC<br>AGCCAGCGACGCCAUCAAGCAGUACUUCAGCGCCUCCAUCGGCGAGUCCUACUAUUGGAAU<br>GACUGCCGCCAGCAGUACUAUGAUCUGUGUCGGGAGCUGGGCGUGGAGGUGUCUGACCUGA<br>CCCACGAUCUGGAGAUCCUGUGCCGGGAGAAGUGUCUGGCCGUGGCCACAGAGAGCAACCA<br>GAACAAUUCUAUCAUCAGCGUGCUGUUUGGCACCGGCGAGAAGGAGGAUAGGUCUGUGAAG<br>CUGCGCAUCACAAAGAAGAUCCUGGAGGCCAUCAGCAACCUGAAGGAGAUCCCAAAGAAUG<br>UGGCCCCCAUCCAGGAGAUCAUCCUGAAUGUGGCCAAGGCCACCAAGGAGACAUUCAGACA<br>GGUGUACGCAGGAAACCUGGGAGCACCAUCCACCCUGGAGAAGUUUAUCGCCAAGGACGGC<br>CAGAAGGAGUUCGAUCUGAAGAAGCUGCAGACAGACCUGAAGAAAGUGAUCCGGGGCAAGU<br>CUAAGGAGAGAGAUUGGUGCUGUCAGGAGGAGCUGAGGAGCUACGUGGAGCAGAAUACCAU<br>CCAGUAUGACCUGUGGGCCUGGGGCGAGAUGUUCAACAAGGCCCACACCGCCCUGAAGAUC<br>AAGUCCACAAGAAACUACAAUUUUGCCAAGCAGAGGCUGGAGCAGUUCAAGGAGAUCCAGU<br>CUCUGAACAAUCUGCUGGUGGUGAAGAAGCUGAACGACUUUUUCGAUAGCGAGUUUUUCUC<br>CGGCGAGGAGACCUACACAAUCUGCGUGCACCACCUGGGCGGCAAGGACCUGUCCAAGCUG<br>UAUAAGGCCUGGGAGGACGAUCCCGCCGAUCCUGAGAAUGCCAUCGUGGUGCUGUGCGACG<br>AUCUGAAGAACAAUUUUAAGAAGGAGCCUAUCAGGAACAUCCUGCGCUACAUCUUCACCAU<br>CCGCCAGGAGUGUAGCGCACAGGACAUCCUGGCAGCAGCAAAGUACAAUCAGCAGCUGGAU<br>CGGUAUAAGAGCCAGAAGGCCAACCCAUCCGUGCUGGGCAAUCAGGGCUUUACCUGGACAA |

TABLE 8-continued

| Cas12i2 mRNA Sequences | |
|---|---|
| Description | mRNA Sequence |
| | ACGCCGUGAUCCUGCCAGAGAAGGCCCAGCGGAACGACAGACCCAAUUCUCUGGAUCUGCG<br>CAUCUGGCUGUACCUGAAGCUGCGGCACCCUGACGGCAGAUGGAAGAAGCACCACAUCCCA<br>UUCUACGAUACCCGGUUUUUCCAGGAGAUCUAUGCCGCCGGCAAUAGCCCUGUGGACACCU<br>GUCAGUUUAGGACACCCCGCUUCGGCUAUCACCUGCCUAAGCUGACCGAUCAGACAGCCAU<br>CCGCGUGAACAAGAAGCACGUGAAGGCAGCAAAGACCGAGGCACGGAUCAGACUGGCCAUC<br>CAGCAGGGCACACUGCCAGUGUCCAAUCUGAAGAUCACCGAGAUCUCCGCCACAAUCAACU<br>CUAAGGGCCAGGUGCGCAUCCCCGUGAAGUUUCGGGUGGGAAGGCAGAAGGGAACCCUGCA<br>GAUCGGCGACCGGUUCUGCGGCUACGAUCAGAACCAGACAGCCUCUCACGCCUAUAGCCUG<br>UGGGAGGUGGUGAAGGAGGGCCAGUACCACAAGGAGCUGCGGUGUCGGGUGCGCUUCAUCU<br>CUAGCGGCGACAUCGUGUCCAUCACCGAGAACCGGGGCAAUCAGUUUGAUCAGCUGUCUUA<br>UGAGGGCCUGGCCUACCCCCAGUAUGCCGACUGGAGAAAGAAGGCCUCCAAGUUCGUGUCU<br>CUGUGGCAGAUCACCAAGAAGAACAAGAAGAAGGAGAUCGUGACAGUGGAGGCCAAGGAGA<br>AGUUUGACGCCAUCUGCAAGUACCAGCCUAGGCUGUAUAAGUUCAACAAGGAGUACGCCUA<br>UCUGCUGCGGGAUAUCGUGAGAGGCAAGAGCCUGGUGGAGCUGCAGCAGAUCAGGCAGGAG<br>AUCUUUCGCUUCAUCGAGCAGGACUGUGGAGUGACCCGCCUGGGAUCUCUGAGCCUGUCCA<br>CCCUGGAGACAGUGAAGGCCGUGAAGGGCAUCAUCUACUCCUAUUUUUCUACAGCCCUGAA<br>UGCCUCUAAGAACAAUCCCAUCAGCGACGAGCAGCGGAAGGAGUUUGAUCCUGAGCUGUUC<br>GCCCUGCUGGAGAAGCUGGAGCUGAUCAGGACUCGGAAGAAGAAGCAGAAGGUGGAGAGAA<br>UCGCCAAUAGCCUGAUCCAGACAUGCCUGGAGAACAAUAUCAAGUUCAUCAGGGGCGAGGG<br>CGACCUGUCCACCACAAACAAUGCCACCAAGAAGAAGGCCAACUCUAGGAGCAUGGAUUGG<br>CUGGCCAGAGGCGUGUUUAAUAAGAUCCGGCAGCUGGCCACCAUGCACAACAUCACCCUGU<br>UCGGCUGCGGCAGCCUGUACACAUCCCACCAGGACCCUCUGGUGCACAGAAACCCAGAUAA<br>GGCCAUGAAGUGUAGAUGGGCAGCAAUCCCAGUGAAGGACAUCGGCGAUUGGGUGCUGAGA<br>AAGCUGUCCCAGAACCUGAGGGCCAAGAAUCGGGGCACCGGCGAGUACUAUCACCAGGGCG<br>UGAAGGAGUUCCUGUCUCACUAUGAGCUGCAGGACCUGGAGGAGGAGCUGCUGAAGUGGCG<br>GUCUGAUAGAAAGAGCAACAUCCCUUGCUGGGUGCUGCAGAAUAGACUGGCCGAGAAGCUG<br>GGCAACAAGGAGGCCGUGGUGUACAUCCCAGUGAGGGGCGGCCGCAUCUAUUUUGCAACCC<br>ACAAGGUGGCAACAGGAGCCGUGAGCAUCGUGUUCGACCAGAAGCAAGUGUGGGUGUGUAA<br>UGCAGAUCACGUGGCAGCAGCAAACAUCGCACUGACCGGCAAGGGCAUCGGCCGGCAGUCC<br>UCUGACGAGGAGAACCCCGAUGGCGGCAGGAUCAAGCUGCAGCUGACAUCUAAAAGGCCGG<br>CGGCCACGAAAAAGGCCGGCCAGGCAAAAAAGAAAAAGUAA (SEQ ID NO: 1090) |

Cas12i2 RNA guides were designed and ordered from Integrated DNA Technologies (IDT) as having 3' end modified phosphorothioated 2' O-methyl bases or 5' end and 3' end modified phosphorothioated 2' O-methyl bases guides, as specified in Table 9. Each variant Cas12i2 mRNA was mixed with a crRNA at a 1:1 (Cas12i2:crRNA) volume ratio (1050:1 crRNA:Cas12i2 molar ratio). The mRNA and crRNA were mixed immediately before electroporation. The primary human hepatocyte cells were cultured and electroporated as described in Example 3.

TABLE 9

| Chemically modified RNA guide sequences | |
|---|---|
| RNA guide | Sequence |
| 3'end modified E2T5 | AGAAAUCCGUCUUUCAUUGACGGCGGAGCAUCCUUGGAUA*mC*mA *mG (SEQ ID NO: 1091) |
| 5' and 3' end modified E2T5 | mA*mG*mA*AAUCCGUCUUUCAUUGACGGCGGAGCAUCCUUGGAUA *mC*mA*mG (SEQ ID NO: 1092) |

Figure 6:
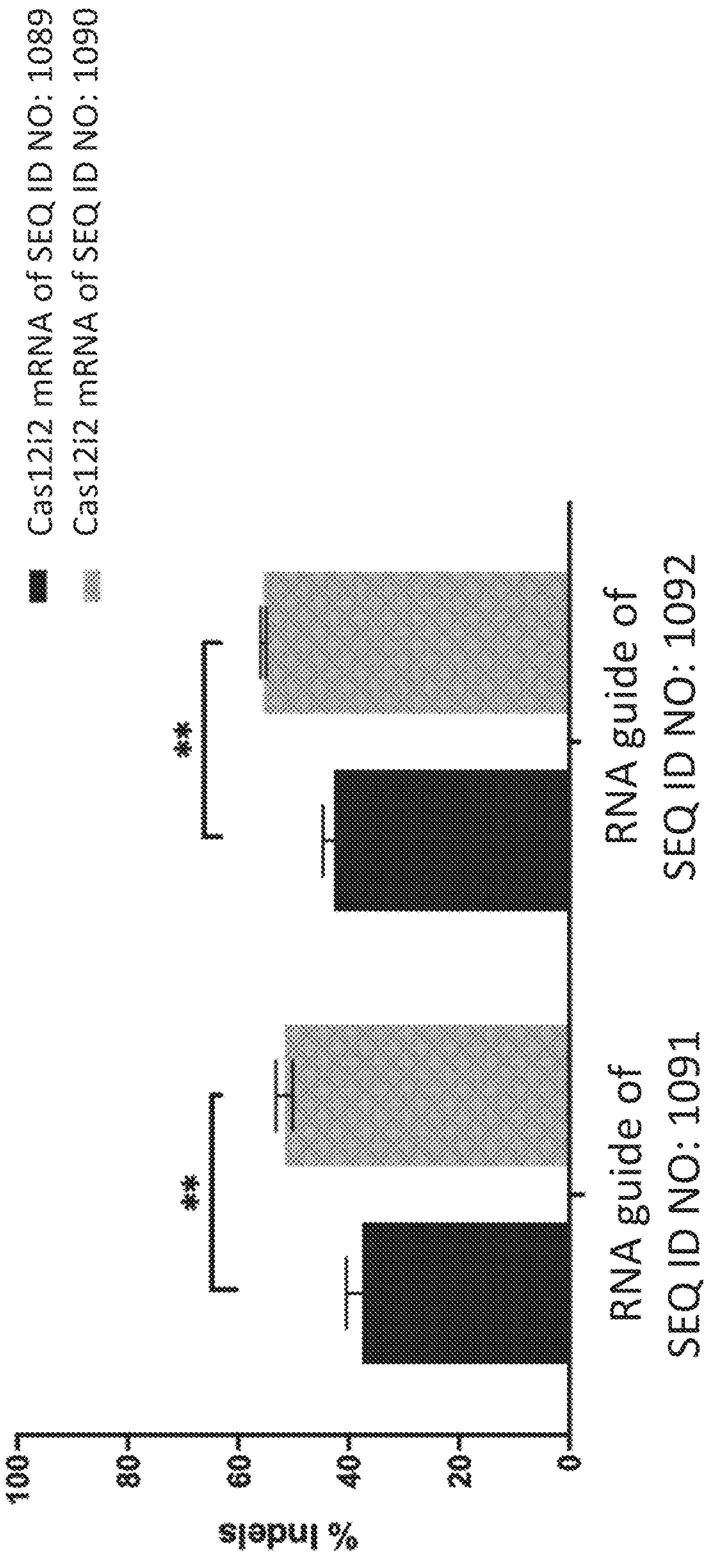
FIG. 6 is a graph showing % indels induced by chemically modified HAO1-targeting crRNAs of SEQ ID NO: 1091 and SEQ ID NO: 1092 and the variant Cas12i2 mRNA of SEQ ID NO: 1089 or SEQ ID NO: 1090.

FIG. 6 shows editing of an HAO1 target site by a variant Cas12i2 mRNA and 3' end modified E2T5 (SEQ ID NO: 1091) or 5' and 3' end modified E2T5 (SEQ ID NO: 1092). Indels in the HAO1 target site were introduced following electroporation of the Cas12i2 mRNA of SEQ ID NO: 1089 or SEQ ID NO: 1090 and either the RNA guide of SEQ ID NO: 1091 or SEQ ID NO: 1092. Approximately 50% NGS reads comprised an indel following electroporation of the Cas12i2 mRNA of SEQ ID NO: 1090 and the RNA guide of SEQ ID NO: 1091 or SEQ ID NO: 1092. Statistically significant higher % indels were observed using variant Cas12i2 mRNA of SEQ ID NO: 1090 compared to variant Cas12i2 mRNA of SEQ ID NO: 1089. No statistical difference was observed using 5' and 3' versus 3' only modifications to RNA guide E2T5.

This Example thus shows that HAO1 can be targeted by Cas12i2 mRNA constructs and chemically modified RNA guides in mammalian cells.

Example 6—Off-Target Analysis of Cas12i2 and HAO1-Targeting RNA Guides

This Example describes on-target versus off-target assessment of a Cas12i2 variant and an HAO1-targeting RNA guide.

HEK293T cells were transfected with a plasmid encoding the variant Cas12i2 of SEQ ID NO: 924 or the variant Cas12i2 of SEQ ID NO: 927 and a plasmid encoding E2T5 (SEQ ID NO: 989), E1T2 (SEQ ID NO: 967), E1T3 (SEQ ID NO: 968), and E2T10 (SEQ ID NO: 994) according to the method described in Example 16 of PCT/US21/25257. The tagmentation-based tag integration site sequencing (TTISS) method described in Example 16 of PCT/US21/25257 was then carried out.

Figure 7A:
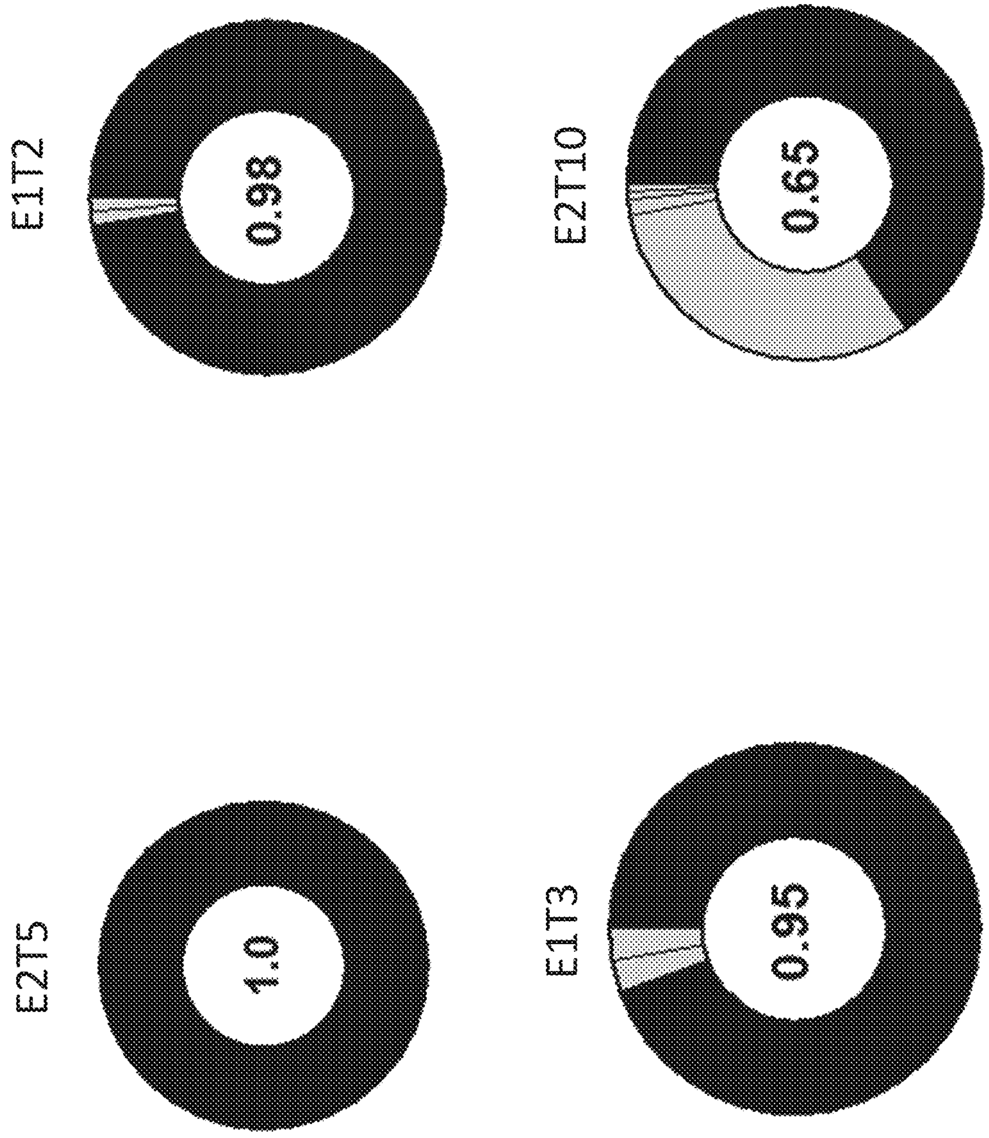
FIG. 7A shows plots depicting tagmentation-based tag integration site sequencing (TTISS) reads for variant Cas12i2 of SEQ ID NO: 924 and HAO1-targeting RNA guides E2T5 (SEQ ID NO: 989), E1T2 (SEQ ID NO: 967), E1T3 (SEQ ID NO: 968), and E2T10 (SEQ ID NO: 994). The black wedge and centered number represent the fraction of on-target TTISS reads. Each gray wedge represents a unique off-target site identified by TTISS. The size of each gray wedge represents the fraction of TTISS reads mapping to a given off-target.
Figure 7B:
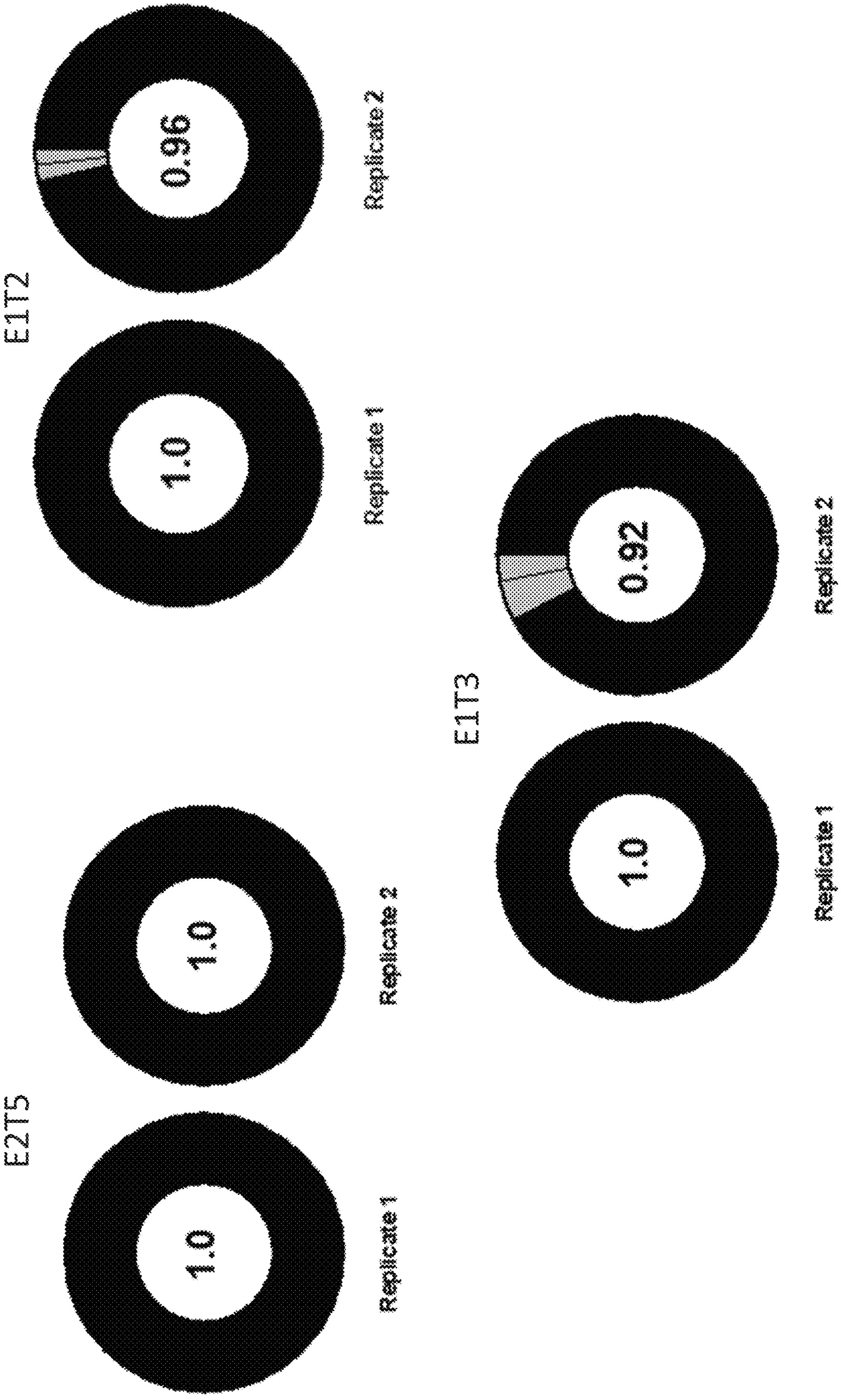
FIG. 7B shows plots depicting two replicates of TTISS reads for variant Cas12i2 of SEQ ID NO: 927 and HAO1-targeting RNA guides E2T5 (SEQ ID NO: 989), E1T2 (SEQ ID NO: 967), and E1T3 (SEQ ID NO: 968). The black wedge and centered number represent the fraction of on-target TTISS reads. Each gray wedge represents a unique off-target site identified by TTISS. The size of each gray wedge represents the fraction of TTISS reads mapping to a given off-target.

FIG. 7A and FIG. 7B show plots depicting on-target and off-target TTISS reads. The black wedge and centered number represent the fraction of on-target TTISS reads. Each grey wedge represents a unique off-target site identified by TTISS. The size of each grey wedge represents the fraction of TTISS reads mapping to a given off-target site. FIG. 7A shows TTISS reads for variant Cas12i2 of SEQ ID NO: 924, and FIG. 7B shows TTISS reads for variant Cas12i2 of SEQ ID NO: 927.

As shown in FIG. 7A, variant Cas12i2 of SEQ ID NO: 924 paired with E2T5 demonstrated a low likelihood of off-target editing, as 100% of TTISS reads mapped to the on-target. No TTISS reads mapped to potential off-target sites. E1T2 also showed a low likelihood of off-target editing. For E1T2, 98% of TTISS reads mapped to the on-target, and two potential off-target sites represented a combined 2% of TTISS reads. For E5T10, 95% of TTISS reads mapped to the on-target, and two potential off-target sites represented a combined 5% of TTISS reads. E2T10 demonstrated a higher likelihood of off-target editing using the TTISS method. For E2T10, only 65% of TTISS reads mapped to the on-target and 4 potential off-target sites represented the remaining combined 35% of TTISS reads. One potential off-target represented the majority of potential off-target TTISS reads for E2T10.

As shown in FIG. 7B, variant Cas12i2 of SEQ ID NO: 927 paired with E2T5 demonstrated a low likelihood of off-target editing, as 100% of TTISS reads mapped to the on-target. No TTISS reads mapped to potential off-target sites. Variant Cas12i2 of SEQ ID NO: 927 paired with the E1T2 or E1T3 also demonstrated a low likelihood of off-target editing. For E1T2, 100% of TTISS reads in replicate 1 and 96% of TTISS reads in replicate 2 mapped to the on-target; two potential off-target sites represented the remaining 4% of TTISS reads in replicate 2. For E1T3, 100% of TTISS reads in replicate 1 and 92% of TTISS reads in replicate 2 mapped to the on-target; two potential off-target sites represented the remaining 8% of TTISS reads in replicate 2.

Therefore, this Example shows that compositions comprising Cas12i2 and HAO1-targeting RNA guides comprise different off-target activity profiles.

Example 7—HAO1 Protein Knockdown with Cas12i2 and HAO1-Targeting RNA Guides

This Example describes use of a Western Blot to identify knockdown of HAO1 protein using variant Cas12i2 of SEQ ID NO: 924 and HAO1-targeting RNA guides.

Primary hepatocyte cells from human donors were thawed from liquid nitrogen very quickly in a 37° C. water bath. The cells were added to pre-warmed hepatocyte recovery media (Thermo Fisher, CM7000) and centrifuged at 100 g for 10 minutes. The cell pellet was resuspended in appropriate volume of hepatocyte plating Medium (Williams' Medium E, Thermo Fisher A1217601 supplemented with Hepatocyte Plating Supplement Pack (serum-containing), Thermo Fisher CM3000). The cells were subjected to trypan blue viability count with an Inucyte disposable hemocytometer (Fisher scientific, 22-600-100). The cells were then washed in PBS and resuspended in P3 buffer+supplement (Lonza, VXP-3032) at a concentration of ~5000 cells/μL. Resuspended cells were dispensed at 500,000 cells/reaction into Lonza electroporation cuvettes For the RNP reactions, E2T5 (SEQ ID NO: 989) was used as the HAO1-targeting RNA guides. RNPs were added to each reaction at a final concentration of 20 μM (Cas12i2), and transfection enhancer oligos were then added at a final concentration of 4 Unelectroporated cells and cells electroporated without cargo were used as negative controls.

The strips were electroporated using an electroporation device (program CA137, Lonza 4D-nucleofector). Immediately following electroporation, pre-warmed Hepatocyte plating medium was added to each well and mixed very gently by pipetting. For each technical replicate plate, 500,000 cells of diluted nucleofected cells were plated into a pre-warmed collagen-coated 24-well plate (Thermo Fisher) with wells containing Hepatocyte plating medium. The cells were then incubated at 37° C. The media was changed to hepatocyte maintenance media (Williams' Medium E, Thermo Fisher A1217601 supplemented with William's E medium Cell Maintenance Cocktail, Thermo Fisher CM 4000) after the cells attached after 24 hours. Fresh hepatocyte maintenance media was replaced every 48 hours.

16 days post RNP electroporation, the media was aspirated, and the cells were washed gently with PBS. Cells were then lysed with RIPA Lysis and Extraction buffer (Thermo Fisher 89901)+1× protease inhibitors (Thermo Fisher 78440) for 30 minutes on ice, mixing the samples every 5 minutes. Cell lysate was quantified via Pierce BCA Protein Assay Kit (Thermo Fisher 23227). 15 μg of total protein per sample was prepared for SDS-PAGE in 1× Laemmlli Sample buffer (BioRad 1610747) and 100 mM DTT, then heated at 95 C for 10 minutes. Samples were run on a 4-15% TGX gel (BioRad 5671084) at 200V for 45 minutes. Samples were transferred to a 0.2 um nitrocellulose membrane (BioRad 1704159) using the Trans Blot Turbo System. The membrane was blocked in Intercept TBS Blocking Buffer (Li-cor 927-60001) for 30 minutes at room temperature. The blot was then incubated in a 1:1000 dilution of primary anti-HAO1 antibody (Genetex GTX81144) and 1:2500 dilution of primary anti-vinculin antibody (Sigma V9131) in blocking buffer at 4 C overnight. The blot was washed three times with TBST (ThermoFisher 28360) for 5 minutes each, then incubated with a 1:12500 dilution of IR680 anti-mouse (ThermoFisher PI35518) and IR800 anti-rabbit secondary antibodies (ThermoFisher PISA535571) in TBST for 1 hour at room temperature. The blot was then washed three times with TBST for 5 minutes each and visualized on the Li-cor Odyssey CLX.

Figure 8:
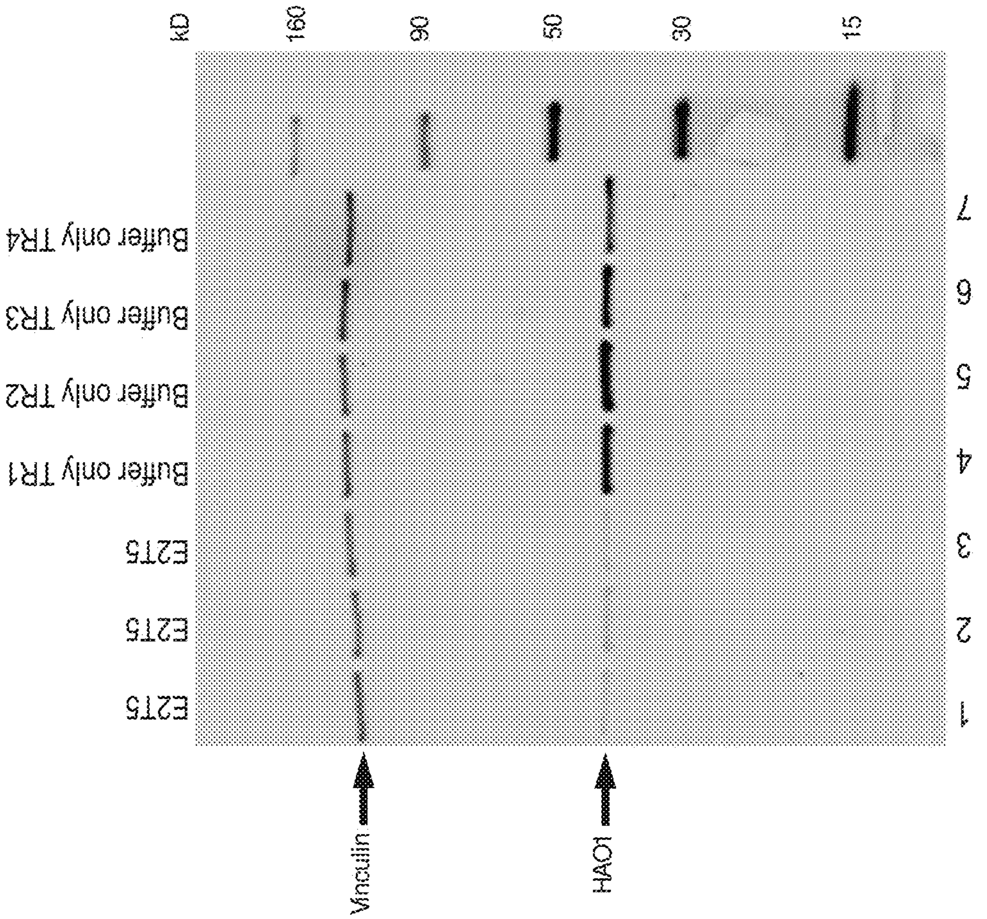
FIG. 8 is a Western Blot showing knockdown of HAO1 protein following electroporation of primary human hepatocytes with variant Cas12i2 of SEQ ID NO: 924 and RNA guide E2T5 (SEQ ID NO: 989).

Knockdown of HAO1 protein was observed in primary human hepatocytes at Day 7 post editing by Cas12i2 RNPs targeting the HAO1 gene with E2T5 (lanes 1-3 of FIG. 8). HAO1 knockdown was not observed for the buffer only controls (lanes 4-7).

This Example thus shows that HAO1 protein levels were decreased following editing with Cas12i2 and HAO1-targeting RNA guides.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e., "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

What is claimed is:

1. A gene editing system for genetic editing of a hydroxyacid oxidase 1 (HAO1) gene, comprising (i) a Cas12i2 polypeptide or a first nucleic acid encoding the Cas12i2 polypeptide, wherein the Cas12i2 polypeptide comprises an amino acid sequence identical to SEQ ID NO: 924 or 927;

(ii) an RNA guide or a second nucleic acid encoding the RNA guide, wherein the RNA guide comprises a spacer sequence specific to a target sequence within an HAO1 gene, the target sequence being adjacent to a protospacer adjacent motif (PAM) comprising the motif of 5'-TTN-3', which is located 5' to the target sequence and wherein the RNA guide comprises the nucleotide sequence of:

(SEQ ID NO: 967)
5'-AGAAAUCCGUCUUUCAUUGACGGCAAAGUCUAUAUAUGACUAU-3'.

2. The gene editing system of claim 1, which comprises the first nucleic acid encoding the Cas12i2 polypeptide.

3. The gene editing system of claim 2, wherein the first nucleic acid is a messenger RNA (mRNA), and/or is included in a viral vector.

4. The gene editing system of claim 3, wherein the viral vector comprises both the first nucleic acid encoding the Cas12i2 polypeptide and the second nucleic acid encoding the RNA guide.

5. The gene editing system of claim 4, wherein the system comprises the first nucleic acid encoding the Cas12i2 polypeptide, which is located in a first vector, and wherein the system comprises the second nucleic acid encoding the RNA guide, which is located in a second vector; or wherein the system comprises one or more lipid nanoparticles (LNPs), which encompass (i), (ii), or both.

6. The gene editing system of claim 5, wherein the system comprises the LNP, which encompass (i), and wherein the system comprises a viral vector comprising the second nucleic acid encoding the RNA guide; or wherein the system comprises the LNP, which encompass (ii), and wherein the system comprises a viral vector comprising the first nucleic acid encoding Cas12i2 polypeptide.

7. The gene editing system of claim 6, wherein the viral vector is an AAV vector.

8. The gene editing system of claim 1, wherein the system comprises the second nucleic acid encoding the RNA guide, or wherein the nucleic acid encoding the RNA guide is located in a viral vector.

9. A pharmaceutical composition comprising the gene editing system set forth in claim 1.

10. A kit comprising the elements (i) and (ii) of the gene editing system set forth in claim 1.

11. A method for editing a hydroxyacid oxidase 1 (HAO1) gene in a cell, the method comprising contacting a host cell with the gene editing system for editing the HAO1 gene set forth in claim 1 to genetically edit the HAO1 gene in the host cell.

12. A method for treating primary hyperoxaluria (PH) in a subject, comprising administering to a subject in need thereof a gene editing system for editing a hydroxyacid oxidase 1 (HAO1) gene set forth in claim 1.

13. The gene editing system of claim 1, wherein the first nucleic acid is a messenger RNA (mRNA).

14. The gene editing system of claim 13, wherein the system comprises (i) the messenger RNA, and (ii) the RNA guide; and wherein the system comprises one or more lipid nanoparticles (LNPs), which encompass (i), (ii), or both.

* * * * *